(12) United States Patent
Ellmark et al.

(10) Patent No.: US 11,873,348 B2
(45) Date of Patent: Jan. 16, 2024

(54) PEPTIDES

(71) Applicant: ALLIGATOR BIOSCIENCE AB, Lund (SE)

(72) Inventors: Peter Ellmark, Lund (SE); Karin Hagerbrand, Hjarup (SE); Laura Varas, Lund (SE); Mattias Levin, Lund (SE); Anna Säll, Lund (SE); Laura von Schantz, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 0 days.

(21) Appl. No.: 17/980,751

(22) Filed: Nov. 4, 2022

(65) Prior Publication Data

US 2023/0312754 A1 Oct. 5, 2023

(30) Foreign Application Priority Data

| Nov. 5, 2021 | (GB) | 2115925 |
| Mar. 30, 2022 | (GB) | 2204539 |
| Sep. 2, 2022 | (GB) | 2212801 |

(51) Int. Cl.
| *A61K 39/395* | (2006.01) |
| *A61K 39/00* | (2006.01) |
| *C07K 16/46* | (2006.01) |
| *A61P 35/00* | (2006.01) |

(52) U.S. Cl.
CPC ............ *C07K 16/468* (2013.01); *A61P 35/00* (2018.01); *C07K 2317/31* (2013.01); *C07K 2317/565* (2013.01); *C07K 2317/77* (2013.01)

(58) Field of Classification Search
None
See application file for complete search history.

(56) References Cited

U.S. PATENT DOCUMENTS

| 4,235,871 | A | 11/1980 | Papahadjapoulos | |
| 4,816,567 | A | 3/1989 | Cabilly et al. | |
| 5,851,451 | A | 12/1998 | Takechi et al. | |
| 2012/0251531 | A1 | 10/2012 | Baehner et al. | |
| 2019/0336615 | A1* | 11/2019 | Thompson | A61K 47/6879 |
| 2022/0073635 | A1* | 3/2022 | Sall | C07K 16/32 |
| 2022/0372155 | A1* | 11/2022 | Wang | C07K 16/32 |

FOREIGN PATENT DOCUMENTS

| EP | 213303 A2 | 3/1987 | |
| WO | WO-2013034904 A1 * | 3/2013 | A61K 39/395 |
| WO | 2020/127354 A2 | 6/2020 | |
| WO | 2021/081303 A1 | 4/2021 | |
| WO | WO-2021081303 A1 * | 4/2021 | A61P 35/00 |

OTHER PUBLICATIONS

Thiemann et al; Abstract 4460: Novel bispecific molecules combining HERA-CD40L with anti-CEA or with anti-PD-L1 for targeting. Cancer Res Aug. 15, 2020; 80 (16_Supplement):4460 (Year: 2020).*
Hagerbrand et al. Bispecific antibodies targeting CD40 and tumor-associated antigens promote cross-priming of T cells resulting in an antitumor response superior to monospecific antibodies. J Immunother Cancer. Nov. 2022;10(11):e005018. (Year: 2022).*
Altschul, et al., "A Protein Alignment Scoring System Sensitive at All Evolutionary Distances" J. Mol. Evol. (1993) 36:290-300.
Karlin, et al., "Applications and statistics for multiple high-scoring segments in molecular sequences" Proc. Natl. Acad. Sci. (1993) 90:5873-5877.
Altschul, et al., "Basic Local Alignment Search Tool" J. Mol. Biol. (1990) 215:403-410.
Angov, et al., "Codon usage: Nature's roadmap to expression and folding of proteins" Biotechnol. J. (2011) 6:650-659.
Attucci, et al., "EPI-hNE4, a Proteolysis-Resistant Inhibitor of Human Neutrophil Elastase and Potential Anti-Inflammatory Drug for Treating Cystic Fibrosis" J. Pharmacol. Exper. Therap. (2006) 318:803-809.
Banereau, et al., "The CD40 Antigen and Its Ligand" Annu. Rev. Immunol. (1994) 12:881-922.
Beatty, et al., "CD40 Agonists Alter Tumor Stroma and Show Efficacy Against Pancreatic Carcinoma in Mice and Humans" Science (2011) 331(6024):1612-1616.
Beatty, et al., "Cancer immunotherapy: activating innate and adaptive immunity through CD40 agonists" Expert. Rev. Anticancer Ther. (2017) 17(2):175-186.
Binz, et al., "High-affinity binders selected from designed ankyrin repeat protein libraries" Nat. Biotech. (2004) 22(5):575-582.
Boerner, et al., "Production of Antigen-Specific Human Monoclonal Antibodies From in Vitro-Primed Human Splenocytes" J. Immunol. (1991) 147:86-95.
Borghouts, et al., "Peptide aptamers: recent developments for cancer therapy" Expert Opin. Biol. Ther. (2005) 5(6):783-797.
Bouchlaka, et al., "Aging predisposes to acute inflammatory induced pathology after tumor immunotherapy" J. Exp. Med. (2013) 210:2223-2237.
Broz, et al., "Dissecting the Tumor Myeloid Compartment Reveals Rare Activating Antigen-Presenting Cells Critical for T Cell Immunity" Cancer Cell (2014) 26:638-652.
Bruhns, et al., "Specificity and affinity of human FcGamma receptors and their polymorphic variants for human IgG subclasses" Blood (2009) 113:3716-3725.
Bruhns, P., "Properties of mouse and human IgG receptors and their contribution to disease models" Blood (2012) 119(24):5640-5649.
Byrne, et al., "CD40 Stimulation Obviates Innate Sensors and Drives T Cell Immunity in Cancer" Cell Reports (2016) 15:2719-2732.
Caceci, et al., "Fitting Curves to Data" Byte (1984) 340-362.
Carenza, et al., "Costimulatory Molecules and Immune Checkpoints Are Differentially Expressed on Different Subsets of Dendritic Cells" Frontiers Immunol. (2019) 10:1325.

(Continued)

*Primary Examiner* — Maher M Haddad
(74) *Attorney, Agent, or Firm* — Robert C. Netter, Jr.; Dann, Dorfman, Herrell & Skillman

(57) ABSTRACT

The present invention relates to novel bispecific polypeptides, such as antibodies, and their use in the treatment of cancers, particularly cancers expressing carcinoembryonic antigen (CEA).

7 Claims, 60 Drawing Sheets

Specification includes a Sequence Listing.

(56) References Cited

OTHER PUBLICATIONS

Caux, et al., "Activation of Human Dendritic Cells through CD40 Cross-linking" J. Exp. Med. (1994) 180:1263-1272.
Chan, et al., "Therapeutic antibodies for autoimmunity and inflammation" Nat. Rev. (2010) 10:301-316.
Chevrier, et al., "An Immune Atlas of Clear Cell Renal Cell Carcinoma" Cell (2017) 169:736-749.
Cole, et al., "Human monoclonal antibodies" Molecular and Cellular Biochemistry (1984) 62:109-120.
Cole, et al., "The EBV-Hybridoma Technique and Its Application to Human Lung Cancer" Monoclonal Antibodies and Cancer Therapy (1985) 77-96.
Dereveux, et al., "A comprehensive set of sequence analysis programs for the VAX" Nucleic Acids Res. (1984) 12:387-395.
Elgueta, et al., "Molecular mechanism and function of CD40/CD40L engagement in the immune system" Immunol. Rev. (2009) 229(1):152-72.
Eliopoulos, et al., "The role of the CD40 pathway in the pathogenesis and treatment of cancer" Current Opinion in Pharmacology (2004) 4:360-367.
Flamar, et al., "Targeting concatenated HIV antigens to human CD40 expands a broad repertoire of multifunctional CD4+ and CD8+ T cells" AIDS (2013) 27(13):2041-51.
Gebauer, et al., "Engineered protein scaffolds as next-generation antibody therapeutics" Current Opinion in Chemical Biology (2009) 13:245-255.
Gladue, et al., "The CD40 agonist antibody CP-870,893 enhances dendritic cell and B-cell activity and promotes anti-tumor efficacy in SCID-hu mice" Cancer Immunol. Immunother. (2011) 60(7):1009-17.
Hedge, et al., "Dendritic Cell Paucity Leads to Dysfunctional Immune Surveillance in Pancreatic Cancer" Cancer Cell (2020) 37:289-307.
Henikoff, et al., "Amino acid substitution matrices from protein blocks" Proc. Natl. Acad. Sci. (1992) 89:10915-10919.
Hey, et al., "Artificial, non-antibody binding proteins for pharmaceutical and industrial applications" Trends in Biotechnology (2005) 23(10):514-522.
Hezareh, et al., "Effector Function Activities of a Panel of Mutants of a Broadly Neutralizing Antibody against Human Immunodeficiency Virus Type 1" Journal of Virology (2001) 75:12161-12168.
Hildner, et al., "Batf3 Deficiency Reveals a Critical Role for CD8α+ Dendritic Cells in Cytotoxic T Cell Immunity" Science (2008) 322(5904):1097-1100.
Hinton, et al., "Engineered Human IgG Antibodies with Longer Serum Half-lives in Primates" The Journal of Biological Chemistry (2004) 279(8):6213-6216.
Hogarth, et al., "Fc receptor-targeted therapies for the treatment of inflammation, cancer and beyond" Nat. Rev. (2012) 11:311-331.
Hoogenboom, et al., "Multi-subunit proteins on the surface of filamentous phage: methodologies for displaying antibody (Fab) heavy and light chains" Nucleic Acids Research (1991) 19(15):4133-4137.
Huffman, et al., "CCL5 mediates CD40-driven CD4+ T cell tumor infiltration and immunity" JCI Insight (2020) 5(10): e137263.
Hurrell, J.G.R., "Monoclonal Hybridoma Antibodies: Techniques and Applications" CRC Press., Boca Raton, Florida, 1982, pp. 1-57.
Jackaman, et al., "CD40-activated B cells contribute to mesothelioma tumor regression" Immunology and Cell Biology (2011) 89:255-267.
Jones, et al., "Replacing the complementarily—determining regions in a human antibody with those from a mouse" Nature (1986) 321:522-525.
Ju, et al., "Aglycosylated full-length IgG antibodies: steps toward next-generation immunotherapeutics" Current Opinion in Biotechnology (2014) 30:128-139.
Khong, et al., "The Use of Agonistic Anti-CD40 Therapy in Treatments for Cancer" International Reviews of Immunology (2012) 31:246-266.
Kiefer, et al., "Immunocytokines and bispecific antibodies: two complementary strategies for the selective activation of immune cells at the tumor site" Immunol Rev. (2016) 270(1):178-192.
Kohler, et al., "Continuous cultures of fused cells secreting antibody of predefined specificity" Nature (1975) 256(5517):495-497.
Arndt, et al., "Protein Engineering Protocols" Humana Press, New Jersey, 2007, pp. 1-312.
Kornbluth, et al., "Design of CD40 Agonists and their use in growing B cells for cancer immunotherapy" Int Rev Immunol. (2012) 31(4):279-88.
Korniluk, et al., "Multifunctional CD40L: pro- and anti-neoplastic activity" Tumor Biol. (2014) 35:9447-9457.
Kozbor, et al., "Specific Immunoglobulin Production and Enhanced Tumorigenicity Following Ascites Growth of Human Hybridomas" J. Immunol. Methods (1985) 81:31-42.
Krause, et al., "Grafting of thrombopoietin-mimetic peptides into cystine knot miniproteins yields high-affinity thrombopoietin antagonists and agonists" FEBS Journal (2007) 274:86-95.
Leabman, et al., "Effects of altered FcγR binding on antibody pharmacokinetics in cynomolgus monkeys" mAbs (2013) 5:896-903.
Liu, et al., "A new perspective: Exploring future therapeutic strategies for cancer by understanding the dual role of B lymphocytes in tumor immunity" Int. J. Cancer (2019) 144:2909-2917.
Long, et al., "IFN g and CCL2 Cooperate to Redirect Tumor-Infiltrating Monocytes to Degrade Fibrosis and Enhance Chemotherapy Efficacy in Pancreatic Carcinoma" Cancer Discov. (2016) 6(4):400-13.
Luheshi, et al., "Transformation of the tumour microenvironment by a CD40 agonist antibody correlates with improved responses to PD-L1 blockade in a mouse orthotopic pancreatic tumour model" Oncotarget (2016) 7:18508-18520.
Lum, et al., "In vivo CD40 ligation can induce T cell-independent antitumor effects that involve macrophages" J. Leukoc. Biol. (2006) 79:1181-1192.
Ma, et al., "The role of CD40 and CD40L in Dendritic Cells" Semin. Immunol. (2009) 21(5):265-272.
MacDonald, et al., "Characterization of human blood dendritic cell subsets" Blood (2002) 100:4512-4520.
Machiels, et al., "Phase Ib study of anti-CSF-1R antibody emactuzumab in combination with CD40 agonist selicrelumab in advanced solid tumor patients" Journal for Immuno Therapy of Cancer (2020) 8:e001153.
Mangsbo, et al., "The Human Agonistic CD40 Antibody ADC-1013 Eradicates Bladder Tumors and Generates T-cell-Dependent Tumor Immunity" Clin Cancer Res. (2015) 21(5):1115-26.
Marks, et al., "By-passing Immunization: Human Antibodies from V-gene Libraries Displayed on Phage" J. Mol. Biol. (1991) 222:581-597.
Medina-Echeverz, et al., "Systemic Agonistic Anti-CD40 Treatment of Tumor-Bearing Mice Modulates Hepatic Myeloid-Suppressive Cells and Causes Immune-Mediated Liver Damage" Cancer Immunol Res. (2015) 3(5):557-66.
Mirsoian, et al., "Adiposity induces lethal cytokine storm after systemic administration of stimulatory immunotherapy regimens in aged mice" J. Exp. Med. (2014) 211(12):2373-2383.
Moran, et al., "The TNFRs OX40, 4-1BB, and CD40 as targets for cancer immunotherapy" Curr. Opin. Immunol. (2013) 25(2):230-7.
Morrison, et al., "Sufficiency of CD40 activation and immune checkpoint blockade for T cell priming and tumor immunity" PNAS (2020) 117:8022-8031.
Nygren, P., "Alternative binding proteins: Affibody binding proteins developed from a small three-helix bundle scaffold" FEBS Journal (2008) 275:2668-2676.
Oganesyan, et al., "Structural characterization of a mutated, ADCC-enhanced human Fc fragment" Molecular Immunology (2008) 45:1872-1882.
Orlandi, et al., "Cloning immunoglobulin variable domains for expression by the polymerase chain reaction" Proc. Natl. Acad. Sci. (1989) 86:3833-3837.
Peters, et al., "CD40 and Autoimmunity: The Dark Side of a Great Activator" Semin Immunol. (2009) 21(5):293-300.

(56) References Cited

OTHER PUBLICATIONS

Presta, L.G., "Antibody engineering" Current Opinion in Biotechnology (1992) 3:394-398.
Pule, et al., "Artificial T-cell receptors" Cytotherapy (2003) 5:211-226.
Rakhilevich, et al., "T-cell-independent Antitumor Effects of CD40 Ligation" Int Rev Immunol. (2012) 31(4):267-278.
Riechmann, et al., "Reshaping human antibodies for therapy" Nature (1988) 332:323-327.
Sanchez-Paulete, et al., "Cancer immunotherapy with immunomodulatory anti-CD137 and anti-PD-1 monoclonal antibodies requires Batf3-dependent dendritic cells" Cancer Discov. (2016) 6(1):71-79.
Sanchez-Paulete, et al., "Antigen cross-presentation and T-cell cross-priming in cancer immunology and immunotherapy" Annals of Oncology (2017) 28(Supplement 12):xii44-xii55.
Sazinsky, et al., "Aglycosylated immunoglobulin G1 variants productively engage activating Fc receptors" PNAS (2008) 105(51):20167-20172.
Schlehuber, et al., "Lipocalins in drug discovery: from natural ligand-binding proteins to 'anticalins'" Drug Discovery Today (2005) 10(1):23-33.
Schroeder, et al., "Abstract 1587: Generation and characterization of novel bispecific molecules combining single chain-CD40L with anti-CEA, anti-CD95L, or anti-PD-L1 targeting moieties" Cancer Res. (2021) 81:1587.
Shields, et al., "High Resolution Mapping of the Binding Site on Human IgG1 for FcgRI, FcgRII, FcgRIII, and FcRn and Design of IgG1 Variants with Improved Binding to the FcgR" J. Biol. Chem. (2001) 276:6591-6604.
Silverman, et al., "Multivalent avimer proteins evolved by exon shuffling of a family of human receptor domains" Nat. Biotech. (2005) 23:1556-1561.
Stewart, et al., "The role of Fc gamma receptors in the activity of immunomodulatory antibodies for cancer" Journal for ImmunoTherapy of Cancer (2014) 2:29.
Strohl, W.R., "Optimization of Fc-mediated effector functions of monoclonal antibodies" Current Opinion in Biotechnology (2009) 20:685-691.
Thompson, et al., "CLUSTAL W: improving the sensitivity of progressive multiple sequence alignment through sequence weighting, position-specific gap penalties and weight matrix choice" Nucleic Acids Research (1994) 22(22):4673-4680.
Thorsett, et al., "Dipeptide Mimics. Conformationally Restricted Inhibitors of Angiotensin-Converting Enzyme" Biochemical and Biophysical Research Communications (1983) 111(1):166-171.
Turner, et al., "Anti-CD40 Antibody Induces Antitumor and Antimetastatic Exects: The Role of NK Cells" J Immunol. (2001) 166(1):89-94.
Tutt, et al., "T Cell Immunity to Lymphoma Following Treatment with Anti-CD40 Monoclonal Antibody" J Immunol. (2002) 168(6):2720-2728.
Vaccaro, et al., "Engineering the Fc region of immunoglobulin G to modulate in vivo antibody levels" Nat. Biotech. (2005) 23:1283-1288.
Vankooten, et al., "Functions of CD40 on B cells, dendritic cells and other cells" Current Opinion in Immunology (1997) 9:330-33.
Vanmierlo, et al., "CD40 stimulation leads to effective therapy of CD40-tumors through induction of strong systemic cytotoxic T lymphocyte immunity" PNAS (2002) 99(8):5561-5566.
Veber, et al., "Conformationally restricted bicyclic analogs of somatostatin" Proc. Natl. Acad. Sci. (1978) 75(6):2636-2640.
Verhoeyen, et al., "Reshaping Human Antibodies: Grafting an Antilysozyme Activity" Science (1988) 239:1534-1536.
Vidarson, et al., "IgG subclasses and allotypes: from structure to effector functions" Frontiers in Immunology (2014) 5:520.
Vonderheide, et al., "Agonistic CD40 antibodies and cancer therapy" Clin. Cancer Res. (2013) 19(5):1035-1043.
Werneburg, et al., "Molecular Characterization of CD40 Signaling Intermediates" J. Biol. Chem. (2001) 276 (46):43334-43342.
Winter, et al., "Man-made antibodies" Nature (1991) 349:293-299.
Wong, et al., "A double-filter method for nitrocellulose-filter binding: Application to protein-nucleic acid interactions" Proc. Natl. Acad. Sci. (1993) 90:5428-5432.
Xu, et al., "Production of bispecific antibodies in "knobs-into-holes" using a cell-free expression system" mAbs (2015) 7:1-12.
Zarnegar, et al., "Unique CD40-mediated biological program in B cell activation requires both type 1 and type 2 NF-kB activation pathways" PNAS (2004) 101:8108-8113.
Hong, et al., "Innate immune cells and their interaction with T cells in hepatocellular carcinoma (Review)" Oncology Letters (2021) 21:57.
Zhang, et al., "Single-Cell Analyses Inform Mechanisms of Myeloid-Targeted Therapies in Colon Cancer" Cell (2020) 181:442-459.
Zheng, et al., "A Novel Anti-CEACAM5 Monoclonal Antibody, CC4, Suppresses Colorectal Tumor Growth and Enhances NK Cells-Mediated Tumor Immunity" PLoS ONE (2011) 6(6):e21146.
Han, et al., "The old CEACAMs find their new role in tumor immunotherapy" Investigational New Drugs (2020) 38(6):1888-1898.
Zhang, et al., "Landscape and Dynamics of Single Immune Cells in Hepatocellular Carcinoma" Cell (2019) 179(4):829-845.

* cited by examiner

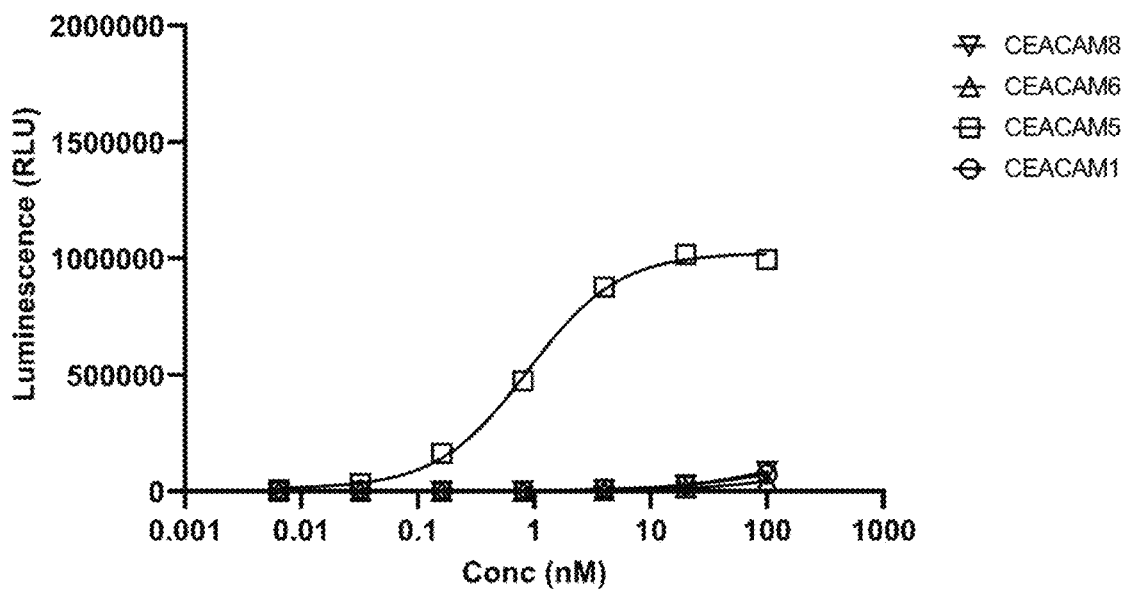
FIG. 3C Multi37
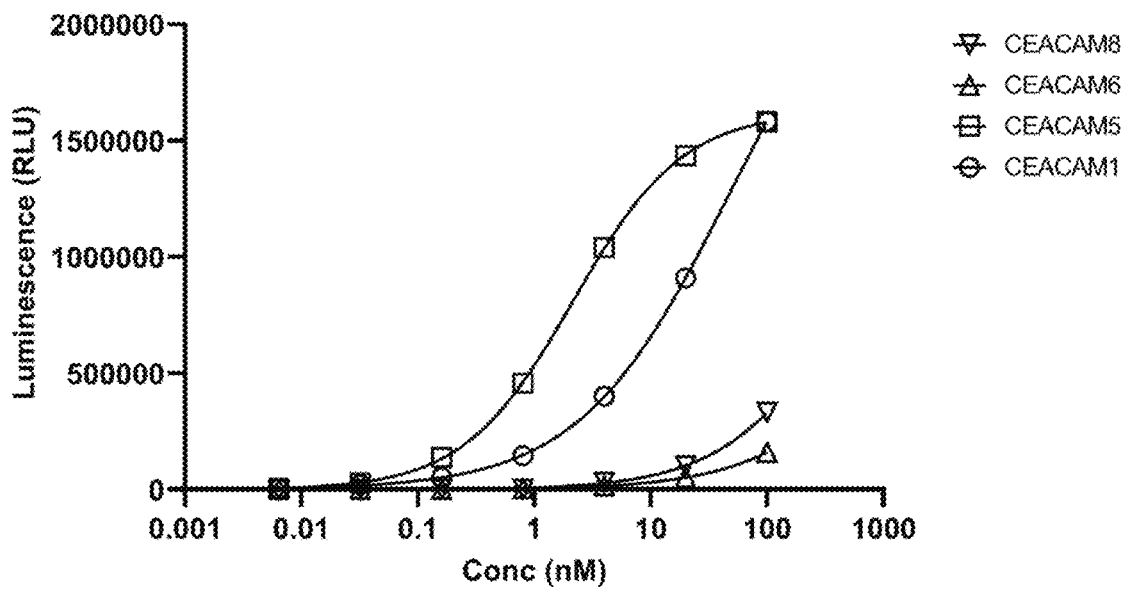
FIG. 3D Multi38

Multi41

Multi42

Multi48

Multi49

IgG-scFv

Kih alt. Cross Mab     scFv₂-Fc     BiTE/scFv₂     DVD-Ig

DART₂-Fc     DART-Fc     DART

DNL-Fab3     scFv-HSA-scFv

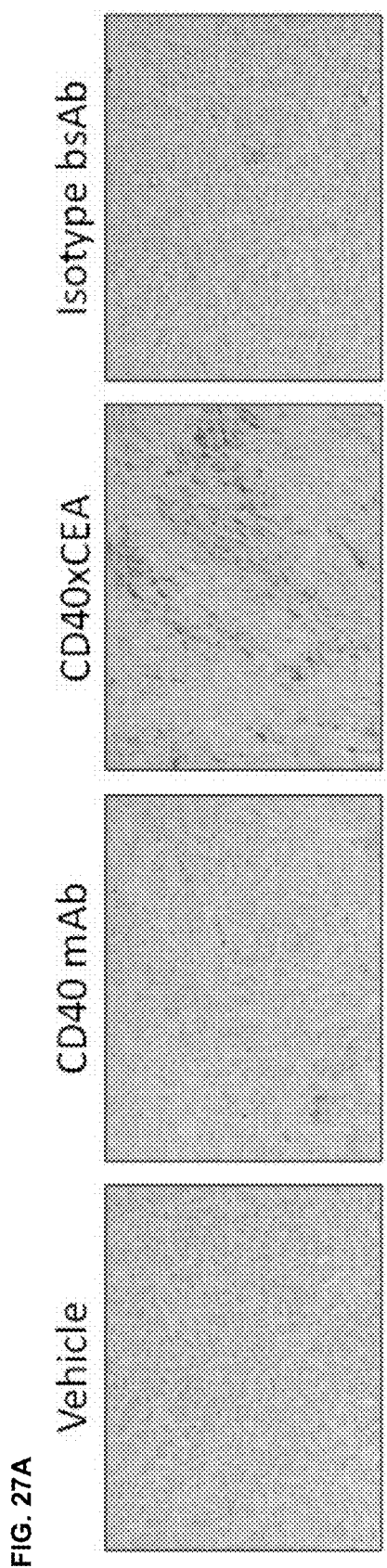
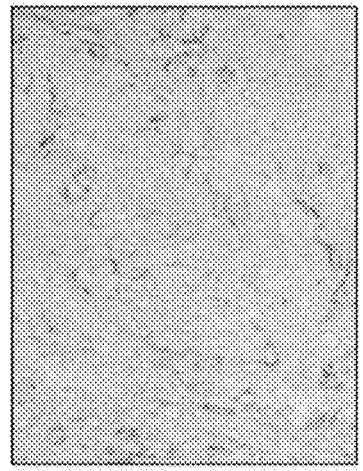
FIG. 27A
FIG. 27B

CD4	CD8

CD3	CD45

|  | B16, #6 | B16, #7 | B16, #9 | MB49, #2 | MB49, #4 | MB49, #5 | spleen |
|---|---|---|---|---|---|---|---|
| CD4 | 0-1+ | 1+ | 1-2+ | 3+ | 2-3+ | 3+ | 3+ |
| CD8 | 0-1+ | 0-1+ | 1+ | 3+ | 2-3+ | 2-3 | 3+ |
| CD3 | 0-1+ | 1+ | 1-2+ | 3+ | 3+ | 2-3+ | 3+ |
| CD45 | 2+ | 2+ | 2-3+ | 4+ | 4+ | 4+ | 4+ |

| Dose level | Sex | Day1 | | | Day8 | | |
|---|---|---|---|---|---|---|---|
| | | 0h | 4h | 24h | 0h | 4h | 24h |
| 10 mg/kg | M | <LLOQ | 158 | <LLOQ | <LLOQ | <LLOQ | <LLOQ |
| 10 mg/kg | F | <LLOQ | <LLOQ | <LLOQ | <LLOQ | <LLOQ | <LLOQ |
| 37.5 mg/kg | M | <LLOQ | <LLOQ | <LLOQ | <LLOQ | <LLOQ | <LLOQ |
| 37.5 mg/kg | F | <LLOQ | <LLOQ | <LLOQ | <LLOQ | <LLOQ | <LLOQ |

LLOQ = 37.5 pg/mL

TNFa (pg/ml)

| Dose level | Sex | Day1 | | | Day8 | | |
|---|---|---|---|---|---|---|---|
| | | 0h | 4h | 24h | 0h | 4h | 24h |
| 10 mg/kg | M | 176 | 237 | <LLOQ | <LLOQ | 273 | <LLOQ |
| 10 mg/kg | F | <LLOQ | <LLOQ | <LLOQ | <LLOQ | <LLOQ | <LLOQ |
| 37.5 mg/kg | M | <LLOQ | 111 | <LLOQ | <LLOQ | <LLOQ | <LLOQ |
| 37.5 mg/kg | F | <LLOQ | <LLOQ | <LLOQ | <LLOQ | <LLOQ | <LLOQ |

LLOQ = 37.5 pg/mL

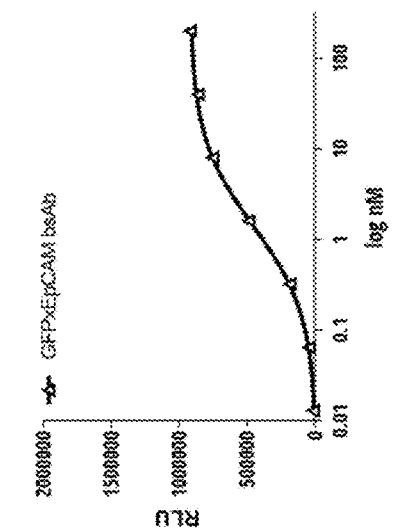
FIG. 30A
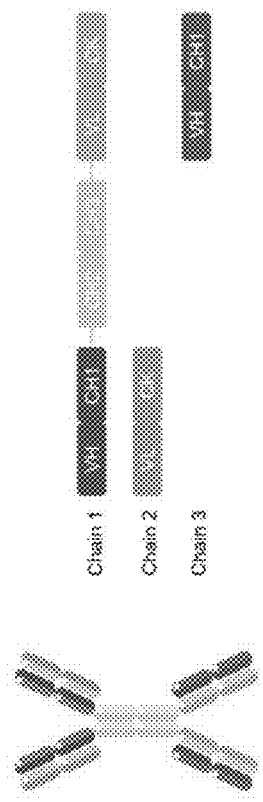
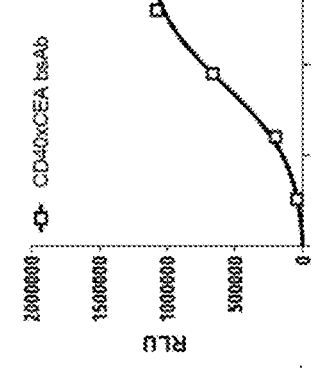
FIG. 30B
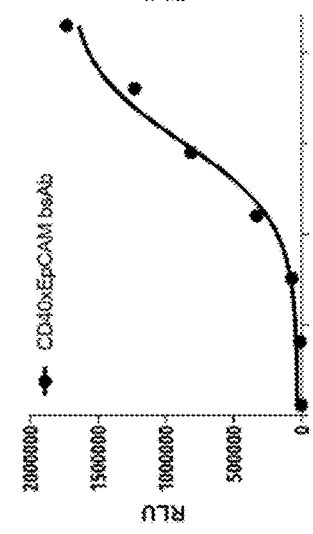
FIG. 30E
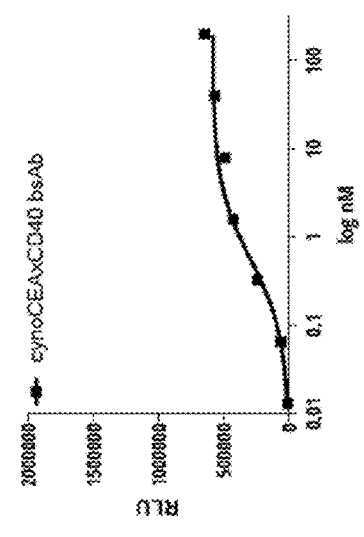
FIG. 30C
FIG. 30D
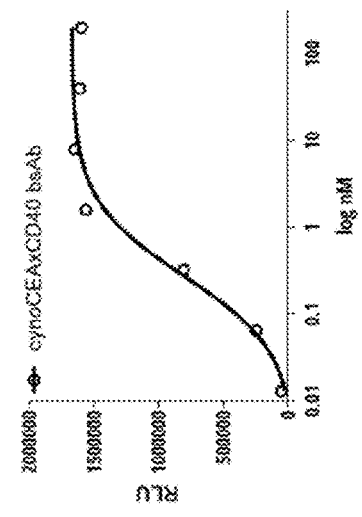
FIG. 30F

```
                         SEQUENCE LISTING

Sequence total quantity: 437
SEQ ID NO: 1              moltype = AA  length = 107
FEATURE                   Location/Qualifiers
source                    1..107
                          mol_type = protein
                          organism = synthetic construct
SEQUENCE: 1
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ YGRNPPTFGQ GTKLEIK                107

SEQ ID NO: 2              moltype = DNA  length = 321
FEATURE                   Location/Qualifiers
source                    1..321
                          mol_type = other DNA
                          organism = synthetic construct
SEQUENCE: 2
gatattcaga tgacccagag cccgagcagc ctgagcgcga gcgtgggcga tcgcgtgacc   60
attacctgcc gcgcgagcca gagcattagc agctatctga actggtatca gcagaaaccg  120
ggcaaagcgc cgaaactgct gatttatgcg gcgagcagcc tgcagagcgg cgtgccgagc  180
cgctttagcg gcagcggcag cggcaccgat tttaccctga ccattagcag cctgcagccg  240
gaagattttg cgacctatta ttgccagcag tatggccgca acccgccgac ctttggccag  300
ggcaccaaac tggaaattaa a                                            321

SEQ ID NO: 3              moltype = AA  length = 117
FEATURE                   Location/Qualifiers
source                    1..117
                          mol_type = protein
                          organism = synthetic construct
SEQUENCE: 3
EVQLLESGGG LVQPGGSLRL SCAASGFTFS SYAMSWVRQA PGKGLEWVSG IGSYGGGTYY   60
ADSVKGRFTI SRDNSKNTLY LQMNSLRAED TAVYYCARYV NFGMDYWGQG TLVTVSS    117

SEQ ID NO: 4              moltype = DNA  length = 351
FEATURE                   Location/Qualifiers
source                    1..351
                          mol_type = other DNA
                          organism = synthetic construct
SEQUENCE: 4
gaagtgcagc tgctggaaag cggcggcggc ctggtgcagc cgggcggcag cctgcgcctg   60
agctgcgcgg cgagcggctt tacctttagc agctatgcga tgagctgggt gcgccaggcg  120
ccgggcaaag gcctggaatg ggtgagcggc attggcagct atggcggcgg cacctattat  180
gcggatagcg tgaaaggccg ctttaccatt agccgcgata cagcaaaaa cacccctgtat  240
ctgcagatga acagcctgcg cgcggaagat accgcggtgt attattgcgc gcgctatgtg  300
aactttggca tggattattg gggccagggc accctggtga ccgtgagcag c           351

SEQ ID NO: 5              moltype = AA  length = 107
FEATURE                   Location/Qualifiers
source                    1..107
                          mol_type = protein
                          organism = synthetic construct
SEQUENCE: 5
DIQMTQSPSS LSASVGDHVT ITCRASQSIS SYLNWYQQKP GKAPKLLIYA ASSLQSGVPS   60
RFSGSGSGTD FTLTISSLQP EDFATYYCQQ YGSAPPTFGQ GTKLEIK                107

SEQ ID NO: 6              moltype = DNA  length = 321
FEATURE                   Location/Qualifiers
source                    1..321
                          mol_type = other DNA
                          organism = synthetic construct
SEQUENCE: 6
gatattcaga tgacccagag cccgagcagc ctgagcgcga gcgtgggcga tcatgtgacc   60
attacctgcc gcgcgagcca gagcattagc agctatctga actggtatca gcagaaaccg  120
ggcaaagcgc cgaaactgct gatttatgcg gcgagcagcc tgcagagcgg cgtgccgagc  180
```

```
cgctttagcg gcagcggcag cggcaccgat tttaccctga ccattagcag cctgcagccg    240
gaagattttg cgacctatta ttgccagcag tatggcagcg cgccgccgac ctttggccag    300
ggcaccaaac tggaaattaa a                                              321
```

| SEQ ID NO: 7 | moltype = AA  length = 117 |
|---|---|
| FEATURE | Location/Qualifiers |
| source | 1..117 |
| | mol_type = protein |
| | organism = synthetic construct |

SEQUENCE: 7
```
EVQLLESGGG LVQPGGSLRL SCAASGFTFS SYAMSWVRQA PGKGLEWVSG IGGSSSYTSY    60
ADSVKGRFTI SRDNSKNTLY LQMNSLRAED TAVYYCARYY SYHMDYWGQG TLVTVSS      117
```

| SEQ ID NO: 8 | moltype = DNA  length = 351 |
|---|---|
| FEATURE | Location/Qualifiers |
| source | 1..351 |
| | mol_type = other DNA |
| | organism = synthetic construct |

SEQUENCE: 8
```
gaagtgcagc tgctggaaag cggcggcggc ctggtgcagc cgggcggcag cctgcgcctg    60
agctgcgcgc cgagcggctt tacctttagc agctatgcga tgagctgggt gcgccaggcg   120
ccgggcaaag gcctggaatg ggtgagcggc attggcggca gcagctatac cagctat      180
gcggatagcg tgaaaggccg ctttaccatt agccgcgata acagcaaaaa cacccctgtat  240
ctgcagatga cagcctgcg cgcggaagat accgcggtgt attattgcgc gcgctattat    300
agctatcata tggattattg gggccagggc accctggtga ccgtgagcag c            351
```

| SEQ ID NO: 9 | moltype = AA  length = 107 |
|---|---|
| FEATURE | Location/Qualifiers |
| source | 1..107 |
| | mol_type = protein |
| | organism = synthetic construct |

SEQUENCE: 9
```
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPYTFGQ GTKLEIK                 107
```

| SEQ ID NO: 10 | moltype = DNA  length = 321 |
|---|---|
| FEATURE | Location/Qualifiers |
| source | 1..321 |
| | mol_type = other DNA |
| | organism = synthetic construct |

SEQUENCE: 10
```
gatattcaga tgacccagag cccgagcagc ctgagcgcga gcgtgggcga tcgcgtgacc    60
attacctgcc gcgcgagcca gagcattagc agctatctga actggtatca gcagaaaccg   120
ggcaaagcgc cgaaactgct gatttatgcg gcgagcagcc tgcagagcgg cgtgccgagc   180
cgctttagcg gcagcggcag cggcaccgat tttaccctga ccattagcag cctgcagccg   240
gaagattttg cgacctatta ttgccagcag agctatagca ccccgtatac ctttggccag   300
ggcaccaaac tggaaattaa a                                              321
```

| SEQ ID NO: 11 | moltype = AA  length = 119 |
|---|---|
| FEATURE | Location/Qualifiers |
| source | 1..119 |
| | mol_type = protein |
| | organism = synthetic construct |

SEQUENCE: 11
```
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARGP VYSSVFDYWG QGTLVTVSS   119
```

| SEQ ID NO: 12 | moltype = DNA  length = 357 |
|---|---|
| FEATURE | Location/Qualifiers |
| source | 1..357 |
| | mol_type = other DNA |
| | organism = synthetic construct |

SEQUENCE: 12
```
gaagtgcagc tgctggaaag cggcggcggc ctggtgcagc cgggcggcag cctgcgcctg    60
agctgcgcgg cgagcggctt tacctttagc agctatgcga tgagctgggt gcgccaggcg   120
ccgggcaaag gcctggaatg ggtgagcgcg attagcggca gcggcggcag cacctattat   180
gcggatagcg tgaaaggccg ctttaccatt agccgcgata acagcaaaaa cacccctgtat  240
ctgcagatga cagcctgcg cgcggaagat accgcggtgt attattgcgc gcgcggcccg    300
gtgtatagca gcgtgtttga ttattggggc cagggcaccc tggtgaccgt gagcagc     357
```

| SEQ ID NO: 13 | moltype = AA  length = 107 |
|---|---|
| FEATURE | Location/Qualifiers |
| source | 1..107 |
| | mol_type = protein |
| | organism = synthetic construct |

SEQUENCE: 13
```
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ YGVYPFTFGQ GTKLEIK                 107
```

```
SEQ ID NO: 14              moltype = DNA  length = 321
FEATURE                    Location/Qualifiers
source                     1..321
                           mol_type = other DNA
                           organism = synthetic construct
SEQUENCE: 14
gatattcaga tgacccagag cccgagcagc ctgagcgcga gcgtgggcga tcgcgtgacc    60
attacctgcc gcgcgagcca gagcattagc agctatctga actggtatca gcagaaaccg   120
ggcaaagcgc cgaaactgct gatttatgcg gcgagcagcc tgcagagcgg cgtgccgagc   180
cgctttagcg gcagcggcag cggcaccgat tttaccctga ccattagcag cctgcagccg   240
gaagattttg cgacctatta ttgccagcag tatggcgtgt atccgtttac ctttggccag   300
ggcaccaaac tggaaattaa a                                             321

SEQ ID NO: 15              moltype = AA  length = 116
FEATURE                    Location/Qualifiers
source                     1..116
                           mol_type = protein
                           organism = synthetic construct
SEQUENCE: 15
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARRV WGFDYWGQGT LVTVSS       116

SEQ ID NO: 16              moltype = DNA  length = 348
FEATURE                    Location/Qualifiers
source                     1..348
                           mol_type = other DNA
                           organism = synthetic construct
SEQUENCE: 16
gaagtgcagc tgctggaaag cggcggcggc ctggtgcagc cgggcggcag cctgcgcctg    60
agctgcgcgg cgagcggctt tacctttagc agctatgcga tgagctgggt gcgccaggcg   120
ccgggcaaag gcctgaatg gtgagcgcg attagcggca gcggcggcag cacctattat    180
gcggatagcg tgaaaggccg ctttaccatt agcgcgata acagcaaaaa cacccctgtat  240
ctgcagatga cagcctgcg cgcggaagat accgcggtgt attattgcg cgccgcgtg    300
tggggctttg attattgggg ccagggcacc ctggtgaccg tgagcagc              348

SEQ ID NO: 17              moltype = AA  length = 112
FEATURE                    Location/Qualifiers
source                     1..112
                           mol_type = protein
                           organism = synthetic construct
SEQUENCE: 17
QSVLTQPPSA SGTPGQRVTI SCTGSSSNIG AGYNVYWYQQ LPGTAPKLLI YGNINRPSGV    60
PDRFSGSKSG TSASLAISGL RSEDEADYYC AAWDKSISGL VFGGGTKLTV LG           112

SEQ ID NO: 18              moltype = DNA  length = 336
FEATURE                    Location/Qualifiers
source                     1..336
                           mol_type = other DNA
                           organism = synthetic construct
SEQUENCE: 18
cagagcgtgc tgacccagcc gccgagcgcg agcggcaccc cgggccagcg cgtgaccatt    60
agctgcaccg gcagcagcag caacattggc gcgggctata acgtgtattg gtatcagcag   120
ctgccgggca ccgcgccgaa actgctgatt tatggcaaca ttaaccgccc gagcggcgtg   180
ccggatcgct ttagcggcag caaaagcggc accagcgcga gcctggcgat tagcggcctg   240
cgcagcgaag atgaagcgga ttattattgc gcggcgtggg ataaaagcat tagcggcctg   300
gtgtttggcg gcggcaccaa actgaccgtg ctgggg                             336

SEQ ID NO: 19              moltype = AA  length = 119
FEATURE                    Location/Qualifiers
source                     1..119
                           mol_type = protein
                           organism = synthetic construct
SEQUENCE: 19
EVQLLESGGG LVQPGGSLRL SCAASGFTFS TYGMHWVRQA PGKGLEWLSY ISGGSSYIFY    60
ADSVRGRFTI SRDNSENALY LQMNSLRAED TAVYYCARIL RGGSGMDLWG QGTLVTVSS    119

SEQ ID NO: 20              moltype = DNA  length = 357
FEATURE                    Location/Qualifiers
source                     1..357
                           mol_type = other DNA
                           organism = synthetic construct
SEQUENCE: 20
gaagtgcagc tgctggaaag cggcggcggc ctggtgcagc cgggcggcag cctgcgcctg    60
agctgcgcgg cgagcggctt tacctttagc acctatggca tgcattgggt gcgccaggcg   120
ccgggcaaag gcctgaatg gctgagctat attagcggcg gcagcagcta tatttttat   180
gcggatagcg tgcgcggccg ctttaccatt agcgcgata acagcgaaaa cgcgctgtat   240
ctgcagatga acagcctgcg cgcggaagat accgcggtgt attattgcg cgcgattctg   300
cgcggcggca gcggcatgga tctgtggggc cagggcaccc tggtgaccgt gagcagc      357
```

```
SEQ ID NO: 21              moltype = AA   length = 108
FEATURE                    Location/Qualifiers
source                     1..108
                           mol_type = protein
                           organism = synthetic construct
SEQUENCE: 21
DIQMTQSPSS LSASVGDRVT IKCQASQSIS SRLAWYQQKP GKPPKLLIYR ASTLASGVPS   60
RFSGSGSGTD FTLTISSLQP EDVATYYCQC TGYGISWPIG GGTKVEIK               108

SEQ ID NO: 22              moltype = DNA   length = 324
FEATURE                    Location/Qualifiers
source                     1..324
                           mol_type = other DNA
                           organism = synthetic construct
SEQUENCE: 22
gatattcaga tgacccagag cccgagcagc ctgagcgcga gcgtgggcga tcgcgtgacc    60
attaaatgcc aggcgagcca gagcattagc agccgcctgg cgtggtatca gcagaaaccg   120
ggcaaaaccg cgaaactgct gatttatcgc gcgagcaccc tggcgagcgg cgtgccgagc   180
cgctttagcg gcagcggcag cggcaccgat tttacccctga ccattagcag cctgcagccg  240
gaagatgtgg cgacctatta ttgccagtgc accggctatg gcattagctg gccgattggc   300
ggcggcacca aagtggaaat taaa                                          324

SEQ ID NO: 23              moltype = AA   length = 120
FEATURE                    Location/Qualifiers
source                     1..120
                           mol_type = protein
                           organism = synthetic construct
SEQUENCE: 23
QVQLVESGGG VVQPGRSLRL SCAASGFSFS STYVCWVRQA PGKGLEWIAC IYTGDGTNYS    60
ASWAKGRFTI SKDSSKNTVY LQMNSLRAED TAVYFCARPD ITYGFAINFW GPGTLVTVSS   120

SEQ ID NO: 24              moltype = DNA   length = 360
FEATURE                    Location/Qualifiers
source                     1..360
                           mol_type = other DNA
                           organism = synthetic construct
SEQUENCE: 24
caggtgcagc tggtggaaag cggcggcggc gtggtgcagc cgggccgcag cctgcgcctg    60
agctgcgcgg cgagcggctt tagctttagc agcacctatg tgtgctgggt gcgccaggcg   120
ccgggcaaag cgctggaatg gattgcgtgc atttataccg gcgatggcac caactatagc   180
gcgagctggg cgaaaggccg ctttaccatt agcaaagata gcagcaaaaa caccgtgtat   240
ctgcagatga acagcctgcg cgcggaagat accgcggtgt atttttgcgc gcgcccggat   300
attacctatg gctttgcgat taacttttgg ggcccgggca ccctggtgac cgtgagcagc   360

SEQ ID NO: 25              moltype = AA   length = 107
FEATURE                    Location/Qualifiers
source                     1..107
                           mol_type = protein
                           organism = synthetic construct
SEQUENCE: 25
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIK                 107

SEQ ID NO: 26              moltype = DNA   length = 321
FEATURE                    Location/Qualifiers
source                     1..321
                           mol_type = other DNA
                           organism = synthetic construct
SEQUENCE: 26
gatattcaga tgacccagag cccgagcagc gtgagcgcga gcgtgggcga tcgcgtgacc    60
attacctgcc gcgcgagcca gggcatttat agctggctgg cgtggtatca gcagaaaccg   120
ggcaaagcgc cgaacctgct gatttatacc gcgagcaccc tgcagagcgg cgtgccgagc   180
cgctttagcg gcagcggcag cggcaccgat tttacccctga ccattagcag cctgcagccg  240
gaagattttg cgacctatta ttgccagcag gcgaacattt ttccgctgac ctttggcggc   300
ggcaccaaag tggaaattaa a                                             321

SEQ ID NO: 27              moltype = AA   length = 126
FEATURE                    Location/Qualifiers
source                     1..126
                           mol_type = protein
                           organism = synthetic construct
SEQUENCE: 27
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSS                                                              126

SEQ ID NO: 28              moltype = DNA   length = 378
FEATURE                    Location/Qualifiers
source                     1..378
```

```
                        mol_type = other DNA
                        organism = synthetic construct
SEQUENCE: 28
caggtgcagc tggtgcagag cggcgcggaa gtgaaaaaac cgggcgcgag cgtgaaagtg    60
agctgcaaag cgagcggcta taccttacc ggctattata tgcattgggt gcgccaggcg    120
ccgggccagg gcctggaatg gatgggctgg attaacccgg atagcggcgg caccaactat    180
gcgcagaaat ttcagggccg cgtgaccatg acccgcgata ccagcattag caccgcgtat    240
atggaactga accgcctgcg cagcgatgat accgcgtgt attattgcgc gcgcgatcag    300
ccgctgggct attgcaccaa cggcgtgtgc agctattttg attattgggg ccagggcacc    360
ctggtgaccg tgagcagc                                                  378

SEQ ID NO: 29          moltype = AA    length = 119
FEATURE                Location/Qualifiers
source                 1..119
                       mol_type = protein
                       organism = synthetic construct
SEQUENCE: 29
EVQLLESGGG LVQPGGSLRL SCAASGFTFS TYGMHWVRQA PGKGLEWLSY ISGGSSYIFY    60
ADSVKGRFTI SRDNSKNTLY LQMNSLRAED TAVYYCARIL RGGSGMDLWG QGTLVTVSS    119

SEQ ID NO: 30          moltype = DNA    length = 357
FEATURE                Location/Qualifiers
source                 1..357
                       mol_type = other DNA
                       organism = synthetic construct
SEQUENCE: 30
gaagtgcagc tgctggaaag cggcggcggc ctggtgcagc cgggcggcag cctgcgcctg    60
agctgcgcgg cgagcggctt tacctttagc acctatggca tgcattgggt gcgccaggcg    120
ccgggcaaag gcctggaatg gctgagctat attagcggcg gcagcagcta tatttttat    180
gcggatagcg tgaagggccg ctttaccatt agccgcgata acagcaaaaa cacgctgtat    240
ctgcagatga acagcctgcg cgcggaagat accgcggtgt attattgcgc gcgcattctg    300
cgcggcggca cggcatggga tctgtggggc cagggcaccc tggtgaccgt gagcagc      357

SEQ ID NO: 31          moltype = AA    length = 106
FEATURE                Location/Qualifiers
source                 1..106
                       mol_type = protein
                       organism = synthetic construct
SEQUENCE: 31
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                   106

SEQ ID NO: 32          moltype = DNA    length = 318
FEATURE                Location/Qualifiers
source                 1..318
                       mol_type = other DNA
                       organism = synthetic construct
SEQUENCE: 32
gacatccaga tgacccagtc tccatcctcc ctgagcgcat ctgtaggaga ccgcgtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag gctggtaacc cgcacacttt tggccagggg    300
accaagctgg agatcaaa                                                  318

SEQ ID NO: 33          moltype = AA    length = 121
FEATURE                Location/Qualifiers
source                 1..121
                       mol_type = protein
                       organism = synthetic construct
SEQUENCE: 33
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHLDY WGQGTLVTVS    120
S                                                                    121

SEQ ID NO: 34          moltype = DNA    length = 363
FEATURE                Location/Qualifiers
source                 1..363
                       mol_type = other DNA
                       organism = synthetic construct
SEQUENCE: 34
gaggtgcagc tgttggagag cggggggaggc ttggtacagc ctgggggtc cctgcgcctc    60
tcctgtgcag ccagcggatt cacctttct tcttcttaca tgggttgggt ccgccaggct    120
ccagggaagg ggctggagtg ggtctcatct attggttctg gttcttactc tacatcttat    180
gcagactccg tgaagggccg gttcaccatc tccgtgaca attccaagaa cacgctgtat    240
ctgcaaatga acagcctgcg tgccgaggac acggctgtat attattgtgc gcgctacccg    300
tctgttccgt tcccgcctca tttggactat tggggccagg gaaccctggt caccgtctcc    360
tca                                                                  363
```

```
SEQ ID NO: 35               moltype = AA   length = 106
FEATURE                     Location/Qualifiers
source                      1..106
                            mol_type = protein
                            organism = synthetic construct
SEQUENCE: 35
DIQMTQSPSS LSASVGDRVT ITCRASQSIR DYLNWYQQKP GKAPKLLIYA ASSLQSGVPS    60
RFSGSGSGTD FTLTISSLQP EDFATYYCQQ GTFPFTFGQG TKLEIK                  106

SEQ ID NO: 36               moltype = DNA   length = 318
FEATURE                     Location/Qualifiers
source                      1..318
                            mol_type = other DNA
                            organism = synthetic construct
SEQUENCE: 36
gacatccaga tgacccagtc tccatcctcc ctgagcgcat ctgtaggaga ccgcgtcacc    60
atcacttgcc gggcaagtca gtctattagg gactatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag ggtactttcc cgttcacttt tggccagggg   300
accaagctgg agatcaaa                                                 318

SEQ ID NO: 37               moltype = AA   length = 117
FEATURE                     Location/Qualifiers
source                      1..117
                            mol_type = protein
                            organism = synthetic construct
SEQUENCE: 37
EVQLLESGGG LVQPGGSLRL SCAASGFTFG SYYMSWVRQA PGKGLEWVSG ISGYGYYTGY    60
ADSVKGRFTI SRDNSKNTLY LQMNSLRAED TAVYYCARHG YGVIDYWGQG TLVTVSS      117

SEQ ID NO: 38               moltype = DNA   length = 351
FEATURE                     Location/Qualifiers
source                      1..351
                            mol_type = other DNA
                            organism = synthetic construct
SEQUENCE: 38
gaggtgcagc tgttggagag cggggaggc ttggtacagc ctggggggtc cctgcgcctc     60
tcctgtgcag ccagcggatt caccttggt tcttactaca tgtcttggg ccgccaggct    120
ccagggaagg ggctggagtg ggtctcaggt atttctggtt acggttacta cacaggttat   180
gcagactccg tgaagggccg gttcaccatc tcccgtgaca attccaagaa cacgctgtat   240
ctgcaaatga acagcctgcg tgccgaggac acggctgtat attattgtgc gcgccatggt   300
tacggtgtta ttgactattg gggccaggga accctggtca ccgtctcctc a            351

SEQ ID NO: 39               moltype = AA   length = 107
FEATURE                     Location/Qualifiers
source                      1..107
                            mol_type = protein
                            organism = synthetic construct
SEQUENCE: 39
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ GAYVPYTFGQ GTKLEIK                 107

SEQ ID NO: 40               moltype = DNA   length = 321
FEATURE                     Location/Qualifiers
source                      1..321
                            mol_type = other DNA
                            organism = synthetic construct
SEQUENCE: 40
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag ggtgcttacg ttccgtacac ttttggccag   300
gggaccaagc tggagatcaa a                                             321

SEQ ID NO: 41               moltype = AA   length = 117
FEATURE                     Location/Qualifiers
source                      1..117
                            mol_type = protein
                            organism = synthetic construct
SEQUENCE: 41
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARYG YTHFDYWGQG TLVTVSS      117

SEQ ID NO: 42               moltype = DNA   length = 351
FEATURE                     Location/Qualifiers
source                      1..351
                            mol_type = other DNA
```

```
                    organism = synthetic construct
SEQUENCE: 42
gaggtgcagc tgttggagag cgggggaggc ttggtacagc ctgggggtc cctgcgcctc    60
tcctgtgcag ccagcggatt cacctttagc agctatgcca tgagctgggt ccgccaggct  120
ccagggaagg ggctggagtg ggtctcagct attagtggta gtggtggtag cacatactat  180
gcagactccg tgaagggccg gttcaccatc tcccgtgaca attccaagaa cacgctgtat  240
ctgcaaatga acagcctgcg tgccgaggac acggctgtat attattgtgc gcgctacggt  300
tacactcatt ttgactattg gggccaggga accctggtca ccgtctcctc a           351

SEQ ID NO: 43           moltype = AA  length = 107
FEATURE                 Location/Qualifiers
source                  1..107
                        mol_type = protein
                        organism = synthetic construct
SEQUENCE: 43
DIQMTQSPSS LSASVGDRVT ITCRASQAIS GYLNWYQQKP GKAPKLLIYS ASSLQSGVPS    60
RFSGSGSGTD FTLTISSLQP EDFATYYCQQ SYSTPYTFGQ GTKLEIK                 107

SEQ ID NO: 44           moltype = DNA  length = 321
FEATURE                 Location/Qualifiers
source                  1..321
                        mol_type = other DNA
                        organism = synthetic construct
SEQUENCE: 44
gacatccaga tgacccagtc tccatcctcc ctgagcgcat ctgtaggaga ccgcgtcacc    60
atcacttgcc gggcaagtca ggctattagc ggttatttaa attggtatca gcagaaacca  120
gggaaagccc ctaagctcct gatctattct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag agttacagta ccccttatac ttttggccag  300
gggaccaagc tggagatcaa a                                             321

SEQ ID NO: 45           moltype = AA  length = 119
FEATURE                 Location/Qualifiers
source                  1..119
                        mol_type = protein
                        organism = synthetic construct
SEQUENCE: 45
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARYR WHGSVFDYWG QGTLVTVSS   119

SEQ ID NO: 46           moltype = DNA  length = 357
FEATURE                 Location/Qualifiers
source                  1..357
                        mol_type = other DNA
                        organism = synthetic construct
SEQUENCE: 46
gaggtgcagc tgttggagag cgggggaggc ttggtacagc ctgggggtc cctgcgcctc    60
tcctgtgcag ccagcggatt cacctttagc agctatgcca tgagctgggt ccgccaggct  120
ccagggaagg ggctggagtg ggtctcagct attagtggta gtggtggtag cacatactat  180
gcagactccg tgaagggccg gttcaccatc tcccgtgaca attccaagaa cacgctgtat  240
ctgcaaatga acagcctgcg tgccgaggac acggctgtat attattgtgc gcgctaccgt  300
tggcatggtt ctgttttga ctattggggc caggaaccc tggtcaccgt ctcctca       357

SEQ ID NO: 47           moltype = AA  length = 108
FEATURE                 Location/Qualifiers
source                  1..108
                        mol_type = protein
                        organism = synthetic construct
SEQUENCE: 47
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ YPWYFPYTFG QGTKLEIK                108

SEQ ID NO: 48           moltype = DNA  length = 324
FEATURE                 Location/Qualifiers
source                  1..324
                        mol_type = other DNA
                        organism = synthetic construct
SEQUENCE: 48
gacatccaga tgacccagtc tccatcctcc ctgagcgcat ctgtaggaga ccgcgtcacc    60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag tacccgtggt acttcccgta cacttttggc  300
caggggacca agctggagat caaa                                          324

SEQ ID NO: 49           moltype = AA  length = 117
FEATURE                 Location/Qualifiers
source                  1..117
                        mol_type = protein
```

-continued

```
SEQUENCE: 49
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARYG YSVLDYWGQG TLVTVSS      117

SEQ ID NO: 50           moltype = DNA   length = 351
FEATURE                 Location/Qualifiers
source                  1..351
                        mol_type = other DNA
                        organism = synthetic construct
SEQUENCE: 50
gaggtgcagc tgttggagag cggggggaggc ttggtacagc ctgggggtc cctgcgcctc    60
tcctgtgcag ccagcggatt cacctttagc agctatgcca tgagctgggt ccgccaggct  120
ccagggaagg ggctggagtg ggtctcagct attagtggta gtggtggtag cacatactat  180
gcagactccg tgaagggccg gttcaccatc tcccgtgaca attccaagaa cacgctgtat  240
ctgcaaatga acagcctgcg tgccgaggac acggctgtat attattgtgc gcgctacggt  300
tactctgttt tggactattg gggccaggga accctggtca ccgtctcctc a           351

SEQ ID NO: 51           moltype = AA    length = 106
FEATURE                 Location/Qualifiers
source                  1..106
                        mol_type = protein
                        organism = synthetic construct
SEQUENCE: 51
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 52           moltype = DNA   length = 318
FEATURE                 Location/Qualifiers
source                  1..318
                        mol_type = other DNA
                        organism = synthetic construct
SEQUENCE: 52
gacatccaga tgacccagtc tccatcctcc ctgagcgcat ctgtaggaga ccgcgtcacc    60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                  318

SEQ ID NO: 53           moltype = AA    length = 121
FEATURE                 Location/Qualifiers
source                  1..121
                        mol_type = protein
                        organism = synthetic construct
SEQUENCE: 53
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPPLDY WGQGTLVTVS  120
S                                                                    121

SEQ ID NO: 54           moltype = DNA   length = 363
FEATURE                 Location/Qualifiers
source                  1..363
                        mol_type = other DNA
                        organism = synthetic construct
SEQUENCE: 54
gaggtacagc tgcttgagtc tggaggtgga ctggtacagc ccggggggtc cctgaggctc    60
tcctgtgctg cctccggttt cacctttagc agctcttata tggggtgggt caggcaggct  120
cctgggtaagg gcctcgagtg ggtgtccagc atcggaagcg gatcatacag cacgagttac  180
gccgactcag taaagggtag attcaccatt tcacgcgaca acagcaagaa cacattgtat  240
ctccaaatga attctctgag agcggaagac acagcagtgt actattgcgc cagatatcct  300
tccgtgccct tcctccacc ccttgattac tggggacagg gtactcttgt gactgtctcc  360
tca                                                                  363

SEQ ID NO: 55           moltype = AA    length = 106
FEATURE                 Location/Qualifiers
source                  1..106
                        mol_type = protein
                        organism = synthetic construct
SEQUENCE: 55
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 56           moltype = DNA   length = 318
FEATURE                 Location/Qualifiers
source                  1..318
                        mol_type = other DNA
                        organism = synthetic construct
SEQUENCE: 56
```

```
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                318

SEQ ID NO: 57           moltype = AA  length = 121
FEATURE                 Location/Qualifiers
source                  1..121
                        mol_type = protein
                        organism = synthetic construct
SEQUENCE: 57
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCARYP SVPFPPLLDY WGQGTLVTVS  120
S                                                                  121

SEQ ID NO: 58           moltype = DNA  length = 363
FEATURE                 Location/Qualifiers
source                  1..363
                        mol_type = other DNA
                        organism = synthetic construct
SEQUENCE: 58
gaggttcagt tgctggagtc agggggcgga ttggtgcagc ctggtggtag tctccgtctt   60
agctgcgcgt cttcagggtt cacttttagc agctcataca tgggctgggt gcggcaggca  120
ccaggaaagg gcctgaatg gtgagtagt ataggatcgt gcagctatac tacttcatat  180
gctgatagtg tgaaaggacg atttactatc tctcgtgaca attcaaaaaa caccctttac  240
ttgcagatga atagccttag gcggaggat accgcggttt actattgtgc tcgttatccg  300
agcgtgcctt tccccccct tttggactac tggggacaag gcaccctcgt gacagtctcc  360
tca                                                                363

SEQ ID NO: 59           moltype = AA  length = 106
FEATURE                 Location/Qualifiers
source                  1..106
                        mol_type = protein
                        organism = synthetic construct
SEQUENCE: 59
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                 106

SEQ ID NO: 60           moltype = DNA  length = 318
FEATURE                 Location/Qualifiers
source                  1..318
                        mol_type = other DNA
                        organism = synthetic construct
SEQUENCE: 60
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                318

SEQ ID NO: 61           moltype = AA  length = 121
FEATURE                 Location/Qualifiers
source                  1..121
                        mol_type = protein
                        organism = synthetic construct
SEQUENCE: 61
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCARYP SVPFQPHLDY WGQGTLVTVS  120
S                                                                  121

SEQ ID NO: 62           moltype = DNA  length = 363
FEATURE                 Location/Qualifiers
source                  1..363
                        mol_type = other DNA
                        organism = synthetic construct
SEQUENCE: 62
gaagtacagc tgctggaaag cggtggagga ctcgtgcagc ctggtgggtc cctcaggctc   60
tcctgtgcag cgagcggttt tacattctct agttcatata tggggtgggt acggcaggcc  120
ccaggtaagg gcttagagtg ggtaagcagt attggatccg ggtcatacag tacatccat  180
gccgactccg tcaagggtag gttcacgatc agccgggata actcaaagaa tactctctac  240
ctccaaatga attcactgcg ggccgaggat acagcagttt actattgtgc aagatatcca  300
tccgtgccct ttcagcccca cctggactac tggggtcagg aacccctggt aacagtctcc  360
tca                                                                363

SEQ ID NO: 63           moltype = AA  length = 106
FEATURE                 Location/Qualifiers
```

```
source                  1..106
                        mol_type = protein
                        organism = synthetic construct
SEQUENCE: 63
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 64           moltype = DNA  length = 318
FEATURE                 Location/Qualifiers
source                  1..318
                        mol_type = other DNA
                        organism = synthetic construct
SEQUENCE: 64
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                 318

SEQ ID NO: 65           moltype = AA  length = 117
FEATURE                 Location/Qualifiers
source                  1..117
                        mol_type = protein
                        organism = synthetic construct
SEQUENCE: 65
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARYH PYSFDYWGQG TLVTVSS      117

SEQ ID NO: 66           moltype = DNA  length = 351
FEATURE                 Location/Qualifiers
source                  1..351
                        mol_type = other DNA
                        organism = synthetic construct
SEQUENCE: 66
gaggtgcagc tgttggagag cggggggaggc ttggtacagc ctggggggtc cctgcgcctc   60
tcctgtgcag ccagcggatt cacctttagc agctatgcca tgagctgggt ccgccaggct   120
ccagggaagg ggctggagtg ggtctcagct attagtggta gtggtggtag cacatactat   180
gcagactccg tgaagggccg gttcaccatc tcccgtgaca attccaagaa cacgctgtat   240
ctgcaaatga acagcctgcg tgccgaggac acggctgtat attattgtgc gcgctaccac   300
ccgtactctt ttgactattg gggccaggga accctggtca ccgtctcctc a            351

SEQ ID NO: 67           moltype = AA  length = 108
FEATURE                 Location/Qualifiers
source                  1..108
                        mol_type = protein
                        organism = synthetic construct
SEQUENCE: 67
DIQMTQSPSS LSASVGDRVT ITCRASQSIR GYLNWYQQKP GKAPKLLIYA ASSLQSGVPS    60
RFSGSGSGTD FTLTISSLQP EDFATYYCQQ PSYPSLFTFG QGTKLEIK                108

SEQ ID NO: 68           moltype = DNA  length = 324
FEATURE                 Location/Qualifiers
source                  1..324
                        mol_type = other DNA
                        organism = synthetic construct
SEQUENCE: 68
gatattcaga tgacgcagag ccctagttct ctgtctgctt ccgttgggga ccgtgtaacc    60
atcacctgta gggctagtca gtccatacgc ggatatttaa actggtatca gcagaaacca   120
gggaaagctc caaagttgct catttatgca gcatcaagct tacagagcgg cgtgcccagc   180
cgtttcagcg ggtcaggaag cgggacggac ttcacggtga ccatatcttc tctgcagccc   240
gaggatttcg cgacctacta ttgtcagcaa ccaagctacc cgtctctgtt cacttttcggc  300
caaggaacga agcttgaaat caag                                          324

SEQ ID NO: 69           moltype = AA  length = 117
FEATURE                 Location/Qualifiers
source                  1..117
                        mol_type = protein
                        organism = synthetic construct
SEQUENCE: 69
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARYS PYVLDYWGQG TLVTVSS      117

SEQ ID NO: 70           moltype = DNA  length = 351
FEATURE                 Location/Qualifiers
source                  1..351
                        mol_type = other DNA
                        organism = synthetic construct
SEQUENCE: 70
```

```
gaggtgcaac tgctggagag cggcggaggc ctggtccagc caggcgggtc tctcagactg    60
agttgcgccg ccagcggctt tacttttttcc tcttatgcta tgagctgggt acgacaggcg   120
cccggaaaag gcctggaatg ggtttccgcc atctctggct ccggcggttc tacctactac   180
gctgattccg tcaagggcag gtttaccatc agcagggaca atagcaagaa cacactgtac   240
ctccagatga actctttgcg cgcagaggac acagccgttt actattgcgc caggtacagc   300
ccatacgtgc tcgactactg gggccagggt acactcgtga cggtctcctc a            351

SEQ ID NO: 71           moltype = AA  length = 106
FEATURE                 Location/Qualifiers
source                  1..106
                        mol_type = protein
                        organism = synthetic construct
SEQUENCE: 71
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VDGLFTFGQG TKLEIK                  106

SEQ ID NO: 72           moltype = DNA  length = 318
FEATURE                 Location/Qualifiers
source                  1..318
                        mol_type = other DNA
                        organism = synthetic construct
SEQUENCE: 72
gatattcaga tgactcagag ccccctcatcc ctgtccgcta gcgtggggga ccgagtgact    60
attacatgca gagcctctca gtccatatca tcctatctga attggtacca gcaaaagccc   120
ggaaaagcac caaaactgct catttatgcc gctagttcac ttcagtctgg ggttccgtct   180
cggtttagcg gatctggcag cggtacagac tttacactta ccatcagcag tctgcagcca   240
gaggactttg cgacgtacta ttgtcaacaa gtcgacggct tattcacctt tggacagggc   300
accaagttgg agattaaa                                                  318

SEQ ID NO: 73           moltype = AA  length = 8
FEATURE                 Location/Qualifiers
source                  1..8
                        mol_type = protein
                        organism = synthetic construct
SEQUENCE: 73
GFTFSSYA                                                              8

SEQ ID NO: 74           moltype = AA  length = 8
FEATURE                 Location/Qualifiers
source                  1..8
                        mol_type = protein
                        organism = synthetic construct
SEQUENCE: 74
IGSYGGGT                                                              8

SEQ ID NO: 75           moltype = AA  length = 10
FEATURE                 Location/Qualifiers
source                  1..10
                        mol_type = protein
                        organism = synthetic construct
SEQUENCE: 75
ARYVNFGMDY                                                           10

SEQ ID NO: 76           moltype = AA  length = 8
FEATURE                 Location/Qualifiers
source                  1..8
                        mol_type = protein
                        organism = synthetic construct
SEQUENCE: 76
IGGSSSYT                                                              8

SEQ ID NO: 77           moltype = AA  length = 10
FEATURE                 Location/Qualifiers
source                  1..10
                        mol_type = protein
                        organism = synthetic construct
SEQUENCE: 77
ARYYSYHMDY                                                           10

SEQ ID NO: 78           moltype = AA  length = 8
FEATURE                 Location/Qualifiers
source                  1..8
                        mol_type = protein
                        organism = synthetic construct
SEQUENCE: 78
ISGSGGST                                                              8

SEQ ID NO: 79           moltype = AA  length = 12
FEATURE                 Location/Qualifiers
```

```
source                       1..12
                             mol_type = protein
                             organism = synthetic construct
SEQUENCE: 79
ARGPVYSSVF DY                                                                   12

SEQ ID NO: 80                moltype = AA   length = 9
FEATURE                      Location/Qualifiers
source                       1..9
                             mol_type = protein
                             organism = synthetic construct
SEQUENCE: 80
ARRVWGFDY                                                                        9

SEQ ID NO: 81                moltype = AA   length = 8
FEATURE                      Location/Qualifiers
source                       1..8
                             mol_type = protein
                             organism = synthetic construct
SEQUENCE: 81
GFTFSTYG                                                                         8

SEQ ID NO: 82                moltype = AA   length = 8
FEATURE                      Location/Qualifiers
source                       1..8
                             mol_type = protein
                             organism = synthetic construct
SEQUENCE: 82
ISGGSSYI                                                                         8

SEQ ID NO: 83                moltype = AA   length = 12
FEATURE                      Location/Qualifiers
source                       1..12
                             mol_type = protein
                             organism = synthetic construct
SEQUENCE: 83
ARILRGGSGM DL                                                                   12

SEQ ID NO: 84                moltype = AA   length = 8
FEATURE                      Location/Qualifiers
source                       1..8
                             mol_type = protein
                             organism = synthetic construct
SEQUENCE: 84
GFSFSSTY                                                                         8

SEQ ID NO: 85                moltype = AA   length = 8
FEATURE                      Location/Qualifiers
source                       1..8
                             mol_type = protein
                             organism = synthetic construct
SEQUENCE: 85
IYTGDGTN                                                                         8

SEQ ID NO: 86                moltype = AA   length = 13
FEATURE                      Location/Qualifiers
source                       1..13
                             mol_type = protein
                             organism = synthetic construct
SEQUENCE: 86
ARPDITYGFA INF                                                                  13

SEQ ID NO: 87                moltype = AA   length = 8
FEATURE                      Location/Qualifiers
source                       1..8
                             mol_type = protein
                             organism = synthetic construct
SEQUENCE: 87
GYTFTGYY                                                                         8

SEQ ID NO: 88                moltype = AA   length = 8
FEATURE                      Location/Qualifiers
source                       1..8
                             mol_type = protein
                             organism = synthetic construct
SEQUENCE: 88
INPDSGGT                                                                         8

SEQ ID NO: 89                moltype = AA   length = 19
```

```
FEATURE              Location/Qualifiers
source               1..19
                     mol_type = protein
                     organism = synthetic construct
SEQUENCE: 89
ARDQPLGYCT NGVCSYFDY                                                    19

SEQ ID NO: 90        moltype = AA  length = 6
FEATURE              Location/Qualifiers
source               1..6
                     mol_type = protein
                     organism = synthetic construct
SEQUENCE: 90
QSISSY                                                                   6

SEQ ID NO: 91        moltype =     length =
SEQUENCE: 91
000

SEQ ID NO: 92        moltype = AA  length = 9
FEATURE              Location/Qualifiers
source               1..9
                     mol_type = protein
                     organism = synthetic construct
SEQUENCE: 92
QQYGRNPPT                                                                9

SEQ ID NO: 93        moltype = AA  length = 9
FEATURE              Location/Qualifiers
source               1..9
                     mol_type = protein
                     organism = synthetic construct
SEQUENCE: 93
QQYGSAPPT                                                                9

SEQ ID NO: 94        moltype = AA  length = 9
FEATURE              Location/Qualifiers
source               1..9
                     mol_type = protein
                     organism = synthetic construct
SEQUENCE: 94
QQSYSTPYT                                                                9

SEQ ID NO: 95        moltype = AA  length = 9
FEATURE              Location/Qualifiers
source               1..9
                     mol_type = protein
                     organism = synthetic construct
SEQUENCE: 95
QQYGVYPFT                                                                9

SEQ ID NO: 96        moltype = AA  length = 9
FEATURE              Location/Qualifiers
source               1..9
                     mol_type = protein
                     organism = synthetic construct
SEQUENCE: 96
SSNIGAGYN                                                                9

SEQ ID NO: 97        moltype =     length =
SEQUENCE: 97
000

SEQ ID NO: 98        moltype = AA  length = 11
FEATURE              Location/Qualifiers
source               1..11
                     mol_type = protein
                     organism = synthetic construct
SEQUENCE: 98
AAWDKSISGL V                                                            11

SEQ ID NO: 99        moltype = AA  length = 6
FEATURE              Location/Qualifiers
source               1..6
                     mol_type = protein
                     organism = synthetic construct
SEQUENCE: 99
QSISSR                                                                   6
```

-continued

```
SEQ ID NO: 100         moltype =    length =
SEQUENCE: 100
000

SEQ ID NO: 101         moltype = AA   length = 10
FEATURE                Location/Qualifiers
source                 1..10
                       mol_type = protein
                       organism = synthetic construct
SEQUENCE: 101
QCTGYGISWP                                                            10

SEQ ID NO: 102         moltype = AA   length = 6
FEATURE                Location/Qualifiers
source                 1..6
                       mol_type = protein
                       organism = synthetic construct
SEQUENCE: 102
QGIYSW                                                                 6

SEQ ID NO: 103         moltype =    length =
SEQUENCE: 103
000

SEQ ID NO: 104         moltype = AA   length = 9
FEATURE                Location/Qualifiers
source                 1..9
                       mol_type = protein
                       organism = synthetic construct
SEQUENCE: 104
QQANIFPLT                                                              9

SEQ ID NO: 105         moltype =    length =
SEQUENCE: 105
000

SEQ ID NO: 106         moltype = AA   length = 118
FEATURE                Location/Qualifiers
source                 1..118
                       mol_type = protein
                       organism = synthetic construct
SEQUENCE: 106
EVQLLESGGG LVQPGGSLRL SCAASGFTFS SYAMSWVRQA PGKGLEWVSA ISGSGGSTYY      60
ADSVKGRFTI SRDNSKNTLY LQMNSLRAED TAVYYCARVY YPAVMDYWGQ GTLVTVSS      118

SEQ ID NO: 107         moltype = DNA   length = 354
FEATURE                Location/Qualifiers
source                 1..354
                       mol_type = other DNA
                       organism = synthetic construct
SEQUENCE: 107
gaagtacagc tgttggagtc tggaggtgga ttggttcagc cgggggggag ccttaggctg      60
agttgtgcag cttcaggatt tactttcagt tcctacgcta tgtcatgggt cagacaggcg    120
ccagggaagg gactggaatg ggtgtctgct atcagcggaa gtgagggtc tacttactac     180
gcagactctg ttaagggccg gtttaccatc tcccgagata acagcaagaa tactttatac    240
ctgcagatga actcccttcg cgccgaagac actgctgtct actattgcgc tcgggtatat    300
tatcctgccg tcatggacta ttggggccag ggaaccctcg tcactgtctc ctca           354

SEQ ID NO: 108         moltype = AA   length = 106
FEATURE                Location/Qualifiers
source                 1..106
                       mol_type = protein
                       organism = synthetic construct
SEQUENCE: 108
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ AGNPHTFGQG TKLEIK                   106

SEQ ID NO: 109         moltype = DNA   length = 318
FEATURE                Location/Qualifiers
source                 1..318
                       mol_type = other DNA
                       organism = synthetic construct
SEQUENCE: 109
gacatccaga tgacccagtc tccatcctcc ctgagcgcat ctgtaggaga ccgcgtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag gctggtaacc cgcacacttt tggccagggg    300
accaagctgg agatcaaa                                                   318
```

| SEQ ID NO: 110 | moltype = AA   length = 121 |
| --- | --- |
| FEATURE | Location/Qualifiers |
| source | 1..121 |
| | mol_type = protein |
| | organism = synthetic construct |

SEQUENCE: 110
```
EVQLLESGGG LVQPGGSLRL SCAASGFTFG SYYMYWVRQA PGKGLEWVSS IGGYSGSTYY   60
ADSVKGRFTI SRDNSKNTLY LQMNSLRAED TAVYYCARNT PFPGGSGLDY WGQGTLVTVS  120
S                                                                121
```

| SEQ ID NO: 111 | moltype = DNA   length = 363 |
| --- | --- |
| FEATURE | Location/Qualifiers |
| source | 1..363 |
| | mol_type = other DNA |
| | organism = synthetic construct |

SEQUENCE: 111
```
gaggtgcagc tgttggagag cggggaggc ttggtacagc ctgggggtc cctgcgcctc    60
tcctgtgcag ccagcggatt cacctttggt tcttactaca tgtactgggt ccgccaggct  120
ccagggaagg gctggagtg gtctcatct attggtggtt actctggttc tacatactat   180
gcagactccg tgaagggccg gttcaccatc tcccgtgaca attccaagaa cacgctgtat  240
ctgcaaatga acagcctgcg tgccgaggac acggctgtat attattgtgc gcgcaacact  300
ccgttcccgg gtggttctgg tttggactat ggggccagg gaaccctggt caccgtctcc   360
tca                                                                363
```

| SEQ ID NO: 112 | moltype = AA   length = 106 |
| --- | --- |
| FEATURE | Location/Qualifiers |
| source | 1..106 |
| | mol_type = protein |
| | organism = synthetic construct |

SEQUENCE: 112
```
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                 106
```

| SEQ ID NO: 113 | moltype = DNA   length = 318 |
| --- | --- |
| FEATURE | Location/Qualifiers |
| source | 1..318 |
| | mol_type = other DNA |
| | organism = synthetic construct |

SEQUENCE: 113
```
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                318
```

| SEQ ID NO: 114 | moltype = AA   length = 121 |
| --- | --- |
| FEATURE | Location/Qualifiers |
| source | 1..121 |
| | mol_type = protein |
| | organism = synthetic construct |

SEQUENCE: 114
```
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCAHYP SVPFPPHLDY WGQGTLVTVS  120
S                                                                121
```

| SEQ ID NO: 115 | moltype = DNA   length = 363 |
| --- | --- |
| FEATURE | Location/Qualifiers |
| source | 1..363 |
| | mol_type = other DNA |
| | organism = synthetic construct |

SEQUENCE: 115
```
gaggtccagc tgcttgaatc cggaggcggc ctggtccaac caggcggaag tctccgctta   60
tcatgcgccg catccggctt tacgttcagt tcatcatata tggggtgggt ccggcaggcg  120
ccaggtaagg gccttgaatg ggtctcctca attggctcag gatcctattc caccagctat  180
gctgattccg tgaagggccg ctttacaatc agtcgcgaca attctaagaa cacccctgtac 240
ctgcagatga actctctgag agcagaagat acagccgttt attattgtgc acactatcct  300
tccgtgccat tccacctca tctggattac tggggccagg gacgctggt cactgtctcc   360
tca                                                                363
```

| SEQ ID NO: 116 | moltype = AA   length = 106 |
| --- | --- |
| FEATURE | Location/Qualifiers |
| source | 1..106 |
| | mol_type = protein |
| | organism = synthetic construct |

SEQUENCE: 116
```
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                 106
```

```
SEQ ID NO: 117          moltype = DNA  length = 318
FEATURE                 Location/Qualifiers
source                  1..318
                        mol_type = other DNA
                        organism = synthetic construct
SEQUENCE: 117
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtccccatca 180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                318

SEQ ID NO: 118          moltype = AA  length = 121
FEATURE                 Location/Qualifiers
source                  1..121
                        mol_type = protein
                        organism = synthetic construct
SEQUENCE: 118
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCARYP PVPFPPHLDY WGQGTLVTVS  120
S                                                                  121

SEQ ID NO: 119          moltype = DNA  length = 363
FEATURE                 Location/Qualifiers
source                  1..363
                        mol_type = other DNA
                        organism = synthetic construct
SEQUENCE: 119
gaggtgcagc ttctggagag tgggggcggg ctcgtgcagc ctgggggtc cctccgtctc    60
agttgtgcag cttcaggctt tacctttagt agttcataca tgggatgggt ccgtcaggct  120
cctgggaagg gcttagaatg ggtgtcatca attggctccg gctcctattc tacatcctac  180
gccgacagtg ttaagggtcg ttttaccatt agcaggata acagtaagaa tacattgtac   240
ctccaaatga attctctgcg ggcggaagat actgccgtgt actattcgc aagataccca   300
cctgtcccgt tccctccgca ccttgattac tgggggcagg gtactctggt gaccgtctcc  360
tca                                                                363

SEQ ID NO: 120          moltype = AA  length = 106
FEATURE                 Location/Qualifiers
source                  1..106
                        mol_type = protein
                        organism = synthetic construct
SEQUENCE: 120
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                 106

SEQ ID NO: 121          moltype = DNA  length = 318
FEATURE                 Location/Qualifiers
source                  1..318
                        mol_type = other DNA
                        organism = synthetic construct
SEQUENCE: 121
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtccccatca 180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                318

SEQ ID NO: 122          moltype = AA  length = 121
FEATURE                 Location/Qualifiers
source                  1..121
                        mol_type = protein
                        organism = synthetic construct
SEQUENCE: 122
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCARYP SVLFPPHLDY WGQGTLVTVS  120
S                                                                  121

SEQ ID NO: 123          moltype = DNA  length = 363
FEATURE                 Location/Qualifiers
source                  1..363
                        mol_type = other DNA
                        organism = synthetic construct
SEQUENCE: 123
gaagtgcagc ttctggagtc tggtggaggt ctggtgcagc ctggggggtc tctgagactt   60
agttgtgcag catctggttt tacctttcagc tcaagctaca tgggctgggt gagacaggca  120
cccgaaaaag gattagagtg ggtgagctcc atcgggtctg gcagctactc tacctcctac  180
```

```
gctgactctg ttaagggacg attcaccatt tccagagaca atagcaaaaa cacactgtac   240
ttacaaatga attctctccg tgctgaggat acagcggtct actattgtgc tcgatacccg   300
tctgttcttt tccccctca ccttgattat tgggggcagg gcacgctggt gacagtctcc   360
tca                                                                363

SEQ ID NO: 124          moltype = AA   length = 106
FEATURE                 Location/Qualifiers
source                  1..106
                        mol_type = protein
                        organism = synthetic construct
SEQUENCE: 124
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                  106

SEQ ID NO: 125          moltype = DNA   length = 318
FEATURE                 Location/Qualifiers
source                  1..318
                        mol_type = other DNA
                        organism = synthetic construct
SEQUENCE: 125
gacatccaga tgacccagtc tccatcctcc ctgagcgcat ctgtaggaga ccgcgtcacc   60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                318

SEQ ID NO: 126          moltype = AA   length = 121
FEATURE                 Location/Qualifiers
source                  1..121
                        mol_type = protein
                        organism = synthetic construct
SEQUENCE: 126
EVQLLESGGG LVQPGGSLRL SCAASGFTFS SSYMGWVRQA PGKGLEWVSS IGSGSYSTSY   60
ADSVKGRFTI SRDNSKNTLY LQMNSLRAED TAVYYCARYP SVPFPHHLDY WGQGTLVTVS   120
S                                                                  121

SEQ ID NO: 127          moltype = DNA   length = 363
FEATURE                 Location/Qualifiers
source                  1..363
                        mol_type = other DNA
                        organism = synthetic construct
SEQUENCE: 127
gaagtccagt tgttagagag tgggggcggg ctggtgcagc cagggggttc tcttaggttg   60
tcatgtgccg cctccggctt cacttttctct tcttcctaca tgggctgggt gcggcaggca   120
ccgggaaagg gtctggagtg gtgtctagt attggctccg gctcctacag tacttcatac   180
gcagattcag tgaaagggag gttcaccatc tcaagagata acagcaaaaa cacccctgtac   240
ttgcagatga attccctgcg ggccgaagat accgccgtct actactgcgc acggtacccc   300
tccgttccct tccccacca tctggactac tggggtcaag gcactttggt cacagtctcc   360
tca                                                                363

SEQ ID NO: 128          moltype = AA   length = 106
FEATURE                 Location/Qualifiers
source                  1..106
                        mol_type = protein
                        organism = synthetic construct
SEQUENCE: 128
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                  106

SEQ ID NO: 129          moltype = DNA   length = 318
FEATURE                 Location/Qualifiers
source                  1..318
                        mol_type = other DNA
                        organism = synthetic construct
SEQUENCE: 129
gacatccaga tgacccagtc tccatcctcc ctgagcgcat ctgtaggaga ccgcgtcacc   60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                318

SEQ ID NO: 130          moltype = AA   length = 121
FEATURE                 Location/Qualifiers
source                  1..121
                        mol_type = protein
                        organism = synthetic construct
SEQUENCE: 130
```

```
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPLHLDY WGQGTLVTVS   120
S                                                                  121

SEQ ID NO: 131          moltype = DNA  length = 363
FEATURE                 Location/Qualifiers
source                  1..363
                        mol_type = other DNA
                        organism = synthetic construct
SEQUENCE: 131
gaggtgcagc tgttggagtc agggggaggc ttggtgcagc ccggaggctc cctgcgcctg    60
tcatgcgcag cctctgggtt tacattctct agctcttata tgggctgggt gaggcaagct   120
cctggcaagg gactcgagtg ggtctcttcc atcggctccg gtagctacag tacgagttat   180
gcagacagtg tgaaaggtag atttactatc tccaggaca actccaagaa taccctctac   240
ctgcagatga attccctcag agccgaagat actgcagtgt actattgcgc caggtacccc   300
tccgtcccat tccccctcca ccttgattac tggggacagg gaaccctggt aactgtctcc   360
tca                                                                363

SEQ ID NO: 132          moltype = AA  length = 106
FEATURE                 Location/Qualifiers
source                  1..106
                        mol_type = protein
                        organism = synthetic construct
SEQUENCE: 132
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 133          moltype = DNA  length = 318
FEATURE                 Location/Qualifiers
source                  1..318
                        mol_type = other DNA
                        organism = synthetic construct
SEQUENCE: 133
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                 318

SEQ ID NO: 134          moltype = AA  length = 121
FEATURE                 Location/Qualifiers
source                  1..121
                        mol_type = protein
                        organism = synthetic construct
SEQUENCE: 134
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHFDY WGQGTLVTVS   120
S                                                                  121

SEQ ID NO: 135          moltype = DNA  length = 363
FEATURE                 Location/Qualifiers
source                  1..363
                        mol_type = other DNA
                        organism = synthetic construct
SEQUENCE: 135
gaagtacaat tgttagagag cggagggga ctcgttcagc ccggaggatc actgcgcctg    60
tcatgtgcag ctagcggttt cactttagt tcatcctaca tgggttgggt cagacaggcc   120
ccaggggaaag gccttgagtg ggtgtcctcc attgggtctg gtagctactc aacatcatac   180
gctgacagcg tcaagggacg attcaccatt agtcgcgaca actctaagaa tacactctac   240
ctccagatga actctctcag ggccgaggac acagccgtgt attactgtgc acgctatccc   300
tctgtaccct ttcctccaca ttttgactat tggggtcagg gaccttggt cactgtctcc   360
tca                                                                363

SEQ ID NO: 136          moltype = AA  length = 106
FEATURE                 Location/Qualifiers
source                  1..106
                        mol_type = protein
                        organism = synthetic construct
SEQUENCE: 136
DIQMTQSPSS LSASVGDRVT ITCRASQSIS SDLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 137          moltype = DNA  length = 318
FEATURE                 Location/Qualifiers
source                  1..318
                        mol_type = other DNA
                        organism = synthetic construct
SEQUENCE: 137
```

```
gatattcaga tgacacagtc ccccagtagt ctgagcgcct cagttggtga cagagtgaca    60
ataacctgta gggcttctca gagcatatcc agcgatctga actggtatca gcagaaacca   120
gggaaggccc ccaaattgct catctatgcc gcatccagcc ttcagagcgg agtgccttca   180
cggttcagtg gttcagggtc aggaacagac ttcacgctca cgatcagttc tctgcaaccc   240
gaagatttcg caacttacta ctgtcaacag gccggcaacc ctcataccct cggtcaggga   300
acgaaattgg agatcaag                                                 318

SEQ ID NO: 138           moltype = AA  length = 121
FEATURE                  Location/Qualifiers
source                   1..121
                         mol_type = protein
                         organism = synthetic construct
SEQUENCE: 138
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHLDY WGQGTLVTVS   120
S                                                                   121

SEQ ID NO: 139           moltype = DNA  length = 363
FEATURE                  Location/Qualifiers
source                   1..363
                         mol_type = other DNA
                         organism = synthetic construct
SEQUENCE: 139
gaggtgcagc tgttagaaag tgggggaggc cttgtccaac caggaggtag tctgcgcctc    60
agttgcgccg cgtctggctt tacttttctct tcaagctata tgggtgggt gcgacaggct   120
ccaggcaagg gactggaatg ggtgtcttca attggttcga gttcctactc aacaagctat   180
gcggattcag tgaagggtag atttacgatc agtaggacaa atagcaagaa caccctctac   240
ctccagatga actcacttag agccgaggat acagccgtgt actattgtgc taggtatcca   300
tccgtgccct tccccctca ccttgactac tggggccaag gtacactcgt gaccgtctcc   360
tca                                                                 363

SEQ ID NO: 140           moltype = AA  length = 106
FEATURE                  Location/Qualifiers
source                   1..106
                         mol_type = protein
                         organism = synthetic construct
SEQUENCE: 140
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 141           moltype = DNA  length = 318
FEATURE                  Location/Qualifiers
source                   1..318
                         mol_type = other DNA
                         organism = synthetic construct
SEQUENCE: 141
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                 318

SEQ ID NO: 142           moltype = AA  length = 121
FEATURE                  Location/Qualifiers
source                   1..121
                         mol_type = protein
                         organism = synthetic construct
SEQUENCE: 142
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHVDY WGQGTLVTVS   120
S                                                                   121

SEQ ID NO: 143           moltype = DNA  length = 363
FEATURE                  Location/Qualifiers
source                   1..363
                         mol_type = other DNA
                         organism = synthetic construct
SEQUENCE: 143
gaggttcaac ttttagagag tggtggtggg ctggtgcagc ctggcggag cctccgcctc    60
tcatgcgcag ccagtgggtt tacctttagc tccagttaca tgggctgggt gagacaggcc   120
cctggaaaag gctggaatg ggtgtctagc atcggcagcg gctcatattc tacgtcttac   180
gctgacagcg ttaaaggcag gtttaccatc tccagggaca attcaaagaa cactctgtat   240
cttcagatga cagtgtctcag agctgaggac accgtgtgt attattgcgc ccgataccct   300
tccgtgccat tcccaccccg cgtagactac tggggccagg ggaccctcgt cacggtctcc   360
tca                                                                 363

SEQ ID NO: 144           moltype = AA  length = 106
FEATURE                  Location/Qualifiers
```

```
source                 1..106
                       mol_type = protein
                       organism = synthetic construct
SEQUENCE: 144
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 145         moltype = DNA   length = 318
FEATURE                Location/Qualifiers
source                 1..318
                       mol_type = other DNA
                       organism = synthetic construct
SEQUENCE: 145
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                 318

SEQ ID NO: 146         moltype = AA    length = 121
FEATURE                Location/Qualifiers
source                 1..121
                       mol_type = protein
                       organism = synthetic construct
SEQUENCE: 146
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHWDY WGQGTLVTVS   120
S                                                                   121

SEQ ID NO: 147         moltype = DNA   length = 363
FEATURE                Location/Qualifiers
source                 1..363
                       mol_type = other DNA
                       organism = synthetic construct
SEQUENCE: 147
gaagtacagc tgctggagag tggtggtggt ctggtgcagc cgggggggctc cctgcggctt   60
tcctgtgccg cgtctggctt caccttcagc tcatcttaca tgggctgggt tcgacaggca   120
cctggaaagg gtttagagtg ggtgtctagc attgggagtg gtcctattc aacatcctac   180
gcagatagtg tgaagggccg gttaccatc tctagagaca acagcaagaa taccttatac   240
ttacaaatga atagcctgag agcagaggat accgctgtct attattgtgc acggtaccct   300
agcgtccccgt tccccctca ctgggactat tggggccagg ggactctggt gaccgtctcc   360
tca                                                                 363

SEQ ID NO: 148         moltype = AA    length = 106
FEATURE                Location/Qualifiers
source                 1..106
                       mol_type = protein
                       organism = synthetic construct
SEQUENCE: 148
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 149         moltype = DNA   length = 318
FEATURE                Location/Qualifiers
source                 1..318
                       mol_type = other DNA
                       organism = synthetic construct
SEQUENCE: 149
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                 318

SEQ ID NO: 150         moltype = AA    length = 121
FEATURE                Location/Qualifiers
source                 1..121
                       mol_type = protein
                       organism = synthetic construct
SEQUENCE: 150
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPSHLDY WGQGTLVTVS   120
S                                                                   121

SEQ ID NO: 151         moltype = DNA   length = 363
FEATURE                Location/Qualifiers
source                 1..363
```

```
SEQUENCE: 151
gaggtgcagc tgttggaatc tggaggaggc ctcgtgcagc caggaggttc cctgaggctg    60
tcttgcgccg cctcaggttt cacctttagc tcttcctaca tgggatgggt gcggcaagca   120
cccggaaaag ggctggagtg ggtgagctcc atcggctcag gttcttatag cacttcttat   180
gcggactccg ttaaaggccg ctttactatc agcagggaca actccaagaa tacactgtat   240
ctgcagatga acagcctgcg tgctgaagac accgcagtct attactgcgc aagatatccg   300
tccgttccat ttccaagcca cctggattac tggggccagg gacactggt  gaccgtctcc   360
tca                                                                  363

SEQ ID NO: 152           moltype = AA  length = 106
FEATURE                  Location/Qualifiers
source                   1..106
                         mol_type = protein
                         organism = synthetic construct
SEQUENCE: 152
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 153           moltype = DNA  length = 318
FEATURE                  Location/Qualifiers
source                   1..318
                         mol_type = other DNA
                         organism = synthetic construct
SEQUENCE: 153
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                  318

SEQ ID NO: 154           moltype = AA  length = 121
FEATURE                  Location/Qualifiers
source                   1..121
                         mol_type = protein
                         organism = synthetic construct
SEQUENCE: 154
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFRPHLDY WGQGTLVTVS   120
S                                                                   121

SEQ ID NO: 155           moltype = DNA  length = 363
FEATURE                  Location/Qualifiers
source                   1..363
                         mol_type = other DNA
                         organism = synthetic construct
SEQUENCE: 155
gaggtgcagc tgctggagtc aggggggaggc cttgttcaac cggggaggcag tctgagatta   60
tcatgcgcag cttcaggggtt taccttctcc agtagttata tgggctgggt ccgccaagca   120
ccaggtaagg ggttggaatg ggtgtcttct atcggctctg gatcctattc tacgtcctac   180
gccgattctg tcaaaggaag gttcaccatc tccagggata attctaagaa taccctctac   240
ctgcaaatga actccctgcg agccgaagat acagccgttt actactgcgc gagataccccg   300
agcgtgcctt tcaggcccca tctggattac tggggacagg gacacttgt  gacagtctcc   360
tca                                                                  363

SEQ ID NO: 156           moltype = AA  length = 106
FEATURE                  Location/Qualifiers
source                   1..106
                         mol_type = protein
                         organism = synthetic construct
SEQUENCE: 156
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 157           moltype = DNA  length = 318
FEATURE                  Location/Qualifiers
source                   1..318
                         mol_type = other DNA
                         organism = synthetic construct
SEQUENCE: 157
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag gctggtaacc cgcacacttt tggccagggg   300
accaagctgg agatcaaa                                                  318
```

```
SEQ ID NO: 158            moltype = AA   length = 121
FEATURE                   Location/Qualifiers
source                    1..121
                          mol_type = protein
                          organism = synthetic construct
SEQUENCE: 158
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFSPHLDY WGQGTLVTVS   120
S                                                                   121

SEQ ID NO: 159            moltype = DNA   length = 363
FEATURE                   Location/Qualifiers
source                    1..363
                          mol_type = other DNA
                          organism = synthetic construct
SEQUENCE: 159
gaagtgcagc tccttgagtc cggtgggggc ctcgtccagc ccggcggatc cctgaggctg    60
tcatgcgctg caagcggctt cacatttagc agcagttata tgggctgggt tagacaggct   120
ccgggcaagg gactgaatgg gtcagcagt attggtagcg gtcatatag tacttcatac     180
gccgatagtg tgaagggccg gttcacaatt tccaggata actccaaaaa tacactgtat    240
ctgcaaatga actctctgcg agcggaagac actgctgttt actactgtgc caggtatccg   300
agtgtgccct tttctccaca cctggactat tggggccaag aacccttgt gaccgtctcc    360
tca                                                                 363

SEQ ID NO: 160            moltype = AA   length = 106
FEATURE                   Location/Qualifiers
source                    1..106
                          mol_type = protein
                          organism = synthetic construct
SEQUENCE: 160
DIQMTQSPSS LSASVGDRVT ITCRASQSIR DYLNWYQQKP GKAPKLLIYA ASSLQSGVPS    60
RFSGSGSGTD FTLTISSLQP EDFATYYCQQ GTFPPFTFGQG TKLEIK                 106

SEQ ID NO: 161            moltype = DNA   length = 318
FEATURE                   Location/Qualifiers
source                    1..318
                          mol_type = other DNA
                          organism = synthetic construct
SEQUENCE: 161
gacatccaga tgacccagtc tccatcctcc ctgagcgcat ctgtaggaga ccgcgtcacc    60
atcacttgcc gggcaagtca gtctattagg gactatttaa attggtatca gcagaaacca   120
gggaaagccc ctaagctcct gatctatgct gcatccagtt gcaaagtgg ggtcccatca    180
cgtttcagtg gcagtggaag cgggacagat ttcactctca ccatcagcag tctgcaacct   240
gaagattttg caacttatta ctgtcaacag gtacttttcc cgttcacttt tggccagggg   300
accaagctgg agatcaaa                                                 318

SEQ ID NO: 162            moltype = AA   length = 117
FEATURE                   Location/Qualifiers
source                    1..117
                          mol_type = protein
                          organism = synthetic construct
SEQUENCE: 162
EVQLLESGGG LVQPGGSLRL SCAASGFTFG SYYMSWVRQA PGKGLEWVSG ISGYGYYTGY    60
ADSVKGRFTI SRDNSKNTLY LQMNSLRAED TAVYYCARNG YGVIDYWGQG TLVTVSS      117

SEQ ID NO: 163            moltype = DNA   length = 351
FEATURE                   Location/Qualifiers
source                    1..351
                          mol_type = other DNA
                          organism = synthetic construct
SEQUENCE: 163
gaggtccagc tcctggaatc aggtggtggg ctcgtacagc caggaggttc acttcggctg    60
tcttgcgcag ccagcgggtt cacatttggc tcttactaca tgtcttgggt caggcaggcc   120
cctggcaagg gtttagagtg ggtcagtgga atatctgtt atggtgtacta cacaggttat   180
gcggacagcg tcaagggcag gtttaccata tctagagaca atagtaagaa cacccttat    240
ttgcagatga actctctgag agctgaagac acagccgttt attattgcgc ccggaacggg   300
tatggagtga ttgattattg ggggcagggt actctggtta cagtctcctc a            351

SEQ ID NO: 164            moltype = AA   length = 106
FEATURE                   Location/Qualifiers
source                    1..106
                          mol_type = protein
                          organism = synthetic construct
SEQUENCE: 164
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIK                  106

SEQ ID NO: 165            moltype = DNA   length = 318
FEATURE                   Location/Qualifiers
```

```
source                   1..318
                         mol_type = other DNA
                         organism = synthetic construct
SEQUENCE: 165
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                 318

SEQ ID NO: 166           moltype = AA   length = 117
FEATURE                  Location/Qualifiers
source                   1..117
                         mol_type = protein
                         organism = synthetic construct
SEQUENCE: 166
EVQLLESGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCARYG YTHFDYWGQG TLVTVSS     117

SEQ ID NO: 167           moltype = DNA   length = 351
FEATURE                  Location/Qualifiers
source                   1..351
                         mol_type = other DNA
                         organism = synthetic construct
SEQUENCE: 167
gaggtgcagc tgttggagag cggggggaggc ttggtacagc ctggggggtc cctgcgcctc   60
tcctgtgcag ccagcggatt cacctttagc agctatgcca tgagctgggt ccgccaggct  120
ccagggaagg ggctggagtg ggtctcagct attagtggta gtggtggtag cacatactat  180
gcagactccg tgaagggccg gttcaccatc tcccgtgaca attccaagaa cacgctgtat  240
ctgcaaatga acagcctgcg tgccgaggac acgactgtgt attattgtgc gcgctacggt  300
tacactcatt ttgactattg gggccaggga accctggtca ccgtctcctc a           351

SEQ ID NO: 168           moltype = AA   length = 106
FEATURE                  Location/Qualifiers
source                   1..106
                         mol_type = protein
                         organism = synthetic construct
SEQUENCE: 168
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ AGNPHTFGQG TKLEIK                 106

SEQ ID NO: 169           moltype = DNA   length = 318
FEATURE                  Location/Qualifiers
source                   1..318
                         mol_type = other DNA
                         organism = synthetic construct
SEQUENCE: 169
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
gaagattttg caacttatta ctgtcaacag gctggtaacc cgcacacttt tggccagggg  300
accaagctgg agatcaaa                                                 318

SEQ ID NO: 170           moltype = AA   length = 121
FEATURE                  Location/Qualifiers
source                   1..121
                         mol_type = protein
                         organism = synthetic construct
SEQUENCE: 170
EVQLLESGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCARYW SSYYGYLDY WGQGTLVTVS   120
S                                                                  121

SEQ ID NO: 171           moltype = DNA   length = 363
FEATURE                  Location/Qualifiers
source                   1..363
                         mol_type = other DNA
                         organism = synthetic construct
SEQUENCE: 171
gaagttcaac tcctcgaatc tggtgggggt ctggtccagc ccggggggcag ccttaggctc   60
agttgcgctg ccagcggttt cacattctct agctacgcca tgagttgggt gcggcaggca  120
ccaggaaagg gattggaatg ggtcagtgca atctcaggca gtggcggctc cacttactat  180
gctgattccg ttaaggggcg attcaccatc agtcgtgata attctaaaaa tacactgtat  240
ctgcagatga attctttgcg cgctgaggac acagctgtgt attattgcgc ccggtattgg  300
tggtccagct attacgggta tctggactat tggggtcagg gactcttgt acagtctcc   360
tca                                                                 363
```

```
SEQ ID NO: 172         moltype = AA   length = 108
FEATURE                Location/Qualifiers
source                 1..108
                       mol_type = protein
                       organism = synthetic construct
SEQUENCE: 172
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SSHGPLLTFG QGTKLEIK                108

SEQ ID NO: 173         moltype = DNA   length = 324
FEATURE                Location/Qualifiers
source                 1..324
                       mol_type = other DNA
                       organism = synthetic construct
SEQUENCE: 173
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag tcctcacacg gcccttttgc tacttttggc   300
cagggggacca agctggagat caaa                                          324

SEQ ID NO: 174         moltype = AA   length = 118
FEATURE                Location/Qualifiers
source                 1..118
                       mol_type = protein
                       organism = synthetic construct
SEQUENCE: 174
QVQLVQSGAE VKKPGSSVKV SCKASGGTFG YYAIHWVRQA PGQGLEWMGG IGSIFGTANY    60
AQKFQGRVTI TADESTSTAY MELSSLRSED TAVYYCARAW SSDHMDYWGQ GTLVTVSS     118

SEQ ID NO: 175         moltype = DNA   length = 354
FEATURE                Location/Qualifiers
source                 1..354
                       mol_type = other DNA
                       organism = synthetic construct
SEQUENCE: 175
caggttcagc tggttcagag cggtgcagaa gttaaaaaac cgggtagcag cgttaaagtt    60
agctgtaaag caagcggtgg cacctttggc tattatgcaa ttcactgggt tcgtcaggca   120
cctggtcaag gtctggaatg gatgggtggt attggttcga tttttggcac cgcaaattat   180
gcccagaaat tcagggtcg tgttaccatt accgcagatg aaagcaccag caccgcatat   240
atggaactga gcagcctgcg tagcgaagat accgcagtgt attattgtgc acgtgcatgg   300
agttcggatc atatggacta ctggggccag ggaaccctgg tcaccgtctc ctca         354

SEQ ID NO: 176         moltype = AA   length = 107
FEATURE                Location/Qualifiers
source                 1..107
                       mol_type = protein
                       organism = synthetic construct
SEQUENCE: 176
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ WRSHLFTFGQ GTKLEIK                 107

SEQ ID NO: 177         moltype = DNA   length = 321
FEATURE                Location/Qualifiers
source                 1..321
                       mol_type = other DNA
                       organism = synthetic construct
SEQUENCE: 177
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag tggcgctcac acctttttac ttttggccag   300
gggaccaagc tggagatcaa a                                              321

SEQ ID NO: 178         moltype = AA   length = 117
FEATURE                Location/Qualifiers
source                 1..117
                       mol_type = protein
                       organism = synthetic construct
SEQUENCE: 178
QVQLVQSGAE VKKPGSSVKV SCKASGGTFH DGAISWVRQA PGQGLEWMGH IIPIDGTAGY    60
AQKFQGRVTI TADESTSTAY MELSSLRSED TAVYYCARYR FYGIDYWGQG TLVTVSS      117

SEQ ID NO: 179         moltype = DNA   length = 351
FEATURE                Location/Qualifiers
source                 1..351
                       mol_type = other DNA
```

```
                                                  organism = synthetic construct
SEQUENCE: 179
caggttcagc tggttcagag cggtgcagaa gttaaaaaac cgggtagcag cgttaaagtt    60
agctgtaaag caagcggtgg cacctttcac gatggtgcaa ttagctgggt tcgtcaggca   120
cctggtcaag gtctggaatg gatggtcac attattccga ttgatggcac cgcaggatat   180
gcccagaaat ttcagggtcg tgttaccatt accgcagatg aaagcaccag caccgcatat   240
atggaactga gcagcctgcg tagcgaagat accgcagtgt attattgtgc acgttaccgt   300
ttctatggaa tcgactactg gggccaggga accctggtca ccgtctcctc a            351

SEQ ID NO: 180          moltype = AA  length = 107
FEATURE                 Location/Qualifiers
source                  1..107
                        mol_type = protein
                        organism = synthetic construct
SEQUENCE: 180
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYWYPLTFGQ GTKLEIK                  107

SEQ ID NO: 181          moltype = DNA  length = 321
FEATURE                 Location/Qualifiers
source                  1..321
                        mol_type = other DNA
                        organism = synthetic construct
SEQUENCE: 181
gaaattgttc tgacccagag tccgggtaca ctgagcctgt caccgggtga acgtgcaacc    60
ctgagctgtc gtgcaagcca gagcgttagc agcagctatc tggcatggta tcagcagaaa   120
cctggtcagg caccgcgtct gctgatttat ggtgcaagca gccgtgcaac cggtattccg   180
gatcgtttta gcggtagcgg tagtggcacc gatttacc tgaccattag ccgtctggaa     240
ccggaagatt ttgcagtgta ttattgtcag cagtattggt accctctgac ttttggccag   300
gggaccaagc tggagatcaa a                                              321

SEQ ID NO: 182          moltype = AA  length = 121
FEATURE                 Location/Qualifiers
source                  1..121
                        mol_type = protein
                        organism = synthetic construct
SEQUENCE: 182
QVQLVQSGAE VKKPGSSVKV SCKASGGTFS SSSIHWVRQA PGQGLEWMGH IYPSFGTANY    60
AQKFQGRVTI TADESTSTAY MELSSLRSED TAVYYCARHS GSRFFSPMDY WGQGTLVTVS   120
S                                                                    121

SEQ ID NO: 183          moltype = DNA  length = 363
FEATURE                 Location/Qualifiers
source                  1..363
                        mol_type = other DNA
                        organism = synthetic construct
SEQUENCE: 183
caggttcagc tggttcagag cggtgcagaa gttaaaaaac cgggtagcag cgttaaagtt    60
agctgtaaag caagcggtgg cacctttagc agcagcagta ttcactgggt tcgtcaggca   120
cctggtcaag gtctggaatg gatgggtcat atttacccgt cttttggcac cgcaaattat   180
gcccagaaat ttcagggtcg tgttaccatt accgcagatg aaagcaccag caccgcatat   240
atggaactga gcagcctgcg tagcgaagat accgcagtgt attattgtgc acgtcacagc   300
ggatctcgct ttttagtccc gatggactac tggggccagg gaaccctggt caccgtctcc   360
tca                                                                  363

SEQ ID NO: 184          moltype = AA  length = 107
FEATURE                 Location/Qualifiers
source                  1..107
                        mol_type = protein
                        organism = synthetic construct
SEQUENCE: 184
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ PWTYLFTFGQ GTKLEIK                  107

SEQ ID NO: 185          moltype = DNA  length = 321
FEATURE                 Location/Qualifiers
source                  1..321
                        mol_type = other DNA
                        organism = synthetic construct
SEQUENCE: 185
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag ccatggacct acttgtttac ttttggccag   300
gggaccaagc tggagatcaa a                                              321

SEQ ID NO: 186          moltype = AA  length = 120
FEATURE                 Location/Qualifiers
```

```
source                  1..120
                        mol_type = protein
                        organism = synthetic construct
SEQUENCE: 186
QVQLVQSGAE VKKPGSSVKV SCKASGGTFD DHAISWVRQA PGQGLEWMGG IIPIFSYAYY   60
AQKFQGRVTI TADESTSTAY MELSSLRSED TAVYYCARGR FYFPPSLDYW GQGTLVTVSS  120

SEQ ID NO: 187          moltype = DNA   length = 360
FEATURE                 Location/Qualifiers
source                  1..360
                        mol_type = other DNA
                        organism = synthetic construct
SEQUENCE: 187
caggttcagc tggttcagag cggtgcagaa gttaaaaaac cgggtagcag cgttaaagtt   60
agctgtaaag caagcggtgg cacctttgac gatcacgcaa ttagctgggt tcgtcaggca  120
cctggtcaag gtctggaatg gatgggtggt attattccga tttttagcta cgcatattat  180
gcccagaaat tcagggtcg tgttaccatt accgcagatg aaagcaccag caccgcatat  240
atggaactga gcagcctgcg tagcgaagat accgcagtgt attattgtgc acgtgggcgt  300
ttctactttc cccgtccct cgactactgg ggccaggaa ccctggtcac cgtctcctca   360

SEQ ID NO: 188          moltype = AA   length = 108
FEATURE                 Location/Qualifiers
source                  1..108
                        mol_type = protein
                        organism = synthetic construct
SEQUENCE: 188
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QPAAYLPTFG QGTKLEIK              108

SEQ ID NO: 189          moltype = DNA   length = 324
FEATURE                 Location/Qualifiers
source                  1..324
                        mol_type = other DNA
                        organism = synthetic construct
SEQUENCE: 189
gaaattgttc tgacccagag tccgggtaca ctgagcctgt caccgggtga acgtgcaacc   60
ctgagctgtc gtgcaagcca gagcgttagc agcagctatc tggcatggta tcagcagaaa  120
cctggtcagg caccgcgtct gctgatttat ggtgcaagca gccgtgcaac cggtattccg  180
gatcgtttta gcggtagcgg tagtggcacc gatttttacc cgaccattag ccgtctggaa  240
ccggaagatt ttgcagtgta ttattgtcag cagcctgcag cttaccttcc aacttttggc  300
caggggacca agctggagat caaa                                          324

SEQ ID NO: 190          moltype = AA   length = 119
FEATURE                 Location/Qualifiers
source                  1..119
                        mol_type = protein
                        organism = synthetic construct
SEQUENCE: 190
QVQLVQSGAE VKKPGSSVKV SCKASGGTFG SDAIGWVRQA PGQGLEWMGG IIPHFDTAYY   60
AQKFQGRVTI TADESTSTAY MELSSLRSED TAVYYCARTY YTYAFFDYWG QGTLVTVSS   119

SEQ ID NO: 191          moltype = DNA   length = 357
FEATURE                 Location/Qualifiers
source                  1..357
                        mol_type = other DNA
                        organism = synthetic construct
SEQUENCE: 191
caggttcagc tggttcagag cggtgcagaa gttaaaaaac cgggtagcag cgttaaagtt   60
agctgtaaag caagcggtgg cacctttgga agcgatgcaa ttgggtgggt tcgtcaggca  120
cctggtcaag gtctggaatg gatgggtggt attattccgc attttgatac cgcatattat  180
gcccagaaat tcagggtcg tgttaccatt accgcagatg aaagcaccag caccgcatat  240
atggaactga gcagcctgcg tagcgaagat accgcagtgt attattgtgc acgtacttat  300
tacacgtatg ccttcttga ctactggggc cagggaaccc tggtcaccgt ctcctca     357

SEQ ID NO: 192          moltype = AA   length = 109
FEATURE                 Location/Qualifiers
source                  1..109
                        mol_type = protein
                        organism = synthetic construct
SEQUENCE: 192
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QHVYGAPYTF GQGTKLEIK              109

SEQ ID NO: 193          moltype = DNA   length = 327
FEATURE                 Location/Qualifiers
source                  1..327
                        mol_type = other DNA
                        organism = synthetic construct
SEQUENCE: 193
```

```
gaaattgttc tgacccagag tccgggtaca ctgagcctgt caccgggtga acgtgcaacc    60
ctgagctgtc gtgcaagcca gagcgttagc agcagctatc tggcatggta tcagcagaaa   120
cctggtcagg caccgcgtct gctgatttat ggtgcaagca gccgtgcaac cggtattccg   180
gatcgtttta gcggtagcgg tagtggcacc gattttaccc tgaccattag ccgtctggaa   240
ccggaagatt ttgcagtgta ttattgtcag cagcatgtgt atggagctcc atacactttt   300
ggccagggga ccaagctgga gatcaaa                                       327

SEQ ID NO: 194          moltype = AA   length = 116
FEATURE                 Location/Qualifiers
source                  1..116
                        mol_type = protein
                        organism = synthetic construct
SEQUENCE: 194
QVQLVQSGAE VKKPGSSVKV SCKASGGTFS GGYISWVRQA PGQGLEWMGG IIPYFHHANY    60
AQKFQGRVTI TADESTSTAY MELSSLRSED TAVYYCARGV WRLDYWGQGT LVTVSS       116

SEQ ID NO: 195          moltype = DNA   length = 348
FEATURE                 Location/Qualifiers
source                  1..348
                        mol_type = other DNA
                        organism = synthetic construct
SEQUENCE: 195
caggttcagc tggttcagag cggtgcagaa gttaaaaaac cgggtagcag cgttaaagtt    60
agctgtaaag caagcggtgg cacctttagc ggtggctaca ttagctgggt tcgtcaggca   120
cctggtcaag gtctggaatg gatgggtggt attattccgt attttcatca tgcaaattat   180
gcccagaaat ttcagggtcg tgttaccatt accgcagata aagcaccaac caccgcatat   240
atggaactga gcagcctgcg tagcgaagat accgcagtgt attattgtgc acgtggcgtg   300
tggcgtctcg actactgggg ccagggaacc ctggtcaccg tctcctca               348

SEQ ID NO: 196          moltype = AA   length = 106
FEATURE                 Location/Qualifiers
source                  1..106
                        mol_type = protein
                        organism = synthetic construct
SEQUENCE: 196
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ WGYLLTFGQG TKLEIK                  106

SEQ ID NO: 197          moltype = DNA   length = 318
FEATURE                 Location/Qualifiers
source                  1..318
                        mol_type = other DNA
                        organism = synthetic construct
SEQUENCE: 197
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag tggggatacc tgttgacttt tggccagggg   300
accaagctgg agatcaaa                                                 318

SEQ ID NO: 198          moltype = AA   length = 118
FEATURE                 Location/Qualifiers
source                  1..118
                        mol_type = protein
                        organism = synthetic construct
SEQUENCE: 198
EVQLLESGGG LVQPGGSLRL SCAASGFTFS SDHMYWVRQA PGKGLEWVSA IYGSHGSTSY    60
ADSVKGRFTI SRDNSKNTLY LQMNSLRAED TAVYYCARYP RYGSIDYWGQ GTLVTVSS     118

SEQ ID NO: 199          moltype = DNA   length = 354
FEATURE                 Location/Qualifiers
source                  1..354
                        mol_type = other DNA
                        organism = synthetic construct
SEQUENCE: 199
gaggtgcagc tgttggagtc tgggggaggc ttggtacagc ctgggggtc cctgagactc     60
tcctgtgcag cctctggatt caccttagc agcgatcata tgtattgggt ccgccaggct   120
ccagggaagg ggctggagtg ggtctcagct atttacggta gtcatggtag cacaagctat   180
gcagactccg tgaagggccg gttcaccatc tccagagaca attccaagaa cacgctgtat   240
ctgcaaatga acagcctgag agccgaggac acggccgtat attactgtgc gcgctatccg   300
cggtacggat ctattgacta ctggggccag ggaaccctgg tcaccgtctc ctca        354

SEQ ID NO: 200          moltype = AA   length = 107
FEATURE                 Location/Qualifiers
source                  1..107
                        mol_type = protein
                        organism = synthetic construct
SEQUENCE: 200
```

-continued

```
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSGPPTFGQ GTKLEIK                 107

SEQ ID NO: 201           moltype = DNA   length = 321
FEATURE                  Location/Qualifiers
source                   1..321
                         mol_type = other DNA
                         organism = synthetic construct
SEQUENCE: 201
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag tcatattcag gacctccgac ttttggccag   300
gggaccaagc tggagatcaa a                                             321

SEQ ID NO: 202           moltype = AA   length = 118
FEATURE                  Location/Qualifiers
source                   1..118
                         mol_type = protein
                         organism = synthetic construct
SEQUENCE: 202
EVQLLESGGG LVQPGGSLRL SCAASGFTFG DHAMSWVRQA PGKGLEWVSA ISGYGHSTGY    60
ADSVKGRFTI SRDNSKNTLY LQMNSLRAED TAVYYCARNH YRVGLDYWGQ GTLVTVSS    118

SEQ ID NO: 203           moltype = DNA   length = 354
FEATURE                  Location/Qualifiers
source                   1..354
                         mol_type = other DNA
                         organism = synthetic construct
SEQUENCE: 203
gaggtgcagc tgttggagtc tgggggaggc ttggtacagc ctggggggtc cctgagactc    60
tcctgtgcag cctctggatt cacctttggc gaccatgcca tgagctgggt ccgccaggct   120
ccagggaagg ggctggagtg ggtctcagct attagtggtt acggtcatag cacaggctat   180
gcagactccg tgaagggccg gttcaccatc tccagagaca attccaagaa cacgctgtat   240
ctgcaaatga acagcctgag agccgaggac acggccgtat attactgtgc gcgcaatcat   300
taccgcgtag gcctggacta ctgggggcag ggaaccctgg tcaccgtctc ctca         354

SEQ ID NO: 204           moltype = AA   length = 108
FEATURE                  Location/Qualifiers
source                   1..108
                         mol_type = protein
                         organism = synthetic construct
SEQUENCE: 204
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ NSSSRLLTFG QGTKLEIK                108

SEQ ID NO: 205           moltype = DNA   length = 324
FEATURE                  Location/Qualifiers
source                   1..324
                         mol_type = other DNA
                         organism = synthetic construct
SEQUENCE: 205
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag aattcatcta gccggctttt gacttttggc   300
caggggacca agctggagat caaa                                          324

SEQ ID NO: 206           moltype = AA   length = 120
FEATURE                  Location/Qualifiers
source                   1..120
                         mol_type = protein
                         organism = synthetic construct
SEQUENCE: 206
EVQLLESGGG LVQPGGSLRL SCAASGFTFG DYDMSWVRQA PGKGLEWVSG IGHSGGSTYY    60
ADSVKGRFTI SRDNSKNTLY LQMNSLRAED TAVYYCARAS DWYPSGFDYW GQGTLVTVSS  120

SEQ ID NO: 207           moltype = DNA   length = 360
FEATURE                  Location/Qualifiers
source                   1..360
                         mol_type = other DNA
                         organism = synthetic construct
SEQUENCE: 207
gaggtgcagc tgttggagtc tgggggaggc ttggtacagc ctggggggtc cctgagactc    60
tcctgtgcag cctctggatt cacctttggc gactatgata tgagctgggt ccgccaggct   120
ccagggaagg ggctggagtg ggtctcaggg attggtcata gtggtggtag cacatactac   180
gcagactccg tgaagggccg gttcaccatc tccagagaca attccaagaa cacgctgtat   240
```

```
ctgcaaatga acagcctgag agccgaggac acggccgtat attactgtgc gcgcgcctcc   300
gattggtacc catctggatt cgactactgg ggccagggaa ccctggtcac cgtctcctca   360
```

SEQ ID NO: 208          moltype = AA   length = 107
FEATURE                 Location/Qualifiers
source                  1..107
                        mol_type = protein
                        organism = synthetic construct
SEQUENCE: 208
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SFSHPPTFGQ GTKLEIK                107

SEQ ID NO: 209          moltype = DNA   length = 321
FEATURE                 Location/Qualifiers
source                  1..321
                        mol_type = other DNA
                        organism = synthetic construct
SEQUENCE: 209
```
gacatccaga tgacccagtc tccatcctcc ctgtctgcat ctgtaggaga cagagtcacc   60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agcttttctc acccaccgac ttttggccag   300
gggaccaagc tggagatcaa a                                             321
```

SEQ ID NO: 210          moltype = AA   length = 119
FEATURE                 Location/Qualifiers
source                  1..119
                        mol_type = protein
                        organism = synthetic construct
SEQUENCE: 210
EVQLLESGGG LVQPGGSLRL SCAASGFTFY DHAMSWVRQA PGKGLEWVSA ISGSYGSTGY   60
ADSVKGRFTI SRDNSKNTLY LQMNSLRAED TAVYYCARWG GWAGDIDYWG QGTLVTVSS   119

SEQ ID NO: 211          moltype = DNA   length = 357
FEATURE                 Location/Qualifiers
source                  1..357
                        mol_type = other DNA
                        organism = synthetic construct
SEQUENCE: 211
```
gaggtgcagc tgttggagtc tgggggaggc ttggtacagc ctggggggtc cctgagactc   60
tcctgtgcag cctctggatt cacctttac gaccatgcca tgagctgggt ccgccaggct   120
ccagggaagg ggctggagtg ggtctcagct attagtggta gttacggtag cacaggatac   180
gcagactccg tgaagggccg gttcaccatc tccagagaca attccaagaa cacgctgtat   240
ctgcaaatga acagcctgag agccgaggac acggccgtat attactgtgc gcgctggggt   300
ggatgggccg gagacatcga ctactggggc caggaaccc tggtcaccgt ctcctca      357
```

SEQ ID NO: 212          moltype = AA   length = 109
FEATURE                 Location/Qualifiers
source                  1..109
                        mol_type = protein
                        organism = synthetic construct
SEQUENCE: 212
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QRDWFPLFTF GQGTKLEIK              109

SEQ ID NO: 213          moltype = DNA   length = 327
FEATURE                 Location/Qualifiers
source                  1..327
                        mol_type = other DNA
                        organism = synthetic construct
SEQUENCE: 213
```
gaaattgttc tgacccagag tccgggtaca ctgagcctgt caccgggtga acgtgcaacc   60
ctgagctgtc gtgcaagcca gagcgttagc agcagctatc tggcatggta tcagcagaaa   120
cctggtcagg caccgcgtct gctgatttat ggtgcaagca gccgtgcaac cggtattccg   180
gatcgtttta gcggtagcgg tagtggcacc gattttaccc tgaccattag ccgtctggaa   240
ccggaagatt ttgcagtgta ttattgtcag cagcgtgact ggtttccttt atttactttt   300
ggccagggga ccaagctgga gatcaaa                                       327
```

SEQ ID NO: 214          moltype = AA   length = 119
FEATURE                 Location/Qualifiers
source                  1..119
                        mol_type = protein
                        organism = synthetic construct
SEQUENCE: 214
EVQLLESGGG LVQPGGSLRL SCAASGFTFS DHAMHWVRQA PGKGLEWVSA ISGYGGYTHY   60
ADSVKGRFTI SRDNSKNTLY LQMNSLRAED TAVYYCARYG GYSGDFDYWG QGTLVTVSS   119

SEQ ID NO: 215          moltype = DNA   length = 357

| FEATURE | Location/Qualifiers |
|---|---|
| source | 1..357<br>mol_type = other DNA<br>organism = synthetic construct |

SEQUENCE: 215

```
gaggtgcagc tgttggagtc tgggggaggc ttggtacagc ctgggggtc cctgagactc      60
tcctgtgcag cctctggatt cacctttagc gatcacgcca tgcattgggt ccgccaggct    120
ccagggaagg ggctggagtg ggtctcagct attagtggtt atggtggtta tacacactac    180
gcagactccg tgaagggccg gttcaccatc tccagagaca attccaagaa cacgctgtat    240
ctgcaaatga acagcctgag agccgaggac acggccgtat attactgtgc gcgctatggc    300
ggatatagtg gggattttga ctactggggc cagggaaccc tggtcaccgt ctcctca       357
```

| SEQ ID NO: 216 | moltype = AA length = 8 |
|---|---|
| FEATURE | Location/Qualifiers |
| source | 1..8<br>mol_type = protein<br>organism = synthetic construct |

SEQUENCE: 216
GFTFSSSY                                                                8

| SEQ ID NO: 217 | moltype = AA length = 8 |
|---|---|
| FEATURE | Location/Qualifiers |
| source | 1..8<br>mol_type = protein<br>organism = synthetic construct |

SEQUENCE: 217
IGSGSYST                                                                8

| SEQ ID NO: 218 | moltype = AA length = 14 |
|---|---|
| FEATURE | Location/Qualifiers |
| source | 1..14<br>mol_type = protein<br>organism = synthetic construct |

SEQUENCE: 218
ARYPSVPFPP HLDY                                                        14

| SEQ ID NO: 219 | moltype = AA length = 8 |
|---|---|
| FEATURE | Location/Qualifiers |
| source | 1..8<br>mol_type = protein<br>organism = synthetic construct |

SEQUENCE: 219
GFTFGSYY                                                                8

| SEQ ID NO: 220 | moltype = AA length = 8 |
|---|---|
| FEATURE | Location/Qualifiers |
| source | 1..8<br>mol_type = protein<br>organism = synthetic construct |

SEQUENCE: 220
ISGYGYYT                                                                8

| SEQ ID NO: 221 | moltype = AA length = 10 |
|---|---|
| FEATURE | Location/Qualifiers |
| source | 1..10<br>mol_type = protein<br>organism = synthetic construct |

SEQUENCE: 221
ARHGYGVIDY                                                             10

| SEQ ID NO: 222 | moltype = AA length = 8 |
|---|---|
| FEATURE | Location/Qualifiers |
| source | 1..8<br>mol_type = protein<br>organism = synthetic construct |

SEQUENCE: 222
GFTFSSYA                                                                8

| SEQ ID NO: 223 | moltype = AA length = 8 |
|---|---|
| FEATURE | Location/Qualifiers |
| source | 1..8<br>mol_type = protein<br>organism = synthetic construct |

SEQUENCE: 223
ISGSGGST                                                                8

| SEQ ID NO: 224 | moltype = AA length = 10 |
|---|---|
| FEATURE | Location/Qualifiers |
| source | 1..10 |

```
                              mol_type = protein
                              organism = synthetic construct
SEQUENCE: 224
ARYGYTHFDY                                                              10

SEQ ID NO: 225                moltype = AA  length = 12
FEATURE                       Location/Qualifiers
source                        1..12
                              mol_type = protein
                              organism = synthetic construct
SEQUENCE: 225
ARYRWHGSVF DY                                                           12

SEQ ID NO: 226                moltype = AA  length = 10
FEATURE                       Location/Qualifiers
source                        1..10
                              mol_type = protein
                              organism = synthetic construct
SEQUENCE: 226
ARYGYSVLDY                                                              10

SEQ ID NO: 227                moltype = AA  length = 14
FEATURE                       Location/Qualifiers
source                        1..14
                              mol_type = protein
                              organism = synthetic construct
SEQUENCE: 227
ARYPSVPFPP PLDY                                                         14

SEQ ID NO: 228                moltype = AA  length = 14
FEATURE                       Location/Qualifiers
source                        1..14
                              mol_type = protein
                              organism = synthetic construct
SEQUENCE: 228
ARYPSVPFPP LLDY                                                         14

SEQ ID NO: 229                moltype = AA  length = 14
FEATURE                       Location/Qualifiers
source                        1..14
                              mol_type = protein
                              organism = synthetic construct
SEQUENCE: 229
ARYPSVPFQP HLDY                                                         14

SEQ ID NO: 230                moltype = AA  length = 10
FEATURE                       Location/Qualifiers
source                        1..10
                              mol_type = protein
                              organism = synthetic construct
SEQUENCE: 230
ARYHPYSFDY                                                              10

SEQ ID NO: 231                moltype = AA  length = 10
FEATURE                       Location/Qualifiers
source                        1..10
                              mol_type = protein
                              organism = synthetic construct
SEQUENCE: 231
ARYSPYVLDY                                                              10

SEQ ID NO: 232                moltype = AA  length = 11
FEATURE                       Location/Qualifiers
source                        1..11
                              mol_type = protein
                              organism = synthetic construct
SEQUENCE: 232
ARVYYPAVMD Y                                                            11

SEQ ID NO: 233                moltype = AA  length = 8
FEATURE                       Location/Qualifiers
source                        1..8
                              mol_type = protein
                              organism = synthetic construct
SEQUENCE: 233
IGGYSGST                                                                8

SEQ ID NO: 234                moltype = AA  length = 14
FEATURE                       Location/Qualifiers
```

```
source                  1..14
                        mol_type = protein
                        organism = synthetic construct
SEQUENCE: 234
ARNTPFPGGS GLDY                                                          14

SEQ ID NO: 235          moltype = AA   length = 14
FEATURE                 Location/Qualifiers
source                  1..14
                        mol_type = protein
                        organism = synthetic construct
SEQUENCE: 235
AHYPSVPFPP HLDY                                                          14

SEQ ID NO: 236          moltype = AA   length = 14
FEATURE                 Location/Qualifiers
source                  1..14
                        mol_type = protein
                        organism = synthetic construct
SEQUENCE: 236
ARYPPVPFPP HLDY                                                          14

SEQ ID NO: 237          moltype = AA   length = 14
FEATURE                 Location/Qualifiers
source                  1..14
                        mol_type = protein
                        organism = synthetic construct
SEQUENCE: 237
ARYPSVLFPP HLDY                                                          14

SEQ ID NO: 238          moltype = AA   length = 14
FEATURE                 Location/Qualifiers
source                  1..14
                        mol_type = protein
                        organism = synthetic construct
SEQUENCE: 238
ARYPSVPFPH HLDY                                                          14

SEQ ID NO: 239          moltype = AA   length = 14
FEATURE                 Location/Qualifiers
source                  1..14
                        mol_type = protein
                        organism = synthetic construct
SEQUENCE: 239
ARYPSVPFPL HLDY                                                          14

SEQ ID NO: 240          moltype = AA   length = 14
FEATURE                 Location/Qualifiers
source                  1..14
                        mol_type = protein
                        organism = synthetic construct
SEQUENCE: 240
ARYPSVPFPP HFDY                                                          14

SEQ ID NO: 241          moltype = AA   length = 14
FEATURE                 Location/Qualifiers
source                  1..14
                        mol_type = protein
                        organism = synthetic construct
SEQUENCE: 241
ARYPSVPFPP HVDY                                                          14

SEQ ID NO: 242          moltype = AA   length = 14
FEATURE                 Location/Qualifiers
source                  1..14
                        mol_type = protein
                        organism = synthetic construct
SEQUENCE: 242
ARYPSVPFPP HWDY                                                          14

SEQ ID NO: 243          moltype = AA   length = 14
FEATURE                 Location/Qualifiers
source                  1..14
                        mol_type = protein
                        organism = synthetic construct
SEQUENCE: 243
ARYPSVPFPS HLDY                                                          14

SEQ ID NO: 244          moltype = AA   length = 14
```

```
FEATURE            Location/Qualifiers
source             1..14
                   mol_type = protein
                   organism = synthetic construct
SEQUENCE: 244
ARYPSVPFRP HLDY                                                           14

SEQ ID NO: 245     moltype = AA   length = 14
FEATURE            Location/Qualifiers
source             1..14
                   mol_type = protein
                   organism = synthetic construct
SEQUENCE: 245
ARYPSVPFSP HLDY                                                           14

SEQ ID NO: 246     moltype = AA   length = 10
FEATURE            Location/Qualifiers
source             1..10
                   mol_type = protein
                   organism = synthetic construct
SEQUENCE: 246
ARNGYGVIDY                                                                10

SEQ ID NO: 247     moltype = AA   length = 14
FEATURE            Location/Qualifiers
source             1..14
                   mol_type = protein
                   organism = synthetic construct
SEQUENCE: 247
ARYWWSSYYG YLDY                                                           14

SEQ ID NO: 248     moltype = AA   length = 8
FEATURE            Location/Qualifiers
source             1..8
                   mol_type = protein
                   organism = synthetic construct
SEQUENCE: 248
GGTFGYYA                                                                  8

SEQ ID NO: 249     moltype = AA   length = 8
FEATURE            Location/Qualifiers
source             1..8
                   mol_type = protein
                   organism = synthetic construct
SEQUENCE: 249
IGSIFGTA                                                                  8

SEQ ID NO: 250     moltype = AA   length = 11
FEATURE            Location/Qualifiers
source             1..11
                   mol_type = protein
                   organism = synthetic construct
SEQUENCE: 250
ARAWSSDHMD Y                                                              11

SEQ ID NO: 251     moltype = AA   length = 8
FEATURE            Location/Qualifiers
source             1..8
                   mol_type = protein
                   organism = synthetic construct
SEQUENCE: 251
GGTFHDGA                                                                  8

SEQ ID NO: 252     moltype = AA   length = 8
FEATURE            Location/Qualifiers
source             1..8
                   mol_type = protein
                   organism = synthetic construct
SEQUENCE: 252
IIPIDGTA                                                                  8

SEQ ID NO: 253     moltype = AA   length = 10
FEATURE            Location/Qualifiers
source             1..10
                   mol_type = protein
                   organism = synthetic construct
SEQUENCE: 253
ARYRFYGIDY                                                                10
```

```
SEQ ID NO: 254          moltype = AA   length = 8
FEATURE                 Location/Qualifiers
source                  1..8
                        mol_type = protein
                        organism = synthetic construct
SEQUENCE: 254
GGTFSSSS                                                                    8

SEQ ID NO: 255          moltype = AA   length = 8
FEATURE                 Location/Qualifiers
source                  1..8
                        mol_type = protein
                        organism = synthetic construct
SEQUENCE: 255
IYPSFGTA                                                                    8

SEQ ID NO: 256          moltype = AA   length = 14
FEATURE                 Location/Qualifiers
source                  1..14
                        mol_type = protein
                        organism = synthetic construct
SEQUENCE: 256
ARHSGSRFFS PMDY                                                            14

SEQ ID NO: 257          moltype = AA   length = 8
FEATURE                 Location/Qualifiers
source                  1..8
                        mol_type = protein
                        organism = synthetic construct
SEQUENCE: 257
GGTFDDHA                                                                    8

SEQ ID NO: 258          moltype = AA   length = 8
FEATURE                 Location/Qualifiers
source                  1..8
                        mol_type = protein
                        organism = synthetic construct
SEQUENCE: 258
IIPIFSYA                                                                    8

SEQ ID NO: 259          moltype = AA   length = 13
FEATURE                 Location/Qualifiers
source                  1..13
                        mol_type = protein
                        organism = synthetic construct
SEQUENCE: 259
ARGRFYFPPS LDY                                                             13

SEQ ID NO: 260          moltype = AA   length = 8
FEATURE                 Location/Qualifiers
source                  1..8
                        mol_type = protein
                        organism = synthetic construct
SEQUENCE: 260
GGTFGSDA                                                                    8

SEQ ID NO: 261          moltype = AA   length = 8
FEATURE                 Location/Qualifiers
source                  1..8
                        mol_type = protein
                        organism = synthetic construct
SEQUENCE: 261
IIPHFDTA                                                                    8

SEQ ID NO: 262          moltype = AA   length = 12
FEATURE                 Location/Qualifiers
source                  1..12
                        mol_type = protein
                        organism = synthetic construct
SEQUENCE: 262
ARTYYTYAFF DY                                                              12

SEQ ID NO: 263          moltype = AA   length = 8
FEATURE                 Location/Qualifiers
source                  1..8
                        mol_type = protein
                        organism = synthetic construct
SEQUENCE: 263
GGTFSGGY                                                                    8
```

```
SEQ ID NO: 264          moltype = AA   length = 8
FEATURE                 Location/Qualifiers
source                  1..8
                        mol_type = protein
                        organism = synthetic construct
SEQUENCE: 264
IIPYFHHA                                                                 8

SEQ ID NO: 265          moltype = AA   length = 9
FEATURE                 Location/Qualifiers
source                  1..9
                        mol_type = protein
                        organism = synthetic construct
SEQUENCE: 265
ARGVWRLDY                                                                9

SEQ ID NO: 266          moltype = AA   length = 8
FEATURE                 Location/Qualifiers
source                  1..8
                        mol_type = protein
                        organism = synthetic construct
SEQUENCE: 266
GFTFSSDH                                                                 8

SEQ ID NO: 267          moltype = AA   length = 8
FEATURE                 Location/Qualifiers
source                  1..8
                        mol_type = protein
                        organism = synthetic construct
SEQUENCE: 267
IYGSHGST                                                                 8

SEQ ID NO: 268          moltype = AA   length = 11
FEATURE                 Location/Qualifiers
source                  1..11
                        mol_type = protein
                        organism = synthetic construct
SEQUENCE: 268
ARYPRYGSID Y                                                            11

SEQ ID NO: 269          moltype = AA   length = 8
FEATURE                 Location/Qualifiers
source                  1..8
                        mol_type = protein
                        organism = synthetic construct
SEQUENCE: 269
GFTFGDHA                                                                 8

SEQ ID NO: 270          moltype = AA   length = 8
FEATURE                 Location/Qualifiers
source                  1..8
                        mol_type = protein
                        organism = synthetic construct
SEQUENCE: 270
ISGYGHST                                                                 8

SEQ ID NO: 271          moltype = AA   length = 11
FEATURE                 Location/Qualifiers
source                  1..11
                        mol_type = protein
                        organism = synthetic construct
SEQUENCE: 271
ARNHYRVGLD Y                                                            11

SEQ ID NO: 272          moltype = AA   length = 8
FEATURE                 Location/Qualifiers
source                  1..8
                        mol_type = protein
                        organism = synthetic construct
SEQUENCE: 272
GFTFGDYD                                                                 8

SEQ ID NO: 273          moltype = AA   length = 13
FEATURE                 Location/Qualifiers
source                  1..13
                        mol_type = protein
                        organism = synthetic construct
SEQUENCE: 273
```

ARASDWYPSG FDY 13

SEQ ID NO: 274    moltype = AA  length = 8
FEATURE           Location/Qualifiers
source            1..8
                  mol_type = protein
                  organism = synthetic construct

SEQUENCE: 274
GFTFYDHA 8

SEQ ID NO: 275    moltype = AA  length = 8
FEATURE           Location/Qualifiers
source            1..8
                  mol_type = protein
                  organism = synthetic construct

SEQUENCE: 275
ISGSYGST 8

SEQ ID NO: 276    moltype = AA  length = 12
FEATURE           Location/Qualifiers
source            1..12
                  mol_type = protein
                  organism = synthetic construct

SEQUENCE: 276
ARWGGWAGDI DY 12

SEQ ID NO: 277    moltype = AA  length = 8
FEATURE           Location/Qualifiers
source            1..8
                  mol_type = protein
                  organism = synthetic construct

SEQUENCE: 277
GFTFSDHA 8

SEQ ID NO: 278    moltype = AA  length = 8
FEATURE           Location/Qualifiers
source            1..8
                  mol_type = protein
                  organism = synthetic construct

SEQUENCE: 278
ISGYGGYT 8

SEQ ID NO: 279    moltype = AA  length = 12
FEATURE           Location/Qualifiers
source            1..12
                  mol_type = protein
                  organism = synthetic construct

SEQUENCE: 279
ARYGGYSGDF DY 12

SEQ ID NO: 280    moltype = AA  length = 10
FEATURE           Location/Qualifiers
source            1..10
                  mol_type = protein
                  organism = synthetic construct

SEQUENCE: 280
GFTFSSSYMG 10

SEQ ID NO: 281    moltype = AA  length = 10
FEATURE           Location/Qualifiers
source            1..10
                  mol_type = protein
                  organism = synthetic construct

SEQUENCE: 281
SIGSGSYSTS 10

SEQ ID NO: 282    moltype = AA  length = 10
FEATURE           Location/Qualifiers
source            1..10
                  mol_type = protein
                  organism = synthetic construct

SEQUENCE: 282
GFTFGSYYMS 10

SEQ ID NO: 283    moltype = AA  length = 10
FEATURE           Location/Qualifiers
source            1..10
                  mol_type = protein
                  organism = synthetic construct

```
SEQUENCE: 283
GISGYGYYTG                                                                   10

SEQ ID NO: 284         moltype = AA  length = 10
FEATURE                Location/Qualifiers
source                 1..10
                       mol_type = protein
                       organism = synthetic construct
SEQUENCE: 284
GFTFSSYAMS                                                                   10

SEQ ID NO: 285         moltype = AA  length = 10
FEATURE                Location/Qualifiers
source                 1..10
                       mol_type = protein
                       organism = synthetic construct
SEQUENCE: 285
AISGSGGSTY                                                                   10

SEQ ID NO: 286         moltype = AA  length = 10
FEATURE                Location/Qualifiers
source                 1..10
                       mol_type = protein
                       organism = synthetic construct
SEQUENCE: 286
GFTFGSYYMY                                                                   10

SEQ ID NO: 287         moltype = AA  length = 10
FEATURE                Location/Qualifiers
source                 1..10
                       mol_type = protein
                       organism = synthetic construct
SEQUENCE: 287
SIGGYSGSTY                                                                   10

SEQ ID NO: 288         moltype = AA  length = 10
FEATURE                Location/Qualifiers
source                 1..10
                       mol_type = protein
                       organism = synthetic construct
SEQUENCE: 288
GFTFSSYAMS                                                                   10

SEQ ID NO: 289         moltype = AA  length = 10
FEATURE                Location/Qualifiers
source                 1..10
                       mol_type = protein
                       organism = synthetic construct
SEQUENCE: 289
GGTFGYYAIH                                                                   10

SEQ ID NO: 290         moltype = AA  length = 10
FEATURE                Location/Qualifiers
source                 1..10
                       mol_type = protein
                       organism = synthetic construct
SEQUENCE: 290
GIGSIFGTAN                                                                   10

SEQ ID NO: 291         moltype = AA  length = 10
FEATURE                Location/Qualifiers
source                 1..10
                       mol_type = protein
                       organism = synthetic construct
SEQUENCE: 291
GGTFHDGAIS                                                                   10

SEQ ID NO: 292         moltype = AA  length = 10
FEATURE                Location/Qualifiers
source                 1..10
                       mol_type = protein
                       organism = synthetic construct
SEQUENCE: 292
HIIPIDGTAG                                                                   10

SEQ ID NO: 293         moltype = AA  length = 10
FEATURE                Location/Qualifiers
source                 1..10
                       mol_type = protein
```

```
SEQUENCE: 293
GGTFSSSSIH                                                                    10

SEQ ID NO: 294           moltype = AA   length = 10
FEATURE                  Location/Qualifiers
source                   1..10
                         mol_type = protein
                         organism = synthetic construct
SEQUENCE: 294
HIYPSFGTAN                                                                    10

SEQ ID NO: 295           moltype = AA   length = 10
FEATURE                  Location/Qualifiers
source                   1..10
                         mol_type = protein
                         organism = synthetic construct
SEQUENCE: 295
GGTFDDHAIS                                                                    10

SEQ ID NO: 296           moltype = AA   length = 10
FEATURE                  Location/Qualifiers
source                   1..10
                         mol_type = protein
                         organism = synthetic construct
SEQUENCE: 296
GIIPIFSYAY                                                                    10

SEQ ID NO: 297           moltype = AA   length = 10
FEATURE                  Location/Qualifiers
source                   1..10
                         mol_type = protein
                         organism = synthetic construct
SEQUENCE: 297
GGTFGSDAIG                                                                    10

SEQ ID NO: 298           moltype = AA   length = 10
FEATURE                  Location/Qualifiers
source                   1..10
                         mol_type = protein
                         organism = synthetic construct
SEQUENCE: 298
GIIPHFDTAY                                                                    10

SEQ ID NO: 299           moltype = AA   length = 10
FEATURE                  Location/Qualifiers
source                   1..10
                         mol_type = protein
                         organism = synthetic construct
SEQUENCE: 299
GGTFSGGYIS                                                                    10

SEQ ID NO: 300           moltype = AA   length = 10
FEATURE                  Location/Qualifiers
source                   1..10
                         mol_type = protein
                         organism = synthetic construct
SEQUENCE: 300
GIIPYFHHAN                                                                    10

SEQ ID NO: 301           moltype = AA   length = 10
FEATURE                  Location/Qualifiers
source                   1..10
                         mol_type = protein
                         organism = synthetic construct
SEQUENCE: 301
GFTFSSDHMY                                                                    10

SEQ ID NO: 302           moltype = AA   length = 10
FEATURE                  Location/Qualifiers
source                   1..10
                         mol_type = protein
                         organism = synthetic construct
SEQUENCE: 302
AIYGSHGSTS                                                                    10

SEQ ID NO: 303           moltype = AA   length = 10
FEATURE                  Location/Qualifiers
source                   1..10
```

```
                              -continued mol_type = protein
                        organism = synthetic construct
SEQUENCE: 303
GFTFGDHAMS                                                          10

SEQ ID NO: 304          moltype = AA  length = 10
FEATURE                 Location/Qualifiers
source                  1..10
                        mol_type = protein
                        organism = synthetic construct
SEQUENCE: 304
AISGYGHSTG                                                          10

SEQ ID NO: 305          moltype = AA  length = 10
FEATURE                 Location/Qualifiers
source                  1..10
                        mol_type = protein
                        organism = synthetic construct
SEQUENCE: 305
GFTFGDYDMS                                                          10

SEQ ID NO: 306          moltype = AA  length = 10
FEATURE                 Location/Qualifiers
source                  1..10
                        mol_type = protein
                        organism = synthetic construct
SEQUENCE: 306
GIGHSGGSTY                                                          10

SEQ ID NO: 307          moltype = AA  length = 10
FEATURE                 Location/Qualifiers
source                  1..10
                        mol_type = protein
                        organism = synthetic construct
SEQUENCE: 307
GFTFYDHAMS                                                          10

SEQ ID NO: 308          moltype = AA  length = 10
FEATURE                 Location/Qualifiers
source                  1..10
                        mol_type = protein
                        organism = synthetic construct
SEQUENCE: 308
AISGSYGSTG                                                          10

SEQ ID NO: 309          moltype = AA  length = 10
FEATURE                 Location/Qualifiers
source                  1..10
                        mol_type = protein
                        organism = synthetic construct
SEQUENCE: 309
GFTFSDHAMH                                                          10

SEQ ID NO: 310          moltype = AA  length = 10
FEATURE                 Location/Qualifiers
source                  1..10
                        mol_type = protein
                        organism = synthetic construct
SEQUENCE: 310
AISGYGGYTH                                                          10

SEQ ID NO: 311          moltype = AA  length = 8
FEATURE                 Location/Qualifiers
source                  1..8
                        mol_type = protein
                        organism = synthetic construct
SEQUENCE: 311
QQAGNPHT                                                             8

SEQ ID NO: 312          moltype = AA  length = 6
FEATURE                 Location/Qualifiers
source                  1..6
                        mol_type = protein
                        organism = synthetic construct
SEQUENCE: 312
QSIRDY                                                               6

SEQ ID NO: 313          moltype = AA  length = 8
FEATURE                 Location/Qualifiers
```

```
                                      267                                268
                                                    -continued source                  1..8
                        mol_type = protein
                        organism = synthetic construct
SEQUENCE: 313
QQGTFPFT                                                                   8

SEQ ID NO: 314          moltype = AA   length = 9
FEATURE                 Location/Qualifiers
source                  1..9
                        mol_type = protein
                        organism = synthetic construct
SEQUENCE: 314
QQGAYVPYT                                                                  9

SEQ ID NO: 315          moltype = AA   length = 6
FEATURE                 Location/Qualifiers
source                  1..6
                        mol_type = protein
                        organism = synthetic construct
SEQUENCE: 315
QAISGY                                                                     6

SEQ ID NO: 316          moltype =    length =
SEQUENCE: 316
000

SEQ ID NO: 317          moltype = AA   length = 10
FEATURE                 Location/Qualifiers
source                  1..10
                        mol_type = protein
                        organism = synthetic construct
SEQUENCE: 317
QQYPWYFPYT                                                                10

SEQ ID NO: 318          moltype = AA   length = 6
FEATURE                 Location/Qualifiers
source                  1..6
                        mol_type = protein
                        organism = synthetic construct
SEQUENCE: 318
QSIRGY                                                                     6

SEQ ID NO: 319          moltype = AA   length = 10
FEATURE                 Location/Qualifiers
source                  1..10
                        mol_type = protein
                        organism = synthetic construct
SEQUENCE: 319
QQPSYPSLFT                                                                10

SEQ ID NO: 320          moltype = AA   length = 8
FEATURE                 Location/Qualifiers
source                  1..8
                        mol_type = protein
                        organism = synthetic construct
SEQUENCE: 320
QQVDGLFT                                                                   8

SEQ ID NO: 321          moltype = AA   length = 6
FEATURE                 Location/Qualifiers
source                  1..6
                        mol_type = protein
                        organism = synthetic construct
SEQUENCE: 321
QSISSD                                                                     6

SEQ ID NO: 322          moltype = AA   length = 10
FEATURE                 Location/Qualifiers
source                  1..10
                        mol_type = protein
                        organism = synthetic construct
SEQUENCE: 322
QQSSHGPLLT                                                                10

SEQ ID NO: 323          moltype = AA   length = 9
FEATURE                 Location/Qualifiers
source                  1..9
                        mol_type = protein
                        organism = synthetic construct
```

-continued

```
SEQUENCE: 323
QQWRSHLFT                                                                   9

SEQ ID NO: 324         moltype = AA  length = 7
FEATURE                Location/Qualifiers
source                 1..7
                       mol_type = protein
                       organism = synthetic construct
SEQUENCE: 324
QSVSSSY                                                                     7

SEQ ID NO: 325         moltype =     length =
SEQUENCE: 325
000

SEQ ID NO: 326         moltype = AA  length = 8
FEATURE                Location/Qualifiers
source                 1..8
                       mol_type = protein
                       organism = synthetic construct
SEQUENCE: 326
QQYWYPLT                                                                    8

SEQ ID NO: 327         moltype = AA  length = 9
FEATURE                Location/Qualifiers
source                 1..9
                       mol_type = protein
                       organism = synthetic construct
SEQUENCE: 327
QQPWTYLFT                                                                   9

SEQ ID NO: 328         moltype = AA  length = 9
FEATURE                Location/Qualifiers
source                 1..9
                       mol_type = protein
                       organism = synthetic construct
SEQUENCE: 328
QQPAAYLPT                                                                   9

SEQ ID NO: 329         moltype = AA  length = 10
FEATURE                Location/Qualifiers
source                 1..10
                       mol_type = protein
                       organism = synthetic construct
SEQUENCE: 329
QQHVYGAPYT                                                                 10

SEQ ID NO: 330         moltype = AA  length = 8
FEATURE                Location/Qualifiers
source                 1..8
                       mol_type = protein
                       organism = synthetic construct
SEQUENCE: 330
QQWGYLLT                                                                    8

SEQ ID NO: 331         moltype = AA  length = 9
FEATURE                Location/Qualifiers
source                 1..9
                       mol_type = protein
                       organism = synthetic construct
SEQUENCE: 331
QQSYSGPPT                                                                   9

SEQ ID NO: 332         moltype = AA  length = 10
FEATURE                Location/Qualifiers
source                 1..10
                       mol_type = protein
                       organism = synthetic construct
SEQUENCE: 332
QQNSSSRLLT                                                                 10

SEQ ID NO: 333         moltype = AA  length = 9
FEATURE                Location/Qualifiers
source                 1..9
                       mol_type = protein
                       organism = synthetic construct
SEQUENCE: 333
QQSFSHPPT                                                                   9
```

```
SEQ ID NO: 334            moltype = AA  length = 10
FEATURE                   Location/Qualifiers
source                    1..10
                          mol_type = protein
                          organism = synthetic construct
SEQUENCE: 334
QQRDWFPLFT                                                                  10

SEQ ID NO: 335            moltype = AA  length = 8
FEATURE                   Location/Qualifiers
source                    1..8
                          mol_type = protein
                          organism = synthetic construct
SEQUENCE: 335
IGHSGGST                                                                     8

SEQ ID NO: 336            moltype = AA  length = 330
FEATURE                   Location/Qualifiers
source                    1..330
                          mol_type = protein
                          organism = Homo sapiens
SEQUENCE: 336
ASTKGPSVFP LAPSSKSTSG GTAALGCLVK DYFPEPVTVS WNSGALTSGV HTFPAVLQSS            60
GLYSLSSVVT VPSSSLGTQT YICNVNHKPS NTKVDKKVEP KSCDKTHTCP PCPAPEAAGG           120
PSVFLFPPKP KDTLMISRTP EVTCVVVDVS HEDPEVKFNW YVDGVEVHNA KTKPREEQYN           180
STYRVVSVLT VLHQDWLNGK EYKCKVSNKA LPAPIEKTIS KAKGQPREPQ VYTLPPSRDE           240
LTKNQVSLTC LVKGFYPSDI AVEWESNGQP ENNYKTTPPV LDSDGSFFLY SKLTVDKSRW           300
QQGNVFSCSV MHEALHNHYT QKSLSLSPGK                                            330

SEQ ID NO: 337            moltype = AA  length = 11
FEATURE                   Location/Qualifiers
source                    1..11
                          mol_type = protein
                          organism = synthetic construct
SEQUENCE: 337
SGGGGSGGGG S                                                                11

SEQ ID NO: 338            moltype = AA  length = 13
FEATURE                   Location/Qualifiers
source                    1..13
                          mol_type = protein
                          organism = synthetic construct
SEQUENCE: 338
SGGGGSGGGG SAP                                                              13

SEQ ID NO: 339            moltype = AA  length = 5
FEATURE                   Location/Qualifiers
source                    1..5
                          mol_type = protein
                          organism = synthetic construct
SEQUENCE: 339
NFSQP                                                                        5

SEQ ID NO: 340            moltype = AA  length = 5
FEATURE                   Location/Qualifiers
source                    1..5
                          mol_type = protein
                          organism = synthetic construct
SEQUENCE: 340
KRTVA                                                                        5

SEQ ID NO: 341            moltype = AA  length = 8
FEATURE                   Location/Qualifiers
source                    1..8
                          mol_type = protein
                          organism = synthetic construct
SEQUENCE: 341
GGGSGGGG                                                                     8

SEQ ID NO: 342            moltype = AA  length = 10
FEATURE                   Location/Qualifiers
source                    1..10
                          mol_type = protein
                          organism = synthetic construct
SEQUENCE: 342
GGGGSGGGGS                                                                  10

SEQ ID NO: 343            moltype = AA  length = 15
FEATURE                   Location/Qualifiers
```

```
                                      -continued
source              1..15
                    mol_type = protein
                    organism = synthetic construct
SEQUENCE: 343
GGGGSGGGGS GGGGS                                                    15

SEQ ID NO: 344      moltype = AA  length = 18
FEATURE             Location/Qualifiers
source              1..18
                    mol_type = protein
                    organism = synthetic construct
SEQUENCE: 344
GSTSGSGKPG SGEGSTKG                                                 18

SEQ ID NO: 345      moltype = AA  length = 15
FEATURE             Location/Qualifiers
source              1..15
                    mol_type = protein
                    organism = synthetic construct
SEQUENCE: 345
THTCPPCPEP KSSDK                                                    15

SEQ ID NO: 346      moltype = AA  length = 4
FEATURE             Location/Qualifiers
source              1..4
                    mol_type = protein
                    organism = synthetic construct
SEQUENCE: 346
GGGS                                                                 4

SEQ ID NO: 347      moltype = AA  length = 13
FEATURE             Location/Qualifiers
source              1..13
                    mol_type = protein
                    organism = synthetic construct
SEQUENCE: 347
EAAKEAAKGG GGS                                                      13

SEQ ID NO: 348      moltype = AA  length = 8
FEATURE             Location/Qualifiers
source              1..8
                    mol_type = protein
                    organism = synthetic construct
SEQUENCE: 348
EAAKEAAK                                                             8

SEQ ID NO: 349      moltype = AA  length = 330
FEATURE             Location/Qualifiers
source              1..330
                    mol_type = protein
                    organism = Homo sapiens
SEQUENCE: 349
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 350      moltype = AA  length = 107
FEATURE             Location/Qualifiers
source              1..107
                    mol_type = protein
                    organism = Homo sapiens
SEQUENCE: 350
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 351      moltype = AA  length = 327
FEATURE             Location/Qualifiers
source              1..327
                    mol_type = protein
                    organism = synthetic construct
SEQUENCE: 351
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
```

```
NVFSCSVMHE ALHNRYTQKS LSLSLGK                                          327

SEQ ID NO: 352           moltype = AA  length = 327
FEATURE                  Location/Qualifiers
source                   1..327
                         mol_type = protein
                         organism = synthetic construct
SEQUENCE: 352
ASTKGPSVFP LAPCSRSTSE STAALGCLVK DYFPEPVTVS WNSGALTSGV HTFPAVLQSS        60
GLYSLSSVVT VPSSSLGTKT YTCNVDHKPS NTKVDKRVES KYGPPCPPCP APEFLGGPSV       120
FLFPPKPKDT LMISRTPEVT CVVVDVSQED PEVQFNWYVD GVEVHNAKTK PREEQFNSTY       180
RVVSVLTVLH QDWLNGKEYK CKVSNKGLPS SIEKTISKAK GQPREPQVYT LPPSQEEMTK       240
NQVSLTCLVK GFYPSDIAVE WESNGQPENN YKTTPPVLDS DGSFFLYSRL TVDKSRWQEG       300
NVFSCSVMHE ALHNHYTQKS LSLSLGK                                          327

SEQ ID NO: 353           moltype = AA  length = 327
FEATURE                  Location/Qualifiers
source                   1..327
                         mol_type = protein
                         organism = Homo sapiens
SEQUENCE: 353
ASTKGPSVFP LAPCSRSTSE STAALGCLVK DYFPEPVTVS WNSGALTSGV HTFPAVLQSS        60
GLYSLSSVVT VPSSSLGTKT YTCNVDHKPS NTKVDKRVES KYGPPCPSCP APEFLGGPSV       120
FLFPPKPKDT LMISRTPEVT CVVVDVSQED PEVQFNWYVD GVEVHNAKTK PREEQFNSTY       180
RVVSVLTVLH QDWLNGKEYK CKVSNKGLPS SIEKTISKAK GQPREPQVYT LPPSQEEMTK       240
NQVSLTCLVK GFYPSDIAVE WESNGQPENN YKTTPPVLDS DGSFFLYSRL TVDKSRWQEG       300
NVFSCSVMHE ALHNHYTQKS LSLSLGK                                          327

SEQ ID NO: 354           moltype = AA  length = 103
FEATURE                  Location/Qualifiers
source                   1..103
                         mol_type = protein
                         organism = synthetic construct
SEQUENCE: 354
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSC                        103

SEQ ID NO: 355           moltype = AA  length = 107
FEATURE                  Location/Qualifiers
source                   1..107
                         mol_type = protein
                         organism = synthetic construct
SEQUENCE: 355
RTVAAPSVFI FPPSDEQLKS GTASVVCLLN NFYPREAKVQ WKVDNALQSG NSQESVTEQD        60
SKDSTYSLSS TLTLSKADYE KHKVYACEVT HQGLSSPVTK SFNRGEC                    107

SEQ ID NO: 356           moltype = AA  length = 106
FEATURE                  Location/Qualifiers
source                   1..106
                         mol_type = protein
                         organism = Homo sapiens
SEQUENCE: 356
GQPKANPTVT LFPPSSEELQ ANKATLVCLI SDFYPGAVTV AWKADGSPVK AGVETTKPSK        60
QSNNKYAASS YLSLTPEQWK SHRSYSCQVT HEGSTVEKTV APTECS                     106

SEQ ID NO: 357           moltype = AA  length = 106
FEATURE                  Location/Qualifiers
source                   1..106
                         mol_type = protein
                         organism = Homo sapiens
SEQUENCE: 357
GQPKAAPSVT LFPPSSEELQ ANKATLVCLI SDFYPGAVTV AWKADSSPVK AGVETTTPSK        60
QSNNKYAASS YLSLTPEQWK SHRSYSCQVT HEGSTVEKTV APTECS                     106

SEQ ID NO: 358           moltype = AA  length = 106
FEATURE                  Location/Qualifiers
source                   1..106
                         mol_type = protein
                         organism = Homo sapiens
SEQUENCE: 358
GQPKAAPSVT LFPPSSEELQ ANKATLVCLI SDFYPGAVTV AWKADSSPVK AGVETTTPSK        60
QSNNKYAASS YLSLTPEQWK SHKSYSCQVT HEGSTVEKTV APTECS                     106

SEQ ID NO: 359           moltype = AA  length = 679
FEATURE                  Location/Qualifiers
source                   1..679
                         mol_type = protein
                         organism = synthetic construct
SEQUENCE: 359
```

```
EVQLLESGGG LVQPGGSLRL SCAASGFTFS TYGMHWVRRA PGKGLEWLSY ISGGSSYIFY    60
ADSVKGRFTI SRDNSKNTLY LQMNSLRAED TAVYYCARIL RGGSGMDLWG QGTLVTVSSA   120
STKGPSVFPL APSSKSTSGG TAALGCLVKD YFPEPVTVSW NSGALTSGVA TGPAVLQSSG   180
LYSLSSVVTV PSSSLGTQTY ICNVNHKPSN TKVDKKVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGGSDIQMTQ SPSSLSASVG   480
DRVTITCRAS QSISSYLNWY QRKPGKAPKL LIYAASSLQS GVPSRFSGSG SGTDFTLTIS   540
SLQPEDFATY YCQQSSHGPL LTFGQGTKLE IKRPVAAPAV FIFPPSDEQL KSGTASVVCL   600
LKNFYPREAK VQWKVDNALQ SGNSQESVTE QDSKDSTYSL SSTLTLSKAD YEKHKVYACE   660
VTHQGLSSPV TKSFNRGEC                                                679

SEQ ID NO: 360          moltype = AA   length = 217
FEATURE                 Location/Qualifiers
source                  1..217
                        mol_type = protein
                        organism = synthetic construct
SEQUENCE: 360
QSVLTQPPSA SGTPGQRVTI SCTGSSSNIG AGYNVYWYQE LPGTAPKLLI YGNINRPSGV    60
PDRFSGSKSG TSASLAISGL RSEDEADYYC AAWDKSISGL VFGGGTKLTV LGQPKAAPSV   120
TLFPPSSEEL QANKATLVCY ISDFYPGAVT VAWKADSSPV KAGVETTTPS KQSNNKYAAW   180
SYLSLTPEQW KSHRSYSCQV THEGSTVEKT VAPTECS                            217

SEQ ID NO: 361          moltype = AA   length = 221
FEATURE                 Location/Qualifiers
source                  1..221
                        mol_type = protein
                        organism = synthetic construct
SEQUENCE: 361
QVQLVQSGAE VKKPGSSVKV SCKASGGTFG YYAIHWVREA PGQGLEWMGG IGSIFGTANY    60
AQKFQGRVTI TADESTSTAY MELSSLRSED TAVYYCARAW SSDHMDYWGQ GTLVTVSSAS   120
TKGPSVFPLA PSSKSTSGGT AALGCLVKDY FPEPVTVSWN SGALTSGVHT FPAVLQSSGL   180
YSLTSVVEVP SSSLGTQTYI CNVNHKPSNT KVDKKVEPKS C                       221

SEQ ID NO: 362          moltype = AA   length = 683
FEATURE                 Location/Qualifiers
source                  1..683
                        mol_type = protein
                        organism = synthetic construct
SEQUENCE: 362
QVQLVQSGAE VKKPGSSVKV SCKASGGTFS SSSIHWVRRA PGQGLEWMGH IYPSFGTANY    60
AQKFQGRVTI TADESTSTAY MELSSLRSED TAVYYCARHS GSRFFSPMDY WGQGTLVTVS   120
SASTKGPSVF PLAPSSKSTS GGTAALGCLV KDYFPEPVTV SWNSGALTSG VATGPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQSVL TQPPSASGTP   480
GQRVTISCTG SSSNIGAGYN VYWYQRLPGT APKLLIYGNI NRPSGVPDRF SGSKSGTSAS   540
LAISGLRSED EADYYCAAWD KSISGLVFGG GTKLTVLGQP KAAPAVTLFP PSSEELQANK   600
ATLVCLIKDF YPGAVTVAWK ADSSPVKAGV ETTTPSKQSN NKYAAWSYLS LTPEQWKSHR   660
SYSCQVTHEG STVEKTVAPT ECS                                           683

SEQ ID NO: 363          moltype = AA   length = 214
FEATURE                 Location/Qualifiers
source                  1..214
                        mol_type = protein
                        organism = synthetic construct
SEQUENCE: 363
EIVLTQSPGT LSLSPGERAT LSCRASQSVS SSYLAWYQEK PGQAPRLLIY GASSRATGIP    60
DRFSGSGSGT DFTLTISRLE PEDFAVYYCQ QYWYPLTFGQ GTKLEIKRTV AAPSVFIFPP   120
SDEQLKSGTA SVVCYLNNFY PREAKVQWKV DNALQSGNSQ ESVTEQDSKD STYSLWSTLT   180
LSKADYEKHK VYACEVTHQG LSSPVTKSFN RGEC                               214

SEQ ID NO: 364          moltype = AA   length = 222
FEATURE                 Location/Qualifiers
source                  1..222
                        mol_type = protein
                        organism = synthetic construct
SEQUENCE: 364
EVQLLESGGG LVQPGGSLRL SCAASGFTFS TYGMHWVREA PGKGLEWLSY ISGGSSYIFY    60
ADSVKGRFTI SRDNSKNTLY LQMNSLRAED TAVYYCARIL RGGSGMDLWG QGTLVTVSSA   120
STKGPSVFPL APSSKSTSGG TAALGCLVKD YFPEPVTVSW NSGALTSGVH TFPAVLQSSG   180
LYSLTSVVEV PSSSLGTQTY ICNVNHKPSN TKVDKKVEPK SC                      222

SEQ ID NO: 365          moltype = AA   length = 677
FEATURE                 Location/Qualifiers
source                  1..677
```

```
                          mol_type = protein
                          organism = synthetic construct
SEQUENCE: 365
EVQLLESGGG LVQPGGSLRL SCAASGFTFS SYAMSWVRRA PGKGLEWVSG IGSYGGGTYY    60
ADSVKGRFTI SRDNSKNTLY LQMNSLRAED TAVYYCARYV NFGMDYWGQG TLVTVSSAST   120
KGPSVFPLAP SSKSTSGGTA ALGCLVKDYF PEPVTVSWNS GALTSGVATG PAVLQSSGLY   180
SLSSVVTVPS SSLGTQTYIC NVNHKPSNTK VDKKVEPKSC DKTHTCPPCP APEAAGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKGGG GSGGGGSGGG GSDIQMTQSP SSLSASVGDR   480
VTITCRASQS ISSYLNWYQR KPGKAPKLLI YAASSLQSGV PSRFSGSGSG TDFTLTISSL   540
QPEDFATYYC QQSSHGPLLT FGQGTKLEIK RPVAAPAVFI FPPSDEQLKS GTASVVCLLK   600
NFYPREAKVQ WKVDNALQSG NSQESVTEQD SKDSTYSLSS TLTLSKADYE KHKVYACEVT   660
HQGLSSPVTK SFNRGEC                                                  677

SEQ ID NO: 366            moltype = AA  length = 221
FEATURE                   Location/Qualifiers
source                    1..221
                          mol_type = protein
                          organism = synthetic construct
SEQUENCE: 366
QVQLVQSGAE VKKPGSSVKV SCKASGGTFG YYAIHWVREA PGQGLEWMGG IGSIFGTANY    60
AQKFQGRVTI TADESTSTAY MELSSLRSED TAVYYCARAW SSDHMDYWGQ GTLVTVSSAS   120
TKGPSVFPLA PSSKSTSGGT AALGCLVKDY FPEPVTVSWN SGALTSGVHT FPAVLQSSGL   180
YSLTSVVEVP SSSLGTQTYI CNVNHKPSNT KVDKKVEPKS C                       221

SEQ ID NO: 367            moltype = AA  length = 683
FEATURE                   Location/Qualifiers
source                    1..683
                          mol_type = protein
                          organism = synthetic construct
SEQUENCE: 367
EVQLLESGGG LVQPGGSLRL SCAASGFTFS SSYMGWVRRA PGKGLEWVSS IGSGSYSTSY    60
ADSVKGRFTI SRDNSKNTLY LQMNSLRAED TAVYYCARYP SVPFPLHLDY WGQGTLVTVS   120
SASTKGPSVF PLAPSSKSTS GGTAALGCLV KDYFPEPVTV SWNSGALTSG VATGPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQSVL TQPPSASGTP   480
GQRVTISCTG SSSNIGAGYN VYWYQRLPGT APKLLIYGNI NRPSGVPDRF SGSKSGTSAS   540
LAISGLRSED EADYYCAAWD KSISGLVFGG GTKLTVLGQP KAAPAVTLFP PSSEELQANK   600
ATLVCLIKDF YPGAVTVAWK ADSSPVKAGV ETTTPSKQSN NKYAAWSYLS LTPEQWKSHR   660
SYSCQVTHEG STVEKTVAPT ECS                                           683

SEQ ID NO: 368            moltype = AA  length = 213
FEATURE                   Location/Qualifiers
source                    1..213
                          mol_type = protein
                          organism = synthetic construct
SEQUENCE: 368
DIQMTQSPSS LSASVGDRVT ITCRASQSIS SYLNWYQEKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCYLNNFYP REAKVQWKVD NALQSGNSQE SVTEQDSKDS TYSLWSTLTL   180
SKADYEKHKV YACEVTHQGL SSPVTKSFNR GEC                                213

SEQ ID NO: 369            moltype = AA  length = 222
FEATURE                   Location/Qualifiers
source                    1..222
                          mol_type = protein
                          organism = synthetic construct
SEQUENCE: 369
EVQLLESGGG LVQPGGSLRL SCAASGFTFS TYGMHWVREA PGKGLEWLSY ISGGSSYIFY    60
ADSVKGRFTI SRDNSKNTLY LQMNSLRAED TAVYYCARIL RGGSGMDLWG QGTLVTVSSA   120
STKGPSVFPL APSSKSTSGG TAALGCLVKD YFPEPVTVSW NSGALTSGVH TFPAVLQSSG   180
LYSLTSVVEV PSSSLGTQTY ICNVNHKPSN TKVDKKVEPK SC                      222

SEQ ID NO: 370            moltype =     length =
SEQUENCE: 370
000

SEQ ID NO: 371            moltype = AA  length = 447
FEATURE                   Location/Qualifiers
source                    1..447
                          mol_type = protein
                          organism = synthetic construct
SEQUENCE: 371
EVQLLESGGG LVQPGGSLRL SCAASGFTFS SYAMSWVRRA PGKGLEWVSG IGSYGGGTYY    60
```

```
ADSVKGRFTI SRDNSKNTLY LQMNSLRAED TAVYYCARYV NFGMDYWGQG TLVTVSSAST  120
KGPSVFPLAP SSKSTSGGTA ALGCLVKDYF PEPVTVSWNS GALTSGVATG PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 372          moltype = AA   length = 214
FEATURE                 Location/Qualifiers
source                  1..214
                        mol_type = protein
                        organism = synthetic construct
SEQUENCE: 372
DIQMTQSPSS LSASVGDRVT ITCRASQSIS SYLNWYQEKP GKAPKLLIYA ASSLQSGVPS   60
RFSGSGSGTD FTLTISSLQP EDFATYYCQQ YGRNPPTFGQ GTKLEIKRTV AAPSVFIFPP  120
SDEQLKSGTA SVVCYLNNFY PREAKVQWKV DNALQSGNSQ ESVTEQDSKD STYSLWSTLT  180
LSKADYEKHK VYACEVTHQG LSSPVTKSFN RGEC                              214

SEQ ID NO: 373          moltype = DNA   length = 59
FEATURE                 Location/Qualifiers
source                  1..59
                        mol_type = other DNA
                        organism = synthetic construct
SEQUENCE: 373
acactctttc cctacacgac gctcttccga tctnnnnncc tctcctgtgc agccagcgg    59

SEQ ID NO: 374          moltype = DNA   length = 42
FEATURE                 Location/Qualifiers
source                  1..42
                        mol_type = other DNA
                        organism = synthetic construct
SEQUENCE: 374
agacgtgtgc tcttccgatc tctccagctt ggtccctgg cc                      42

SEQ ID NO: 375          moltype = DNA   length = 58
FEATURE                 Location/Qualifiers
source                  1..58
                        mol_type = other DNA
                        organism = synthetic construct
SEQUENCE: 375
aatgatacgg cgaccaccga gatctacact agatcgcaca ctctttccct acacgacg    58

SEQ ID NO: 376          moltype = DNA   length = 58
FEATURE                 Location/Qualifiers
source                  1..58
                        mol_type = other DNA
                        organism = synthetic construct
SEQUENCE: 376
aatgatacgg cgaccaccga gatctacacc tctctataca ctctttccct acacgacg    58

SEQ ID NO: 377          moltype = DNA   length = 66
FEATURE                 Location/Qualifiers
source                  1..66
                        mol_type = other DNA
                        organism = synthetic construct
SEQUENCE: 377
caagcagaag acggcatacg agattcgcct tagtgactgg agttcagacg tgtgctcttc   60
cgatct                                                             66

SEQ ID NO: 378          moltype = AA   length = 447
FEATURE                 Location/Qualifiers
source                  1..447
                        mol_type = protein
                        organism = synthetic construct
SEQUENCE: 378
EVQLLESGGG LVQPGGSLRL SCAASGFTFS SYAMSWVRQA PGKGLEWVSG IGSYGGGTYY   60
ADSVKGRFTI SRDNSKNTLY LQMNSLRAED TAVYYCARYV NFGMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 379          moltype = AA   length = 214
FEATURE                 Location/Qualifiers
source                  1..214
                        mol_type = protein
```

```
                                -continued
                           organism = synthetic construct
SEQUENCE: 379
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ YGRNPPTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 380         moltype = AA  length = 449
FEATURE                Location/Qualifiers
source                 1..449
                       mol_type = protein
                       organism = synthetic construct
SEQUENCE: 380
EVQLLESGGG LVQPGGSLRL SCAASGFTFS TYGMHWVRQA PGKGLEWLSY ISGGSSYIFY    60
ADSVRGRFTI SRDNSENALY LQMNSLRAED TAVYYCARIL RGGSGMDLWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 381         moltype = AA  length = 217
FEATURE                Location/Qualifiers
source                 1..217
                       mol_type = protein
                       organism = synthetic construct
SEQUENCE: 381
QSVLTQPPSA SGTPGQRVTI SCTGSSSNIG AGYNVYWYQQ LPGTAPKLLI YGNINRPSGV    60
PDRFSGSKSG TSASLAISGL RSEDEADYYC AAWDKSISGL VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 382         moltype = AA  length = 449
FEATURE                Location/Qualifiers
source                 1..449
                       mol_type = protein
                       organism = synthetic construct
SEQUENCE: 382
EVQLLESGGG LVQPGGSLRL SCAASGFTFS TYGMHWVRQA PGKGLEWLSY ISGGSSYIFY    60
ADSVKGRFTI SRDNSKNTLY LQMNSLRAED TAVYYCARIL RGGSGMDLWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 383         moltype = AA  length = 217
FEATURE                Location/Qualifiers
source                 1..217
                       mol_type = protein
                       organism = synthetic construct
SEQUENCE: 383
QSVLTQPPSA SGTPGQRVTI SCTGSSSNIG AGYNVYWYQQ LPGTAPKLLI YGNINRPSGV    60
PDRFSGSKSG TSASLAISGL RSEDEADYYC AAWDKSISGL VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 384         moltype = AA  length = 107
FEATURE                Location/Qualifiers
source                 1..107
                       mol_type = protein
                       organism = synthetic construct
SEQUENCE: 384
DIQMTQSPSS LSASVGDRVT ITCRASENIF SYLAWYQQKP GKAPKLLIYN TRTLQSGVPS    60
RFSGSGSGTD FTLTISSLQP EDFATYYCQH HYGTPFTFGQ GTKLEIK                107

SEQ ID NO: 385         moltype = DNA  length = 321
FEATURE                Location/Qualifiers
source                 1..321
                       mol_type = other DNA
                       organism = synthetic construct
SEQUENCE: 385
gacatccaga tgacacagag ccctagcagc ctgtctgcca gcgtgggaga cagagtgacc    60
atcacctgta gagccagcga gaacatcttc agctacctgg cctggtatca gcagaagcct   120
ggcaaggccc ctaagctgct gatctacaac acccggacac tgcagagcgg cgtgccaagc   180
agatttctg gcagcggctc tggcaccgac ttcaccctga ccatatctag cctgcagcct   240
gaggacttcg ccacctacta ctgccagcac cactacggca cccctttcac atttggccag   300
```

```
ggcaccaagc tggaaatcaa g                                            321

SEQ ID NO: 386           moltype = AA  length = 120
FEATURE                  Location/Qualifiers
source                   1..120
                         mol_type = protein
                         organism = synthetic construct
SEQUENCE: 386
EVQLVESGGG LVQPGGSLRL SCAASGFVFS SYDMSWVRQA PGKGLEWVSY ISSGGGITYY  60
ADSVKGRFTI SRDNSKNTLY LQMNSLRAED TAVYYCAAHY FGSSGPFAYW GQGTLVTVSS 120

SEQ ID NO: 387           moltype = DNA  length = 360
FEATURE                  Location/Qualifiers
source                   1..360
                         mol_type = other DNA
                         organism = synthetic construct
SEQUENCE: 387
gaggtgcagc tggttgaatc tggcggagga ctggttcagc ctggcggatc tctgagactg  60
tcttgtgccg ccagcggctt cgtgttcagc agctacgata tgagctgggt ccgacaggcc 120
cctggcaaag gacttgagtg ggtgtcctac atcagcagcg gcggaggcat cacctactac 180
gccgattctg tgaagggcag attcaccatc agccgggaca cagcaagaa caccctgtac 240
ctgcagatga acagcctgag agccgaggac accgccgtgt actattgtgc cgctcactac 300
ttcggcagct ctggcccttt tgcctattgg ggccagggca cactggtcac cgttagctct 360

SEQ ID NO: 388           moltype = AA  length = 213
FEATURE                  Location/Qualifiers
source                   1..213
                         mol_type = protein
                         organism = synthetic construct
SEQUENCE: 388
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ AGNPHTFGQG TKLEIKRTVA APSVFIFPPS 120
DEQLKSGTAS VVCLLNNFYP REAKVQWKVD NALQSGNSQE SVTEQDSKDS TYSLSSTLTL 180
SKADYEKHKV YACEVTHQGL SSPVTKSFNR GEC                              213

SEQ ID NO: 389           moltype = AA  length = 451
FEATURE                  Location/Qualifiers
source                   1..451
                         mol_type = protein
                         organism = synthetic construct
SEQUENCE: 389
EVQLLESGGG LVQPGGSLRL SCAASGFTFS SSYMGWVRQA PGKGLEWVSS IGSGSYSTSY  60
ADSVKGRFTI SRDNSKNTLY LQMNSLRAED TAVYYCARYP SVPFPPHLDY WGQGTLVTVS 120
SASTKGPSVF PLAPSSKSTS GGTAALGCLV KDYFPEPVTV SWNSGALTSG VHTFPAVLQS 180
SGLYSLSSVV TVPSSSLGTQ TYICNVNHKP SNTKVDKKVE PKSCDKTHTC PPCPAPELLG 240
GPSVFLFPPK PKDTLMISRT PEVTCVVVDV SHEDPEVKFN WYVDGVEVHN AKTKPREEQY 300
NSTYRVVSVL TVLHQDWLNG KEYKCKVSNK ALPAPIEKTI SKAKGQPREP QVYTLPPSRD 360
ELTKNQVSLT CLVKGFYPSD IAVEWESNGQ PENNYKTTPP VLDSDGSFFL YSKLTVDKSR 420
WQQGNVFSCS VMHEALHNHY TQKSLSLSPG K                                451

SEQ ID NO: 390           moltype = AA  length = 213
FEATURE                  Location/Qualifiers
source                   1..213
                         mol_type = protein
                         organism = synthetic construct
SEQUENCE: 390
DIQMTQSPSS LSASVGDRVT ITCRASQSIR DYLNWYQQKP GKAPKLLIYA ASSLQSGVPS  60
RFSGSGSGTD FTLTISSLQP EDFATYYCQQ GTFPFTFGQG TKLEIKRTVA APSVFIFPPS 120
DEQLKSGTAS VVCLLNNFYP REAKVQWKVD NALQSGNSQE SVTEQDSKDS TYSLSSTLTL 180
SKADYEKHKV YACEVTHQGL SSPVTKSFNR GEC                              213

SEQ ID NO: 391           moltype = AA  length = 447
FEATURE                  Location/Qualifiers
source                   1..447
                         mol_type = protein
                         organism = unidentified
SEQUENCE: 391
EVQLLESGGG LVQPGGSLRL SCAASGFTFG SYYMSWVRQA PGKGLEWVSG ISGYGYYTGY  60
ADSVKGRFTI SRDNSKNTLY LQMNSLRAED TAVYYCARHG YGVIDYWGQG TLVTVSSAST 120
KGPSVFPLAP SSKSTSGGTA ALGCLVKDYF PEPVTVSWNS GALTSGVHTF PAVLQSSGLY 180
SLSSVVTVPS SSLGTQTYIC NVNHKPSNTK VDKKVEPKSC DKTHTCPPCP APELLGGPSV 240
FLFPPKPKDT LMISRTPEVT CVVVDVSHED PEVKFNWYVD GVEVHNAKTK PREEQYNSTY 300
RVVSVLTVLH QDWLNGKEYK CKVSNKALPA PIEKTISKAK GQPREPQVYT LPPSRDELTK 360
NQVSLTCLVK GFYPSDIAVE WESNGQPENN YKTTPPVLDS DGSFFLYSKL TVDKSRWQQG 420
NVFSCSVMHE ALHNHYTQKS LSLSPGK                                    447

SEQ ID NO: 392           moltype = AA  length = 214
FEATURE                  Location/Qualifiers
source                   1..214
```

```
                        mol_type = protein
                        organism = synthetic construct
SEQUENCE: 392
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ GAYVPYTFGQ GTKLEIKRTV AAPSVFIFPP    120
SDEQLKSGTA SVVCLLNNFY PREAKVQWKV DNALQSGNSE ESVTEQDSKD STYSLSSTLT    180
LSKADYEKHK VYACEVTHQG LSSPVTKSFN RGEC                                214

SEQ ID NO: 393          moltype = AA  length = 447
FEATURE                 Location/Qualifiers
source                  1..447
                        mol_type = protein
                        organism = synthetic construct
SEQUENCE: 393
EVQLLESGGG LVQPGGSLRL SCAASGFTFS SYAMSWVRQA PGKGLEWVSA ISGSGGSTYY     60
ADSVKGRFTI SRDNSKNTLY LQMNSLRAED TAVYYCARYG YTHFDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 394          moltype = AA  length = 214
FEATURE                 Location/Qualifiers
source                  1..214
                        mol_type = protein
                        organism = synthetic construct
SEQUENCE: 394
DIQMTQSPSS LSASVGDRVT ITCRASQAIS GYLNWYQQKP GKAPKLLIYS ASSLQSGVPS     60
RFSGSGSGTD FTLTISSLQP EDFATYYCQQ SYSTPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 395          moltype = AA  length = 449
FEATURE                 Location/Qualifiers
source                  1..449
                        mol_type = protein
                        organism = synthetic construct
SEQUENCE: 395
EVQLLESGGG LVQPGGSLRL SCAASGFTFS SYAMSWVRQA PGKGLEWVSA ISGSGGSTYY     60
ADSVKGRFTI SRDNSKNTLY LQMNSLRAED TAVYYCARYR WHGSVFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 396          moltype = AA  length = 215
FEATURE                 Location/Qualifiers
source                  1..215
                        mol_type = protein
                        organism = synthetic construct
SEQUENCE: 396
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ YPWYFPYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 397          moltype = AA  length = 447
FEATURE                 Location/Qualifiers
source                  1..447
                        mol_type = protein
                        organism = synthetic construct
SEQUENCE: 397
EVQLLESGGG LVQPGGSLRL SCAASGFTFS SYAMSWVRQA PGKGLEWVSA ISGSGGSTYY     60
ADSVKGRFTI SRDNSKNTLY LQMNSLRAED TAVYYCARYG YSVLDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 398          moltype = AA  length = 213
FEATURE                 Location/Qualifiers
source                  1..213
                        mol_type = protein
```

```
                            organism = synthetic construct
SEQUENCE: 398
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 399          moltype = AA  length = 451
FEATURE                 Location/Qualifiers
source                  1..451
                        mol_type = protein
                        organism = unidentified
SEQUENCE: 399
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPPLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 400          moltype = AA  length = 213
FEATURE                 Location/Qualifiers
source                  1..213
                        mol_type = protein
                        organism = synthetic construct
SEQUENCE: 400
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 401          moltype = AA  length = 451
FEATURE                 Location/Qualifiers
source                  1..451
                        mol_type = protein
                        organism = synthetic construct
SEQUENCE: 401
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFQPHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 402          moltype = AA  length = 213
FEATURE                 Location/Qualifiers
source                  1..213
                        mol_type = protein
                        organism = synthetic construct
SEQUENCE: 402
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 403          moltype = AA  length = 451
FEATURE                 Location/Qualifiers
source                  1..451
                        mol_type = protein
                        organism = synthetic construct
SEQUENCE: 403
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVLFPPHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 404          moltype = AA  length = 213
FEATURE                 Location/Qualifiers
source                  1..213
                        mol_type = protein
                        organism = synthetic construct
```

```
SEQUENCE: 404
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ AGNPHTFGQG TKLEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 405         moltype = AA  length = 451
FEATURE                Location/Qualifiers
source                 1..451
                       mol_type = protein
                       organism = synthetic construct
SEQUENCE: 405
EVQLLESGGG LVQPGGSLRL SCAASGFTFS SSYMGWVRQA PGKGLEWVSS IGSGSYSTSY      60
ADSVKGRFTI SRDNSKNTLY LQMNSLRAED TAVYYCARYP SVPFPHHLDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPELLG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRD     360
ELTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                    451

SEQ ID NO: 406         moltype = AA  length = 213
FEATURE                Location/Qualifiers
source                 1..213
                       mol_type = protein
                       organism = synthetic construct
SEQUENCE: 406
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ AGNPHTFGQG TKLEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 407         moltype = AA  length = 451
FEATURE                Location/Qualifiers
source                 1..451
                       mol_type = protein
                       organism = synthetic construct
SEQUENCE: 407
EVQLLESGGG LVQPGGSLRL SCAASGFTFS SSYMGWVRQA PGKGLEWVSS IGSGSYSTSY      60
ADSVKGRFTI SRDNSKNTLY LQMNSLRAED TAVYYCARYP SVPFPLHLDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPELLG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRD     360
ELTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                    451

SEQ ID NO: 408         moltype = AA  length = 213
FEATURE                Location/Qualifiers
source                 1..213
                       mol_type = protein
                       organism = synthetic construct
SEQUENCE: 408
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ AGNPHTFGQG TKLEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 409         moltype = AA  length = 451
FEATURE                Location/Qualifiers
source                 1..451
                       mol_type = protein
                       organism = synthetic construct
SEQUENCE: 409
EVQLLESGGG LVQPGGSLRL SCAASGFTFS SSYMGWVRQA PGKGLEWVSS IGSGSYSTSY      60
ADSVKGRFTI SRDNSKNTLY LQMNSLRAED TAVYYCARYP SVPFPPHFDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPELLG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRD     360
ELTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                    451

SEQ ID NO: 410         moltype = AA  length = 213
FEATURE                Location/Qualifiers
source                 1..213
                       mol_type = protein
                       organism = synthetic construct
SEQUENCE: 410
```

```
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 411          moltype = AA  length = 451
FEATURE                 Location/Qualifiers
source                  1..451
                        mol_type = protein
                        organism = synthetic construct
SEQUENCE: 411
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHVDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 412          moltype = AA  length = 213
FEATURE                 Location/Qualifiers
source                  1..213
                        mol_type = protein
                        organism = synthetic construct
SEQUENCE: 412
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 413          moltype = AA  length = 451
FEATURE                 Location/Qualifiers
source                  1..451
                        mol_type = protein
                        organism = synthetic construct
SEQUENCE: 413
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFPPHWDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 414          moltype = AA  length = 213
FEATURE                 Location/Qualifiers
source                  1..213
                        mol_type = protein
                        organism = synthetic construct
SEQUENCE: 414
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ AGNPHTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 415          moltype = AA  length = 451
FEATURE                 Location/Qualifiers
source                  1..451
                        mol_type = protein
                        organism = synthetic construct
SEQUENCE: 415
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFRPHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 416          moltype = AA  length = 213
FEATURE                 Location/Qualifiers
source                  1..213
                        mol_type = protein
                        organism = synthetic construct
SEQUENCE: 416
DIQMTQSPSS LSASVGDRVT ITCRASQSIS SYLNWYQQKP GKAPKLLIYA ASSLQSGVPS    60
```

```
RFSGSGSGTD FTLTISSLQP EDFATYYCQQ AGNPHTFGQG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 417          moltype = AA  length = 451
FEATURE                 Location/Qualifiers
source                  1..451
                        mol_type = protein
                        organism = synthetic construct
SEQUENCE: 417
EVQLLESGGG LVQPGGSLRL SCAASGFTFS SSYMGWVRQA PGKGLEWVSS IGSGSYSTSY    60
ADSVKGRFTI SRDNSKNTLY LQMNSLRAED TAVYYCARYP SVPFSPHLDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 418          moltype = AA  length = 215
FEATURE                 Location/Qualifiers
source                  1..215
                        mol_type = protein
                        organism = synthetic construct
SEQUENCE: 418
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SSHGPLLTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 419          moltype = AA  length = 448
FEATURE                 Location/Qualifiers
source                  1..448
                        mol_type = protein
                        organism = synthetic construct
SEQUENCE: 419
QVQLVQSGAE VKKPGSSVKV SCKASGGTFG YYAIHWVRQA PGQGLEWMGG IGSIFGTANY    60
AQKFQGRVTI TADESTSTAY MELSSLRSED TAVYYCARAW SSDHMDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSRDELT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                       448

SEQ ID NO: 420          moltype = AA  length = 214
FEATURE                 Location/Qualifiers
source                  1..214
                        mol_type = protein
                        organism = synthetic construct
SEQUENCE: 420
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYWYPLTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 421          moltype = AA  length = 451
FEATURE                 Location/Qualifiers
source                  1..451
                        mol_type = protein
                        organism = synthetic construct
SEQUENCE: 421
QVQLVQSGAE VKKPGSSVKV SCKASGGTFS SSSIHWVRQA PGQGLEWMGH IYPSFGTANY    60
AQKFQGRVTI TADESTSTAY MELSSLRSED TAVYYCARHS GSRFFSPMDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 422          moltype = AA  length = 120
FEATURE                 Location/Qualifiers
source                  1..120
                        mol_type = protein
                        organism = Homo sapiens
SEQUENCE: 422
EVQLLEQSGA ELVRPGTSVK ISCKASGYAF TNYWLGWVKQ RPGHGLEWIG DIFPGSGNIH    60
YNEKFKGKAT LTADKSSSTA YMQLSSLTFE DSAVYFCARL RNWDEPMDYW GQGTTVTVSS    120
```

```
SEQ ID NO: 423          moltype = DNA  length = 360
FEATURE                 Location/Qualifiers
source                  1..360
                        mol_type = other DNA
                        organism = synthetic construct
SEQUENCE: 423
gaggtgcagc tgctggaaca gtctggcgcc gaactcgtta gacctggcac aagcgtgaag   60
atcagctgca aggccagcgg ctacgccttc acaaattatt ggctcggctg ggtcaaacag  120
aggccaggac acggactgga atggatcggc gatatcttcc ccggcagcgg caacatccac  180
tacaacgaga agttcaaggg caaagccaca ctgaccgccg acaagagcag cagcacagcc  240
tatatgcagc tgagcagcct gaccttcgag gacagcgccg tgtacttctg cgccaggctg  300
agaaactggg acgagcctat ggattactgg ggccagggca ccacagtgac agtgtctagc  360

SEQ ID NO: 424          moltype = AA  length = 113
FEATURE                 Location/Qualifiers
source                  1..113
                        mol_type = protein
                        organism = Homo sapiens
SEQUENCE: 424
ELVMTQSPSS LTVTAGEKVT MSCKSSQSLL NSGNQKNYLT WYQQKPGQPP KLLIYWASTR   60
ESGVPDRFTG SGSGTDFTLT ISSVQAEDLA VYYCQNDYSY PLTFGAGTKL EIK         113

SEQ ID NO: 425          moltype = DNA  length = 339
FEATURE                 Location/Qualifiers
source                  1..339
                        mol_type = other DNA
                        organism = synthetic construct
SEQUENCE: 425
gaactggtta tgacacagag ccctagcagc ctgacagtga cagccggcga gaaagtgaca   60
atgagctgca agagcagcca gagcctgctg aacagcggca accagaagaa ctacctgacc  120
tggtatcagc agaagcccgg acagcctcct aagctgctga tctattgggc cagcaccaga  180
gaaagcggcg tgcccgatag attcacaggc agcggcagcg gaaccgactt taccctgaca  240
attagcagcg tgcaggccga ggactggccc gtgtattatt gtcagaacga ctacagctac  300
cctctgacct tcggagccgg caccaagctg gaaatcaag                         339

SEQ ID NO: 426          moltype = AA  length = 121
FEATURE                 Location/Qualifiers
source                  1..121
                        mol_type = protein
                        organism = Homo sapiens
SEQUENCE: 426
EVQLLESGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCARYY GGYYSAWMDY WGQGTLVTVS  120
S                                                                  121

SEQ ID NO: 427          moltype = DNA  length = 363
FEATURE                 Location/Qualifiers
source                  1..363
                        mol_type = other DNA
                        organism = synthetic construct
SEQUENCE: 427
gaggtgcagc tgctcgagag cggggggaggc ttggtacagc ctgggggggtc cctgcgcctc   60
tcctgtgcag ccagcggatt cacctttagc agctatgcca tgagctgggt ccgccaggct  120
ccagggaagg ggctggagtg ggtctcagct attagtggta gtggtggtag cacatactat  180
gcagactccg tgaagggccg gttcaccatc tcccgtgaca attccaagaa cacgctgtat  240
ctgcaaatga acagcctgcg tgccgaggac acggctgtat attattgtgc gcgctactac  300
ggtggttact actctgcttg gatggactat tggggccagg gaaccctggt caccgtctcc  360
tca                                                                363

SEQ ID NO: 428          moltype = AA  length = 107
FEATURE                 Location/Qualifiers
source                  1..107
                        mol_type = protein
                        organism = Homo sapiens
SEQUENCE: 428
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ TYGYLHTFGQ GTKLEIK                107

SEQ ID NO: 429          moltype = DNA  length = 321
FEATURE                 Location/Qualifiers
source                  1..321
                        mol_type = other DNA
                        organism = synthetic construct
SEQUENCE: 429
gacatccaga tgacccagtc tccatcctcc ctgagcgcat ctgtaggaga ccgcgtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
cgtttcagtg gcagtggaag cgggacagat ttcactctca ccatcagcag tctgcaacct  240
```

```
gaagattttg caacttatta ctgtcaacag acttacggtt acctgcacac ttttggccag    300
gggaccaagc tggagatcaa a                                              321

SEQ ID NO: 430         moltype = AA  length = 111
FEATURE                Location/Qualifiers
source                 1..111
                       mol_type = protein
                       organism = synthetic construct
SEQUENCE: 430
QSVLTQPPSA SGTPGQRVTI SCTGSSSNIG AGYNVYWYQR LPGTAPKLLI YGNINRPSGV    60
PDRFSGSKSG TSASLAISGL RSEDEADYYC AAWDKSISGL VFGGGTKLTV L             111

SEQ ID NO: 431         moltype = AA  length = 119
FEATURE                Location/Qualifiers
source                 1..119
                       mol_type = protein
                       organism = synthetic construct
SEQUENCE: 431
EVQLLESGGG LVQPGGSLRL SCAASGFTFS TYGMHWVREA PGKGLEWLSY ISGGSSYIFY    60
ADSVKGRFTI SRDNSKNTLY LQMNSLRAED TAVYYCARIL RGGSGMDLWG QGTLVTVSS     119

SEQ ID NO: 432         moltype = AA  length = 106
FEATURE                Location/Qualifiers
source                 1..106
                       mol_type = protein
                       organism = synthetic construct
SEQUENCE: 432
DIQMTQSPSS LSASVGDRVT ITCRASQSIS SYLNWYQEKP GKAPKLLIYA ASSLQSGVPS    60
RFSGSGSGTD FTLTISSLQP EDFATYYCQQ AGNPHTFGQG TKLEIK                   106

SEQ ID NO: 433         moltype = AA  length = 121
FEATURE                Location/Qualifiers
source                 1..121
                       mol_type = protein
                       organism = synthetic construct
SEQUENCE: 433
EVQLLESGGG LVQPGGSLRL SCAASGFTFS SSYMGWVRRA PGKGLEWVSS IGSGSYSTSY    60
ADSVKGRFTI SRDNSKNTLY LQMNSLRAED TAVYYCARYP SVPFPLHLDY WGQGTLVTVS    120
S                                                                    121

SEQ ID NO: 434         moltype = DNA  length = 336
FEATURE                Location/Qualifiers
source                 1..336
                       mol_type = other DNA
                       organism = synthetic construct
SEQUENCE: 434
cagagcgtgc tgacccagcc gccgagcgcg agcggcaccc cgggccagcg cgtgaccatt    60
agctgcaccg gcagcagcag caacattggc gcgggctata acgtgtattg gtatcagcgg    120
ctgccgggca ccgcgccgaa actgctgatt tatggcaaca ttaaccgccc gagcggcgtg    180
ccggatcgct ttagcggcag caaaagcggc accagcgcga gcctggcgat tagcggcctg    240
cgcagcgaag atgaagcgga ttattattgc gcggcgtggg ataaaagcat tagcggcctg    300
gtgtttggcg gcggcaccaa actgaccgtg ctgggg                              336

SEQ ID NO: 435         moltype = DNA  length = 357
FEATURE                Location/Qualifiers
source                 1..357
                       mol_type = other DNA
                       organism = synthetic construct
SEQUENCE: 435
gaagtgcagc tgctggaaag cggcggcggc ctggtgcagc cggcggcag cctgcgcctg    60
agctgcgcgg cgagcggctt tacctttagc acctatggca tgcattgggt gcgcgaggcg    120
ccgggcaaag cctggaatg gctgagctat attagcggcg gcagcagcta tatttttat     180
gcggatagcg tgaagggccg ctttaccatt agccgcgata cagcaaaaa cacgctgtat    240
ctgcagatga cagcctgcg cgcggaagat accgcggtgt attattgcg gcgcattctg    300
cgcggcggca gcggcatgga tctgtggggc cagggcaccc tggtgaccgt gagcagc      357

SEQ ID NO: 436         moltype = DNA  length = 317
FEATURE                Location/Qualifiers
source                 1..317
                       mol_type = other DNA
                       organism = synthetic construct
SEQUENCE: 436
acatccagat gacccagtct ccatcctccc tgagcgcatc tgtaggagac cgcgtcacca    60
tcacttgccg ggcaagtcag agcattagca gctatttaaa ttggtatcag agaaaccag    120
ggaaagcccc taagtcctg atctatgctg catccagttt gcaaagtggg gtcccatcac    180
gtttcagtgg cagtggaagc gggacagatt tcactctcac catcagcagt ctgcaacctg    240
aagattttgc aacttattac tgtcaacagg ctggtaaccc gcacactttt ggccagggga    300
ccaagctgga gatcaaa                                                   317
```

```
SEQ ID NO: 437         moltype = DNA  length = 363
FEATURE                Location/Qualifiers
source                 1..363
                       mol_type = other DNA
                       organism = synthetic construct
SEQUENCE: 437
gaggtgcagc tgttggagtc aggggggaggc ttggtgcagc ccggaggctc cctgcgcctg   60
tcatgcgcag cctctgggtt tacattctct agctcttata tgggctgggt gaggcgagct  120
cctggcaagg gactcgagtg ggtctcttcc atcggctccg gtagctacag tacgagttat  180
gcagacagtg tgaaaggtag atttactatc tccagggaca actccaagaa taccctctac  240
ctgcagatga attccctcag agccgaagat actgcagtgt actattgcgc caggtacccc  300
tccgtcccat tccccctcca ccttgattac tggggacagg gaaccctggt aactgtctcc  360
tca                                                                363
```

PEPTIDES

This application claims priority to GB 2115925.6, filed Nov. 5, 2021; GB 2204539.7, filed Mar. 30, 2022; and GB 2212801.1, filed Sep. 2, 2022. The foregoing applications are incorporated by reference herein.

Incorporated herein by reference in its entirety is the Sequence Listing being concurrently submitted as a XML file named SeqList, created Jun. 26, 2023, and having a size of 439,242 bytes.

FIELD OF INVENTION

The present invention relates to novel bispecific polypeptides, such as antibodies, and their use in the treatment of cancers, particularly cancers expressing carcinoembryonic antigen (CEA).

BACKGROUND

Immunotherapy of Cancer

Cancer is a leading cause of premature deaths in the developed world. Immunotherapy of cancer aims to mount an effective immune response against tumour cells. This may be achieved by, for example, breaking tolerance against tumour antigen, augmenting anti-tumour immune responses, and stimulating local cytokine responses at the tumour site. The key effector cell of a long-lasting anti-tumour immune response is the activated tumour-specific effector T cell. Potent expansion of activated tumour-specific effector T cells can redirect the immune response towards the tumour. In this context, various immunosuppressive mechanisms induced by the tumour microenvironment suppress the activity of effector T cells. Several immunosuppressive mediators are expressed by the tumour cells. Such mediators inhibit T cell activation, either directly, or indirectly by inducing e.g. regulatory T cells (Treg) or myeloid-derived suppressor cells. Depleting, inhibiting, reverting or inactivating such regulatory cells may therefore provide anti-tumour effects and revert the immune suppression in the tumour microenvironment. Further, incomplete activation of effector T cells by, for example, dendritic cells (DC) can result in suboptimally activated or anergic T cells, resulting in an inefficient anti-tumour response. In contrast, adequate induction by DC can generate a potent expansion of activated effector T cells, redirecting and enhancing the immune response towards the tumour. In addition, natural killer (NK) cells play an important role in tumour immunology by attacking tumour cells with down-regulated human leukocyte antigen (HLA) expression and by inducing antibody dependent cellular cytotoxicity (ADCC). Stimulation of NK cells may thus also reduce tumour growth.

CD40

CD40, a 48 kDa transmembrane cell surface glycoprotein, is a co-stimulatory receptor belonging to the tumor necrosis factor receptor (TNFR) superfamily (Banchereau J, Bazan F, Blanchard D, et al. The CD40 antigen and its ligand. Annu Rev Immunol. 1994; 12:881-922; R, Benson M J, de Vries V C, et al. Molecular mechanism and function of CD40/CD40L engagement in the immune system. Immunol Rev. 2009 May; 229(1):152-72). CD40 is expressed in diverse cell types and can be detected on antigen-presenting cells (APC), including dendritic cells (DC), B cells, and macrophages. In addition, CD40 is expressed on granulocytes, endothelial cells, smooth muscle cells, fibroblasts, and epithelial cells (Banchereau J, Bazan F, Blanchard D, et al. The CD40 antigen and its ligand. Annu Rev Immunol. 1994; 12:881-922; Elgueta R, Benson M J, de Vries V C, et al. Molecular mechanism and function of CD40/CD40L engagement in the immune system. Immunol Rev. 2009 May; 229(1):152-72; Korniluk A, Kemona H, Dymicka-Piekarska V. Multifunctional CD40L: pro- and anti-neoplastic activity. Tumour Biol. 2014 October; 35(10):9447-57; Peters A L, Stunz L L, Bishop G A. CD40 and autoimmunity: the dark side of a great activator. Semin Immunol. 2009 October; 21(5):293-300). Consistent with its widespread expression on normal cells, CD40 is also present on the membranes of a wide range of malignant cells, including non-Hodgkin and Hodgkin lymphomas, myelomas, and certain types of carcinomas, including those of the nasopharynx, bladder, cervix, kidney, and ovary (Elgueta R, Benson M J, de Vries V C, et al. Molecular mechanism and function of CD40/CD40L engagement in the immune system. Immunol Rev. 2009 May; 229(1):152-72; Eliopoulos A G, Young L S. The role of the CD40 pathway in the pathogenesis and treatment of cancer. Curr Opin Pharmacol. 2004 August; 4(4):360-7).

CD40 interacts with a single ligand, CD40L (CD154), a transmembrane protein that is expressed by activated T cells, but also on B cells, platelets, mast cells, macrophages, basophils, natural killer (NK) cells, and non-hematopoietic cells (smooth muscle cells, endothelial cells, and epithelial cells) (Elgueta R, Benson M J, de Vries V C, et al. Molecular mechanism and function of CD40/CD40L engagement in the immune system. Immunol Rev. 2009 May; 229(1):152-72; Korniluk A, Kemona H, Dymicka-Piekarska V. Multifunctional CD40L: pro- and anti-neoplastic activity. Tumour Biol. 2014 October; 35(10):9447-57). The binding of CD40 to CD40L, as part of a cell-cell interaction, activates an intracellular signal transduction pathway that involves a series of adapter molecules known as TNFR activation factors (TRAF). To initiate this intracellular signal transduction, multiple CD40 receptor trimers must form a higher order cluster on the cell membrane (Peters A L, Stunz L L, Bishop G A. CD40 and autoimmunity: the dark side of a great activator. Semin Immunol. 2009 October; 21(5):293-300; Werneburg B G, Zoog S J, Dang T T, et al. Molecular characterization of CD40 signaling intermediates. J Biol Chem. 2001 Nov. 16; 276(46):43334-42). The CD40 clustering forms a signaling complex that allows multiple TRAF to assemble, which in turn leads to the activation of downstream transcription factors, including NFκB (Elgueta R, Benson M J, de Vries V C, et al. Molecular mechanism and function of CD40/CD40L engagement in the immune system. Immunol Rev. 2009 May; 229(1):152-72; Kornbluth R S, Stempniak M, Stone G W. Design of CD40 agonists and their use in growing B cells for cancer immunotherapy. Int Rev Immunol. 2012 August; 31(4):279-88).

The molecular consequences of CD40 signaling depend on the cell type expressing CD40 and their microenvironment (Vonderheide R H, Glennie M J. Agonistic CD40 antibodies and cancer therapy. Clin Cancer Res. 2013 Mar. 1; 19(5):1035-43). The 'licensing' of APC, in particular DC, results in up-regulation of membrane co-stimulatory molecules and MHC, as well as the production of pro-inflammatory cytokines (Caux C, Massacrier C, Vanbervliet B, et al. Activation of human dendritic cells through CD40 cross-linking. J Exp Med. 1994 Oct. 1; 180(4):1263-72; van Kooten C, Banchereau J. Functions of CD40 on B cells, dendritic cells and other cells. Curr Opin Immunol. 1997 June; 9(3):330-7). Thus, CD40 is involved in the functional maturation of APC and consequently the activation of antigen-specific T cells (Ma D Y, Clark E A. The role of CD40 and CD154/CD40L in dendritic cells. Semin Immunol. 2009

October; 21(5):265-72; Moran A E, Kovacsovics-Bankowski M, Weinberg A D. The TNFRs OX40, 4-1BB, and CD40 as targets for cancer immunotherapy. Curr Opin Immunol. 2013 April; 25(2):230-7). CD40 also plays a role in humoral immunity by activating resting B cells and by increasing their antigen-presenting function (Vonderheide R H, Glennie M J. Agonistic CD40 antibodies and cancer therapy. Clin Cancer Res. 2013 Mar. 1; 19(5):1035-43; Zarnegar B, He J Q, Oganesyan G, et al. Unique CD40-mediated biological program in B cell activation requires both type 1 and type 2 NF-kappaB activation pathways. Proc Natl Acad Sci USA. 2004 May 25; 101(21):8108-13). Moreover, CD40 is involved in the induction of innate immunity through stimulation of cells such as macrophages, granulocytes and NK cells (Rakhmilevich A L, Alderson K L, Sondel P M. T-cell-independent antitumor effects of CD40 ligation. Int Rev Immunol. 2012 August; 31(4):267-78).

Monoclonal CD40 agonist antibodies are believed to trigger anti-tumor effects via two distinct mechanisms: (i) tumor-specific immune activation; and (ii) direct tumoricidal effects via e.g., apoptosis, antibody-dependent cellular cytotoxicity (ADCC), and/or complement-dependent cytotoxicity (CDC) (Khong A, Nelson D J, Nowak A K, et al. The use of agonistic anti-CD40 therapy in treatments for cancer. Int Rev Immunol. 2012 August; 31(4):246-66). Treatment with CD40 agonists induces activation of several different immune cells that contribute to the anti-tumor immune response. T cells, and in particular cytotoxic T lymphocytes (CTL), are essential for the anti-tumor effects induced by CD40 agonists, as demonstrated in a range of preclinical models (Byrne K T, Vonderheide R H. CD40 Stimulation Obviates Innate Sensors and Drives T Cell Immunity in Cancer. Cell Rep. 2016 Jun. 21; 15(12):2719-32; Mangsbo S M, Broos S, Fletcher E, et al. The human agonistic CD40 antibody ADC-1013 eradicates bladder tumors and generates T-cell-dependent tumor immunity. Clin Cancer Res. 2015 Mar. 1; 21(5):1115-26; Tutt A L, O'Brien L, Hussain A, et al. T Cell Immunity to Lymphoma Following Treatment with Anti-CD40 Monoclonal Antibody. The Journal of Immunology. 2002; 168(6):2720-2728; van Mierlo G J, den Boer A T, Medema J P, et al. CD40 stimulation leads to effective therapy of CD40(−) tumors through induction of strong systemic cytotoxic T lymphocyte immunity. Proc Natl Acad Sci USA. 2002 Apr. 16; 99(8):5561-6). Activation of DC and subsequent priming of T cells likely plays a central role, as the presence of antigen cross-presenting DC is required for the anti-tumor effects of CD40 agonist treatment in T cell-dependent models (Beatty G L, Chiorean E G, Fishman M P, et al. CD40 agonists alter tumor stroma and show efficacy against pancreatic carcinoma in mice and humans. Science. 2011 Mar. 25; 331(6024):1612-6; Beatty G L, Li Y, Long K B. Cancer immunotherapy: activating innate and adaptive immunity through CD40 agonists. Expert Rev Anticancer Ther. 2017 February; 17(2):175-186; Long K B, Gladney W L, Tooker G M, et al. IFNgamma and CCL2 Cooperate to Redirect Tumor-Infiltrating Monocytes to Degrade Fibrosis and Enhance Chemotherapy Efficacy in Pancreatic Carcinoma. Cancer Discov. 2016 April; 6(4):400-413; Lum H D, Buhtoiarov I N, Schmidt B E, et al. In vivo CD40 ligation can induce T-cell-independent antitumor effects that involve macrophages. J Leukoc Biol. 2006 June; 79(6):1181-92). NK cells are also capable of cytotoxic killing of tumor cells, and have been shown to contribute to the reduction in tumor growth in response to a CD40 agonist (Turner J G, Rakhmilevich A L, Burdelya L, et al. Anti-CD40 Antibody Induces Antitumor and Antimetastatic Effects: The Role of NK Cells. The Journal of Immunology. 2001; 166(1):89). B cells activated through CD40 can further add to the anti-tumor immune response by presenting antigen to T cells and producing tumor-targeting antibodies (Jackaman C, Cornwall S, Graham P T, et al. CD40-activated B cells contribute to mesothelioma tumor regression. Immunol Cell Biol. 2011 February; 89(2):255-67; Liu M, Sun Q, Wang J, et al. A New Perspective: Exploring Future Therapeutic Strategies For Cancer By Understanding The Dual Role Of B Lymphocytes In Tumor Immunity. Int J Cancer. 2018 Sep. 5). Additionally, CD40 agonists have been found to convert tumor-associated macrophages (TAM) to activated macrophages with anti-tumor properties that can promote tumor shrinkage, independent of T cells (Beatty G L, Chiorean E G, Fishman M P, et al. CD40 agonists alter tumor stroma and show efficacy against pancreatic carcinoma in mice and humans. Science. 2011 Mar. 25; 331(6024):1612-6; Beatty G L, Li Y, Long K B. Cancer immunotherapy: activating innate and adaptive immunity through CD40 agonists. Expert Rev Anticancer Ther. 2017 February; 17(2):175-186; Long K B, Gladney W L, Tooker G M, et al. IFNgamma and CCL2 Cooperate to Redirect Tumor-Infiltrating Monocytes to Degrade Fibrosis and Enhance Chemotherapy Efficacy in Pancreatic Carcinoma. Cancer Discov. 2016 April; 6(4):400-413; Lum H D, Buhtoiarov I N, Schmidt B E, et al. In vivo CD40 ligation can induce T-cell-independent antitumor effects that involve macrophages. J Leukoc Biol. 2006 June; 79(6):1181-92).

DC are the most important APC for the generation of antigen-specific T cell responses (Flamar A L, Xue Y, Zurawski S M, et al. Targeting concatenated HIV antigens to human CD40 expands a broad repertoire of multifunctional CD4+ and CD8+ T cells. AIDS. 2013 Aug. 24; 27(13):2041-51). Their central role in inducing anti-tumor immune responses has been shown in preclinical models, where mice deficient in Batf3 and thereby lacking cross-presenting DC (cDC1), show impaired rejection of immunogenic tumors and fail to respond to immunotherapy due to impaired priming of tumor-targeting CTL (Hildner K, Edelson B T, Purtha W E, et al. Batf3 deficiency reveals a critical role for CD8alpha+ dendritic cells in cytotoxic T cell immunity. Science. 2008 Nov. 14; 322(5904):1097-100; Sanchez-Paulete A R, Cueto F J, Martinez-Lopez M, et al. Cancer Immunotherapy with Immunomodulatory Anti-CD137 and Anti-PD-1 Monoclonal Antibodies Requires BATF3-Dependent Dendritic Cells. Cancer Discov. 2016 January; 6(1):71-9). In accordance with these data, the presence of cross-presenting DC in human tumors correlates with CD8+ T cell infiltration and is associated with better prognosis as well as better response to immunotherapy (Broz M L, Binnewies M, Boldajipour B, et al. Dissecting the tumor myeloid compartment reveals rare activating antigen-presenting cells critical for T cell immunity. Cancer Cell. 2014 Nov. 10; 26(5):638-52; Sanchez-Paulete A R, Teijeira A, Cueto F J, et al. Antigen Cross-Presentation and T-Cell Cross-Priming In Cancer Immunology And Immunotherapy. Ann Oncol. 2017 Sep. 1). Signaling through CD40 on DC induces activation of the antigen presentation machinery and upregulation of co-stimulatory molecules such as CD80 and CD86, thereby improving the capacity of the DC to present antigen to and activate T cells (Beatty G L, Li Y, Long K B. Cancer immunotherapy: activating innate and adaptive immunity through CD40 agonists. Expert Rev Anticancer Ther. 2017 February; 17(2):175-186; Gladue R P, Paradis T, Cole S H, et al. The CD40 agonist antibody CP-870,893 enhances dendritic cell and B-cell activity and promotes anti-tumor efficacy in SCID-hu mice. Cancer Immunol Immunother.

2011 July; 60(7):1009-17), and to produce cytokines, notably IL-12, that helps shape the T cell response.

CD40 expression can be detected on all blood DC, with the highest expression found on a subpopulation referred to as cDC1 (Carenza C, Calcaterra F, Oriolo F, et al. Costimulatory Molecules and Immune Checkpoints Are Differentially Expressed on Different Subsets of Dendritic Cells [Original Research]. Frontiers in Immunology. 2019 2019 Jun. 11; 10 (1325); MacDonald K P, Munster D J, Clark G J, et al. Characterization of human blood dendritic cell subsets. Blood. 2002 Dec. 15; 100(13):4512-20). Recent studies have focused on the role of cDC1 in driving T cell responses to tumors, demonstrating a potential for CD40 agonists alone or in combination with other therapies in enhancing cDC1 priming of tumor-targeting T cells (Hegde S, Krisnawan V E, Herzog B H, et al. Dendritic Cell Paucity Leads to Dysfunctional Immune Surveillance in Pancreatic Cancer. Cancer Cell. 2020 Mar. 16; 37(3):289-307 e9; Morrison A H, Diamond M S, Hay C A, et al. Sufficiency of CD40 activation and immune checkpoint blockade for T cell priming and tumor immunity. Proc Natl Acad Sci USA. 2020 Mar. 25; Zhang L, Li Z, Skrzypczynska K M, et al. Single-Cell Analyses Inform Mechanisms of Myeloid-Targeted Therapies in Colon Cancer. Cell. 2020; 181(2):442-459. e29). Single-cell RNA sequencing studies confirm the presence of cDC1 with the potential to respond to CD40 agonists in primary tumor tissue (Chevrier S, Levine J H, Zanotelli V R T, et al. An Immune Atlas of Clear Cell Renal Cell Carcinoma. Cell. 2017; 169(4):736-749. e18; Zhang L, Li Z, Skrzypczynska K M, et al. Single-Cell Analyses Inform Mechanisms of Myeloid-Targeted Therapies in Colon Cancer. Cell. 2020; 181(2):442-459. e29; Zhang Q, He Y, Luo N, et al. Landscape and Dynamics of Single Immune Cells in Hepatocellular Carcinoma. Cell. 2019; 179(4):829-845. e20). Targeting CD40 on DC therefore has the capacity to expand the tumor-specific T cell pool, and potentially represents a way to treat immunologically "cold" tumors.

Carcinoembryonic Antigen (CEA)

Carcinoembryonic antigen (CEA) describes a family of highly-related glycoproteins (some of which are glycosyl phosphatidyl inositol (GPI) cell-surface-anchored), which are involved in cell functions, such as cell adhesion, phagocytosis, proliferation and signal transduction. CEAs are generally characterised as being members of the CD66 family of molecules (with CEA including examples of CD66a, CD66b, CD66c, CD66d, CD66e, and CD66f molecules). Currently 29 CEA family genes have been identified, which are generally referred to as carcinoembryonic antigen-related cell adhesion molecule (CEACAMs). Examples of the CEACAM genes are CEACAM1, CEACAM3, CEACAM4, CEACAM5, CEACAM6, CEACAM7, CEACAM8, CEACAM16, CEACAM18, CEACAM19, CEACAM20, and CEACAM21.

CEA (and, in particular, CEACAM5) is usually produced during the development of a fetus, and is only present at very low levels in the blood of a healthy, human, adult. However, in cancer the levels of CEA found are increased, and in that context it is characterised as a tumour-associated antigen (TAA). CEA has been associated with many types of cancers and tumours, including gastric carcinoma, pancreatic carcinoma, lung carcinoma, breast carcinoma, and medullary thyroid carcinoma. Of particular relevance to cancer and tumours are CEACAM1, CEACAM6, CEACAM7 and CEACAM5 (Zi-Wen Han, Zhi-Wu Lyv, Bin Cui, et al. The old CEACAMs find their new role in tumor immunotherapy. Invest New Drugs volume. 2020 38:1888-1898; Chaogu Zheng, Jing Feng1, Di Lu1, et al. A Novel Anti-CEACAM5 Monoclonal Antibody, CC4, Suppresses Colorectal Tumor Growth and Enhances NK Cells-Mediated Tumor Immunity. PLoS One. 2011; 6 (6): e21146).

Despite progress in the development of immunotherapies for the treatment of various cancers over the last decade, there remains a need for new and efficacious agents for treating cancers, in particular cancers expressing CEA.

Accordingly, the present invention seeks to provide improved polypeptide-based therapies for the treatment of cancer, in particular cancers expressing CEA.

SUMMARY OF THE INVENTION

In a first aspect, the present invention provides a bispecific polypeptide comprising a first binding domain, designated B1, which is capable of binding specifically to CD40, and a second binding domain, designated B2, which is capable of specifically binding to CEA.

Such bispecific compounds can be used to establish a highly effective and safe cancer immunotherapy.

Various types of tumour-localizing immunotherapeutic molecules, such as immunocytokines and bispecific antibodies have shown beneficial immune activation and inhibition of tumor growth in preclinical studies as well as in the clinic (reviewed in Kiefer and Neri, 2016).

The clinical progress with immunocytokines has so far not been impressive and the side effects still remain since the tumor-binding entity only confers limited tumor localization, with the bulk of the immunocytokine ending up in other compartments. Bispecific antibodies that restrict the activity to the tumor as described in this invention would provide a clear advantage over immunocytokines since they are inactive in the absence of cancer and/or tumours, in particular cancer and/or tumours that express CEA.

To avoid affecting part of the immune system not relevant for inducing tumour immunity and avoid systemic toxicity by CD40-activating agents, yet obtain high efficacy in the tumour area, the designs of the molecular formats of CD40 agonists may be optimised. For example, a good efficacy/safety profile can be obtained by a CD40-CEA bispecific antibody that requires crosslinking by binding to the CEA for CD40 activation to occur. Thus, CD40-expressing cells such as dendritic cells, residing in the tumour tissue, will preferentially be activated, whereas CD40-expressing cells in other tissues, where the expression of CEA is low or absent, will not. This would allow focused activation of CD40-expressing cells specifically in the tumour tissue, while limiting toxicity induced by generalised CD40 activation.

Structure of the Bispecific Polypeptide

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The term "bispecific" as used herein means the polypeptide is capable of specifically binding at least two target entities. Accordingly, bispecific as used herein can describe polypeptides that are capable of specifically binding more than two target entities, such as: at least three, at least four or at least five target entities. In a preferred embodiment, the bispecific polypeptide is capable of specifically binding two target entities.

Thus, the first and/or second binding domains may be selected from the group consisting of antibodies and antigen-binding fragments thereof, and CD40 ligands.

By "an antibody or an antigen-binding fragment thereof" we include substantially intact antibody molecules, as well as chimeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include Fv fragments (e.g. single chain Fv and disulphide-bonded Fv), Fab-like fragments (e.g. Fab fragments, Fab' fragments and F(ab)2 fragments), single variable domains (e.g. VH and VL domains) and single domain antibodies (dAbs, including single and dual formats [i.e. dAb-linker-dAb], and nanobodies). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

In one preferred embodiment, the polypeptide is a bispecific antibody (numerous examples of which are described in detail below).

In one embodiment, the antigen-binding fragment is selected from the group consisting of: Fv fragments (such as a single chain Fv fragment, or a disulphide-bonded Fv fragment), Fab-like fragments (such as a Fab fragment; a Fab' fragment or a F(ab)$_2$ fragment) and single domain antibodies.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009 (the disclosures of which are incorporated herein by reference). Exemplary antibody mimics include: affibodies (also called Trinectins; Nygren, 2008, *FEBS J*, 275, 2668-2676); CTLDs (also called Tetranectins; *Innovations Pharmac. Technol.* (2006), 27-30); adnectins (also called monobodies; *Meth. Mol. Biol.,* 352 (2007), 95-109); anticalins (*Drug Discovery Today* (2005), 10, 23-33); DARPins (ankyrins; *Nat. Biotechnol.* (2004), 22, 575-582); avimers (*Nat. Biotechnol.* (2005), 23, 1556-1561); microbodies (*FEBS J*, (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522); affimers (Avacta Life Sciences, Wetherby, UK).

Also included within the scope of the invention are chimeric T cell receptors (also known as chimeric immunoreceptors, and chimeric antigen receptors or CARs) (see Pule et al., 2003, the disclosures of which are incorporated herein by reference). These are engineered receptors, which graft an arbitrary specificity onto an immune effector cell. Typically, CARs are used to graft the specificity of a monoclonal antibody onto a T cell; with transfer of their coding sequence facilitated by retroviral vectors. The most common form of such molecules are fusions comprising a single-chain variable fragment (scFv) derived from a monoclonal antibody fused to CD3-zeta transmembrane and endodomain. When T cells express this fusion molecule, they recognize and kill target cells that express the transferred monoclonal antibody specificity.

Persons skilled in the art will further appreciate that the invention also encompasses modified versions of antibodies and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989; Winter et al., 1991, the disclosures of which are incorporated herein by reference) or generation of monoclonal antibody molecules by cell lines in culture. These include, but are not limited to, the hybridoma technique, the human B cell hybridoma technique, and the Epstein-Barr virus (EBV)-hybridoma technique (Kohler et al., 1975, Kozbor et al., 1985; Cote et al., 1983; Cole et al., 1984., the disclosures of which are incorporated herein by reference).

Suitable methods for the production of monoclonal antibodies are also disclosed in "*Monoclonal Antibodies: A manual of techniques*", H Zola (CRC Press, 1988, the disclosures of which are incorporated herein by reference) and in "Monoclonal *Hybridoma Antibodies: Techniques and Applications*", J G R Hurrell (CRC Press, 1982, the disclosures of which are incorporated herein by reference).

Likewise, antibody fragments can be obtained using methods well known in the art (see, for example, Harlow & Lane, 1988, "*Antibodies: A Laboratory Manual*", Cold Spring Harbor Laboratory, New York, the disclosures of which are incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat or rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986, Riechmann et al., 1988, Presta, 1992, the disclosures of which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, Reichmann et al., 1988, Verhoeyen et al., 1988, U.S. Pat. No. 4,816,567, the disclosures of which are incorporated herein by reference) by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, Marks et al., 1991, Cole et al., 1985, Boerner et al., 1991, the disclosures of which are incorporated herein by reference).

It will be appreciated by persons skilled in the art that the bispecific polypeptides, e.g. antibodies, of the present invention may be of any suitable structural format.

Thus, in exemplary embodiments of the bispecific antibodies of the invention:
(a) binding domain B1 and/or binding domain B2 is an intact IgG antibody (or, together, form an intact IgG antibody);
(b) binding domain B1 and/or binding domain B2 is an Fv fragment (e.g. an scFv);
(c) binding domain B1 and/or binding domain B2 is a Fab fragment; and/or
(d) binding domain B1 and/or binding domain B2 is a single domain antibody (e.g. domain antibodies and nanobodies).

It will be appreciated by persons skilled in the art that the bispecific antibody may comprise a human Fc region, or a variant of a said region, where the region is an IgG1, IgG2, IgG3 or IgG4 region, preferably an IgG1 or IgG4 region.

Engineering the Fc region of a therapeutic monoclonal antibody or Fc fusion protein allows the generation of molecules that are better suited to the pharmacology activity required of them (Strohl, 2009, the disclosures of which are incorporated herein by reference).

By "CD40 ligands", we include non-antibody molecules that are capable of binding to CD40; for example CD40L (CD154, such as GenBank: D31797.2) or fragments or variants of CD40L that retain their ability to bind to CD40.
(a) Engineered Fc Regions for Increased Half-Life One approach to improve the efficacy of a therapeutic antibody is to increase its serum persistence, thereby allowing higher circulating levels, less frequent administration and reduced doses.

The half-life of an IgG depends on its pH-dependent binding to the neonatal receptor FcRn. FcRn, which is expressed on the surface of endothelial cells, binds the IgG in a pH-dependent manner and protects it from degradation.

Some antibodies that selectively bind the FcRn at pH 6.0, but not pH 7.4, exhibit a higher (to put another way longer) half-life in a variety of animal models. Additionally, some antibodies that bind the FcRn with a higher affinity at pH 6.0, but with a remained low affinity at pH 7.4 exhibit a longer half-life.

Several mutations located at the interface between the CH2 and CH3 domains, such as T250Q/M428L (Hinton et al., 2004, the disclosures of which are incorporated herein by reference) and M252Y/S254T/T256E+H433K/N434F (Vaccaro et al., 2005, the disclosures of which are incorporated herein by reference), have been shown to increase the binding affinity to FcRn and the half-life of IgG1 in vivo.
(b) Engineered Fc Regions for Altered Effector Function To ensure lack of CD40 activation in the absence of CEA, the Fc portion of the bispecific antibody should bind with no or very low affinity to FcγR, since FcγR-mediated crosslinking of a CD40 antibody may induce activation. By "very low affinity" we include that the Fc portion exhibits at least 10 times reduced affinity to FcγRI, FcγRII and III compared to wild-type IgG1, as determined by the concentration where half maximal binding is achieved in flow cytometric analysis of FcγR expressing cells (Hezareh et al., 2001) or by FcγR ELISA (Shields et al., 2001).

Another factor to take into account is that engagement of FcγRs may also induce antibody-dependent cellular cytotoxicity (ADCC), antibody-dependent cellular phagocytosis (ADCP) and complement-dependent cytotoxicity (CDC) of cells coated with antibodies. In one embodiment, to enhance tumour-dependent CD40 activation as well as to avoid depletion of CD40-expressing cells, the isotype of a CD40-CEA bispecific antibody should preferably be silent.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009, the disclosures of which are incorporated herein by reference). IgG1 molecules have the highest affinity and capacity to induce effector functions, whereas IgG2, IgG3 and IgG4 are less effective (Bruhns, 2012; Hogarth and Pietersz, 2012; Stewart et al., 2014) (Wang et al. 2015; Vidarson et al. 2014). In addition, certain mutations in the Fc region of IgG1 dramatically reduce FcγR affinity and effector function while retaining neonatal FcR (FcRn) interaction (Ju and Jung, 2014; Leabman et al., 2013; Oganesyan et al., 2008; Sazinsky et al., 2008).

The most widely used IgG1 mutants are N297A alone or in combination with D265A, as well as mutations at positions L234 and L235, including the so-called "LALA" double mutant L234A/L235A. Another position described to further silence IgG1 by mutation is P329 (see US 2012/0251531).

Thus, choosing a mutated IgG1 format with low effector function but retained binding to FcRn may result in a bispecific antibody with CEA-dependent activation of CD40, and exhibiting a favorable efficacy/safety profile and good PK properties.

Advantageously, the polypeptide is incapable of inducing antibody-dependent cell cytotoxicity (ADCC), antibody-dependent cellular phagocytosis (ADCP), and/or complement-dependent cytotoxicity (CDC). By "incapable" we include that the ability of the polypeptide to induce ADCC, etc., is at least 10-fold lower than compared to wild-type IgG1 as shown by e.g. monocyte-dependent ADCC or CDC assays described by Hezareh et al. 2001.

In one embodiment, the Fc region may be a variant of a human IgG1 Fc region comprising a mutation at one or more of the following positions:

L234, L235, P239, D265, N297 and/or P329.

Advantageously, alanine may be present at the mutated position(s).

Optionally, the IgG1 variant may be a variant of a human IgG1 Fc region comprising mutations L234A and L235A (i.e. the LALA double mutant; see SEQ ID NO: 336).

It will be appreciated by persons skilled in the art that the bispecific polypeptides of the invention may be of several different structural formats (for example, see Chan & Carter, 2016, the disclosures of which are incorporated herein by reference).

In exemplary embodiments, the bispecific antibody is selected from the groups consisting of:
  (a) bivalent bispecific antibodies, such as IgG-scFv bispecific antibodies (for example, wherein B1 is an intact IgG and B2 is an scFv attached to B1 at the N-terminus of a light chain and/or at the C-terminus of a light chain and/or at the N-terminus of a heavy chain and/or at the C-terminus of a heavy chain of the IgG, or vice versa);
  (b) monovalent bispecific antibodies, such as a Duo-Body® (Genmab AS, Copenhagen, Denmark) or 'knob-in-hole' bispecific antibody (for example, an scFv-KIH, scFv-KIH$^r$, a BiTE-KIH or a BiTE-KIH$^r$ (see Xu et al., 2015, mAbs 7(1):231-242));
  (c) scFv$_2$-Fc bispecific antibodies (such as ADAPTIR™ bispecific antibodies from Aptevo Therapeutics);
  (d) BiTE/scFv$_2$ bispecific antibodies;
  (e) DVD-Ig bispecific antibodies;
  (f) DART-based bispecific antibodies (for example, DART$_2$-Fc or DART);
  (g) DNL-Fab$_3$ bispecific antibodies; and
  (h) scFv-HSA-scFv bispecific antibodies.

For example, the bispecific antibody may be an IgG-scFv antibody. The IgG-scFv antibody may be in either VH-VL or VL-VH orientation. In one embodiment, the scFv may be stabilised by a S—S bridge between VH and VL.

In one embodiment, binding domain B1 and binding domain B2 are fused directly to each other.

In an alternative embodiment, binding domain B1 and binding domain B2 are joined via a polypeptide linker. For example, a polypeptide linker may be a short linker peptide between about 10 to about 25 amino acids. The linker is usually rich in glycine for flexibility, as well as serine or threonine for solubility, and can either connect the N-terminus of the VH with the C-terminus of the VL, or vice versa.

Thus, the linker may be selected from the group consisting of the amino acid sequence SGGGGSGGGGS (SEQ ID NO: 337), SGGGGSGGGGSAP (SEQ ID NO: 338), NFSQP (SEQ ID NO: 339), KRTVA (SEQ ID NO: 340), GGGSGGGG (SEQ ID NO: 341), GGGGSGGGGS, (SEQ ID NO: 342), GGGGSGGGGSGGGGS (SEQ ID NO: 343), GSTSGSGKPGSGEGSTKG (SEQ ID NO: 344) (Whitlow et al. 1993) THTCPPCPEPKSSDK (SEQ ID NO: 345), GGGS (SEQ ID NO: 346), EAAKEAAKGGGGS (SEQ ID NO: 347), EAAKEAAK (SEQ ID NO: 348), or (SG)m, where m=1 to 7.

In a preferred embodiment, the linker may be selected from the group consisting of: SEQ ID NO: 341, SEQ ID NO: 342 and SEQ ID NO: 343. In a particularly preferred embodiment, the linker is GGGGSGGGGSGGGGS (SEQ ID NO: 343).

The term "amino acid" as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides as defined herein comprise or consist of L-amino acids.

It will be appreciated by persons skilled in the art that the polypeptides of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997), which is incorporated herein by reference. This approach involves making pseudo-peptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will also be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978 and Thursell et al., 1983, which are incorporated herein by reference.

In one embodiment of the invention, one of binding domain B1 or binding domain B2 is an immunoglobulin molecule, and one of binding domain B1 or binding domain B2 is a Fab fragment, wherein the Fab fragment is fused to the C terminus of the heavy chain of the immunoglobulin via the light chain of the Fab fragment.

For example, the polypeptide may have a format as shown in FIG. 23. Such a format is referred to as the "RUBY™ format" (as described in pending UK patent application 1820556.7 and the PCT application WO 2020/127354). Antibodies in the "RUBY™ format" and "optimised RUBY™ format", as described herein, are particularly preferred, for the bispecific polypeptides of the invention.

The bispecific polypeptide may comprise one or more mutations to promote association of the heavy chain polypeptide of the immunoglobulin with the light chain polypeptide of the immunoglobulin and/or to promote association of the heavy chain polypeptide of the Fab with the light chain polypeptide of the Fab.

In one embodiment the one or more mutations prevent the formation of aggregates and a Fab by-product.

It will be appreciated by persons skilled in the art, that in one embodiment the mutations may prevent the formation of aggregates and/or a Fab by-product by generating steric hindrance and/or incompatibility between charges.

By "steric hindrance" we mean the slowing of a reaction due to steric bulk, i.e. the size of an amino acid molecule prevents association of two protein surfaces that may otherwise occur if a smaller amino acid is present.

By "incompatibility between charges" we mean that an unwanted product will not form as the charges are incompatible and prevent the product from forming, e.g. there may be two negatively charged portions which repel and prevent an unwanted product from forming.

As described above, said mutations limit the formation of a Fab by-product and/or aggregates by, for example, creating surfaces that limit the formation of aggregates or by-product Fab fragments. In one embodiment, the mutations prevent formation of a Fab by-product by generating steric hindrance and/or incompatibility between charges (leading to charge incompatibility of wrong chains). The mutations may also promote interactions between correct chains (i.e. between the first heavy chain polypeptide and the first light chain polypeptide, and/or between the second heavy chain polypeptide and the second light chain polypeptide) by, for example, creating salt or disulphide bridges.

Thus, the mutations may favour formation of the bispecific polypeptide.

In one embodiment, the percentage of aggregates formed during manufacturing is less than or equal to 25%. Optionally the percentage of aggregates is less than or equal to 20%, 17.5%, 15%, 13.5% or 10%. Preferably the percentage of aggregates is less than 10%. Optionally these measurements are carried out when the chains of the bispecific polypeptide are transfected at equal ratios, e.g. at a ratio of 1:1:1 when 3 chains are used during production.

Alternatively, the chain transfection ratio may be optimised. Optionally the % of aggregates when the chain transfection ratio is optimised may be less than or equal to 3.5%, 3%, 2.5% or 2%.

In one embodiment, the bispecific polypeptide comprises one or more mutation pairs each comprising two functionally compatible mutations.

By "functionally compatible mutations" we mean the mutations have complementary functions, e.g. one mutation of the pair (in one chain) may be a mutation that forms a positively charged region, and the other mutation (in another chain) forms a negatively charged region. Together these mutations act in a functionally compatible way promoting association of the respective chains.

In one embodiment, the bispecific polypeptide comprises one or more mutation pairs in one or more of the following region groups:
  (a) the CH1 and CKappa or CLambda region of the immunoglobulin; and/or
  (b) the CH1 and CKappa or CLambda region of the Fab; and/or
  (c) the VL and VH regions of the immunoglobulin; and/or
  (d) the VL and VH regions of the Fab.

Thus, in one embodiment, the mutation pairs are in the CH1 and CKappa or CLambda regions of the Fab and/or the immunoglobulin, and the mutation pairs are selected from:
  (a) cavity and protruding surface mutations (i.e. steric mutations); and/or
  (b) hydrophobic swap mutations; and/or
  (c) charged mutations (i.e. salt mutations); and/or
  (d) mutations resulting in the formation of a disulphide bridge.

The mutation pairs may alternatively or additionally be in the VH and VL regions of the Fab and/or the immunoglobulin, the mutation pairs in the VH and VL regions are selected from:
  (a) charged mutations (i.e. salt mutations); and/or
  (b) double charged mutations; and/or
  (c) mutations resulting in the formation of a disulphide bridge.

In one embodiment of the invention the mutations are at positions selected from the group consisting of:
  (a) one or more of the following positions in the CH1 domain: H168, F170, L145, S183 and T187 (according to EU numbering system); and/or
  (b) a position selected from the one or more of the following position ranges in the CKappa or CLambda domain: position 132 to 138, position 173 to 179, position 130 to 136, position 111 to 117 and position 134 to 140 (according to EU numbering system); and/or
  (c) a position selected from one or more of the following position ranges in the VL: position 41 to 47, position 117 to 123 and position 46 to 52 (according to IMGT numbering system); and/or
  (d) a position selected from one or more of the following position ranges in the VH: position 41 to 47, position 46 to 52 and position 117 to 123 (according to IMGT numbering system).

In one embodiment of the invention the mutations are at positions selected from the group consisting of:
  (a) one or more of the following positions in the CH1 domain: H168, F170, L145, S183 and T187 (according to EU numbering system); and/or
  (b) a position selected from the one or more of the following position ranges in the CKappa or CLambda domain: position 132 to 138, position 173 to 179, position 130 to 136, position 111 to 117 and position 134 to 140 (according to Kabat numbering system); and/or (c) a position selected from one or more of the following position ranges in the VL: position 41 to 47, position 117 to 123 and position 46 to 52 (according to IMGT numbering system); and/or (d) a position selected from one or more of the following position ranges in the VH: position 41 to 47, position 46 to 52 and position 117 to 123 (according to IMGT numbering system).

In one embodiment of the invention the mutations are at positions selected from the group consisting of:

(a) one or more of the following positions in the CH1 domain: H168, F170, L145, S183 and T187 (according to EU numbering system); and/or (b) a position selected from the one or more of the following position ranges in the CKappa or CLambda domain: position 132 to 138, position 173 to 179, position 130 to 136, position 111 to 117 and position 134 to 140 (according to EU numbering system); and/or (c) a position selected from one or more of the following position ranges in the VL: position 41 to 47, position 117 to 123 and position 46 to 52 (according to IMGT numbering system); and/or (d) a position selected from one or more of the following position ranges in the VH: position 41 to 47, position 46 to 52 and position 117 to 123 (according to IMGT numbering system).

One mutation in each of the ranges given above will be the relevant functional mutation as it will be a position that makes contact with the amino acid in the corresponding domain/chain, and is therefore the relevant interface between chains.

It will therefore be appreciated by persons skilled in the art that mutations in the position ranges given above are suitable, as the relevant functional feature is whether the position contacts a corresponding position on the other chain, i.e. a position in the VH chain that contacts a corresponding position in a VL chain is the relevant position, or a position in a CLambda that contacts a position in a CH1 chain is the relevant position.

In one embodiment the mutations are selected from the group consisting of:
VH X44R/E/D/K, X49C, X120K
VL X44R/E/D/K, X49D X120C
CH1 H168A/G, F170G/A, L145Q, S183V, T187E/D,
CKappa/CLambda S/T114A, V133T, L135Y/W, N/S137K/R/H, S176W/V/Y
numbering according to IMGT system for VH/VL domains and according to EU numbering system for constant domains
X refers to any amino acid The use of "/" in the context of discussing mutations is to illustrate alternative possible amino acids; for example, "X44R/E/D/K" indicates that R or E or D or K can be included at position 44, as a substitute for the amino acid "X".

In one embodiment the mutations are selected from the group consisting of:
VH X44R/E/D/K, X49C, X120K
VL X44R/E/D/K, X49D X120C
CH1 H168A/G, F170G/A, L145Q, S183V, T187E/D,
CKappa/CLambda S/T114A, V133T, L135Y/W, N/S137K/R/H, S176W/V/Y
numbering according to IMGT system for VH/VL domains and according to Kabat numbering system for constant domains
X refers to any amino acid In one embodiment of the invention, the mutations are at positions selected from the group consisting of:

(a) one or more of the following positions in the CH1 domain: H168, F170, L145, S183 and T187 (according to EU numbering system); and/or (b) one or more of the following positions in the CKappa domain: L135, S176, V133, S114 and N137 (according to EU numbering system) and/or one or more of the following positions in the CLambda domain: L135, S176, V133, T114 and S137 (according to EU numbering system); and/or (c) one or more of the following positions in the VL: Q44, Q120 and A49 (according to IMGT numbering system); and/or (d) one or more of the following positions in the VH: Q44, G49 and Q120 (according to IMGT numbering system).

In one embodiment of the invention, the mutations are at positions selected from the group consisting of:

(a) one or more of the following positions in the CH1 domain: H168, F170, L145, S183 and T187 (according to EU numbering system); and/or (b) one or more of the following positions in the CKappa domain: L135, S176, V133, S114 and N137 (according to Kabat numbering system) and/or one or more of the following positions in the CLambda domain: L135, S176, V133, T114 and S137 (according to Kabat numbering system); and/or (c) one or more of the following positions in the VL: Q44, Q120 and A49 (according to IMGT numbering system); and/or (d) one or more of the following positions in the VH: Q44, G49 and Q120 (according to IMGT numbering system).

For example, the mutations may be selected from the group consisting of:

(a) one or more of the following mutations in the CH1 domain: H168A, F170G, L145Q, S183V and T187E (according to EU numbering system); and/or (b) one or more of the following mutations in the CKappa domain: L135Y, S176W, V133T, S176V, S114A and N137K (according to EU numbering system) and/or one or more of the following mutations in the CLambda domain: L135Y, S176W, V133T, S176V, T114A and S137K (according to EU numbering system); and/or (c) one or more of the following mutations in the VL: Q44R, Q44E, Q120C, Q44D and A49D (according to IMGT numbering system); and/or (d) one or more of the following mutations in the VH: Q44E, Q44R, G49C, Q44K and Q120K (according to IMGT numbering system).

For example, the mutations may be selected from the group consisting of:

(a) one or more of the following mutations in the CH1 domain: H168A, F170G, L145Q, S183V and T187E (according to EU numbering system); and/or (b) one or more of the following mutations in the CKappa domain: L135Y, S176W, V133T, S176V, S114A and N137K (according to Kabat numbering system) and/or one or more of the following mutations in the CLambda domain: L135Y, S176W, V133T, S176V, T114A and S137K (according to Kabat numbering system); and/or (c) one or more of the following mutations in the VL: Q44R, Q44E, Q120C, Q44D and A49D (according to IMGT numbering system); and/or (d) one or more of the following mutations in the VH: Q44E, Q44R, G49C, Q44K and Q120K (according to IMGT numbering system).

The above mutations are those of the "RUBY™ format".

In a further embodiment, the polypeptide may have a format as shown in FIG. 23 with further optimised mutations, which is referred to as the "optimised RUBY™ format".

Although bispecific polypeptides in the "RUBY™ format" can be reproducibly produced with an excellent level of purity, bispecific polypeptides in the "optimised RUBY™ format" can be reproducibly produced at an even higher level of purity. Further, bispecific polypeptides in the "optimised RUBY™ format" have been engineered to carry a reduced risk of provoking immunogenic responses directed against the bispecific polypeptide itself.

The optimised mutations are described below as "optimised mutation set 1" and "optimised mutation set 2"—including "set 2a" and/or "set 2b". It will be appreciated by the skilled person various combinations of these optimised mutations could be used in a bispecific polypeptide of the invention, as well as in combination with any of the "RUBY™ format" mutations described above. The combinations of the "RUBY™ format" mutations and "optimised RUBY™ format" mutations, used in the same bispecific antibody, are described below. It will also be appreciated that the variations of those mutations as described herein would also work as part of the invention. All mutations in variable domains (VH or VL) are numbered according to the IMGT numbering system, and all mutations in the constant domains are numbered according to the EU numbering system.

Mutation set 1—Mutations in the variable domain heavy (VH): T65E, T65A, T65I.

Mutation set 2—any individual and/or any combination of the mutations listed in set 2a and set 2b. Set 2a—mutations in the CH1: Y180A, Y180G, Y180I, Y180N, Y180S, Y180T, Y180V, or Y180W, and/or S183N or S183T, and/or V188G; preferably, Y180T. Set 2b—mutations in the CKappa domain: A111R, A111T, A111W or A111V, and/or T109P; preferably: T109P and/or A111V; and/or mutations in the variable domain light (VL): I126A, I126G, I126H, I126N, I126P, I126Q, I126S, or I126T.

In one embodiment of the invention the mutations are at positions selected from the group consisting of:
(a) the T65 position in the VH (according to the IMGT numbering system); and/or
(b) one or more of the following positions in the CH1: Y180; S183; and V188, preferably Y180 (according to the EU numbering system); and/or
(c) one or more of the following positions in the CKappa domain: A111 and T109 (according to the EU or Kabat numbering systems); and/or
(d) the I126 position in the VL (according to the IMGT numbering system).

In a particular embodiment, the mutation is at the T65 position in the variable domain heavy (VH)(according to the IMGT numbering system).

In a particular embodiment, the mutations are one or more of the following positions in the CH1: Y180; S183; and V188, preferably Y180 (according to the EU numbering system).

In a particular embodiment, the mutations are one or more of the following positions in the CKappa domain: A111 and T109 (according to the EU numbering system); and/or the I126 position in the VL (according to the IMGT numbering system).

In one embodiment of the invention the mutations are selected from the group consisting of:
(a) X65E/A/I in the VH (according to the IMGT numbering system); and/or
(b) one or more of the following mutations in the CH1: X180A/G/I/N/S/T/V/W; X183N/T; and X188G; preferably, X180T (according to the EU numbering system); and/or
(c) one or more of the following mutations in the CKappa domain: X111R/T/W/V; and X109P, preferably X111V and X109P (according to the EU or Kabat numbering systems); and/or
(d) X126A/G/H/N/P/Q/S/T in the VL (according to the IMGT numbering system).

X refers to any amino acid

In a particular embodiment, the mutation is X65E/A/I in the VH (according to the IMGT numbering system).

X refers to any amino acid

In a particular embodiment, the mutation is one or more of the following mutations in the CH1: X180A/G/I/N/S/T/V/W; X183N/T; and X188G; preferably, X180T (according to the EU numbering system).

X refers to any amino acid

In a particular embodiment, the mutation is one or more of the following mutations in the CKappa domain: X111R/T/W/V; and X109P, preferably X111V and X109P (according to the EU or Kabat numbering systems); and/or the mutation is X126A/G/H/N/P/Q/S/T in the VL (according to the IMGT numbering system).

X refers to any amino acid

For example, the mutations may be selected from the group consisting of:
(a) one or more of the following mutations in the VH: T65E; T65A; and T65I (according to the IMGT numbering system); and/or
(b) one or more of the following mutations in the CH1: Y180A; Y180G; Y180I; Y180N; Y180S; Y180T; Y180V; Y180W; S183N; S183T; V188G, preferably Y180T (according to the EU numbering system); and/or
(c) one or more of the following mutations in the CKappa domain: A111R; A111T; A111W; A111V; and T109P, preferably T109P and A111V (according to the EU or Kabat numbering systems); and/or
(d) one or more of the following mutations in the VL: I126A; I126G; I126H; I126N; I126P; I126Q; I126S; and I126T (according to the IMGT numbering system).

In a particular example, the mutations are one or more of the following mutations in the VH: T65E; T65A; and T65I (according to the IMGT numbering system).

In a particular example, the mutations are one or more of the following mutations in the CH1: Y180A; Y180G; Y180I; Y180N; Y180S; Y180T; Y180V; Y180W; S183N; S183T; V188G, preferably Y180T (according to the EU numbering system).

In a particular example, the mutations are one or more of the following mutations in the CKappa domain: A111R; A111T; A111W; A111V; and T109P, preferably T109P and A111V (according to the EU or Kabat numbering systems); and/or one or more of the following mutations in the VL: I126A; I126G; I126H; I126N; I126P; I126Q; I126S; and I126T (according to the IMGT numbering system).

As discussed above, any combination of the "RUBY™ format" mutations and "optimised RUBY™ format" mutations can be used in the same bispecific polypeptide, such as any one or more of the following "RUBY™ format" mutations in (a) to (d), or variations described herein, being combined with any one or more of the following "optimised RUBY™ format" mutations in (e) to (g), or variations described herein:

(a) one or more of the following mutations in the CH1 domain: H168A, F170G and/or T187E (according to EU numbering system);
(b) one or more of the following mutations in the CKappa domain: L135Y, S176W, S114A and/or N137K (according to EU or Kabat numbering systems) and/or one or more of the following mutations in the CLambda domain: L135Y, S176W, T114A and/or S137K (according to Kabat numbering system);
(c) mutations in the VL: Q44R or Q44E (according to IMGT numbering system); and
(d) mutations in the VH: Q44E or Q44R (according to IMGT numbering system);
(e) mutations in the VH: T65E, T65A or T65I (according to IMGT numbering system);
(f) mutation in the CH1: Y180T (according to EU numbering system); and/or
(g) mutations in the CKappa: T109P and/or A111V (according to EU or Kabat numbering systems).

Accordingly, in a particular embodiment, a bispecific antibody with combined "RUBY™ format" mutations and "optimised RUBY™ format" mutations could include the following mutations:

one or more of the following mutations in the CH1 domain: H168A, F170G, Y180T and/or T187E (according to EU numbering system);
one or more of the following mutations in the CKappa domain: T109P, A111V, L135Y, S176W, S114A and/or N137K (according to EU or Kabat numbering systems) and/or one or more of the following mutations in the CLambda domain: L135Y, S176W, T114A and/or S137K (according to Kabat numbering system);
mutations in the VL: Q44R or Q44E (according to IMGT numbering system); and/or
one or more of the following mutations in the VH: Q44E or Q44R, and/or T65E, T65A or T65I (according to IMGT numbering system).

In one embodiment, the one or more Fab fragment(s) is linked to the C-terminal end of the immunoglobulin via a linker.

In one embodiment of the first aspect of the invention, the bispecific polypeptide is tetravalent, capable of binding bivalently to each of the two antigens.

In one embodiment, the bispecific polypeptide comprises an immunoglobulin arranged as an antibody with two arms and therefore two binding sites for the first antigen, and two of the Fab fragments, each providing a binding site for the second antigen. Thus, there are two binding sites for the first antigen and two binding sites for the second antigen. The bispecific polypeptide of this embodiment may comprise three polypeptide chains: (1) chain H1 which comprises the heavy chain of the IgG a linker and the light chain of a Fab; (2) chain L1 is the light chain for the IgG; and (3) chain H2 is the heavy chain for the appended (attached) Fab. In a preferred embodiment, the bispecific polypeptide may comprise six polypeptide chains: (a) two chain H1, which comprise the heavy chain of the IgG a linker and the light chain of a Fab; (b) two chain L1, which are the light chain for the IgG; and (c) two chain H2, which are the heavy chain for the appended (attached) Fab. This structure can be used for both the "RUBY™ format" and "optimised RUBY™ format" antibodies.

In one embodiment, binding domain B1 is an immunoglobulin and binding domain B2 is a Fab. In an alternative embodiment, binding domain B1 is a Fab and binding domain B2 is an immunoglobulin.

In one embodiment, the bispecific polypeptide may modulate the activity of and/or activate a target immune system cell, wherein said modulation is an increase or decrease in the activity of said cell. Such cells include T cells, dendritic cells and natural killer cells.

In another embodiment, the bispecific polypeptide may modulate the activity of and/or activate myeloid cells, such as macrophages, monocytes and myeloid-derived suppressor cells.

Monocytes and macrophages also express CD40 and may promote immune responses against tumors. Indeed, the murine anti-CD40 surrogate antibody FGK45 was shown to be capable of mediating anti-tumor activity involving macrophages, independent of T cell and NK cell function (Lum H D, Buhtoiarov I N, Schmidt B E, et al. In vivo CD40 ligation can induce T-cell-independent antitumor effects that involve macrophages. J Leukoc Biol. 2006 June; 79(6): 1181-92). However, the effects of CD40 agonists on macrophages and other myeloid cell populations also result in increased production of IFN-γ and CCL5, which promote improved influx of T cells to the tumor (Huffman A P, Lin J H, Kim S I, et al. CCL5 mediates CD40-driven CD4+ T cell tumor infiltration and immunity. JCI Insight. 2020 May 21; 5 (10)).

Several studies have indicated that CD40 agonist antibodies can convert TAM into activated macrophages with an anti-tumor phenotype. FGK45 interacts with TAM following treatment in vivo, and results in their increased expression of MHCII and CD86 (Beatty G L, Chiorean E G, Fishman M P, et al. CD40 agonists alter tumor stroma and show efficacy against pancreatic carcinoma in mice and humans. *Science*. 2011 Mar. 25; 331(6024):1612-6). Similar effects have been observed on CD11b+ F4/80+ macrophages in the spleen (Luheshi N M, Coates-Ulrichsen J, Harper J, et al. Transformation of the tumour microenvironment by a CD40 agonist antibody correlates with improved responses to PD-L1 blockade in a mouse orthotopic pancreatic tumour model. Oncotarget. 2016 Apr. 5; 7(14):18508-20), and the liver, where the treatment may result in hepatotoxicity due to the strong effect on macrophages (Byrne K T, Vonderheide R H. CD40 Stimulation Obviates Innate Sensors and Drives T Cell Immunity in Cancer. Cell Rep. 2016 Jun. 21; 15(12):2719-32; Medina-Echeverz J, Ma C, Duffy A G, et al. Systemic Agonistic Anti-CD40 Treatment of Tumor-Bearing Mice Modulates Hepatic Myeloid-Suppressive Cells and Causes Immune-Mediated Liver Damage. *Cancer Immunol Res*. 2015 May; 3(5):557-66). Interestingly, aged and obese mice were shown to be more susceptible to systemic toxicity after immunotherapy such as anti-CD40, and it was further demonstrated that macrophages were the cells primarily responsible for these effects (Bouchlaka M N, Sckisel G D, Chen M, et al. Aging predisposes to acute inflammatory induced pathology after tumor immunotherapy. *J Exp Med*. 2013 Oct. 21; 210(11):2223-37; Mirsoian A, Bouchlaka M N, Sckisel G D, et al. Adiposity induces lethal cytokine storm after systemic administration of stimulatory immunotherapy regimens in aged mice. *J Exp Med*. 2014 Nov. 17; 211(12):2373-83). Macrophage-mediated hepatotoxicity following anti-CD40 treatment was later shown to be alleviated by combination treatment with anti-CSF-1R antibody, which blocked CSF-1R signalling supporting differentiation, proliferation and function of monocytes and macrophages (Byrne K T, Vonderheide R H. CD40 Stimulation Obviates Innate Sensors and Drives T Cell Immunity in Cancer. Cell Rep. 2016 Jun. 21; 15(12):2719-32). Combination therapy with anti-CD40 and anti-CSF-1R is currently being explored in clinical studies (Machiels J P, Gomez-Roca C, Michot J M, et al. Phase Ib study of anti-CSF-1R antibody emactuzumab in combination with CD40 agonist selicrelumab in advanced solid tumor patients. J Immunother Cancer. 2020 October; 8(2)).

The immune system cell (for example, the target immune cell) is typically a dendritic cell. For example, the bispecific polypeptide may be capable of inducing activation of dendritic cells, which are then capable of internalising tumour associated debris or extracellular vesicles containing CEA and tumour neoantigens.

For example, the polypeptide may be capable of inducing:
(a) tumour-specific immune activation; and/or
(b) activation of dendritic cells; and/or
(c) internalisation of associated tumour debris and/or extracellular vesicles containing CEA as well as tumour neoantigens; and/or
(d) cross-presentation of peptides derived from internalised tumour antigens on MHC; and/or
(e) priming and activation of effector T cells; and/or
(f) direct tumoricidal effects, selected from the list consisting of: apoptosis, necroptosis, antibody-dependent cellular cytotoxicity (ADCC) and complement-dependent cytotoxicity (CDC).

It will be appreciated by persons skilled in the art, that said activation of dendritic cells may be an increase in the expression of the co-stimulatory molecules CD40, CD80 or CD86, or increased IL-12 production. Alternatively, activation of dendritic cells can be determined by the increased ability to cross-present antigens, e.g. tumour neoantigens, on MHC class I or II to T cells, generating an enhanced activation of T cells recognizing said antigen, by the antigen-presenting cell.

In one embodiment, the bispecific antibody induces an increase in the uptake of tumour debris or tumour extracellular vesicles by an antigen-presenting cell, such as a dendritic cell. It will be appreciated by persons skilled in the art, that said increase in uptake may be measured by the co-localization or internalization of the tumour debris or tumour extracellular vesicles by the antigen-presenting cell.

The increased uptake of tumour debris or tumour extracellular vesicles by the antigen-presenting cells would subsequently result in an effective presentation of neoantigens contained within the tumour debris or tumour extracellular vesicles in the context of MHC molecules, which in turn results in a broader tumor specific T cell repertoire and, thus, more effective T cell-mediated tumour eradication. Methods for determining the expansion of tumour-antigen specific T cells are well known and include, for example, the use of MHC-peptide multimers, e.g. tetramers or pentamers. Such expansion may be measured by inoculating mice with tumours expressing a specific tumour antigen or tumours transfected with a tumour model antigen (e.g., ovalbumin), alternatively by inoculating mice with the same cells that have been heat shocked to induce necrosis, followed by measuring the expansion of tumour antigen-specific T cells by use of various MHC-tumour (model) antigen peptide tetramers or pentamers by flow cytometry-based methods. Alternatively, such expansion may be measured by culturing dendritic cells with antigen-specific TCR transgenic T cells labelled with a proliferative dye and tumour debris or tumour-derived extracellular vesicles derived from tumours transfected with a model antigen (e.g., ovalbumin). Expansion of the antigen-specific T cells can be assessed by analysing dilution of the proliferative dye using flow cytometry.

The polypeptide or binding domains of the invention can also be characterised and defined by their binding abilities. Standard assays to evaluate the binding ability of ligands towards targets are well known in the art, including for example, ELISA, Western blot, RIA, and flow cytometry analysis. The binding kinetics (e.g., binding affinity) of the polypeptide can also be assessed by standard assays known in the art, such as by surface plasmon resonance analysis or bio-layer interferometry.

The terms "binding activity" and "binding affinity" are intended to refer to the tendency of a polypeptide molecule to bind or not to bind to a target. Binding affinity may be quantified by determining the dissociation constant ($K_D$) for a polypeptide and its target. A lower $K_D$ is indicative of a higher affinity for a target. Similarly, the specificity of binding of a polypeptide to its target may be defined in terms of the comparative dissociation constants ($K_D$) of the polypeptide for its target as compared to the dissociation constant with respect to the polypeptide and another, non-target molecule.

The value of this dissociation constant can be determined directly by well-known methods, and can be computed even for complex mixtures by methods such as those, for example, set forth in Caceci et al., 1984 (the disclosures of which are incorporated herein by reference). For example, the $K_D$ may be established using a double-filter nitrocellulose filter binding assay such as that disclosed by Wong & Lohman, 1993.

Other standard assays to evaluate the binding ability of ligands such as antibodies towards targets are known in the art, including for example, ELISA, Western blot, RIA, and flow cytometry analysis. The binding kinetics (e.g., binding affinity) of the polypeptide also can be assessed by standard assays known in the art, such as by surface plasmon resonance (by use of e.g., Biacore™ system analysis) or by bio-layer interferometry (by use of e.g. Octet® system analysis).

A competitive binding assay can be conducted in which the binding of the polypeptide to the target is compared to the binding of the target by another, known ligand of that target, such as another polypeptide. The concentration at which 50% inhibition occurs is known as the Ki. Under ideal conditions, the Ki is equivalent to $K_D$. The Ki value will never be less than the $K_D$, so measurement of Ki can conveniently be substituted to provide an upper limit for $K_D$.

Alternative measures of binding affinity include EC50 or IC50. In this context EC50 indicates the concentration at which a polypeptide achieves 50% of its maximum binding to a fixed quantity of target. IC50 indicates the concentration at which a polypeptide inhibits 50% of the maximum binding of a fixed quantity of competitor to a fixed quantity of target. In both cases, a lower level of EC50 or IC50 indicates a higher affinity for a target. The EC50 and IC50 values of a ligand for its target can both be determined by well-known methods, for example ELISA. Suitable assays to assess the EC50 and IC50 of polypeptides are set out in the Examples.

A polypeptide of the invention is preferably capable of binding to its target with an affinity that is at least two-fold, 10-fold, 50-fold, 100-fold or greater than its affinity for binding to another non-target molecule.

In one embodiment, the bispecific polypeptide is capable of:
  (a) activation of a B-cell, in the presence of a CEA (preferably CEACAM5); and/or
  (b) activation of dendritic cells in the presence of CEA (preferably CEACAM5); and/or
  (c) capable of increased dendritic cell cross-presentation of neoantigens; and/or
  (d) inducing proliferation of neoantigen specific T cells.

In one embodiment, the bispecific polypeptide promotes uptake of tumor derived material, derived from tumor cells overexpressing CEA (preferably CEACAM5). In a particular embodiment, the uptake of tumor derived material is by antigen presenting cells.

It will be appreciated by persons skilled in the art, that said activation of B-cell activation can be characterised by CD86 upregulation, as well as, optionally, other markers of B-cell activation.

CD40 Binding Domains

The bispecific polypeptides of the invention comprise a binding domain (B1) which is capable of specifically binding to CD40. Preferably, B1 is an agonistic CD40 binding domain.

Binding domain B1 specifically binds to CD40, i.e. it binds to CD40 but does not bind, or binds at a lower affinity, to other molecules. The term CD40, as used herein, typically refers to human CD40. The sequence of human CD40 is set out in GenBank: X60592.1.

Binding domain B1 may have some binding affinity for CD40 from other mammals, such as CD40 from a non-human primate (for example *Macaca fascicularis* (cynomolgus monkey), *Macaca mulatta*). Binding domain B1 preferably does not bind to murine CD40 and/or does not bind to other human TNFR superfamily members, for example human CD137 or OX40.

Advantageously, binding domain B1 binds to human CD40 with a $K_D$ of less than $2\times10^{-7}$M or less than $1.5\times10^{-7}$M or less than $8.5\times10^{-8}$M or less than $8\times10^{-8}$M or less than $7.5\times10^{-8}$M or less than $7\times10^{-8}$M or less than $9\times10^{-8}$M or less than $9\times10^{-9}$M or less than $5\times10^{-10}$M or less than $3\times10^{-10}$M, preferably less than $8.5\times10^{-8}$M, more preferably less than $5\times10^{-10}$M or less than $3\times10^{-10}$M. Preferably, the $K_D$ is measured in Octet; for example, as explained in the Examples.

For example, binding domain B1 preferably does not bind to murine CD40 or any other TNFR superfamily member, such as CD137 or OX40. Therefore, typically, the $K_D$ for the binding domain with respect to human CD40 will be 2-fold, preferably 5-fold, more preferably 10-fold less than $K_D$ with respect to the other, non-target molecules, such as murine CD40, other TNFR superfamily members, or any other unrelated material or accompanying material in the environment. More preferably, the $K_D$ will be 50-fold less, even more preferably 100-fold less, and yet more preferably 200-fold less.

Binding domain B1 is preferably capable of binding to its target with an affinity that is at least two-fold, 10-fold, 50-fold, 100-fold or greater than its affinity for binding to another non-target molecule.

In summary therefore, binding domain B1 preferably exhibits at least one of the following functional characteristics:
  a) binding to human CD40 with a $K_D$ value which is less than $2\times10^{-7}$M, more preferably less than $5\times10^{-10}$M;
  b) does not bind to murine CD40;
  c) does not bind to other human TNFR superfamily members, for example human CD137 or OX40.

In one embodiment, binding domain B1 comprises one or more light chain CDR sequences selected from those in Table C(2), and/or one or more heavy chain CDR sequences selected from Table C(1). Thus binding domain B1 may comprise one or more CDR sequences selected from the groups consisting of:
  (a) CD40 heavy chain CDRs, SEQ ID NOs: 73 to 89; and/or
  (b) CD40 light chain CDRs, SEQ ID NOs: 90 to 104.

In one embodiment binding domain B1 comprises one, two or three light chain CDR sequences from a particular row for an individual antibody reference in Table C(2), and/or one, two or three heavy chain CDR sequences from the corresponding row for the antibody with the same reference in Table C(1). For example, binding domain B1 might comprise one or more of the light chain CDR sequences for 1132 (SEQ ID NOs: 90 and 92, and AAS) and one or more of the heavy chain CDR sequences for 1132 (SEQ ID NOs: 73, 74 and 75), or binding domain B1 might comprise one or more of the light chain CDR sequences for 1132 (SEQ ID NOs: 96 and 98, and GNI) and one or more of the heavy chain CDR sequences for 1132 (SEQ ID NOs: 81, 82 and 83). Most preferably, B1 comprises the CDRs and/or the VL and VH of 1132. Also most preferably, B1 comprises the CDRs and/or the VL and VH of G12 or G12-mut.

The CDRs of G12-mut are shared by ffAC_05337. Accordingly, in a preferred embodiment B1 comprises the CDRs of ffAC_05337, which are SEQ ID NOs: 81-83 and 96-98.

Preferred CD40 binding domains may comprise at least a heavy chain CDR3 as defined in any individual row of Table C(1) and/or a light chain CDR3 as defined in in any individual row of Table C(2).

Accordingly, in one embodiment binding domain B1 comprises all six CDR sequences for a given antibody (VH/VL) reference, for example binding domain B1 might comprise all six CDR sequences of antibody 1132 or all six CDR sequences of antibody G12 (as also present in G12_mut and ffAC_05337).

In one embodiment, binding domain B1 comprises a VH and/or a VL amino acid sequence as given in Table A. In one embodiment, binding domain B1 comprises a VH and VL amino acid sequence as given in Table A for a particular antibody reference. For example, binding domain B1 may comprise the VH sequence of 1132 (SEQ ID NO: 3) and/or the VL sequence of 1132 (SEQ ID NO: 1), or the VH sequence of G12 (SEQ ID NO: 19) and/or the VL sequence of G12 (SEQ ID NO: 17), the VH sequence of G12-mut (SEQ ID NO: 29) and/or the VL sequence of G12_mut (SEQ ID NO: 17), the VH sequence of ffAC_05337 (SEQ ID NO: 431) and/or the VL sequence of ffAC_05337 (SEQ ID NO: 430).

In a preferred embodiment B1 comprises the VL and VH of ffAC_05337, which are SEQ ID NO: 430 and 431.

In one embodiment the CD40 binding domain of B1 is selected from: 1132; 1150, 1140, 1107, G12, APX005 and 21.4.1. Preferably, the CD40 binding domain of B1 is G12 and/or 1132. Most preferably, the CD40 binding domain of B1 is G12. In an alternative most preferred embodiment, the CD40 binding domain of B1 is G12_mut.

Thus, the CDR or VH and VL sequences of binding domain B1 might be selected from antibodies from the group consisting of:
  (a) 1132 (heavy chain CDRs: SEQ ID NOs: 73, 74 and 75; light chain CDRs: SEQ ID NOs: 90 and 92, and AAS; VL: SEQ ID NO: 1; VH: SEQ ID NO: 3)

(b) 1150 (heavy chain CDRs: SEQ ID NOs: 73, 76 and 77; light chain CDRs: SEQ ID NOs: 90 and 93, and AAS; VL: SEQ ID NO: 5; VH: SEQ ID NO: 7)

(c) 1140 (heavy chain CDRs: SEQ ID NOs: 73, 78 and 79; light chain CDRs: SEQ ID NOs: 90 and 94, and AAS; VL: SEQ ID NO: 9; VH: SEQ ID NO: 11)

(d) 1107 (heavy chain CDRs: SEQ ID NOs: 73, 78 and 80; light chain CDRs: SEQ ID NOs: 90 and 95, and AAS; VL: SEQ ID NO: 13; VH: SEQ ID NO: 15)

(e) G12 (heavy chain CDRs: SEQ ID NOs: 81, 82 and 83; light chain CDRs: SEQ ID NOs: 96 and 98, and GNI; VL: SEQ ID NO: 17; VH: SEQ ID NO: 19)

(f) APX005 (heavy chain CDRs: SEQ ID NOs: 84, 85 and 86; light chain CDRs: SEQ ID NOs: 99 and 101, and RAS; VL: SEQ ID NO: 21; VH: SEQ ID NO: 23)

(g) 21.4.1 (heavy chain CDRs: SEQ ID NOs: 87, 88 and 89; light chain CDRs: SEQ ID NOs: 102 and 104, and TAS; VL: SEQ ID NO: 25, VH: SEQ ID NO: 27)

(h) G12_mut (heavy chain CDRs: SEQ ID NOs: 81, 82 and 83; light chain CDRs: SEQ ID NOs: 96 and 98, and GNI; VL: SEQ ID NO: 17; VH: SEQ ID NO: 29)

(i) ffAC_05337 (heavy chain CDRs: SEQ ID NOs: 81, 82 and 83; light chain CDRs: SEQ ID NOs: 96 and 98, and GNI; VL: SEQ ID NO: 431; VH: SEQ ID NO: 430).

The numbering of the antibody (e.g. Antibody X/Y) defines the heavy chain variable region (X) and the light chain variable region (Y), respectively (or, where a single number is indicated, the heavy chain variable region [X] only is defined). As described above, the sequences may be one or more CDR sequence, or the VH and/or VL sequence. As described above, the sequences of the bispecific polypeptide may comprise specified mutations.

In one embodiment binding domain B1 is specific for CD40, typically human CD40 and may comprise any one, two, three, four, five or all six features independently selected from the following:

(a) a heavy chain CDR1 sequence which consists of the sequence "G, F, T, F, S, S, Y, A";

(b) a heavy chain CDR2 sequence which is 8 amino acids in length and comprises the consensus sequence: "I, G/S, S/G, Y/S, G/S, G/S, G/Y/S, T";

(c) a heavy chain CDR3 sequence which is 9 to 12 amino acids in length and which comprises the consensus sequence of: "A, R, Y/R/G, Y/P/V/–, N/S/V, F/Y/W, G/H/S, –/S, –/V, M/F, D, Y"

(d) a light chain CDR1 sequence which consists of the sequence: "Q, S, I, S, S, Y";

(e) a light chain CDR2 sequence which consists of the sequence: "A, A, S";

(f) a light chain CDR3 sequence which is 9 amino acids in length and comprises the consensus sequence: "Q, Q, Y/S, G/Y, R/S/V, N/A/Y/T, P, P/F/Y, T".

The use of "," in the context of discussing amino acid sequences is to illustrate a list of amino acids when further nomenclature, such as "/", is included; for example, "G, F, T, F, S, S, Y, A" indicates that the sequence of amino acids is GFTFSSYA and "A, R, Y/R/G" indicates that the sequence of amino acids could be ARY or ARR or ARG. The use of "–" in the context of discussing amino acid sequences is to illustrate that there might not be an amino acid present at that respective position; for example, "–/V, M/F, D" indicates that the sequence of amino acids could be VMD or VFD or MD or FD.

Binding domain B1 may comprise at least a heavy chain CDR3 as defined in (c) and/or a light chain CDR3 as defined in (f). Binding domain B1 may comprise all three heavy chain CDR sequences of (a), (b) and (c) and/or all three light chain CDR sequences of (d), (e) and (f).

Examples of complete heavy and light chain variable region amino acid sequences for binding domain B1 are shown in Table A. Exemplary nucleic acid sequences encoding each amino acid sequence are also shown. The numbering of said VH and VL regions in Table A corresponds to the numbering system used as in Table C(1) and C(2). Thus, for example, the amino acid sequence for "1132, light chain VL (also known as 1133)" is an example of a complete VL region sequence comprising all three CDRs of VL number 1132 (1133) shown in Table C(2) and the amino acid sequence for "1132, heavy chain VH" is an example of a complete VH region sequence comprising all three CDRs of VH number 1132 shown in Table C(1).

In exemplary embodiments, binding domain B1 comprises:

(a) the three CDRs of the heavy chain and/or the three CDRs of the light chain of antibody 1132/1133 (SEQ ID NOs: 73, 74 and 75; and/or SEQ ID NOs: 90 and 92, and AAS);

(b) the three CDRs of the heavy chain and/or the three CDRs of the light chain of antibody 1150/1151 (SEQ ID NOs: 73, 76 and 77; and/or SEQ ID NOs:90 and 93, and AAS);

(c) the three CDRs of the heavy chain and/or the three CDRs of the light chain of antibody 1140/1135 (SEQ ID NOs: 73, 78 and 79; and/or SEQ ID NOs: 90 and 94, and AAS);

(d) the three CDRs of the heavy chain and/or the three CDRs of the light chain of antibody 1107/1108 (SEQ ID NOs: 73, 78 and 80; and/or SEQ ID NOs: 90 and 95, and AAS);

(e) the three CDRs of the heavy chain and/or the three CDRs of the light chain of antibody G12 or G12_mut or ffAC_05337 (SEQ ID NOs: 81, 82 and 83; and/or SEQ ID NOs: 96 and 98, and GNI);

(f) the three CDRs of the heavy chain and/or the three CDRs of the light chain of antibody APX005 (SEQ ID NOs: 84, 85 and 86; and/or SEQ ID NOs: 99 and 101, and RAS); or (g) the three CDRs of the heavy chain and/or the three CDRs of the light chain of antibody 21.4.1 (SEQ ID NOs: 87, 88 and 89; and/or SEQ ID NOs: 102 and 104, and TAS).

Thus, binding domain B1 may comprise:

(a) the heavy chain variable region and/or the light chain variable region of antibody 1132/1133 (SEQ ID NO: 3 and/or SEQ ID NO: 1);

(b) the heavy chain variable region and/or the light chain variable region of antibody 1150/1151 (SEQ ID NO: 7 and/or SEQ ID NO: 5);

(c) the heavy chain variable region and/or the light chain variable region of antibody 1140/1135 (SEQ ID NO: 11 and/or SEQ ID NO: 9);

(d) the heavy chain variable region and/or the light chain variable region of antibody 1107/1108 (SEQ ID NO:15 and/or SEQ ID NO: 13);

(e) the heavy chain variable region and/or the light chain variable region of antibody G12 (SEQ ID NO: 19 and/or SEQ ID NO: 17);

(f) the heavy chain variable region and/or the light chain variable region of antibody APX005 (SEQ ID NO: 23 and/or SEQ ID NO: 21);

(g) the heavy chain variable region and/or the light chain variable region of antibody 21.4.1 (SEQ ID NO: 27 and/or SEQ ID NO: 25);

(h) the heavy chain variable region and/or the light chain variable region of antibody G12_mut (SEQ ID NO: 29 and/or SEQ ID NO: 17); or (h) the heavy chain variable region and/or the light chain variable region of antibody ffAC_05337 (SEQ ID NO: 431 and/or SEQ ID NO: 430).

In an exemplary embodiment, binding domain B1 comprises:

the three CDRs of the heavy chain and/or the three CDRs of the light chain of antibody 1132/1133 (SEQ ID NOs: 73, 74 and 75 and/or SEQ ID NOs: 90 and 92, and AAS), or the exemplary heavy and light chain variable regions (SEQ ID NO: 3 and SEQ ID NO: 1), or heavy and light antibody chains, which comprise said CDRs, as detailed above.

In a further exemplary embodiment, binding domain B1 comprises:

the three CDRs of the heavy chain and/or the three CDRs of the light chain of antibody G12 (SEQ ID NOs: 81, 82 and 83 and/or SEQ ID NOs: 96 and 98, and GNI), or the exemplary heavy and light chain variable regions (SEQ ID NO: 19 and SEQ ID NO: 17), or heavy and light antibody chains, which comprise said CDRs, as detailed above.

In a further exemplary embodiment, binding domain B1 comprises:

the three CDRs of the heavy chain and/or the three CDRs of the light chain of antibody G12_mut (SEQ ID NOs: 81, 82 and 83 and/or SEQ ID NOs: 96 and 98, and GNI), or the exemplary heavy and light chain variable regions (SEQ ID NO: 29 and SEQ ID NO: 17), or heavy and light antibody chains, which comprise said CDRs, as detailed above.

In a further, and preferred, exemplary embodiment, binding domain B1 comprises:

the three CDRs of the heavy chain and/or the three CDRs of the light chain of antibody ffAC_05337 (SEQ ID NOs: 81, 82 and 83 and/or SEQ ID NOs: 96 and 98, and GNI), or the exemplary heavy and light chain variable regions (SEQ ID NO: 431 and SEQ ID NO: 430), or heavy and light antibody chains, which comprise said CDRs, as detailed above.

The numbering of the antibody (e.g. Antibody X/Y) defines the heavy chain variable region (X) and the light chain variable region (Y), respectively (or, where a single number is indicated, the heavy chain variable region [X] only is defined).

It will be appreciated by persons skilled in the art that the bispecific polypeptides of the invention may alternatively comprise variants of the above-defined variable regions (or variants of the CDR sequences of the B1 and/or B2 binding domains).

A variant of any one of the heavy or light chain amino acid sequences or CDR sequences recited herein may be a substitution, deletion or addition variant of said sequence. A variant may comprise 1, 2, 3, 4, 5, up to 10, up to 20, up to 30 or more amino acid substitutions and/or deletions from the said sequence. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala, A | aliphatic, hydrophobic, neutral | Met, M | hydrophobic, neutral |
| Cys, C | polar, hydrophobic, neutral | Asn, N | polar, hydrophilic, neutral |
| Asp, D | polar, hydrophilic, charged (−) | Pro, P | hydrophobic, neutral |
| Glu, E | polar, hydrophilic, charged (−) | Gln, Q | polar, hydrophilic, neutral |
| Phe, F | aromatic, hydrophobic, neutral | Arg, R | polar, hydrophilic, charged (+) |
| Gly, G | aliphatic, neutral | Ser, S | polar, hydrophilic, neutral |
| His, H | aromatic, polar, hydrophilic, charged (+) | Thr, T | polar, hydrophilic, neutral |
| Ile, I | aliphatic, hydrophobic, neutral | Val, V | aliphatic, hydrophobic, neutral |
| Lys, K | polar, hydrophilic, charged (+) | Trp, W | aromatic, hydrophobic, neutral |
| Leu, L | aliphatic, hydrophobic, neutral | Tyr, Y | aromatic, polar, hydrophobic |

Amino acids herein may be referred to by full name, three letter code or single letter code.

Preferred "derivatives" or "variants" include those in which instead of the naturally occurring amino acid the amino acid which appears in the sequence is a structural analog thereof. Amino acids used in the sequences may also be derivatised or modified, e.g. labelled, providing the function of the polypeptide is not significantly adversely affected.

Derivatives and variants as described above may be prepared during synthesis of the polypeptide or by post-production modification, or when the polypeptide is in recombinant form using the known techniques of site-directed mutagenesis, random mutagenesis, or enzymatic cleavage and/or ligation of nucleic acids.

Preferably variants have an amino acid sequence which has more than 60%, or more than 70%, e.g. 75 or 80%, preferably more than 85%, e.g. more than 90 or 95% amino acid identity to a sequence as shown in the sequences disclosed herein. This level of amino acid identity may be seen across the full length of the relevant SEQ ID NO sequence or over a part of the sequence, such as across 20, 30, 50, 75, 100, 150, 200 or more amino acids, depending on the size of the full-length polypeptide.

In connection with amino acid sequences, "sequence identity" refers to sequences which have the stated value when assessed using ClustalW (Thompson et al., 1994; the disclosures of which are incorporated herein by reference) with the following parameters: Pairwise alignment parameters—Method: accurate, Matrix: PAM, Gap open penalty: 10.00, Gap extension penalty: 0.10.

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatised.

In one embodiment, binding domain B1 comprises the light chain of antibody 1132/1133 (SEQ ID NO: 372 or 379) and/or the heavy chain of antibody 1132/1133 (SEQ ID NO: 371 or 378).

In one embodiment, binding domain B1 comprises the light chain of antibody G12 (SEQ ID NO: 381) and/or the heavy chain of antibody G12 (SEQ ID NO: 380).

In one embodiment, binding domain B1 comprises the light chain of antibody G12_mut (SEQ ID NO: 383) and/or the heavy chain of antibody G12_mut (SEQ ID NO: 382).

It will be appreciated by the skilled person, and it is included herein, that mutations described herein for the RUBY™ format and/or the optimised RUBY™ format can be applied to the above light chain and/or the heavy chain sequences of G12 and/or G12_mut.

Thus, in one embodiment binding domain B1 may comprise one or more variants of the above-defined light chain variable regions and/or said heavy chain variable regions (and/or light chain and/or said heavy chain) having at least 90% sequence identity thereto or 95% sequence identity thereto or 99% sequence identity thereto. Binding domain B1 may also comprise variants of the CDR sequences specified herein, for example variants where up one, two, three, four or five amino acid residues are substituted, deleted to added compared to the specified reference sequences.

For reference, the antibody reference used in this application, possible alternative names for the same antibody/binding domain, and the target of the antibody/binding domain, is laid out in Table i below.

TABLE i

Alternative names for particular CD40 antibodies/binding domains

| Antibody reference | Alternative names |
|---|---|
| 1132 | 1132/1133 |
| 1150 | 1150/1151 |
| 1140 | 1140/1135 |
| 1107 | 1107/1108 |
| G12 | ADC-1013 |
| APX005 | |
| 21.4.1 | |
| G12_mut | |

The "G12_mut" antibody largely corresponds to the sequence of "G12"; however, G12_mut includes three mutations in the VH framework. The CDRs and the VL sequences of G12_mut are the same as the G12.

Accordingly, in a further independent aspect of the present invention is a polypeptide which is capable of binding specifically to CD40 comprising a heavy variable region comprising SEQ ID NO: 29 and/or a light chain variable region comprising SEQ ID NO: 17, preferably wherein the polypeptide is monospecific, further preferably wherein the polypeptide is an agonistic CD40 polypeptide, further preferably wherein the light chain comprises SEQ ID NO: 383 and/or the heavy chain comprises SEQ ID NO: 382, and further preferably wherein the polypeptide is the antibody G12_mut.

Embodiments of the other aspects of the invention (such as aspect one and/or aspect two) can be incorporated into this aspect of the invention, of the polypeptide capable of binding specifically to CD40 comprising a heavy variable region comprising SEQ ID NO: 29 and/or a light chain variable region comprising SEQ ID NO: 17.

Carcinoembryonic Antigen (CEA) Binders

The bispecific polypeptides of the invention further comprise a binding domain (B2) which is capable of specifically binding a carcinoembryonic antigen (CEA).

Binding domain B2 specifically binds to CEA, i.e. it binds to CEA but does not bind, or binds at a lower affinity, to other molecules. The term CEA, as used herein, typically refers to human CEA. Binding domain B2 may have some binding affinity for CEA from other mammals, such as CEA from a non-human primate (for example *Macaca fascicularis* (cynomolgus monkey), *Macaca mulatta*). Binding domain B2 preferably does not bind to non-target molecules, such as CTLA-4-Fc and/or human ubiquitin.

In one embodiment, the CEA is a tumor-associated CEA. By "tumor-associated CEA" we include a member of the CEA family whose presence and/or overexpression is correlated with the existence of cancer and/or tumours; for example, a CEA that is known or suspected to be overexpressed by cancer and/or tumour cells. Members of the CEA family that are associated with tumours and/or cancer would be known to the skilled person; for example, CEACAM1, CEACAM6, CEACAM7 and/or CEACAM5.

In one embodiment, the CEA is a carcinoembryonic antigen-related cell adhesion molecule (CEACAM).

In one embodiment, the CEACAM is one or more selected from the listing consisting of: CEACAM1 (such as, GenBank: NG_029051.2); CEACAM3 (such as, GenBank: D90278.1); CEACAM4 (such as, GenBank: D90276.1); CEACAM5 (such as, GenBank: M17303.1); CEACAM6 (such as, GenBank: M29541.1); CEACAM7 (such as, GenBank: L31792.1); CEACAM8 (such as, GenBank: X52378.1); CEACAM16 (such as, GenBank: EU021223.1); CEACAM18 (such as, GenBank: AC020914.9); CEACAM19 (such as, GenBank: BC083499.1); CEACAM20 (such as, GenBank: AY358129.1); and CEACAM21 (such as, GenBank: BC106727.1). It will be appreciated that the reference to the aforementioned CEACAM molecules includes splice variants.

Preferably, the CEACAM is one or more selected from the listing consisting of: CEACAM1; CEACAM5; and CEACAM6. Preferably, the CEACAM is CEACAM1. Most preferably, the CEACAM is CEACAM5.

In a preferred embodiment, B2 is capable of specifically binding to CEACAM5 but not other CEACAMs, particularly not CEACAM1.

In one embodiment, B2 which is capable of specifically binding to CEA on a target cell.

Preferably, the target cell is a cancer cell and/or a tumour cell.

Preferably, the CEA on the target cell is an intermediate level of CEA or a high level of CEA.

In one embodiment, the intermediate level of CEA expression is characterised by the target cell expressing about 10,000 or more CEA receptors per target cell; for example, about 11,000 or more; about 12,000 or more; about 13,000 or more; about 14,000 or more; about 15,000 or more; about 16,000 or more; about 17,000 or more; about 18,000 or more; about 19,000 or more; about 20,000 or more; about 25,000 or more; about 30,000 or more; about 35,000 or more; about 40,000 or more; about 50,000 or more; about 60,000 or more; about 70,000 or more; about 80,000 or more; about 90,000 or more; about 100,000 or more; about 125,000 or more; about 150,000 or more; or about 175,000 or more CEA receptors per target cell. In another embodiment, the intermediate level of CEA expression is characterised by the target cell expressing about 10,000 to about 200,000 CEA receptors per target cell; for example, about 20,000 to about 175,000 CEA receptors per target cell or 20,000 to about 200,000 CEA receptors per target cell or about 50,000 to about 175,000 CEA receptors per target cell or about 50,000 to about 200,000 CEA receptors per target cell. Preferably, the CEA receptors are CEACAM5 receptors.

In one embodiment, the high level of CEA expression is characterised by the target cell expressing about 200,000 or more CEA receptors per target cell; for example, about 225,000 or more; about 250,000 or more; about 275,000 or more; about 300,000 or more; about 325,000 or more; about 350,000 or more; about 375,000 or more; about 400,000 or more; about 425,000 or more; about 450,000 or more; about 475,000 or more; about 500,000 or more; about 600,000 or more; about 700,000 or more; about 800,000 or more; about 900,000 or more; or about 1,000,000 CEA receptors per target cell, preferably about 300,000 of more CEA receptors per target cell. In another embodiment, the high level of CEA expression is characterised by the target cell expressing about 200,000 to about 1,000,000 CEA receptors per target cell; for example, about 200,000 to about 500,000 CEA receptors per target cell or about 300,000 to about 500,000 CEA receptors per target cell. Preferably, the CEA receptors are CEACAM5 receptors.

In one embodiment, B2 is not capable of specifically binding to a cell with no CEA expression or a low level of CEA expression. In one embodiment, the low level of CEA expression is characterised by a cell expressing about 10,000 or fewer CEA receptors per cell; for example, about 9,000 or fewer; about 8,000 or fewer; about 7,000 or fewer; about 6,000 or fewer; about 5,000 or fewer; about 4,000 or fewer; about 3,000 or fewer; about 2,000 or fewer; or about 1,000 or fewer CEA receptors per cell.

Advantageously, binding domain B2 binds to human CEA with a $K_D$ of less than $2 \times 10^{-6}$M or less than $1.5 \times 10^{-8}$M or less than $2.5 \times 10^{-9}$M or less than $2 \times 10^{-9}$M or less than $1.5 \times 10^{-12}$M or less than $1 \times 10^{-12}$M, preferably less than $1.5 \times 10^{-8}$M or less than $2.5 \times 10^{-9}$M or less than $1.5 \times 10^{-12}$M. Preferably, the $K_D$ is measured in Octet; for example, as explained in the Examples.

For example, binding domain B2 preferably does not bind to non-target molecules, such as CTLA-4-Fc and/or human ubiquitin. In a particular embodiment relating to a specific CEACAM, the non-target molecule may be a different CEACAM; for example, for CEACAM5 the non-target molecule may be CEACAM, and vice versa. Therefore, typically, the $K_D$ for the binding domain with respect to human CEA will be 2-fold, preferably 5-fold, more preferably 10-fold less than $K_D$ with respect to the other, non-target molecules, such as CTLA-4-Fc and/or human ubiquitin or any other unrelated material or accompanying material in the environment. More preferably, the $K_D$ will be 50-fold less, even more preferably 100-fold less, and yet more preferably 200-fold less.

Binding domain B2 is preferably capable of binding to its target with an affinity that is at least two-fold, 10-fold, 50-fold, 100-fold or greater than its affinity for binding to another non-target molecule.

In summary therefore, binding domain B2 preferably exhibits at least one of the following functional characteristics:

a) binding to human CEA with a $K_D$ value which is less than $2 \times 10^{-6}$M, more preferably less than $2.5 \times 10^{-9}$M or less than $1.5 \times 10^{-12}$M, more preferably less than $1.5 \times 10^{-12}$M;

b) does not bind to non-target molecules, such as CTLA-4-Fc and/or human ubiquitin.

In one embodiment, binding domain B2 binds preferentially to CEA on a cell over soluble CEA. By "binds preferentially to CEA on a cell over soluble CEA", we include that when in the presence of CEA on a cell (such as, on the surface of a cell) and soluble CEA, B2 will be more likely to bind to CEA on the cell than the soluble CEA.

In one embodiment, binding domain B2 comprises one or more light chain CDR sequences selected from those in Table D(2) and/or one or more heavy chain CDR sequences selected from Table D(1a) and/or Table D(1b). Thus binding domain B2 may comprise one or more CDR sequences selected from the groups consisting of:

(a) CEA heavy chain CDRs, SEQ ID NOs: 216 to 310, 335; and/or (b) CEA light chain CDRs, SEQ ID NOs: 90, 94, 311 to 334, and AAS.

In one embodiment binding domain B2 comprises one, two or three light chain CDR sequences from a particular row for an individual antibody reference in Table D(2), and/or one, two or three heavy chain CDR sequences from the corresponding row for the antibody with the same reference in Table D(1a) and/or Table D(1b). For example, binding domain B2 might comprise one or more of the light chain CDR sequences for AC_05059 (SEQ ID NOs: 90 and 311, and AAS) and one or more of the heavy chain CDR sequences for AC_05059 (SEQ ID NOs: 216, 217, and 218 or 280, 281 and 218) or one or more of the light chain CDR sequences for AC_05060 (SEQ ID NOs: 312 and 313, and AAS) and one or more of the heavy chain CDR sequences for AC_05060 (SEQ ID NOs: 219, 220, and 221 or 282, 283 and 221) or one or more of the light chain CDR sequences for AC_05061 (SEQ ID NOs: 90 and 314, and AAS) and one or more of the heavy chain CDR sequences for AC_05061 (SEQ ID NOs: 222, 223 and 224 or 284, 285 and 224) or one or more of the light chain CDR sequences for AC_05062 (SEQ ID NOs: 315 and 94, and SAS) and one or more of the heavy chain CDR sequences for AC_05062 (SEQ ID NOs: 222, 223 and 225 or 284, 285 and 225) or one or more of the light chain CDR sequences for AC_05064 (SEQ ID NOs: 90 and 317, and AAS) and one or more of the heavy chain CDR sequences for AC_05064 (SEQ ID NOs: 222, 223 and 226 or 284, 285 and 226) or one or more of the light chain CDR sequences for AC_05079 (SEQ ID NOs: 90 and 311, and AAS) and one or more of the heavy chain CDR sequences for AC_05079 (SEQ ID NOs: 216, 217 and 227 or 280, 281 and 227) or one or more of the light chain CDR sequences for AC_05081 (SEQ ID NOs: 90 and 311, and AAS) and one or more of the heavy chain CDR sequences for AC_05081 (SEQ ID NOs: 216, 217 and 229 or 280, 281 and 229) or one or more of the light chain CDR sequences for AC_05088 (SEQ ID NOs: 90 and 311, and AAS) and one or more of the heavy chain CDR sequences for AC_05088 (SEQ ID NOs: 216, 217 and 237 or 280, 281 and 237) or one or more of the light chain CDR sequences for AC_05089 (SEQ ID NOs: 90 and 311, and AAS) and one or more of the heavy chain CDR sequences for AC_05089 (SEQ ID NOs: 216, 217, and 238 or 280, 281 and 238) or one or more of the light chain CDR sequences for AC_05090 (SEQ ID NOs: 90 and 311, and AAS) and one or more of the heavy chain CDR sequences for AC_05090 or ffAC_05337 (SEQ ID NOs: 216, 217 and 239 or 280, 281 and 239) or one or more of the light chain CDR sequences for AC_05091 (SEQ ID NOs: 90 and 311, and AAS) and one or more of the heavy chain CDR sequences for AC_05091 (SEQ ID NOs: 216, 217 and 240 or 280, 281 and 240) or one or more of the light chain CDR sequences for AC_05093 (SEQ ID NOs: 90 and 311, and AAS) and one or more of the heavy chain CDR sequences for AC_05093 (SEQ ID NOs: 216, 217 and 241 or 280, 281 and 241) or one or more of the light chain CDR sequences for AC_05094 (SEQ ID NOs: 90 and 311, and AAS) and one or more of the heavy chain CDR sequences for AC_05094 (SEQ ID NOs: 216, 217 and 242 or 280, 281 and 242) or one or more of the light chain CDR sequences for AC_05096 (SEQ ID NOs: 90 and 311, and AAS) and one or more of the heavy chain CDR sequences for AC_05096 (SEQ ID NOs: 216, 217 and 244 or 280, 281 and 244) or one or more of the light chain CDR sequences for AC_05097 (SEQ ID NOs: 90 and 311, and AAS) and one or more of the heavy chain CDR sequences for AC_05097 (SEQ ID NOs: 216, 217 and 245 or 280, 281 and 245) or one or more of the light chain CDR sequences for Fab1 (SEQ ID NOs: 90 and 322, and AAS) and one or more of the heavy chain CDR sequences for Fab1 (SEQ ID NOs: 248, 249 and 250 or 289, 290 and 250) or one or more of the light chain CDR sequences for Fab3 (SEQ ID NOs: 324 and 326, and GAS) and one or more of the heavy chain CDR sequences for Fab3 (SEQ ID NOs: 254, 255 and 256 or 293, 294 and 256). Most preferably, B2 comprises the CDRs and/or the VL and VH of AC_05088, AC_05090/ ffAC_05337, AC_05093, AC_05097, Fab1, and/or Fab3.

As explained further in the Examples, the references to exemplary B2 polypeptides (such as "Fab1") are nomenclature based on the libraries from which the particular binders were identified, and are not specific references to particular types, or fragments, of antibodies. To put another way, "Fab1" is not necessarily a Fab fragment. Accordingly, the CDRs, VL and VH amino acid sequences defined for each of the exemplary B2 polypeptides can be used in any compatible antibody format, or fragment thereof.

Preferred CEA binding domains may comprise at least a heavy chain CDR3 as defined in any individual row of Table D(1a) and/or a light chain CDR3 as defined in in any individual row of Table D(2).

Accordingly, in one embodiment binding domain B2 comprises all six CDR sequences for a given antibody (VH/VL) reference, for example binding domain B2 might comprise all six CDR sequences of an antibody selected from the list consisting of: AC_05059; AC_05060; AC_05061; AC_05062; AC_05064; AC_05079; AC_05080; AC_05081; AC_05082; AC_05083; AC_05084; AC_05085; AC_05086; AC_05087; AC_05088; AC_05089; AC_05090; AC_05091; AC_05092; AC_05093; AC_05094; AC_05095; AC_05096; AC_05097; AC_05098; AC_05099; AC_05100; Fab1; Fab2; Fab3; Fab4; Fab5; Fab6; Fab7; Fab8; Fab9; Fab10; Fab11; ffAC_05337 and mAb2, preferably: AC_05059; AC_05060; AC_05061; AC_05062; AC_05064; AC_05079; AC_05081; AC_05088; AC_05089; AC_05090; AC_05091; AC_05093; AC_05094; AC_05096; AC_05097; Fab1; ffAC_05337 and Fab3, most preferably AC_05088; AC_05090; the CEA binding domain of ffAC_05337; AC_05093; AC_05097; Fab1; and Fab3.

In one embodiment, binding domain B2 comprises a VH and/or a VL amino acid sequence as given in Table B. In one embodiment, binding domain B2 comprises a VH and VL amino acid sequence as given in Table B for a particular antibody reference. For example, binding domain B2 may comprise the VH sequence of AC_05059 (SEQ ID NO: 33) and/or the VL sequence of AC_05059 (SEQ ID NO: 31) or binding domain B2 may comprise the VH sequence of AC_05060 (SEQ ID NO: 37) and/or the VL sequence of AC_05060 (SEQ ID NO: 35) or binding domain B2 may comprise the VH sequence of AC_05062 (SEQ ID NO: 45) and/or the VL sequence of AC_05062 (SEQ ID NO: 43) or binding domain B2 may comprise the VH sequence of AC_05064 (SEQ ID NO: 49) and/or the VL sequence of AC_05064 (SEQ ID NO: 47) or binding domain B2 may comprise the VH sequence of AC_05079 (SEQ ID NO: 53) and/or the VL sequence of AC_05079 (SEQ ID NO: 51) or binding domain B2 may comprise the VH sequence of AC_05081 (SEQ ID NO: 61) and/or the VL sequence of AC_05081 (SEQ ID NO: 59) or binding domain B2 may comprise the VH sequence of AC_05088 (SEQ ID NO: 122) and/or the VL sequence of AC_05088 (SEQ ID NO: 120) or binding domain B2 may comprise the VH sequence of AC_05089 (SEQ ID NO: 126) and/or the VL sequence of AC_05089 (SEQ ID NO: 124) or binding domain B2 may comprise the VH sequence of AC_05090 (SEQ ID NO: 130) and/or the VL sequence of AC_05090 (SEQ ID NO: 128) or binding domain B2 may comprise the VH sequence of AC_05091 (SEQ ID NO: 134) and/or the VL sequence of AC_05091 (SEQ ID NO: 132) or binding domain B2 may comprise the VH sequence of AC_05093 (SEQ ID NO: 142) and/or the VL sequence of AC_05093 (SEQ ID NO: 140) or binding domain B2 may comprise the VH sequence of AC_05094 (SEQ ID NO: 146) and/or the VL sequence of AC_05094 (SEQ ID NO: 144) or binding domain B2 may comprise the VH sequence of AC_05096 (SEQ ID NO: 154) and/or the VL sequence of AC_05096 (SEQ ID NO: 152) or binding domain B2 may comprise the VH sequence of AC_05097 (SEQ ID NO: 158) and/or the VL sequence of AC_05097 (SEQ ID NO: 156) or binding domain B2 may comprise the VH sequence of Fab1 (SEQ ID NO: 174) and/or the VL sequence of Fab1 (SEQ ID NO: 172) or binding domain B2 may comprise the VH sequence of Fab3 (SEQ ID NO: 182) and/or the VL sequence of Fab3 (SEQ ID NO: 180) or binding domain B2 may comprise the VH sequence of ffAC_05337 (SEQ ID NO: 433) and/or the VL sequence of ffAC_05337 (SEQ ID NO: 432).

In one embodiment the CEA binding domain of B2 is selected from: AC_05059; AC_05060; AC_05061; AC_05062; AC_05064; AC_05079; AC_05080; AC_05081; AC_05082; AC_05083; AC_05084; AC_05085; AC_05086; AC_05087; AC_05088; AC_05089; AC_05090; AC_05091; AC_05092; AC_05093; AC_05094; AC_05095; AC_05096; AC_05097; AC_05098; AC_05099; AC_05100; Fab1; Fab2; Fab3; Fab4; Fab5; Fab6; Fab7; Fab8; Fab9; Fab10; Fab11; the CEA binding domain of ffAC_05337 and mAb2, preferably: AC_05059; AC_05060; AC_05061; AC_05062; AC_05064; AC_05079; AC_05081; AC_05088; AC_05089; AC_05090; AC_05091; AC_05093; AC_05094; AC_05096; AC_05097; Fab1; the CEA binding domain of ffAC_05337; and Fab3, most preferably AC_05088; AC_05090; the CEA binding domain of ffAC_05337; AC_05093; AC_05097; Fab1; and Fab3.

Thus, the CDR or VH and VL sequences of binding domain B2 might be selected from antibodies from the group consisting of:
(a) AC_05059 (heavy chain CDRs: SEQ ID NOs: 216, 217 and 218 or 280, 281 and 218; light chain CDRs: SEQ ID NOs: 90 and 311, and AAS; VL: SEQ ID NO: 31; VH: SEQ ID NO: 33)
(b) AC_05060 (heavy chain CDRs: SEQ ID NOs: 219, 220 and 221 or 282, 283 and 221; light chain CDRs: SEQ ID NOs: 312 and 313, and AAS; VL: SEQ ID NO: 35; VH: SEQ ID NO: 37)

(c) AC_05061 (heavy chain CDRs: SEQ ID NOs: 222, 223 and 224 or 284, 285 and 224; light chain CDRs: SEQ ID NOs: 90 and 314, and AAS; VL: SEQ ID NO: 39; VH: SEQ ID NO: 41)

(d) AC_05062 (heavy chain CDRs: SEQ ID NOs: 222, 223 and 225 or 284, 285 and 225; light chain CDRs: SEQ ID NOs: 315 and 94, and SAS; VL: SEQ ID NO: 43; VH: SEQ ID NO: 45)

(e) AC_05064 (heavy chain CDRs: SEQ ID NOs: 222, 223 and 226 or 284, 285 and 226; light chain CDRs: SEQ ID NOs: 90 and 317, and AAS; VL: SEQ ID NO: 47; VH: SEQ ID NO: 49)

(f) AC_05079 (heavy chain CDRs: SEQ ID NOs: 216, 217 and 227 or 280, 281 and 227; light chain CDRs: SEQ ID NOs: 90 and 311, and AAS; VL: SEQ ID NO: 51; VH: SEQ ID NO: 53)

(g) AC_05080 (heavy chain CDRs: SEQ ID NOs: 216, 217 and 228 or 280, 281 and 228; light chain CDRs: SEQ ID NOs: 90 and 311, and AAS; VL: SEQ ID NO: 55; VH: SEQ ID NO: 57)

(h) AC_05081 (heavy chain CDRs: SEQ ID NOs: 216, 217 and 229 or 280, 281 and 229; light chain CDRs: SEQ ID NOs: 90 and 311, and AAS; VL: SEQ ID NO: 59; VH: SEQ ID NO: 61)

(i) AC_05082 (heavy chain CDRs: SEQ ID NOs: 222, 223 and 230 or 284, 285 and 230; light chain CDRs: SEQ ID NOs: 90 and 311, and AAS; VL: SEQ ID NO: 63; VH: SEQ ID NO: 65)

(j) AC_05083 (heavy chain CDRs: SEQ ID NOs: 222, 223 and 231 or 284, 285 and 231; light chain CDRs: SEQ ID NOs: 318 and 319, and AAS; VL: SEQ ID NO: 67; VH: SEQ ID NO: 69)

(k) AC_05084 (heavy chain CDRs: SEQ ID NOs: 222, 223 and 232 or 284, 285 and 232; light chain CDRs: SEQ ID NOs: 90 and 320, and AAS; VL: SEQ ID NO: 71; VH: SEQ ID NO: 106)

(l) AC_05085 (heavy chain CDRs: SEQ ID NOs: 219, 233 and 234 or 286, 287 and 234; light chain CDRs: SEQ ID NOs: 90 and 311, and AAS; VL: SEQ ID NO: 108; VH: SEQ ID NO: 110)

(m) AC_05086 (heavy chain CDRs: SEQ ID NOs: 216, 217 and 235 or 280, 281 and 235; light chain CDRs: SEQ ID NOs: 90 and 311, and AAS; VL: SEQ ID NO: 112; VH: SEQ ID NO: 114)

(n) AC_05087 (heavy chain CDRs: SEQ ID NOs: 216, 217 and 236 or 280, 281 and 236; light chain CDRs: SEQ ID NOs: 90 and 311, and AAS; VL: SEQ ID NO: 116; VH: SEQ ID NO: 118)

(o) AC_05088 (heavy chain CDRs: SEQ ID NOs: 216, 217 and 237 or 280, 281 and 237; light chain CDRs: SEQ ID NOs: 90 and 311, and AAS; VL: SEQ ID NO: 120; VH: SEQ ID NO: 122)

(p) AC_05089 (heavy chain CDRs: SEQ ID NOs: 216, 217 and 238 or 280, 281 and 238; light chain CDRs: SEQ ID NOs: 90 and 311, and AAS; VL: SEQ ID NO: 124; VH: SEQ ID NO: 126)

(q) AC_05090 (heavy chain CDRs: SEQ ID NOs: 216, 217 and 239 or 280, 281 and 239; light chain CDRs: SEQ ID NOs: 90 and 311, and AAS; VL: SEQ ID NO: 128; VH: SEQ ID NO: 130)

(r) AC_05091 (heavy chain CDRs: SEQ ID NOs: 216, 217 and 240 or 280, 281 and 240; light chain CDRs: SEQ ID NOs: 90 and 311, and AAS; VL: SEQ ID NO: 132; VH: SEQ ID NO: 134)

(s) AC_05092 (heavy chain CDRs: SEQ ID NOs: 216, 217 and 218 or 280, 281 and 218; light chain CDRs: SEQ ID NOs: 321 and 311, and AAS; VL: SEQ ID NO: 136; VH: SEQ ID NO: 138)

(t) AC_05093 (heavy chain CDRs: SEQ ID NOs: 216, 217 and 241 or 280, 281 and 241; light chain CDRs: SEQ ID NOs: 90 and 311, and AAS; VL: SEQ ID NO: 140; VH: SEQ ID NO: 142)

(u) AC_05094 (heavy chain CDRs: SEQ ID NOs: 216, 217 and 242 or 280, 281 and 242; light chain CDRs: SEQ ID NOs: 90 and 311, and AAS; VL: SEQ ID NO: 144; VH: SEQ ID NO: 146)

(v) AC_05095 (heavy chain CDRs: SEQ ID NOs: 216, 217 and 243 or 280, 281 and 243; light chain CDRs: SEQ ID NOs: 90 and 311, and AAS; VL: SEQ ID NO: 148; VH: SEQ ID NO: 150)

(w) AC_05096 (heavy chain CDRs: SEQ ID NOs: 216, 217 and 244 or 280, 281 and 244; light chain CDRs: SEQ ID NOs: 90 and 311, and AAS; VL: SEQ ID NO: 152; VH: SEQ ID NO: 154)

(x) AC_05097 (heavy chain CDRs: SEQ ID NOs: 217, 216 and 245 or 280, 281 and 245; light chain CDRs: SEQ ID NOs: 90 and 311, and AAS; VL: SEQ ID NO: 156; VH: SEQ ID NO: 158)

(y) AC_05098 (heavy chain CDRs: SEQ ID NOs: 219, 220 and 246 or 282, 283 and 246; light chain CDRs: SEQ ID NOs: 312 and 313, and AAS; VL: SEQ ID NO: 160; VH: SEQ ID NO: 162)

(z) AC_05099 (heavy chain CDRs: SEQ ID NOs: 222, 223 and 224 or 288, 285 and 224; light chain CDRs: SEQ ID NOs: 90 and 311, and AAS; VL: SEQ ID NO: 164; VH: SEQ ID NO: 166)

(aa) AC_05100 (heavy chain CDRs: SEQ ID NOs: 222, 223 and 247 or 288, 285 and 247; light chain CDRs: SEQ ID NOs: 90 and 311, and AAS; VL: SEQ ID NO: 168; VH: SEQ ID NO: 170)

(ab) Fab1 (heavy chain CDRs: SEQ ID NOs: 248, 249 and 250 or 289, 290 and 250; light chain CDRs: SEQ ID NOs: 90 and 322, and AAS; VL: SEQ ID NO: 172; VH: SEQ ID NO: 174)

(ac) Fab2 (heavy chain CDRs: SEQ ID NOs: 251, 252 and 253 or 291, 292 and 253; light chain CDRs: SEQ ID NOs: 90 and 323, and AAS; VL: SEQ ID NO: 176; VH: SEQ ID NO: 178)

(ad) Fab3 (heavy chain CDRs: SEQ ID NOs: 254, 255 and 256 or 293, 294 and 256; light chain CDRs: SEQ ID NOs: 324 and 326, and GAS; VL: SEQ ID NO: 180; VH: SEQ ID NO: 182)

(ae) Fab4 (heavy chain CDRs: SEQ ID NOs: 257, 258 and 259 or 295, 296 and 259; light chain CDRs: SEQ ID NOs: 90 and 327, and AAS; VL: SEQ ID NO: 184; VH: SEQ ID NO: 186)

(af) Fab5 (heavy chain CDRs: SEQ ID NOs: 260, 261 and 262 or 297, 298 and 262; light chain CDRs: SEQ ID NOs: 324 and 328, and GAS; VL: SEQ ID NO: 188; VH: SEQ ID NO: 190)

(ag) Fab6 (heavy chain CDRs: SEQ ID NOs: 263, 264 and 265 or 299, 300 and 265; light chain CDRs: SEQ ID NOs: 324 and 329, and GAS; VL: SEQ ID NO: 192; VH: SEQ ID NO: 194)

(ah) Fab7 (heavy chain CDRs: SEQ ID NOs: 266, 267 and 268 or 301, 302 and 268; light chain CDRs: SEQ ID NOs: 90 and 330, and AAS; VL: SEQ ID NO: 196; VH: SEQ ID NO: 198)

(ai) Fab8 (heavy chain CDRs: SEQ ID NOs: 269, 270 and 271 or 303, 304 and 271; light chain CDRs: SEQ ID NOs: 90 and 331, and AAS; VL: SEQ ID NO: 200; VH: SEQ ID NO: 202)

(aj) Fab9 (heavy chain CDRs: SEQ ID NOs: 272, 335 and 273 or 305, 306 and 273; light chain CDRs: SEQ ID NOs: 90 and 332, and AAS; VL: SEQ ID NO: 204; VH: SEQ ID NO: 206)

(ak) Fab10 (heavy chain CDRs: SEQ ID NOs: 274, 275 and 276 or 307, 308 and 276; light chain CDRs: SEQ ID NOs: 90 and 333, and AAS; VL: SEQ ID NO: 208; VH: SEQ ID NO: 210)

(al) Fab11 (heavy chain CDRs: SEQ ID NOs: 277, 278 and 279 or 309, 310 and 279; light chain CDRs: SEQ ID NOs: 324 and 334, and GAS; VL: SEQ ID NO: 212; VH: SEQ ID NO: 214) and/or (am) ffAC_05337 (heavy chain CDRs: SEQ ID NOs: 216, 217 and 239; light chain CDRs: SEQ ID NOs: 90 and 311, and AAS; VL: SEQ ID NO: 432; VH: SEQ ID NO: 433), preferably (am) ffAC_05337 (heavy chain CDRs: SEQ ID NOs: 216, 217 and 239; light chain CDRs: SEQ ID NOs: 90 and 311, and AAS; VL: SEQ ID NO: 432; VH: SEQ ID NO: 433).

The numbering of the antibody (e.g. Antibody X/Y) defines the heavy chain variable region (X) and the light chain variable region (Y), respectively (or, where a single number is indicated, the heavy chain variable region [X] only is defined). As described above, the sequences may be one or more CDR sequence, or the VH and/or VL sequence. As described above, the sequences of the bispecific polypeptide may comprise specified mutations.

A variant of any one of the heavy or light chain amino acid sequences or CDR sequences recited herein may be a substitution, deletion or addition variant of said sequence. A variant may comprise 1, 2, 3, 4, 5, up to 10, up to 20, up to 30 or more amino acid substitutions and/or deletions from the said sequence. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala, A | aliphatic, hydrophobic, neutral | Met, M | hydrophobic, neutral |
| Cys, C | polar, hydrophobic, neutral | Asn, N | polar, hydrophilic, neutral |
| Asp, D | polar, hydrophilic, charged (-) | Pro, P | hydrophobic, neutral |
| Glu, E | polar, hydrophilic, charged (-) | Gln, Q | polar, hydrophilic, neutral |
| Phe, F | aromatic, hydrophobic, neutral | Arg, R | polar, hydrophilic, charged (+) |
| Gly, G | aliphatic, neutral | Ser, S | polar, hydrophilic, neutral |
| His, H | aromatic, polar, hydrophilic, charged (+) | Thr, T | polar, hydrophilic, neutral |
| Ile, I | aliphatic, hydrophobic, neutral | Val, V | aliphatic, hydrophobic, neutral |
| Lys, K | polar, hydrophilic, charged (+) | Trp, W | aromatic, hydrophobic, neutral |
| Leu, L | aliphatic, hydrophobic, neutral | Tyr, Y | aromatic, polar, hydrophobic |

Amino acids herein may be referred to by full name, three letter code or single letter code.

Preferred "derivatives" or "variants" include those in which instead of the naturally occurring amino acid the amino acid which appears in the sequence is a structural analog thereof. Amino acids used in the sequences may also be derivatised or modified, e.g. labelled, providing the function of the polypeptide is not significantly adversely affected.

Derivatives and variants as described above may be prepared during synthesis of the polypeptide or by post-production modification, or when the polypeptide is in recombinant form using the known techniques of site-directed mutagenesis, random mutagenesis, or enzymatic cleavage and/or ligation of nucleic acids.

Preferably variants have an amino acid sequence which has more than 60%, or more than 70%, e.g. 75 or 80%, preferably more than 85%, e.g. more than 90 or 95% amino acid identity to a sequence as shown in the sequences disclosed herein. This level of amino acid identity may be seen across the full length of the relevant SEQ ID NO sequence or over a part of the sequence, such as across 20, 30, 50, 75, 100, 150, 200 or more amino acids, depending on the size of the full-length polypeptide.

In one embodiment binding domain B2 is specific for CEA, typically human CEA and may comprise any one, two, three, four, five or all six features independently selected from the following:

(a) a heavy chain CDR1 sequence which consists of the sequence: "G, F, T, F, S, S, S, Y" or which comprises the consensus sequence of: "G, F, T, F, G/S, S, Y, Y/A";

(b) a heavy chain CDR2 sequence which consists of the sequence: "I, G, S, G, S, Y, S, T" or which comprises the consensus sequence of: "I, S, G, Y/S, G, Y/G, S, T";

(c) a heavy chain CDR3 sequence which comprises the consensus sequence of: "A, R, Y, P, S, V, P/L, F, P, Q, S, P/H/L, H/P/L, L/F/V/W, D, Y" or which comprises the consensus sequence of: "A, R, H/Y, G, Y, G/S/T, V/H, L/F, D, Y";

(d) a light chain CDR1 sequence which consists of the sequence: "Q, S, I, S, S, Y" or which comprises the consensus sequence of: "Q, S, I, R/S, S, Y";

(e) a light chain CDR2 sequence which consists of the sequence: "A, A, S";

(f) a light chain CDR3 sequence which consists of the sequence: "Q, Q, A, G, N, P, H, T" or which comprises the consensus sequence of: "Q, Q, G/Y, T/P/A, W/−, Y/−, F/V, P, F/Y, T".

In an alternative embodiment binding domain B2 is specific for CEA, typically human CEA and may comprise any one, two, three, four, five or all six features independently selected from the following:

(a) a heavy chain CDR1 sequence which consists of the sequence: "G, F, T, F, S, S, S, Y";

(b) a heavy chain CDR2 sequence which consists of the sequence: "I, G, S, G, S, Y, S, T";

(c) a heavy chain CDR3 sequence which comprises the consensus sequence of: "A, R, Y, P, S, V, P/L, F, P, Q, S, P/H/L, H/P/L, L/F/V/W, D, Y";

(d) a light chain CDR1 sequence which consists of the sequence: "Q, S, I, S, S, Y";
(e) a light chain CDR2 sequence which consists of the sequence: "A, A, S";
(f) a light chain CDR3 sequence which consists of the sequence: "Q, Q, A, G, N, P, H, T". Binding domain B2 may comprise at least a heavy chain CDR3 as defined in (c) of this embodiment and/or a light chain CDR3 as defined in (f). Binding domain B2 may comprise all three heavy chain CDR sequences of (a), (b) and (c) and/or all three light chain CDR sequences of (d), (e) and (f).

In a further alternative embodiment binding domain B2 is specific for CEA, typically human CEA and may comprise any one, two, three, four, five or all six features independently selected from the following:
(a) a heavy chain CDR1 sequence which comprises the consensus sequence of: "G, F, T, F, G/S, S, Y, Y/A";
(b) a heavy chain CDR2 sequence which comprises the consensus sequence of: "I, S, G, Y/S, G, Y/G, S, T";
(c) a heavy chain CDR3 sequence which comprises the consensus sequence of: "A, R, H/Y, G, Y, G/S/T, V/H, L/F, D, Y";
(d) a light chain CDR1 sequence which comprises the consensus sequence of: "Q, S, I, R/S, S, Y";
(e) a light chain CDR2 sequence which consists of the sequence: "A, A, S";
(f) a light chain CDR3 sequence which comprises the consensus sequence of: "Q, Q, G/Y, T/P/A, W/–, Y/–, F/V, P, F/Y, T".

Binding domain B2 may comprise at least a heavy chain CDR3 as defined in (c) of this embodiment and/or a light chain CDR3 as defined in (f). Binding domain B2 may comprise all three heavy chain CDR sequences of (a), (b) and (c) and/or all three light chain CDR sequences of (d), (e) and (f).

Examples of complete heavy and light chain variable region amino acid sequences for binding domain B2 are shown in Table B. Exemplary nucleic acid sequences encoding each amino acid sequence are also shown. The numbering of said VH and VL regions in Table B corresponds to the numbering system used as in Table D(1a), Table D(1b) and/or Table D(2). Thus, for example, the amino acid sequence for "AC_05088, light chain VL" is an example of a complete VL region sequence comprising all three CDRs of VL number AC_05088 shown in Table D(2) and the amino acid sequence for "AC_05088, heavy chain VH" is an example of a complete VH region sequence comprising all three CDRs of VH number AC_05088 shown in Table D(1a) and/or Table D(1b).

In exemplary embodiments, binding domain B2 comprises:
(a) the three CDRs of the heavy chain and/or the three CDRs of the light chain of antibody AC_05059 (SEQ ID NOs: 216, 217 and 218 or 280, 281 and 218 and/or SEQ ID NOs: 90 and 311, and AAS)
(b) the three CDRs of the heavy chain and/or the three CDRs of the light chain of antibody AC_05060 (SEQ ID NOs: 219, 220 and 221 or 282, 283 and 221 and/or SEQ ID NOs: 312 and 313, and AAS)
(c) the three CDRs of the heavy chain and/or the three CDRs of the light chain of antibody AC_05061 (SEQ ID NOs: 222, 223 and 224 or 284, 285 and 224 and/or SEQ ID NOs: 90 and 314, and AAS)
(d) the three CDRs of the heavy chain and/or the three CDRs of the light chain of antibody AC_05062 (SEQ ID NOs: 222, 223 and 225 or 284, 285 and 225 and/or SEQ ID NOs: 315 and 94, and SAS)
(e) the three CDRs of the heavy chain and/or the three CDRs of the light chain of antibody AC_05064 (SEQ ID NOs: 222, 223 and 226 or 284, 285 and 226 and/or SEQ ID NOs: 90 and 317, and AAS)
(f) the three CDRs of the heavy chain and/or the three CDRs of the light chain of antibody AC_05079 (SEQ ID NOs: 216, 217 and 227 or 280, 281 and 227 and/or SEQ ID NOs: 90 and 311, and AAS)
(g) the three CDRs of the heavy chain and/or the three CDRs of the light chain of antibody AC_05080 (SEQ ID NOs: 216, 217 and 228 or 280, 281 and 228 and/or SEQ ID NOs: 90 and 311, and AAS)
(h) the three CDRs of the heavy chain and/or the three CDRs of the light chain of antibody AC_05081 (SEQ ID NOs: 216, 217 and 229 or 280, 281 and 229 and/or SEQ ID NOs: 90 and 311, and AAS)
(i) the three CDRs of the heavy chain and/or the three CDRs of the light chain of antibody AC_05082 (SEQ ID NOs: 222, 223 and 230 or 284, 285 and 230 and/or SEQ ID NOs: 90 and 311, and AAS)
(j) the three CDRs of the heavy chain and/or the three CDRs of the light chain of antibody AC_05083 (SEQ ID NOs: 222, 223 and 231 or 284, 285 and 231 and/or SEQ ID NOs: 318 and 319, and AAS)
(k) the three CDRs of the heavy chain and/or the three CDRs of the light chain of antibody AC_05084 (SEQ ID NOs: 222, 223 and 232 or 284, 285 and 232 and/or SEQ ID NOs: 90 and 320, and AAS)
(l) the three CDRs of the heavy chain and/or the three CDRs of the light chain of antibody AC_05085 (SEQ ID NOs: 219, 233 and 234 or 286, 287 and 234 and/or SEQ ID NOs: 90 and 311, and AAS)
(m) the three CDRs of the heavy chain and/or the three CDRs of the light chain of antibody AC_05086 (SEQ ID NOs: 216, 217 and 235 or 280, 281 and 235 and/or SEQ ID NOs: 90 and 311, and AAS)
(n) the three CDRs of the heavy chain and/or the three CDRs of the light chain of antibody AC_05087 (SEQ ID NOs: 216, 217 and 236 or 280, 281 and 236 and/or SEQ ID NOs: 90 and 311, and AAS)
(o) the three CDRs of the heavy chain and/or the three CDRs of the light chain of antibody AC_05088 (SEQ ID NOs: 216, 217 and 237 or 280, 281 and 237 and/or SEQ ID NOs: 90 and 311, and AAS)
(p) the three CDRs of the heavy chain and/or the three CDRs of the light chain of antibody AC_05089 (SEQ ID NOs: 216, 217 and 238 or 280, 281 and 238 and/or SEQ ID NOs: 90 and 311, and AAS)
(q) the three CDRs of the heavy chain and/or the three CDRs of the light chain of antibody AC_05090/ ffAC_05337 (SEQ ID NOs: 216, 217 and 239 or 280, 281 and 239 and/or SEQ ID NOs: 90 and 311, and AAS)
(r) the three CDRs of the heavy chain and/or the three CDRs of the light chain of antibody AC_05091 (SEQ ID NOs: 216, 217 and 240 or 280, 281 and 240 and/or SEQ ID NOs: 90 and 311, and AAS)
(s) the three CDRs of the heavy chain and/or the three CDRs of the light chain of antibody AC_05092 (SEQ ID NOs: 216, 217 and 218 or 280, 281 and 218 and/or SEQ ID NOs: 321 and 311, and AAS)
(t) the three CDRs of the heavy chain and/or the three CDRs of the light chain of antibody AC_05093 (SEQ ID NOs: 216, 217 and 241 or 280, 281 and 241 and/or SEQ ID NOs: 90 and 311, and AAS)

(u) the three CDRs of the heavy chain and/or the three CDRs of the light chain of antibody AC_05094 (SEQ ID NOs: 216, 217 and 242 or 280, 281 and 242 and/or SEQ ID NOs: 90 and 311, and AAS)
(v) the three CDRs of the heavy chain and/or the three CDRs of the light chain of antibody AC_05095 (SEQ ID NOs: 216, 217 and 243 or 280, 281 and 243 and/or SEQ ID NOs: 90 and 311, and AAS)
(w) the three CDRs of the heavy chain and/or the three CDRs of the light chain of antibody AC_05096 (SEQ ID NOs: 216, 217 and 244 or 280, 281 and 244 and/or SEQ ID NOs: 90 and 311, and AAS)
(x) the three CDRs of the heavy chain and/or the three CDRs of the light chain of antibody AC_05097 (SEQ ID NOs: 217, 216 and 245 or 280, 281 and 245 and/or SEQ ID NOs: 90 and 311, and AAS)
(y) the three CDRs of the heavy chain and/or the three CDRs of the light chain of antibody AC_05098 (SEQ ID NOs: 219, 220 and 246 or 282, 283 and 246 and/or SEQ ID NOs: 312 and 313, and AAS)
(z) the three CDRs of the heavy chain and/or the three CDRs of the light chain of antibody AC_05099 (SEQ ID NOs: 222, 223 and 224 or 288, 285 and 224 and/or SEQ ID NOs: 90 and 311, and AAS)
(aa) the three CDRs of the heavy chain and/or the three CDRs of the light chain of antibody AC_05100 (SEQ ID NOs: 222, 223 and 247 or 288, 285 and 247 and/or SEQ ID NOs: 90 and 311, and AAS)
(ab) the three CDRs of the heavy chain and/or the three CDRs of the light chain of antibody Fab1 (SEQ ID NOs: 248, 249 and 250 or 289, 290 and 250 and/or SEQ ID NOs: 90 and 322, and AAS)
(ac) the three CDRs of the heavy chain and/or the three CDRs of the light chain of antibody Fab2 (SEQ ID NOs: 251, 252 and 253 or 291, 292 and 253 and/or SEQ ID NOs: 90 and 323, and AAS)
(ad) the three CDRs of the heavy chain and/or the three CDRs of the light chain of antibody Fab3 (SEQ ID NOs: 254, 255 and 256 or 293, 294 and 256 and/or SEQ ID NOs: 324 and 326, and GAS)
(ae) the three CDRs of the heavy chain and/or the three CDRs of the light chain of antibody Fab4 (SEQ ID NOs: 257, 258 and 259 or 295, 296 and 259 and/or SEQ ID NOs: 90 and 327, and AAS)
(af) the three CDRs of the heavy chain and/or the three CDRs of the light chain of antibody Fab5 (SEQ ID NOs: 260, 261 and 262 or 297, 298 and 262 and/or SEQ ID NOs: 324 and 328, and GAS)
(ag) the three CDRs of the heavy chain and/or the three CDRs of the light chain of antibody Fab6 (SEQ ID NOs: 263, 264 and 265 or 299, 300 and 265 and/or SEQ ID NOs: 324 and 329, and GAS)
(ah) the three CDRs of the heavy chain and/or the three CDRs of the light chain of antibody Fab7 (SEQ ID NOs: 266, 267 and 268 or 301, 302 and 268 and/or SEQ ID NOs: 90 and 330, and AAS)
(ai) the three CDRs of the heavy chain and/or the three CDRs of the light chain of antibody Fab8 (SEQ ID NOs: 269, 270 and 271 or 303, 304 and 271 and/or SEQ ID NOs: 90 and 331, and AAS)
(aj) the three CDRs of the heavy chain and/or the three CDRs of the light chain of antibody Fab9 (SEQ ID NOs: 272, 335 and 273 or 305, 306 and 273 and/or SEQ ID NOs: 90 and 332, and AAS)
(ak) the three CDRs of the heavy chain and/or the three CDRs of the light chain of antibody Fab10 (SEQ ID NOs: 274, 275 and 276 or 307, 308 and 276 and/or SEQ ID NOs: 90 and 333, and AAS) and/or
(al) the three CDRs of the heavy chain and/or the three CDRs of the light chain of antibody Fab11 (SEQ ID NOs: 277, 278 and 279 or 309, 310 and 279 and/or SEQ ID NOs: 324 and 334, and GAS).

Thus, binding domain B2 may comprise:
(a) the heavy chain variable region and/or the light chain variable region of antibody AC_05059 (SEQ ID NO: 33 and/or SEQ ID NO: 31)
(b) the heavy chain variable region and/or the light chain variable region of antibody AC_05060 (SEQ ID NO: 37 and/or SEQ ID NO: 35)
(c) the heavy chain variable region and/or the light chain variable region of antibody AC_05061 (SEQ ID NO: 41 and/or SEQ ID NO: 39)
(d) the heavy chain variable region and/or the light chain variable region of antibody AC_05062 (SEQ ID NO: 45 and/or SEQ ID NO: 43)
(e) the heavy chain variable region and/or the light chain variable region of antibody AC_05064 (SEQ ID NO: 49 and/or SEQ ID NO: 47)
(f) the heavy chain variable region and/or the light chain variable region of antibody AC_05079 (SEQ ID NO: 53 and/or SEQ ID NO: 51)
(g) the heavy chain variable region and/or the light chain variable region of antibody AC_05080 (SEQ ID NO: 57 and/or SEQ ID NO: 55)
(h) the heavy chain variable region and/or the light chain variable region of antibody AC_05081 (SEQ ID NO: 61 and/or SEQ ID NO: 59)
(i) the heavy chain variable region and/or the light chain variable region of antibody AC_05082 (SEQ ID NO: 65 and/or SEQ ID NO: 63)
(j) the heavy chain variable region and/or the light chain variable region of antibody AC_05083 (SEQ ID NO: 69 and/or SEQ ID NO: 67)
(k) the heavy chain variable region and/or the light chain variable region of antibody AC_05084 (SEQ ID NO: 106 and/or SEQ ID NO: 71)
(l) the heavy chain variable region and/or the light chain variable region of antibody AC_05085 (SEQ ID NO: 110 and/or SEQ ID NO: 108)
(m) the heavy chain variable region and/or the light chain variable region of antibody AC_05086 (SEQ ID NO: 114 and/or SEQ ID NO: 112)
(n) the heavy chain variable region and/or the light chain variable region of antibody AC_05087 (SEQ ID NO: 118 and/or SEQ ID NO: 116)
(o) the heavy chain variable region and/or the light chain variable region of antibody AC_05088 (SEQ ID NO: 122 and/or SEQ ID NO: 120)
(p) the heavy chain variable region and/or the light chain variable region of antibody AC_05089 (SEQ ID NO: 126 and/or SEQ ID NO: 124)
(q) the heavy chain variable region and/or the light chain variable region of antibody AC_05090 (SEQ ID NO: 130 and/or SEQ ID NO: 128)
(r) the heavy chain variable region and/or the light chain variable region of antibody AC_05091 (SEQ ID NO: 134 and/or SEQ ID NO: 132)
(s) the heavy chain variable region and/or the light chain variable region of antibody AC_05092 (SEQ ID NO: 138 and/or SEQ ID NO: 136)
(t) the heavy chain variable region and/or the light chain variable region of antibody AC_05093 (SEQ ID NO: 142 and/or SEQ ID NO: 140)

(u) the heavy chain variable region and/or the light chain variable region of antibody AC_05094 (SEQ ID NO: 146 and/or SEQ ID NO: 144)
(v) the heavy chain variable region and/or the light chain variable region of antibody AC_05095 (SEQ ID NO: 150 and/or SEQ ID NO: 148)
(w) the heavy chain variable region and/or the light chain variable region of antibody AC_05096 (SEQ ID NO: 154 and/or SEQ ID NO: 152)
(x) the heavy chain variable region and/or the light chain variable region of antibody AC_05097 (SEQ ID NO: 158 and/or SEQ ID NO: 156)
(y) the heavy chain variable region and/or the light chain variable region of antibody AC_05098 (SEQ ID NO: 162 and/or SEQ ID NO: 160)
(z) the heavy chain variable region and/or the light chain variable region of antibody AC_05099 (SEQ ID NO: 166 and/or SEQ ID NO: 164)
(aa) the heavy chain variable region and/or the light chain variable region of antibody AC_05100 (SEQ ID NO: 170 and/or SEQ ID NO: 168)
(ab) the heavy chain variable region and/or the light chain variable region of antibody Fab1 (SEQ ID NO: 174 and/or SEQ ID NO: 172)
(ac) the heavy chain variable region and/or the light chain variable region of antibody Fab2 (SEQ ID NO: 178 and/or SEQ ID NO: 176)
(ad) the heavy chain variable region and/or the light chain variable region of antibody Fab3 (SEQ ID NO: 182 and/or SEQ ID NO: 180)
(ae) the heavy chain variable region and/or the light chain variable region of antibody Fab4 (SEQ ID NO: 186 and/or SEQ ID NO: 184)
(af) the heavy chain variable region and/or the light chain variable region of antibody Fab5 (SEQ ID NO: 190 and/or SEQ ID NO: 188)
(ag) the heavy chain variable region and/or the light chain variable region of antibody Fab6 (SEQ ID NO: 194 and/or SEQ ID NO: 192)
(ah) the heavy chain variable region and/or the light chain variable region of antibody Fab7 (SEQ ID NO: 198 and/or SEQ ID NO: 196)
(ai) the heavy chain variable region and/or the light chain variable region of antibody Fab8 (SEQ ID NO: 202 and/or SEQ ID NO: 200)
(aj) the heavy chain variable region and/or the light chain variable region of antibody Fab9 (SEQ ID NO: 206 and/or SEQ ID NO: 204)
(ak) the heavy chain variable region and/or the light chain variable region of antibody Fab10 (SEQ ID NO: 210 and/or SEQ ID NO: 208)
(al) the heavy chain variable region and/or the light chain variable region of antibody Fab11 (SEQ ID NO: 214 and/or SEQ ID NO: 212)
(am) the heavy chain variable region and/or the light chain variable region of antibody mAb2 (SEQ ID NO: 387 and/or SEQ ID NO: 385) and/or
(an) the heavy chain variable region and/or the light chain variable region of antibody ffAC_05337 (SEQ ID NO: 433 and/or SEQ ID NO: 432).

In one embodiment, binding domain B2 may comprise:
(a) the light chain and/or the heavy chain of antibody AC_05059 (SEQ ID NO: 388 and/or SEQ ID NO: 389)
(b) the light chain and/or the heavy chain of antibody AC_05060 (SEQ ID NO: 390 and/or SEQ ID NO: 391)
(c) the light chain and/or the heavy chain of antibody AC_05061 (SEQ ID NO: 392 and/or (SEQ ID NO: 393)
(d) the light chain and/or the heavy chain of antibody AC_05062 (SEQ ID NO: 394 and/or SEQ ID NO: 395)
(e) the light chain and/or the heavy chain of antibody AC_05064 (SEQ ID NO: 396 and/or SEQ ID NO: 397)
(f) the light chain and/or the heavy chain of antibody AC_05079 (SEQ ID NO: 398 and/or SEQ ID NO: 399)
(g) the light chain and/or the heavy chain of antibody AC_05081 (SEQ ID NO: 400 and/or SEQ ID NO: 401)
(h) the light chain and/or the heavy chain of antibody AC_05088 (SEQ ID NO: 402 and/or SEQ ID NO: 403)
(i) the light chain and/or the heavy chain of antibody AC_05089 (SEQ ID NO: 404 and/or SEQ ID NO: 405)
(j) the light chain and/or the heavy chain of antibody AC_05090 (SEQ ID NO: 406 and/or SEQ ID NO: 407)
(k) the light chain and/or the heavy chain of antibody AC_05091 (SEQ ID NO: 408 and/or SEQ ID NO: 409)
(l) the light chain and/or the heavy chain of antibody AC_05093 (SEQ ID NO: 410 and/or SEQ ID NO: 411)
(m) the light chain and/or the heavy chain of antibody AC_05094 (SEQ ID NO: 412 and/or SEQ ID NO: 413)
(n) the light chain and/or the heavy chain of antibody AC_05096 (SEQ ID NO: 414 and/or SEQ ID NO: 415)
(o) the light chain and/or the heavy chain of antibody AC_05097 (SEQ ID NO: 416 and/or SEQ ID NO: 417)
(p) the light chain and/or the heavy chain of antibody Fab1 (SEQ ID NO: 418 and/or SEQ ID NO: 419) and/or
(q) the light chain and/or the heavy chain of antibody Fab3 (SEQ ID NO: 420 and/or
(SEQ ID NO: 421).

It will be appreciated by the skilled person, and it is included herein, that mutations described herein for the RUBY™ format and/or the optimised RUBY™ format can be applied to the above light chain and/or the heavy chain sequences of the binding domain B2.

In one embodiment binding domain B2 may comprise one or more variants of the above-defined light chain variable regions and/or said heavy chain variable regions (and/or light chain and/or heavy chain) having at least 90% sequence identity thereto or 95% sequence identity thereto or 99% sequence identity thereto. Binding domain B2 may also comprise variants of the CDR sequences specified herein, for example variants where up one, two, three, four or five amino acid residues are substituted, deleted to added compared to the specified reference sequences.

In a second aspect, the present invention provides a polypeptide comprising a binding domain, designated B2, as defined herein, which is capable of specifically binding to CEA. Preferably, the polypeptide of the second aspect of the invention is monospecific. In an alternative preferred embodiment, the polypeptide of the second aspect of the invention is bispecific, preferably a bispecific antibody.

All of the features of B2 as discussed for the first aspect of the invention are relevant to, and included in, the second aspect of the invention. Accordingly, in one embodiment the CEA binding domain of B2 is selected from: AC_05059; AC_05060; AC_05061; AC_05062; AC_05064; AC_05079; AC_05080; AC_05081; AC_05082; AC_05083; AC_05084; AC_05085; AC_05086; AC_05087; AC_05088; AC_05089; AC_05090; AC_05091; AC_05092; AC_05093; AC_05094; AC_05095; AC_05096; AC_05097; AC_05098; AC_05099; CEA binding domain of ffAC_05337 and AC_05100; Fab1; Fab2; Fab3; Fab4; Fab5; Fab6; Fab7; Fab8; Fab9; Fab10; Fab11; and mAb2, preferably: AC_05059; AC_05060;

AC_05061; AC_05062; AC_05064; AC_05079; AC_05081; AC_05088; AC_05089; AC_05090; AC_05091; AC_05093; AC_05094; AC_05096; and AC_05097; Fab1; and Fab3, most preferably AC_05088; AC_05090; AC_05093; and AC_05097; Fab1; the CEA binding domain of ffAC_05337 and Fab3. The CDRs, VL, VH, light chain and/or heavy chain of the above antibodies as described in the first aspect of the invention are relevant to, and included in, the second aspect of the invention.

Advantageously, binding domain B2 of the second aspect of the invention binds to human CEA with a $K_D$ of less than $2\times10^{-6}$M or less than $1.5\times10^{-7}$M or less than $1.5\times10^{-8}$M or less than $2.5\times10^{-8}$M or less than $4.5\times10^{-8}$M or less than $5.5\times10^{-8}$M or less than $6.5\times10^{-9}$M or less than $2.5\times10^{-9}$M or less than $2\times10^{-9}$M or less than $9.5\times10^{-10}$M or less than $4.5\times10^{-10}$M or less than $7.5\times10^{-11}$M or less than $8.5\times10^{-12}$M or less than $1.5\times10^{-12}$M or less than $1\times10^{-12}$M, preferably less than $1.5\times10^{-8}$M or less than $2.5\times10^{-9}$M or less than $1.5\times10^{-12}$M. Preferably, the $K_D$ is measured in Octet; for example, as explained in the Examples. Preferably, the $K_D$ is measured in Octet; for example, as explained in the Examples.

In a third aspect, the present invention provides a bispecific polypeptide comprising a first binding domain, designated B3, which is capable of binding specifically to a target antigen that is not CD40, and a second binding domain, designated B2, as defined herein, which is capable of specifically binding to CEA.

All of the features of B2 as discussed for the first and second aspect of the invention are relevant to, and included in, the third aspect of the invention. Accordingly, in one embodiment the CEA binding domain of B2 is selected from: AC_05059; AC_05060; AC_05061; AC_05062; AC_05064; AC_05079; AC_05080; AC_05081; AC_05082; AC_05083; AC_05084; AC_05085; AC_05086; AC_05087; AC_05088; AC_05089; AC_05090; AC_05091; AC_05092; AC_05093; AC_05094; AC_05095; AC_05096; AC_05097; AC_05098; AC_05099; and AC_05100; Fab1; Fab2; Fab3; Fab4; Fab5; Fab6; Fab7; Fab8; Fab9; Fab10; Fab11; CEA binding domain of ffAC_05337 and mAb2, preferably: AC_05059; AC_05060; AC_05061; AC_05062; AC_05064; AC_05079; AC_05081; AC_05088; AC_05089; AC_05090; AC_05091; AC_05093; AC_05094; AC_05096; and AC_05097; Fab1; and Fab3, most preferably AC_05088; AC_05090; AC_05093; and AC_05097; Fab1; CEA binding domain of ffAC_05337 and Fab3. The CDRs, VL, VH, light chain and/or heavy chain of the above antibodies as described in the first aspect of the invention are relevant to, and included in, the second aspect of the invention.

Preferably, the target antigen is protein and/or a peptide.

In one embodiment, B3 is capable of targeting an immune cell, such that the target antigen is an immune cell target antigen. The immune cell may be any immune cell described herein, including a T cell, a NK cell, a myeloid cell, and/or an antigen presenting cell (such as a dendritic cell).

In one embodiment, B3 is capable of targeting a dendritic cell (DC), such that the target antigen is a DC target antigen.

Binding domain B3 specifically binds to the DC target antigen, i.e. it binds to the DC target antigen but does not bind, or binds at a lower affinity, to other molecules. Binding domain B3 may have some binding affinity for the same DC target antigen from other mammals, such as from a non-human primate (for example *Macaca fascicularis* (cynomolgus monkey), *Macaca mulatta*). Binding domain B3 preferably does not bind non-target molecules.

Binding domain B3 is preferably capable of binding to its target with an affinity that is at least two-fold, 10-fold, 50-fold, 100-fold or greater than its affinity for binding to another non-target molecule.

In one embodiment, the DC target antigen is capable of mediating internalisation.

In one embodiment, the DC target antigen is capable of mediating cross-presentation.

In one embodiment, the DC target antigen is specifically expressed on mature DCs.

In one embodiment, the DC target antigen is specifically expressed on immature DCs.

In a preferred embodiment of the third aspect of the invention, the bispecific polypeptide is a bispecific antibody, such as a bispecific antibody in the RUBY™ format or optimised RUBY™ format, as both described herein.

Exemplary CD40-CEA Bispecific Antibodies

In one embodiment of the bispecific polypeptides of the invention, binding domain B1 is an IgG and binding domain B2 is an scFv. Conversely, binding domain B1 may be an scFv and binding domain B2 may be an IgG.

In one embodiment binding domain B1 is an immunoglobulin and binding domain B2 is a Fab. Conversely, binding domain B1 may be a Fab and binding domain B2 may be an immunoglobulin. The bispecific polypeptide may optionally be in the RUBY™ format or optimised RUBY™ format, as both described herein. The bispecific polypeptide format is as described above and as laid out in FIG. 23, and the bispecific polypeptide may comprise certain mutations as described above.

Bispecific polypeptides of the invention may comprise the CDRs of the light chains of any of the B1 domains described above (as laid out in Table C(2) below), and/or the CDRs of the heavy chains of any of the B1 domains described above (as laid out in Table C(1) below), in combination with any of the CDRs of the light chains of any of the B2 domains described above (as laid out in Table D(2)), and/or the CDRs of the heavy chains of any of the B2 domains described above (as laid out in Table D(1a) and/or Table D(1b)).

Bispecific polypeptides of the invention may comprise the light chain variable regions of any of the B1 domains described above (as laid out in Table A below), and/or the CDRs of the heavy chain variable regions of any of the B1 domains described above (as laid out in Table A below), in combination with any of the light chain variable regions of any of the B2 domains described above (as laid out in Table B), and/or the heavy chain variable regions of any of the B2 domains described above (as laid out in Table B).

Thus, in certain embodiments B1 and B2 comprise the respective variable regions comprising the CDRs identified above. For example, B1 may comprise the heavy chain variable region and/or the light chain variable region of antibody G12 (SEQ ID NO: 19 and/or SEQ ID NO: 17) or G12_mut (SEQ ID NO: 29 and/or SEQ ID NO: 17) and B2 may comprise the heavy chain variable region and/or the light chain variable region of any of the reference CEA antibodies:

(a) the heavy chain variable region and/or the light chain variable region of antibody AC_05059 (SEQ ID NO: 33 and/or SEQ ID NO: 31)

(b) the heavy chain variable region and/or the light chain variable region of antibody AC_05060 (SEQ ID NO: 37 and/or SEQ ID NO: 35)

(c) the heavy chain variable region and/or the light chain variable region of antibody AC_05061 (SEQ ID NO: 41 and/or SEQ ID NO: 39)

(d) the heavy chain variable region and/or the light chain variable region of antibody AC_05062 (SEQ ID NO: 45 and/or SEQ ID NO: 43)
(e) the heavy chain variable region and/or the light chain variable region of antibody AC_05064 (SEQ ID NO: 49 and/or SEQ ID NO: 47)
(f) the heavy chain variable region and/or the light chain variable region of antibody AC_05079 (SEQ ID NO: 53 and/or SEQ ID NO: 51)
(g) the heavy chain variable region and/or the light chain variable region of antibody AC_05080 (SEQ ID NO: 57 and/or SEQ ID NO: 55)
(h) the heavy chain variable region and/or the light chain variable region of antibody AC_05081 (SEQ ID NO: 61 and/or SEQ ID NO: 59)
(i) the heavy chain variable region and/or the light chain variable region of antibody AC_05082 (SEQ ID NO: 65 and/or SEQ ID NO: 63)
(j) the heavy chain variable region and/or the light chain variable region of antibody AC_05083 (SEQ ID NO: 69 and/or SEQ ID NO: 67)
(k) the heavy chain variable region and/or the light chain variable region of antibody AC_05084 (SEQ ID NO: 106 and/or SEQ ID NO: 71)
(l) the heavy chain variable region and/or the light chain variable region of antibody AC_05085 (SEQ ID NO: 110 and/or SEQ ID NO: 108)
(m) the heavy chain variable region and/or the light chain variable region of antibody AC_05086 (SEQ ID NO: 114 and/or SEQ ID NO: 112)
(n) the heavy chain variable region and/or the light chain variable region of antibody AC_05087 (SEQ ID NO: 118 and/or SEQ ID NO: 116)
(o) the heavy chain variable region and/or the light chain variable region of antibody AC_05088 (SEQ ID NO: 122 and/or SEQ ID NO: 120)
(p) the heavy chain variable region and/or the light chain variable region of antibody AC_05089 (SEQ ID NO: 126 and/or SEQ ID NO: 124)
(q) the heavy chain variable region and/or the light chain variable region of antibody AC_05090 (SEQ ID NO: 130 and/or SEQ ID NO: 128)
(r) the heavy chain variable region and/or the light chain variable region of antibody AC_05091 (SEQ ID NO: 134 and/or SEQ ID NO: 132)
(s) the heavy chain variable region and/or the light chain variable region of antibody AC_05092 (SEQ ID NO: 138 and/or SEQ ID NO: 136)
(t) the heavy chain variable region and/or the light chain variable region of antibody AC_05093 (SEQ ID NO: 142 and/or SEQ ID NO: 140)
(u) the heavy chain variable region and/or the light chain variable region of antibody AC_05094 (SEQ ID NO: 146 and/or SEQ ID NO: 144)
(v) the heavy chain variable region and/or the light chain variable region of antibody AC_05095 (SEQ ID NO: 150 and/or SEQ ID NO: 148)
(w) the heavy chain variable region and/or the light chain variable region of antibody AC_05096 (SEQ ID NO: 154 and/or SEQ ID NO: 152)
(x) the heavy chain variable region and/or the light chain variable region of antibody AC_05097 (SEQ ID NO: 158 and/or SEQ ID NO: 156)
(y) the heavy chain variable region and/or the light chain variable region of antibody AC_05098 (SEQ ID NO: 162 and/or SEQ ID NO: 160)
(z) the heavy chain variable region and/or the light chain variable region of antibody AC_05099 (SEQ ID NO: 166 and/or SEQ ID NO: 164)
(aa) the heavy chain variable region and/or the light chain variable region of antibody AC_05100 (SEQ ID NO: 170 and/or SEQ ID NO: 168)
(ab) the heavy chain variable region and/or the light chain variable region of antibody Fab1 (SEQ ID NO: 174 and/or SEQ ID NO: 172)
(ac) the heavy chain variable region and/or the light chain variable region of antibody Fab2 (SEQ ID NO: 178 and/or SEQ ID NO: 176)
(ad) the heavy chain variable region and/or the light chain variable region of antibody Fab3 (SEQ ID NO: 182 and/or SEQ ID NO: 180)
(ae) the heavy chain variable region and/or the light chain variable region of antibody Fab4 (SEQ ID NO: 186 and/or SEQ ID NO: 184)
(af) the heavy chain variable region and/or the light chain variable region of antibody Fab5 (SEQ ID NO: 190 and/or SEQ ID NO: 188)
(ag) the heavy chain variable region and/or the light chain variable region of antibody Fab6 (SEQ ID NO: 194 and/or SEQ ID NO: 192)
(ah) the heavy chain variable region and/or the light chain variable region of antibody Fab7 (SEQ ID NO: 198 and/or SEQ ID NO: 196)
(ai) the heavy chain variable region and/or the light chain variable region of antibody Fab8 (SEQ ID NO: 202 and/or SEQ ID NO: 200)
(aj) the heavy chain variable region and/or the light chain variable region of antibody Fab9 (SEQ ID NO: 206 and/or SEQ ID NO: 204)
(ak) the heavy chain variable region and/or the light chain variable region of antibody Fab10 (SEQ ID NO: 210 and/or SEQ ID NO: 208)
(al) the heavy chain variable region and/or the light chain variable region of antibody Fab11 (SEQ ID NO: 214 and/or SEQ ID NO: 212) and/or
(am) the heavy chain variable region and/or the light chain variable region of antibody mAb2 (SEQ ID NO: 387 and/or SEQ ID NO: 385).

In a preferred embodiment, B1 may comprise the heavy chain variable region and/or the light chain variable region of antibody ffAC_05337 (SEQ ID NO: 430 and/or SEQ ID NO: 431) and B2 may comprise the heavy chain variable region and/or the light chain variable region of antibody ffAC_05337 (SEQ ID NO: 433 and/or SEQ ID NO: 432).

The B1 domain may comprise the light chain variable region and/or the heavy chain variable region of any B1 domain described above, and the B2 domain may comprise the light chain variable region and/or the heavy chain variable region of any B2 domain described above, or variants of said light chain variable regions and/or said heavy chain variable regions having at least 90% sequence identity thereto.

Typically, the bispecific polypeptides of the invention will comprise constant region sequences, in addition to the above-defined variable region sequences. Bispecific polypeptides of the invention may be in any suitable format. For example, bispecific polypeptides may be in the RUBY™ format or optimised RUBY™ format (as described above, and shown in FIG. 23), or in the Morrison format.

An exemplary heavy chain constant region amino acid sequence which may be combined with any VH region sequence disclosed herein (to form a complete heavy chain) is the following IgG1 heavy chain constant region sequence:

(SEQ ID NO: 349)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Likewise, an exemplary light chain constant region amino acid sequence which may be combined with any VL region sequence disclosed herein (to form a complete light chain) is the Kappa chain constant region sequence reproduced here:

(SEQ ID NO: 350)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Other light chain constant region sequences are known in the art and could also be combined with any VL region disclosed herein.

In one embodiment, the polypeptide may comprise the following constant region amino acid sequences:

(a) Reference sequence CH1 (SEQ ID NO: 354):
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSC

(wherein the bold and underlined section is part of the hinge region, but is present in the Fab fragment)
and/or
(b) Reference sequence CKappa (SEQ ID
NO: 355):
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
and/or

Reference sequence CLambda (SEQ ID NO: 356)
GQPKANPTVTLFPPSSEELQANKATLVCLISDFYPGAVTVAWKADGSPVK

AGVETTKPSKQSNNKYAASSYLSLTPEQWKSHRSYSCQVTHEGSTVEKTV

APTECS
and/or

Reference sequence CLambda (SEQ ID NO: 357)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS
and/or

Reference sequence CLambda (SEQ ID NO: 358)
GQPKAAPSVTLFPPSSEELQANKATLVCLISDFYPGAVTVAWKADSSPVK

AGVETTTPSKQSNNKYAASSYLSLTPEQWKSHKSYSCQVTHEGSTVEKTV

APTECS

As described above, these reference sequences may comprise one or more mutations to prevent the formation of aggregates and/or a Fab by-product. Such mutation positions (identified earlier in the description) may be given relative to any of the above constant region sequences.

In one embodiment, the bispecific polypeptide is in the RUBY™ format or in the optimised RUBY™ format, comprising an immunoglobulin and a Fab fragment, wherein the Fab fragment is fused to the C-terminus of the heavy chain of the immunoglobulin via the light chain of the Fab fragment.

Thus in one embodiment, binding domain B1 is an immunoglobulin, and binding domain B2 is a Fab fragment, and the Fab fragment is fused to the C-terminus of the heavy chain of the immunoglobulin via the light chain of the Fab fragment. In an alternative embodiment, binding domain B2 is an immunoglobulin, and binding domain B1 is a Fab fragment, and the Fab fragment is fused to the C-terminus of the heavy chain of the immunoglobulin via the light chain of the Fab fragment. Additionally, the bispecific polypeptide comprises one or more mutations selected from those described above for the RUBY™ format and/or the optimised RUBY™ format.

In one embodiment, the bispecific polypeptide comprises a binding domain B1 and/or a binding domain 2 comprising the light chain CDRs and/or heavy chain CDRs, and/or the format, of an antibody selected from the list consisting of: side Multi1; Multi2; Multi3; Multi4; Multi5; Multi6; Multi7; Multi8; Multi9; Multi10; Multi11; Multi12; Multi13; Multi14; Multi17; Multi18; Multi19; Multi20; Multi23; Multi24; Multi25; Multi26; Multi27; Multi28; Multi29; Multi30; Multi31; Multi32; Multi33; Multi34; Multi35; Multi37; Multi38; Multi39; Multi40; Multi41; Multi42; Multi44; Multi46; Multi47; Multi48; Multi49; AC_05333; AC_05334; AC_05336; AC_05337; AC_05338; AC_05339; AC_05341; ffAC_05337; ffAC_05339; and/or AC_05355, preferably Multi34; Multi42; Multi46 and/or ffAC_05337.

In one embodiment, the bispecific polypeptide comprises a binding domain B1 and/or a binding domain 2 comprising the light chain variable region and/or heavy chain variable region, and/or the format, of an antibody selected from the list consisting of: Multi1; Multi2; Multi3; Multi4; Multi5; Multi6; Multi7; Multi8; Multi9; Multi10; Multi11; Multi12; Multi13; Multi14; Multi17; Multi18; Multi19; Multi20; Multi23; Multi24; Multi25; Multi26; Multi27; Multi28; Multi29; Multi30; Multi31; Multi32; Multi33; Multi34; Multi35; Multi37; Multi38; Multi39; Multi40; Multi41; Multi42; Multi44; Multi46; Multi47; Multi48; Multi49; AC_05333; AC_05334; AC_05336; AC_05337; AC_05338; AC_05339; AC_05341; ffAC_05337; ffAC_05339; and/or AC_05355, preferably Multi34; Multi42; Multi46 and/or ffAC_05337.

In one embodiment, the bispecific polypeptide comprises a binding domain B1 and/or a binding domain 2 comprising the light chain and/or heavy chain, and/or the format, of an antibody selected from the list consisting of: Multi1; Multi2; Multi3; Multi4; Multi5; Multi6; Multi7; Multi8; Multi9; Multi10; Multi11; Multi12; Multi13; Multi14; Multi17;

Multi18; Multi19; Multi20; Multi23; Multi24; Multi25; Multi26; Multi27; Multi28; Multi29; Multi30; Multi31; Multi32; Multi33; Multi34; Multi35; Multi37; Multi38; Multi39; Multi40; Multi41; Multi42; Multi44; Multi46; Multi47; Multi48; Multi49; AC_05333; AC_05334; AC_05336; AC_05337; AC_05338; AC_05339; AC_05341; ffAC_05337; ffAC_05339; and/or AC_05355, preferably Multi34; Multi42; Multi46 and/or ffAC_05337.

In one embodiment, the bispecific polypeptide comprises a Chain H1 comprising a sequence selected from the listing consisting of: SEQ ID NO: 359; SEQ ID NO: 362; SEQ ID NO: 365; and/or SEQ ID NO: 367.

In one embodiment, the bispecific polypeptide comprises a Chain L1 comprising a sequence selected from the listing consisting of: SEQ ID NO: 360; SEQ ID NO: 363; SEQ ID NO: 372; and/or SEQ ID NO: 368.

In one embodiment, the bispecific polypeptide comprises a Chain H2 comprising a sequence selected from the listing consisting of: SEQ ID NO: 361; SEQ ID NO: 364; SEQ ID NO: 366; and/or SEQ ID NO: 369.

In one embodiment, the bispecific polypeptide:
comprises a Chain H1 comprising a sequence selected from the listing consisting of: SEQ ID NO: 359; SEQ ID NO: 362; SEQ ID NO: 365; and/or SEQ ID NO: 367; and/or
comprises a Chain L1 comprising a sequence selected from the listing consisting of: SEQ ID NO: 360; SEQ ID NO: 363; SEQ ID NO: 372; and/or SEQ ID NO: 368; and/or
comprises a Chain H2 comprising a sequence selected from the listing consisting of: SEQ ID NO: 361; SEQ ID NO: 364; SEQ ID NO: 366; and/or SEQ ID NO: 369.

In one embodiment, the bispecific polypeptide:
comprises two Chain H1 each comprising a sequence selected from the listing consisting of: SEQ ID NO: 359; SEQ ID NO: 362; SEQ ID NO: 365; and/or SEQ ID NO: 367; and/or
comprises two Chain L1 each comprising a sequence selected from the listing consisting of: SEQ ID NO: 360; SEQ ID NO: 363; SEQ ID NO: 372; and/or SEQ ID NO: 368; and/or
comprises two Chain H2 each comprising a sequence selected from the listing consisting of: SEQ ID NO: 361; SEQ ID NO: 364; SEQ ID NO: 366; and/or SEQ ID NO: 369.

In one embodiment the bispecific polypeptide may comprise one or more variants of the above-defined Chain H1, Chain L1, and/or Chain H2 having at least 90% sequence identity thereto or 95% sequence identity thereto or 99% sequence identity thereto.

In one embodiment, the bispecific polypeptide:
comprises a Chain H1 comprising SEQ ID NO: 359; and/or
comprises a Chain L1 comprising SEQ ID NO: 360; and/or
comprises a Chain H2 comprising SEQ ID NO: 361.

In one embodiment, the bispecific polypeptide:
comprises a Chain H1 comprising SEQ ID NO: 362; and/or
comprises a Chain L1 comprising SEQ ID NO: 363; and/or
comprises a Chain H2 comprising SEQ ID NO: 364;

In one embodiment, the bispecific polypeptide:
comprises a Chain H1 comprising SEQ ID NO: 365; and/or
comprises a Chain L1 comprising SEQ ID NO: 372; and/or
comprises a Chain H2 comprising SEQ ID NO: 366.

In one embodiment, the bispecific polypeptide:
comprises a Chain H1 comprising SEQ ID NO: 367; and/or
comprises a Chain L1 comprising SEQ ID NO: 368; and/or
comprises a Chain H2 comprising SEQ ID NO: 369.

In one embodiment, the bispecific polypeptide:
comprises two Chain H1 comprising SEQ ID NO: 359; and/or
comprises two Chain L1 comprising SEQ ID NO: 360; and/or
comprises two Chain H2 comprising SEQ ID NO: 361.

In one embodiment, the bispecific polypeptide:
comprises two Chain H1 comprising SEQ ID NO: 362; and/or
comprises two Chain L1 comprising SEQ ID NO: 363; and/or
comprises two Chain H2 comprising SEQ ID NO: 364;

In one embodiment, the bispecific polypeptide:
comprises two Chain H1 comprising SEQ ID NO: 365; and/or
comprises two Chain L1 comprising SEQ ID NO: 372; and/or
comprises two Chain H2 comprising SEQ ID NO: 366.

In one embodiment, the bispecific polypeptide:
comprises two Chain H1 comprising SEQ ID NO: 367; and/or
comprises two Chain L1 comprising SEQ ID NO: 368; and/or
comprises two Chain H2 comprising SEQ ID NO: 369.

In one embodiment, the bispecific polypeptide is an antibody selected from the list consisting of: Multi1; Multi2; Multi3; Multi4; Multi5; Multi6; Multi7; Multi8; Multi9; Multi10; Multi11; Multi12; Multi13; Multi14; Multi17; Multi18; Multi19; Multi20; Multi23; Multi24; Multi25; Multi26; Multi27; Multi28; Multi29; Multi30; Multi31; Multi32; Multi33; Multi34; Multi35; Multi37; Multi38; Multi39; Multi40; Multi41; Multi42; Multi44; Multi46; Multi47; Multi48; Multi49; AC_05333; AC_05334; AC_05336; AC_05337; AC_05338; AC_05339; AC_05341; ffAC_05337; ffAC_05339; and/or AC_05355, preferably Multi34; Multi42; Multi46 and/or ffAC_05337.

In one embodiment the bispecific polypeptide may comprise one or more variants of the above-defined Multi1; Multi2; Multi3; Multi4; Multi5; Multi6; Multi7; Multi8; Multi9; Multi10; Multi11; Multi12; Multi13; Multi14; Multi17; Multi18; Multi19; Multi20; Multi23; Multi24; Multi25; Multi26; Multi27; Multi28; Multi29; Multi30; Multi31; Multi32; Multi33; Multi34; Multi35; Multi37; Multi38; Multi39; Multi40; Multi41; Multi42; Multi44; Multi46; Multi47; Multi48; Multi49; AC_05333; AC_05334; AC_05336; AC_05337; AC_05338; AC_05339; AC_05341; ffAC_05337; ffAC_05339; and/or AC_05355 having at least 90% sequence identity thereto or 95% sequence identity thereto or 99% sequence identity thereto.

Exemplary full heavy and light chain sequences
Binding domain B1:
1132/1133 Heavy chain, including RUBY mutations
(VH: Q44R, CH1: H168A, F170G, CH2: L234A, L235A)
(SEQ ID NO: 371):
EVQLLESGGGLVQPGGSLRLSCAASGFTFSSYAMSWVRRAPGKGLEWVSGIGSYGGGTYYAD

SVKGRFTISRDNSKNTLYLQMNSLRAEDTAVYYCARYVNFGMDYWGQGTLVTVSSASTKGPS

VFPLAPSSKSTSGGTAALGCLVKDYFPEPVTVSWNSGALTSGVATGPAVLQSSGLYSLSSVV

TVPSSSLGTQTYICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

1132/1133 Light chain, including RUBY mutations
(VL: Q44E, CKappa: L135Y, S176W) (SEQ ID NO: 372):
DIQMTQSPSSLSASVGDRVTITCRASQSISSYLNWYQEKPGKAPKLLIYAASSLQSGVPSRF

SGSGSGTDFTLTISSLQPEDFATYYCQQYGRNPPTFGQGTKLEIKRTVAAPSVFIFPPSDEQ

LKSGTASVVCYLNNFYPREAKVQWKVDNALQSGNSQESVTEQDSKDSTYSLWSTLTLSKADY

EKHKVYACEVTHQGLSSPVTKSFNRGEC

1132/1133 Heavy chain (SEQ ID NO: 378):
EVQLLESGGGLVQPGGSLRLSCAASGFTFSSYAMSWVRQAPGKGLEWVSGIGSYGGGTYYAD

SVKGRFTISRDNSKNTLYLQMNSLRAEDTAVYYCARYVNFGMDYWGQGTLVTVSSASTKGPS

VFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

1132/1133 Light chain (SEQ ID NO: 379):
DIQMTQSPSSLSASVGDRVTITCRASQSISSYLNWYQQKPGKAPKLLIYAASSLQSGVPSRF

SGSGSGTDFTLTISSLQPEDFATYYCQQYGRNPPTFGQGTKLEIKRTVAAPSVFIFPPSDEQ

LKSGTASVVCLLNNFYPREAKVQWKVDNALQSGNSQESVTEQDSKDSTYSLSSTLTLSKADY

EKHKVYACEVTHQGLSSPVTKSFNRGEC

G12 Heavy chain (SEQ ID NO: 380):
EVQLLESGGGLVQPGGSLRLSCAASGFTFSTYGMHWVRQAPGKGLEWLSYISGGSSYIFYAD

SVRGRFTISRDNSENALYLQMNSLRAEDTAVYYCARILRGGSGMDLWGQGTLVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEAL

HNHYTQKSLSLSPGK

G12 Light chain (SEQ ID NO: 381):
QSVLTQPPSASGTPGQRVTISCTGSSSNIGAGYNVYWYQQLPGTAPKLLIYGNINRPSGVPD

RFSGSKSGTSASLAISGLRSEDEADYYCAAWDKSISGLVFGGGTKLTVLGQPKAAPSVTLFP

PSSEELQANKATLVCLISDFYPGAVTVAWKADSSPVKAGVETTTPSKQSNNKYAASSYLSLT

PEQWKSHRSYSCQVTHEGSTVEKTVAPTECS

G12_mut Heavy chain (SEQ ID NO: 382):
EVQLLESGGGLVQPGGSLRLSCAASGFTFSTYGMHWVRQAPGKGLEWLSYISGGSSYIFYAD

SVKGRFTISRDNSKNTLYLQMNSLRAEDTAVYYCARILRGGSGMDLWGQGTLVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEAL

HNHYTQKSLSLSPGK

G12_mut Light chain (SEQ ID NO: 383):
QSVLTQPPSASGTPGQRVTISCTGSSSNIGAGYNVYWYQQLPGTAPKLLIYGNINRPSGVPD

RFSGSKSGTSASLAISGLRSEDEADYYCAAWDKSISGLVFGGGTKLTVLGQPKAAPSVTLFP

PSSEELQANKATLVCLISDFYPGAVTVAWKADSSPVKAGVETTTPSKQSNNKYAASSYLSLT

PEQWKSHRSYSCQVTHEGSTVEKTVAPTECS

Binding domain B2:
AC_05059, light chain (SEQ ID NO: 388):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05059, heavy chain (SEQ ID NO: 389):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFPPHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05060, light chain (SEQ ID NO: 390):
DIQMTQSPSSLSASVGDRVTITCRASQSIRDYLNWYQQKPGKAPKLLIYAASSLQSGVPSRF

SGSGSGTDFTLTISSLQPEDFATYYCQQGTFPFTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05060, heavy chain (SEQ ID NO: 391):
EVQLLESGGGLVQPGGSLRLSCAASGFTFGSYYMSWVRQAPGKGLEWVSGISGYGYYTGYAD

SVKGRFTISRDNSKNTLYLQMNSLRAEDTAVYYCARHGYGVIDYWGQGTLVTVSSASTKGPS

VFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

AC_05061, light chain (SEQ ID NO: 392):
DIQMTQSPSSLSASVGDRVTITCRASQSISSYLNWYQQKPGKAPKLLIYAASSLQSGVPSRF

SGSGSGTDFTLTISSLQPEDFATYYCQQGAYVPYTFGQGTKLEIKRTVAAPSVFIFPPSDEQ

LKSGTASVVCLLNNFYPREAKVQWKVDNALQSGNSQESVTEQDSKDSTYSLSSTLTLSKADY

EKHKVYACEVTHQGLSSPVTKSFNRGEC

AC_05061, heavy chain (SEQ ID NO: 393):
EVQLLESGGGLVQPGGSLRLSCAASGFTFSSYAMSWVRQAPGKGLEWVSAISGSGGSTYYAD

SVKGRFTISRDNSKNTLYLQMNSLRAEDTAVYYCARYGYTHFDYWGQGTLVTVSSASTKGPS

VFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

AC_05062, light chain (SEQ ID NO: 394):
DIQMTQSPSSLSASVGDRVTITCRASQAISGYLNWYQQKPGKAPKLLIYSASSLQSGVPSRF

SGSGSGTDFTLTISSLQPEDFATYYCQQSYSTPYTFGQGTKLEIKRTVAAPSVFIFPPSDEQ

LKSGTASVVCLLNNFYPREAKVQWKVDNALQSGNSQESVTEQDSKDSTYSLSSTLTLSKADY

EKHKVYACEVTHQGLSSPVTKSFNRGEC

AC_05062, heavy chain (SEQ ID NO: 395):
EVQLLESGGGLVQPGGSLRLSCAASGFTFSSYAMSWVRQAPGKGLEWVSAISGSGGSTYYAD

SVKGRFTISRDNSKNTLYLQMNSLRAEDTAVYYCARYRWHGSVFDYWGQGTLVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEAL

HNHYTQKSLSLSPGK

AC_05064, light chain (SEQ ID NO: 396):
DIQMTQSPSSLSASVGDRVTITCRASQSISSYLNWYQQKPGKAPKLLIYAASSLQSGVPSRF

SGSGSGTDFTLTISSLQPEDFATYYCQQYPWYFPYTFGQGTKLEIKRTVAAPSVFIFPPSDE

QLKSGTASVVCLLNNFYPREAKVQWKVDNALQSGNSQESVTEQDSKDSTYSLSSTLTLSKAD

YEKHKVYACEVTHQGLSSPVTKSFNRGEC

AC_05064, heavy chain (SEQ ID NO: 397):
EVQLLESGGGLVQPGGSLRLSCAASGFTFSSYAMSWVRQAPGKGLEWVSAISGSGGSTYYAD

SVKGRFTISRDNSKNTLYLQMNSLRAEDTAVYYCARYGYSVLDYWGQGTLVTVSSASTKGPS

VFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

AC_05079, light chain (SEQ ID NO: 398):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05079, heavy chain (SEQ ID NO: 399):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFPPPLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05081, light chain (SEQ ID NO: 400):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05081, heavy chain (SEQ ID NO: 401):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFQPHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05088, light chain (SEQ ID NO: 402):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05088, heavy chain (SEQ ID NO: 403):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVLFPPHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

-continued

AC_05089, light chain (SEQ ID NO: 404):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05089, heavy chain (SEQ ID NO: 405):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFPHHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05090, light chain (SEQ ID NO: 406):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05090, heavy chain (SEQ ID NO: 407):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFPPLHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05091, light chain (SEQ ID NO: 408):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05091, heavy chain (SEQ ID NO: 409):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFPPHFDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

AC_05093, light chain (SEQ ID NO: 410):
DIQMTQSPSSLSASVGDRVTITCRASQSISSYLNWYQQKPGKAPKLLIYAASSLQSGVPSRF
SGSGSGTDFTLTISSLQPEDFATYYCQQAGNPHTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC AC_05093, heavy chain (SEQ ID NO: 411):
EVQLLESGGGLVQPGGSLRLSCAASGFTFSSSYMGWVRQAPGKGLEWVSSIGSGSYSTSYAD
SVKGRFTISRDNSKNTLYLQMNSLRAEDTAVYYCARYPSVPFPPHVDYWGQGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGK AC_05094, light chain (SEQ ID NO: 412):
DIQMTQSPSSLSASVGDRVTITCRASQSISSYLNWYQQKPGKAPKLLIYAASSLQSGVPSRF
SGSGSGTDFTLTISSLQPEDFATYYCQQAGNPHTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC AC_05094, heavy chain (SEQ ID NO: 413):
EVQLLESGGGLVQPGGSLRLSCAASGFTFSSSYMGWVRQAPGKGLEWVSSIGSGSYSTSYAD
SVKGRFTISRDNSKNTLYLQMNSLRAEDTAVYYCARYPSVPFPPHWDYWGQGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGK AC_05096, light chain (SEQ ID NO: 414):
DIQMTQSPSSLSASVGDRVTITCRASQSISSYLNWYQQKPGKAPKLLIYAASSLQSGVPSRF
SGSGSGTDFTLTISSLQPEDFATYYCQQAGNPHTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC AC_05096, heavy chain (SEQ ID NO: 415):
EVQLLESGGGLVQPGGSLRLSCAASGFTFSSSYMGWVRQAPGKGLEWVSSIGSGSYSTSYAD
SVKGRFTISRDNSKNTLYLQMNSLRAEDTAVYYCARYPSVPFRPHLDYWGQGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGK -continued

```
AC_05097, light chain (SEQ ID NO: 416):
DIQMTQSPSSLSASVGDRVTITCRASQSISSYLNWYQQKPGKAPKLLIYAASSLQSGVPSRF

SGSGSGTDFTLTISSLQPEDFATYYCQQAGNPHTFGQGTKLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

AC_05097, heavy chain (SEQ ID NO: 417):
EVQLLESGGGLVQPGGSLRLSCAASGFTFSSSYMGWVRQAPGKGLEWVSSIGSGSYSTSYAD

SVKGRFTISRDNSKNTLYLQMNSLRAEDTAVYYCARYPSVPFSPHLDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK

Fab1, light chain (SEQ ID NO: 418):
DIQMTQSPSSLSASVGDRVTITCRASQSISSYLNWYQQKPGKAPKLLIYAASSLQSGVPSRF

SGSGSGTDFTLTISSLQPEDFATYYCQQSSHGPLLTFGQGTKLEIKRTVAAPSVFIFPPSDE

QLKSGTASVVCLLNNFYPREAKVQWKVDNALQSGNSQESVTEQDSKDSTYSLSSTLTLSKAD

YEKHKVYACEVTHQGLSSPVTKSFNRGEC

Fab1, heavy chain (SEQ ID NO: 419):
QVQLVQSGAEVKKPGSSVKVSCKASGGTFGYYAIHWVRQAPGQGLEWMGGIGSIFGTANYAQ

KFQGRVTITADESTSTAYMELSSLRSEDTAVYYCARAWSSDHMDYWGQGTLVTVSSASTKGP

SVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALH

NHYTQKSLSLSPGK

Fab3, light chain (SEQ ID NO: 420):
EIVLTQSPGTLSLSPGERATLSCRASQSVSSSYLAWYQQKPGQAPRLLIYGASSRATGIPDR

FSGSGSGTDFTLTISRLEPEDFAVYYCQQYWYPLTFGQGTKLEIKRTVAAPSVFIFPPSDEQ

LKSGTASVVCLLNNFYPREAKVQWKVDNALQSGNSQESVTEQDSKDSTYSLSSTLTLSKADY

EKHKVYACEVTHQGLSSPVTKSFNRGEC

Fab3, heavy chain (SEQ ID NO: 421):
QVQLVQSGAEVKKPGSSVKVSCKASGGTFSSSSIHWVRQAPGQGLEWMGHIYPSFGTANYAQ

KFQGRVTITADESTSTAYMELSSLRSEDTAVYYCARHSGSRFFSPMDYWGQGTLVTVSSAST

KGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHE

ALHNHYTQKSLSLSPGK
```

As discussed above, methods for the production of polypeptides of the invention are well known in the art.

Conveniently, the polypeptide is or comprises a recombinant polypeptide. Suitable methods for the production of such recombinant polypeptides are well known in the art, such as expression in prokaryotic or eukaryotic hosts cells (for example, see Green & Sambrook, 2012, Molecular Cloning, *A Laboratory Manual*, Fourth Edition, Cold Spring Harbor, New York, the relevant disclosures in which document are hereby incorporated by reference).

Polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis).

Polynucleotides, Vectors and Cells

A fourth aspect of the invention provides an isolated nucleic acid molecule encoding a bispecific polypeptide according to any one of the preceding claims, or a component polypeptide chain thereof. For example, the nucleic acid molecule may comprise any of the nucleotide sequences provided in Tables A and B.

Thus, a polynucleotide of the invention may encode any polypeptide as described herein, or all or part of B1 or all or part of B2. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Representative polynucleotides which encode examples of a heavy chain or light chain amino acid sequence of an antibody may comprise or consist of any one of the nucleotide sequences disclosed herein, for example the sequences set out in Tables A and B.

A suitable polynucleotide sequence may alternatively be a variant of one of these specific polynucleotide sequences. For example, a variant may be a substitution, deletion or addition variant of any of the above nucleic acid sequences.

A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al, 1984; the disclosures of which are incorporated herein by reference).

The PILEUP and BLAST algorithms can also be used to calculate homology or line up sequences (typically on their default settings), for example as described in Altschul, 1993; Altschul et al, 1990, the disclosures of which are incorporated herein by reference).

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff & Henikoff, 1992; the disclosures of which are incorporated herein by reference) alignments (B) of 50, expectation (E) of 10, M=5, N=4, and a comparison of both strands.

The BLAST algorithm performs a statistical analysis of the similarity between two sequences; see e.g. Karlin & Altschul, 1993; the disclosures of which are incorporated herein by reference. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

A polypeptide of the invention may thus be produced from or delivered in the form of a polynucleotide which encodes, and is capable of expressing, it.

Polynucleotides of the invention can be synthesised according to methods well known in the art, as described by way of example in Green & Sambrook (2012, Molecular Cloning—a laboratory manual, 4th edition; Cold Spring Harbor Press; the disclosures of which are incorporated herein by reference).

The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art (see Green & Sambrook, supra).

The invention also includes cells that have been modified to express a polypeptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a polypeptide of the invention include mammalian human embryonic kidney (HEK) (for example, HEK293T), CHO, HeLa, NSO and COS cells. Preferably the cell line selected will be one which is not only stable, but also allows for mature glycosylation and cell surface expression of a polypeptide.

Such cell lines of the invention may be cultured using routine methods to produce a polypeptide of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In one embodiment, the nucleic acid molecule encodes an antibody heavy chain or variable region thereof.

In one embodiment, the nucleic acid molecule encodes an antibody light chain or variable region thereof.

By "nucleic acid molecule" we include DNA (e.g. genomic DNA or complementary DNA) and mRNA molecules, which may be single- or double-stranded. By "isolated" we mean that the nucleic acid molecule is not located or otherwise provided within a cell.

In one embodiment, the nucleic acid molecule is a cDNA molecule.

It will be appreciated by persons skilled in the art that the nucleic acid molecule may be codon-optimised for expression of the antibody polypeptide in a particular host cell, e.g. for expression in human cells (for example, see Angov, 2011, the disclosures of which are incorporated herein by reference).

Also included within the scope of the invention are the following:
- (a) a fifth aspect of the invention provides a vector (such as an expression vector) comprising a nucleic acid molecule according to the fourth aspect of the invention;
- (b) a sixth aspect of the invention provides a host cell (such as a mammalian cell, e.g. human cell, or Chinese hamster ovary cell, e.g. CHOK1SV cells) comprising a nucleic acid molecule according to the fourth aspect of the invention or a vector according to the fifth aspect of the invention; and
- (c) a seventh aspect of the invention provides a method of making a polypeptide according to the first, second or third aspect of the invention comprising culturing a population of host cells according to the sixth aspect of the invention under conditions in which said polypeptide is expressed, and isolating the polypeptide therefrom.

Methods of Production

In an eighth aspect, the present invention provides compositions comprising molecules of the invention, such as the antibodies, bispecific polypeptides, polypeptides, polynucleotides, vectors and cells described herein. For example, the invention provides a composition comprising one or more molecules of the invention, such as one or more antibodies and/or bispecific polypeptides of the invention, and at least one pharmaceutically acceptable carrier.

It will be appreciated by persons skilled in the art that additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals.

For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the CD40 and CEA-binding activity of the bispecific polypeptide of the invention. Such pharmaceutically acceptable buffers, carriers or excipients are well-known in the art (see *Remington's Pharmaceutical Sciences*, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the polypeptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the polypeptide of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethyleneglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The polypeptides of the invention may be formulated into any type of pharmaceutical composition known in the art to be suitable for the delivery thereof.

In one embodiment, the pharmaceutical compositions of the invention may be in the form of a liposome, in which the polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethyleneglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the polypeptide may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

Particularly preferred compositions are formulated for systemic administration.

The composition may preferably be formulated for sustained release over a period of time. Thus the composition may be provided in or as part of a matrix facilitating sustained release. Preferred sustained release matrices may comprise a montanide or γ-polyglutamic acid (PGA) nanoparticles.

The bispecific polypeptides can be formulated at various concentrations, depending on the efficacy/toxicity of the polypeptide being used. For example, the formulation may comprise the active polypeptide at a concentration of between 0.1 µM and 1 mM, more preferably between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM, between 500 µM and 600 µM, between 600 µM and 700 µM, between 800 µM and 900 µM or between 900 µM and 1 mM. Typically, the formulation comprises the active polypeptide at a concentration of between 300 µM and 700 µM.

Typically, the therapeutic dose of the bispecific polypeptide (with or without a therapeutic moiety) in a human patient will be in the range of 100 µg to 700 mg per administration (based on a body weight of 70 kg). For example, the maximum therapeutic dose may be in the range of 0.1 to 20 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of cancers and/or tumours, such as antimetabolites, alkylating agents, anthracyclines and other cytotoxic antibiotics, *vinca* alkyloids, etoposide, platinum compounds, taxanes, topoisomerase I inhibitors, other cytostatic drugs, antiproliferative immunosuppressants, antiangiogenic drugs, cancer vaccines, adoptive cell transfer (T cells/DC, NK cells), corticosteroids, sex hormones and hormone antagonists, and other therapeutic antibodies (such as antibodies against a CEA or an immune checkpoint modulator).

For example, the pharmaceutical compositions of the invention may be administered in combination with an immunotherapeutic agent that binds a target selected from the group consisting of PD-1/PD-L1, VGFR, EGFR, HER2, CTLA-4, CD137, OX40, GITR, LAG3, TIM3, CD27, VISTA and KIR.

Thus, the invention encompasses combination therapies comprising a bispecific polypeptide of the invention together with a further immunotherapeutic agent, effective in the treatment of cancer and/or a tumour, which specifically binds to an immune checkpoint molecule. It will be appreciated that the therapeutic benefit of the further immunotherapeutic agent may be mediated by attenuating the function of an inhibitory immune checkpoint molecule and/or by activating the function of a stimulatory immune checkpoint or co-stimulatory molecule.

In one embodiment, the further immunotherapeutic agent is selected from the group consisting of:

(a) an immunotherapeutic agent that inhibits the function of PD-1 and/or PD-L1;
(b) an immunotherapeutic agent that inhibits the function of CTLA-4;
(c) an immunotherapeutic agent that activates the function of CD137;
(d) an immunotherapeutic agent that binds activates the function of OX40;
(e) an immunotherapeutic agent that inhibits the function of LAG3;
(f) an immunotherapeutic agent that inhibits the function of TIM3;
(g) an immunotherapeutic agent that inhibits the function of VISTA;
(h) an immunotherapeutic agent that inhibits the function of VGFR;
(i) an immunotherapeutic agent that inhibits the function of EGFR; and
(j) an immunotherapeutic agent that inhibits the function of HER2.

Thus, the further immunotherapeutic agent may be a PD-1 inhibitor, such as an anti-PD-1 antibody, or antigen-binding fragment thereof capable of inhibiting PD-1 function (for example, Nivolumab, Pembrolizumab, Lambrolizumab, PDR-001, MEDI-0680 and AMP-224). Alternatively, the PD-1 inhibitor may comprise or consist of an anti-PD-L1 antibody, or antigen-binding fragment thereof capable of inhibiting PD-1 function (for example, Durvalumab, Atezolizumab, Avelumab and MDX-1105).

In another embodiment, the further immunotherapeutic agent is a CTLA-4 inhibitor, such as an anti-CTLA-4 antibody or antigen-binding portion thereof.

In a further embodiment, the further immunotherapeutic agent activates CD137, such as an agonistic anti-CD137 antibody or antigen-binding portion thereof.

In a further embodiment, the further immunotherapeutic agent activates OX40, such as an agonistic anti-OX40 antibody or antigen-binding portion thereof.

In a further embodiment, the further immunotherapeutic agent inhibits the function of LAG3, TIM3 or VISTA (Lines et al. 2014).

In another embodiment, the further immunotherapeutic agent is a VGFR inhibitor, such as an anti-VGFR antibody or antigen-binding portion thereof.

In a further embodiment, the further immunotherapeutic agent activates EGFR, such as an agonistic anti-EGFR antibody or antigen-binding portion thereof.

In a further embodiment, the further immunotherapeutic agent activates HER2, such as an agonistic anti-HER2 antibody or antigen-binding portion thereof.

It will be appreciated by persons skilled in the art that the presence of the two active agents (as detailed above) may provide a synergistic benefit in the treatment of a tumour in a subject. By "synergistic" we include that the therapeutic effect of the two agents in combination (e.g. as determined by reference to the rate of growth or the size of the tumour) is greater than the additive therapeutic effect of the two agents administered on their own. Such synergism can be identified by testing the active agents, alone and in combination, in a relevant cell line model of the solid tumour.

Also within the scope of the present invention are kits comprising polypeptides or other compositions of the invention and instructions for use. The kit may further contain one or more additional reagents, such as an additional therapeutic or prophylactic agent as discussed above.

Medical Uses and Methods

The polypeptides in accordance with the present invention may be used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount".

In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means.

Thus, a ninth aspect of the invention provides a bispecific polypeptide according to the first or third aspect of the invention or polypeptide according to the second aspect of the invention for use in medicine.

A tenth aspect of the invention provides a bispecific polypeptide according to the first or third aspect of the invention or polypeptide according to the second aspect of the invention for use in treating cancer and/or a tumour and/or a non-cancer condition in a subject. A cancer and/or a tumour may be referred to as a neoplastic disorder.

An eleventh aspect of the invention provides a use of a bispecific polypeptide according to the first or third aspect of the invention or polypeptide according to the second aspect of the invention in the preparation of a medicament for treating cancer and/or a tumour and/or a non-cancer condition in a subject.

In one embodiment, the bispecific polypeptide or polypeptide for the use of the tenth aspect of the invention, or the use of the eleventh aspect of the invention, is for use in combination with one or more additional therapeutic agents.

In one embodiment, the one or more additional therapeutic agents is/are an immunotherapeutic agent that binds a target selected from the group consisting of PD-1/PD-L1, VGFR, EGFR, HER2, CTLA-4, CD137, OX40, GITR, LAG3, TIM3, CD27, VISTA and KIR.

In one embodiment, the bispecific polypeptide or polypeptide for the use of the tenth aspect of the invention, or the use of the eleventh aspect of the invention, is for administration systemically.

A twelfth aspect of the invention provides a method for the treatment and/or diagnosis of cancer and/or a tumour and/or a non-cancer condition in a subject, comprising the step of administering to the subject an effective amount of a bispecific polypeptide according to the first or third aspect of the invention or polypeptide according to the second aspect of the invention.

An alternative twelfth aspect of the invention, invention provides an in vitro method for the diagnosis of cancer and/or a tumour, comprising using a according to the first or third aspect of the invention or polypeptide according to the second aspect of the invention.

In one embodiment, the method comprises administering the bispecific polypeptide systemically.

In one embodiment, the methods further comprise administering to the subject one or more additional therapeutic agents.

By 'treatment' we include both therapeutic and prophylactic treatment of the patient.

The term 'prophylactic' is used to encompass the use of an agent, or formulation thereof, as described herein which either prevents or reduces the likelihood of a neoplastic disorder, or the spread, dissemination, or metastasis of cancer cells in a patient or subject. The term 'prophylactic' also encompasses the use of an agent, or formulation thereof, as described herein to prevent recurrence of a neoplastic disorder in a patient who has previously been treated for the cancer and/or tumour.

Preferably, the cancer and/or the tumour is a cancer and/or the tumour associated with CEA; for example, CEA expression. By "associated with CEA", we include that the CEA is cancer and/or the tumour is caused by CEA and/or CEA is a marker for the cancer and/or the tumour.

In one embodiment, the cancer and/or the tumour comprises target cells comprising expression of CEA.

Preferably, the expression of CEA is an intermediate level of CEA expression or a high level of CEA expression.

In one embodiment, the intermediate level of CEA expression is characterised by the target cell expressing about 10,000 or more CEA receptors per target cell; for example, about 11,000 or more; about 12,000 or more; about 13,000 or more; about 14,000 or more; about 15,000 or more; about 16,000 or more; about 17,000 or more; about 18,000 or more; about 19,000 or more; about 20,000 or more; about 25,000 or more; about 30,000 or more; about 35,000 or more; about 40,000 or more; about 50,000 or more; about 60,000 or more; about 70,000 or more; about 80,000 or more; about 90,000 or more; about 100,000 or more; about 125,000 or more; about 150,000 or more; or about 175,000 or more CEA receptors per target cell. In another embodiment, the intermediate level of CEA expression is characterised by the target cell expressing about 10,000 to about 200,000 CEA receptors per target cell; for example, about 20,000 to about 175,000 CEA receptors per target cell or 20,000 to about 200,000 CEA receptors per target cell or about 50,000 to about 175,000 CEA receptors per target cell or about 50,000 to about 200,000 CEA receptors per target cell. Preferably, the CEA receptors are CEACAM5 receptors.

In one embodiment, the high level of CEA expression is characterised by the target cell expressing about 200,000 or more CEA receptors per target cell; for example, about 225,000 or more; about 250,000 or more; about 275,000 or more; about 300,000 or more; about 325,000 or more; about 350,000 or more; about 375,000 or more; about 400,000 or more; about 425,000 or more; about 450,000 or more; about 475,000 or more; about 500,000 or more; about 600,000 or more; about 700,000 or more; about 800,000 or more; about 900,000 or more; or about 1,000,000 CEA receptors per target cell, preferably about 300,000 of more CEA receptors per target cell. In another embodiment, the high level of CEA expression is characterised by the target cell expressing about 200,000 to about 1,000,000 CEA receptors per target cell; for example, about 200,000 to about 500,000 CEA receptors per target cell or about 300,000 to about 500,000 CEA receptors per target cell. Preferably, the CEA receptors are CEACAM5 receptors.

In one embodiment, the cancer and/or the tumour does not comprise a cell with no or a low level of CEA expression. In one embodiment, the low level of CEA expression is characterised by the cell expressing about 10,000 or fewer CEA receptors per target cell; for example, about 9,000 or fewer; about 8,000 or fewer; about 7,000 or fewer; about 6,000 or fewer; about 5,000 or fewer; about 4,000 or fewer; about 3,000 or fewer; about 2,000 or fewer; or about 1,000 or fewer CEA receptors per cell.

In one embodiment, the CEA is a tumor-associated CEA. Preferably, the CEA is a CEACAM.

In one embodiment, the CEACAM is one or more selected from the listing consisting of: CEACAM1; CEACAM3; CEACAM4; CEACAM5; CEACAM6; CEACAM7; CEACAM8; CEACAM16; CEACAM18; CEACAM19; CEACAM20; and CEACAM21. It will be appreciated that the reference to the aforementioned CEACAM molecules includes splice variants.

Preferably, the CEACAM is one or more selected from the listing consisting of: CEACAM1; CEACAM5; and CEACAM6. Preferably, the CEACAM is CEACAM1. Most preferably, the CEACAM is CEACAM5.

In a preferred embodiment, B2 is capable of specifically binding to CEACAM5 but not other CEACAMs, particularly not CEACAM1.

In one embodiment, the cancer and/or the tumour is one or more cancer and/or tumour selected from the list consisting of: prostate cancer and/or a prostate tumour; breast cancer and/or a breast tumour; lung cancer and/or a lung tumour; colorectal cancer and/or a colorectal tumour; melanomas; bladder cancer and/or a bladder tumour; brain/CNS cancer and/or a brain/CNS tumour; cervical cancer and/or a cervical tumour; oesophageal cancer and/or a oesophageal tumour; gastric cancer and/or a gastric tumour; head/neck cancer and/or a head/neck tumour; kidney cancer and/or a kidney tumour; liver cancer and/or a liver tumour; a carcinoma; leukaemia; lymphomas; ovarian cancer and/or an ovarian tumour; pancreatic cancer and/or a pancreatic tumour; tonsil cancer and/or a tonsil tumour; and sarcomas. Preferably, a carcinoma.

Preferably, the one or more cancer and/or tumour selected from the list consisting of: breast cancer and/or a breast tumour; lung cancer and/or a lung tumour; colorectal cancer and/or a colorectal tumour; gastric cancer and/or a gastric tumour; and/or pancreatic cancer and/or a pancreatic tumour.

In a preferred embodiment, the cancer and/or tumour is a colorectal cancer and/or a colorectal tumour.

In a preferred embodiment, the cancer and/or tumour is a tonsil cancer and/or a tonsil tumour.

Preferably, the carcinoma is one or more carcinoma selected from the listing consisting of: gastric carcinoma; oesophageal carcinoma; colorectal carcinoma; pancreatic carcinoma; lung carcinoma; breast carcinoma; cervical carcinoma; cholangiocarcinoma; and medullary thyroid carcinoma.

In a preferred embodiment, the carcinoma is a colorectal carcinoma.

Preferably, the tumour is a solid tumour.

In one embodiment, the non-cancer condition is a non-cancer condition is one associated with CEA; for example, CEA expression. By "associated with CEA", we include that the CEA is non-cancer condition is caused by CEA and/or CEA is a marker for the non-cancer condition.

In one embodiment, the non-cancer condition comprises target cells comprising expression of CEA.

Preferably, the expression of CEA is an intermediate level of CEA expression or a high level of CEA expression, as discussed herein.

Preferably, the one or more non-cancer condition is selected from the list consisting of: ulcerative colitis, pancreatitis; cirrhosis; COPD; Crohn's disease; and/or hypothyroidism.

In one embodiment, the subject is human.

Optimised RUBY™ Format

A thirteenth aspect of the invention provides a bispecific polypeptide comprising the optimised RUBY™ format, preferably wherein the bispecific polypeptide has specificity for a first antigen and a second antigen.

In a particular embodiment, the bispecific polypeptide comprises:
(a) an immunoglobulin molecule having specificity for a first antigen, the immunoglobulin molecule comprising a first heavy chain polypeptide and a first light chain polypeptide; and
(b) at least one Fab fragment having specificity for a second antigen, the Fab fragment comprising a second heavy chain polypeptide and a second light chain polypeptide
wherein the second light chain polypeptide is fused to the C-terminus of the first heavy chain polypeptide
and wherein the bispecific antibody comprises one or more mutations discussed in relation to the optimised RUBY™ format to promote association of the polypeptide; in particular, of the first heavy chain polypeptide with the first light chain polypeptide and/or to promote association of the second heavy chain polypeptide with the second light chain polypeptide.

All of the features of the optimised RUBY™ format, and the necessary associated embodiments of the RUBY™ format, as discussed for the first aspect of the invention are relevant to, and included in, the thirteenth aspect of the invention. In particular, the features discussed below.

The optimised RUBY™ format has the structure shown in FIG. 23 with further optimised mutations, when compared to the RUBY™ format. As will be appreciated by the skilled person, technology relating to antibody format has wide applicability to a wide range of different target antigens.

Although bispecific polypeptides in the "RUBY™ format" can be reproducibly produced with an excellent level of purity, bispecific polypeptides in the "optimised RUBY™ format" can be reproducibly produced at an even higher level of purity. Further, bispecific polypeptides in the "optimised RUBY™ format" have been engineered to carry a reduced risk of provoking immunogenic responses directed against the bispecific polypeptide itself.

In one embodiment of the thirteenth aspect of the invention, the bispecific polypeptide is a bispecific antibody.

In one embodiment, the bispecific polypeptide comprises an immunoglobulin arranged as an antibody with two arms and therefore two binding sites for the first antigen, and two of the Fab fragments, each providing a binding site for the second antigen. Thus, there are two binding sites for the first antigen and two binding sites for the second antigen. In a preferred embodiment of the thirteenth aspect of the invention, the first antigen and/or second antigen are not CD40 and/or CEA. In a further preferred embodiment of the thirteenth aspect of the invention the first antigen and/or second antigen are a protein and/or peptide that is not CD40 and/or CEA.

In one embodiment, the one or more Fab fragment(s) is linked to the C-terminal end of the immunoglobulin via a linker.

In one embodiment of the first aspect of the invention, the bispecific polypeptide is tetravalent, capable of binding bivalently to each of the two antigens.

The optimised mutations are described below as "optimised mutation set 1" and "optimised mutation set 2"—including "set 2a" and/or "set 2b". It will be appreciated by the skilled person various combinations of these optimised mutations could be used in a bispecific polypeptide of the invention, as well as in combination with any of the "RUBY™ format" mutations described above. It will also be appreciated that the variations of those mutations as described herein would also work as part of the invention. All mutations in variable domains (VH or VL) are numbered according to the IMGT numbering system, and all mutations in the constant domains are numbered according to the EU numbering system.

Mutation set 1—Mutations in the variable domain heavy (VH):

T65E, T65A, T65I.

Mutation set 2—any individual and/or any combination of the mutations listed in set 2a and set 2b. Set 2a—mutations in the CH1: Y180A, Y180G, Y180I, Y180N, Y180S, Y180T, Y180V, or Y180W, and/or S183N or S183T, and/or V188G; preferably, Y180T. Set 2b—mutations in the CKappa domain: A111R, A111T, A111W or A111V, and/or T109P; preferably: T109P and/or A111V; and/or mutations in the variable domain light (VL): I126A, I126G, I126H, I126N, I126P, I126Q, I126S, or I126T.

In one embodiment of the invention the mutations are at positions selected from the group consisting of:
(a) the T65 position in the VH (according to the IMGT numbering system); and/or
(b) one or more of the following positions in the CH1: Y180; S183; and V188, preferably Y180 (according to the EU numbering system); and/or
(c) one or more of the following positions in the CKappa domain: A111 and T109
(according to the EU or Kabat numbering systems); and/or
(d) the I126 position in the VL (according to the IMGT numbering system).

In a particular embodiment, the mutation is at the T65 position in the variable domain heavy (VH) (according to the IMGT numbering system).

In a particular embodiment, the mutations are one or more of the following positions in the CH1: Y180; S183; and V188, preferably Y180 (according to the EU numbering system).

In a particular embodiment, the mutations are one or more of the following positions in the CKappa domain: A111 and T109 (according to the EU or Kabat numbering systems); and/or the I126 position in the VL (according to the IMGT numbering system).

In one embodiment of the invention the mutations are selected from the group consisting of:
(a) X65E/A/I in the VH (according to the IMGT numbering system); and/or
(b) one or more of the following mutations in the CH1: X180A/G/I/N/S/T/V/W; X183N/T; and X188G; preferably, X180T (according to the EU numbering system); and/or
(c) one or more of the following mutations in the C-Kappa domain: X111R/T/W/V; and X109P, preferably X111V and X109P (according to the EU or Kabat numbering systems); and/or
(d) X126A/G/H/N/P/Q/S/T in the VL (according to the IMGT numbering system).

X refers to any amino acid

In a particular embodiment, the mutation is X65E/A/I in the VH chain (according to the IMGT numbering system).

X refers to any amino acid

In a particular embodiment, the mutation is one or more of the following mutations in the CH1: X180A/G/I/N/S/T/

V/W; X183N/T; and X188G; preferably, X180T (according to the EU numbering system).

X refers to any amino acid

In a particular embodiment, the mutation is one or more of the following mutations in the CKappa domain: X111R/T/W/V; and X109P, preferably X111V and X109P (according to the IMGT numbering system); and/or the mutation is X126A/G/H/N/P/Q/S/T in the VL (according to the IMGT numbering system).

X refers to any amino acid

For example, the mutations may be selected from the group consisting of:
- (a) one or more of the following mutations in the VH: T65E; T65A; and T65I
  (according to the IMGT numbering system); and/or
- (b) one or more of the following mutations in the CH1: Y180A; Y180G; Y180I; Y180N; Y180S; Y180T; Y180V; Y180W; S183N; S183T; V188G, preferably Y180T (according to the EU numbering system); and/or
- (c) one or more of the following mutations in the CKappa domain: A111R; A111T; A111W; A111V; and T109P, preferably T109P and A111V (according to the EU numbering system); and/or
- (d) one or more of the following mutations in the VL: I126A; I126G; I126H; I126N; I126P; I126Q; I126S; and I126T (according to the IMGT numbering system).

In a particular example, the mutations are one or more of the following mutations in the VH: T65E; T65A; and T65I (according to the IMGT numbering system).

In a particular example, the mutations are one or more of the following mutations in the CH1: Y180A; Y180G; Y180I; Y180N; Y180S; Y180T; Y180V; Y180W; S183N; S183T; V188G, preferably Y180T (according to the EU numbering system).

In a particular example, the mutations are one or more of the following mutations in the C-kappa domain: A111R; A111T; A111W; A111V; and T109P, preferably T109P and A111V (according to the EU or Kabat numbering systems); and/or one or more of the following mutations in the VL: I126A; I126G; I126H; I126N; I126P; I126Q; I126S; and I126T (according to the IMGT numbering system).

As discussed above, any combination of the "RUBY™ format" mutations and "optimised RUBY™ format" mutations can be used in the same bispecific antibody, such as any one or more of the following "RUBY™ format" mutations in (a) to (d), or variations described herein, being combined with any one or more of the following "optimised RUBY™ format" mutations in (e) to (g), or variations described herein:
- (a) one or more of the following mutations in the CH1 domain: H168A, F170G and/or T187E (according to EU numbering system);
- (b) one or more of the following mutations in the CKappa domain: L135Y, S176W, S114A and/or N137K (according to EU or Kabat numbering systems) and/or one or more of the following mutations in the CLambda domain: L135Y, S176W, T114A and/or S137K (according to Kabat numbering system);
- (c) mutations in the VL: Q44R or Q44E (according to IMGT numbering system); ad
- (d) mutations in the VH: Q44E or Q44R (according to IMGT numbering system);
- (e) mutations in the VH: T65E, T65A or T65I (according to IMGT numbering system);
- (f) mutation in the CH1: Y180T (according to EU numbering system); and/or
- (g) mutations in the CKappa: T109P and/or A111V (according to EU numbering system).

Accordingly, in a particular embodiment, a bispecific antibody with combined "RUBY™ format" mutations and "optimised RUBY™ format" mutations could include the following mutations:
- one or more of the following mutations in the CH1 domain: H168A, F170G, Y180T and/or T187E (according to EU numbering system);
- one or more of the following mutations in the CKappa domain: T109P, A111V, L135Y, S176W, S114A and/or N137K (according to EU or Kabat numbering systems) and/or one or more of the following mutations in the CLambda domain: L135Y, S176W, T114A and/or S137K (according to Kabat numbering system);
- mutations in the VL: Q44R or Q44E (according to IMGT numbering system); and/or
- one or more of the following mutations in the VH: Q44E or Q44R, and/or T65E, T65A or T65I (according to IMGT numbering system).

The listing or discussion of an apparently prior-published document in this specification should not necessarily be taken as an acknowledgement that the document is part of the state of the art or is common general knowledge.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF FIGURES

Preferred, non-limiting examples which embody certain aspects of the invention will now be described, with reference to the following figures:

FIG. 2A shows binding curves for Multi34, Multi35, Multi37 and Multi38. FIG. 2B shows binding curves for Multi39, Multi40, Multi41 and Multi42. FIG. 2C shows binding curves for Multi44, Multi45, Multi46 and Multi47. Lastly, FIG. 2D shows binding curves for Multi48, Multi4 and AC_05339.

FIG. 6A shows binding curves for Multi34 and Multi35. FIG. 6B shows binding curves for Multi41, Multi42, Multi44 and ffAC_5339. FIG. 6C shows binding curves for Multi46, Multi47, Multi48 and Multi49. FIG. 6D shows binding curves for ffAC_5337 and AC_5339. FIG. 6E shows binding curves for AC_05355 and AC_05339.

FIGS. 27A-27B. Accumulation of the CD40×CEA bsAb, but not corresponding CD40 mAb, in CEA-expressing tumors. Human CD40 transgenic mice were inoculated with MC38-hCEA tumor cells (MC-38-CEA-2, Kerafast) s.c. and were administered with 100 μg anti-CD40 antibody or a molar equivalent dose (167 μg) CD40×CEA bsAb or Isotype bsAb i.p. on days 10 and 13. On day 14, tumors were dissected. Frozen tumor sections were stained for human IgG to assess accumulation of administered antibodies, and for CEA to assess CEA expression pattern in the tumors. Representative images of (FIG. 27A) IgG staining and (FIG. 27B) CEA staining are shown. The staining pattern obtained following treatment with CD40×CEA is significantly stronger than for the controls, and the staining pattern is consistent with the CEA-staining of the tumor.

FIG. 28A) representative images from MB49 tumors. FIG. 28B) The immunohistochemical staining was judged as follows; negative (0), few positive cells (1+), moderate numbers of positive cells (2+), high numbers of positive cells (3+) or very high numbers of positive cells (4+). The analysis shows that a marked higher degree of infiltrating T cells are seen in the MB49 tumors compared to the B16 tumors used as control. Antibodies used for staining: CD4: Rat IgG, Affymetrix, 14-0042 1:200, CD8 Rat IgG, Affymetrix, 14-0081 1:200, CD3 Rabbit, Dako, A0452 1:100, CD45 Rat IgG, Biodesign 1:100. FIG. 28C) Immune cell population frequencies in MB49-EpCAM tumors, with similar in vivo growth and immune infiltration as MB49 tumors. Human CD40 transgenic mice were injected with MB49-hEpCAM cells (0.25×106) s.c. into the right flank in 100 ul of PBS. 12 days after tumor inoculation, tumors were dissected, dissociated and stained for flow cytometry analysis of immune cell content. The frequencies of NK cells (CD45+, CD11b-, CD19- MHC II-, TCRbeta-, NK1.1+), T cells (CD45+, CD11b-, CD19- MHC II-, TCRbeta+, NK1.1-), B cells (CD45+, Ly6G-, CD3-, NK1.1-, CD19+), monocytes/macrophages (CD45+, Ly6G-, CD3-, NK1.1-, CD64+) and DCs (CD45+, Ly6G-, CD3-, NK1.1-, CD64-, CD11c+, MHC II+) within the total viable CD45+ population was assessed.

FIGS. 29A-29C. Data from NHP study. FIG. 29A) B cell activation of the cynoCEA×CD40 RUBY™ on cynomolgus and human B cells in the presence of CEA transfected cells (macaque CEA, NP_001040590.1). Primary cynomolgus B cells were cultured with titrated antibodies in the presence CEA expressed on CHO cells. After 2 days, expression of CD86 on B cells was analyzed by FACS. The graphs show pooled data from two cynomolgus and four human donors. The data demonstrate that CEA×CD40 bsAbs in the RUBY™ format induce upregulation of CD86 on cynomolgus and human B cells to a similar degree. The CEA-conditional activation of CD40 on cynomolgus B cells and human B cells is similar to what is observed with the human CEA×CD40 bsAb in RUBY™ used for the in vitro assays. The cynoCEA×CD40 bsAb binds with similar affinity to human and cynomolgus monkey CEA (hCEA vs cCEA, right panel). In FIG. 29B and FIG. 29C key data from the toxicology assessment in cynomolgus monkey is presented. The cynoCEA×CD40 bispecific antibody was administered once weekly via intravenous infusion for 2 weeks to cynomolgus monkeys at two different dose levels (10 mg/kg and 37.5 mg/kg). One female and one male were evaluated at each dose level. FIG. 29B) Data on L-aspartate aminotransferase (ASAT) and L-alanine aminotransferase (ALAT) and FIG. 29 C) levels of IL-6 and TNFalpha over time. In addition, plasma levels for the following cytokines were measured by a bead-based multiplex immunoassay: IL-2, IL-6, IL-8, IL-10, MCP-1, IFN-γ and TNF-α. The conclusion from the study was that there were no findings associated with cyoCEA×CD40 bsAb at the evaluated dose levels.

FIGS. 30A-30F. Structure of RUBY™ bsAb and binding of RUBY™ bsAb to their various antigen targets as measured by ELISA. (FIG. 30A) Chain 1 consists of the IgG heavy chain, a short polypeptide linker and the light chain of the additional Fab fragment, chain 2 is a light chain that binds to the VH and CH1 domains of the IgG part and chain 3 is a short heavy chain that binds to the light chain appended to the IgG. (FIG. 30B) Dual ELISA showing simultaneous binding of CD40×EpCAM RUBY™ bsAb to its respective antigen targets. ELISA plates were coated with human CD40, bsAb was added followed by detection using biotinylated EpCAM. (FIG. 30C) Dual ELISA showing simultaneous binding of CD40×CEA RUBY™ bsAb to its respective antigen targets. ELISA plates were coated with human CEACAM5, bsAb was added followed by detection using biotinylated CD40. (FIG. 30D) Mono ELISA showing binding of GFPxEpCAM control RUBY™ bsAb to human EpCAM. ELISA plates were coated with human EpCAM, bsAb was added followed by detection using goat anti human-kappa light chain-HRP. (FIG. 30E) Mono ELISA showing binding of cynoCEA×CD40 RUBY™ bsAb to human CD40. ELISA plates were coated with human CD40 followed by addition of cynoCEA×CD40 RUBY™ bsAb and detection using goat anti human-kappa light chain-HRP. (FIG. 30F) Mono ELISA showing binding of cynoCEA× CD40 RUBY™ bsAb to human CEACAM5. ELISA plates were coated with human CEA followed by addition of cynoCEA×CD40 RUBY™ bsAb and detection using goat anti human-kappa light chain-HRP. In summary, Bispecific antibodies were successfully generated in the RUBY™ format and the generated bsAbs displayed good binding to their respective antigen targets as illustrated by the ELISA binding evaluations.

SEQUENCE TABLES

TABLE A

Figure 1:
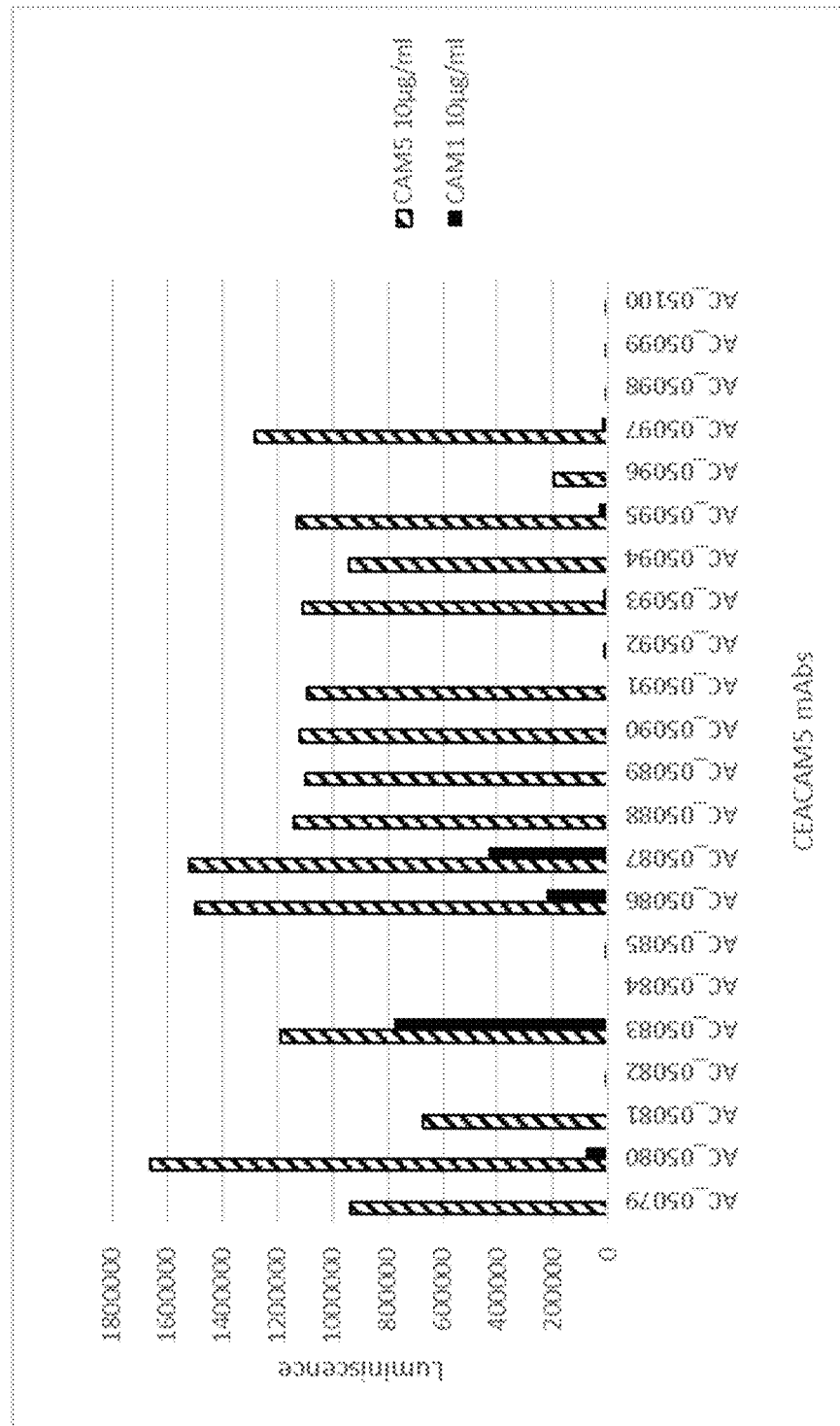
FIG. 1. ELISA analysis of 22 CEA antibodies isolated using phage displayed combined with next generation sequencing. Binders in IgG1 format were analysed for binding to human CEACAM5 (abbreviated CAM5) (diagonal bars) or human CEACAM1 (abbreviated CAM1) (back bars).
Figure 2A:
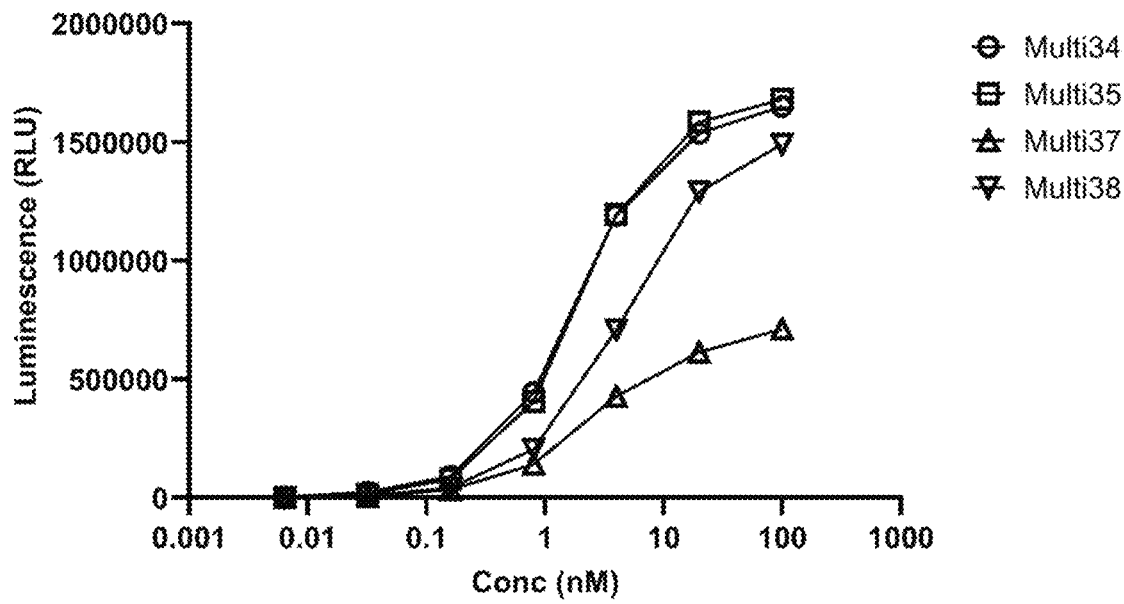
FIGS. 2A-2D. Ability of CD40 and CEACAM5 targeting RUBY™ bsAbs to bind both antigens simultaneously, as measured by dual target ELISA.
Figure 2B:
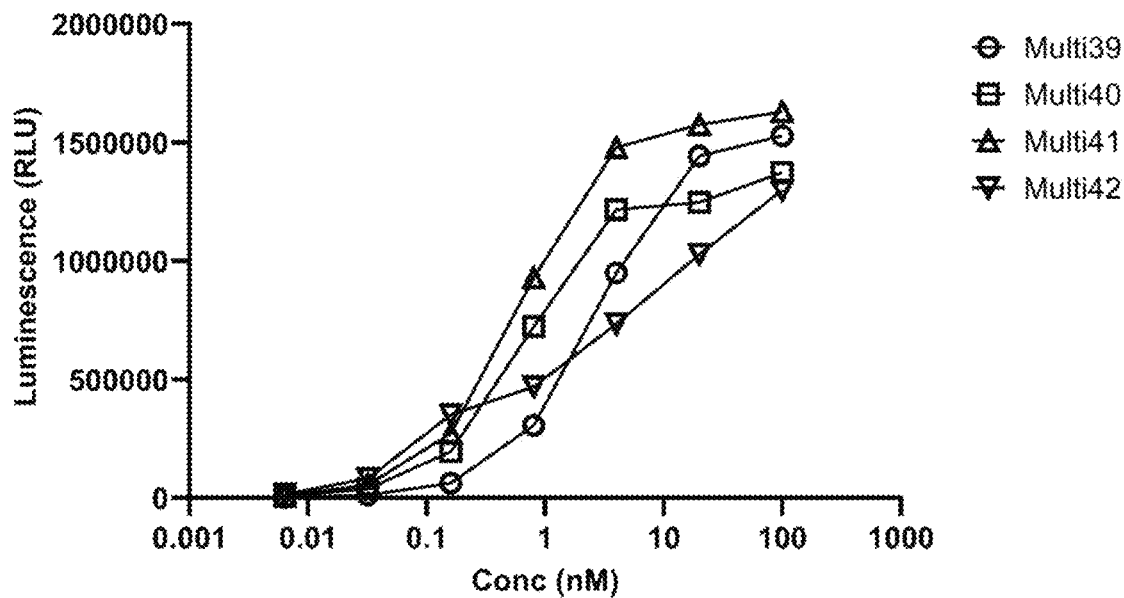
Figure 2C:
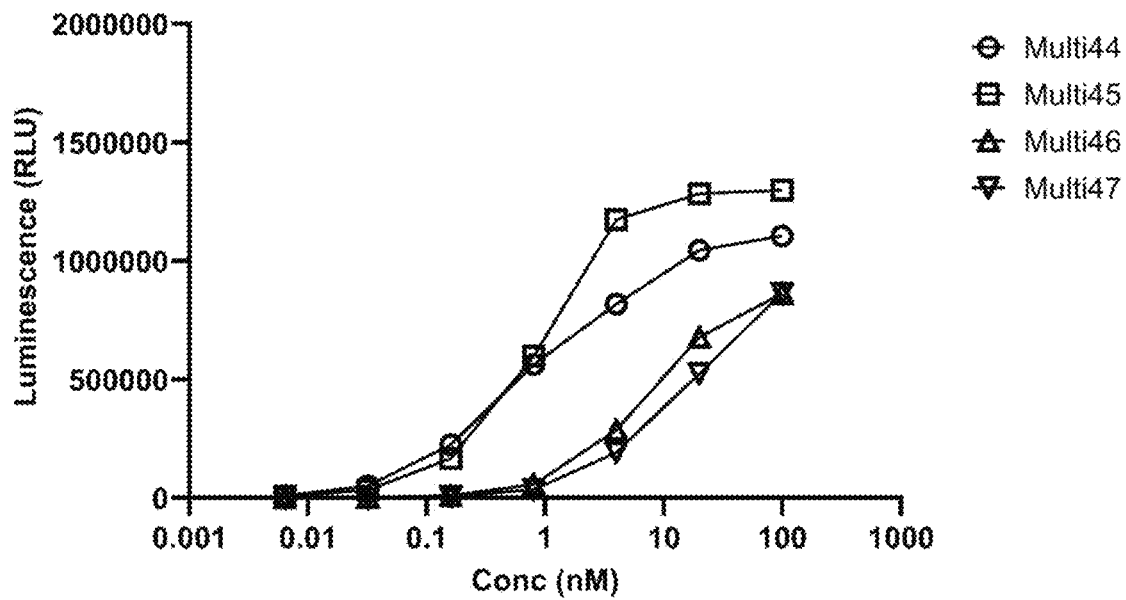
Figure 2D:
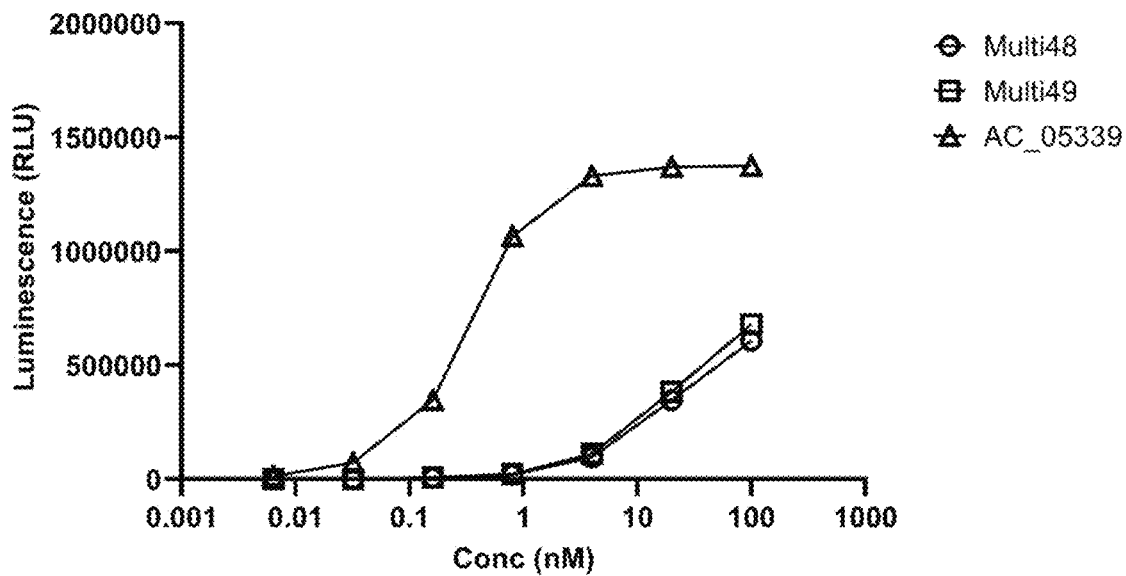
Figure 3A:
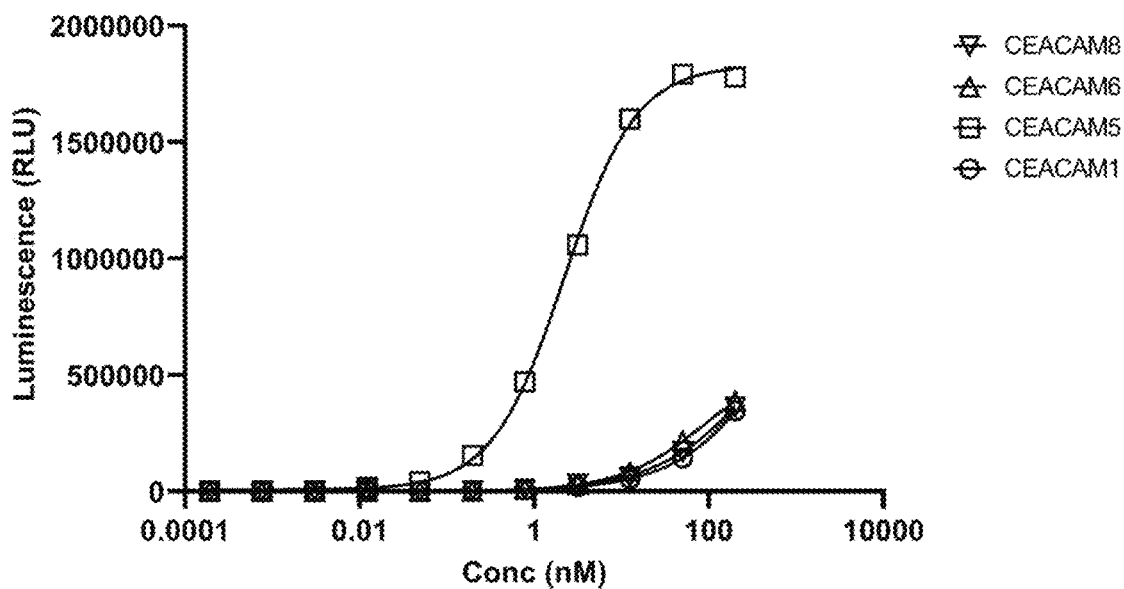
FIGS. 3A-3N. Cross-reactivity of RUBY™ bsAbs (Mult34, Multi35, Multi37-Multi42, Multi44-Multi49) with CEA protein family members CEACAM1, 5, 6 and 8, evaluated in ELISA.
Figure 3B:
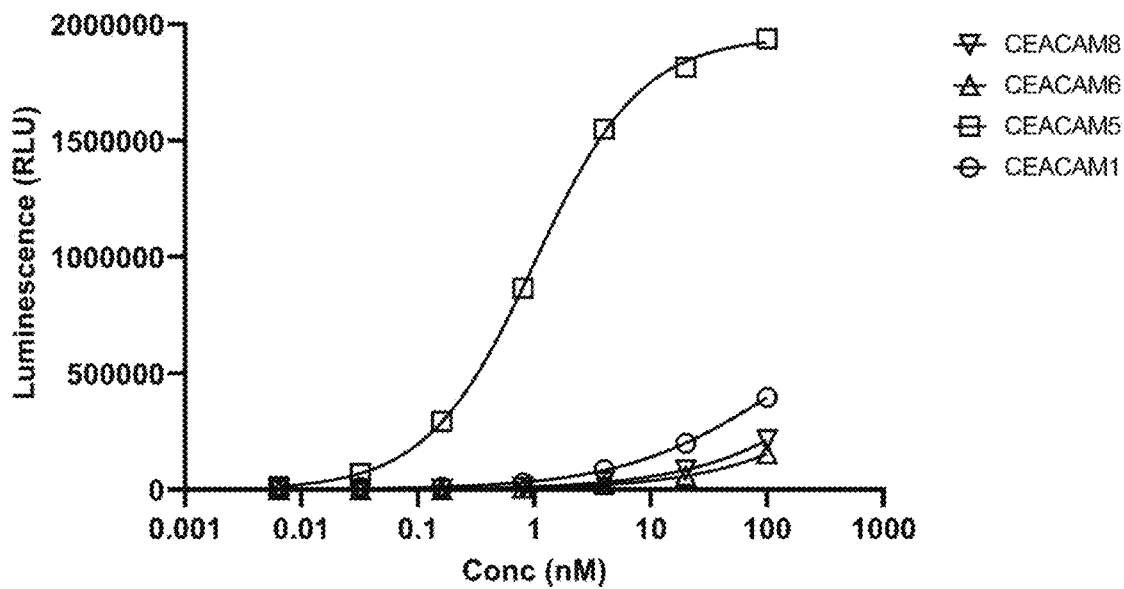
Figure 3E:
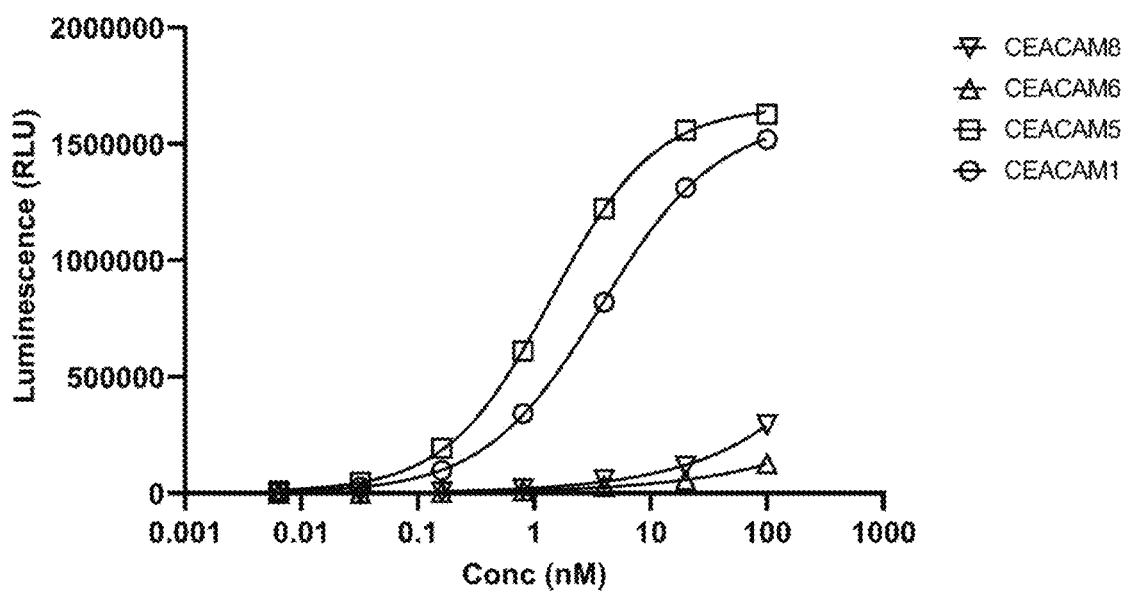
Figure 3F:
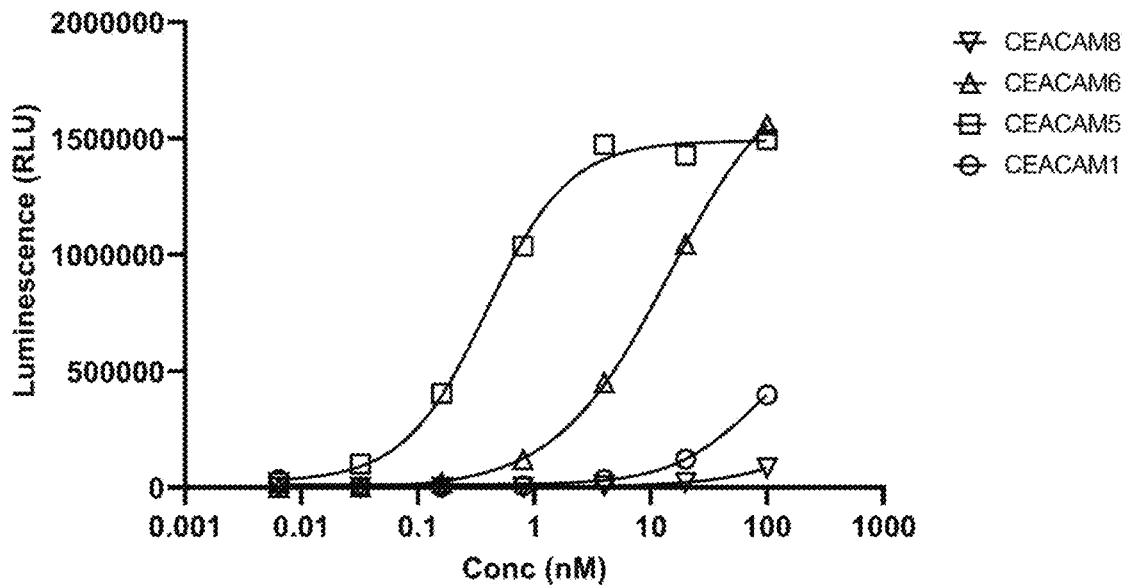
Figure 3G:
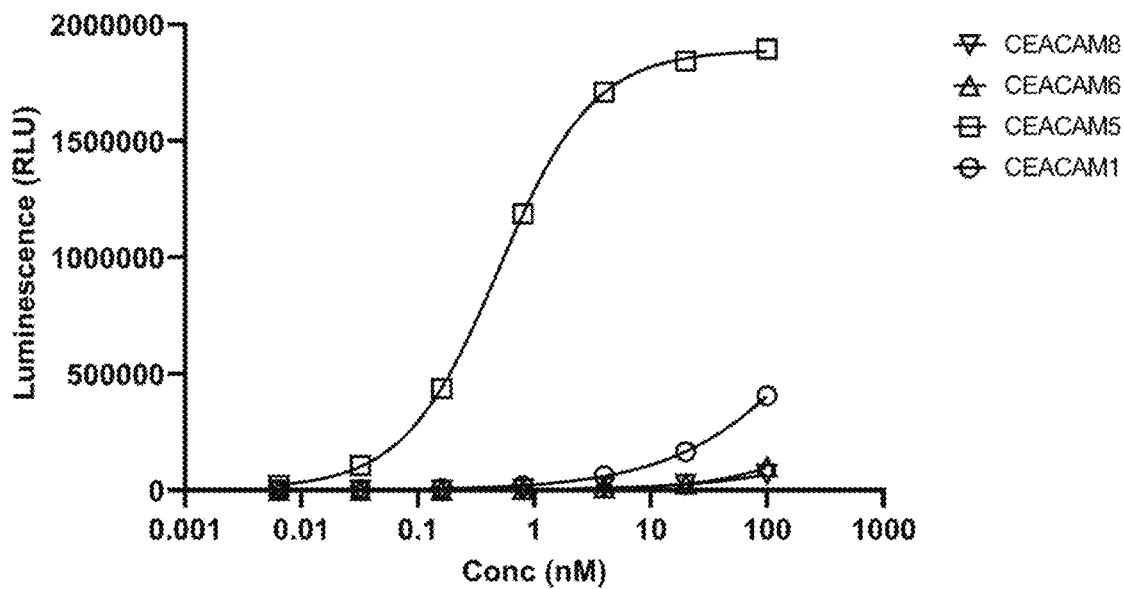
Figure 3H:
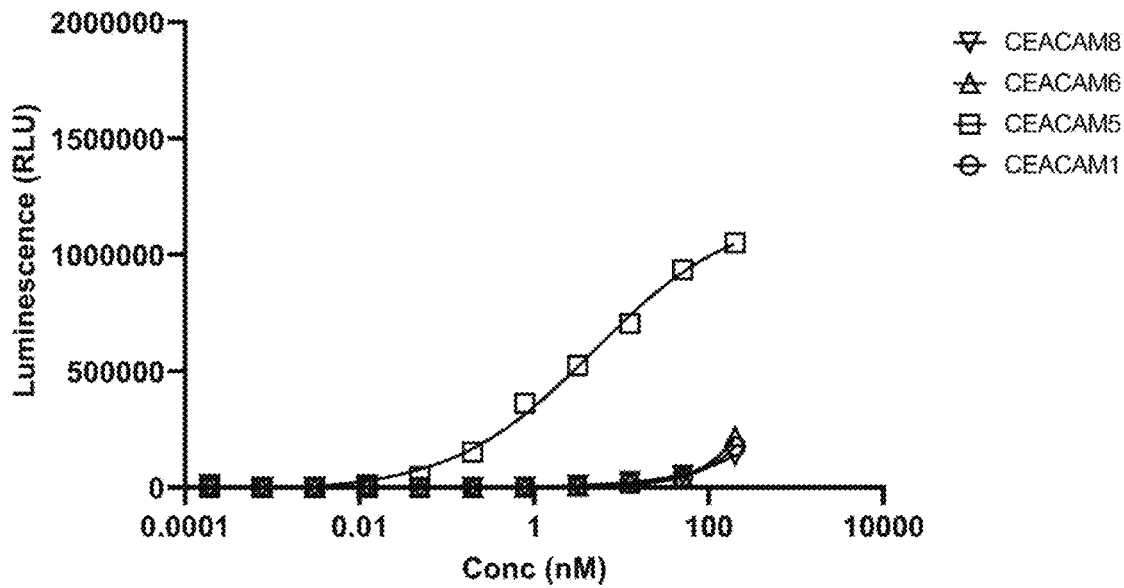
Figure 3I:
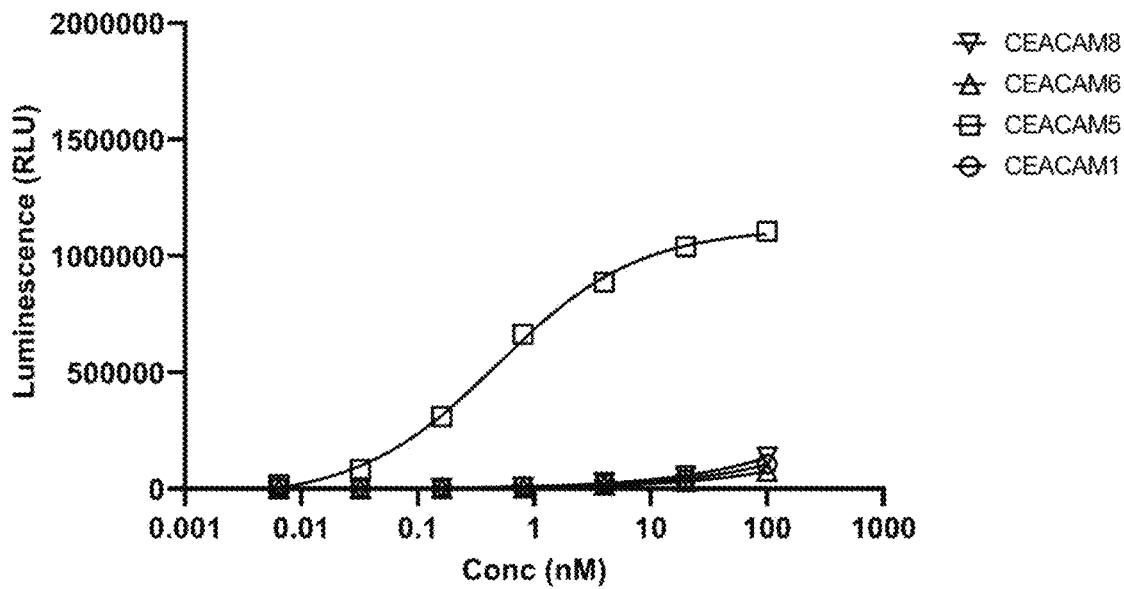
Figure 3J:
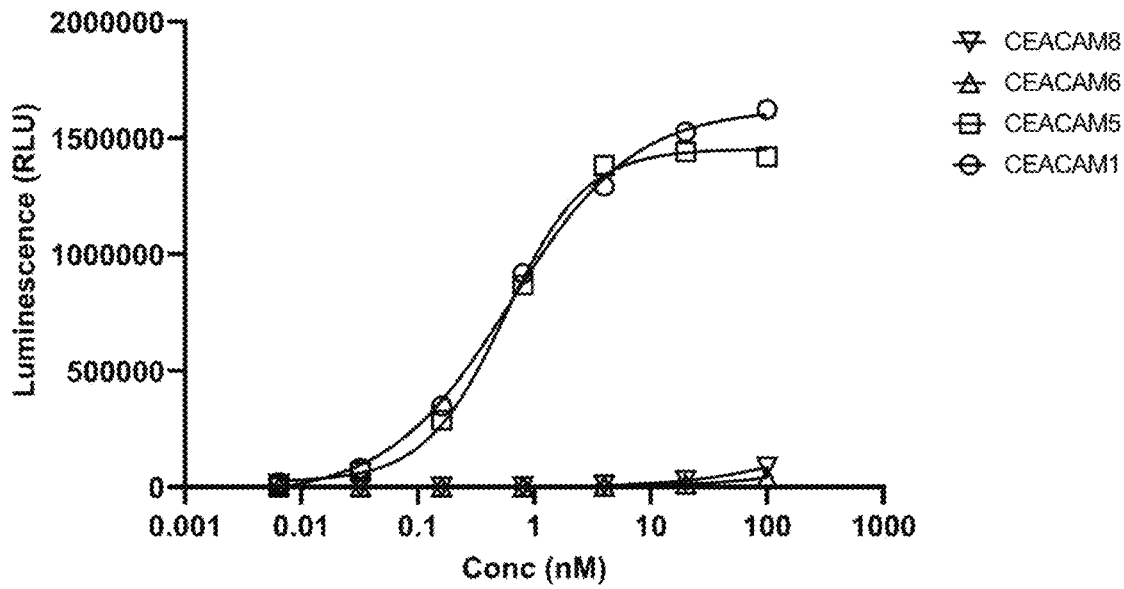
Figure 3K:
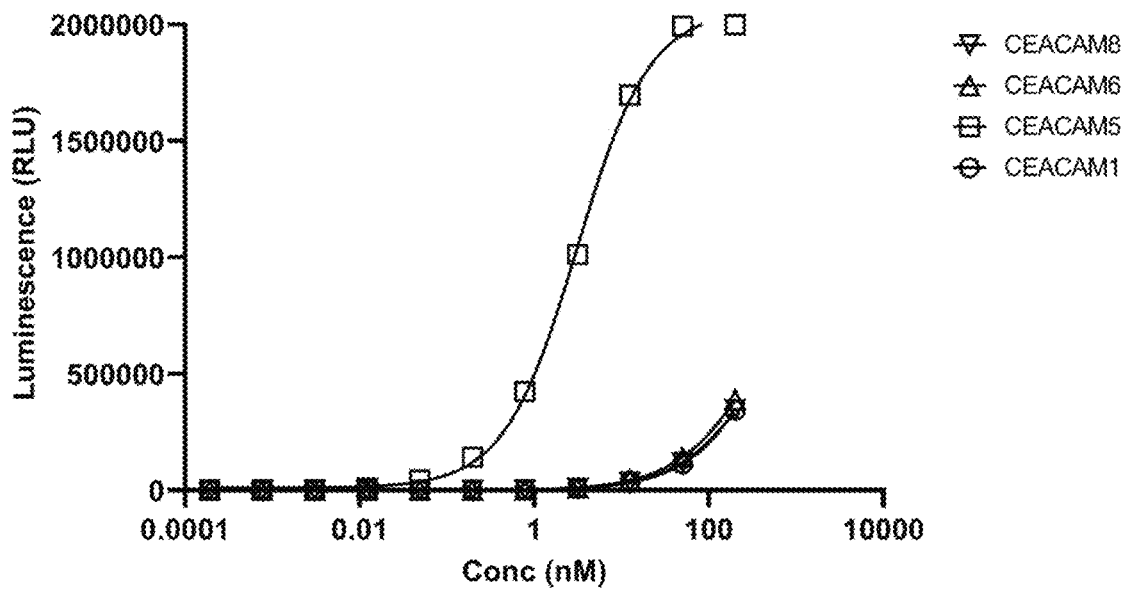
Figure 3L:
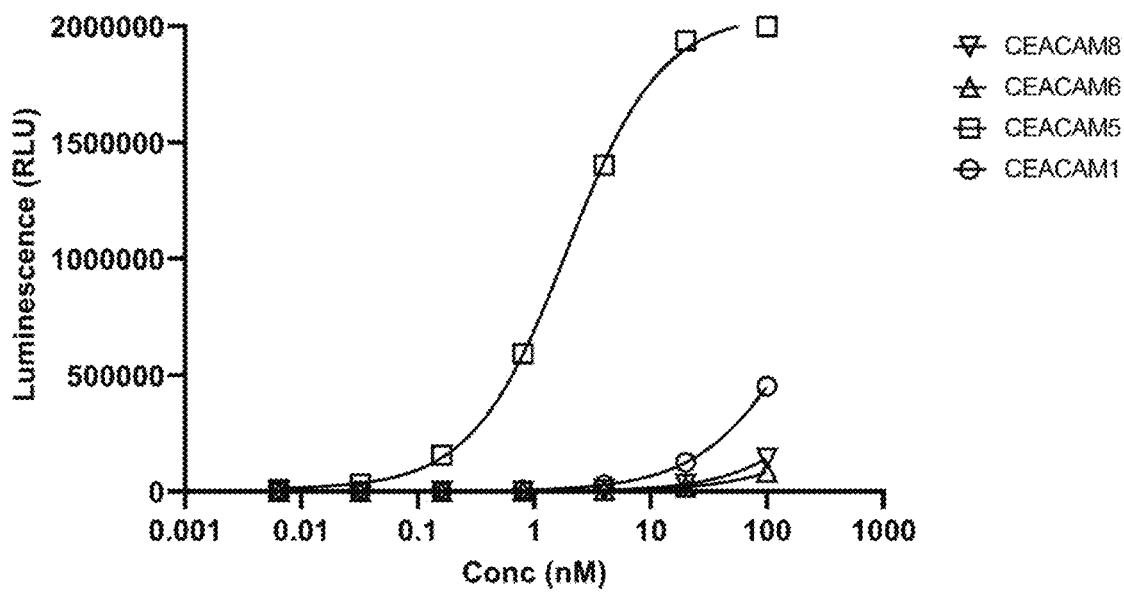
Figure 3M:
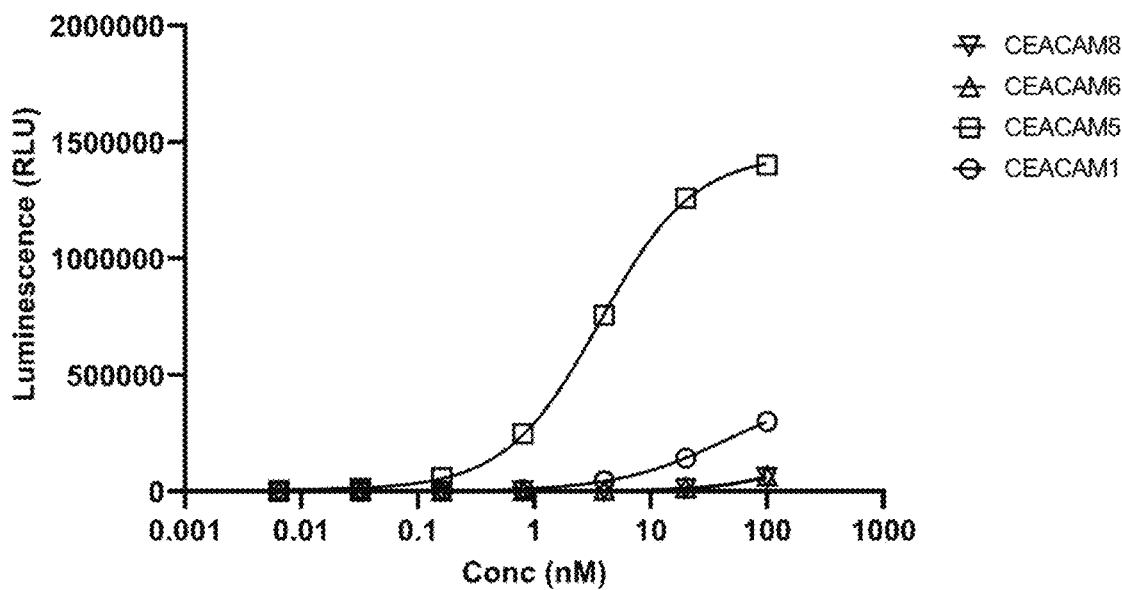
Figure 3N:
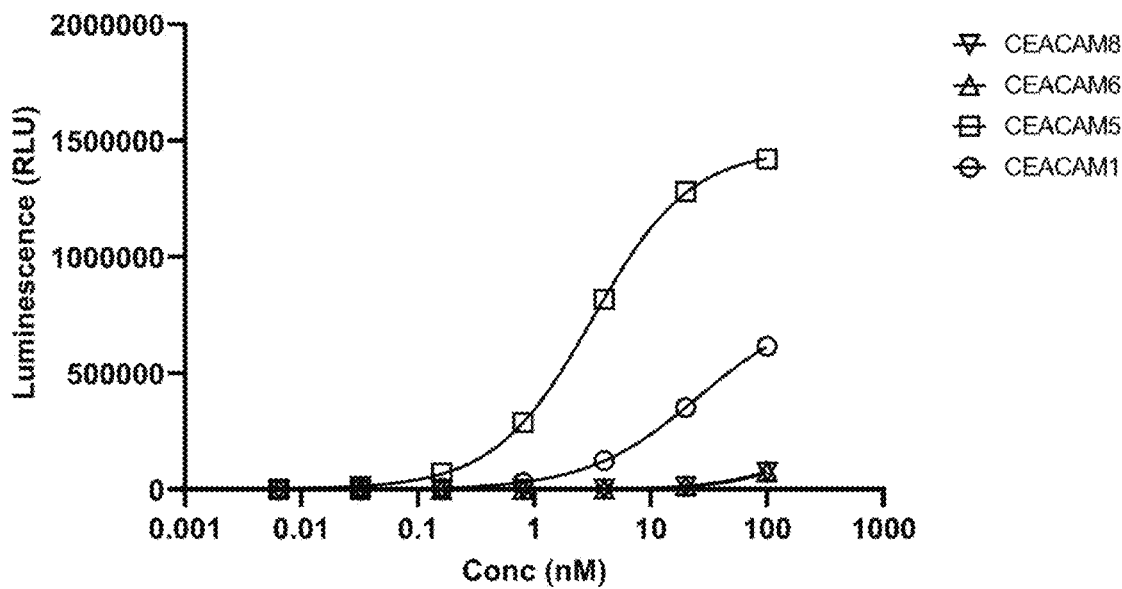

Binding domain B1 VL and VH amino acid (aa) and nucleotide (nt) sequences

| SEQ ID NO. | ANTIBODY REF | TYPE | SEQUENCE |
| --- | --- | --- | --- |
| 1 | 1132, light chain VL (also known as 1133) | aa | DIQMTQSPSSLSASVGDRVTITCRASQSISSYLNWYQQKPGKA PKLLIYAASSLQSGVPSRFSGSGSGTDFTLTISSLQPEDFATY YCQQYGRNPPTFGQGTKLEIK |
| 2 | 1132, light chain VL (also known as 1133) | nt | gatattcagatgacccagagcccgagcagcctgagcgcgagcg tgggcgatcgcgtgaccattacctgccgcgcgagccagagcat tagcagctatctgaactggtatcagcagaaacccgggcaaagcg ccgaaactgctgatttatgcggcgagcagcctgcagagcggcg tgccgagccgctttagcggcagcggcagcggcaccgattttac cctgaccattagcagcctgcagccggaagattttgcgacctat tattgccagcagtatggccgcaacccgccgacctttggccagg gcaccaaactggaaattaaa |
| 3 | 1132, heavy chain VH | aa | EVQLLESGGGLVQPGGSLRLSCAASGFTFSSYAMSWVRQAPGK GLEWVSGIGSYGGGTYYADSVKGRFTISRDNSKNTLYLQMNSL RAEDTAVYYCARYVNFGMDYWGQGTLVTVSS |
| 4 | 1132, heavy chain VH | nt | ggcggcagcctgcgcctgagctgcgcggcgagcggctttacct tagcagctatgcgatgagctgggtgcgccaggcgccgggcaa aggcctggaatgggtgagcggcattggcagctatggcggcggc acctattatgcggatagcgtgaaaggccgctttaccattagcc gcgataacagcaaaaacaccctgtatctgcagatgaacagcct gcgcgcggaagataccgcggtgtattattgcgcgcgctatgtg aactttggcatggattattgggccagggcaccctggtgaccg tgagcagc |
| 5 | 1150, light chain VL (also known as 1151) | aa | DIQMTQSPSSLSASVGDHVTITCRASQSISSYLNWYQQKPGKA PKLLIYAASSLQSGVPSRFSGSGSGTDFTLTISSLQPEDFATY YCQQYGSAPPTFGQGTKLEIK |
| 6 | 1150, light chain VL (also known as 1151) | nt | gatattcagatgacccagagcccgagcagcctgagcgcgagcg tgggcgatcatgtgaccattacctgccgcgcgagccagagcat tagcagctatctgaactggtatcagcagaaacccgggcaaagcg ccgaaactgctgatttatgcggcgagcagcctgcagagcggcg |

TABLE A-continued

Binding domain B1 VL and VH amino acid (aa) and nucleotide (nt) sequences

| SEQ ID NO. | ANTIBODY REF | TYPE | SEQUENCE |
|---|---|---|---|
| | | | tgccgagccgctttagcggcagcggcagcggcaccgatttttac cctgaccattagcagcctgcagccggaagattttgcgacctat tattgccagcagtatggcagcgcgccgccgaccttggccagg gcaccaaactggaaattaaa |
| 7 | 1150, heavy chain VH | aa | EVQLLESGGGLVQPGGSLRLSCAASGFTFSSYAMSWVRQAPGK GLEWVSGIGGSSSYTSYADSVKGRFTISRDNSKNTLYLQMNSL RAEDTAVYYCARYYSYHMDYWGQGTLVTSS |
| 8 | 1150, heavy chain VH | nt | gaagtgcagctgctggaaagcggcggcggcctggtgcagccgg gcggcagcctgcgcctgagctgcgcggcgagcggctttacctt tagcagctatgcgatgagctgggtgcgccaggcgccgggcaaa ggcctggaatgggtgagcggcattggcggcagcagcagctata ccagctatgcggatagcgtgaaaggccgctttaccattagccg cgataacagcaaaaacaccctgtatctgcagatgaacagcctg cgcgcggaagataccgcggtgtattattgcgcgcgctattata gctatcatatggattattggggccagggcaccctggtgaccgt gagcagc |
| 9 | 1140, light chain VL (also known as 1135) | aa | DIQMTQSPSSLSASVGDRVTITCRASQSISSYLNWYQQKPGKA PKLLIYAASSLQSGVPSRFSGSGSGTDFTLTISSLQPEDFATY YCQQSYSTPYTFGQGTKLEIK |
| 10 | 1140, light chain VL (also known as 1135) | nt | gatattcagatgacccagagcccgagcagcctgagcgcgagcg tgggcgatcgcgtgaccattacctgccgcgcgagccagagcat tagcagctatctgaactggtatcagcagaaaccgggcaaagcg ccgaaactgctgatttatgcggcgagcagcctgcagagcggcg tgccgagccgctttagcggcagcggcagcggcaccgatttttac cctgaccattagcagcctgcagccggaagattttgcgacctat tattgccagcagagctatagcaccccgtataccttggccagg gcaccaaactggaaattaaa |
| 11 | 1140, heavy chain VH | aa | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARGPVYSSVFDYWGQGTLVTSS |
| 12 | 1140, heavy chain VH | nt | gaagtgcagctgctggaaagcggcggcggcctggtgcagccgg gcggcagcctgcgcctgagctgcgcggcgagcggctttacctt tagcagctatgcgatgagctgggtgcgccaggcgccgggcaaa ggcctggaatgggtgagcgcgattagcggcagcggcggcagca cctattatgcggatagcgtgaaaggccgctttaccattagccg cgataacagcaaaaacaccctgtatctgcagatgaacagcctg cgcgcggaagataccgcggtgtattattgcgcgcgcggcccgg tgtatagcagcgtgtttgattattggggccagggcaccctggt gaccgtgagcagc |
| 13 | 1107, light chain VL (also known as 1108) | aa | DIQMTQSPSSLSASVGDRVTITCRASQSISSYLNWYQQKPGKA PKLLIYAASSLQSGVPSRFSGSGSGTDFTLTISSLQPEDFATY YCQQYGVYPFTFGQGTKLEIK |
| 14 | 1107, light chain VL (also known as 1108) | nt | gatattcagatgacccagagcccgagcagcctgagcgcgagcg tgggcgatcgcgtgaccattacctgccgcgcgagccagagcat tagcagctatctgaactggtatcagcagaaaccgggcaaagcg ccgaaactgctgatttatgcggcgagcagcctgcagagcggcg tgccgagccgctttagcggcagcggcagcggcaccgatttttac cctgaccattagcagcctgcagccggaagattttgcgacctat tattgccagcagtatggcgtgtatccgtttacctttggccagg gcaccaaactggaaattaaa |
| 15 | 1107, heavy chain VH | aa | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCARRVWGFDYWGQGTLVTSS |
| 16 | 1107, heavy chain VH | nt | gaagtgcagctgctggaaagcggcggcggcctggtgcagccgg gcggcagcctgcgcctgagctgcgcggcgagcggctttacctt tagcagctatgcgatgagctgggtgcgccaggcgccgggcaaa ggcctggaatgggtgagcgcgattagcggcagcggcggcagca cctattatgcggatagcgtgaaaggccgctttaccattagccg cgataacagcaaaaacaccctgtatctgcagatgaacagcctg cgcgcggaagataccgcggtgtattattgcgcgcgccgcgtgt ggggctttgattattggggccagggcaccctggtgaccgtgag cagc |

TABLE A-continued

Binding domain B1 VL and VH amino acid (aa) and nucleotide (nt) sequences

| SEQ ID NO. | ANTIBODY REF | TYPE | SEQUENCE |
|---|---|---|---|
| 17 | G12, light chain VL | aa | QSVLTQPPSASGTPGQRVTISCTGSSSNIGAGYNVYWYQQLPG TAPKLLIYGNINRPSGVPDRFSGSKSGTSASLAISGLRSEDEA DYYCAAWDKSISGLVFGGGTKLTVLG |
| 18 | G12, light chain VL | nt | cagagcgtgctgacccagccgccgagcgcgagcggcacccgg gccagcgcgtgaccattagctgcaccggcagcagcagcaacat tggcgcgggctataacgtgtattggtatcagcagctgccgggc accgcgccgaaactgctgatttatggcaacattaaccgcccga gcggcgtgccggatcgctttagcggcagcaaaagcggcaccag cgcgagcctggcgattagcggcctgcgcagcgaagatgaagcg gattattattgcgcggcgtgggataaaagcattagcggcctgg tgtttggcggcggcaccaaactgaccgtgctgggg |
| 19 | G12, heavy chain VH | aa | EVQLLESGGGLVQPGGSLRLSCAASGFTFSTYGMHWVRQAPGK GLEWLSYISGGSSYIFYADSVRGRFTISRDNSENALYLQMNSL RAEDTAVYYCARILRGGSGMDLWGQGTLVTVSS |
| 20 | G12, heavy chain VH | nt | gaagtgcagctgctggaaagcggcggcggcctggtgcagccgg gcggcagcctgcgcctgagctgcgcggcgagcggctttacctt tagcacctatggcatgcattgggtgcgccaggcgccgggcaaa ggcctggaatggctgagctatattagcggcggcagcagctata ttttttatgcggatagcgtgcgcggccgctttaccattagccg cgataacagcgaaaacgcgctgtatctgcagatgaacagcctg cgcgcggaagataccgcggtgtattattgcgcgcgcattctgc gcggcggcagcggcatggatctgtggggccagggcaccctggt gaccgtgagcagc |
| 21 | APX005, light chain VL | aa | DIQMTQSPSSLSASVGDRVTIKCQASQSISSRLAWYQQKPGKP PKLLIYRASTLASGVPSRFSGSGSGTDFTLTISSLQPEDVATY YCQCTGYGISWPIGGGTKVEIK |
| 22 | APX005, light chain VL | nt | gatattcagatgacccagagcccgagcagcctgagcgcgagcg tgggcgatcgcgtgaccattaaatgccaggcgagccagagcat tagcagccgcctggcgtggtatcagcagaaaccgggcaaacg ccgaaactgctgatttatcgcgcgagcaccctggcgagcggcg tgccgagccgctttagcggcagcggcagcggcaccgatttac cctgaccattagcagcctgcagccggaagatgtggcgacctat tattgccagtgcaccggctatggcattagctggccgattggcg gcggcaccaaagtggaaattaaa |
| 23 | APX005, heavy chain VH | aa | QVQLVESGGGVVQPGRSLRLSCAASGFSFSSTYVCWVRQAPGK GLEWIACIYTGDGTNYSASWAKGRFTISKDSSKNTVYLQMNSL RAEDTAVYFCARPDITYGFAINFWGPGTLVTVSS |
| 24 | APX005, heavy chain VH | nt | caggtgcagctggtggaaagcggcggcggcgtggtgcagccgg gccgcagcctgcgcctgagctgcgcggcgagcggctttagctt tagcagcacctatgtgtgctgggtgcgccaggcgccgggcaaa ggcctggaatggattgcgtgcatttataccggcgatggcacca actatagcgcgagctgggcgaaaggccgctttaccattagcaa agatagcagcaaaaacaccgtgtatctgcagatgaacagcctg cgcgcggaagataccgcggtgtattttgcgcgcgccccggata ttacctatggctttgcgattaacttttggggcccgggcaccct ggtgaccgtgagcagc |
| 25 | 21.4.1, light chain VL | aa | DIQMTQSPSSVSASVGDRVTITCRASQGIYSWLAWYQQKPGKA PNLLIYTASTLQSGVPSRFSGSGSGTDFTLTISSLQPEDFATY YCQQANIFPLTFGGGTKVEIK |
| 26 | 21.4.1, light chain VL | nt | gatattcagatgacccagagcccgagcagcgtgagcgcgagcg tgggcgatcgcgtgaccattacctgccgcgcgagccagggcat ttatagctggctggcgtggtatcagcagaaaccgggcaaagcg ccgaacctgctgatttataccgcgagcaccctgcagagcggcg tgccgagccgctttagcggcagcggcagcggcaccgatttac cctgaccattagcagcctgcagccggaagattttgcgacctat tattgccagcaggcgaacattttccgctgaccttggcggcg gcaccaaagtggaaattaaa |
| 27 | 21.4.1, heavy chain VH | aa | QVQLVQSGAEVKKPGASVKVSCKASGYTFTGYYMHWVRQAPGQ GLEWMGWINPDSGGTNYAQKFQGRVTMTRDTSISTAYMELNRL RSDDTAVYYCARDQPLGYCTNGVCSYFDYWGQGTLVTVSS |

TABLE A-continued

Binding domain B1 VL and VH amino acid (aa) and nucleotide (nt) sequences

| SEQ ID NO. | ANTIBODY REF | TYPE | SEQUENCE |
|---|---|---|---|
| 28 | 21.4.1, heavy chain VH | nt | caggtgcagctggtgcagagcggcgcggaagtgaaaaaaccgg gcgcgagcgtgaaagtgagctgcaaagcgagcggctatacctt taccggctattatatgcattgggtgcgccaggcgccgggccag ggcctggaatggatgggctggattaacccggatagcggcggca ccaactatgcgcagaaatttcagggccgcgtgaccatgacccg cgataccagcattagcaccgcgtatatggaactgaaccgcctg cgcagcgatgataccgcggtgtattattgcgcgcgcgatcagc cgctgggctattgcaccaacggcgtgtgcagctattttgatta ttggggccagggcaccctggtgaccgtgagcagc |
| 17 | G12_mut, light chain VL | aa | QSVLTQPPSASGTPGQRVTISCTGSSSNIGAGYNVYWYQQLPG TAPKLLIYGNINRPSGVPDRFSGSKSGTSASLAISGLRSEDEA DYYCAAWDKSISGLVFGGGTKLTVL |
| 18 | G12_mut, light chain VL | nt | cagagcgtgctgacccagccgccgagcgcgagcggcacccccgg gccagcgcgtgaccattagctgcaccggcagcagcagcaacat ggcgcgggctataacgtgtattggtatcagcagctgccgggc accgcgccgaaactgctgatttatggcaacattaaccgcccga gcggcgtgccggatcgctttagcggcagcaaaagcggcaccag cgcgagcctggcgattagcggcctgcgcagcgaagatgaagcg gattattattgcgcggcgtgggataaaagcattagcggcctgg tgtttggcggcggcaccaaactgaccgtgctgggg |
| 29 | G12_mut, heavy chain VH | aa | EVQLLESGGGLVQPGGSLRLSCAASGFTFSTYGMHWVRQAPGK GLEWLSYISGGSSYIFYADSVKGRFTISRDNSKNTLYLQMNSL RAEDTAVYYCARILRGGSGMDLWGQGTLVTVSS |
| 30 | G12_mut, heavy chain VH | nt | gaagtgcagctgctggaaagcggcggcggcctggtgcagccgg gcggcagcctgcgcctgagctgcgcggcgagcggctttacctt tagcacctatggcatgcattgggtgcgccaggcgccgggcaaa ggcctggaatggctgagctatattagcggcggcagcagctata tttttatgcggatagcgtgaagggccgctttaccattagccg cgataacagcaaaaacacgctgtatctgcagatgaacagcctg cgcgcggaagataccgcggtgtattattgcgcgcgcattctgc gcggcggcagcggcatggatctgtggggccagggcaccctggt gaccgtgagcagc |
| 430 | ffAC_05337 light chain VL CD40 binder | aa | QSVLTQPPSASGTPGQRVTISCTGSSSNIGAGYNVYWYQRLPG TAPKLLIYGNINRPSGVPDRFSGSKSGTSASLAISGLRSEDEA DYYCAAWDKSISGLVFGGGTKLTVL |
| 434 | ffAC_05337 light chain VL CD40 binder | nt | cagagcgtgctgacccagccgccgagcgcgagcggcacccccgg gccagcgcgtgaccattagctgcaccggcagcagcagcaacat ggcgcgggctataacgtgtattggtatcagcggctgccgggc accgcgccgaaactgctgatttatggcaacattaaccgcccga gcggcgtgccggatcgctttagcggcagcaaaagcggcaccag cgcgagcctggcgattagcggcctgcgcagcgaagatgaagcg gattattattgcgcggcgtgggataaaagcattagcggcctgg tgtttggcggcggcaccaaactgaccgtgctgggg |
| 431 | ffAC_05337 heavy chain VH CD40 binder | aa | EVQLLESGGGLVQPGGSLRLSCAASGFTFSTYGMHWVREAPGK GLEWLSYISGGSSYIFYADSVKGRFTISRDNSKNTLYLQMNSL RAEDTAVYYCARILRGGSGMDLWGQGTLVTVSS |
| 435 | ffAC_05337 heavy chain VH CD40 binder | nt | gaagtgcagctgctggaaagcggcggcggcctggtgcagccgg gcggcagcctgcgcctgagctgcgcggcgagcggctttacctt tagcacctatggcatgcattgggtgcgcgaggcgccgggcaaa ggcctggaatggctgagctatattagcggcggcagcagctata tttttatgcggatagcgtgaagggccgctttaccattagccg cgataacagcaaaaacacgctgtatctgcagatgaacagcctg cgcgcggaagataccgcggtgtattattgcgcgcgcattctgc gcggcggcagcggcatggatctgtggggccagggcaccctggt gaccgtgagcagc |

TABLE B

Binding domain B2 VL and VH amino acid (aa) and nucleotide (nt) sequences

| SEQ ID NO. | ANTIBODY REF | TYPE | SEQUENCE |
|---|---|---|---|
| 31 | AC_05059, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 32 | AC_05059, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 33 | AC_05059, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPHLDYWGQGTLVTVSS |
| 34 | AC_05059, heavy chain VH | nt | gaggtgcagctgttggagagcggggggaggcttggtacagcctgg ggggtccctgcgcctctcctgtgcagccagcggattcaccttt cttcttcttacatgggttgggtccgccaggctccagggaagggg ctggagtgggtctcatctattggttctggttcttactctacatc ttatgcagactccgtgaagggccggttcaccatctcccgtgaca attccaagaacacgctgtatctgcaaatgaacagcctgcgtgcc gaggacacggctgtatattattgtgcgcgctacccgtctgttcc gttcccgcctcatttggactattggggccagggaaccctggtca ccgtctcctca |
| 35 | AC_05060, light chain VL | aa | DIQMTQSPSSLSASVGDRVTITCRASQSIRDYLNWYQQKPGKAP KLLIYAASSLQSGVPSRFSGSGSGTDFTLTISSLQPEDFATYYC QQGTFPPFTFGQGTKLEIK |
| 36 | AC_05060, light chain VL | nt | gacatccagatgacccagtctccatcctccctgagcgcatctgt aggagaccgcgtcaccatcacttgccgggcaagtcagtctatta gggactatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacagggtactttcccgttcacttttggccaggggaccaagct ggagatcaaa |
| 37 | AC_05060, heavy chain VH | aa | EVQLLESGGGLVQPGGSLRLSCAASGFTFGSYYMSWVRQAPGKG LEWVSGISGYGYYTGYADSVKGRFTISRDNSKNTLYLQMNSLRA EDTAVYYCARHGYGVIDYWGQGTLVTVSS |
| 38 | AC_05060, heavy chain VH | nt | gaggtgcagctgttggagagcggggggaggcttggtacagcctgg ggggtccctgcgcctctcctgtgcagccagcggattcaccttg gttcttactacatgtcttgggtccgccaggctccagggaaggggg ctggagtgggtctcaggtatttctggttacggttactacacagg ttatgcagactccgtgaagggccggttcaccatctcccgtgaca attccaagaacacgctgtatctgcaaatgaacagcctgcgtgcc gaggacacggctgtatattattgtgcgcgccatggttacggtgt tattgactattggggccagggaaccctggtcaccgtctcctca |
| 39 | AC_05061, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQGAYVPYTFGQGTKLEIK |
| 40 | AC_05061, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacagggtgcttacgttccgtacacttttggccaggggaccaa gctggagatcaaa |
| 41 | AC_05061, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYGYTHFDYWGQGTLVTVSS |
| 42 | AC_05061, heavy chain VH | nt | gaggtgcagctgttggagagcggggggaggcttggtacagcctgg ggggtccctgcgcctctcctgtgcagccagcggattcaccttta gcagctatgccatgagctgggtccgccaggctccagggaagggg |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| | | | ctggagtgggtctcagctattagtggtagtggtggtagcacata ctatgcagactccgtgaagggccggttcaccatctcccgtgaca attccaagaacacgctgtatctgcaaatgaacagcctgcgtgcc gaggacacggctgtatattattgtgcgcgctaccggttacactca ttttgactattggggccagggaaccctggtcaccgtctcctca |
| 43 | AC_05062, light chain VL | aa | DIQMTQSPSSLSASVGDRVTITCRASQAISGYLNWYQQKPGKAP KLLIYSASSLQSGVPSRFSGSGSGTDFTLTISSLQPEDFATYYC QQSYSTPYTFGQGTKLEIK |
| 44 | AC_05062, light chain VL | nt | gacatccagatgacccagtctccatcctccctgagcgcatctgt aggagaccgcgtcaccatcacttgccgggcaagtcaggctatta gcggttatttaaattggtatcagcagaaaccagggaaagcccct aagctcctgatctattctgcatccagtttgcaaagtggggtccc atcacgtttcagtggcagtggaagcgggacagatttcactctca ccatcagcagtctgcaacctgaagattttgcaacttattactgt caacagagttacagtacccctatactttggccaggggaccaa gctggagatcaaa |
| 45 | AC_05062, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYRWHGSVFDYWGQGTLVTVSS |
| 46 | AC_05062, heavy chain VH | nt | gaggtgcagctgttggagagcggggggaggcttggtacagcctgg ggggtccctgcgcctctcctgtgcagccagcggattcaccttta gcagctatgccatgagctgggtccgccaggctccagggaagggg ctggagtgggtctcagctattagtggtagtggtggtagcacata ctatgcagactccgtgaagggccggttcaccatctcccgtgaca attccaagaacacgctgtatctgcaaatgaacagcctgcgtgcc gaggacacggctgtatattattgtgcgcgctaccgttggcatgg ttctgttttgactattggggccagggaaccctggtcaccgtct cctca |
| 47 | AC_05064, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQYPWYFPYTFGQGTKLEIK |
| 48 | AC_05064, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc aatccgtttcagtggcagtggaagcgggacagatttcactctca ccatcagcagtctgcaacctgaagattttgcaacttattactgt caacagtacccgtggtacttcccgtacacttttggccaggggac caagctggagatcaaa |
| 49 | AC_05064, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYGYSVLDYWGQGTLVTVSS |
| 50 | AC_05064, heavy chain VH | nt | gaggtgcagctgttggagagcggggggaggcttggtacagcctgg ggggtccctgcgcctctcctgtgcagccagcggattcaccttta gcagctatgccatgagctgggtccgccaggctccagggaagggg ctggagtgggtctcagctattagtggtagtggtggtagcacata ctatgcagactccgtgaagggccggttcaccatctcccgtgaca attccaagaacacgctgtatctgcaaatgaacagcctgcgtgcc gaggacacggctgtatattattgtgcgcgctaccggttactctgt tttggactattggggccagggaaccctggtcaccgtctcctca |
| 51 | AC_05079, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 52 | AC_05079, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaaccgcacacttttggccaggggaccaagct ggagatcaaa |

TABLE B-continued

Binding domain B2 VL and VH amino acid (aa) and
nucleotide (nt) sequences

| SEQ ID NO. | ANTIBODY REF | TYPE | SEQUENCE |
|---|---|---|---|
| 53 | AC_05079, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPPLDYWGQGTLVTSS |
| 54 | AC_05079, heavy chain VH | nt | gaggtacagctgcttgagtctggaggtggactggtacagcccgg ggggtccctgaggctctcctgtgctgcctccggtttcaccttta gcagctcttatatggggtgggtcaggcaggctcctggtaagggc ctcgagtgggtgtccagcatcggaagcggatcatacagcacgag ttacgccgactcagtaaagggtagattcaccattttcacgcgaca acagcaagaacacattgtatctccaaatgaattctctgagagcg gaagacacagcagtgtactattgcgccagatatccttccgtgcc ctttcctccaccccttgattactggggacagggtactcttgtga ctgtctcctca |
| 55 | AC_05080, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 56 | AC_05080, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 57 | AC_05080, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPLLDYWGQGTLVTSS |
| 58 | AC_05080, heavy chain VH | nt | gaggttcagttgctggagtcaggggggcggattggtgcagcctgg tggtagtctccgtcttagctgcgcggcttcagggttcactttta gcagctcatacatgggctgggtgcggcaggcaccaggaaagggc ctggaatgggtgagtagtataggatctggcagctatagtacttc atatgctgatagtgtgaaaggacgatttactatctctcgtgaca attcaaaaaacacccttacttgcagatgaatagccttagggcg gaggataccgcggtttactattgtgctcgttatccgagcgtgcc tttccccccctttggactactggggacaaggcaccctcgtga cagtctcctca |
| 59 | AC_05081, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 60 | AC_05081, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 61 | AC_05081, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPQPHLDYWGQGTLVTSS |
| 62 | AC_05081, heavy chain VH | nt | gaagtacagctgctggaaaagcggtggaggactcgtgcagcctgg tgggtccctcaggctctcctgtgcagcgagcggttttacattct ctagttcatatatggggtgggtacggcaggcccaggtaagggc ttagagtgggtaagcagtattggatccgggtcatacagtacatc ctatgccgactccgtcaagggtaggttcacgatcagccgggata actcaaagaatactctctacctccaaatgaattcactgcgggcc gaggatacagcagtttactattgtgcaagatatccatccgtgcc ctttcagccccacctggactactggggtcagggaaccctggtaa cagtctcctca |
| 63 | AC_05082, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 64 | AC_05082, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 65 | AC_05082, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYHPYSFDYWGQGTLVTVSS |
| 66 | AC_05082, heavy chain VH | nt | gaggtgcagctgttggagagcgggggaggcttggtacagcctgg ggggtccctgcgcctctcctgtgcagccagcggattcacctta gcagctatgccatgagctgggtccgccaggctccagggaagggg ctggagtgggtctcagctattagtggtagtggtggtagcacata ctatgcagactccgtgaagggccggttcaccatctccgtgaca attccaagaacacgctgtatctgcaaatgaacagcctgcgtgcc gaggacacggctgtatattattgtgcgcgctaccacccgtactc ttttgactattggggccagggaaccctggtcaccgtctcctca |
| 67 | AC_05083, light chain VL | aa | DIQMTQSPSSLSASVGDRVTITCRASQSIRGYLNWYQQKPGKAP KLLIYAASSLQSGVPSRFSGSGSGTDFTLTISSLQPEDFATYYC QQPSYPSLFTFGQGTKLEIK |
| 68 | AC_05083, light chain VL | nt | gatattcagatgacgcagagccctagttctctgtctgcttccgt tggggaccgtgtaaccatcacgtgtagggctagtcagtccatac gcggatatttgaactggtatcagcagaaaccagggaaagctcca aagttgctcatttatgcagcatcaagcttacagagcggcgtgcc cagccgtttcagcgggtcaggaagcgggacttcacgttga ccatatcttctctgcagcccgaggatttcgcgacctactattgt cagcaaccaagctacccgtctctgttcactttcggccaaggaac gaagcttgaaatcaag |
| 69 | AC_05083, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYSPYVLDYWGQGTLVTVSS |
| 70 | AC_05083, heavy chain VH | nt | gaggtgcaactgctggagagcggcggaggcctggtccagccagg cgggtctctcagactgagttgcgccgccagcggctttactttt cctcttatgctatgagctgggtacgacaggcgcccggaaaaggc ctggaatgggtttccgccatctctggctccggcggttctaccta ctacgctgattccgtcaagggcaggtttaccatcagcagggaca atagcaagaacacactgtacctccagatgaactctttgcgcgca gaggacacagccgttactattgcgccaggtacagcccatacgt gctcgactactggggccaggtacactcgtgacggtctcctca |
| 71 | AC_05084, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQVDGLFTFGQGTKLEIK |
| 72 | AC_05084, light chain VL | nt | gatattcagatgactcagagcccctcatccctgtccgctagcgt gggggaccgagtgactattacatgcagagcctctcagtccatat catcctatctgaattggtaccagcaaaagcccggaaaagcacca aaactgctcatttatgccgctagttcacttcagtctggggttcc gtctcggtttagcggatctggcagcggtacagactttacactta ccatcagcagtctgcagccagaggactttgcgacgtactattgt caacaagtcgacggcttattcacctttggacagggcaccaagtt ggagattaaa |
| 106 | AC_05084, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARVYYPAVMDYWGQGTLVTVSS |
| 107 | AC_05084, heavy chain VH | nt | gaagtacagctgttggagtctggaggtggattggttcagcccgg ggggagccttaggctgagttgtgcagcttcaggattacttca gttcctacgctatgtcatgggtcagacaggcgcagggaaggga ctggaatgggtgtctgctatcagcggaagtggagggtctactta ctacgcagactctgttaagggccggtttaccatctcccgagata acagcaagaatacttttatacctgcagatgaactcccttcgcgcc |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| | | | gaagacactgctgtctactattgcgctcgggtatattatcctgc cgtcatggactattggggccagggaaccctcgtcactgtctcct ca |
| 108 | AC_05085, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 109 | AC_05085, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 110 | AC_05085, heavy chain VH | aa | EVQLLESGGGLVQPGGSLRLSCAASGFTFGSYYMYWVRQAPGKG LEWVSSIGGYSGSTYYADSVKGRFTISRDNSKNTLYLQMNSLRA EDTAVYYCARNTPFPGGSGLDYWGQGTLVTVSS |
| 111 | AC_05085, heavy chain VH | nt | gaggtgcagctgttggagagcggggggaggcttggtacagcctgg ggggtccctgcgcctctcctgtgcagccagcggattcaccttg gttcttactacatgtactgggtccgccaggctccagggaaggg ctggagtgggtctcatctattggtggttactctggttctacata ctatgcagactccgtgaagggccggttcaccatctcccgtgaca attccaagaacacgctgtatctgcaaatgaacagcctgcgtgcc gaggacacggctgtatattattgtgcgcgcaacactccgttccc gggtggttctggttttggactattggggccagggaaccctggtca ccgtctcctca |
| 112 | AC_05086, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 113 | AC_05086, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 114 | AC_05086, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCAHYPSVPFPPHLDYWGQGTLVTVSS |
| 115 | AC_05086, heavy chain VH | nt | gaggtccagctgcttgaatccggaggcggcctggtccaaccagg cggaagtctccgcttatcatgcgccgcatccggctttacgttca gttcatcatatatggggtgggtccggcaggcgccaggtaagggc cttgaatgggtctcctcaattggctcaggatcctattccaccag ctatgctgattccgtgaagggccgctttacaatcagtcgcgaca attctaagaacaccctgtacctgcagatgaactctctgagagca gaagatacagccgtttattattgtgcacactatccttccgtgcc attcccacctcatctggattactggggccaggggacgctggtca ctgtctcctca |
| 116 | AC_05087, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 117 | AC_05087, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |

TABLE B-continued

Binding domain B2 VL and VH amino acid (aa) and
nucleotide (nt) sequences

| SEQ ID NO. | ANTIBODY REF | TYPE | SEQUENCE |
|---|---|---|---|
| 118 | AC_05087, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPPVPFPPHLDYWGQGTLVTSS |
| 119 | AC_05087, heavy chain VH | nt | gaggtgcagcttctggagagtgggggcgggctcgtgcagcctgg ggggtccctccgtctcagttgtgcagcttcaggcttttaccttta gtagttcatacatgggatgggtccgtcaggctcctgggaagggc ttagaatgggtgtcatcaattggctccggctcctattctacatc ctacgccgacagtgttaagggtcgttttaccattagcagggata acagtaagaatacattgtacctccaaatgaattctctgcgggcg gaagatactgccgtgtactattgcgcaagatacccacctgtccc gttccctccgccacttgattactgggggcagggtactctggtga ccgtctcctca |
| 120 | AC_05088, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 121 | AC_05088, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 122 | AC_05088, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVLFPPHLDYWGQGTLVTSS |
| 123 | AC_05088, heavy chain VH | nt | gaagtgcagcttctggagtctggtggaggtctggtgcagcctgg agggtctctgagacttagttgtgcagcatctggttttaccttca gctcaagctacatgggctgggtgagacaggcaccggaaaagga ttagagtgggtgagctccatcgggtctggcagctactctacctc ctacgctgactctgttaagggacgattcaccatttccagagaca atagcaaaaacacactgtacttacaaatgaattctctccgtgct gaggatacagcggtctactattgtgctcgataccgtctgttct tttccccctcaccttgattattgggggcagggcacgctggtga cagtctcctca |
| 124 | AC_05089, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 125 | AC_05089, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 126 | AC_05089, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPHLDYWGQGTLVTSS |
| 127 | AC_05089, heavy chain VH | nt | gaagtccagttgttagagagtgggggcgggctggtgcagccagg gggttctcttaggttgtcatgtgccgcctccggcttcactttct cttcttcctacatgggctgggtgcggcaggcaccgggaaagggt ctggagtgggtgtctagtattggctccggctcctacagtacttc atacgcagattcagtgaaaggaggttcaccatctcaagagata acagcaaaaacaccctgtacttcagatgaattccctgcgggcc gaagataccgcgtctactactgcgcacggtaccctccgttcc cttcccccaccatctggactactgggtcaaggcactttggtca cagtctcctca |
| 128 | AC_05090, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 129 | AC_05090, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 130 | AC_05090, heavy chain VH | aa | EVQLLESGGGLVQPGGSLRLSCAASGFTFSSSYMGWVRQAPGK GLEWVSSIGSGSYSTSYADSVKGRFTISRDNSKNTLYLQMNSLRA EDTAVYYCARYPSVPFPPLHLDYWGQGTLVTVSS |
| 131 | AC_05090, heavy chain VH | nt | gaggtgcagctgttggagtcaggggaggcttggtgcagcccgg aggctccctgcgcctgtcatgcgcagcctctgggtttacattct ctagctcttatatgggctgggtgaggcaagctcctggcaaggga ctcgagtgggtctcttccatcggtccggtagctacagtacgag ttatgcagacagtgtgaaaggtagatttactatctccagggaca actccaagaatacctctacctgcagatgaattccctcagagcc gaagatactgcagtgtactattgcgccaggtacccctccgtccc attccccctccaccttgattactggggacagggaaccctggtaa ctgtctcctca |
| 132 | AC_05091, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 133 | AC_05091, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 134 | AC_05091, heavy chain VH | aa | EVQLLESGGGLVQPGGSLRLSCAASGFTFSSSYMGWVRQAPGK GLEWVSSIGSGSYSTSYADSVKGRFTISRDNSKNTLYLQMNSLRA EDTAVYYCARYPSVPFPPHFDYWGQGTLVTVSS |
| 135 | AC_05091, heavy chain VH | nt | gaagtacaattgttagagagcggagggggactcgttcagcccgg aggatcactgcgcctgtcatgtgcagctagcggtttcacttttta gttcatcctacatgggttgggtcagacaggcccagggaaagc cttgagtgggtgtcctccattgggtctggtagctactcaacatc atacgctgacagcgtcaagggacgattcaccattagtcgcgaca actctaagaatacactctacctccagatgaactctctcagggcc gaggacacagccgtgtattactgtgcacgctatccctctgtacc ctttcctccacattttgactattgggtcaggggaccttggtca ctgtctcctca |
| 136 | AC_05092, light chain VL | aa | DIQMTQSPSSLSASVGDRVTITCRASQSISSDLNWYQQKPGKAP KLLIYAASSLQSGVPSRFSGSGSGTDFTLTISSLQPEDFATYYC QQAGNPHTFGQGTKLEIK |
| 137 | AC_05092, light chain VL | nt | gatattcagatgacacagtcccccagtagtctgagcgcctcagt tggtgacagagtgacaataacctgtagggcttctcagagcatat ccagcgatctgaactggtatcagcagaaaccagggaaggccccc aaattgctcatctatgccg catccagccttcagagcggagtgc cttcacggttcagtggttcagggtcaggaacagacttcacgctc acgatcagttctctgcaacccgaagatttcgcaacttactactg tcaacaggccggcaaccctcataccttcggtcagggaacgaaat tggagatcaag |
| 138 | AC_05092, heavy chain VH | aa | EVQLLESGGGLVQPGGSLRLSCAASGFTFSSSYMGWVRQAPGK GLEWVSSIGSGSYSTSYADSVKGRFTISRDNSKNTLYLQMNSLRA EDTAVYYCARYPSVPFPPPHLDYWGQGTLVTVSS |
| 139 | AC_05092, heavy chain VH | nt | gaggtgcagctgttagaaagtgggggaggccttgtccaaccagg aggtagtctgcgcctcagttgcgccgcgtctggctttactttct cttcaagctatatgggtgggtgcgacaggctccaggcaaggga ctggaatgggtgtcttcaattggttcaggttcctactcaacaag ctatgcggattcagtgaagggtagatttcgatcagtagggaca atagcaagaacaccctctacctccagatgaactcacttagagcc |

TABLE B-continued

Binding domain B2 VL and VH amino acid (aa) and
nucleotide (nt) sequences

| SEQ ID NO. | ANTIBODY REF | TYPE | SEQUENCE |
|---|---|---|---|
| | | | gaggatacagccgtgtactattgtgctaggtatccatccgtgcc cttcccccctcaccttgactactggggccaaggtacactcgtga ccgtctcctca |
| 140 | AC_05093, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 141 | AC_05093, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 142 | AC_05093, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPHVDYWGQGTLVTVSS |
| 143 | AC_05093, heavy chain VH | nt | gaggttcaacttttagagagtggtggtggtggtctggtgcagcctgg cgggagcctccgcctctcatgcgcagccagtgggtttaccttta gctccagttacatgggctgggtgagacaggcccctggaaaaggg ctggaatgggtgtctagcatcggcagcggctcatattctacgtc ttacgctgacagcgttaaaggcaggtttaccatctccagggaca attcaaagaacactctgtatcttcagatgaacagtctcagagct gaggacaccgctgtgtattattgcgcccgatacccttccgtgcc attcccaccccacgtagactactggggccaggggaccctcgtca cggtctcctca |
| 144 | AC_05094, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 145 | AC_05094, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 146 | AC_05094, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPPHWDYWGQGTLVTVSS |
| 147 | AC_05094, heavy chain VH | nt | gaagtacagctgctggagagtggtggtggtctggtgcagcccgg gggctccctgcggctttcctgtgccgcgtctggcttcaccttca gctcatcttacatgggctgggttcgacaggcacctgggaaggt ttagagtgggtgtctagcattgggagtgggtcctattcaacatc ctacgcagatagtgtgaagggccggtttaccatctctagagaca acagcaagaataccttatacttacaaatgaatagcctgagagca gaggataccgctgtctattattgtgcacggtaccctagcgtccc gtttccccctcactgggactattggggccaggggactctggtga ccgtctcctca |
| 148 | AC_05095, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 149 | AC_05095, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 150 | AC_05095, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFPSHLDYWGQGTLVTSS |
| 151 | AC_05095, heavy chain VH | nt | gaggtgcagctgttggaatctggaggaggcctcgtgcagccagg aggttccctgaggctgtcttgcgccgcctcaggtttcaccttta gctcttcctacatgggatgggtgcggcaagcacccggaaaaggg ctggagtgggtgagctccatcggctcaggttcttatagcacttc ttatgcggactccgttaaaggccgctttactatcagcagggaca actccaagaatacactgtatctgcagatgaacagcctgcgtgct gaagacaccgcagtctattactgcgcaagatatccgtccgttcc atttccaagccacctggattactggggccaggggacactggtga ccgtctcctca |
| 152 | AC_05096, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 153 | AC_05096, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtgggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 154 | AC_05096, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFRPHLDYWGQGTLVTSS |
| 155 | AC_05096, heavy chain VH | nt | gaggtgcagctgctggagtcaggggggaggccttgttcaaccggg aggcagtctgagattatcatgtgcggcttcagggtttaccttct ccagtagttatatgggctgggtccgccaggctccaggtaaggg ttggaatgggtgtcttctatcggctctggatcctattctacgtc ctacgccgattctgtcaaaggaaggttcaccatctccagggata attctaagaatacctctacctgcaaatgaactccctgcgagcc gaagatacagccgtttactactgcgcgagataccccgagcgtgcc tttcaggcccccatctggattactggggacaggggacacttgtga cagtctcctca |
| 156 | AC_05097, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 157 | AC_05097, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtgggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 158 | AC_05097, heavy chain VH | aa | EVQLLESGGGLVQPGGSLRLSCAASGFTFSSSYMGWVRQAPGKG LEWVSSIGSGSYSTSYADSVKGRFTISRDNSKNTLYLQMNSLRA EDTAVYYCARYPSVPFSPHLDYWGQGTLVTSS |
| 159 | AC_05097, heavy chain VH | nt | gaagtgcagctccttgagtccggtgggggcctcgtccagcccgg cggatccctgaggctgtcatgcgctgcaagcggcttcacattta gcagcagttatatgggctgggttagacaggctccgggcaaggga ctggaatgggtcagcagtattggtagcgggtcatatagtacttc atacgccgatagtgtgaagggccggttcacaatttccagggata actccaaaaatacactgtatctgcaaatgaactctctgcgagcg gaagacactgctgtttactactgtgccaggtatccgagtgtgcc ctttctccacacctggactattggggccaaggaacccttgtga ccgtctcctca |
| 160 | AC_05098, light chain VL | aa | DIQMTQSPSSLSASVGDRVTITCRASQSIRDYLNWYQQKPGKAP KLLIYAASSLQSGVPSRFSGSGSGTDFTLTISSLQPEDFATYYC QQGTFPFTFGQGTKLEIK |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 161 | AC_05098, light chain VL | nt | gacatccagatgacccagtctccatcctccctgagcgcatctgt aggagaccgcgtcaccatcacttgccgggcaagtcagtctatta gggactatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacagggtactttcccgttcacttttggccaggggaccaagct ggagatcaaa |
| 162 | AC_05098, heavy chain VH | aa | EVQLLESGGGLVQPGGSLRLSCAASGFTFGSYYMSWVRQAPGKG LEWVSGISGYGYYTGYADSVKGRFTISRDNSKNTLYLQMNSLRA EDTAVYYCARNGYGVIDYWGQGTLVTVSS |
| 163 | AC_05098, heavy chain VH | nt | gaggtccagctcctggaatcaggtggtgggctcgtacagccagg aggttcacttcggctgtcttgcgcagccagcgggttcacatttg gctcttactacatgtcttgggtcaggcaggcccctggcaagggt ttagagtgggtcagtggaatatctggttatgggtactacacagg ttatgcggacagcgtcaagggcaggtttaccatatctagagaca atagtaagaaccccctttatttgcagatgaactctctgagagct gaagacacagccgtttattattgcgcccggaacgggtatggagt gattgattattgggggcagggtactctggttacagtctcctca |
| 164 | AC_05099, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 165 | AC_05099, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 166 | AC_05099, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYGYTHFDYWGQGTLVTVSS |
| 167 | AC_05099, heavy chain VH | nt | gaggtgcagctgttggagagcgggggaggcttggtacagcctgg ggggtccctgcgcctctcctgtgcagccagcggattcacctta gcagctatgccatgagctgggtccgccaggctccagggaagggg ctggagtgggtctcagctattagtggtagtggtggtagcacata ctatgcagactccgtgaagggccggttcaccatctcccgtgaca attccaagaacacgctgtatctgcaaatgaacagcctgcgtgcc gaggacacggctgtatattattgtgcgcgctacggttacactca ttttgactattggggccagggaaccctggtcaccgtctcctca |
| 168 | AC_05100, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQAGNPHTFGQGTKLEIK |
| 169 | AC_05100, light chain VL | nt | gacatccagatgacccagtctccatcctccctgagcgcatctgt aggagaccgcgtcaccatcacttgccgggcaagtcagagcatta gcagctatttaaattggtatcagcagaaaccagggaaagcccct aagctcctgatctatgctgcatccagtttgcaaagtggggtccc atcacgtttcagtggcagtggaagcgggacagatttcactctca ccatcagcagtctgcaacctgaagattttgcaacttattactgt caacaggctggtaacccgcacacttttggccaggggaccaagct ggagatcaaa |
| 170 | AC_05100, heavy chain VH | aa | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARYWSSYYGYLDYWGQGTLVTVSS |
| 171 | AC_05100, heavy chain VH | nt | gaagttcaactcctcgaatctggtggggtctggtccagcccgg gggcagccttaggctcagttgcgctgccagcggtttcacattct ctagctacgccatgagttgggtcggcaggcaccaggaaaggga ttggaatgggtcagtgcaatctcaggcagtggcggctccactta ctatgctgattccgttaagggggcgattccaccatcagtcgtgata attctaaaaatacactgtatctgcagatgaattcttgcgcgct |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| | | | gaggacacagctgtgtattattgcgcccggtattggtggtccag ctattacgggtatctggactattggggtcaggggactcttgtta cagtctcctca |
| 172 | Fab1, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQSSHGPLLTFGQGTKLEIK |
| 173 | Fab1, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagccect aagctcctgatctatgctgcatccagtttgcaaagtggggtccc atcaaggttcagtggcagtggatctgggacagatttcactctca ccatcagcagtctgcaacctgaagattttgcaacttactactgt caacagtcctcacacggccctttgctgacttttggccaggggac caagctggagatcaaa |
| 174 | Fab1, heavy chain VH | aa | WVRQAPGQGLEWMGGIGSIFGTANYAQKFQGRVTITADESTSTA YMELSSLRSEDTAVYYCARAWSSDHMDYWGQGTLVTVSS |
| 175 | Fab1, heavy chain VH | nt | caggttcagctggttcagagcggtgcagaagttaaaaaaccggg tagcagcgttaaagttagctgtaaagcaagcggtggcacctttg gctattatgcaattcactgggttcgtcaggcacctggtcaaggt ctggaatggatgggtggtattggttcgattttggcaccgcaaa ttatgcccagaaatttcagggtcgtgttaccattaccgcagatg aaagcaccagcaccgcatatatggaactgagcagcctgcgtagc gaagataccgcagtgtattattgtgcacgtgcatggagttcgga tcatatggactactggggccagggaaccctggtcaccgtctcct ca |
| 176 | Fab2, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQWRSHLFTFGQGTKLEIK |
| 177 | Fab2, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagccect aagctcctgatctatgctgcatccagtttgcaaagtggggtccc atcaaggttcagtggcagtggatctgggacagatttcactctca ccatcagcagtctgcaacctgaagattttgcaacttactactgt caacagtggcgctcacacctttttacttttggccaggggaccaa gctggagatcaaa |
| 178 | Fab2, heavy chain VH | aa | QVQLVQSGAEVKKPGSSVKVSCKASGGTFHDGAISWVRQAPGQG LEWMGHIIPIDGTAGYAQKFQGRVTITADESTSTAYMELSSLRS EDTAVYYCARYRFYGIDYWGQGTLVTVSS |
| 179 | Fab2, heavy chain VH | nt | caggttcagctggttcagagcggtgcagaagttaaaaaaccggg tagcagcgttaaagttagctgtaaagcaagcggtggcacctttc acgatggtgcaattagctgggttcgtcaggcacctggtcaaggt ctggaatggatgggtcacattattccgattgatggcaccgcagg atatgcccagaaatttcagggtcgtgttaccattaccgcagatg aaagcaccagcaccgcatatatggaactgagcagcctgcgtagc gaagataccgcagtgtattattgtgcacgttaccgtttctatgg aatcgactactggggccagggaaccctggtcaccgtctcctca |
| 180 | Fab3, light chain VL | aa | EIVLTQSPGTLSLSPGERATLSCRASQSVSSSYLAWYQQKPGQA PRLLIYGASSRATGIPDRFSGSGSGTDFTLTISRLEPEDFAVYY CQQYWYPLTFGQGTKLEIK |
| 181 | Fab3, light chain VL | nt | gaaattgttctgacccagagtccgggtacactgagcctgtcacc gggtgaacgtgcaaccctgagctgtcgtgcaagccagagcgtta gcagcagctatctggcatggtatcagcagaaacctggtcaggca ccgcgtctgctgatttatggtgcaagcagccgtgcaaccggtat tccggatcgttttagcggtagcggtagtggcaccgattttaccc tgaccattagccgtctggaaccggaagattttgcagtgtattat tgtcagcagtattggtaccctctgacttttggccaggggaccaa gctggagatcaaa |
| 182 | Fab3, heavy chain VH | aa | QVQLVQSGAEVKKPGSSVKVSCKASGGTFSSSSIHWVRQAPGQG LEWMGHIYPSFGTANYAQKFQGRVTITADESTSTAYMELSSLRS EDTAVYYCARHSGSRFFSPMDYWGQGTLVTVSS |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 183 | Fab3, heavy chain VH | nt | caggttcagctggttcagagcggtgcagaagttaaaaaaccggg tagcagcgttaaagttagctgtaaagcaagcggtggcacctttta gcagcagcagtattcactgggttcgtcaggcacctggtcaaggt ctggaatggatgggtcatatttacccgtcttttggcaccgcaaa ttatgcccagaaatttcagggtcgtgttaccattaccgcagatg aaagcaccagcaccgcatatatggaactgagcagcctgcgtagc gaagataccgcagtgtattattgtgcacgtcacagcggatctcg cttttttagtccgatggactactggggccagggaaccctggtca ccgtctcctca |
| 184 | Fab4, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQPWTYLFTFGQGTKLEIK |
| 185 | Fab4, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagcccct aagctcctgatctatgctgcatccagttttgcaaagtggggtccc atcaaggttcagtggcagtggatctgggacagatttcactctca ccatcagcagtctgcaacctgaagattttgcaacttactactgt caacagccatggacctacttgtttacttttggccaggggaccaa gctggagatcaaa |
| 186 | Fab4, heavy chain VH | aa | QVQLVQSGAEVKKPGSSVKVSCKASGGTFDDHAISWVRQAPGQG LEWMGGIIPIFSYAYYAQKFQGRVTITADESTSTAYMELSSLRS EDTAVYYCARGRFYFPPSLDYWGQGTLVTVSS |
| 187 | Fab4, heavy chain VH | nt | caggttcagctggttcagagcggtgcagaagttaaaaaaccggg tagcagcgttaaagttagctgtaaagcaagcggtggcacctttg acgatcacgcaattagctgggttcgtcaggcacctggtcaaggt ctggaatggatgggtggtattattccgattttagctacgcata ttatgcccagaaatttcagggtcgtgttaccattaccgcagatg aaagcaccagcaccgcatatatggaactgagcagcctgcgtagc gaagataccgcagtgtattattgtgcacgtgggcgtttctactt tccccccgtccctcgactactggggccagggaaccctggtcaccg tctcctca |
| 188 | Fab5, light chain VL | aa | EIVLTQSPGTLSLSPGERATLSCRASQSVSSSYLAWYQQKPGQA PRLLIYGASSRATGIPDRFSGSGSGTDFTLTISRLEPEDFAVYY CQQPAAYLPTFGQGTKLEIK |
| 189 | Fab5, light chain VL | nt | gaaattgttctgacccagagtccgggtacactgagcctgtcacc gggtgaacgtgcaaccctgagctgtcgtgcaagccagagcgtta gcagcagctatctggcatggtatcagcagaaacctggtcaggca ccgcgtctgctgatttatggtgcaagcagccgtgcaaccggtat tccggatcgttttagcggtagcggtagtggcaccgattttaccc tgaccattagccgtctggaaccggaagattttgcagtgtattat tgtcagcagcctgcagcttaccttccaacttttggccaggggac caagctggagatcaaa |
| 190 | Fab5, heavy chain VH | aa | QVQLVQSGAEVKKPGSSVKVSCKASGGTFGSDAIGWVRQAPGQG LEWMGGIIPHFDTAYYAQKFQGRVTITADESTSTAYMELSSLRS EDTAVYYCARTYYTYAFFDYWGQGTLVTVSS |
| 191 | Fab5, heavy chain VH | nt | caggttcagctggttcagagcggtgcagaagttaaaaaaccggg tagcagcgttaaagttagctgtaaagcaagcggtggcacctttg gaagcgatgcaattgggtgggttcgtcaggcacctggtcaaggt ctggaatggatgggtggtattattccgcattttgataccgcata ttatgcccagaaatttcagggtcgtgttaccattaccgcagatg aaagcaccagcaccgcatatatggaactgagcagcctgcgtagc gaagataccgcagtgtattattgtgcacgtacttattacacgta tgccttctttgactactggggccagggaaccctggtcaccgtct cctca |
| 192 | Fab6, light chain VL | aa | EIVLTQSPGTLSLSPGERATLSCRASQSVSSSYLAWYQQKPGQA PRLLIYGASSRATGIPDRFSGSGSGTDFTLTISRLEPEDFAVYY CQQHVYGAPYTFGQGTKLEIK |
| 193 | Fab6, light chain VL | nt | gaaattgttctgacccagagtccgggtacactgagcctgtcacc gggtgaacgtgcaaccctgagctgtcgtgcaagccagagcgtta gcagcagctatctggcatggtatcagcagaaacctggtcaggca ccgcgtctgctgatttatggtgcaagcagccgtgcaaccggtat tccggatcgttttagcggtagcggtagtggcaccgatttaccc |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| | | | tgaccattagccgtctggaaccggaagattttgcagtgtattat tgtcagcagcatgtgtatggagctccatacacttttggccaggg gaccaagctggagatcaaa |
| 194 | Fab6, heavy chain VH | aa | QVQLVQSGAEVKKPGSSVKVSCKASGGTFSGGYISWVRQAPGQG LEWMGGIIPYFHHANYAQKFQGRVTITADESTSTAYMELSSLRS EDTAVYYCARGVWRLDYWGQGTLVTVSS |
| 195 | Fab6, heavy chain VH | nt | caggttcagctggttcagagcggtgcagaagttaaaaaaccggg tagcagcgttaaagttagctgtaaagcaagcggtggcaccttta gcggtggctacattagctgggttcgtcaggcacctggtcaaggt ctggaatggatgggtggtattattccgtattttcatcatgcaaa ttatgcccagaaatttcagggtcgtgttaccattaccgcagatg aaagcaccagcaccgcatatatggaactgagcagcctgcgtagc gaagataccgcagtgtattattgtgcacgtggcgtgtggcgtct cgactactggggccagggaaccctggtcaccgtctcctca |
| 196 | Fab7, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQWGYLLTFGQGTKLEIK |
| 197 | Fab7, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagtggggatacctgttgactttggccaggggaccaagct ggagatcaaa |
| 198 | Fab7, heavy chain VH | aa | EVQLLESGGGLVQPGGSLRLSCAASGFTFSSDHMYWVRQAPGKG LEWVSAIYGSHGSTSYADSVKGRFTISRDNSKNTLYLQMNSLRA EDTAVYYCARYPRYGSIDYWGQGTLVTVSS |
| 199 | Fab7, heavy chain VH | nt | gaggtgcagctgttggagtctggggaggcttggtacagcctgg ggggtccctgagactctcctgtgcagcctctggattcacctta gcagcgatcatatgtattgggtccgccaggctccagggaagggg ctggagtgggtctcagctatttacggtagtcatggtagcacaag ctacgcagactccgtgaagggccggttcaccatctccagagaca attccaagaacacgctgtatctgcaaatgaacagcctgagagcc gaggacacggccgtatattactgtgcgcgctatccgcggtacgg atctattgactactggggccagggaaccctggtcaccgtctcct ca |
| 200 | Fab8, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQSYSGPPTFGQGTKLEIK |
| 201 | Fab8, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagtcatattcaggacctccgactttggccaggggaccaa gctggagatcaaa |
| 202 | Fab8, heavy chain VH | aa | EVQLLESGGGLVQPGGSLRLSCAASGFTFGDHAMSWVRQAPGKG LEWVSAISGYGHSTGYADSVKGRFTISRDNSKNTLYLQMNSLRA EDTAVYYCARNHYRVGLDYWGQGTLVTVSS |
| 203 | Fab8, heavy chain VH | nt | gaggtgcagctgttggagtctggggaggcttggtacagcctgg ggggtccctgagactctcctgtgcagcctctggattcacctttg gcgaccatgccatgagctgggtccgccaggctccagggaagggg ctggagtgggtctcagctattagtggttacggtcatagcacagg ctacgcagactccgtgaagggccggttcaccatctccagagaca attccaagaacacgctgtatctgcaaatgaacagcctgagagcc gaggacacggccgtatattactgtgcgcgcaatcattaccgcgt aggcctggactactggggccagggaaccctggtcaccgtctcct ca |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 204 | Fab9, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQNSSSRLLTFGQGTKLEIK |
| 205 | Fab9, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagaattcatctagccggcttttgactttggccaggggac caagctggagatcaaa |
| 206 | Fab9, heavy chain VH | aa | EVQLLESGGGLVQPGGSLRLSCAASGFTFGDYDMSWVRQAPGKG LEWVSGIGHSGGSTYYADSVKGRFTISRDNSKNTLYLQMNSLRA EDTAVYYCARASDWYPSGFDYWGQGTLVTVSS |
| 207 | Fab9, heavy chain VH | nt | gaggtgcagctgttggagtctggggaggcttggtacagcctgg ggggtccctgagactctcctgtgcagcctctggattcacctttg gcgactatgatatgagctgggtccgccaggctccagggaagggg ctggagtgggtctcagggattggtcatagtggtggtagcacata ctacgcagactccgtgaagggccggttcaccatctccagagaca attccaagaacacgctgtatctgcaaatgaacagcctgagagcc gaggacacggccgtatattactgtgcgcgcgcctccgattggta cccatctggattcgactactggggccagggaaccctggtcaccg tctcctca |
| 208 | Fab10, light chain VL | aa | DIQMTQSPSSLSASVGDRVTITCRASQSISSYLNWYQQKPGKAP KLLIYAASSLQSGVPSRFSGSGSGTDFTLTISSLQPEDFATYYC QQSFSHPPTFGQGTKLEIK |
| 209 | Fab10, light chain VL | nt | gacatccagatgacccagtctccatcctccctgtctgcatctgt aggagacagagtcaccatcacttgccgggcaagtcagagcatta gcagctatttaaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagagcttttctcacccaccgactttggccaggggaccaa gctggagatcaaa |
| 210 | Fab10, heavy chain VH | aa | EVQLLESGGGLVQPGGSLRLSCAASGFTFYDHAMSWVRQAPGKG LEWVSAISGSYGSTGYADSVKGRFTISRDNSKNTLYLQMNSLRA EDTAVYYCARWGGWAGDIDYWGQGTLVTVSS |
| 211 | Fab10, heavy chain VH | nt | gaggtgcagctgttggagtctggggaggcttggtacagcctgg ggggtccctgagactctcctgtgcagcctctggattcaccttt acgaccatgccatgagctgggtccgccaggctccagggaagggg ctggagtgggtctcagctattagtggtagttacggtagcacagg atacgcagactccgtgaagggccggttcaccatctccagagaca attccaagaacacgctgtatctgcaaatgaacagcctgagagcc gaggacacggccgtatattactgtgcgcgctggggtggatgggc cggagacatcgactactggggccagggaaccctggtcaccgtct cctca |
| 212 | Fab11, light chain VL | aa | EIVLTQSPGTLSLSPGERATLSCRASQSVSSSYLAWYQQKPGQA PRLLIYGASSRATGIPDRFSGSGSGTDFTLTISRLEPEDFAVYY CQQRDWFPLFTFGQGTKLEIK |
| 213 | Fab11, light chain VL | nt | gaaattgttctgacccagagtccgggtacactgagcctgtcacc gggtgaacgtgcaaccctgagctgtcgtgcaagccagagcgtta gcagcagctatctggcatggtatcagcagaaacctggtcaggca ccgcgtctgctgatttatggtgcaagcagccgtgcaaccggtat tccggatcgttttagcggtagcggtagtggcaccgatttaccc tgaccattagccgtctggaaccggaagattttgcagtgtattat tgtcagcagcgtgactggtttcctttattacttttggccaggg gaccaagctggagatcaaa |
| 214 | Fab11, heavy chain VH | aa | EVQLLESGGGLVQPGGSLRLSCAASGFTFSDHAMHWVRQAPGKG LEWVSAISGYGGYTHYADSVKGRFTISRDNSKNTLYLQMNSLRA EDTAVYYCARYGGYSGDFDYWGQGTLVTVSS |

TABLE B-continued

Binding domain B2 VL and VH amino acid (aa) and nucleotide (nt) sequences

| SEQ ID NO. | ANTIBODY REF | TYPE | SEQUENCE |
|---|---|---|---|
| 215 | Fab11, heavy chain VH | nt | gaggtgcagctgttggagtctgggggaggcttggtacagcctgg ggggtccctgagactctcctgtgcagcctctggattcaccttta gcgatcacgccatgcattgggtccgccaggctccaggaaggggg ctggagtgggtctcagctattagtggttatggtggttatacaca ctacgcagactccgtgaagggccggttcaccatctccagagaca attccaagaacacgctgtatctgcaaatgaacagcctgagagcc gaggacacggccgtatattactgtgcgcgctatggcggatatag tggggattttgactactggggccagggaaccctggtcaccgtct cctca |
| 384 | Mab2, light chain VL | aa | DIQMTQSPSSLSASVGDRVTITCRASENIFSYLAWYQQKPGKAP KLLIYNTRTLQSGVPSRFSGSGSGTDFTLTISSLQPEDFATYYC QHHYGTPFTFGQGTKLEIK |
| 385 | Mab2, light chain VL | nt | gacatccagatgacacagagccctagcagcctgtctgccagcgt gggagacagagtgaccatcacctgtagagccagcgagaacatct tcagctacctggcctggtatcagcagaagcctggcaaggcccct aagctgctgatctacaacacccggacactgcagagcggcgtgcc aagcagattttctggcagcggctctggcaccgacttcaccctga ccatatctagcctgcagcctgaggacttcgccacctactactgc cagcaccactacggcaccccctttcacatttggccagggcaccaa gctggaaatcaag |
| 386 | Mab2, heavy chain VH | aa | EVQLVESGGGLVQPGGSLRLSCAASGFVFSSYDMSWVRQAPGKG LEWVSYISSGGGITYYADSVKGRFTISRDNSKNTLYLQMNSLRA EDTAVYYCAAHYFGSSGPFAYWGQGTLVTVSS |
| 387 | Mab2, heavy chain VH | nt | gaggtgcagctggttgaatctggcggaggactggttcagcctgg cggatctctgagactgtcttgtgccgccagcggcttcgtgttca gcagctacgatatgagctgggtccgacaggcccctggcaaagga cttgagtgggtgtcctacatcagcagcggcggaggcatcaccta ctacgccgattctgtgaagggcagattcaccatcagccgggaca acagcaagaacaccctgtacctgcagatgaacagcctgagagcc gaggacaccgccgtgtactattgtgccgctcactacttcggcag ctctggccccttttgcctattggggccagggcacactggtcaccg ttagctct |
| 432 | ffAC_05337 light chain VL CEA binder | aa | DIQMTQSPSSLSASVGDRVTITCRASQSISSYLNWYQEKPGKAP KLLIYAASSLQSGVPSRFSGSGSGTDFTLTISSLQPEDFATYYC QQAGNPHTFGQGTKLEIK |
| 436 | ffAC_05337 light chain VL CEA binder | nt | acatccagatgacccagtctccatcctccctgagcgcatctgta ggagaccgcgtcaccatcacttgccgggcaagtcagagcattag cagctatttaaattggtatcaggagaaaccagggaaagcccta agctcctgatctatgctgcatccagtttgcaaagtggggtccca tcacgtttcagtggcagtggaagcgggacagatttcactctcac catcagcagtctgcaacctgaagattttgcaacttattactgtc aacaggctggtaacccgcacacttttggccaggggaccaagctg gagatcaaa |
| 433 | ffAC_05337 heavy chain VH CEA binder | aa | EVQLLESGGGLVQPGGSLRLSCAASGFTFSSSYMGWVRRAPGKG LEWVSSIGSGSYSTSYADSVKGRFTISRDNSKNTLYLQMNSLRA EDTAVYYCARYPSVPFPLHLDYWGQGTLVTVSS |
| 437 | ffAC_05337 heavy chain VH CEA binder | nt | gaggtgcagctgttggagtcaggggggaggcttggtgcagccgg aggctcccctgcgcctgtcatgcgcagcctctgggtttacattct ctagctcttatatgggctgggtgaggcgagctcctggcaaggga ctcgagtgggtctcttccatcggctccggtagctacagtacgag ttatgcagacagtgtgaaaggtagatttactatctccagggaca actccaagaatacccctctacctgcagatgaatttcctcagagcc gaagatactgcagtgtactattgcgccaggtaccccctccgtccc attccccctccaccttgattactggggacagggaaccctggtaa ctgtctcctca |

TABLE C(1)

Exemplary heavy chain CDR sequences (binding domain B1)

| Antibody ref (VH) | SEQ | H CDR1 | SEQ | H CDR2 | SEQ | H CDR3 |
|---|---|---|---|---|---|---|
| 1132 | 73 | GFTFSSYA | 74 | IGSYGGGT | 75 | ARYVNFGMDY |
| 1150 | 73 | GFTFSSYA | 76 | IGGSSSYT | 77 | ARYYSYHMDY |
| 1140 | 73 | GFTFSSYA | 78 | ISGSGGST | 79 | ARGPVYSSVFDY |
| 1107 | 73 | GFTFSSYA | 78 | ISGSGGST | 80 | ARRVWGFDY |
| G12 and G12_mut | 81 | GFTFSTYG | 82 | ISGGSSYI | 83 | ARILRGGSGMDL |
| APX005 | 84 | GFSFSSTY | 85 | IYTGDGTN | 86 | ARPDITYGFAINF |
| 21.4.1 | 87 | GYTFTGYY | 88 | INPDSGGT | 89 | ARDQPLGYCTNGVCSYFDY |

TABLE C(2)

Exemplary light chain CDR sequences (binding domain B1)

| Antibody ref (VL) | SEQ | L CDR1 | SEQ | L CDR2 | SEQ | L CDR3 |
|---|---|---|---|---|---|---|
| 1132 (1133) | 90 | QSISSY | | AAS | 92 | QQYGRNPPT |
| 1150 (1151) | 90 | QSISSY | | AAS | 93 | QQYGSAPPT |
| 1140 (1135) | 90 | QSISSY | | AAS | 94 | QQSYSTPYT |
| 1107 (1108) | 90 | QSISSY | | AAS | 95 | QQYGVYPFT |
| G12 and G12_mut | 96 | SSNIGAGYN | | GNI | 98 | AAWDKSISGLV |
| APX005 | 99 | QSISSR | | RAS | 101 | QCTGYGISWP |
| 21.4.1 | 102 | QGIYSW | | TAS | 104 | QQANIFPLT |

TABLE D(1a)

Exemplary heavy chain CDR sequences (binding domain B2)

| Antibody ref (VH) | SEQ | H CDR1 | SEQ | H CDR2 | SEQ | H CDR3 |
|---|---|---|---|---|---|---|
| AC_05059 | 216 | GFTFSSSY | 217 | IGSGSYST | 218 | ARYPSVPFPPHLDY |
| AC_05060 | 219 | GFTFGSYY | 220 | ISGYGYYT | 221 | ARHGYGVIDY |
| AC_05061 | 222 | GFTFSSYA | 223 | ISGSGGST | 224 | ARYGYTHFDY |
| AC_05062 | 222 | GFTFSSYA | 223 | ISGSGGST | 225 | ARYRWHGSVFDY |
| AC_05064 | 222 | GFTFSSYA | 223 | ISGSGGST | 226 | ARYGYSVLDY |
| AC_05079 | 216 | GFTFSSSY | 217 | IGSGSYST | 227 | ARYPSVPFPPPLDY |
| AC_05080 | 216 | GFTFSSSY | 217 | IGSGSYST | 228 | ARYPSVPFPPLLDY |
| AC_05081 | 216 | GFTFSSSY | 217 | IGSGSYST | 229 | ARYPSVPFQPHLDY |
| AC_05082 | 222 | GFTFSSYA | 223 | ISGSGGST | 230 | ARYHPYSFDY |
| AC_05083 | 222 | GFTFSSYA | 223 | ISGSGGST | 231 | ARYSPYVLDY |
| AC_05084 | 222 | GFTFSSYA | 223 | ISGSGGST | 232 | ARVYYPAVMDY |
| AC_05085 | 219 | GFTFGSYY | 233 | IGGYSGST | 234 | ARNTPFPGGSGLDY |
| AC_05086 | 216 | GFTFSSSY | 217 | IGSGSYST | 235 | AHYPSVPFPPHLDY |
| AC_05087 | 216 | GFTFSSSY | 217 | IGSGSYST | 236 | ARYPPVPFPPHLDY |
| AC_05088 | 216 | GFTFSSSY | 217 | IGSGSYST | 237 | ARYPSVLFPPHLDY |
| AC_05089 | 216 | GFTFSSSY | 217 | IGSGSYST | 238 | ARYPSVPFPHHLDY |

TABLE D(1a)-continued

Exemplary heavy chain CDR sequences
(binding domain B2)

| Antibody ref (VH) | SEQ | H CDR1 | SEQ | H CDR2 | SEQ | H CDR3 |
|---|---|---|---|---|---|---|
| AC_05090 | 216 | GFTFSSSY | 217 | IGSGSYST | 239 | ARYPSVPFPLHLDY |
| AC_05091 | 216 | GFTFSSSY | 217 | IGSGSYST | 240 | ARYPSVPFPPHFDY |
| AC_05092 | 216 | GFTFSSSY | 217 | IGSGSYST | 218 | ARYPSVPFPPHLDY |
| AC_05093 | 216 | GFTFSSSY | 217 | IGSGSYST | 241 | ARYPSVPFPPHVDY |
| AC_05094 | 216 | GFTFSSSY | 217 | IGSGSYST | 242 | ARYPSVPFPPHWDY |
| AC_05095 | 216 | GFTFSSSY | 217 | IGSGSYST | 243 | ARYPSVPFPSHLDY |
| AC_05096 | 216 | GFTFSSSY | 217 | IGSGSYST | 244 | ARYPSVPFRPHLDY |
| AC_05097 | 216 | GFTFSSSY | 217 | IGSGSYST | 245 | ARYPSVPFSPHLDY |
| AC_05098 | 219 | GFTFGSYY | 220 | ISGYGYYT | 246 | ARNGYGVIDY |
| AC_05099 | 222 | GFTFSSYA | 223 | ISGSGGST | 224 | ARYGYTHFDY |
| AC_05100 | 222 | GFTFSSYA | 223 | ISGSGGST | 247 | ARYWWSSYYGYLDY |
| Fab1 | 248 | GGTFGYYA | 249 | IGSIFGTA | 250 | ARAWSSDHMDY |
| Fab2 | 251 | GGTFHDGA | 252 | IIPIDGTA | 253 | ARYRFYGIDY |
| Fab3 | 254 | GGTFSSSS | 255 | IYPSFGTA | 256 | ARHSGSRFFSPMDY |
| Fab4 | 257 | GGTFDDHA | 258 | IIPIFSYA | 259 | ARGRFYFPPSLDY |
| Fab5 | 260 | GGTFGSDA | 261 | IIPHFDTA | 262 | ARTYYTYAFFDY |
| Fab6 | 263 | GGTFSGGY | 264 | IIPYFHHA | 265 | ARGVWRLDY |
| Fab7 | 266 | GFTFSSDH | 267 | IYGSHGST | 268 | ARYPRYGSIDY |
| Fab8 | 269 | GFTFGDHA | 270 | ISGYGHST | 271 | ARNHYRVGLDY |
| Fab9 | 272 | GFTFGDYD | 335 | IGHSGGST | 273 | ARASDWYPSGFDY |
| Fab10 | 274 | GFTFYDHA | 275 | ISGSYGST | 276 | ARWGGWAGDIDY |
| Fab11 | 277 | GFTFSDHA | 278 | ISGYGGYT | 279 | ARYGGYSGDFDY |

TABLE D(1b)

Exemplary heavy chain CDR extended sequences
(binding domain B2)

| Antibody ref (VH) | SEQ | Ext H CDR1* | SEQ | Ext H CDR2* |
|---|---|---|---|---|
| AC_05059 | 280 | GFTFSSSYMG | 281 | SIGSGSYSTS |
| AC_05060 | 282 | GFTFGSYYMS | 283 | GISGYGYYTG |
| AC_05061 | 284 | GFTFSSYAMS | 285 | AISGSGGSTY |
| AC_05062 | 284 | GFTFSSYAMS | 285 | AISGSGGSTY |
| AC_05064 | 284 | GFTFSSYAMS | 285 | AISGSGGSTY |
| AC_05079 | 280 | GFTFSSSYMG | 281 | SIGSGSYSTS |
| AC_05080 | 280 | GFTFSSSYMG | 281 | SIGSGSYSTS |
| AC_05081 | 280 | GFTFSSSYMG | 281 | SIGSGSYSTS |
| AC_05082 | 284 | GFTFSSYAMS | 285 | AISGSGGSTY |
| AC_05083 | 284 | GFTFSSYAMS | 285 | AISGSGGSTY |
| AC_05084 | 284 | GFTFSSYAMS | 285 | AISGSGGSTY |
| AC_05085 | 286 | GFTFGSYYMY | 287 | SIGGYSGSTY |
| AC_05086 | 280 | GFTFSSSYMG | 281 | SIGSGSYSTS |
| AC_05087 | 280 | GFTFSSSYMG | 281 | SIGSGSYSTS |
| AC_05088 | 280 | GFTFSSSYMG | 281 | SIGSGSYSTS |
| AC_05089 | 280 | GFTFSSSYMG | 281 | SIGSGSYSTS |
| AC_05090 | 280 | GFTFSSSYMG | 281 | SIGSGSYSTS |
| AC_05091 | 280 | GFTFSSSYMG | 281 | SIGSGSYSTS |

TABLE D(1b)-continued

Exemplary heavy chain CDR extended sequences (binding domain B2)

| Antibody ref (VH) | SEQ | Ext H CDR1* | SEQ | Ext H CDR2* |
|---|---|---|---|---|
| AC_05092 | 280 | GFTFSSSYMG | 281 | SIGSGSYSTS |
| AC_05093 | 280 | GFTFSSSYMG | 281 | SIGSGSYSTS |
| AC_05094 | 280 | GFTFSSSYMG | 281 | SIGSGSYSTS |
| AC_05095 | 280 | GFTFSSSYMG | 281 | SIGSGSYSTS |
| AC_05096 | 280 | GFTFSSSYMG | 281 | SIGSGSYSTS |
| AC_05097 | 280 | GFTFSSSYMG | 281 | SIGSGSYSTS |
| AC_05098 | 282 | GFTFGSYYMS | 283 | GISGYGYYTG |
| AC_05099 | 288 | GFTFSSYAMS | 285 | AISGSGGSTY |
| AC_05100 | 288 | GFTFSSYAMS | 285 | AISGSGGSTY |
| Fab1 | 289 | GGTFGYYAIH | 290 | GIGSIFGTAN |
| Fab2 | 291 | GGTFHDGAIS | 292 | HIIPIDGTAG |
| Fab3 | 293 | GGTFSSSSIH | 294 | HIYPSFGTAN |
| Fab4 | 295 | GGTFDDHAIS | 296 | GIIPIFSYAY |
| Fab5 | 297 | GGTFGSDAIG | 298 | GIIPHFDTAY |
| Fab6 | 299 | GGTFSGGYIS | 300 | GIIPYFHHAN |
| Fab7 | 301 | GFTFSSDHMY | 302 | AIYGSHGSTS |
| Fab8 | 303 | GFTFGDHAMS | 304 | AISGYHSTG |
| Fab9 | 305 | GFTFGDYDMS | 306 | GIGHSGGSTY |
| Fab10 | 307 | GFTFYDHAMS | 308 | AISGSYGSTG |
| Fab11 | 309 | GFTFSDHAMH | 310 | AISGYGGYTH |

*Ext refers to extended sequences-these are sequence variants of the CDRs with additional flanking amino acids; they are functionally comparable to the unextended CDR sequences in Table D1a.

TABLE D(2)

Exemplary light chain CDR sequences (binding domain B2)

| Antibody ref (VL) | SEQ L CDR1 | | SEQ L CDR2 | SEQ L CDR3 | |
|---|---|---|---|---|---|
| AC_05059 | 90 | QSISSY | AAS | 311 | QQAGNPHT |
| AC_05060 | 312 | QSIRDY | AAS | 313 | QQGTFPFT |
| AC_05061 | 90 | QSISSY | AAS | 314 | QQGAYVPYT |
| AC_05062 | 315 | QAISGY | SAS | 94 | QQSYSTPYT |
| AC_05064 | 90 | QSISSY | AAS | 317 | QQYPWYFPYT |
| AC_05079 | 90 | QSISSY | AAS | 311 | QQAGNPHT |
| AC_05080 | 90 | QSISSY | AAS | 311 | QQAGNPHT |
| AC_05081 | 90 | QSISSY | AAS | 311 | QQAGNPHT |
| AC_05082 | 90 | QSISSY | AAS | 311 | QQAGNPHT |
| AC_05083 | 318 | QSIRGY | AAS | 319 | QQPSYPSLFT |
| AC_05084 | 90 | QSISSY | AAS | 320 | QQVDGLFT |
| AC_05085 | 90 | QSISSY | AAS | 311 | QQAGNPHT |
| AC_05086 | 90 | QSISSY | AAS | 311 | QQAGNPHT |
| AC_05087 | 90 | QSISSY | AAS | 311 | QQAGNPHT |
| AC_05088 | 90 | QSISSY | AAS | 311 | QQAGNPHT |
| AC_05089 | 90 | QSISSY | AAS | 311 | QQAGNPHT |
| AC_05090 | 90 | QSISSY | AAS | 311 | QQAGNPHT |
| AC_05091 | 90 | QSISSY | AAS | 311 | QQAGNPHT |
| AC_05092 | 321 | QSISSD | AAS | 311 | QQAGNPHT |
| AC_05093 | 90 | QSISSY | AAS | 311 | QQAGNPHT |
| AC_05094 | 90 | QSISSY | AAS | 311 | QQAGNPHT |
| AC_05095 | 90 | QSISSY | AAS | 311 | QQAGNPHT |
| AC_05096 | 90 | QSISSY | AAS | 311 | QQAGNPHT |
| AC_05097 | 90 | QSISSY | AAS | 311 | QQAGNPHT |
| AC_05098 | 312 | QSIRDY | AAS | 313 | QQGTFPFT |
| AC_05099 | 90 | QSISSY | AAS | 311 | QQAGNPHT |
| AC_05100 | 90 | QSISSY | AAS | 311 | QQAGNPHT |
| Fab1 | 90 | QSISSY | AAS | 322 | QQSSHGPLLT |
| Fab2 | 90 | QSISSY | AAS | 323 | QQWRSHLFT |
| Fab3 | 324 | QSVSSSY | GAS | 326 | QQYWYPLT |
| Fab4 | 90 | QSISSY | AAS | 327 | QQPWTYLFT |
| Fab5 | 324 | QSVSSSY | GAS | 328 | QQPAAYLPT |
| Fab6 | 324 | QSVSSSY | GAS | 329 | QQHVYGAPYT |
| Fab7 | 90 | QSISSY | AAS | 330 | QQWGYLLT |
| Fab8 | 90 | QSISSY | AAS | 331 | QQSYSGPPT |
| Fab9 | 90 | QSISSY | AAS | 332 | QQNSSSRLLT |
| Fab10 | 90 | QSISSY | AAS | 333 | QQSFSHPPT |
| Fab11 | 324 | QSVSSSY | GAS | 334 | QQRDWFPLFT |

Control Antibody Sequences

3174 VH aa
(SEQ ID NO: 422)
EVQLLEQSGAELVRPGTSVKISCKASGYAFTNYWL
GWVKQRPGHGLEWIGDIFPGSGNIHYNEKFKGKAT
LTADKSSSTAYMQLSSLTFEDSAVYFCARLRNWDE
PMDYWGQGTTVTVSS

3174 VH nt (SEQ ID NO: 423)
GAGGTGCAGCTGCTGGAACAGTCTGGCGCCGAACT
CGTTAGACCTGGCACAAGCGTGAAGATCAGCTGCA
AGGCCAGCGGCTACGCCTTCACAAATTATTGGCTC
GGCTGGGTCAAACAGAGGCCAGGACACGGACTGGA
ATGGATCGGCGATATCTTCCCCGGCAGCGGCAACA
TCCACTACAACGAGAAGTTCAAGGGCAAAGCCACA
CTGACCGCCGACAAGAGCAGCAGCACAGCCTATAT
GCAGCTGAGCAGCCTGACCTTCGAGGACAGCGCCG
TGTACTTCTGCGCCAGGCTGAGAAACTGGGACGAG
CCTATGGATTACTGGGGCCAGGGCACCACAGTGAC
AGTGTCTAGC

3174 VL aa (SEQ ID NO: 424)
ELVMTQSPSSLTVTAGEKVTMSCKSSQSLLNSGNQ
KNYLTWYQQKPGQPPKLLIYWASTRESGVPDRFTG
SGSGTDFTLTISSVQAEDLAVYYCONDYSYPLTFG
AGTKLEIK

3174 VL nt (SEQ ID NO: 425)
GAACTGGTTATGACACAGAGCCCTAGCAGCCTGAC
AGTGACAGCCGGCGAGAAAGTGACAATGAGCTGCA
AGAGCAGCCAGAGCCTGCTGAACAGCGGCAACCAG
AAGAACTACCTGACCTGGTATCAGCAGAAGCCCGG
ACAGCCTCCTAAGCTGCTGATCTATTGGGCCAGCA
CCAGAGAAAGCGGCGTGCCCGATAGATTCACAGGC
AGCGGCAGCGGAACCGACTTTACCCTGACAATTAG
CAGCGTGCAGGCCGAGGACCTGGCCGTGTATTATT
GTCAGAACGACTACAGCTACCCTCTGACCTTCGGA
GCCGGCACCAAGCTGGAAATCAAG

1210 VH aa (SEQ ID NO: 426)
EVQLLESGGGLVQPGGSLRLSCAASGFTFSSYAMS
WVRQAPGKGLEWVSAISGSGGSTYYADSVKGRFTI
SRDNSKNTLYLQMNSLRAEDTAVYYCARYYGGYYS
AWMDYWGQGTLVTVSS

1210 VH nt (SEQ ID NO: 427)
GAGGTGCAGCTGCTCGAGAGCGGGGGAGGCTTGGT
ACAGCCTGGGGGGTCCCTGCGCCTCTCCTGTGCAG
CCAGCGGATTCACCTTTAGCAGCTATGCCATGAGC
TGGGTCCGCCAGGCTCCAGGGAAGGGGCTGGAGTG
GGTCTCAGCTATTAGTGGTAGTGGTGGTAGCACAT
ACTATGCAGACTCCGTGAAGGGCCGGTTCACCATC
TCCCGTGACAATTCCAAGAACACGCTGTATCTGCA
AATGAACAGCCTGCGTGCCGAGGACACGGCTGTAT
ATTATTGTGCGCGCTACTACGGTGGTTACTACTCT
GCTTGGATGGACTATTGGGGCCAGGGAACCCTGGT
CACCGTCTCCTCA

1210 VL aa (SEQ ID NO: 428)
DIQMTQSPSSLSASVGDRVTITCRASQSISSYLNW
YQQKPGKAPKLLIYAASSLQSGVPSRFSGSGSGTD
FTLTISSLQPEDFATYYCQQTYGYLHTFGQGTKLE
IK

1210 VL nt (SEQ ID NO: 429)
GACATCCAGATGACCCAGTCTCCATCCTCCCTGAG
CGCATCTGTAGGAGACCGCGTCACCATCACTTGCC
GGGCAAGTCAGAGCATTAGCAGCTATTTAAATTGG
TATCAGCAGAAACCAGGGAAAGCCCCTAAGCTCCT
GATCTATGCTGCATCCAGTTTGCAAAGTGGGGTCC
CATCACGTTTCAGTGGCAGTGGAAGCGGGACAGAT
TTCACTCTCACCATCAGCAGTCTGCAACCTGAAGA
TTTTGCAACTTATTACTGTCAACAGACTTACGGTT
ACCTGCACACTTTTGGCCAGGGGACCAAGCTGGAG
ATCAAA

Mutated IgG1 Antibody Sequence

IgG1 LALA-sequence:
(SEQ ID NO: 336)
ASTKGPSVFPLAPSSKSTSGGTAALGCLVKDYFPE
PVTVSWNSGALTSGVHTFPAVLQSSGLYSLSSVVT
VPSSSLGTQTYICNVNHKPSNTKVDKKVEPKSCDK
THTCPPCPAPEAAGGPSVFLFPPKPKDTLMISRTP
EVTCVVVDVSHEDPEVKFNWYVDGVEVHNAKTKPR
EEQYNSTYRVVSVLTVLHQDWLNGKEYKCKVSNKA
LPAPIEKTISKAKGQPREPQVYTLPPSRDELTKNQ
VSLTCLVKGFYPSDIAVEWESNGQPENNYKTTPPV
LDSDGSFFLYSKLTVDKSRWQQGNVFSCSVMHEAL
HNHYTQKSLSLSPGK Linker Sequences (SEQ ID NO: 337)
SGGGGSGGGGS (SEQ ID NO: 338)
SGGGGSGGGSAP (SEQ ID NO: 339)
NFSQP

```
                     (SEQ ID NO: 340)
KRTVA (SEQ ID NO: 341)
GGGSGGGG (SEQ ID NO: 342)
GGGGSGGGGS (SEQ ID NO: 343)
GGGGSGGGGSGGGGS (SEQ ID NO: 344)
GSTSGSGKPGSGEGSTKG (SEQ ID NO: 345)
THTCPPCPEPKSSDK (SEQ ID NO: 346)
GGGS (SEQ ID NO: 347)
EAAKEAAKGGGGS (SEQ ID NO: 348)
EAAKEAAK (SG)m, where m = 1 to 7.
```

IgG Constant Region Sequences

```
IgG1 heavy chain constant region sequence:
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
[SEQ ID NO: 349]

IgG1 light chain constant region sequence:
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC
[SEQ ID NO: 350]

Modified IgG4 heavy chain constant
region sequence:
ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPPCPAPEFLGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNR

YTQKSLSLSLGK
[SEQ ID NO: 351]

Modified IgG4 heavy chain constant
region sequence:
ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPPCPAPEFLGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNH

YTQKSLSLSLGK
[SEQ ID NO: 352]

Wild type IgG4 heavy chain constant
region sequence:
ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPSCPAPEFLGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNH

YTQKSLSLSLGK
[SEQ ID NO: 353]

Reference sequence CH1 (SEQ ID NO: 354):
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSC

(wherein the bold and underlined section is
part of the hinge region, but is present in
the appended Fab fragment in RUBY bsAb)

Reference sequence CKappa (SEQ ID NO: 355):
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC
```

Reference sequence CLambda, Immunoglobulin
constant lambda 1 (SEQ ID NO: 356)
GQPKANPTVTLFPPSSEELQANKATLVCLISDFYP

GAVTVAWKADGSPVKAGVETTKPSKQSNNKYAASS

YLSLTPEQWKSHRSYSCQVTHEGSTVEKTVAPTEC

S

Reference sequence CLambda, Immunoglobulin
constant lambda 2 (SEQ ID NO: 357)
GQPKAAPSVTLFPPSSEELQANKATLVCLISDFYP

GAVTVAWKADSSPVKAGVETTTPSKQSNNKYAASS

YLSLTPEQWKSHRSYSCQVTHEGSTVEKTVAPTEC

S

Reference sequence CLambda, Immunoglobulin
constant lambda 3 (SEQ ID NO: 358)
GQPKAAPSVTLFPPSSEELQANKATLVCLISDFYP

GAVTVAWKADSSPVKAGVETTTPSKQSNNKYAASS

YLSLTPEQWKSHKSYSCQVTHEGSTVEKTVAPTEC

S

Exemplary Sequences of CD40×CEACAM5 RUBY™ bsAb

Multi34
Chain H1
(SEQ ID NO: 359)
EVQLLESGGGLVQPGGSLRLSCAASGFTFSTYGMH

WVRRAPGKGLEWLSYISGGSSYIFYADSVKGRFTI

SRDNSKNTLYLQMNSLRAEDTAVYYCARILRGGSG

MDLWGQGTLVTVSSASTKGPSVFPLAPSSKSTSGG

TAALGCLVKDYFPEPVTVSWNSGALTSGVATGPAV

LQSSGLYSLSSVVTVPSSSLGTQTYICNVNHKPSN

TKVDKKVEPKSCDKTHTCPPCPAPEAAGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGKGGGGSG

GGGSGGGGSDIQMTQSPSSLSASVGDRVTITCRAS

QSISSYLNWYQRKPGKAPKLLIYAASSLQSGVPSR

FSGSGSGTDFTLTISSLQPEDFATYYCQQSSHGPL

LTFGQGTKLEIKRPVAAPAVFIFPPSDEQLKSGTA

SVVCLLKNFYPREAKVQWKVDNALQSGNSQESVTE

QDSKDSTYSLSSTLTLSKADYEKHKVYACEVTHQG

LSSPVTKSFNRGEC

Chain L1
(SEQ ID NO: 360)
QSVLTQPPSASGTPGQRVTISCTGSSSNIGAGYNV

YWYQELPGTAPKLLIYGNINRPSGVPDRFSGSKSG

TSASLAISGLRSEDEADYYCAAWDKSISGLVFGGG

TKLTVLGQPKAAPSVTLFPPSSEELQANKATLVCY

ISDFYPGAVTVAWKADSSPVKAGVETTTPSKQSNN

KYAAWSYLSLTPEQWKSHRSYSCQVTHEGSTVEKT

VAPTECS

Chain H2
(SEQ ID NO: 361)
QVQLVQSGAEVKKPGSSVKVSCKASGGTFGYYAIH

WVREAPGQGLEWMGGIGSIFGTANYAQKFQGRVTI

TADESTSTAYMELSSLRSEDTAVYYCARAWSSDHM

DYWGQGTLVTVSSASTKGPSVFPLAPSSKSTSGGT

AALGCLVKDYFPEPVTVSWNSGALTSGVHTFPAVL

QSSGLYSLTSVVEVPSSSLGTQTYICNVNHKPSNT

KVDKKVEPKSC

Multi42
Chain H1
(SEQ ID NO: 362)
QVQLVQSGAEVKKPGSSVKVSCKASGGTFSSSSIH

WVRRAPGQGLEWMGHIYPSFGTANYAQKFQGRVTI

TADESTSTAYMELSSLRSEDTAVYYCARHSGSRFF

SPMDYWGQGTLVTVSSASTKGPSVFPLAPSSKSTS

GGTAALGCLVKDYFPEPVTVSWNSGALTSGVATGP

AVLQSSGLYSLSSVVTVPSSSLGTQTYICNVNHKP

SNTKVDKKVEPKSCDKTHTCPPCPAPEAAGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGKGGGG

SGGGGSGGGGSQSVLTQPPSASGTPGQRVTISCTG

SSSNIGAGYNVWYQRLPGTAPKLLIYGNINRPSG

VPDRFSGSKSGTSASLAISGLRSEDEADYYCAAWD

KSISGLVFGGGTKLTVLGQPKAAPAVTLFPPSSEE

LQANKATLVCLIKDFYPGAVTVAWKADSSPVKAGV

ETTTPSKQSNNKYAAWSYLSLTPEQWKSHRSYSCQ

VTHEGSTVEKTVAPTECS

Chain L1
(SEQ ID NO: 363)
EIVLTQSPGTLSLSPGERATLSCRASQSVSSSYLA

WYQEKPGQAPRLLIYGASSRATGIPDRFSGSGSGT

-continued

DFTLTISRLEPEDFAVYYCQQYWYPLTFGQGTKLE

IKRTVAAPSVFIFPPSDEQLKSGTASVVCYLNNFY

PREAKVQWKVDNALQSGNSQESVTEQDSKDSTYSL

WSTLTLSKADYEKHKVYACEVTHQGLSSPVTKSFN

RGEC

Chain H2
(SEQ ID NO: 364)
EVQLLESGGGLVQPGGSLRLSCAASGFTFSTYGMH

WVREAPGKGLEWLSYISGGSSYIFYADSVKGRFTI

SRDNSKNTLYLQMNSLRAEDTAVYYCARILRGGSG

MDLWGQGTLVTVSSASTKGPSVFPLAPSSKSTSGG

TAALGCLVKDYFPEPVTVSWNSGALTSGVHTFPAV

LQSSGLYSLTSVVEVPSSSLGTQTYICNVNHKPSN

TKVDKKVEPKSC

Multi46
Chain H1
(SEQ ID NO: 365)
EVQLLESGGGLVQPGGSLRLSCAASGFTFSSYAMS

WVRRAPGKGLEWVSGIGSYGGGTYYADSVKGRFTI

SRDNSKNTLYLQMNSLRAEDTAVYYCARYVNFGMD

YWGQGTLVTVSSASTKGPSVFPLAPSSKSTSGGTA

ALGCLVKDYFPEPVTVSWNSGALTSGVATGPAVLQ

SSGLYSLSSVVTVPSSSLGTQTYICNVNHKPSNTK

VDKKVEPKSCDKTHTCPPCPAPEAAGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGKGGGGSGGG

GSGGGGSDIQMTQSPSSLSASVGDRVTITCRASQS

ISSYLNWYQRKPGKAPKLLIYAASSLQSGVPSRFS

GSGSGTDFTLTISSLQPEDFATYYCQQSSHGPLLT

FGQGTKLEIKRPVAAPAVFIFPPSDEQLKSGTASV

VCLLKNFYPREAKVQWKVDNALQSGNSQESVTEQD

SKDSTYSLSSTLTLSKADYEKHKVYACEVTHQGLS

SPVTKSFNRGEC

Chain L1
(SEQ ID NO: 372)
DIQMTQSPSSLSASVGDRVTITCRASQSISSYLNW

YQEKPGKAPKLLIYAASSLQSGVPSRFSGSGSGTD

FTLTISSLQPEDFATYYCQQYGRNPPTFGQGTKLE

IKRTVAAPSVFIFPPSDEQLKSGTASVVCYLNNFY

PREAKVQWKVDNALQSGNSQESVTEQDSKDSTYSL

WSTLTLSKADYEKHKVYACEVTHQGLSSPVTKSFN

RGEC

Chain H2
(SEQ ID NO: 366)
QVQLVQSGAEVKKPGSSVKVSCKASGGTFGYYAIH

WVREAPGQGLEWMGGIGSIFGTANYAQKFQGRVTI

TADESTSTAYMELSSLRSEDTAVYYCARAWSSDHM

DYWGQGTLVTVSSASTKGPSVFPLAPSSKSTSGGT

AALGCLVKDYFPEPVTVSWNSGALTSGVHTFPAVL

QSSGLYSLTSVVEVPSSSLGTQTYICNVNHKPSNT

KVDKKVEPKSC ffAC_05337 also known as ffAC_5337,
ffP_A_05337 or ffP_A_5337
Chain H1
(SEQ ID NO: 367)
EVQLLESGGGLVQPGGSLRLSCAASGFTFSSSYMG

WVRRAPGKGLEWVSSIGSGSYSTSYADSVKGRFTI

SRDNSKNTLYLQMNSLRAEDTAVYYCARYPSVPFP

LHLDYWGQGTLVTVSSASTKGPSVFPLAPSSKSTS

GGTAALGCLVKDYFPEPVTVSWNSGALTSGVATGP

AVLQSSGLYSLSSVVTVPSSSLGTQTYICNVNHKP

SNTKVDKKVEPKSCDKTHTCPPCPAPEAAGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGKGGGG

SGGGGSGGGGSQSVLTQPPSASGTPGQRVTISCTG

SSSNIGAGYNVVYWYQRLPGTAPKLLIYGNINRPSG

VPDRFSGSKSGTSASLAISGLRSEDEADYYCAAWD

KSISGLVFGGGTKLTVLGQPKAAPAVTLFPPSSEE

LQANKATLVCLIKDFYPGAVTVAWKADSSPVKAGV

ETTTPSKQSNNKYAAWSYLSLTPEQWKSHRSYSCQ

VTHEGSTVEKTVAPTECS

Chain L1
(SEQ ID NO: 368)
DIQMTQSPSSLSASVGDRVTITCRASQSISSYLNW

YQEKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCYLNNFYP

REAKVQWKVDNALQSGNSQESVTEQDSKDSTYSLW

STLTLSKADYEKHKVYACEVTHQGLSSPVTKSFNR

GEC

-continued

```
Chain H2
                           (SEQ ID NO: 369)
EVQLLESGGGLVQPGGSLRLSCAASGFTFSTYGMH

WVREAPGKGLEWLSYISGGSSYIFYADSVKGRFTI

SRDNSKNTLYLQMNSLRAEDTAVYYCARILRGGSG

MDLWGQGTLVTVSSASTKGPSVFPLAPSSKSTSGG

TAALGCLVKDYFPEPVTVSWNSGALTSGVHTFPAV

LQSSGLYSLTSVVEVPSSSLGTQTYICNVNHKPSN

TKVDKKVEPKSC
```

Exemplary Full Heavy and Light Chain Sequences

```
Binding domain B1:
1132/1133 Heavy chain, including RUBY
mutations (VH: Q44R, CH1: H168A, F170G,
CH2: L234A, L235A) (SEQ ID NO: 371):
EVQLLESGGGLVQPGGSLRLSCAASGFTFSSYAMS

WVRRAPGKGLEWVSGIGSYGGGTYYADSVKGRFTI

SRDNSKNTLYLQMNSLRAEDTAVYYCARYVNFGMD

YWGQGTLVTVSSASTKGPSVFPLAPSSKSTSGGTA

ALGCLVKDYFPEPVTVSWNSGALTSGVATGPAVLQ

SSGLYSLSSVVTVPSSSLGTQTYICNVNHKPSNTK

VDKKVEPKSCDKTHTCPPCPAPEAAGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGK

1132/1133 Light chain, including RUBY
mutations (VL: Q44E, CKappa: L135Y, S176W)
(SEQ ID NO: 372):
DIQMTQSPSSLSASVGDRVTITCRASQSISSYLNW

YQEKPGKAPKLLIYAASSLQSGVPSRFSGSGSGTD

FTLTISSLQPEDFATYYCQQYGRNPPTFGQGTKLE

IKRTVAAPSVFIFPPSDEQLKSGTASVVCYLNNFY

PREAKVQWKVDNALQSGNSQESVTEQDSKDSTYSL

WSTLTLSKADYEKHKVYACEVTHQGLSSPVTKSFN

RGEC

1132/1133 Heavy chain (SEQ ID NO: 378):
EVQLLESGGGLVQPGGSLRLSCAASGFTFSSYAMS

WVRQAPGKGLEWVSGIGSYGGGTYYADSVKGRFTI

SRDNSKNTLYLQMNSLRAEDTAVYYCARYVNFGMD

YWGQGTLVTVSSASTKGPSVFPLAPSSKSTSGGTA

ALGCLVKDYFPEPVTVSWNSGALTSGVHTFPAVLQ

SSGLYSLSSVVTVPSSSLGTQTYICNVNHKPSNTK

VDKKVEPKSCDKTHTCPPCPAPELLGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGK

1132/1133 Light chain (SEQ ID NO: 379):
DIQMTQSPSSLSASVGDRVTITCRASQSISSYLNW

YQQKPGKAPKLLIYAASSLQSGVPSRFSGSGSGTD

FTLTISSLQPEDFATYYCQQYGRNPPTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

G12 Heavy chain (SEQ ID NO: 380):
EVQLLESGGGLVQPGGSLRLSCAASGFTFSTYGMH

WVRQAPGKGLEWLSYISGGSSYIFYADSVRGRFTI

SRDNSENALYLQMNSLRAEDTAVYYCARILRGGSG

MDLWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK

G12 Light chain (SEQ ID NO: 381):
QSVLTQPPSASGTPGQRVTISCTGSSSNIGAGYNV

YWYQQLPGTAPKLLIYGNINRPSGVPDRFSGSKSG

TSASLAISGLRSEDEADYYCAAWDKSISGLVFGGG

TKLTVLGQPKAAPSVTLFPPSSEELQANKATLVCL

ISDFYPGAVTVAWKADSSPVKAGVETTTPSKQSNN

KYAASSYLSLTPEQWKSHRSYSCQVTHEGSTVEKT

VAPTECS

G12_mut Heavy chain (SEQ ID NO: 382):
EVQLLESGGGLVQPGGSLRLSCAASGFTFSTYGMH

WVRQAPGKGLEWLSYISGGSSYIFYADSVKGRFTI

SRDNSKNTLYLQMNSLRAEDTAVYYCARILRGGSG

MDLWGQGTLVTVSSASTKGPSVFPLAPSSKSTSGG

TAALGCLVKDYFPEPVTVSWNSGALTSGVHTFPAV
```

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK

G12_mut Light chain (SEQ ID NO: 383):
QSVLTQPPSASGTPGQRVTISCTGSSSNIGAGYNV

YWYQQLPGTAPKLLIYGNINRPSGVPDRFSGSKSG

TSASLAISGLRSEDEADYYCAAWDKSISGLVFGGG

TKLTVLGQPKAAPSVTLFPPSSEELQANKATLVCL

ISDFYPGAVTVAWKADSSPVKAGVETTTPSKQSNN

KYAASSYLSLTPEQWKSHRSYSCQVTHEGSTVEKT

VAPTECS

Binding domain B2:
AC_05059, light chain (SEQ ID NO: 388):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05059, heavy chain (SEQ ID NO: 389):
EVQLLESGGGLVQPGGSLRLSCAASGFTFSSSYMG

WVRQAPGKGLEWVSSIGSGYSTSYADSVKGRFTI

SRDNSKNTLYLQMNSLRAEDTAVYYCARYPSVPFP

PHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05060, light chain (SEQ ID NO: 390):
DIQMTQSPSSLSASVGDRVTITCRASQSIRDYLNW

YQQKPGKAPKLLIYAASSLQSGVPSRFSGSGSGTD

FTLTISSLQPEDFATYYCQQGTFPFTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05060, heavy chain (SEQ ID NO: 391):
EVQLLESGGGLVQPGGSLRLSCAASGFTFGSYYMS

WVRQAPGKGLEWVSGISGYGYYTGYADSVKGRFTI

SRDNSKNTLYLQMNSLRAEDTAVYYCARHGYGVID

YWGQGTLVTVSSASTKGPSVFPLAPSSKSTSGGTA

ALGCLVKDYFPEPVTVSWNSGALTSGVHTFPAVLQ

SSGLYSLSSVVTVPSSSLGTQTYICNVNHKPSNTK

VDKKVEPKSCDKTHTCPPCPAPELLGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGK

AC_05061, light chain (SEQ ID NO: 392):
DIQMTQSPSSLSASVGDRVTITCRASQSISSYLNW

YQQKPGKAPKLLIYAASSLQSGVPSRFSGSGSGTD

FTLTISSLQPEDFATYYCQQGAYVPYTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

AC_05061, heavy chain (SEQ ID NO: 393):
EVQLLESGGGLVQPGGSLRLSCAASGFTFSSYAMS

WVRQAPGKGLEWVSAISGSGGSTYYADSVKGRFTI

SRDNSKNTLYLQMNSLRAEDTAVYYCARYGYTHFD

YWGQGTLVTVSSASTKGPSVFPLAPSSKSTSGGTA

ALGCLVKDYFPEPVTVSWNSGALTSGVHTFPAVLQ

SSGLYSLSSVVTVPSSSLGTQTYICNVNHKPSNTK

VDKKVEPKSCDKTHTCPPCPAPELLGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGK

AC_05062, light chain (SEQ ID NO: 394):
DIQMTQSPSSLSASVGDRVTITCRASQAISGYLNW

YQQKPGKAPKLLIYSASSLQSGVPSRFSGSGSGTD

FTLTISSLQPEDFATYYCQQSYSTPYTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

AC_05062, heavy chain (SEQ ID NO: 395):
EVQLLESGGGLVQPGGSLRLSCAASGFTFSSYAMS

WVRQAPGKGLEWVSAISGSGGSTYYADSVKGRFTI

SRDNSKNTLYLQMNSLRAEDTAVYYCARYRWHGSV

FDYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK

AC_05064, light chain (SEQ ID NO: 396):
DIQMTQSPSSLSASVGDRVTITCRASQSISSYLNW

YQQKPGKAPKLLIYAASSLQSGVPSRFSGSGSGTD

FTLTISSLQPEDFATYYCQQYPWYFPYTFGQGTKL

EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC

AC_05064, heavy chain (SEQ ID NO: 397):
EVQLLESGGGLVQPGGSLRLSCAASGFTFSSYAMS

WVRQAPGKGLEWVSAISGSGGSTYYADSVKGRFTI

SRDNSKNTLYLQMNSLRAEDTAVYYCARYGYSVLD

YWGQGTLVTVSSASTKGPSVFPLAPSSKSTSGGTA

ALGCLVKDYFPEPVTVSWNSGALTSGVHTFPAVLQ

SSGLYSLSSVVTVPSSSLGTQTYICNVNHKPSNTK

VDKKVEPKSCDKTHTCPPCPAPELLGGPSVFLFPP

KPKDTLMISRTPEVTCVVVDVSHEDPEVKFNWYVD

GVEVHNAKTKPREEQYNSTYRVVSVLTVLHQDWLN

GKEYKCKVSNKALPAPIEKTISKAKGQPREPQVYT

LPPSRDELTKNQVSLTCLVKGFYPSDIAVEWESNG

QPENNYKTTPPVLDSDGSFFLYSKLTVDKSRWQQG

NVFSCSVMHEALHNHYTQKSLSLSPGK

AC_05079, light chain (SEQ ID NO: 398):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05079, heavy chain (SEQ ID NO: 399):
EVQLLESGGGLVQPGGSLRLSCAASGFTFSSYMG

WVRQAPGKGLEWVSSIGSGSYSTSYADSVKGRFTI

SRDNSKNTLYLQMNSLRAEDTAVYYCARYPSVPFP

PPLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05081, light chain (SEQ ID NO: 400):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05081, heavy chain (SEQ ID NO: 401):
EVQLLESGGGLVQPGGSLRLSCAASGFTFSSYMG

WVRQAPGKGLEWVSSIGSGSYSTSYADSVKGRFTI

SRDNSKNTLYLQMNSLRAEDTAVYYCARYPSVPFQ

PHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

-continued
ESNGQPENNYKTTPPVLDSDGSFFLYSKLTVDKSR

WQQGNVFSCSVMHEALHNHYTQKSLSLSPGK

AC_05088, light chain (SEQ ID NO: 402):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05088, heavy chain (SEQ ID NO: 403):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVLFP

PHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05089, light chain (SEQ ID NO: 404):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05089, heavy chain (SEQ ID NO: 405):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFP

HHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

-continued
QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05090, light chain (SEQ ID NO: 406):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05090, heavy chain (SEQ ID NO: 407):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFP

LHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05091, light chain (SEQ ID NO: 408):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05091, heavy chain (SEQ ID NO: 409):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFP

PHFDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05093, light chain (SEQ ID NO: 410):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05093, heavy chain (SEQ ID NO: 411):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFP

PHVDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05094, light chain (SEQ ID NO: 412):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05094, heavy chain (SEQ ID NO: 413):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFP

PHWDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05096, light chain (SEQ ID NO: 414):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05096, heavy chain (SEQ ID NO: 415):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFR

PHLDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

AC_05097, light chain (SEQ ID NO: 416):
DIQMTQSPSSLSASVGDRVTITCRASQSISSYLNW

YQQKPGKAPKLLIYAASSLQSGVPSRFSGSGSGTD

FTLTISSLQPEDFATYYCQQAGNPHTFGQGTKLEI

KRTVAAPSVFIFPPSDEQLKSGTASVVCLLNNFYP

REAKVQWKVDNALQSGNSQESVTEQDSKDSTYSLS

STLTLSKADYEKHKVYACEVTHQGLSSPVTKSFNR

GEC

AC_05097, heavy chain (SEQ ID NO: 417):
EVQLLESGGGLVQPGGSLRLSCAASGFTFSSSYMG

WVRQAPGKGLEWVSSIGSGSYSTSYADSVKGRFTI

SRDNSKNTLYLQMNSLRAEDTAVYYCARYPSVPFS

PHLDYWGQGTLVTVSSASTKGPSVFPLAPSSKSTS

GGTAALGCLVKDYFPEPVTVSWNSGALTSGVHTFP

```
AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK

Fab1, light chain (SEQ ID NO: 418):
DIQMTQSPSSLSASVGDRVTITCRASQSISSYLNW

YQQKPGKAPKLLIYAASSLQSGVPSRFSGSGSGTD

FTLTISSLQPEDFATYYCQQSSHGPLLTFGQGTKL

EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC

Fab1, heavy chain (SEQ ID NO: 419):
QVQLVQSGAEVKKPGSSVKVSCKASGGTFGYYAIH

WVRQAPGQGLEWMGGIGSIFGTANYAQKFQGRVTI

TADESTSTAYMELSSLRSEDTAVYYCARAWSSDHM

DYWGQGTLVTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKKVEPKSCDKTHTCPPCPAPELLGGPSVFLFP

PKPKDTLMISRTPEVTCVVVDVSHEDPEVKFNWYV

DGVEVHNAKTKPREEQYNSTYRVVSVLTVLHQDWL

NGKEYKCKVSNKALPAPIEKTISKAKGQPREPQVY

TLPPSRDELTKNQVSLTCLVKGFYPSDIAVEWESN

GQPENNYKTTPPVLDSDGSFFLYSKLTVDKSRWQQ

GNVFSCSVMHEALHNHYTQKSLSLSPGK

Fab3, light chain (SEQ ID NO: 420):
EIVLTQSPGTLSLSPGERATLSCRASQSVSSSYLA

WYQQKPGQAPRLLIYGASSRATGIPDRFSGSGSGT

DFTLTISRLEPEDFAVYYCQQYWYPLTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

Fab3, heavy chain (SEQ ID NO: 421):
QVQLVQSGAEVKKPGSSVKVSCKASGGTFSSSSIH

WVRQAPGQGLEWMGHIYPSFGTANYAQKFQGRVTI

TADESTSTAYMELSSLRSEDTAVYYCARHSGSRFF

SPMDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK
```

Example 1—Isolation of CEACAM5 Binders

Aim and Background

The aim of the studies were to isolate anti human CEACAM5 binding domains.

Materials and Methods

The studies included the use of two different phage display antibody libraries AlligatorGOLD® and Alligator-FAB. Isolation of binders was performed using phage display using cells displaying the antigens or with biotinylated antigens bound on magnetic beads. Screening of binders was performed using high-throughput (HT) ELISA, FACS or next generation sequencing (NGS).

Phage Selections:

Phage display selections were performed, using either AlligatorGold® or the AlligatorFab libraries, according to selection strategies shown in Table 1. An overview of the different parameters used in the selections rounds during the phage selection process can be seen in Table 2 (Alligator GOLD, soluble antigen), Table 3 and Table 4 (Alligator GOLD, cell selections) or Table 5 (AlligatorFab libraries, soluble antigen). Overall, the starting libraries were thermally challenged at 45° C. for 1 h to ensure that the starting library only contained temperature stable antibody variants. Negative selection steps were added to remove potentially sticky binders as well as binders that were reactive towards the presence of a Fc-part (using ubiquitin-His and CTLA-4-Fc). In addition, pre-selections against other CEACAM family members were performed, to ensure the specificity of the developed clones. The selection strategy was also designed to promote the isolation of clones with high affinity by stepwise decreasing the antigen concentration and increasing the number of wash steps. CEACAM5 from commercial sources was used as soluble antigen (R&D Systems, #4128-CM-050).

TABLE 1

Description of the different selections strategies and tracks performed

| Type of phage selections | Antibody library | Selection Tracks | Pre-selection | Selection antigen |
|---|---|---|---|---|
| Biotinylated antigen on Dyna beads | AlligatorGOLD | 1 | CEACAM1, CEACAM6, CEACAM7, CEACAM8 | CEACAM5 |
| Cells overexpressing target | | 1 | Yes, CEACAM1 + cells | CEACAM1/5+ cells |
| | | 2 | Yes, CEACAM1 + cells | Splice variant CEACAM5+ cells |
| | | 3 | Yes, CEACAM1 + cells | Full-length CEACAM5+ cells |
| | | 3b | Yes, CEACAM1 + cells | Full-length CEACAM5+ cells |
| Biotinylated antigen on Dyna beads | AlligatorFAB libraries | 1 | CEACAM1 | CEACAM5 |

TABLE 2

AlligatorGOLD selections, soluble antigen-Selection parameters

| Selection Round | Antigen conc | Thermal step | Selection time | Wash | Phage input |
|---|---|---|---|---|---|
| R#1 | 100 nM | Yes (45° C., 1 h) | 1 h | 5X 2 min | 500 ul |
| R#2 | 10 nM | No | 1 h | 7X 2 min | 500 ul |
| R#3 | 10 nM | Yes (50° C., 1 h) | 1 h | 7X 2 min | 500 ul |
| R#4 | 1 nM | No | 20 min | 7X 2 min + 1x 30 min | 300 ul |
| R#5 | 0.1 nM | No | 20 min | 7X 2 min + 1x 30 min | 300 ul |
| R#6 | 0.01 nM | No | 20 min | 7X 2 min + 1x 30 min rsh | 300 ul |

TABLE 3

Cell selections-Selection parameters Track 1-3

| Selection Round | Antigen conc | Thermal step | Selection time | Wash | Phage input |
|---|---|---|---|---|---|
| R#1 | 1-5 × 10^6 cells | Yes (45° C., 1 h) | 2 h | 5X 2 min | 500 ul |
| R#2 | 1-5 × 10^6 cells | No | 1.5 h | 8X 2 min PBST/2% BSA, 2X 2 min PBST | 500 ul |
| R#3 | 1-5 × 10^6 cells | No | 1.5 h | 8X 2 min PBST/2% BSA, 2X 2 min PBST | 500 ul |
| R#4 | 1-5 × 10^6 cells | No | 1.5 h | 8X 2 min PBST/2% BSA, 2X 2 min PBST | 300 ul |

TABLE 4

Cell selections-Selection parameters Track 3b

| Selection Round | Antigen conc | Thermal step | Selection time | Wash | Phage input |
|---|---|---|---|---|---|
| R#1 | 1-5 × 10^6 cells | Yes (45° C., 1 h) | 2 h | 5X for 2 min | 500 ul |
| R#2 | 1-5 × 10^6 cells | No | 1 h | 5X for 2 min | 500 ul |
| R#3 | 1-5 × 10^6 cells | Yes (50° C., 1 h) | 1 h | 5X for 2 min | 500 ul |
| R#4 | 1-5 × 10^6 cells | No | 1.5 h | 8X 2 min PBST/2% BSA, 2X 2 min PBST | 300 ul |
| R#5 | 1-5 × 10^6 cells | No | 1.5 h | 8X 2 min PBST/2% BSA, 2X 2 min PBST | 300 ul |
| R#6 | 1-5 × 10^6 cells | No | 1.5 h | 8X 2 min PBST/2% BSA, 2X 2 min PBST | 300 ul |

TABLE 5

Alligator Fab selections - Selection parameters

| Selection Round | Antigen conc | Thermal step | Selection time | Wash | Elution | Phage input |
|---|---|---|---|---|---|---|
| R#1 | 100 nM | Yes (45° C., 1 h) | 1 h | 5X 30 s | Trypsin | 500 ul or 950 µl |
| R#2 | 10 nM | No | 1 h | 5X 30 s | trypsin | 650 ul |
| R#3 | 1 nM | No | 1 h | 7X 30 s | Trypsin | 300 ul |
| R#4 | 0.1 nM or 1 nM | No | 1 h | 7X 30 s | Trypsin | 300 ul |
| R#5 | 0.01 nM or 0.1 nM | No | 1 h | 5X 30 s or 7X 30 s | Trypsin | 300 ul |

Screening of Clones with ELISA

Screening was made on binders displayed on phages (test screenings) or using soluble scFv/Fab in bacterial supernatants. Briefly phage ELISAs were performed using CEACAM5 (#4128-CM-050, R&D Systems) or CTLA-4 Fc coated on microtiter plates to capture scFv/FAb displaying phages. Bound phages were detected with HRP conjugated monoclonal anti-M13 antibody (#27-9421-001, GE Healthcare). Positive phage clones were sequenced (Sanger sequencing at GATC). Unique phage clones were cloned to soluble scFv/Fab format. ELISA with soluble scFv/FAb were performed using the same antigens. Soluble scFv/Fab fragments were produced from bacterial TOP10 cultures. Unpurified supernatants were tested for binding towards antigen. Detection was made with HRP conjugated monoclonal anti-Flag antibody (#A8592, Sigma).

Screening of Clones with FACS

Genes coding for human CEACAM5, human CEACAM1 or a chimera of CEACAM5 and CEACAM1 (CEACAM1/5) were cloned into pcDNA3.1, and stably transfected into CHO cells. FACS screening was performed using either CHO cells transiently transfected for CEACAM5 expression, or control wild type CHO cells, diluted in FACS buffer (DPBS/0.5% BSA). Cells were seeded (150 000 cells/well) on to 96 well microtiter PP plates (#351190, Falcon). Supernatants of soluble Fab domains free of bacteria through centrifugation were diluted 1:1 in FACS buffer and added (50 µl) to seeded CHO cells. After incubation at 4° C. for 90 minutes cells were washed repeatedly with FACS buffer and resuspended in solution containing secondary antibody (α-hIgG F(ab')-PE, #19-116-097, Jackson ImmunoResearch) diluted at 1:1000 ratio. Following incubation for 1 hour at 4° C. cells were washed in FACS buffer and resuspended in Cellfix solution (#340181, BD) and signals were measured in a flow cytometer (BD).

Screening of Clones with Next Generation Sequencing (NGS)

Purified DNA from Phage pools from rounds #4, #5 and #6 from the AlligatorGOLD® selections with soluble antigen was used to amplify scFV encoding DNA in PCR using primers (as listed in Table 6). The PCR was performed using Pfu Ultra II Hotstart PCR Master Mix (#600850, Agilent Technologies). 1 ng of DNA template was denatured at 98° C. for 30 seconds before DNA was amplified in 15 or 18 cycles of PCR reactions (98° C. for 30 s, 58° C. for 30 s and 72° C. for 30 s) and an elongation phase of 2 minutes at 72° C. Material was purified from agarose gel and further tagged with DNA barcode primers (listed in Table 6). 1 ng of DNA template was denatured at 98° C. for 30 seconds before DNA was amplified in 15 or 18 cycles of PCR reactions (98° C. for 10 s, 68° C. for 30 s and 72° C. for 31 s) and an elongation phase of 2 minutes at 72° C. DNA was purified (Purify DNA with GeneRead Size Selection kit, #180514 Qiagen) before sent for Illumina sequencing at the SciLife facility NGI, Stockholm. Data analyses included quality control of obtained sequences and trimming of genes. Top candidates were aligned to sequences from clones isolated with traditional ELISA screening.

TABLE 6

PCR primers for generation of NGS libraries ('N' can correspond to any of A, T, C, or G)

| Purpose of PCR reaction | Type of primer | Sequence (5'- to 3') |
|---|---|---|
| DNA amplification | forward primer | ACACTCTTTCCCTACACGACG CTCTTCCGATCTNNNNNCCTC TCCTGTGCAGCCAGCGG (SEQ ID NO: 373) |
|  | reverse primer | AGACGTGTGCTCTTCCGATC TCTCCAGCTTGGTCCCCTGG CC (SEQ ID NO: 374) |
| Applying NGS barcodes | forward primer | AATGATACGGCGACCACCGA GATCTACACTAGATCGCACA CTCTTTCCCTACACGACG (SEQ ID NO: 375) |
|  | forward primer | AATGATACGGCGACCACCGAG ATCTACACCTCTCTATACACT CTTTCCCTACACGACG (SEQ ID NO: 376) |
|  | reverse primer | CAAGCAGAAGACGGCATACGA GATTCGCCTTAGTGACTGGAG TTCAGACGTGTGCTCTTCCGAT CT (SEQ ID NO: 377) |

Results and Conclusions

The phage selections and screening resulted in the isolation of 38 binding domains against human CEACAM5. 29 clones originated from the AlligatorGOLD® library and 11 clones from the AlligatorFAB libraries.

Example 2—Characterization of CEACAM5 Binding scFv

Aim and Background

The aim of the studies listed in this experiment was to further characterize the CEACAM5 binding single chain fragments (scFv) isolated in Example 1.

Materials and Methods

The scFv were cloned in to IgG1 format and produced from mammalian cultures. Antibodies were analyzed in a set of different assays to test quality, and binding capacity towards CEACAM5 and related CEA family protein CEACAM1.

Expression and QC Analyses

IgG1 antibodies listed in Table 7 and Table 8, and expression control monoclonal antibody 1188, were transiently expressed using Expi293 HEK (Life Technologies) cells at volumes ranging from 600 µl to 30 mL according to manufacturer's protocol. Purification of the antibodies from supernatants was made on protein A using the NGC system (BioRad) or Predictor MabSelectSure 50 µl 96 well plates (GE Healthcare). Aggregation was measured with SE-HPLC in a 1260 Infinity II system (Agilent Technologies) using a TSK gel Super SW mAB HTP 4 µm, 4.6×150 mm column (TOSOH Bioscience) and 100 mM Sodium Phosphate, pH 6.8, 300 mM NaCl as mobile phase at ambient temperature and a flow rate of 0.35 ml/min.

CEACAM5 Cell Binding

CHO cells stably transfected, with pcDNA3.1 carrying either genes for human CEACAM5, human CEACAM1 or CEACAM5/CEACAM1 chimeras, and CHO wild type (wt)

cells were incubated with 0.5 and 5 µg/ml IgG1 antibodies or for selected samples titrated antibody concentrations ranging from 67 nM to 0.4 µM. Binding of the antibodies was detected using fluorochrome-conjugated anti-human IgG and analysed using flow cytometry.

ELISA, CEA Binding and Cross-Reactivity 96-well plates were coated with 0.5 µg/mL antigen, hCEACAM-5 (4128-CM-050, R&D Systems), hCEACAM-1 (2244-CM-050, R&D Systems), hCEACAM-6 (3934-CM-050, R&D Systems) or CEACAM-8 (9639-CM-050, R&D Systems) in PBS over night at 4° C. After washing with PBS/0.05% Tween 20 (PBST), the plates were blocked with PBST, 2% BSA for at least 30 minutes at room temperature before a second round of washing. Antibody samples, diluted to either 0.4 µg/ml, or 10 µg/ml for binders isolated with NGS, or for selected samples titrated from 67 nM to 0.4 µM in PBST, 0.5% BSA, were then added and allowed to bind for at least 1 hour at room temperature. After washing, plates were incubated with 50 µl detection antibody (0.5 µg/ml HRP conjugated goat anti human-kappa light chain, #STAR127P, AbD Serotec). Finally, a final round of washing was performed and bound complexes detected using SuperSignal Pico Luminescent as substrate and luminescence signals were measured using Fluostar Optima.

Octet Binding Studies

Kinetic measurements were performed in the Octet RED96 platform using several different setups. Monoclonal antibodies (listed in Table 9), serially diluted 2 starting at 100 nM, were captured to anti human IgG Fc Capture (AHC) Biosensor tips (Sartorius #18-5060). Human CEACAM5-His (R&D Systems #4128-CM-050) diluted in 1× kinetic buffer (Sartorius) at 100 nM was then added. Binding kinetics was studied in 1× kinetic buffer where association was allowed for 300 sec followed by dissociation for 600 sec.

Sensor tips were regenerated with 10 mM Glycine pH 1.7. Data generated were referenced by subtracting blank or parallel buffer blank, the baseline was aligned to the y-axis, inter-step correction by alignment against dissociation was performed and the data was smoothed by Savitzky-Golay filter in the data analysis software (v9.0.0.14). The processed data was fitted using a 1:1 Langmuir binding model with $R^2$ or $X^2$ as a measurement of fitting accuracy.

Results and Conclusions

Results (summarized in Table 7) demonstrated the phage selection led to the isolation of several antibodies that displayed specific binding toward human CEACAM5. In particular antibodies AC_05059, AC_05060, AC_05061, AC_05062, AC_05064 showed a promising binding profile with selective binding towards human CEACAM5 as demonstrated both in ELISA (against CEACAM5, CEACAM1, CEACAM6, CEACAM7 and CEACAM8) as well as on FACS (with cells expressing CEACAM5, CEACAM1 or a CEACAM1/5 chimera).

In addition, the results also show that clones selected using next generation screening also generated clones with specific binding toward human CEACAM5 as demonstrated in an ELISA study toward CEACAM5 and CEACAM1 (Table 8 and FIG. 1). In particular antibodies AC_05079, AC_05081, AC_05088, AC_05089, AC_05090, AC_05091, AC_05093, AC_05094, AC_05096 and AC_05097 show selective binding for human CEACAM5.

Affinity measurements with Octet demonstrated the analysed antibodies displayed a range of different affinities toward CEACAM5 (Table 9).

TABLE 7

Binding studies with CEA binders in IgG1 format

| AC-name | HPLC (% mono) | Binding to CEACAM5 on cells | Binding to CEACAM1 on cells | Binding to CEACAM1/5 chimera on cells | Cross-reactivity to other CEA family members |
|---|---|---|---|---|---|
| AC_05066 | 97'1 | yes | yes | yes | — |
| AC_05068 | 97'7 | no | no | no | — |
| AC_05069 | 97'2 | yes | yes | yes | — |
| AC_05070 | 97'9 | yes | yes | yes | — |
| AC_05071 | 98'8 | yes | yes | yes | — |
| AC_05073 | 99'3 | yes | yes | yes | — |
| AC_05074 | 95'8 | yes | yes | yes | — |
| AC_05075 | 96'8 | yes | yes | yes | — |
| AC_05076 | 94 | yes | yes | yes | — |
| AC_05077 | 96'6 | yes | yes | yes | — |
| AC_05078 | 98'6 | weak | yes | yes | — |
| AC_05059 | 90'6 | yes | weak | weak | OK |
| AC_05060 | 98'8 | yes | no | no | OK |
| AC_05061 | 97'3 | yes | no | no | OK |
| AC_05062 | 98'1 | yes | no | no | OK |
| AC_05064 | 84'3 | yes | no | no | OK |
| AC_05065 | 94'2 | no | no | no | — |

TABLE 8

Binding towards CEACAM5 and CEACAM1 for antibodies isolated using NGS as shown in ELISA.

| | CEACAM5 | CEACAM1 |
|---|---|---|
| AC_05079 | Yes | No |
| AC_05080 | Yes | Weak |
| AC_05081 | Yes | No |
| AC_05082 | No | No |
| AC_05083 | Yes | Yes |
| AC_05085 | No | No |
| AC_05086 | Yes | Yes |
| AC_05087 | Yes | Yes |
| AC_05088 | Yes | No |
| AC_05089 | Yes | No |
| AC_05090 | Yes | No |
| AC_05091 | Yes | No |
| AC_05092 | No | No |
| AC_05093 | Yes | No |
| AC_05094 | Yes | No |
| AC_05095 | Yes | Weak |
| AC_05096 | Yes | No |
| AC_05097 | Yes | No |
| AC_05098 | No | No |
| AC_05099 | No | No |
| AC_05100 | No | No |

TABLE 9

Affinity measurement against CEACAM5 for antibodies in IgG1 format

| Sample | KD (M) | kon(1/Ms) | kdis(1/s) |
|---|---|---|---|
| AC_05059 | <1.0E−12 | 3E+05 | <1.0E−07 |
| AC_05060 | 6E−09 | 4E+05 | 2E−03 |
| AC_05061 | 2E−08 | 1E+05 | 2E−03 |
| AC_05062 | 9E−10 | 2E+06 | 2E−03 |
| AC_05064 | 4E−10 | 1E+05 | 6E−05 |
| AC_05080 | 8E−12 | 2E+05 | 2E−06 |
| AC_05081 | 1E−07 | 6E+04 | 8E−03 |
| AC_05088 | 2E−08 | 1E+06 | 3E−02 |
| AC_05089 | 4E−08 | 3E+05 | 1E−02 |
| AC_05090 | 2E−08 | 3E+05 | 4E−03 |

TABLE 9-continued

Affinity measurement against CEACAM5 for antibodies in IgG1 format

| Sample | KD (M) | kon(1/Ms) | kdis(1/s) |
|---|---|---|---|
| AC_05091 | 2E−09 | 2E+05 | 3E−04 |
| AC_05093 | 4E−10 | 3E+05 | 1E−04 |
| AC_05094 | 5E−08 | 2E+04 | 8E−04 |
| AC_05097 | 7E−11 | 2E+05 | 2E−05 |

Example 3—Generation and Manufacturability of Bispecific Antibodies Targeting CD40 and CEACAM5

Background and Aim

Bispecific antibodies (bsAbs) were generated by combining above evaluated CEACEAM5 targeting antibodies with any of the CD40 agonistic antibodies 1132, G12 or 'G12_mut' in the RUBY™ format. In brief, bispecific antibodies in the RUBY™ format are generated by appending the antigen-binding fragments (Fab) of an antibody to the c-terminal part of the heavy chain of an IgG via a short peptide linker. A selected set of bsAbs were further transferred into a variant of the RUBY™ format with optimized properties. Generated RUBY™ bsAbs are listed in Table 10. Manufacturability of the listed bsAbs targeting CD40 and CEACAM5 was evaluated in terms of production yields and purity after protein A purification.

Materials and Methods

RUBY™ bsAbs listed in Table 10, and expression control monoclonal antibody 1188, were transiently expressed using Expi293 HEK (Life Technologies) cells at volumes ranging from 600 µl to 30 mL according to manufacturer's protocol. Cells were transfected with three different vectors each encoding one of the three polypeptide chains of RUBY™ bsAbs (i.e., the immunoglobulin heavy chain linked to the linker and Fab light chain (Chain H1), the immunoglobulin light chain (Chain L1) and the Fab heavy chain (Chain H2)). Purification of the antibodies from supernatants was made on protein A using the NGC system (BioRad) or Predictor MabSelectSure 50 µl 96 well plates (GE Healthcare). Different transfection ratios of the three vectors were tested. Aggregation was measured with SE-HPLC in a 1260 Infinity II system (Agilent Technologies) using a TSK gel Super SW mAB HTP 4 µm, 4.6×150 mm column (TOSOH Bioscience) and 100 mM Sodium Phosphate, pH 6.8, 300 mM NaCl as mobile phase at ambient temperature and a flow rate of 0.35 m*/mm.

Results and Conclusions

Bispecific antibodies could be generated in the RUBY™ format by combining CD40 and CEACAM targeting antibodies. Table 11, shows the production yields from high-throughput transient cultures and the monomer fraction as measured by SE-HPLC after protein A high-throughput purification. Generally good productivity and quality was observed. In conclusion, it is possible to generate and produce RUBY™ bsAbs targeting CD40 and CEA of high purity.

TABLE 10

List of generated RUBY™ bsAbs.

| RUBY™ ID | mAb origin IgG position | mAb origin Fab position | Target combination | Format |
|---|---|---|---|---|
| Multi1 | G12 | Fab1 | CD40xCEACAM5 | RUBY™, * |
| Multi2 | G12 | Fab2 | CD40xCEACAM5 | RUBY™, * |
| Multi3 | G12 | Fab3 | CD40xCEACAM5 | RUBY™, * |
| Multi4 | G12 | Fab4 | CD40xCEACAM5 | RUBY™, * |
| Multi5 | G12 | Fab5 | CD40xCEACAM5 | RUBY™, * |
| Multi6 | G12 | Fab6 | CD40xCEACAM5 | RUBY™, * |
| Multi7 | G12 | Fab7 | CD40xCEACAM5 | RUBY™, * |
| Multi8 | G12 | Fab8 | CD40xCEACAM5 | RUBY™, * |
| Multi9 | G12 | Fab9 | CD40xCEACAM5 | RUBY™, * |
| Multi10 | G12 | Fab10 | CD40xCEACAM5 | RUBY™, * |
| Multi11 | G12 | Fab11 | CD40xCEACAM5 | RUBY™, * |
| Multi12 | Fab1 | G12 | CEACAM5xCD40 | RUBY™, * |
| Multi13 | Fab2 | G12 | CEACAM5xCD40 | RUBY™, * |
| Multi14 | Fab3 | G12 | CEACAM5xCD40 | RUBY™, * |
| Multi17 | Fab6 | G12 | CEACAM5xCD40 | RUBY™, * |
| Multi18 | Fab7 | G12 | CEACAM5xCD40 | RUBY™, * |
| Multi19 | Fab8 | G12 | CEACAM5xCD40 | RUBY™, * |
| Multi20 | Fab9 | G12 | CEACAM5xCD40 | RUBY™, * |
| Multi23 | 1132 | Fab1 | CD40xCEACAM5 | RUBY™, * |
| Multi24 | 1132 | Fab2 | CD40xCEACAM5 | RUBY™, * |
| Multi25 | 1132 | Fab3 | CD40xCEACAM5 | RUBY™, * |
| Multi26 | 1132 | Fab4 | CD40xCEACAM5 | RUBY™, * |
| Multi27 | 1132 | Fab5 | CD40xCEACAM5 | RUBY™, * |
| Multi28 | 1132 | Fab6 | CD40xCEACAM5 | RUBY™, * |
| Multi29 | 1132 | Fab7 | CD40xCEACAM5 | RUBY™, * |
| Multi30 | 1132 | Fab8 | CD40xCEACAM5 | RUBY™, * |
| Multi31 | 1132 | Fab9 | CD40xCEACAM5 | RUBY™, * |
| Multi32 | 1132 | Fab10 | CD40xCEACAM5 | RUBY™, * |
| Multi33 | 1132 | Fab11 | CD40xCEACAM5 | RUBY™, * |
| Multi34 | G12_mut | Fab1 | CD40xCEACAM5 | Optimized RUBY™, § |
| Multi35 | G12_mut | Fab2 | CD40xCEACAM5 | Optimized RUBY™, § |
| Multi37 | G12_mut | Fab6 | CD40xCEACAM5 | Optimized RUBY™, § |
| Multi38 | G12_mut | Fab8 | CD40xCEACAM5 | Optimized RUBY™, § |
| Multi39 | G12_mut | Fab10 | CD40xCEACAM5 | Optimized RUBY™, § |
| Multi40 | Fab1 | G12_mut | CEACAM5xCD40 | Optimized RUBY™, § |
| Multi41 | Fab2 | G12_mut | CEACAM5xCD40 | Optimized RUBY™, § |
| Multi42 | Fab3 | G12_mut | CEACAM5xCD40 | Optimized RUBY™, § |
| Multi44 | Fab7 | G12_mut | CEACAM5xCD40 | Optimized RUBY™ |
| Multi46 | 1132 | Fab1 | CD40xCEACAM5 | Optimized RUBY™, § |
| Multi47 | 1132 | Fab2 | CD40xCEACAM5 | Optimized RUBY™, § |
| Multi48 | 1132 | Fab8 | CD40xCEACAM5 | Optimized RUBY™, § |
| Multi49 | 1132 | Fab10 | CD40xCEACAM5 | Optimized RUBY™, § |
| AC_05333 | G12 | 5090 | CD40xCEACAM5 | RUBY™, * |
| AC_05334 | G12 | 5093 | CD40xCEACAM5 | RUBY™, * |
| AC_05336 | 5088 | G12 | CEACAM5xCD40 | RUBY™, * |
| AC_05337 | 5090 | G12 | CEACAM5xCD40 | RUBY™, * |
| AC_05338 | 5093 | G12 | CEACAM5xCD40 | RUBY™, * |
| AC_05339 | 5097 | G12 | CEACAM5xCD40 | RUBY™, * |
| AC_05341 | 1132 | 5090 | CD40xCEACAM5 | RUBY™, * |
| ffAC_05337 | 5090 | G12_mut | CEACAM5xCD40 | Optimized RUBY™, § |

TABLE 10-continued

List of generated RUBY™ bsAbs.

| | mAb origin | | | |
|---|---|---|---|---|
| RUBY™ ID | IgG position | Fab position | Target combination | Format |
| ffAC_05339 | 5097 | G12_mut | CEACAM5xCD40 | Optimized RUBY™, § |
| AC_05355 | mAb2 | G12 | CEACAM5xCD40 | RUBY™, * |

* Carries the following mutations: in Chain H1 Q44R (according to IMGT numbering system) in the VH of the IgG; H168A, F170G (according to the Eu numbering system) in the CH1; Q44R (according to IMGT numbering system) in the VL; and S114A, N137K (according to the Eu numbering system) in CKappa of the appended Fab position; in Chain L1 Q44E (according to the IMGT numbering system) in the VL; and L135Y, S176W (according to the Eu numbering system) in Ckappa; in Chain H2 Q44E (according to the IMGT numbering system) in the VH; and T187E (according of Eu numbering system) in the CH1.

§ Additional mutations included: T109P (according to the Eu numbering system) in the CKappa of the appended Fab.

TABLE 11

Expression volume, production yield and purity of CD40 and CEACAM5 targeted bsAbs

| RUBY™ ID | Expression vol. | Yield (mg/L) | Monomeric fraction (%) |
|---|---|---|---|
| Multi1 | 600 µl | 67 | 96 |
| Multi2 | 600 µl | 66 | 97 |
| Multi3 | 600 µl | 58 | 97 |
| Multi4 | 600 µl | 62 | 100 |
| Multi5 | 600 µl | 55 | 98 |
| Multi6 | 600 µl | 84 | 97 |
| Multi8 | 600 µl | 124 | 88 |
| Multi9 | 600 µl | 85 | 92 |
| Multi10 | 600 µl | 82 | 95 |
| Multi11 | 600 µl | 67 | 96 |
| Multi13 | 600 µl | 24 | 85 |
| Multi14 | 600 µl | 40 | 94 |
| Multi17 | 600 µl | 14 | 100 |
| Multi18 | 600 µl | 11 | 93 |
| Multi19 | 600 µl | 56 | 93 |
| Multi20 | 600 µl | 64 | 85 |
| Multi23 | 600 µl | 29 | 93 |
| Multi24 | 600 µl | 29 | 92 |
| Multi25 | 600 µl | 25 | 94 |
| Multi26 | 600 µl | 29 | 99 |
| Multi27 | 600 µl | 27 | 90 |
| Multi28 | 600 µl | 22 | 93 |
| Multi29 | 600 µl | 26 | 80 |
| Multi30 | 600 µl | 107 | 83 |
| Multi31 | 600 µl | 85 | 86 |
| Multi32 | 600 µl | 39 | 91 |
| Multi33 | 600 µl | 98 | 88 |
| Multi34 | 30 ml | 18 | 96 |
| Multi35 | 30 ml | 79 | 96 |
| Multi37 | 30 ml | 20 | 97 |
| Muli38 | 30 ml | 126 | 87 |
| Multi39 | 30 ml | 101 | 92 |
| Multi40 | 30 ml | 95 | 85 |
| Multi41 | 30 ml | 67 | 84 |
| Multi42 | 30 ml | 16 | 100 |
| Multi44 | 30 ml | 20 | 93 |
| Multi46 | 30 ml | 79 | 94 |
| Multi47 | 30 ml | 91 | 92 |
| Multi48 | 30 ml | 152 | 83 |
| Multi49 | 30 ml | 110 | 82 |
| AC_05333 | 30 ml | 112 | 90 |
| AC_05334 | 30 ml | 107 | 81 |
| AC_05336 | 30 ml | 15 | 99 |
| AC_05337 | 30 ml | 29 | 97 |
| AC_05338 | 30 ml | 30 | 97 |
| AC_05339 | 30 ml | 34 | 97 |
| AC_05341 | 30 ml | 73 | 81 |
| ffAC_05337 | 30 ml | 33 | 98 |
| ffAC_05339 | 30 ml | 72 | 96 |
| AC_05355 | 30 ml | 225 | 96 |
| 1188 | 600 µl | 104-172 | 97-99 |
| 1188 | 30 ml | 70-180 | 99 |

Example 4—Dual Antigen Binding and Binding to CEACAM Variants of CD40 and CEACAM5 Targeting bsAbs by ELISA Aim The aim of the study was to evaluate the ability of selected CD40 and CEACAM5 targeting RUBY™ bsAbs to bind both their targets simultaneously as well as their potential cross-reactivity with additional members of the CEA protein family was evaluated by ELISA.

Materials and Methods 96-well plates were coated with 0.5 µg/mL antigen, hCEACAM-1 (2244-CM-050, R&D Systems), hCEACAM-5 (4128-CM-050, R&D Systems), hCEACAM-6 (3934-CM-050, R&D Systems) or CEACAM-8 (9639-CM-050, R&D Systems) in PBS over night at 4° C. After washing in PBS/0.05% Tween 20 (PBST), the plates were blocked with PBST, 2% BSA for at least 30 minutes at room temperature before a second round of washing. RUBY bsAbs, diluted in PBST, 0.5% BSA, were then added and allowed to bind for at least 1 hour at room temperature. After washing, plates were incubated with either 50 µl detection antibody (0.5 µg/ml HRP conjugated goat anti human-kappa light chain, #STAR127P, AbD Serotec) for analysis of binding to CEACAM protein family proteins or 0.5 µg/ml biotinylated hCD40-muIg (504-030, Ancell) followed by HRP conjugated streptavidin (21126, Pierce) for confirmation of dual antigen binding. Finally, a final round of washing was performed and bound complexes detected using SuperSignal Pico Luminescent as substrate and luminescence signals were measured using Fluostar Optima.

Results and Conclusions

All evaluated RUBY™ bsAbs was indeed able to bind to both CD40 and human CEACAM5 simultaneously (FIG. 2), although with varying potency. In general, bsAbs carrying 1132 as CD40 binding antibody (Multi46-Multi49) displayed lower potency in the dual target ELISA, as compared to bsAbs carrying G12_mut. Also, Multi38 displayed reduced dual target binding compared to other G12_mut based bsAbs, likely due to lower CEACAM5 binding of Fab6 than other evaluated CEACAM5 binding antibodies.

As can be seen in FIG. 3, a majority of the evaluated CD40 and CEACAM5 targeting RUBY™ bsAbs did not cross react with any of the other CEA family members evaluated. However, a limited number of the assayed bsAb did show significant cross-reactivity with CEACAM1 (Multi38, Multi39, Multi45 and Multi 49) or CEACAM6 (Multi40).

All in all, it can be concluded that all evaluated RUBY™ bsAbs have the ability to bind CD40 and CEACAM5 simultaneously and a majority of the set was specific for CEACAM5, with no or little detectable binding to other evaluated members of the CEA protein family.

Example 5—Kinetics of Interaction Between Bispecific Antibodies and CEACAM5 and CD40

Aim and Background

The aim of these studies was to measure the binding affinities of selected CD40×CEACAM5 targeting RUBY™ bsAb using several different assay set ups to obtain a comprehensive understanding of the bsAbs binding kinetics. The assays included both set ups using immobilized CEACAM5 or CD40 or monomeric CEACAM5 or CD40 in solution.

Materials and Methods

Kinetic measurements were performed in the Octet RED96 platform using several different setups. Bispecific antibodies (listed in Table 12-Table 15) or biotinylated human CEACAM5-His (Acro Biosystems #CE5-H82E0) or biotinylated human CD40-mouse Fc (Ancell #504-030) were captured to anti human IgG Fc Capture (AHC) Biosensor tips (Sartorius #18-5060) or Streptavidin Biosensor tips (Sartorius #18-5019). Monomeric human CD40-His-Avi tag (Acro Biosystems #CD0-H5228), monomeric Human CEACAM5-His (R&D Systems #4128-CM-050) or monomeric Cynomolgus CEACAM5-His (Sino Biological #90891-C08H) were ½ serially diluted in 1× kinetic buffer (Sartorius) starting at 500 nM or 100 nM. Bispecific antibodies were 2 serially diluted starting at 50 nM, 25 nM or 10 nM or 1/1.5 serially diluted starting at 15 nM or 5 nM. Binding kinetics was studied in 1× kinetic buffer where association was allowed for 100 sec, 300 sec or 600 sec followed by dissociation for 100 sec, 300 sec or 3600 sec. Sensor tips were regenerated with 10 mM Glycine pH 1.7. Data generated were referenced by subtracting blank or parallel buffer blank, the baseline was aligned to the y-axis, inter-step correction by alignment against dissociation was performed and the data was smoothed by Savitzky-Golay filter in the data analysis software (v9.0.0.14). The processed data was fitted using a 1:1 Langmuir binding model with $R^2$ or $X^2$ as a measurement of fitting accuracy.

Results and Conclusions

Figure 4:
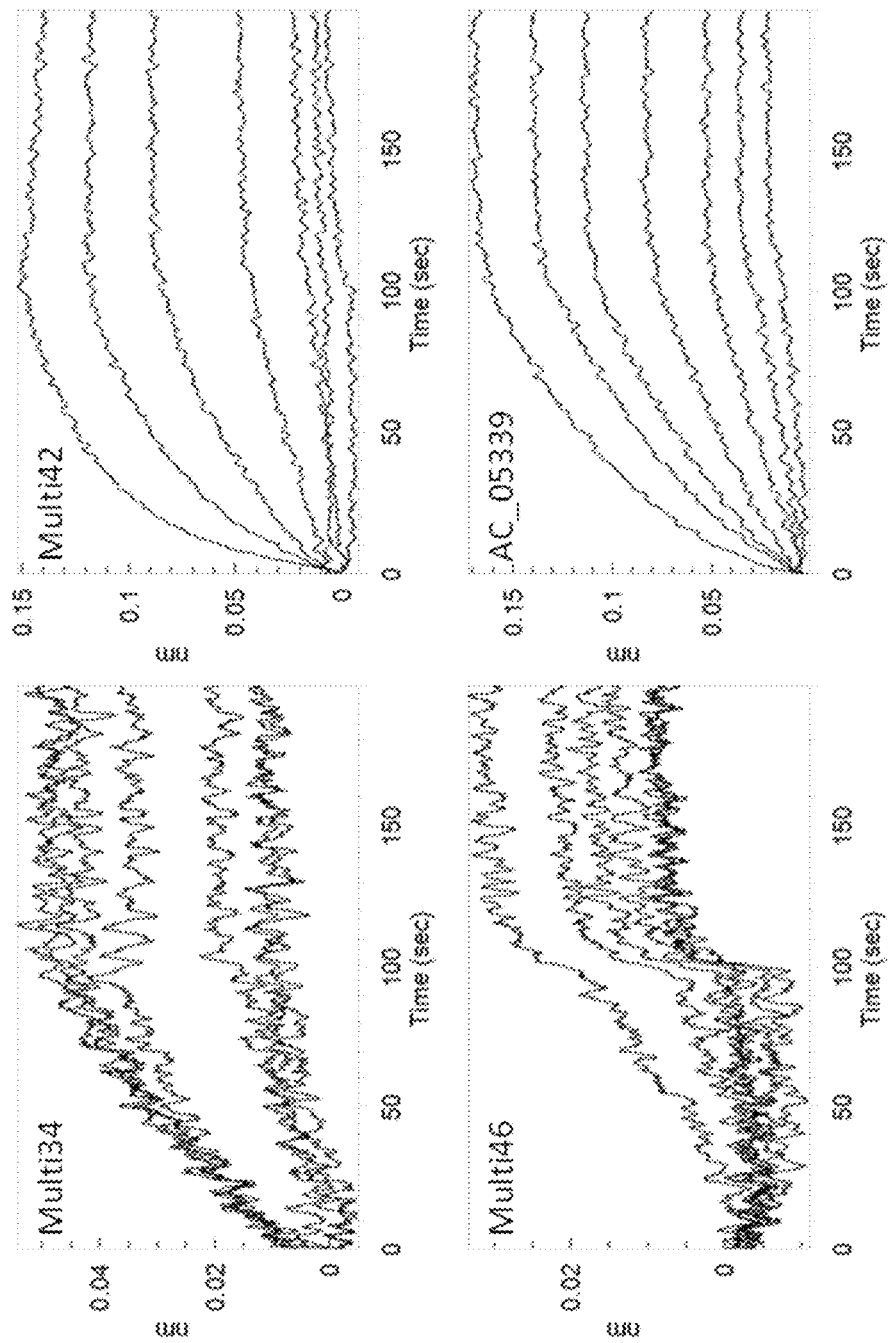
FIG. 4. Kinetic measurement in Octet of interaction between captured CD40 CEACAM5 targeting bispecific antibodies (Multi 34, Multi42, Multi46 and AC_5339) against soluble monomeric human CEACAM5 (at varying concentrations ranging between 100-1.6 nM). Association was measured for 100 sec followed by dissociation for 100 sec into 1× kinetic buffer.
Figure 5:
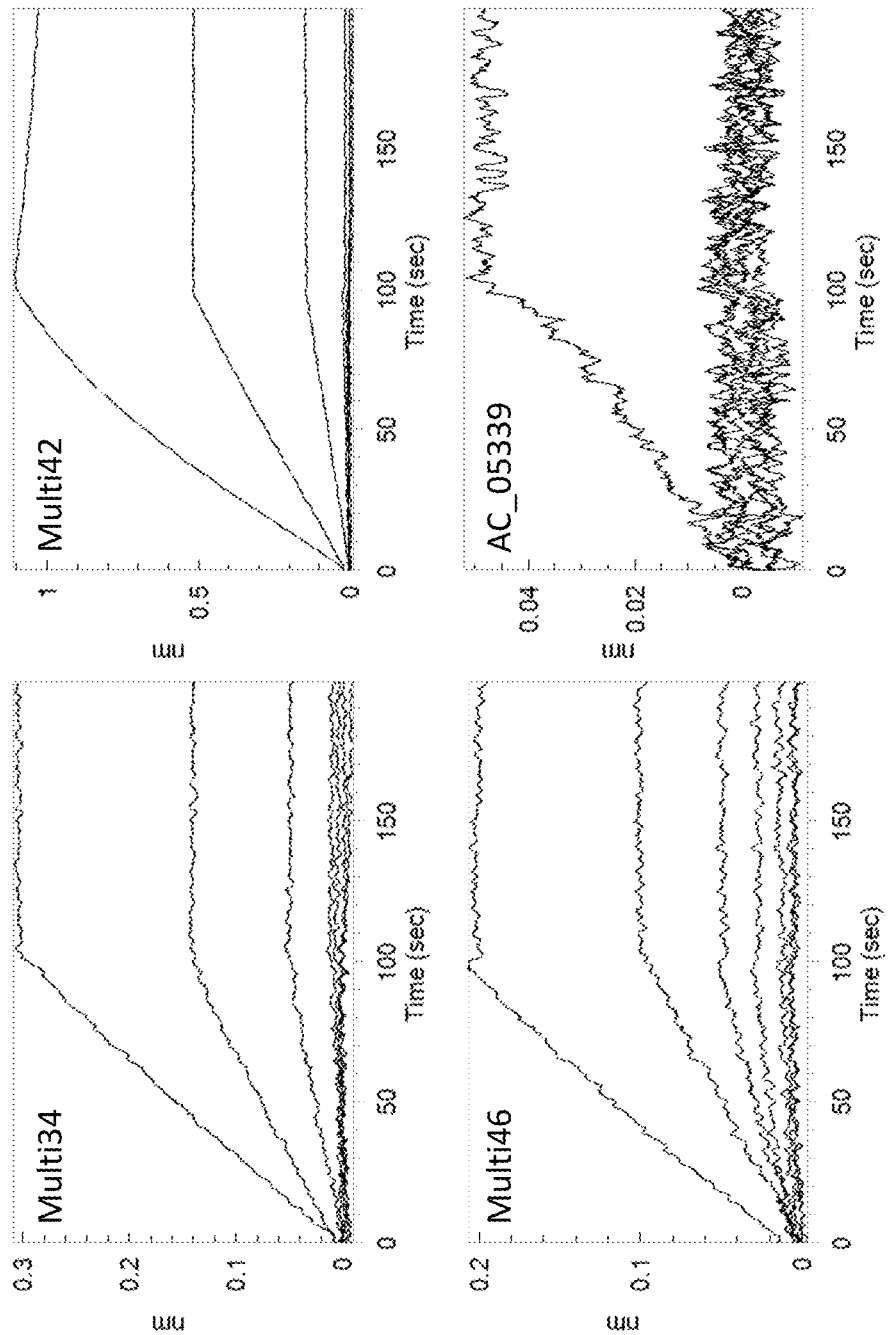
FIG. 5. Kinetic measurement of bispecific antibodies (at varying concentrations ranging between 50-0.8 nM) in solution interacting with captured human CEACAM5-biotin in Octet. Association was measured for 100 sec followed by dissociation for 100 sec into kinetic buffer.
Figure 6A:
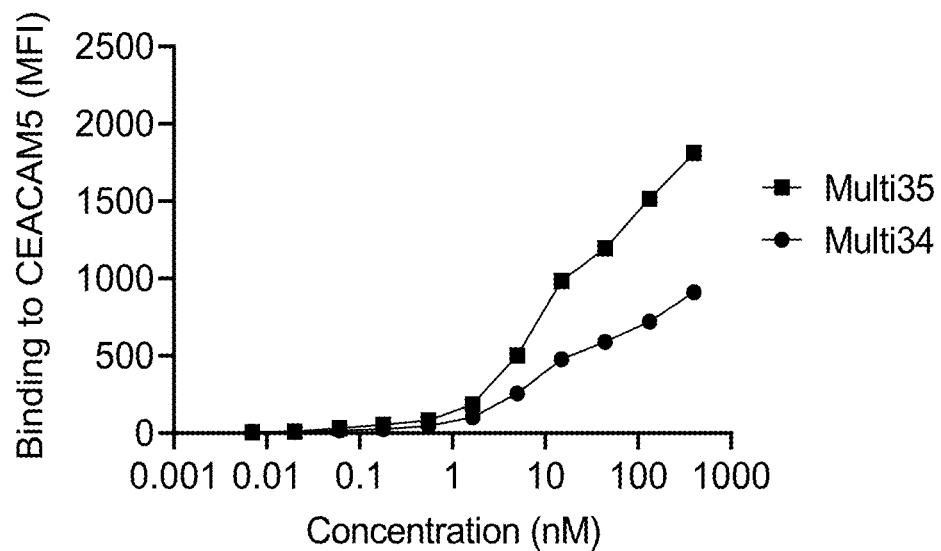
FIGS. 6A-6E. Binding of CD40-CEACAM5 bispecific antibodies to CEACAM5-transfected CHO cells. Binding of CD40-CEA bispecific antibodies was detected by flow cytometry using fluorochrome-conjugated anti-human IgG.
Figure 6B:
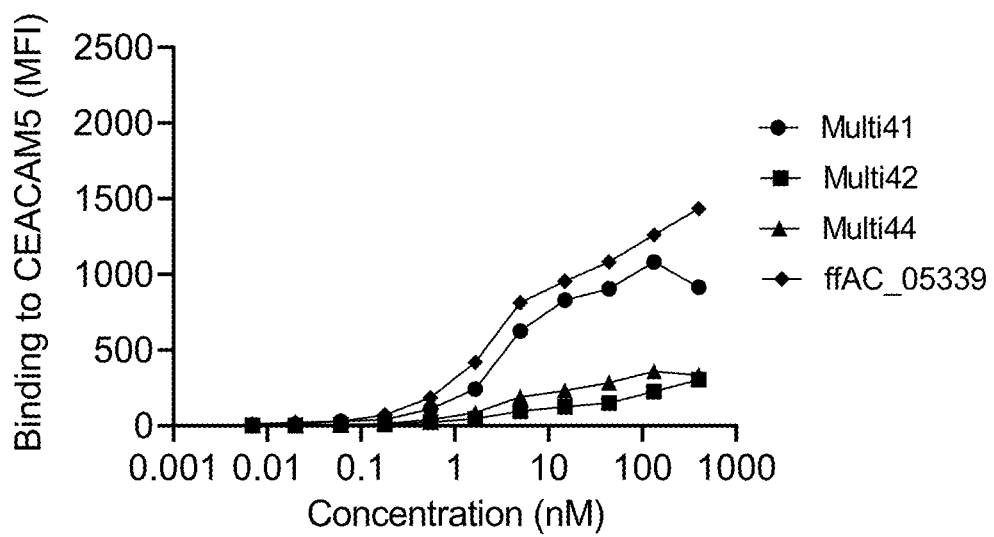
Figure 6C:
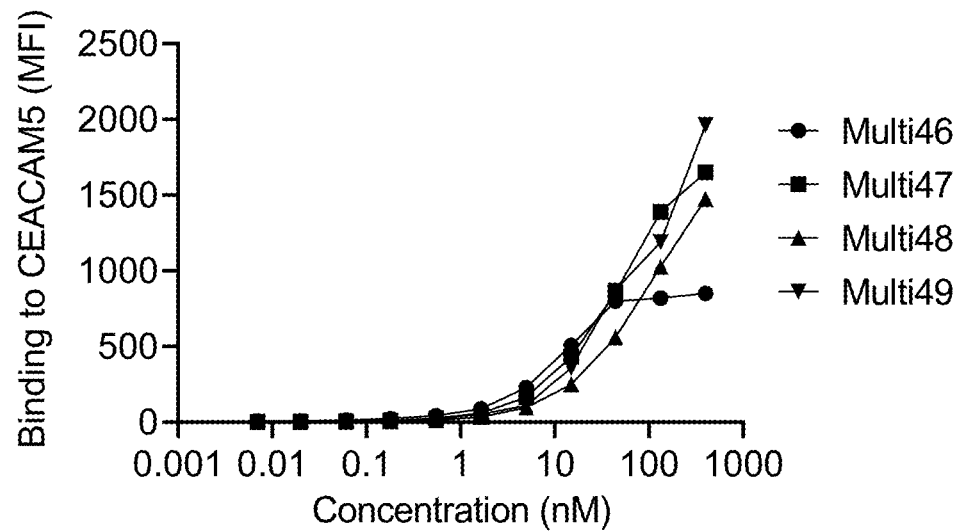
Figure 6D:
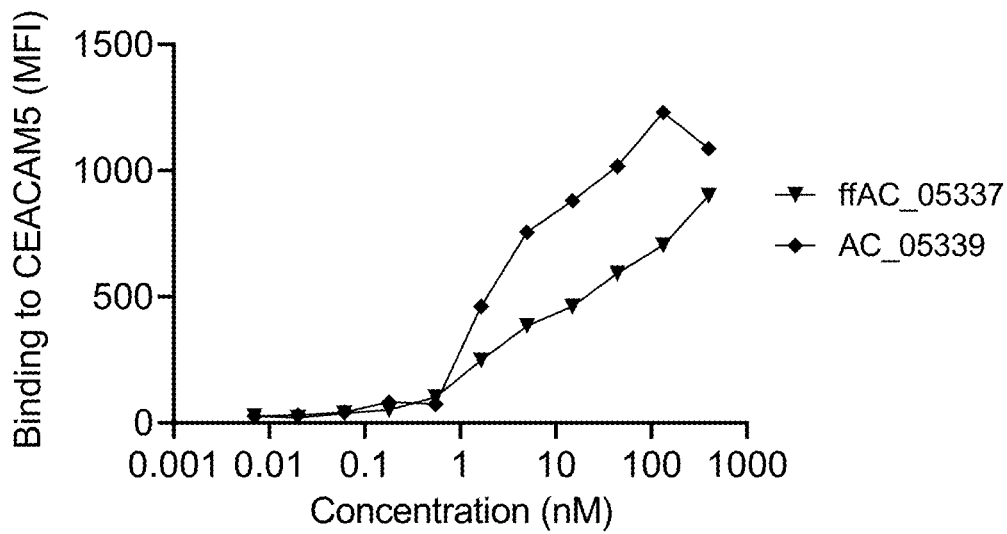
Figure 6E:
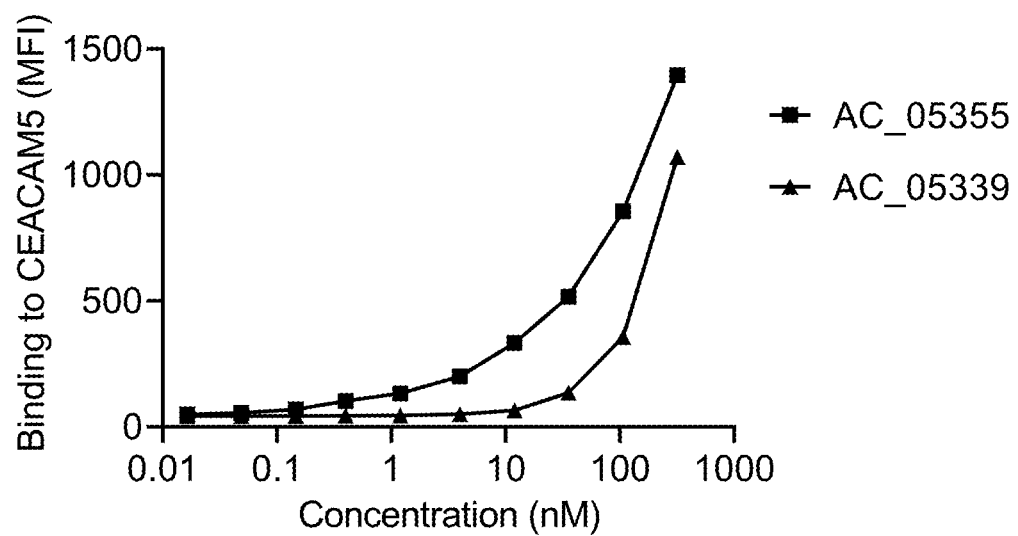
Figure 7A:
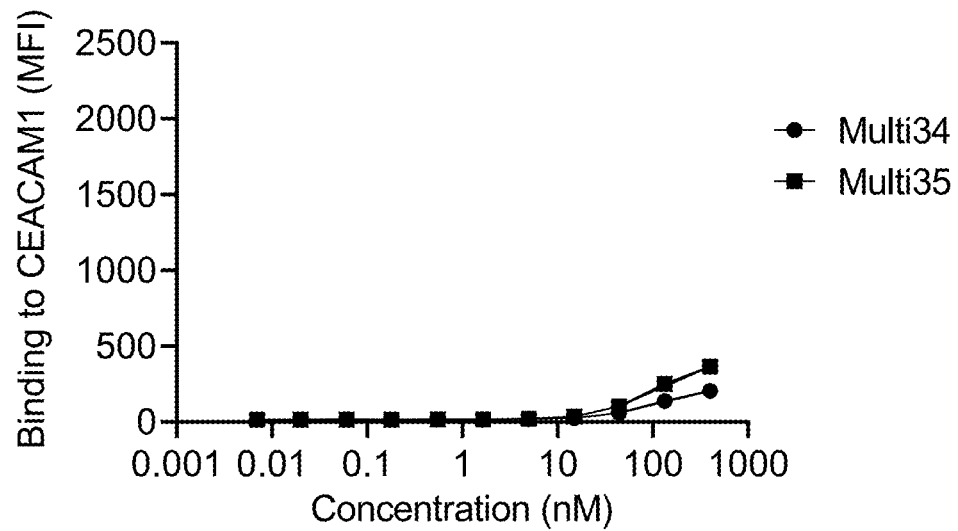
FIGS. 7A-7D. Binding of CD40-CEACAM5 bispecific antibodies to CEACAM1-transfected CHO cells (FIGS. 7A-7C) and to CHO wt cells (FIG. 7D). Binding of CD40-CEACAM5 bispecific antibodies was detected by flow cytometry using fluorochrome-conjugated anti-human IgG.
Figure 7B:
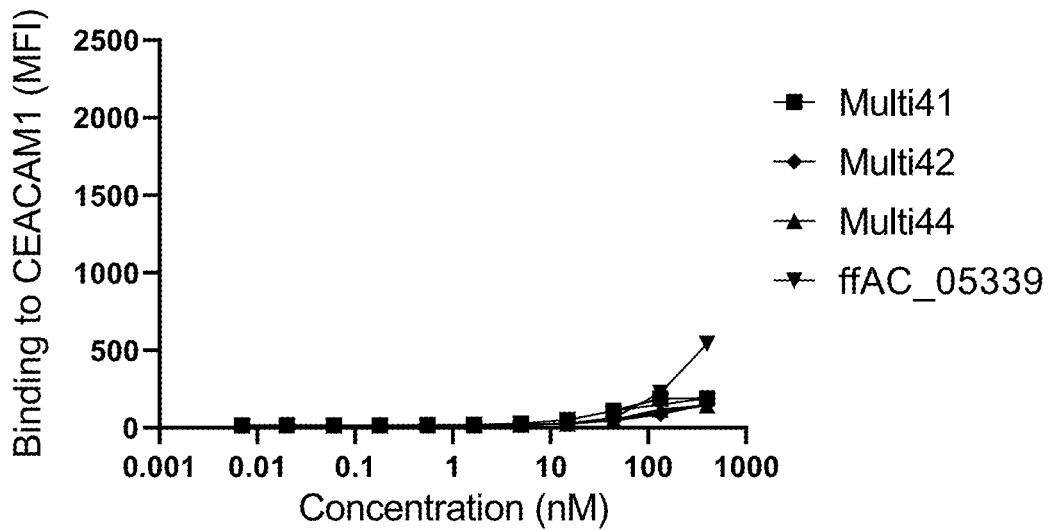
Figure 7C:
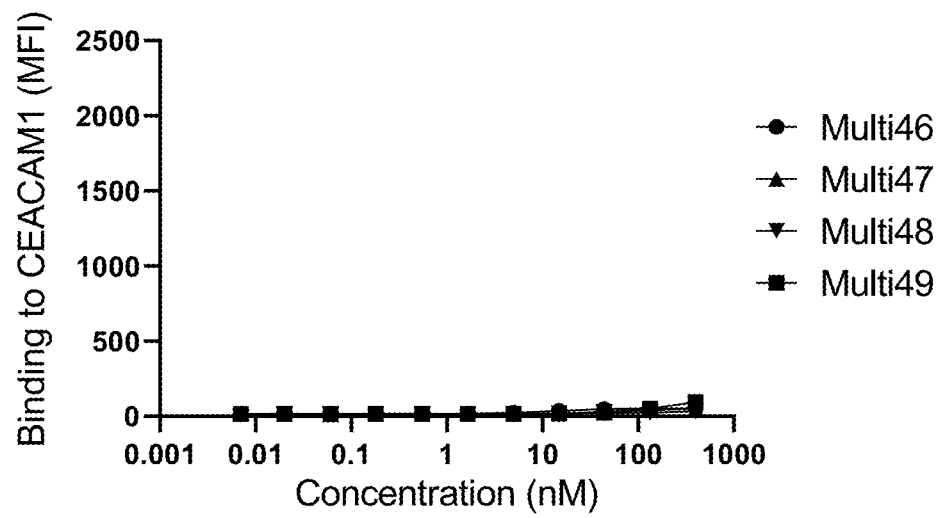
Figure 7D:
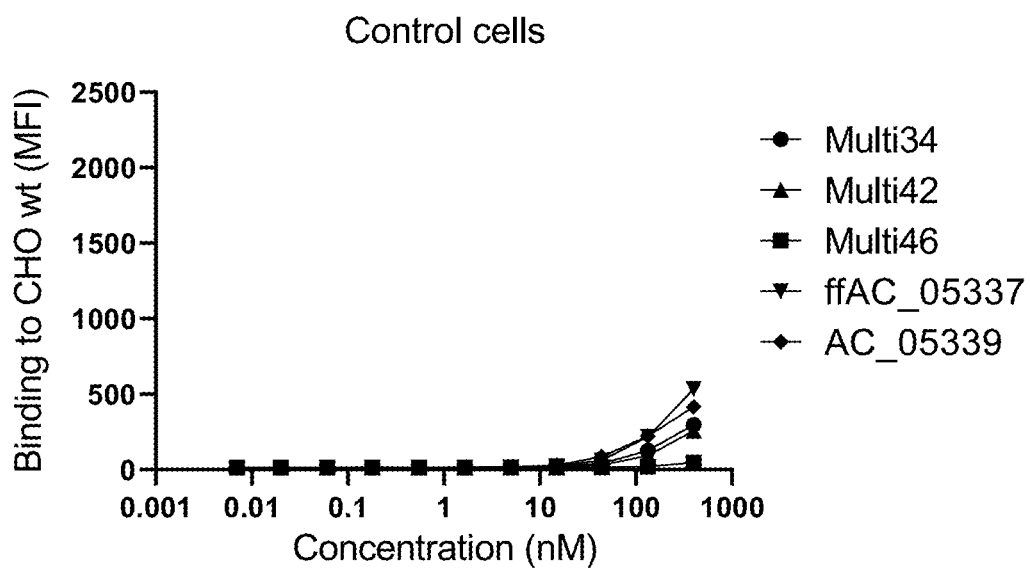

The two anti CD40 binding domains; 1132 and G12 interact with captured CD40 with $K_D$ values in the nM range, but with different kinetic profiles (Table 12). The same anti CD40 binding domains in IgG position or in Fab position in the bispecific antibody interact with similar affinity and kinetics to CD40 (Table 12). A summary of kinetic profiles for the CEACAM5 interactions measured in the Octet is listed in Table 13 and Table 14. Example of sensorgrams of soluble monomeric human CEACAM5 interacting with captured bsAb is shown in FIG. 4. Example of bsAb in solution interacting with capture CEACAM5 is shown in FIG. 5. The kinetic profiles and affinities for the bsAb interacting with human CEACAM5 varies with $K_D$ from higher nM range to sub nM range. The cynomolgus CEACAM5 reactive bsAb AC_05355 were interacting with both human CEACAM5 and cynomolgus CEACAM5 with $K_D$ in the nM range (Table 15).

TABLE 12

Summary of kinetic profiles measured in Octet. Bispecific antibodies in solution (25-0.8 nM, 10-2 or 5-0.7 nM.) interacting with captured CD40mFc-biotin. Association was measured for 300 sec or 600 sec and dissociation was measured for 300 sec or 3600 sec

| Bispecific antibody | BsAb IgG | BsAb Fab | $k_a$(1/Ms) | $k_d$(1/s) | $K_D$ (M) | $R^2$ |
|---|---|---|---|---|---|---|
| AC_05293 | 1132 | control 3174 (comprising SEQ ID NOs: 422 and 424) | 8.3E+03 | 6.2E-04 | 7.6E-08 | 0.96 |
| AC_05300 | control 3174 | 1132 | 5.4E+05 | 4.6E-03 | 8.5E-09 | 0.97 |
| AC_05330 | G12 | control 1210 (comprising SEQ ID NOs: 426 and 428) | 3.5E+04 | 1.6E-05 | 4.5E-10 | 1.00 |
| AC_05331 | control 1210 | G12 | 3.6E+04 | 8.1E-06 | 2.3E-10 | 1.00 |

TABLE 13

Summary of kinetic profiles for soluble monomeric CEACAM5 (100-1.6 nM) interacting with captured BsAb in Octet. Association was measured for 100 sec and dissociation was measured for 100 sec.

| Bispecific antibody | BsAb IgG | BsAb Fab | $k_a$(1/Ms) | $k_d$(1/s) | $K_D$ (M) | $R^2$ |
|---|---|---|---|---|---|---|
| Multi34 | G12_mut | Fab1 | 2.2E+05 | <1.0E-07 | <1.0E-12 | 0.91 |
| Multi35 | G12_mut | Fab2 | 1.6E+05 | <1.0E-07 | <1.0E-12 | 0.93 |
| Multi42 | Fab3 | G12_mut | 4.7E+05 | 9.1E-04 | 2.0E-09 | 1.00 |
| Multi44 | Fab7 | G12_mut | 1.8E+05 | 2.3E-03 | 1.3E-08 | 0.98 |
| Multi46 | 1132 | Fab1 | 1.3E+05 | <1.0E-07 | <1.0E-12 | 0.94 |
| Multi47 | 1132 | Fab2 | 6.3E+02 | 1.1E-03 | 1.8E-06 | 0.82 |
| Multi48 | 1132 | Fab8 | 2.4E+04 | <1.0E-07 | <1.0E-12 | 0.83 |
| Multi49 | 1132 | Fab10 | 2.8E+04 | <1.0E-07 | <1.0E-12 | 0.76 |
| AC_05339 | 5097 | G12 | 2.4E+05 | 4.2E-04 | 1.8E-09 | 0.99 |

TABLE 14

Summary of kinetic profiles of BsAb (100-1.6 nM or 50-0.8 nM) interacting with captured CEACAM5-biotin in Octet. Association was measured for 100 sec and dissociation measured for 100 sec.

| Bispecific antibody | BsAb IgG | BsAb Fab | $k_a$(1/Ms) | $k_d$(1/s) | $K_D$ (M) | $R^2$ |
|---|---|---|---|---|---|---|
| Multi34 | G12_mut | Fab1 | 4.0E+03 | 1.1E-04 | 2.8E-08 | 0.98 |
| Multi35 | G12_mut | Fab2 | 2.8E+03 | 3.7E-04 | 1.3E-07 | 0.94 |
| Multi37 | G12_mut | Fab6 | 1.9E+03 | 2.6E-03 | 1.4E-06 | 0.93 |
| Multi41 | Fab2 | G12_mut | 4.7E+04 | <1.0E-07 | <1.0E-12 | 0.97 |
| Multi42 | Fab3 | G12_mut | 1.8E+03 | 1.5E-03 | 8.4E-07 | 0.97 |
| Multi44 | Fab7 | G12 mut | 1.5E+05 | <1.0E-07 | <1.0E-12 | 1.00 |
| Multi46 | 1132 | Fab1 | 6.7E+04 | 1.3E-04 | 1.9E-09 | 1.00 |

TABLE 15

Summary kinetic profile for soluble
human CEACAM5 (100-1.6 nM) or cynomolgus CEACAM5
(500-8 nM) interacting with captured BsAb in Octet.
Association was measured for 100 sec and dissociation for 300 sec.

| Bispecific Antibody | Antigen | $K_a$(1/Ms) | $K_d$ (1/s) | $K_D$ (M) | $R^2$ |
|---|---|---|---|---|---|
| AC_05339 | human CEACAM5 | 5.2E+05 | <1.0E−07 | <1.0E−12 | 0.99 |
| AC_05355 | human CEACAM5 | 5.1E+05 | 5.3E−04 | 1.0E−09 | 1.00 |
| AC_05355 | cyno CEACAM5 | 1.9E+05 | 3.8E−03 | 2.0E−08 | 1.00 |

Example 6—Binding of CD40-CEACAM5 Bispecific Antibodies to CEACAM5 Expressing Cells Aim and Background The aim of this study was to assess the binding of the CD40-CEA RUBY™ bispecific antibodies to CEACAM5 expressed on cells and evaluate potential cross-reactivity to CEACAM1. In this study both CEACAM5 transfected cells and human tumor cells with endogenous CEACAM5 expression were used.

Materials and Methods

The human CEACAM5 and CEACAM1 genes were cloned into pcDNA3.1, and the vector was subsequently stably transfected into CHO cells. The tumor cell line MKN45, expressing high levels of CEACAM5, LS174T expressing intermediate levels of CEACAM5, and HT29 and LOVO expressing low levels of CEACAM5 (Table 16), CHO-CEACAM5, CHO-CEACAM1 and to CHO wt cells were incubated with titrated concentrations of CD40-CEA bispecific antibodies. Binding of the antibodies was detected using fluorochrome-conjugated anti-human IgG and analyzed using flow cytometry.

Results and Conclusions

Figure 8A:
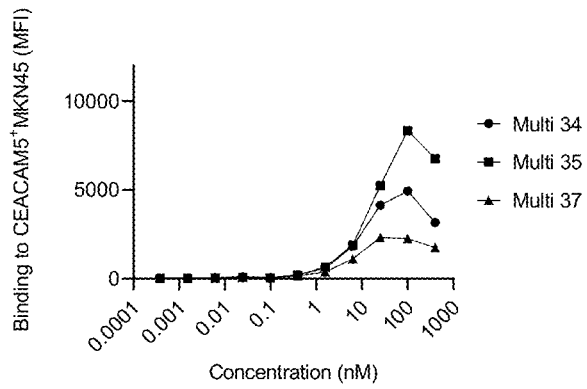
FIGS. 8A-8I. Binding of CD40-CEACAM5 bispecific antibodies to CEACAM5 expressing tumor cells. The tumor cell line MKN45, expressing high levels of CEACAM5 (FIGS. 8A-8C), LS174T expressing intermediate levels of CEACAM5 (FIGS. 8D-8F), and Lovo expressing low levels CEACAM5 (FIGS. 8G-8I). Binding of CD40-CEACAM5 bispecific antibodies was detected by flow cytometry using fluorochrome-conjugated anti-human IgG.
Figure 8B:
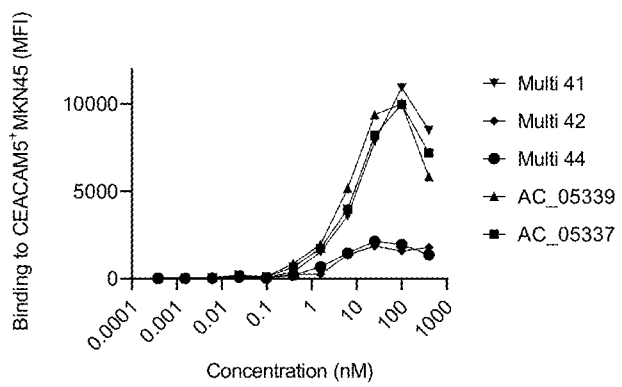
Figure 8C:
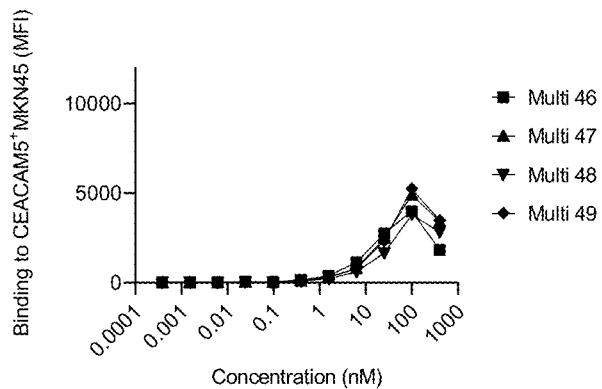
Figure 8D:
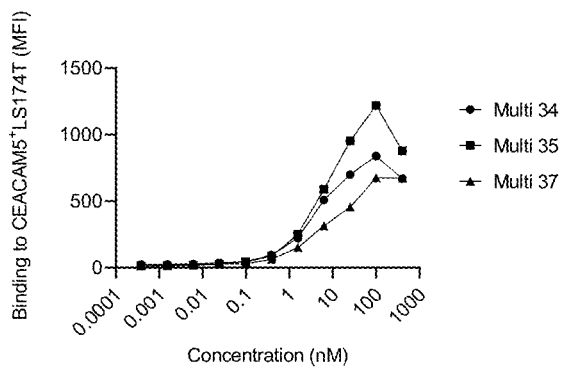
Figure 8E:
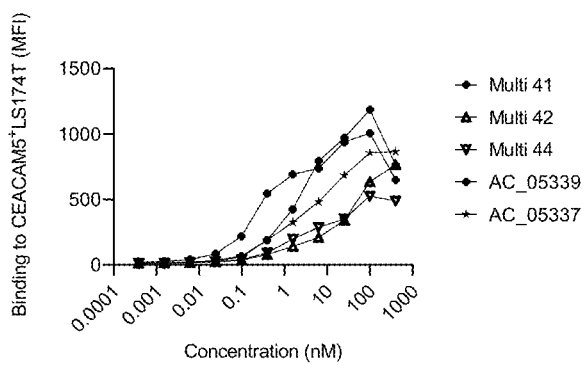
Figure 8F:
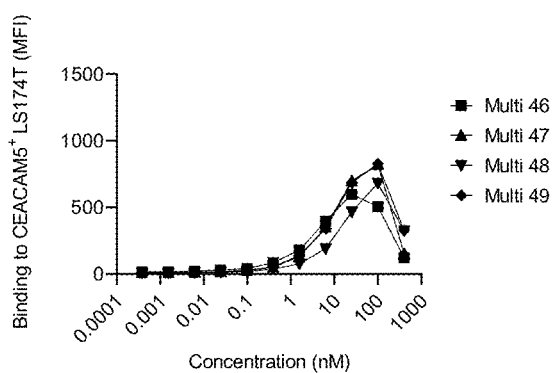
Figure 8G:
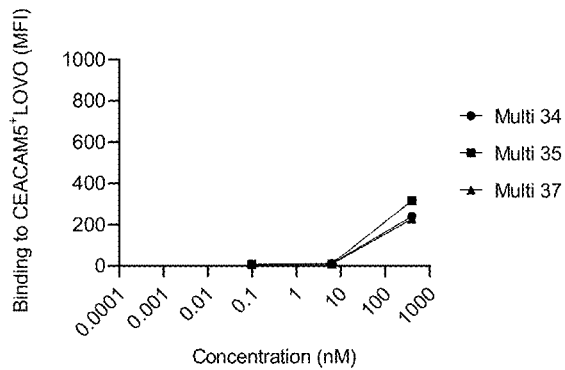
Figure 8H:
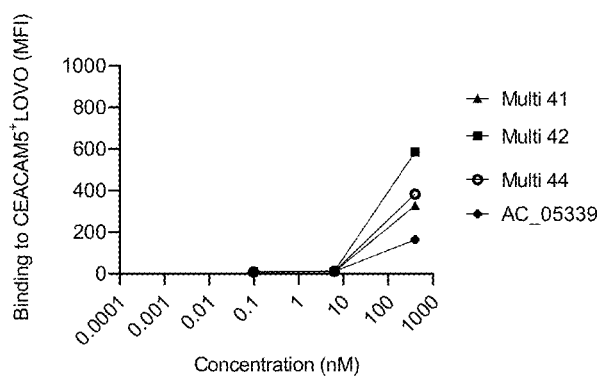
Figure 8I:
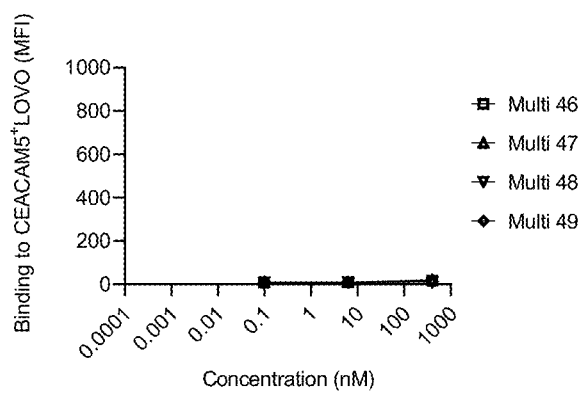
Figure 9A:
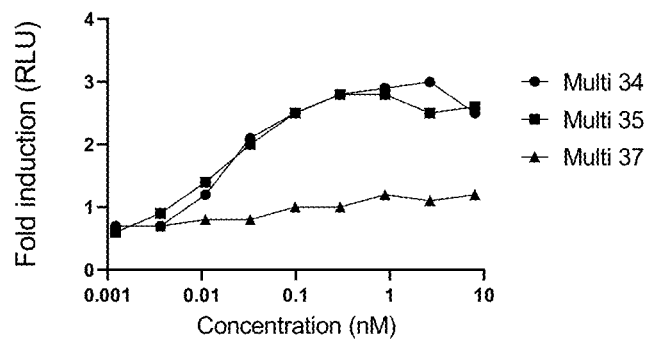
FIGS. 9A-9E. Effect of the CD40-CEACAM5 bispecific antibodies on CD40 reporter cells cultured with titrated antibodies in the presence or absence of CEACAM5 expressed on CHO cells. The response was calculated as fold induction to background.
Figure 9B:
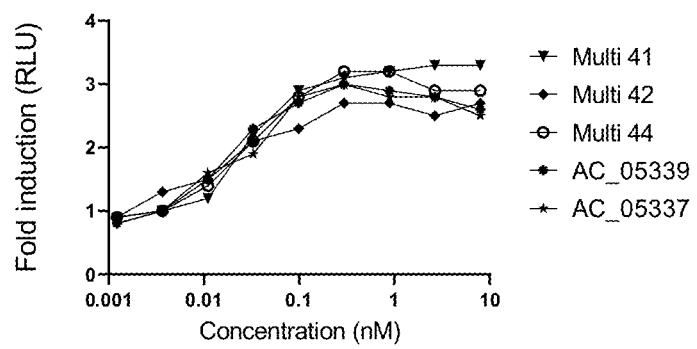
Figure 9C:
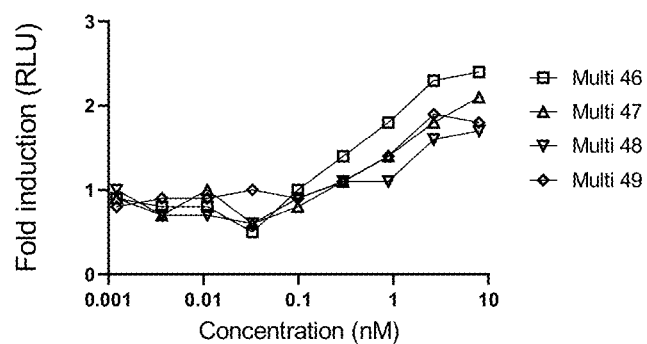
Figure 9D:
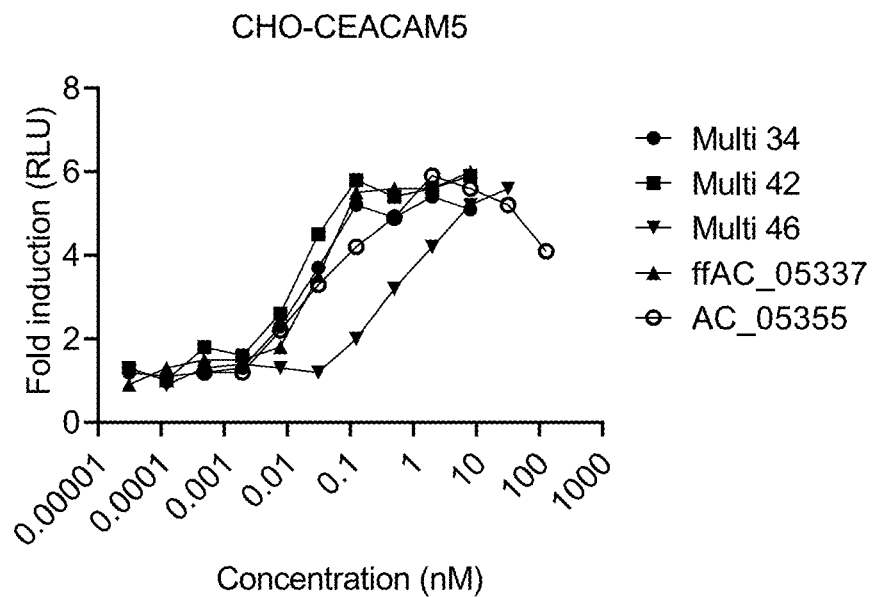
Figure 9E:
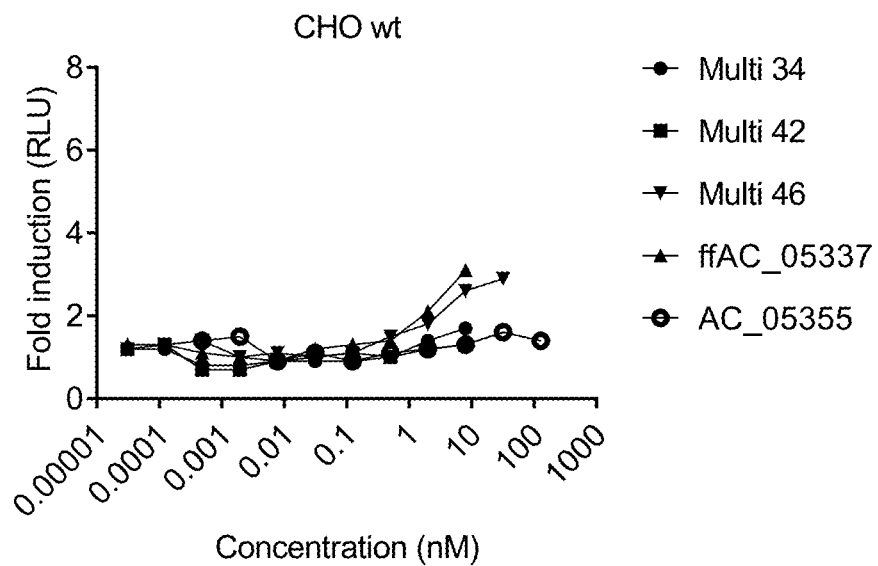
Figure 10A:
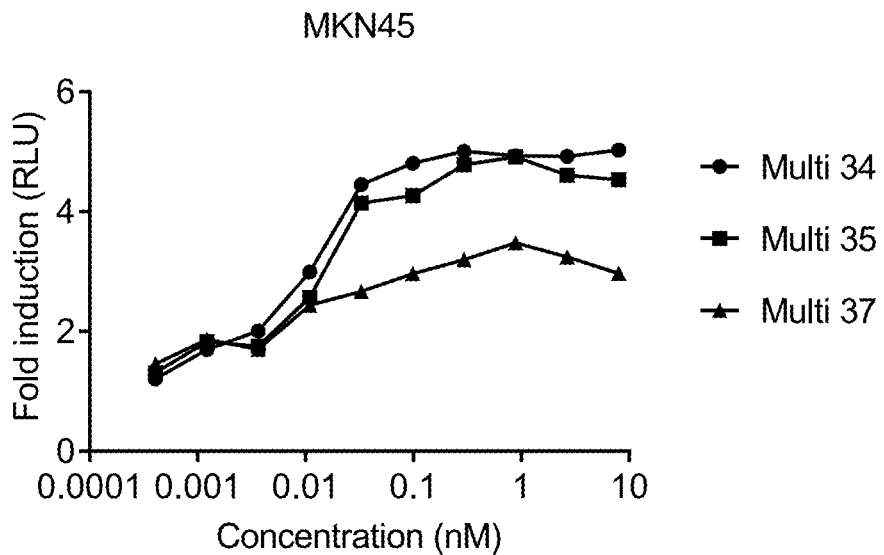
FIGS. 10A-10L. Effect of the CD40-CEACAM5 bispecific antibodies on CD40 reporter cells when co-cultured with tumor cells with different CEACAM5 receptor density. CD40-CEACAM5 containing CD40 clone G12 (FIGS. 10A-10D), CEACAM5-CD40 containing CD40 clone G12 (FIGS. 10E-10H) and CD40-CEACAM5 containing CD40 clone 1132 (FIGS. 10I-10L). The response was calculated as fold induction to background.
Figure 10B:
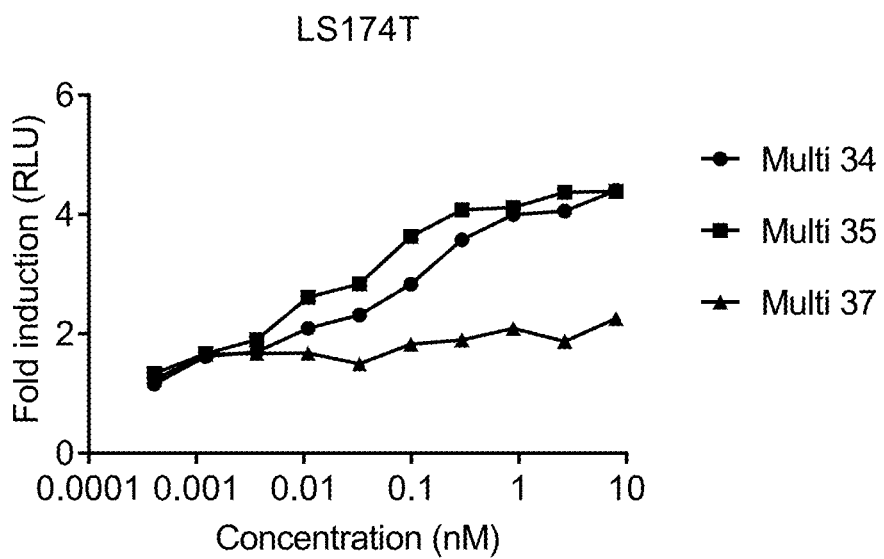
Figure 10C:
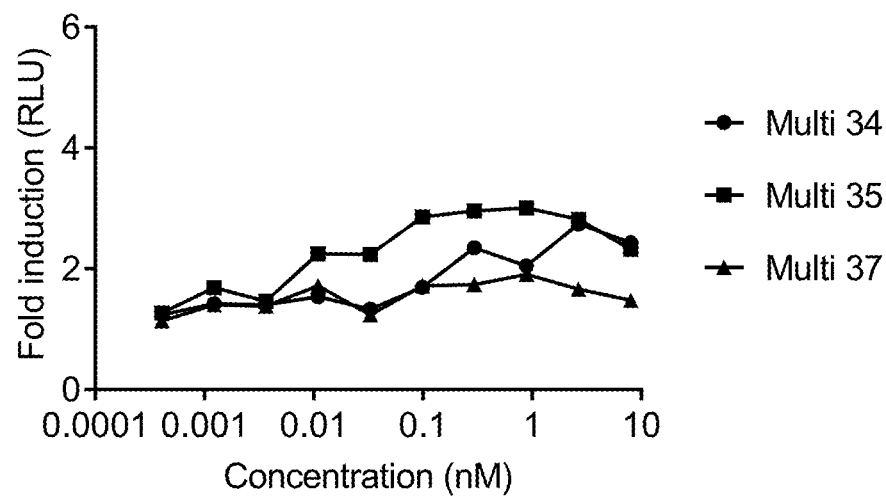
Figure 10D:
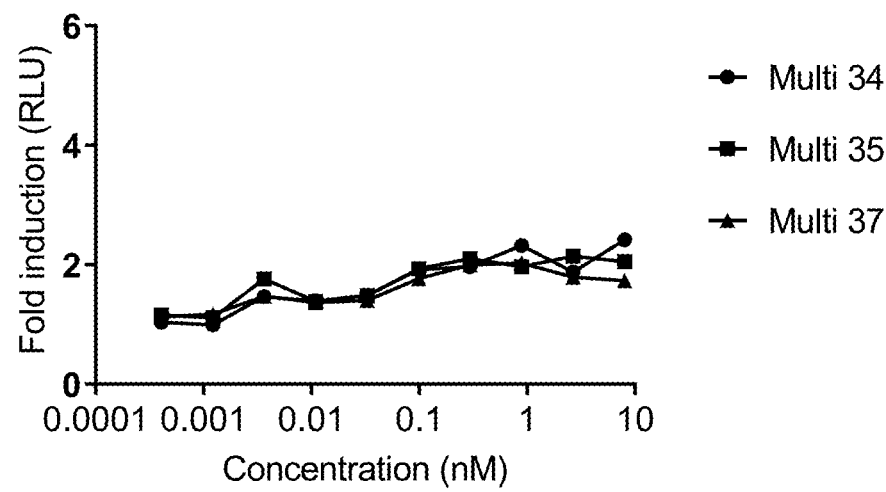
Figure 10E:
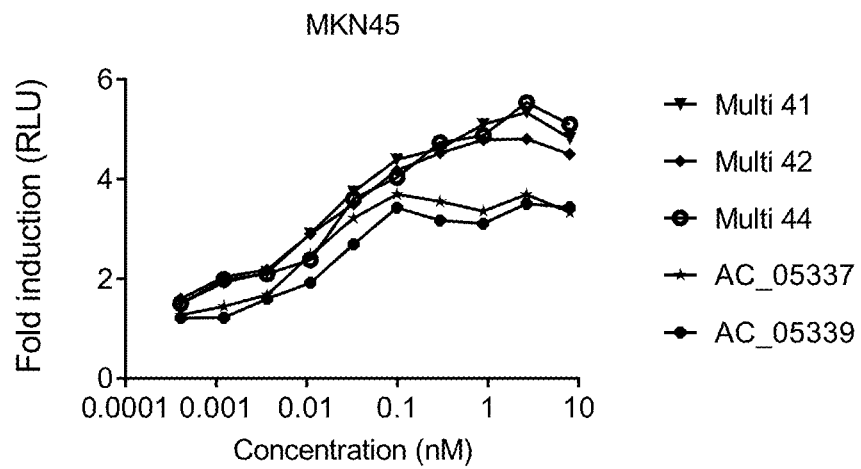
Figure 10F:
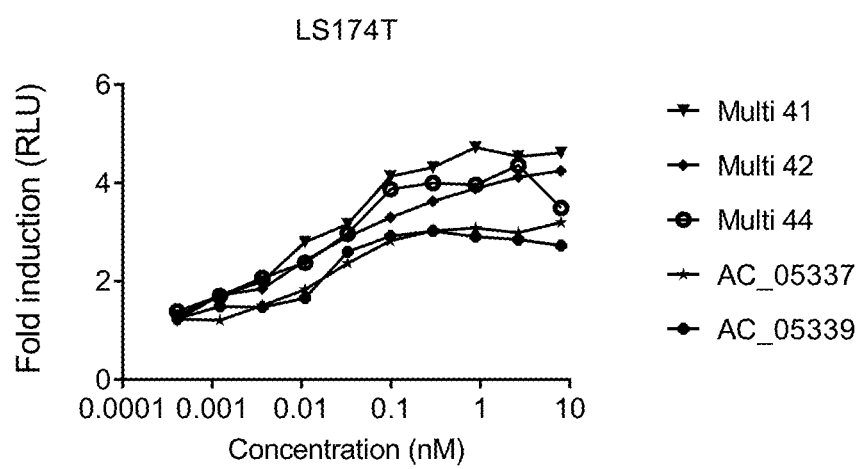
Figure 10G:
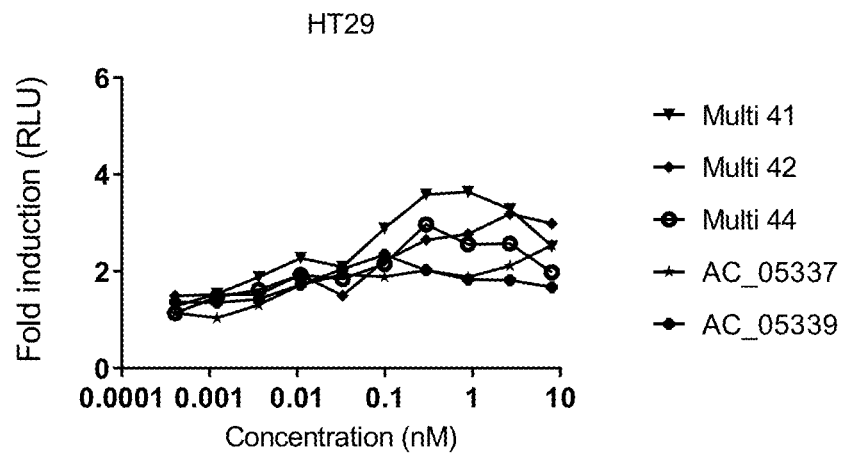
Figure 10H:
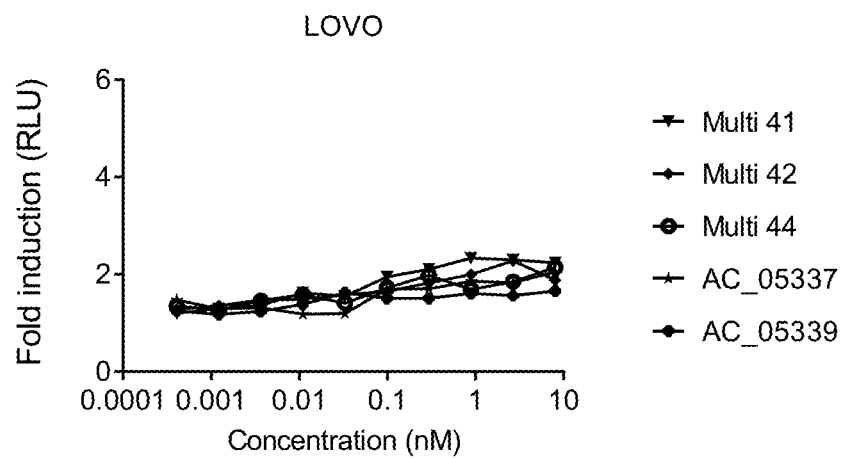
Figure 10I:
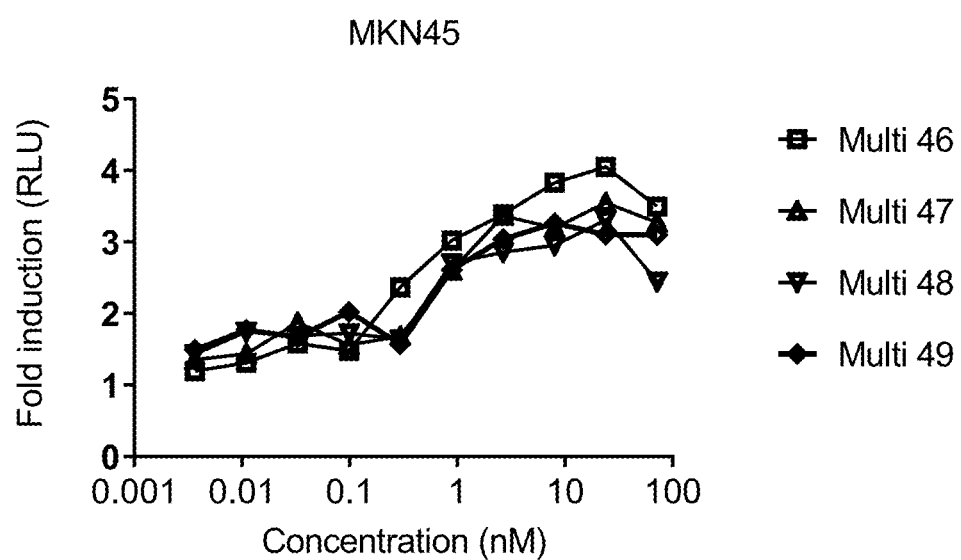
Figure 10J:
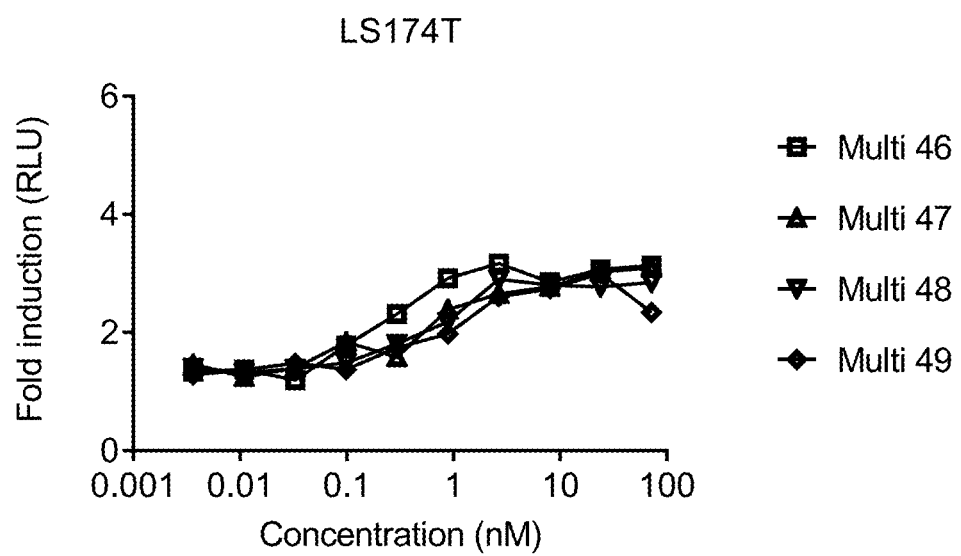
Figure 10K:
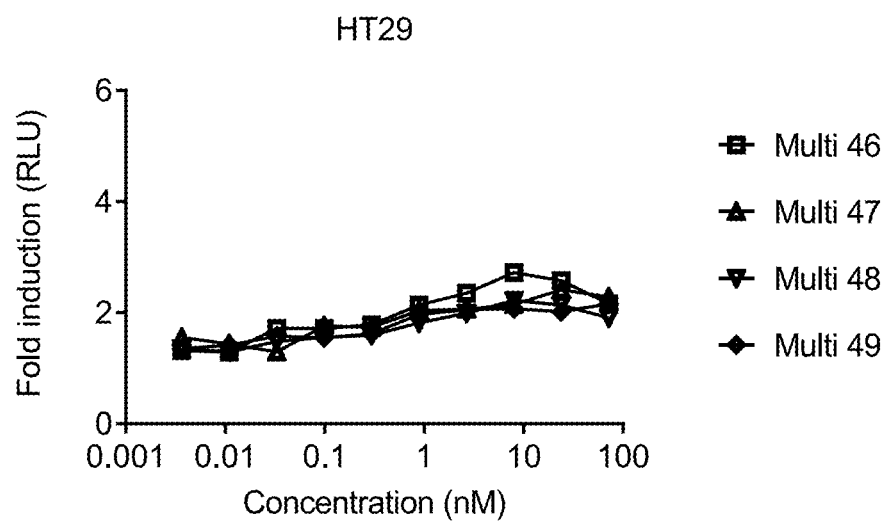
Figure 10L:
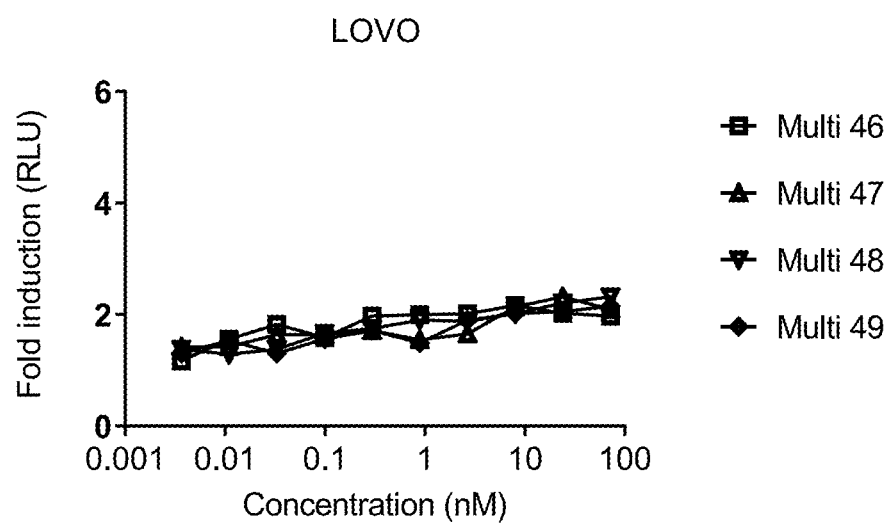
Figure 11A:
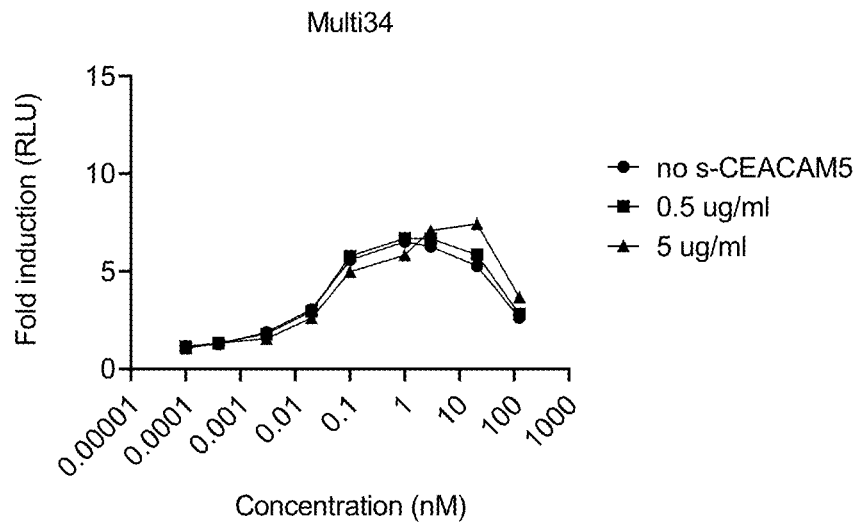
FIGS. 11A-11J. Effect of the CD40-CEACAM5 bispecific antibodies on CD40 reporter cells co-cultured with CEACAM5 expressing CHO cells and titrated antibodies in the presence or absence of soluble CEACAM5. The response was calculated as fold induction to background.
Figure 11B:
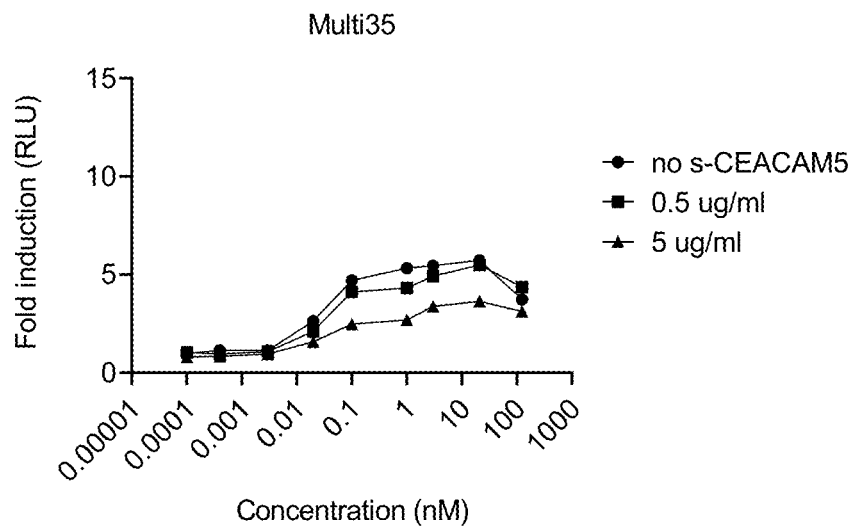
Figure 11C:
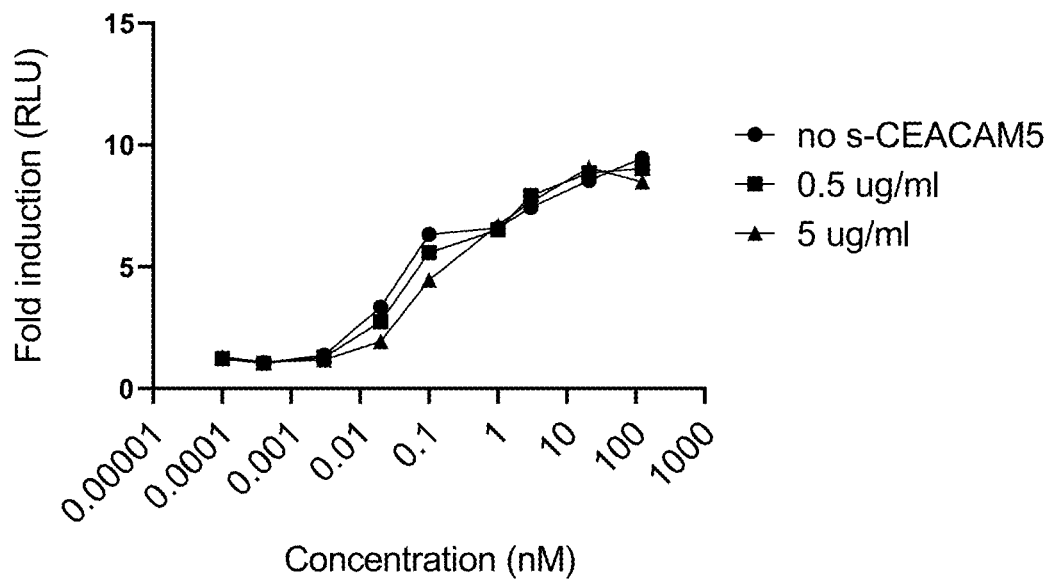
Figure 11D:
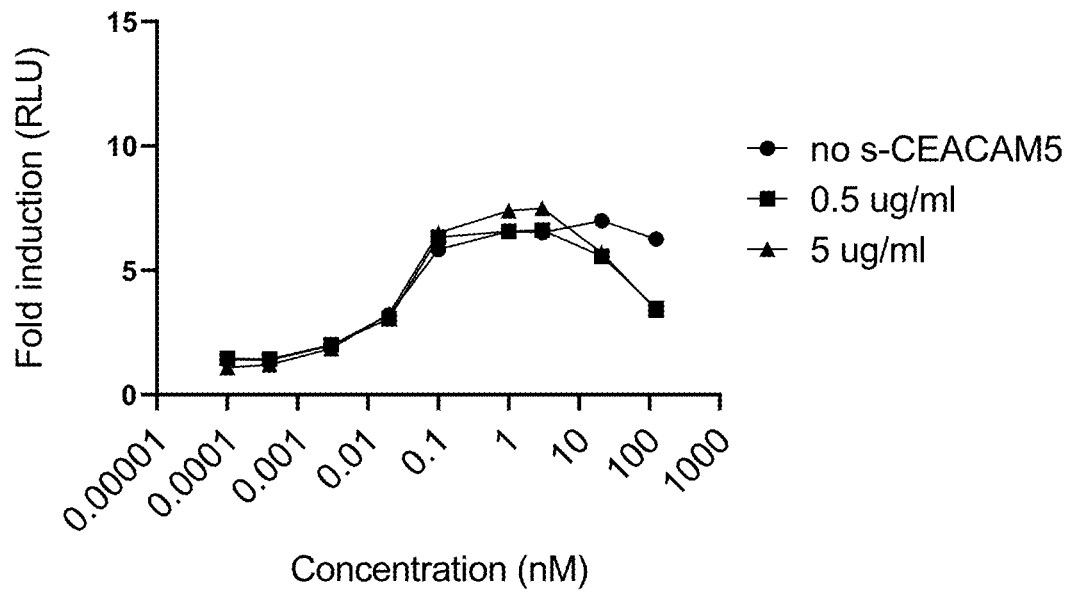
Figure 11E:
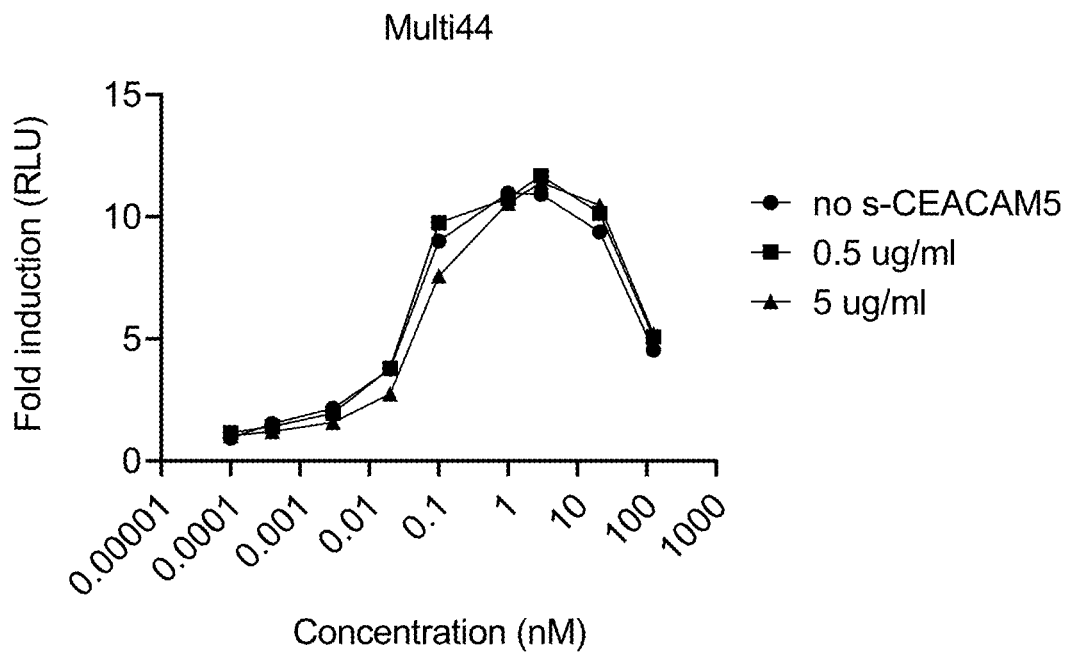
Figure 11F:
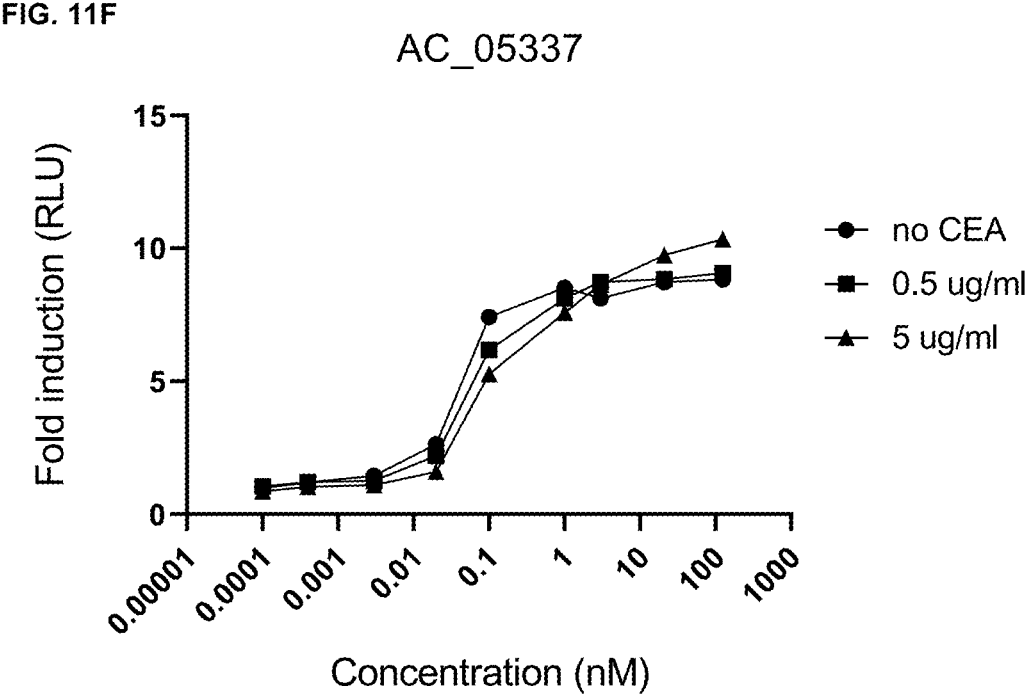
Figure 11G:
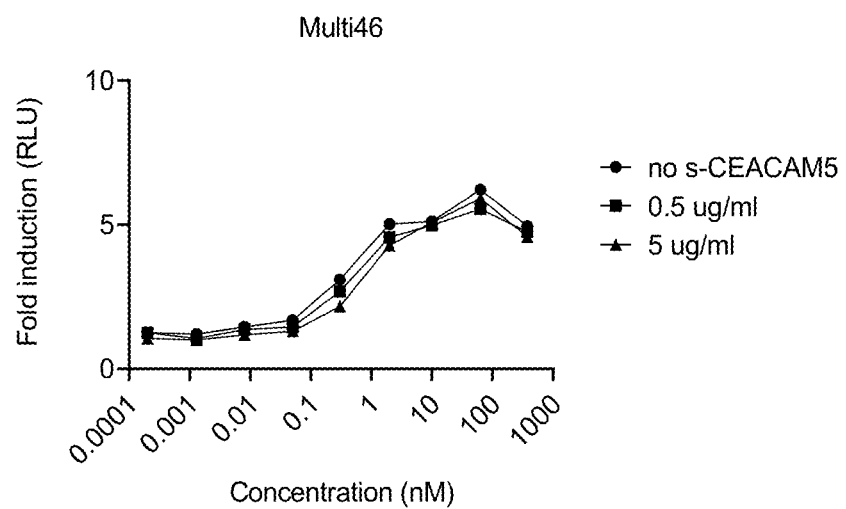
Figure 11H:
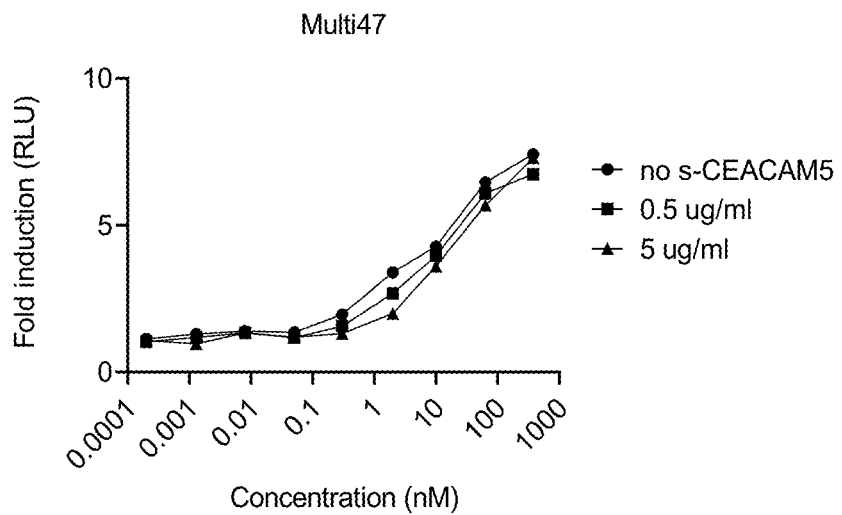
Figure 11I:
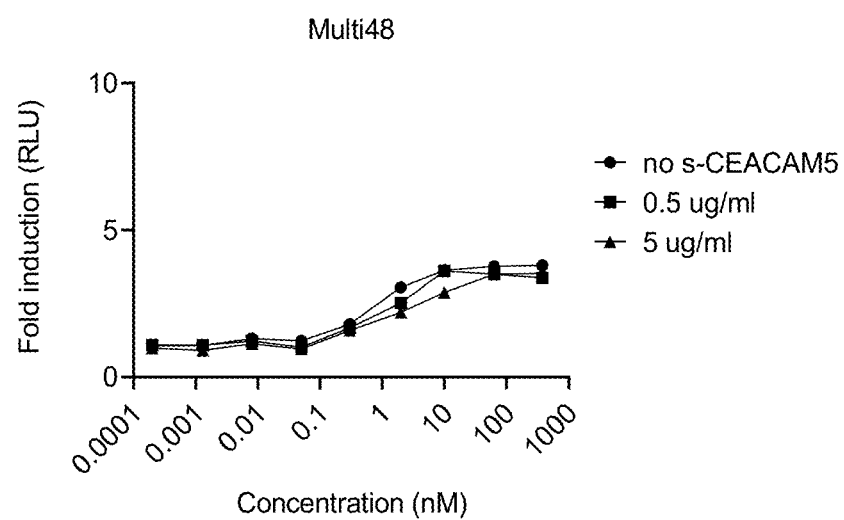
Figure 11J:
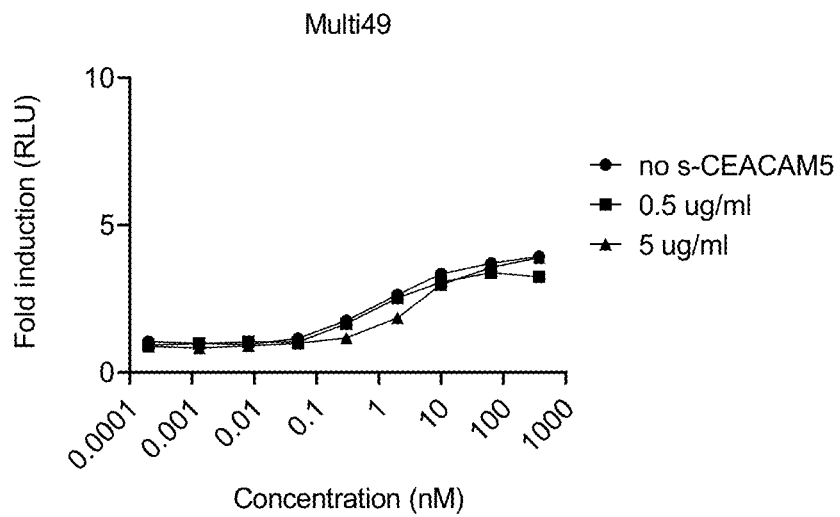

The data demonstrate that all tested CD40-CEACAM5 RUBYs bind to CEACAM5 expressed on CHO-CEACAM5 (FIG. 6A-FIG. 6E), and MKN45 (high expressing) (FIG. 8A-FIG. 8C) and LS174T (intermediate expressing) human tumor cells (FIG. 8D-FIG. 8F). Low or no binding was observed to the CEACAM5 low expressing tumor cells, the LOVO cells (FIG. 8G-FIG. 8I). In addition, a low cross-reactivity to CEACAM1 or stickiness to CHO wt cells was observed with some of the CD40-CEA bispecific antibodies at very high concentrations (FIG. 7). In conclusion, all the CD40-CEA RUBY™ bispecific antibodies bind to CEACAM5 and with low or no binding to CEACAM1.

TABLE 16

Summary of CEA expression levels on CEACAM5 transfected
CHO cells and CEA expressing human tumor cells.

| Tumor cell line and CEA transfected CHO cells | Receptors/cell |
|---|---|
| HT29 | 11 300 |
| LOVO | 5 500 |
| LS174T | 51 500 |
| MKN45 | 353 000 |
| CHO-CEACAM5 | 125 000 |

Example 7—Evaluation of the CD40 Agonistic Function Using the CD40 Reporter Assay Aim and Background The aim of this study was to assess the CD40 agonistic function of the CD40-CEACAM5 RUBY™ bispecific antibodies using the CD40 reporter assay in the presence of CEACAM5 expressing cells. CD40 crosslinking will be mediated by simultaneous binding of CD40, expressed on CD40 reporter cells, and CEACAM5 expressed on CHO cells or CEACAM5 expressing human tumor cells. In addition, since high levels of soluble CEACAM5 can be detected systemically in cancer patients, the agonistic function was also assessed in the presence of physiological relevant concentrations of soluble CEACAM5.

Materials and Methods

Agonistic function of the CD40-CEACAM5 RUBYs was evaluated using a CD40 reporter assay (Promega, CD40 Bioassay Kit CS JA2155). The assay was performed according to the manufacturer's protocol. In brief, CD40 reporter cells and titrating concentrations of CD40-CEACAM5 RUBYs were diluted in RPMI containing 10% FCS and added to the assay plates before the addition of CEACAM5 transfected CHO, CHO wt or CEA expressing human tumor cells. In addition, the assay was also performed in the presence of 0.5 or 5 ug/ml soluble CEA. The assay plates were incubated for 6 h at 37° C. until addition of Bio-Glo™ Luciferase Assay Detection solution and analyzed in the BMG ELISA plate reader.

Results and Conclusions

The results show that all tested CD40-CEA bispecific antibodies induce CD40 activation in the presence of CEA (FIG. 9), and the efficacy correlates to the CEA expression level as seen when the reporter cells were co-cultured with human tumor cells expressing different CEA levels (FIG. 10). The majority of the evaluated CD40-CEA bispecific antibodies were unaffected by the presence soluble CEA in the cultures, except Multi35. The potency of Multi35 was decreased in the presence of soluble CEA (FIG. 11).

Example 8—Assessment of Agonistic Function of CD40-CEACAM5 RUBYs in the B Cell Assay Aim and Background The aim of this study was to assess the effect of the CD40-CEACAM5 bispecific antibodies on B cell activation in vitro in the presence or absence of CEACAM5. CD40 crosslinking will be mediated by simultaneous binding of CD40, expressed on B cells, and CEACAM5 transfected CHO cells.

Materials and Methods

The agonistic effect of CD40-CEACAM5 bispecific antibodies was assessed in a B cell assay, based on primary human B cells. Briefly, B cells were isolated from human peripheral blood mononuclear cells by MACS according to the manufacturer's protocol (Miltenyi Biotec #130-091-151). Human CEACAM5 transfected CHO cells, cynomolgus CEACAM5 transfected CHO cells or CHO wt cells were UV irradiated and seeded in tissue culture treated 96 well flat bottom plates (Eppendorf). B cells were cocultured with the CHO cells in the presence of IL-4 (10 ng/ml, Gibco #PHC0045) and titrated concentrations of CD40-CEACAM5 bispecific. After 2 days, B cells were harvested and expression level of the activation marker CD86 was analyzed by FACS.

Results and Conclusions

Figure 12:
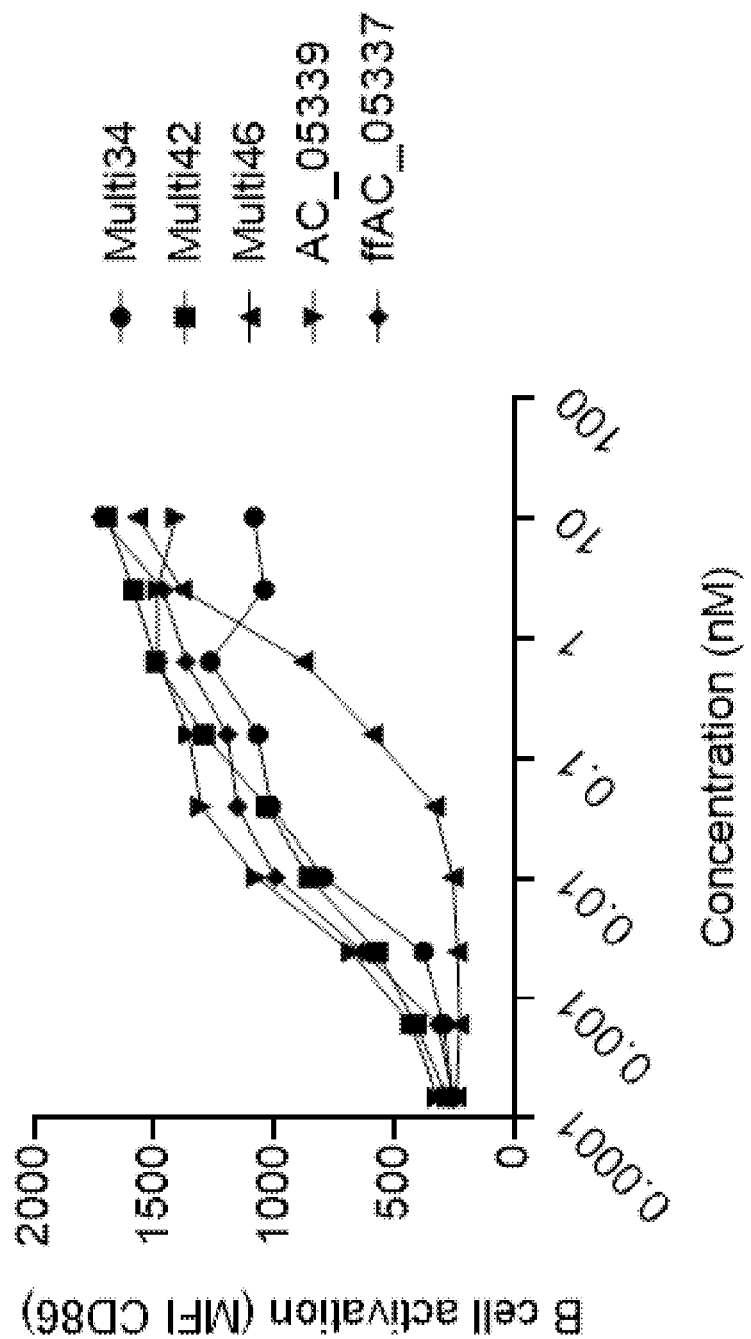
FIG. 12. Effect of the CD40-CEACAM5 bispecific antibodies on B cell activation. Primary human B cells were cultured with titrated antibodies in the presence or absence of CEACAM5 expressed on CHO cells. After 2 days, expression of CD86 on B cells was analyzed by FACS.
Figure 13:
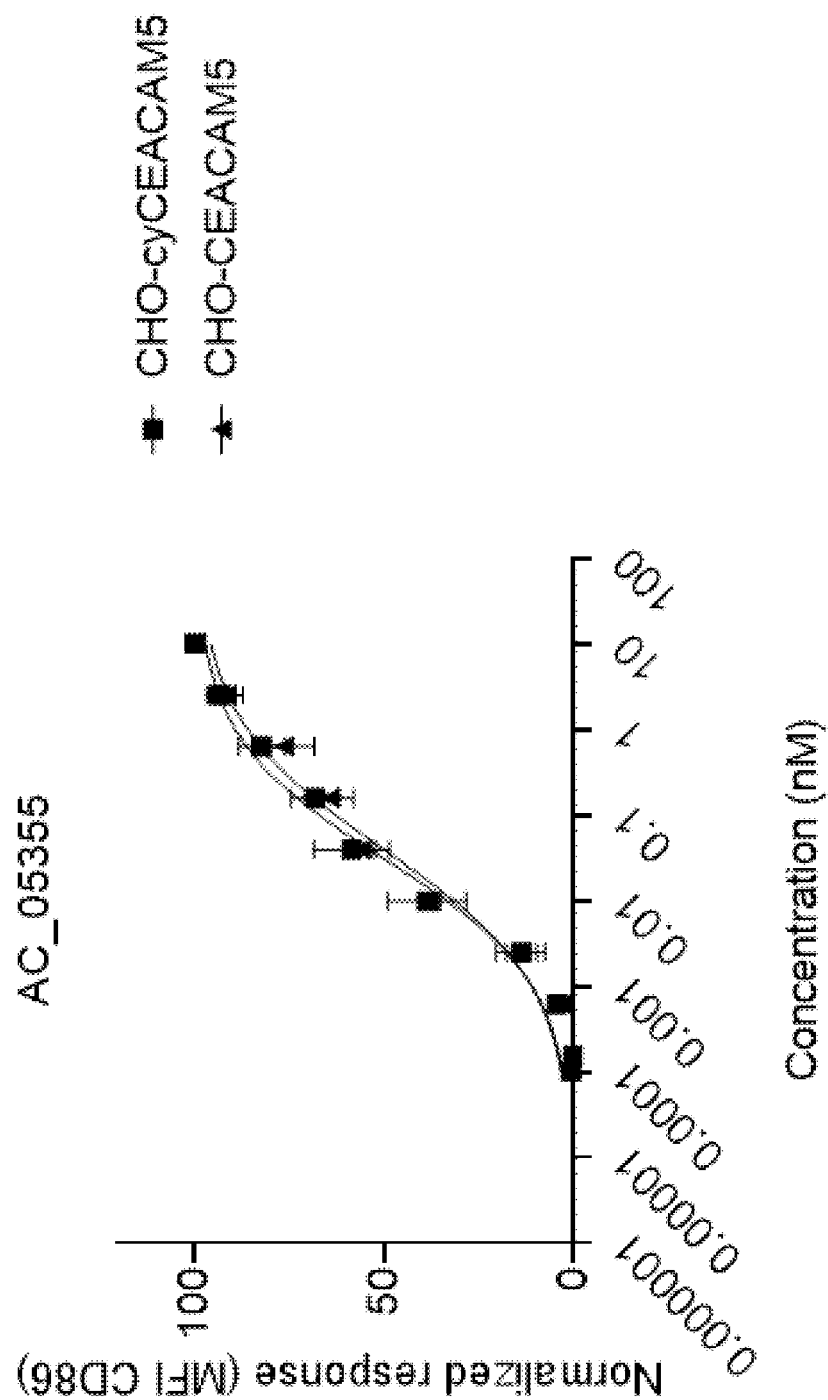
FIG. 13. Effect of the CD40-cCEACAM5 bispecific antibody AC_05355 on B cell activation in the presence of human or cynomolgus CEACAM5 transfected cells. Primary human B cells were cultured with titrated antibodies in the presence of human or cynomolgus CEACAM5 expressed on CHO cells. After 2 days, expression of CD86 on B cells was analyzed by FACS. The graph shows pooled results from 6 donors.

The data demonstrate that tested CD40-CEA RUBYs induce upregulation of CD86 on B cells in the presence of CEA (FIG. 12, FIG. 13).

Example 9—CD40 Sink Assay

Aim and Background

To mimic the CD40 sink effect from CD40 expressing cells in circulation, the functionality of the CD40×CEA bispecific antibodies were evaluated in presence of competing CD40 expressing cells.

Materials and Methods

CHO-cells transfected with human CEACAM5 were used for crosslinking. The CEACAM5 gene was cloned into pcDNA3.1. The vector was subsequently stably transfected into CHO cells. The expression of CEACAM5 was confirmed by staining with commercial antibody targeting CD66e (Invitrogen #PA5-16665). Wild type CHO (CHO-wt) cells were used as control cells for absence of crosslinking.

HEK Blue™ CD40L cells (Invivogen hkb #40) were stably transfected with CD40 and an NF-κB-inducible secreted embryonic alkaline phosphatase (SEAP) construct. Binding to CD40 led to activation of NFκB and production of SEAP, which was monitored using QUANTI-Blue™ substrate (Invivogen #rep-qbs).

A HTS Transwell 96 well permeable support system containing a Transwell receiver plate (Corning #3382) and a Transwell insert with 0.4 μm pore sized membrane (Corning #3391) was used.

HEK Blue CD40L cells (30 000 cells/well) and CHO-CEACAM5 cells or CHO-wt (5000 or 10 000 cells/well) were transferred to the receiver plate. The insert was placed onto the receiver plate. Buffer with increasing number of CD40 expressing sink cells, in this case Raji cells (0-100 000 cells/well), were transferred to the insert. Finally bispecific antibodies (bsAb), listed in Table 17, at one concentration or serially diluted ⅓ from 100 nM or 3 nM were added to the insert. Following 20-24 h incubation the SEAP content in the culture medium in the receiver plate was measured using the QUANTI Blue™ substrate.

Results and Conclusions

Figure 14:
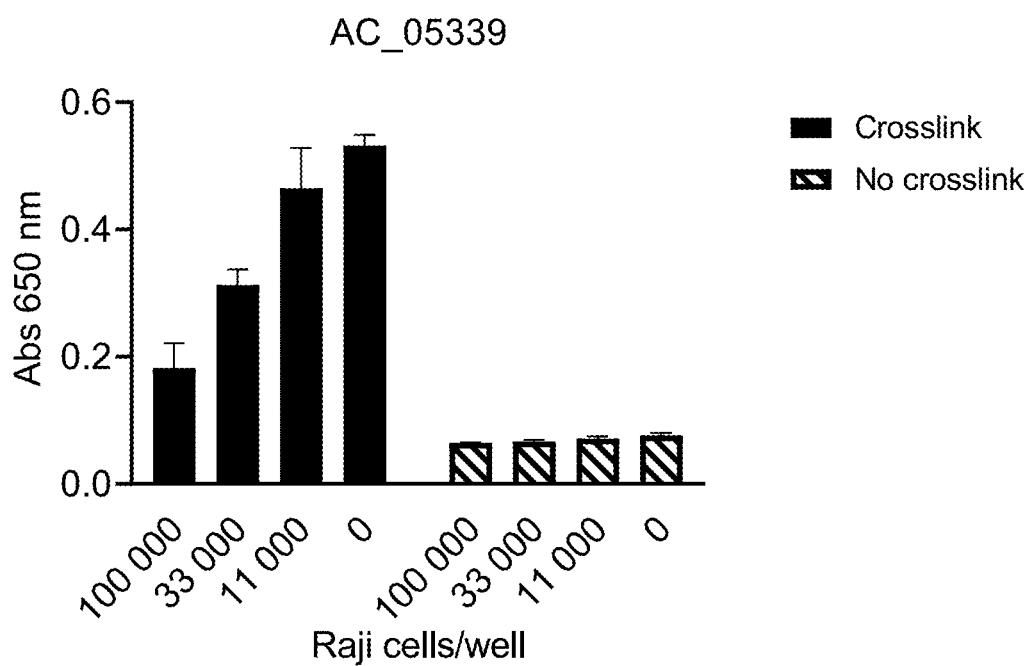
FIG. 14. BsAb AC_05339 (0.02 nM) w/o crosslinking to CHO-CEACAM5 or CHO-wt cells, activating HEK Blue CD40L™ reporter cells in presence of Raji cells after 20h incubation in a Transwell system. Activation monitored as SEAP release into culture medium, measured with QuantiBlue™. Mean+SD of triplicate.
Figure 15:
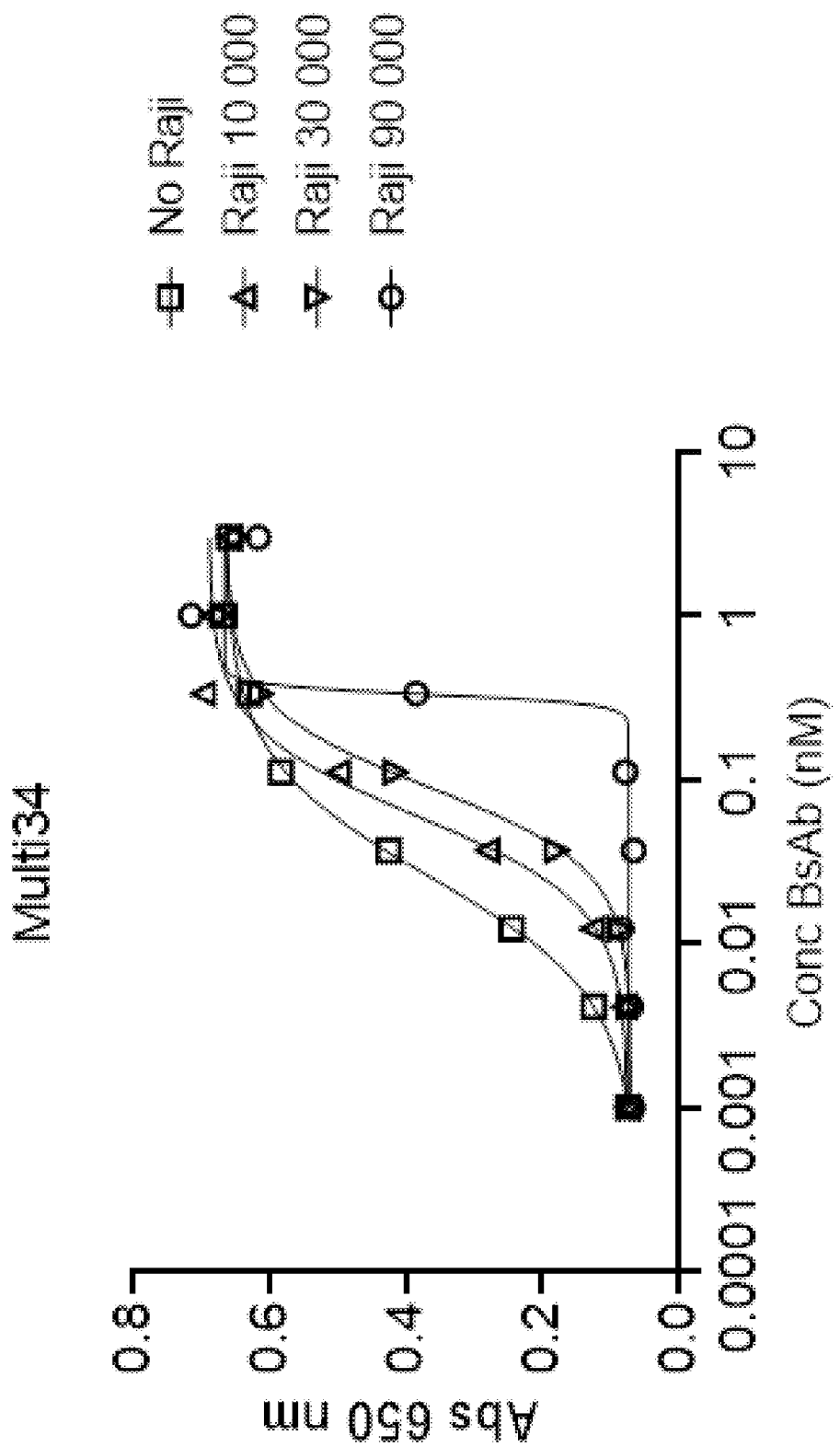
FIG. 15. BsAb Multi34 (3-0.004 nM, single sample) crosslinked to CHO-CEACAM5 cells activating HEK Blue CD40L™ reporter cells w/o of presence of Raji sink cells in a Transwell system. Activation monitored as release of SEAP into culture media following 20 h culture, measured with QuantiBlue™.
Figure 16:
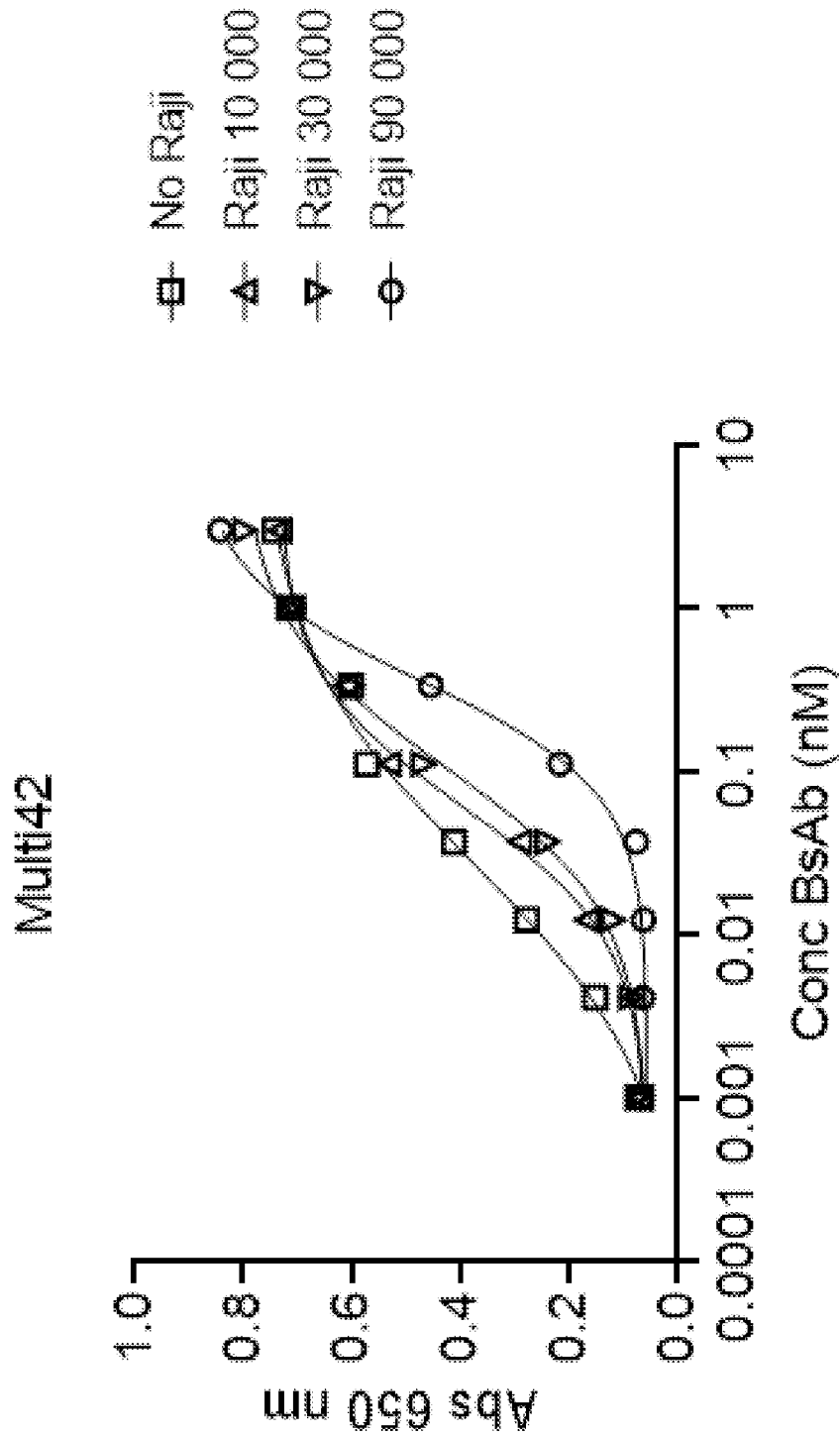
FIG. 16. BsAb Multi42 (3-0.004 nM, single sample) crosslinked to CHO-CEACAM5 cells activating HEK Blue CD40L™ reporter cells w/o of presence of Raji sink cells in a Transwell system. Activation monitored as release of SEAP into culture media following 20 h culture, measured with QuantiBlue™.
Figure 17:
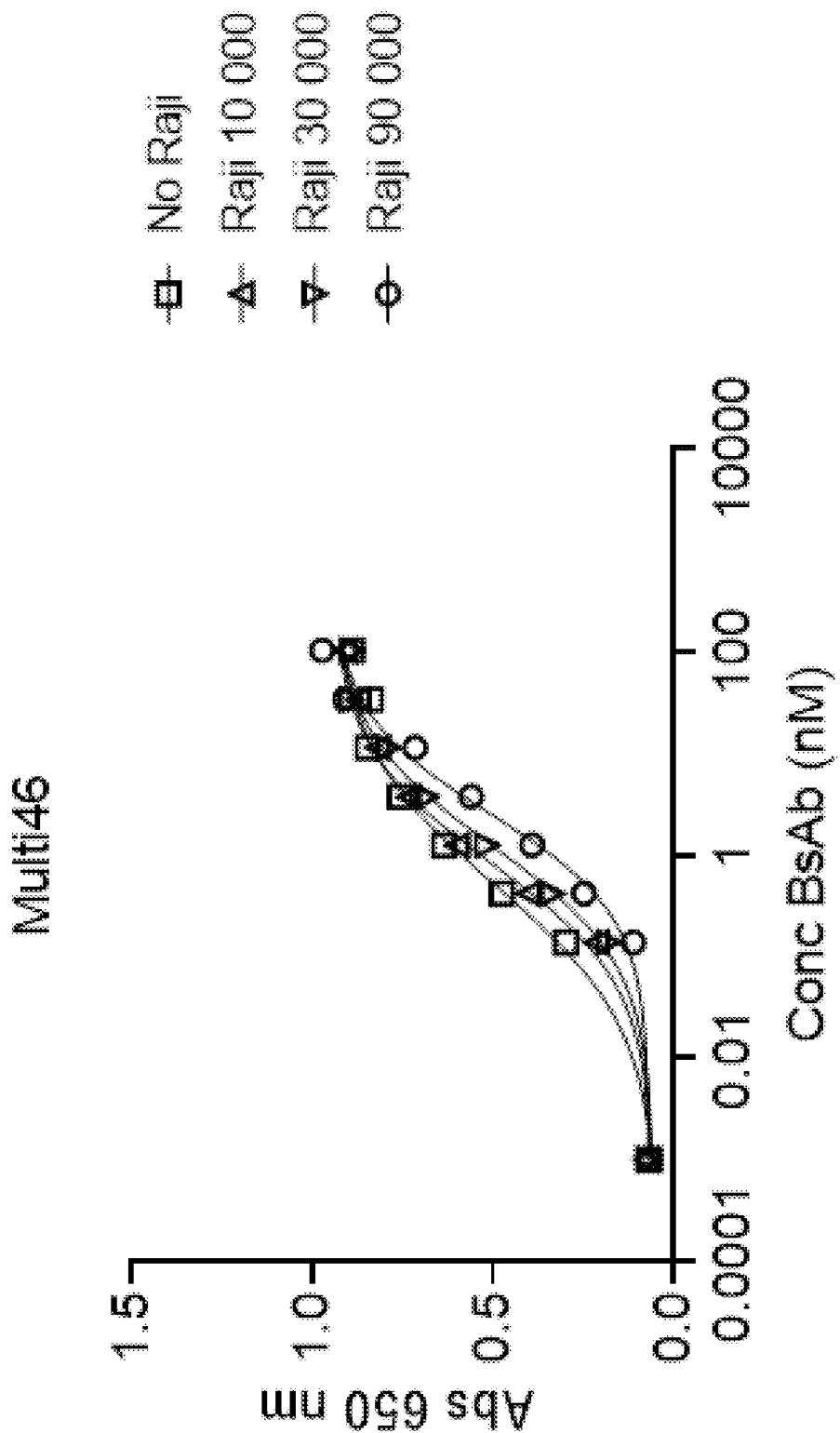
FIG. 17. BsAb Multi46 (100-0.1 nM, single sample) crosslinked to CHO-CEACAM5 cells activating HEK Blue CD40L™ reporter cells w/o of presence of Raji sink cells in a Transwell system. Activation monitored as release of SEAP into culture media following 20 h culture, measured with QuantiBlue™.

As shown in FIG. 14 a crosslinking dependent activation of HEK Blue CD40L cells was received for AC_05339. The activation was inhibited by addition of increasing number of Raji sink cells as seen in FIG. 14, FIG. 15, FIG. 16 and FIG. 17 The inhibition of activation became greater with increasing amount of CD40 sink cells present. A summary of EC50 is shown in Table 17. A 2-fold to 13-fold increase in EC50 was measured when including 90 000 Raji cells. Similar effect was received on antiCD40 G12 in IgG and Fab position of RUBY™ bsAb. A possibly lower effect on antiCD40 1132 was observed. In conclusion, all BsAb's tested were functional in presence of CD40 expressing sink cells, but with a decreased potency.

TABLE 17

Summary of EC50 (nM) measured for BsAb (3-0.004 nM or 100-0.1 nM) as single samples crosslinked to CHO-CEACAM5 cells activating HEK Blue CD40L ™ reporter cells w/o presence of Raji sink cells, monitored as release of SEAP into culture media, measured with QuantiBlue ™.

| BsAb | RUBY™ position | | EC50 (nM) Number of Raji sink cells/well | | | |
|---|---|---|---|---|---|---|
| | IgG | Fab | 0 | 10 000 | 30 000 | 90 000 |
| ffAC_05337 | 5090 | G12 | 0.04 | 0.08 | 0.11 | 0.41 |
| AC_05339 | 5097 | G12 | 0.03 | 0.05 | 0.08 | 0.23 |
| Multi34 | G12 | Fab1 | 0.03 | 0.06 | 0.09 | 0.33 |
| Multi35 | G12 | Fab2 | 0.06 | 0.09 | 0.14 | 0.34 |
| Multi41 | Fab2 | G12 | 0.03 | 0.06 | 0.13 | 0.36 |
| Multi42 | Fab3 | G12 | 0.04 | 0.06 | 0.11 | 0.36 |
| Multi44 | Fab7 | G12 | 0.02 | 0.05 | 0.08 | 0.16 |
| Multi46 | 1132 | Fab1 | 0.5 | 0.81 | 1.2 | 2.5 |
| Multi47 | 1132 | Fab2 | 4.4 | 5.7 | 7.2 | 10.3 |

Example 10—Colocalization of CEACAM5+ Tumor Debris and Raji Cells Induced by CD40-CEA RUBY Aim and Background The aim of this study was to assess the colocalization of CEACAM5 expressing tumor cell debris and CD40 expressing Raji cells induced by CD40-CEA RUBY.

Materials and Methods

A tumor cell line expressing CEACAM5 was stained with the fluorescent membrane dye PKH26 (Sigma-Aldrich) followed by heat shock at 45° C. for 10 min to induce cell death. Heat-shocked tumor cells were incubated at 37° C. overnight, spun down and supernatant containing tumor cell debris was collected.

Raji cells were labelled with the nuclear stain Hoechst 33342 (0.045 ug/ml, Thermo Fisher) and seeded in 96-well flat-bottom plates (Costar). Tumor cell debris and CD40-CEACAM5 (AC_05339) RUBY or CD40 (1132.m2) control mAb were added, and cells were imaged using Cytation5 (BioTek) every two hours. Gen5 software was used to analyze the number of colocalized tumor debris and Raji cells.

Results and Conclusions

Figure 18:
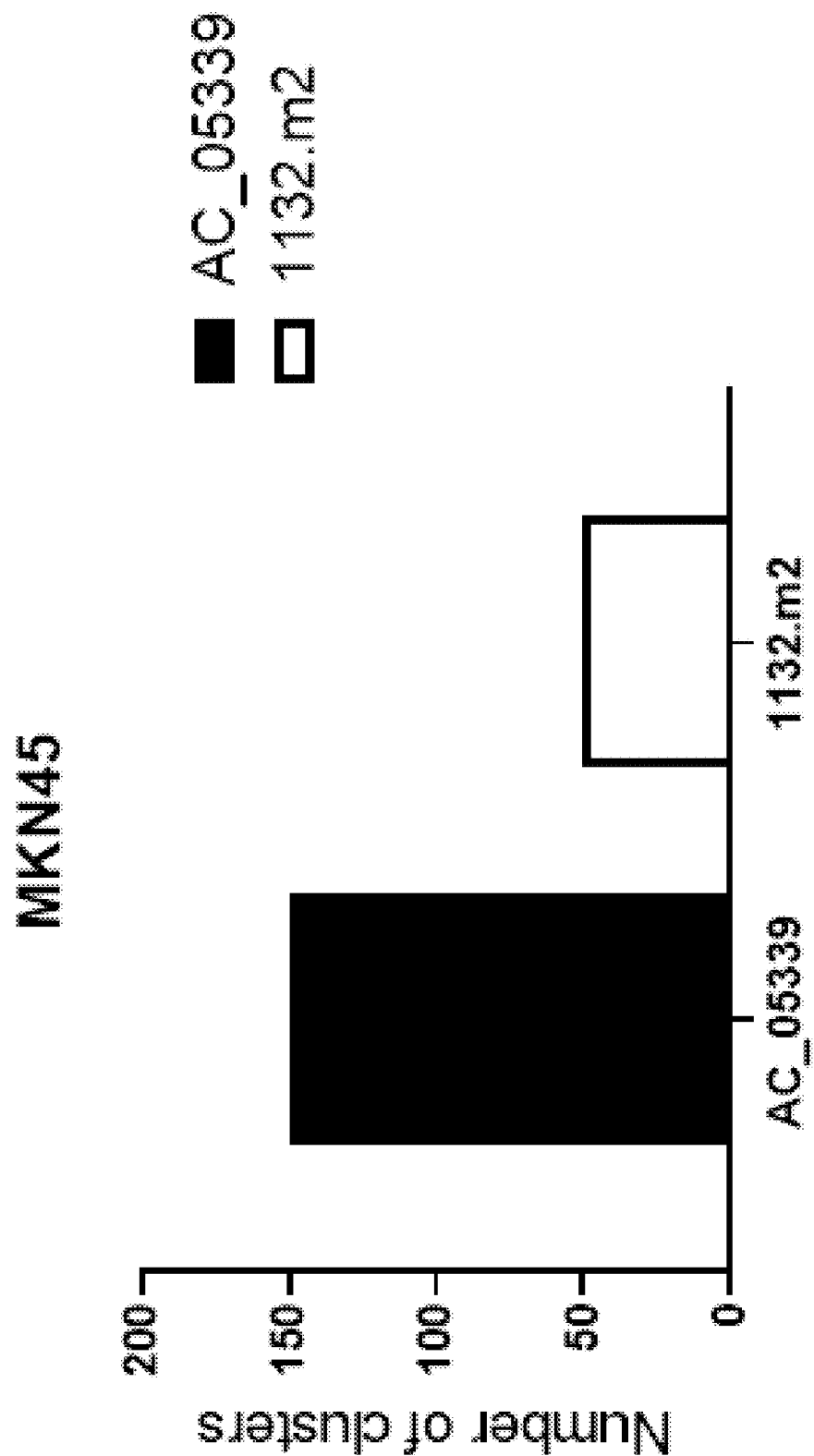
FIG. 18. Colocalization of tumor debris and Raji cells. Raji cells were incubated with CEACAM5 expressing MKN45 tumor debris and AC_05339 or the control antibody 1132 with a silenced Fc, more specifically of the IgG1 isotype and carrying the L234A and L235A mutations (the antibody is herein refer to 1132.m2). Images were captured with a Cytation5 live imaging system and the number of tumor debris colocalized with Raji cells after 4 h was analyzed using Gen5 software.

The results show increased colocalization of CEA expressing tumor cell debris and CD40 expressing Raji cells induced by the CD40-CEA RUBY compared to the CD40 monoclonal antibody (FIG. 18).

Example 11: Anti-Tumor Effect and Immunological Memory Induction of CD40-CEACAM5 Bispecific Antibodies Background and Aim AC_05337 and AC_05339 are CD40-CEA bispecific antibodies in RUBY™ format which have been LALA-mutated to silence Fcg receptor binding.

The aim of this study was to evaluate the anti-tumor effect of AC_05337 and AC_05339 in human CD40 transgenic (hCD40tg) mice inoculated with murine MC38 tumors transfected with human CEA (MC38-CEACAM5), and to assess immunological memory formation in mice cured from the tumors by treatment with CD40-CEA bsAbs.

Materials and Methods

Female hCD40tg mice of 10 weeks of age were inoculated with $1 \times 10^6$ MC38-CEACAM5 cells subcutaneously (s.c.) in the right flank. On days 7, 10, and 13 after inoculation, the mice were administered intraperitoneally (i.p.) with 100 μg of wildtype CD40 monospecific antibody, G12, or 167 μg of the CD40-CEA bsAbs AC_05337 and AC_05339. A group of vehicle-treated mice was also included. The tumors were frequently measured with a caliper in width (w), length (l) and height (h) and the tumor volume was calculated using the formula: $(w/2 \times l/2 \times h/2 \times n \times (4/3))$. Naïve hCD40tg control mice at 10 weeks of age and mice cured from the MC38-CEACAM5 tumors by treatment with AC_05339 (complete responders) were inoculated s.c. in the right flank with $1 \times 10^6$ MC38-wt cells. The tumors were frequently measured with a caliper in width (w), length (l) and height (h) and the tumor volume was calculated using the formula: $(w/2 \times l/2 \times h/2 \times n \times (4/3))$.

Results and Conclusions

Figure 19A:
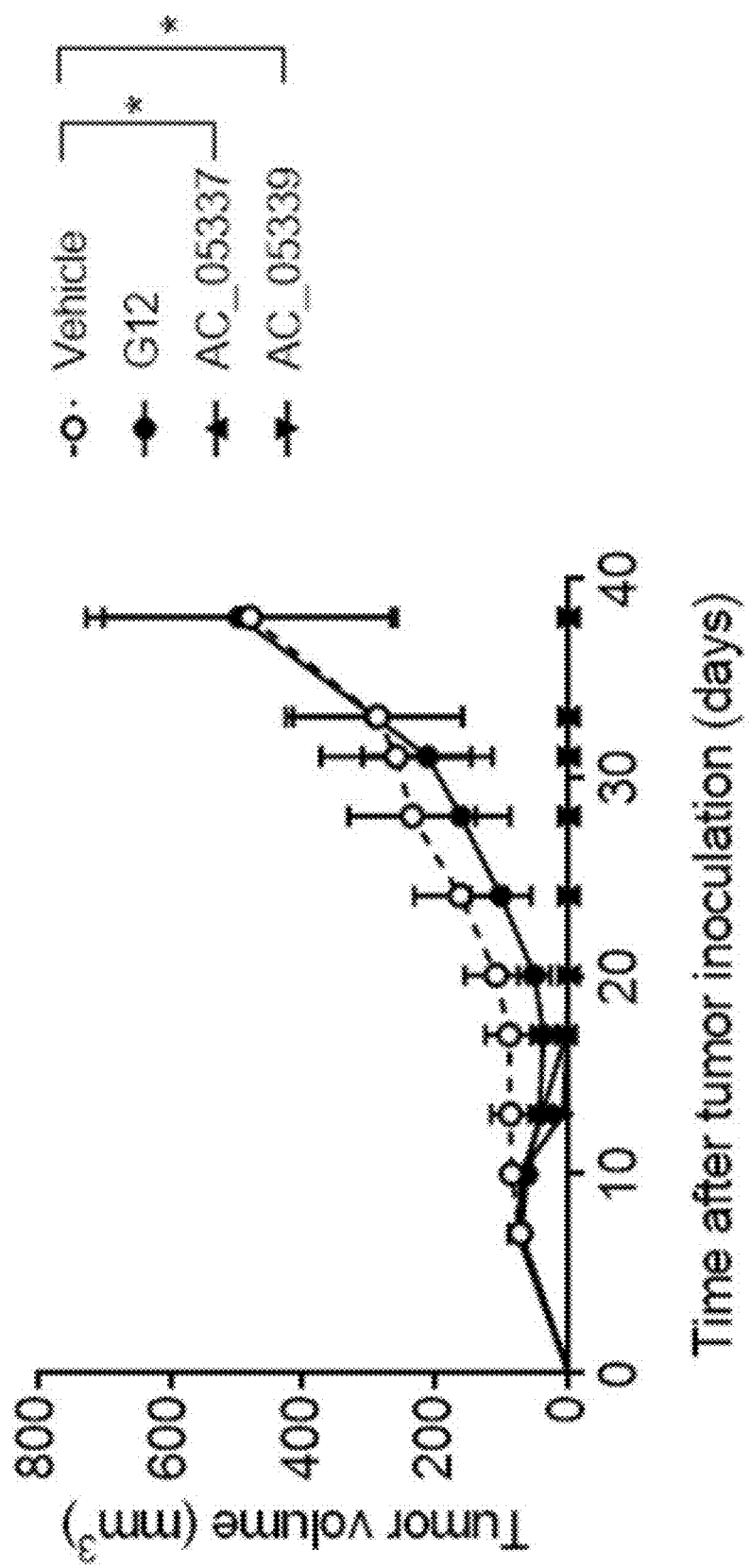
FIGS. 19A-19B. MC38-CEACAM5 tumor growth and MC38-wt rechallenge. hCD40tg mice inoculated with MC38-CEACAM5 tumors were dosed with the indicated treatments on days 7, 10, and 13 post-inoculations. Tumors were frequently measured until the first mouse in any of the treatment groups reached a tumor volume above the ethical limit. Statistical analysis of tumor volumes on day 38 was performed using a Mann-Whitney test (n=10, *p<0.05). Naïve control hCD40tg mice or mice cured from MC38-CEACAM5 tumors by treatment with a CD40-CEACAM5 bsAb (complete responders) were inoculated with MC38-wt tumors (rechallenged). Tumors were frequently measured until the first mouse in any of the treatment groups reached a tumor volume above the ethical limit.
Figure 19B:
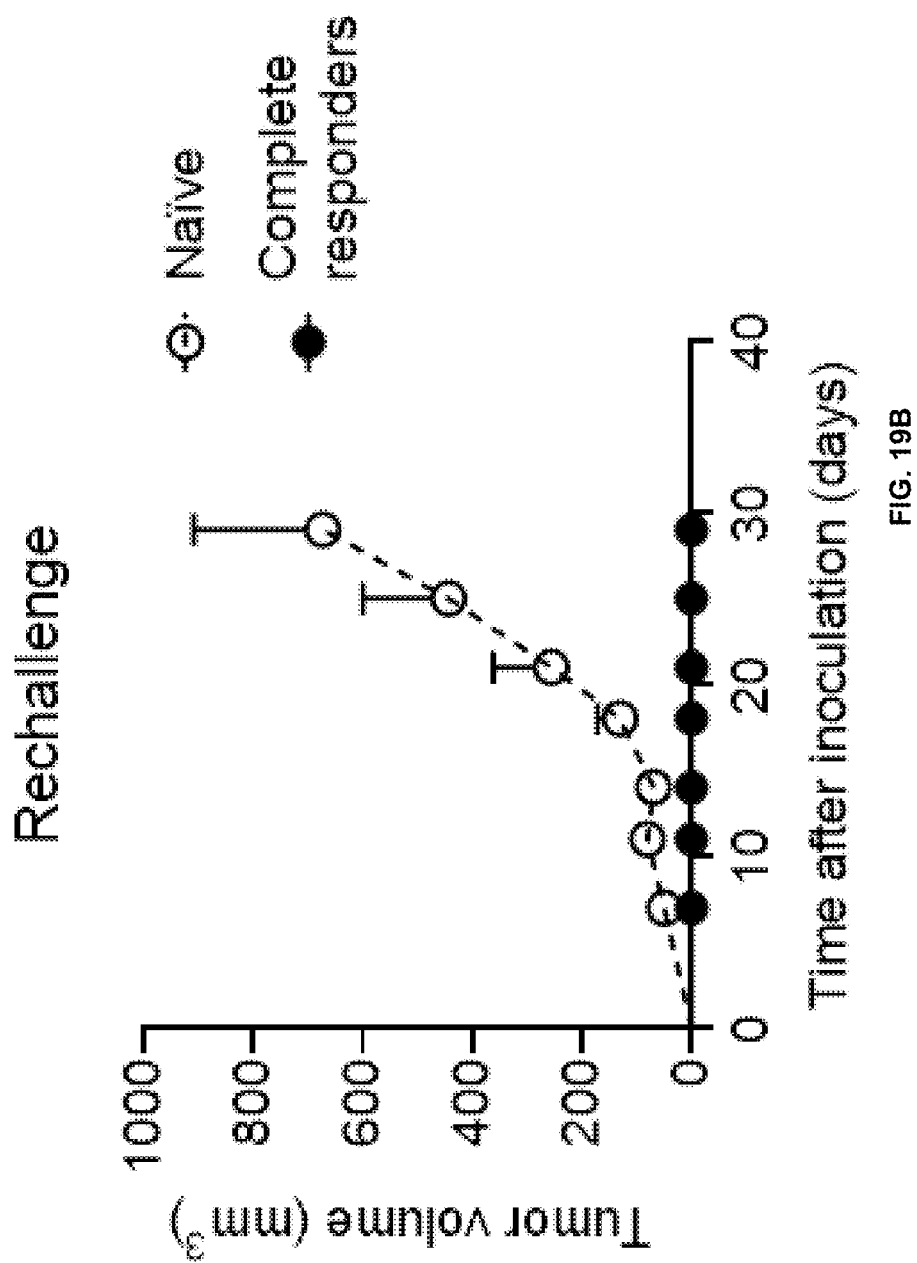

The data demonstrate that treatment with the CD40-CEACAM5 bsAbs AC_05337 and AC_05339, but not the CD40 mAb G12, significantly reduces the MC38-CEA tumor volume compared to vehicle-treated mice (FIG. 19). MC38-wt cells display tumor formation and growth in naïve mice, but not in complete responder mice. This suggests that the rechallenged mice have developed immunological memory against the MC38 tumor following treatment with the CD40-CEACAM5 bsAb AC_05339, and that this immunological memory is not restricted to CEACAM5 (FIG. 19).

Example 12—a 2 Week Toxicity Study of AC_05355, a CD40×CEACAM5 Targeting RUBY™ bsAb, in Cynomolgus Monkeys Background and Aim To facilitate toxicity studies in cynomolgus monkeys a RUBY™ bsAb (AC_05355), cross-reactive between human and cynomolgus variants of CD40 and CEACAM5, was generated. AC_05355 carries mutations L234A, L235A in its Fc, rendering the bsAbs silenced in terms of Fcγ receptor binding and thus dependent on CEACAM5 engagement to stimulate DC40 mediated activation. After confirmation of in vitro and in vivo functionality, the potential toxicity of this bsAb targeting CD40 and CEACAM5, when given via once weekly intravenous infusion for 2 weeks to cynomolgus monkeys, was evaluated.

Material & Methods

In Vitro Functionality

The agonistic effect of AC_05355 was assessed in a B cell assay, based on primary B cells isolated from cynomolgus monkeys. Briefly, B cells were isolated from cynomolgus peripheral blood mononuclear cells by MACS according to the manufacturer's protocol (Miltenyi Biotec, #130-091-105). Cynomolgus CEACAM5 transfected CHO cells were UV irradiated and seeded in tissue culture treated 96 well flat bottom plates (Eppendorf). B cells were cocultured with CHO cells in the presence of IL-4 (10 ng/ml, Gibco #PHC0045) and titrated concentrations of AC_05355. After 2 days, B cells were harvested and expression level of the activation marker CD86 was analyzed by FACS.

In Vivo Functionality

Female hCD40tg mice of 8-14 weeks of age were inoculated with $10 \times 10^6$ MC38-CEACAM5 cells s.c. in the right flank. On days 10, 13 and 16 after inoculation, the mice were administered i.p. with 167 μg of AC_05355 or vehicle control. The tumors were frequently measured with a Caliper instrument in regard to width (w), length (l) and height (h) and the tumor volume was calculated using the formula: $(w/2 \times l/2 \times h/2 \times n \times (4/3))$.

Toxicity Study in Cynomolaus Monkeys

Toxicity testing in cynomolgus monkeys was conducted by Charles River Laboratories Edinburgh Ltd. Cynomolgus monkeys aged 2 to 4 years, weighing 3 to 6 kg, were given the test item AC_05355 at days 1 and 8 via intravenous infusion into the tail vein according to the experimental design in Table 18.

TABLE 18

Experimental design for toxicity testing of AC_05355 in cynomolgus monkeys

| Group No | Test Item | Dose Level (mg/kg/dose) | Dose Volume (mL/kg) | Dose Concentration (mg/mL) | No of Animals |
|---|---|---|---|---|---|
| 1 | AC_05355 | 10 | 7.5 | 1.33 | 1M + 1F |
| 2 | AC_05355 | 37.5 | 7.5 | 5 | 1M + 1F |

Standard in-life assessment, including monitoring of body weight, body temperature and food consumption, was performed continuously during the study and until study termination and necroscopy at day 11. Samples were collected for clinical pathology assessments at days 1 (pre-treatment), 4, 8 (pre-treatment) and 11. Macroscopic and microscopic examination of an extensive list of tissues was performed post necroscopy.

Results

In Vitro Functionality

Figure 20:
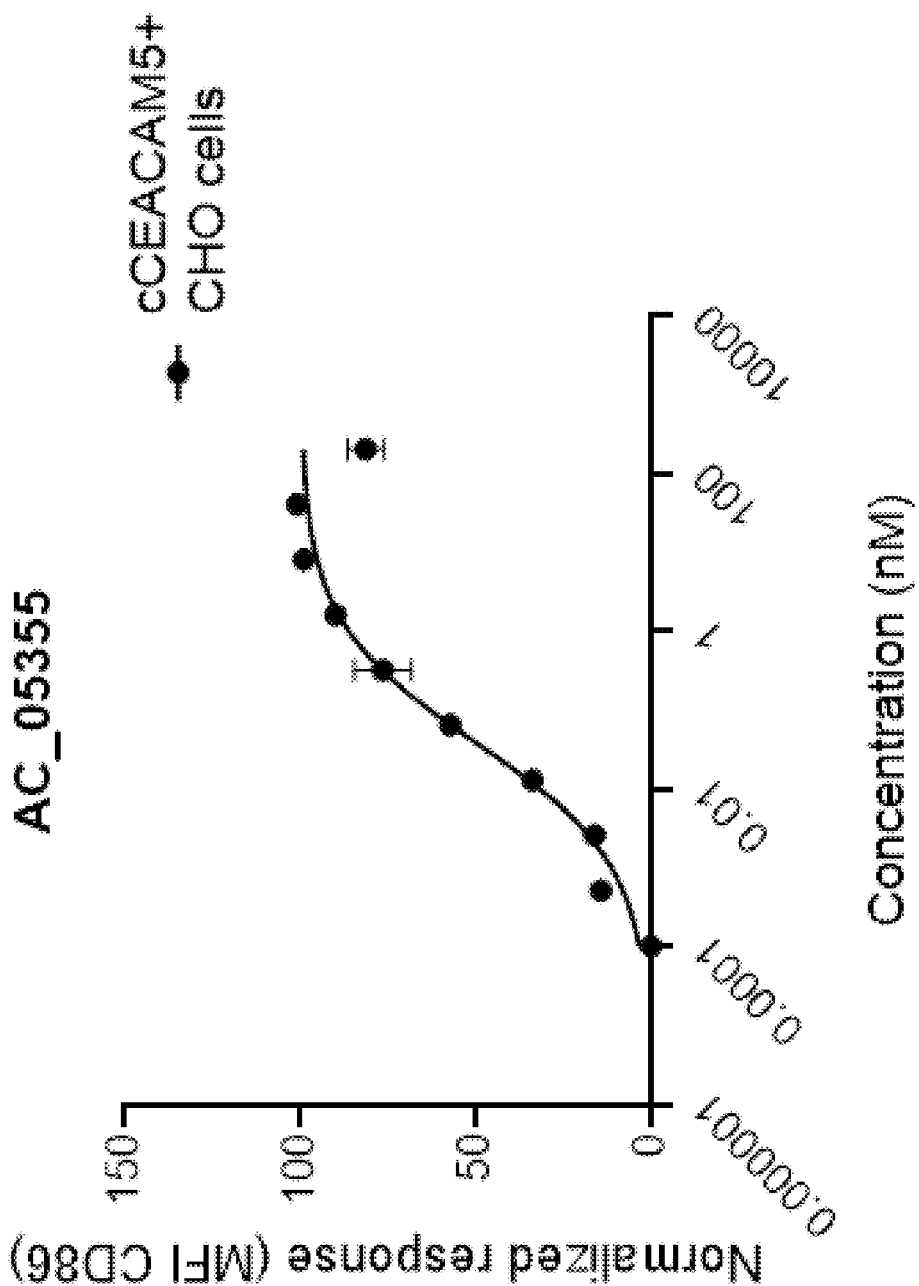
FIG. 20. Effect of the CD40-CEACAM5 bispecific antibody AC_05355 on B cell activation in the presence of cynomolgus CEACAM5 (cCEACAM5) transfected CHO cells. Primary cynomolgus B cells were cultured with titrated antibodies in the presence cCEACAM5 expressed on CHO cells. After 2 days, expression of CD86 on B cells was analyzed by FACS. The graph shows pooled data from 2 donors.

The data demonstrate that the tested CD40×CEACAM5 RUBY™ bsAb AC_05355 induces upregulation of CD86 on cynomolgus B cells in the presence of cynomolgus CEACAM5 expressed on CHO cells (FIG. 20).

In Vivo Functionality

Figure 21:
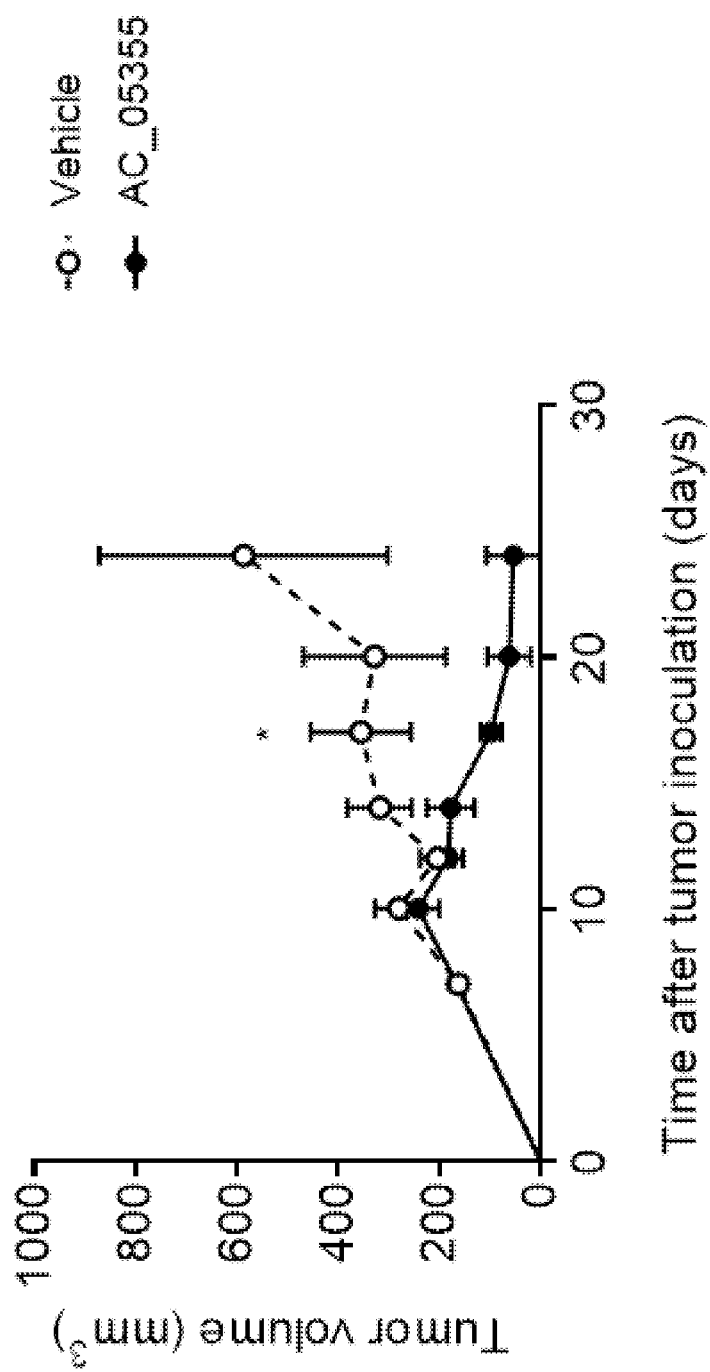
FIG. 21. MC38-CEACAM5 tumor growth. hCD40tg mice inoculated with MC38-CEACAM5 tumors were dosed with the indicated treatments on days 10, 13 and 16 post inoculation. Tumors were frequently measured until the first mouse in any of the treatment groups reached a tumor volume above the ethical limit. Statistical analysis of tumor volumes on day 17 was performed using a Mann-Whitney test (n=10, *p<0.05).
Figure 22:
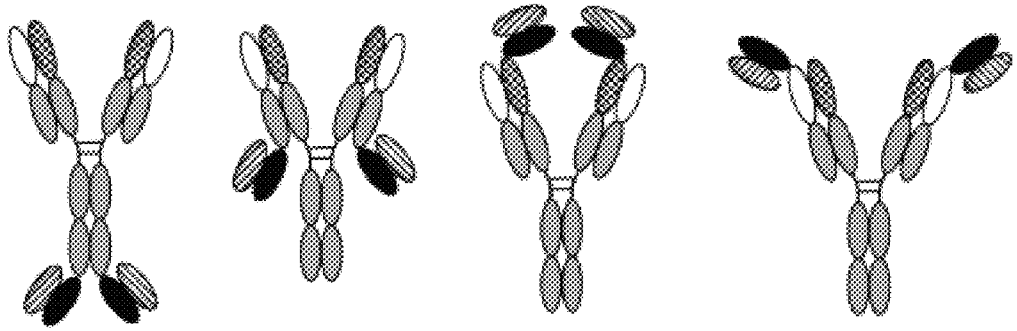
FIG. 22. This shows a schematic representation of the structure of exemplary formats for a bispecific antibody of the invention. In each format, the constant regions are shown as filled light grey; variable heavy chain regions VH1 are shown as chequered black and white; variable light chain regions VL1 are shown as filled white; variable heavy chain regions VH2 are shown as filled black; and variable light chain regions VL2 are shown as white with diagonal lines. CD40 binding domains (binding domain 1) are typically represented as a pair of a chequered black and white domain with a filled white domain (VH1/VL1); CEA binding domains (binding domain 2) are typically represented as a pair of a filled black domain and a white domain with diagonal lines (VH2/VL2). However, in all of the formats shown, it will be appreciated that binding domains 1 and 2 may be switched. That is, a CD40 binding domain may occur in a position shown in this figure for a CEA-binding domain, and vice versa.
Figure 22:
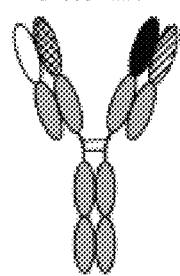
Figure 22:
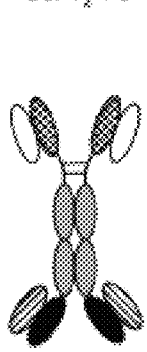
Figure 22:
Figure 22:
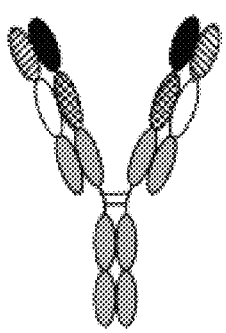
Figure 22:
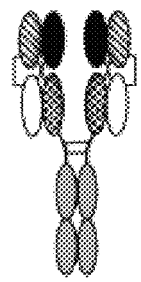
Figure 22:
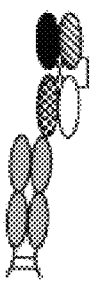
Figure 22:
Figure 22:
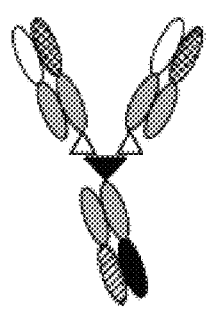
Figure 22:
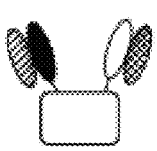
Figure 23:
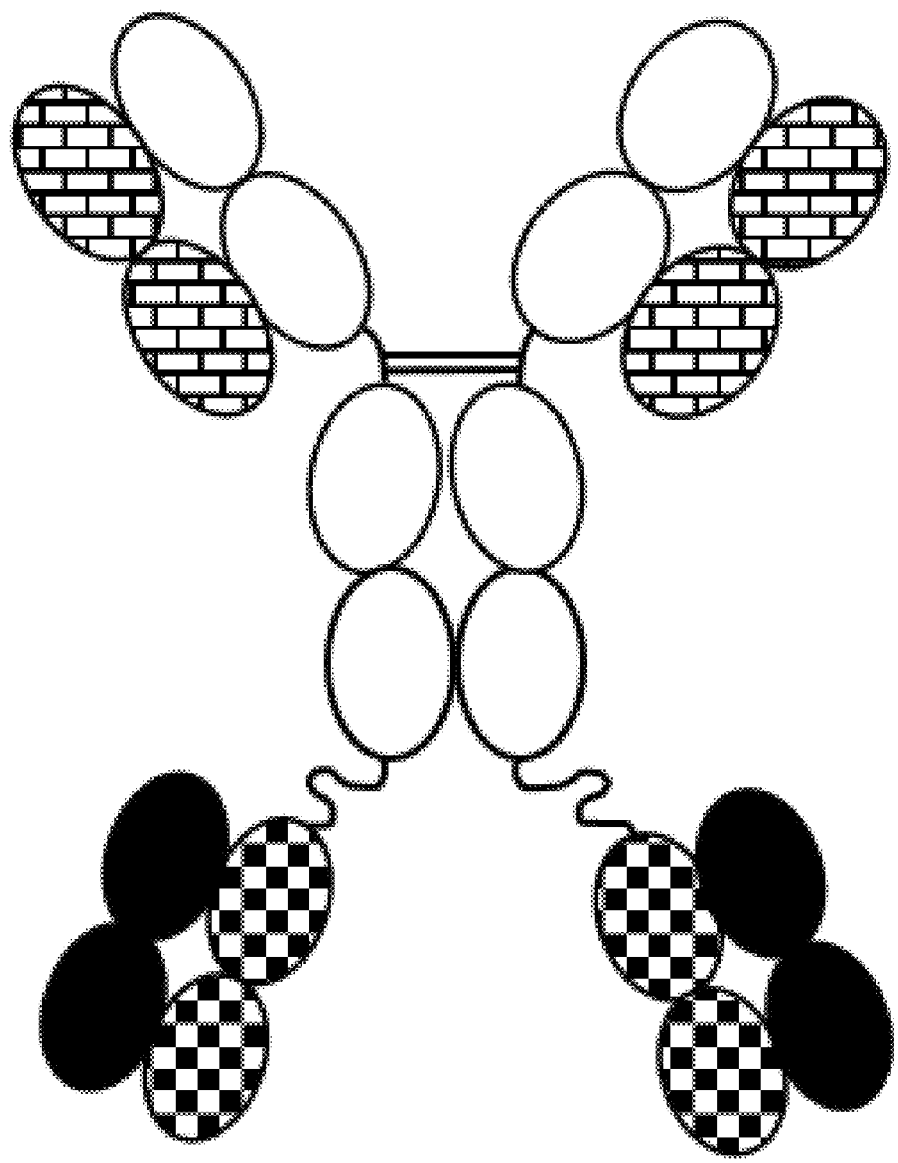
FIG. 23. This shows an example composition of a bispecific antibody construct, in the RUBY™ format. The bispecific antibody of FIG. 21 is made up of three types of polypeptide chains: (1) IgG heavy chains (white) fused to Fab light chains (chequered) via a polypeptide linker. (2) IgG light chains (bricked) and (3) Fab heavy chains (black). Mutations are introduced in the interface between heavy and light chains.

The data demonstrate that treatment with the CD40-CEACAM5 bsAb AC_05355 significantly reduces the MC38-CEACAM5 tumor volume compared to vehicle-treated mice at day 17 after tumor inoculation (FIG. 21).

Toxicity Study in Cynomolaus Monkeys

During the study duration, covering two weekly intravenous doses of AC_05355 at 10 and 37.5 mg/kg to male and female cynomolgus monkeys, no compound related adverse clinical signs were observed. Neither were any macroscopic finding observed post necroscopy, no deviating individual organ weight values obtained, and the microscopic findings observed were of the nature commonly observed in this strain and age of monkey, and, therefore, were considered not to be associated with the administration of AC_05355.

Cytokine levels in samples taken at 0, 4 and 24 h post dosing at day 1 and 8 were in general low and no increases that could be reliably attributed to the dosing with AC_05355 were obtained (Table 18 to Table 23). Levels of IFN-γ, IL-2, IL-6 and IL-10 were below lower limit of quantification (LLOQ) at all time points for three out of four animals and only reached measurable levels at sporadic timepoints in a single monkey. Measurable levels of TNF-α were observed in the two male animals but not in any sampled from female animals (Table 23). However, the slight changes in TNF-α levels did not appear related to the dose level and therefore could not be reliably attributed to dosing with AC_05355.

TABLE 19

IFN-γ levels (pg/mL)

| Group | Dose Level (mg/kg/dose) | Animal sex | Day 1 0 h | Day 1 4 h | Day 1 24 h | Day 8 0 h | Day 8 4 h | Day 8 24 h |
|---|---|---|---|---|---|---|---|---|
| 1 | 10 | M | 43.4 | 53.4 | <LLOQ | <LLOQ | 63.1 | <LLOQ |
|   |    | F | <LLOQ | <LLOQ | <LLOQ | <LLOQ | <LLOQ | <LLOQ |
| 2 | 37.5 | M | <LLOQ | <LLOQ | <LLOQ | <LLOQ | <LLOQ | <LLOQ |
|   |    | F | <LLOQ | <LLOQ | <LLOQ | <LLOQ | O' | <LLOQ |

LLOQ = 37.5 pg/mL

TABLE 20

IL-2 levels (pg/mL)

| Group | Dose Level (mg/kg/dose) | Animal sex | Day 1 0 h | Day 1 4 h | Day 1 24 h | Day 8 0 h | Day 8 4 h | Day 8 24 h |
|---|---|---|---|---|---|---|---|---|
| 1 | 10 | M | 52.7 | 65.2 | <LLOQ | <LLOQ | 65.3 | <LLOQ |
|   |    | F | <LLOQ | <LLOQ | <LLOQ | <LLOQ | <LLOQ | <LLOQ |
| 2 | 37.5 | M | <LLOQ | <LLOQ | <LLOQ | <LLOQ | <LLOQ | <LLOQ |
|   |    | F | <LLOQ | <LLOQ | <LLOQ | <LLOQ | <LLOQ | <LLOQ |

LLOQ = 37.5 pg/mL

TABLE 21

IL-6 levels (pg/mL)

| Group | Dose Level (mg/kg/dose) | Animal sex | Day 1 0 h | Day 1 4 h | Day 1 24 h | Day 8 0 h | Day 8 4 h | Day 8 24 h |
|---|---|---|---|---|---|---|---|---|
| 1 | 10 | M | <LLOQ | 158 | <LLOQ | <LLOQ | <LLOQ | <LLOQ |
|   |    | F | <LLOQ | <LLOQ | <LLOQ | <LLOQ | <LLOQ | <LLOQ |
| 2 | 37.5 | M | <LLOQ | <LLOQ | <LLOQ | <LLOQ | <LLOQ | <LLOQ |
|   |    | F | <LLOQ | <LLOQ | <LLOQ | <LLOQ | <LLOQ | <LLOQ |

LLOQ = 37.5 pg/mL

TABLE 22

IL-10 levels (pg/mL)

| Group | Dose Level (mg/kg/dose) | Animal sex | Day 1 0 h | Day 1 4 h | Day 1 24 h | Day 8 0 h | Day 8 4 h | Day 8 24 h |
|---|---|---|---|---|---|---|---|---|
| 1 | 10 | M | 193 | 230 | <LLOQ | <LLOQ | <LLOQ | <LLOQ |
|   |    | F | <LLOQ | <LLOQ | <LLOQ | <LLOQ | <LLOQ | <LLOQ |
| 2 | 37.5 | M | <LLOQ | <LLOQ | <LLOQ | <LLOQ | <LLOQ | <LLOQ |
|   |    | F | <LLOQ | <LLOQ | <LLOQ | <LLOQ | <LLOQ | <LLOQ |

LLOQ = 188 pg/mL

TABLE 23

TNF-a levels (pg/mL)

| Group | Dose Level (mg/kg/dose) | Animal sex | Day 1 0 h | Day 1 4 h | Day 1 24 h | Day 8 0 h | Day 8 4 h | Day 8 24 h |
|---|---|---|---|---|---|---|---|---|
| 1 | 10 | M | 176 | 237 | <LLOQ | <LLOQ | 273 | <LLOQ |
|   |    | F | <LLOQ | <LLOQ | <LLOQ | <LLOQ | <LLOQ | <LLOQ |
| 2 | 37.5 | M | <LLOQ | 111 | <LLOQ | <LLOQ | <LLOQ | <LLOQ |
|   |    | F | <LLOQ | <LLOQ | <LLOQ | <LLOQ | <LLOQ | <LLOQ |

LLOQ = 37.5 pg/mL

Conclusion

Based on the above presented data, it can be concluded that the CD40×CEACAM5 RUBY™ bsAb AC_05355 is functional both in vitro and in vivo, with the ability to activate cynomolgus B cells in the presence of surface expressed cynomolgus CEACAM5. It can also be concluded that AC_05355 can be safely administered to cynomolgus monkey at two weekly doses up to at least 37.5 mg/kg/dose, without provoking any adverse clinical signs, macro- or microscopic abnormalities or changes in cytokine levels that could be reliably attributed to the dosing with AC_05355.

Example 13

Materials and Methods

MB49 CEA overexpressing cells were labeled with the fluorescent dye PKH26 (Sigma-Aldrich) according to manufacturer's instructions. Labeled MB49-CEA cells were heat-shocked at 45° C. for 10 min to induce necrosis, followed by incubation at 37° C. over night. The heat-shocked cells were then centrifuged and the supernatant containing necrotic tumor cell line debris was collected. Raji cells were labeled with the nuclear dye Hoechst 33342 (Thermo Scientific) and cultured with necrotic debris and titrated antibodies (ffAC_05337 or 1132). Images were captured using a Cytation 5 live cell imager (BioTek) and the number of PKH26-stained tumor debris co-localized with Hoechst-stained Raji cells was quantified using Gen5 software (BioTek).

Results

Figure 24:
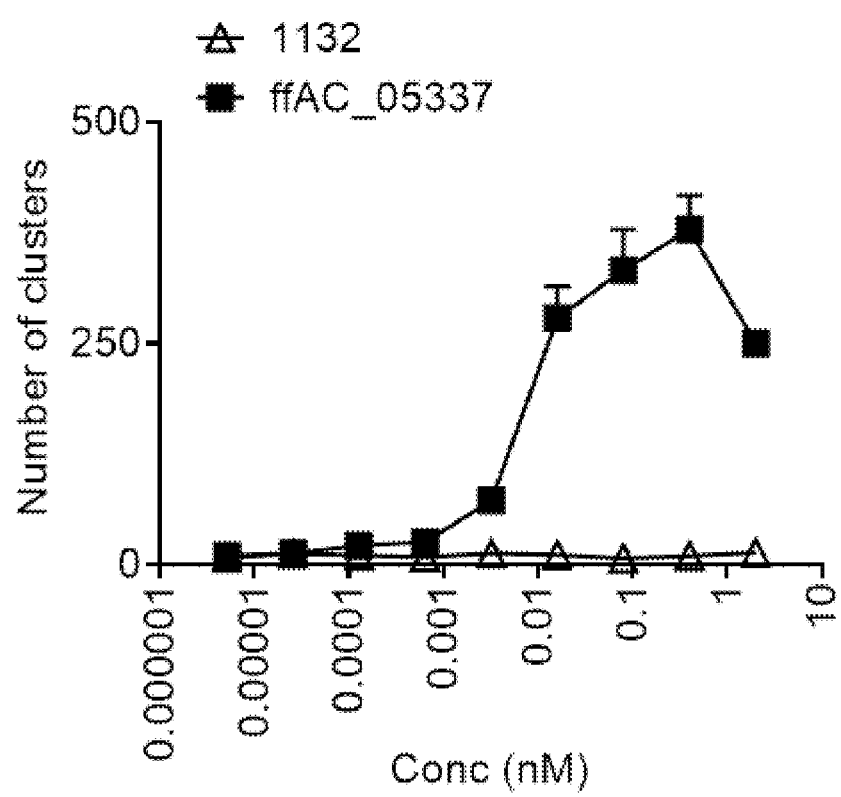
FIG. 24. CD40×TAA bsAbs mediate localization of tumor debris to antigen presenting cells. The number of CEA+ tumor debris clustering with CD40+ cells was quantified after 8 hrs of culture using live cell imaging software. The graphs show the mean (+SD) of duplicate wells in one representative experiment of four (CEA).

A dose-dependent increase in clusters of necrotic debris from a CEA-transfected MB49 tumor cell line with Raji cells was seen when the CD40×CEA targeting ffAC_05337 bsAb was added, but not with the monospecific CD40 Ab 1132 (as shown in FIG. 24).

Example 14—Functional Assays Using Cells Obtained from Primary Human Colorectal Cancer Patients Dissociated primary cells from colorectal cancer patients were purchased from Discovery Life Sciences (Huntsville, AL). Directly after thawing, DTCs were counted using NucleoCounter® NC-200™ (Chemometec, Denmark) and 20,000 viable cells were pipetted into each well. The cancer cells were used to assess functionality in the CD40 bioassay, or alternatively the ability of the primary cancer cells to activate the immune cells in the same tumor sample was analyzed. 200,000 viable cells were pipetted into a Nunc UpCell 96-well plate (Thermo Scientific, 174897). Next, ATOR-4066 or controls were added into the wells. The plate was incubated for 48 hours in a 37° C., 5% CO2 incubator. Next, the cells were harvested, and analyzed by flow cytometry.

TABLE 24

FACs panel for activation staining (22 tubes were stained)

| | | | |
|---|---|---|---|
| CD40 | APC | 555591 | BD Pharmingen |
| CD86 | PE | 555658 | BD Pharmingen |
| CD45 | V450 | 560367 | BD Horizon |
| CD14 | PerCP-Cy5.5 | 562692 | BD Pharmingen |
| CD83 | PE-Cy7 | 561132 | BD Pharmingen |
| CD3 | FITC | 555332 | BD Pharmingen |
| CD56 | FITC | 562794 | BD Pharmingen |

Results

Figure 25:
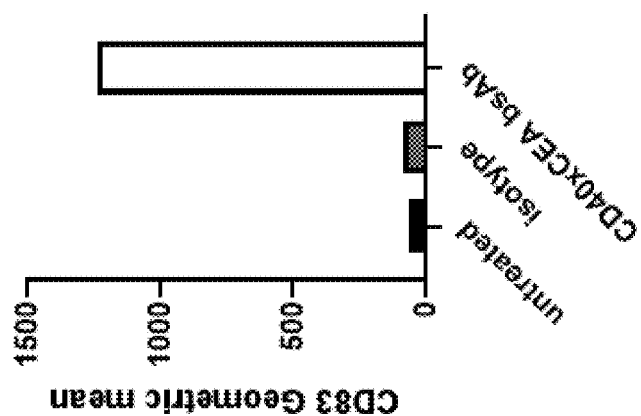
FIG. 25. Dissociated cells from human colorectal cancer tumors were analyzed for: (left) their CEA-expression (gated on total viable cells), (middle) ability to provide cross-linking to CD40×CEA Neo-X-Prime bsAb in a CD40 reporter assay, and (right) CD83 upregulation following stimulation of the tumor infiltrating immune cells (gated on viable CD45+CD3-CD56- cells) using CD40×CEA Neo-X-Prime bsAb or isotypexCD40 bsAb (data from 1 representative experiment out of three).
Figure 25:
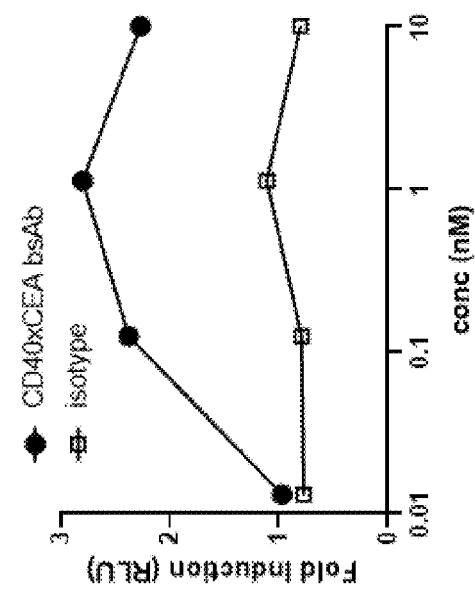
Figure 25:
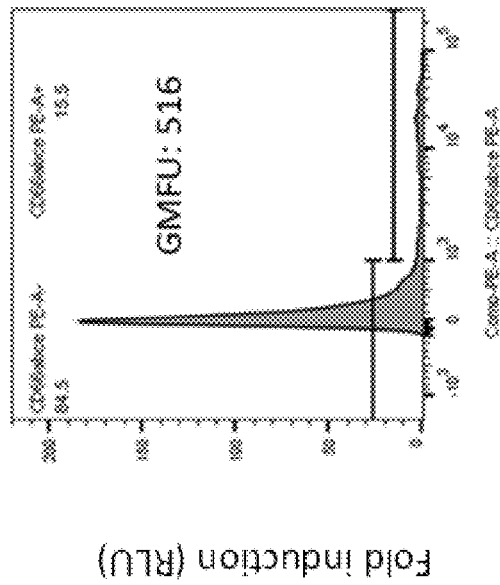

First, it was demonstrated that the CEA densities in patient derived tumors were sufficient to provide cross-linking and induce CD40 stimulation using a reporter cell assay. The results demonstrated patient derived cancer cells can induce similar cross-linking and CD40 activation as the cell lines (FIG. 25). Secondly, when culturing dissociated cells from patient derived colon tumors, it was demonstrated that a CD40×CEA bsAb (ffAC_05337) could activate tumor infiltrating immune cells (FIG. 25).

Example 15—Kinetic Profiles of CD40×CEA and CD40×EpCAM RUBY™ bsAbs

Kinetic measurements were performed in the Octet RED96 platform with bispecific antibodies captured to anti human IgG Fc Capture (AHC) or FAB2G Biosensor tips (Sartorius). Monomeric human CD40-His-Avi tag (Acro Biosystems), monomeric human CEACAM5-His (R&D Systems) or monomeric human EpCAM-His (R&D Systems) were ½ serially diluted in 1× kinetic buffer (Sartorius) starting at 500 nM or 100 nM. Binding kinetics was studied in 1× kinetic buffer where association was allowed for 100 to 300 sec followed by dissociation for 100 to 3600 sec. Sensor tips were regenerated with 10 mM Glycine pH 1.7. Data generated were referenced by subtracting blank or parallel buffer blank, the baseline was aligned to the y-axis, inter-step correction by alignment against dissociation was performed and the data was smoothed by Savitzky-Golay filter in the data analysis software (v9.0.0.14). The processed data was fitted using a 1:1 Langmuir binding model.

TABLE 25

| | CD40 affinity | | | TAA affinity | | |
|---|---|---|---|---|---|---|
| bsAb ID | $K_D$ (M) | $k_{on}$ (1/Ms) | $k_{off}$ (1/s) | $K_D$ (M) | $k_{on}$ (1/Ms) | $k_{off}$ (1/s) |
| CD40xCEA #1 | 9.7E−08 | 4.5E+05 | 4.4E−02 | 1.8E−08 | 2.4E+05 | 4.3E−03 |
| CD40xCEA #2 | 9.7E−08 | 4.5E+05 | 4.4E−02 | 2.1E−09 | 2.4E+05 | 4.2E−04 |
| CD40xEpCAM #1 | 1.9E−06 | 1.1E+05 | 2.1E−01 | 4.8E−07 | 2.0E+04 | 1.0E−02 |
| CD40xEpCAM #2 | 9.7E−08 | 4.5E+05 | 4.4E−02 | 4.8E−07 | 2.0E+04 | 1.0E−02 |

CD40xCEA #1 = ffAC_05337
CD40xCEA #2 = Multi46

Example 16

Materials and Methods

Human Samples

The collection of the tonsillar cancer sample at Lund University Hospital was approved by the Swedish Ethical Review Authority (ref. no. 2017/580), and the participating patient granted written informed consent.

Cell Isolation and Coculture

The tonsillar cancer biopsy was cut into small fragments in RPMI 1640 medium (ThermoFisher Scientific) supplemented with 0.1 mg/mL gentamycin (Sigma-Aldrich). The tissue fragments were enzymatically digested with Collagenase IV (Sigma-Aldrich) (2.0 mg/mL) and DNase I (Sigma Aldrich) (200 Kunits/mL) for 20 minutes at 37° C. Cells were filtered using a 70 μm cell strainer (BD Biosciences) and stained with CD3-PerCPCy5.5, VS620-PECF594, CD45-APCH7 and HLA-DR-BV711 for cell sorting using FACSAria IIu (BD Biosciences). 104 viable CD45+ HLA-DR+CD3− cells were sorted directly into 96-well flat-bottom plates (Nunc UpCell, ThermoFisher Scientific) pre-seeded with 6×104 UV-irradiated CHO-CEA cells, per well. 19 nM of CD40×CEA bsAbs, CD40 mAbs or isotype controls were added to the cocultures for 13 h, after which the supernatants were collected, and the cells were washed and blocked for non-specific binding with ChromPure mouse IgG (Jackson ImmunoResearch) for 15 min at room temperature. Cells were immediately stained with fluorochrome-coupled antibodies (Supplementary Table 1) for flow cytometric analysis using a FACSAria IIu instrument (BD Biosciences). Cytokine analysis was performed using Bio-Plex Pro Human Cytokine 17-plex Assay on the Bio-PlexR 200 system (Bio-Rad Lab).

TABLE 26

Antibodies used for flow cytometry.

| Antigen | Fluorophore | Clone | Company |
|---|---|---|---|
| | | Human cells | |
| CD45 | APCH7 | 2D1 | BD Biosciences |
| HLA-DR | BV711 | G46-6 | BD Biosciences |
| CD11c | BV510 | B-ly6 | BD Biosciences |
| XCR1 | PE | S15046E | BioLegend |
| CD1C | BV786 | L161 | BioLegend |
| CD14 | FITC | TUK4 | Invitrogen |
| CCR2 | APC | K036C2 | BioLegend |
| CD123 | AF700 | 6H6 | BioLegend |
| CD19 | PerCP Cy5.5 | HIB19 | BD Biosciences |
| CD20 | PerCP Cy5.5 | 2H7 | BD Biosciences |
| CD86 | BV605 | IT2.2 | BioLegend |
| CD40 | PE-Cy7 | 5C3 | BD Biosciences |
| CCR7 | BV421 | 2-L1-A | BD Biosciences |

Results

Figure 26:
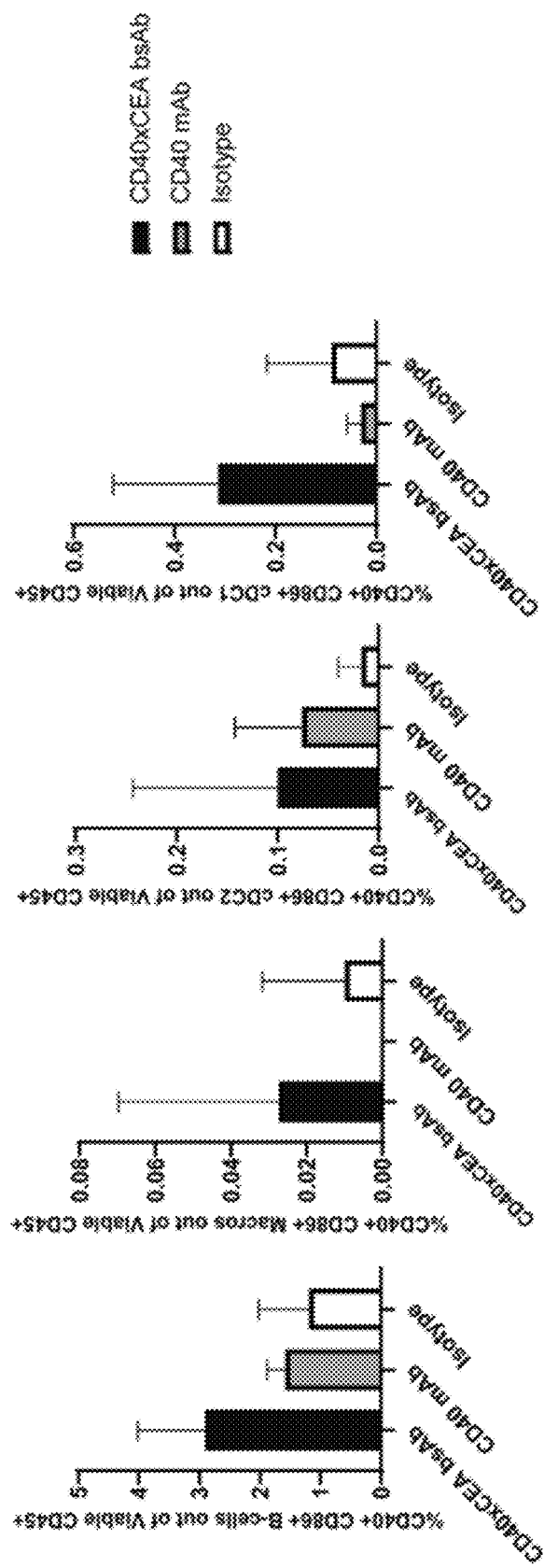
FIG. 26. Simultaneous binding of CD40 and CEA by CD40×CEA bsAbs mediates activation of tonsillar cancer APCs in vitro. Human CD45+ HLA-DR+CD3- cells from a tonsillar cancer biopsy were co-cultured with UV-irradiated CHO cells transfected with human CEA in the presence of CD40×CEA bsAb, CD40 mAb or isotype control. After 13 h culture, cells were harvested and the frequencies of CD86+CD40+ cells were investigated using flow cytometry of CD19+CD20+ B cells, CD14+ macrophages, CD1c+ cDC2s and XCR1+ cDC1s.

As shown in FIG. 26, simultaneous binding of CD40 and CEA by CD40×CEA bsAbs (ffAC_05337) mediates activation of tonsillar cancer APCs in vitro.

Example 17—Tumour Localisation

Materials and Methods

Human CD40 transgenic mice were inoculated with MC38-hCEA tumor cells (MC-38-CEA-2, Kerafast) s.c. and were administered with 100 µg anti-CD40 antibody or a molar equivalent dose (167 µg) CD40×CEA bsAb (ffAC_05337) or Isotype bsAb i.p. on days 10 and 13. On day 14, tumors were dissected. Frozen tumor sections were stained for human IgG to assess accumulation of administered antibodies, and for CEA to assess CEA expression pattern in the tumors.
Results
FIG. 27 shows accumulation of the CD40×CEA bsAb (ffAC_05337), but not corresponding CD40 mAb, in CEA-expressing tumors Example 18—Immune Status MB49

Figures 28A, 28B:
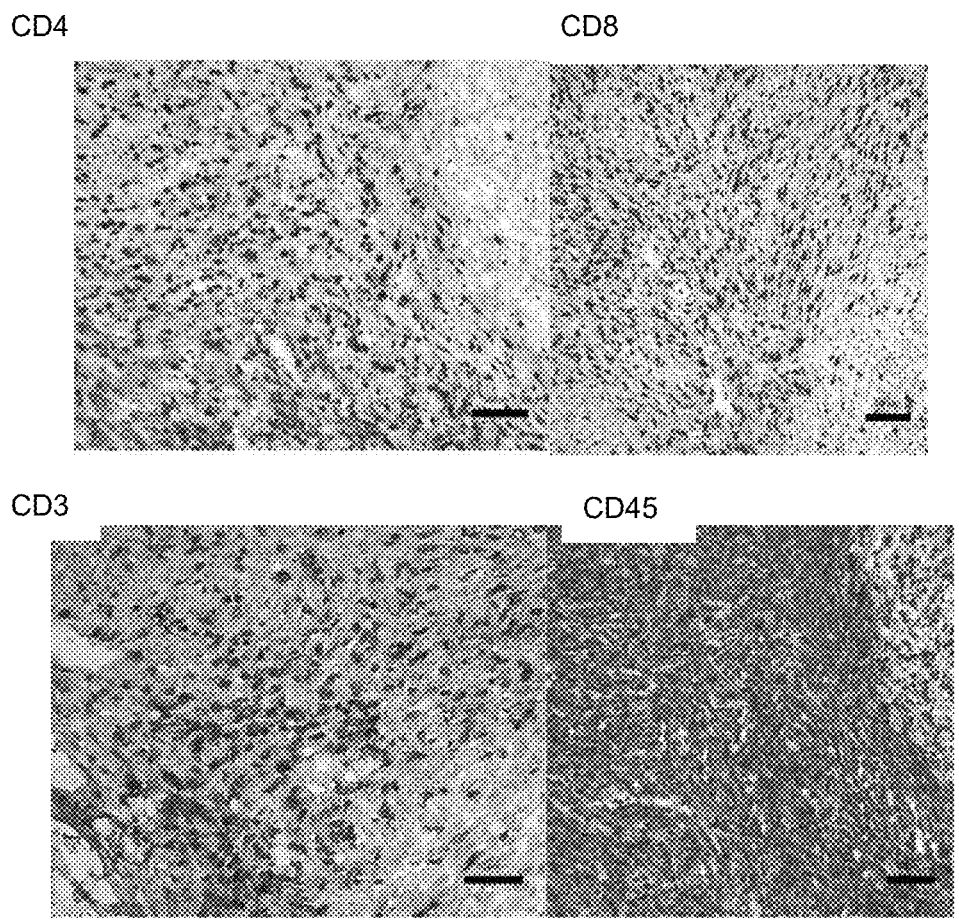
FIGS. 28A-28C. Cryo preserved tumors (B16.F10-hCD40+#6, 7 and 9 used as control, hereafter called B16 AND MB49 #2, 4 and 5) from human CD40 transgenic mice were analyzed. 8 μm cryosections were prepared and stained. Mouse spleen was used as positive control. The sections were analyzed in a Leica DMRX-e microscope and representative photos were taken.
Figure 28C:
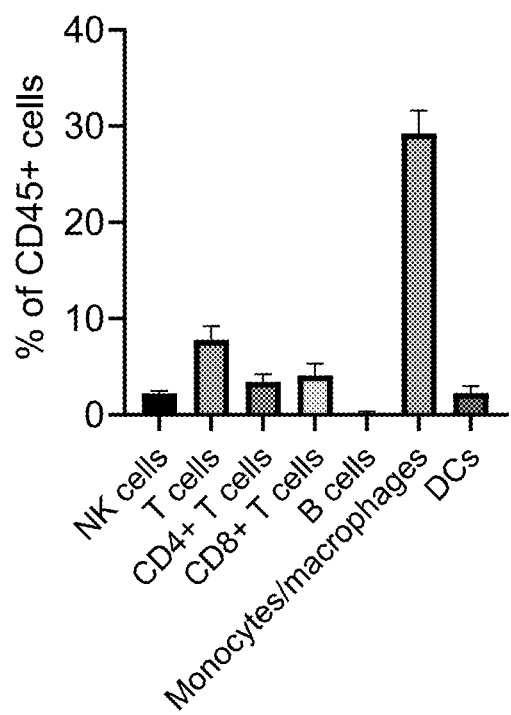

Materials and Methods
Cryo preserved tumors (B16.F10-hCD40+#6, 7 and 9 used as control, hereafter called B16 AND MB49 #2, 4 and 5) from human CD40 transgenic mice were analyzed. 8 µm cryosections were prepared and stained. Mouse spleen was used as positive control.
The sections were analyzed in a Leica DMRX-e microscope and representative photos were taken.
Results
FIG. 28 shows that a marked higher degree of infiltrating T cells are seen in the MB49 tumors compared to the B16 tumors used as control.

Example 19—Receptor Density

The receptor density of CEA on particular cells was determined using a receptor density kit (Quantum Simply Cellular, anti-human IgG) according to manufacturer's instructions.

TABLE 27

Receptor Density

| Cell line | Celltype | |
|---|---|---|
| | | CEA/cell |
| LOVO | Human | 5,500 |
| HT29 | Human | 11,300 |
| LS174T | Human | 51,500 |
| MKN45 | human | 353,000 |
| MC38-CEA1 | Mouse (transfected) | 300,000 |
| CHO-CEA | Human (transfected) | 125,000 |
| | | EpCAM/cell |
| BxPC3 | Human | 260,000 |
| JAR | Human | 2,200,000 |
| MCF7 | Human | 1,500,000 |
| JEG3 | human | 2,400,000 |
| MB49-EpCAM | Mouse (transfected) | 230,000 |
| CHO-EpCAM | Human (transfected) | 350,000 |

Example 20—Surrogate Toxicology Study

Materials and Methods
B cell activation of the cynoCEA×CD40 RUBY™ (AC_05355) on cynomolgus and human B cells in the presence of CEA transfected cells (macaque CEA, NP_001040590.1). Primary cynomolgus B cells were cultured with titrated antibodies in the presence CEA expressed on CHO cells. After 2 days, expression of CD86 on B cells was analyzed by FACS.

Figures 29A, 29B:
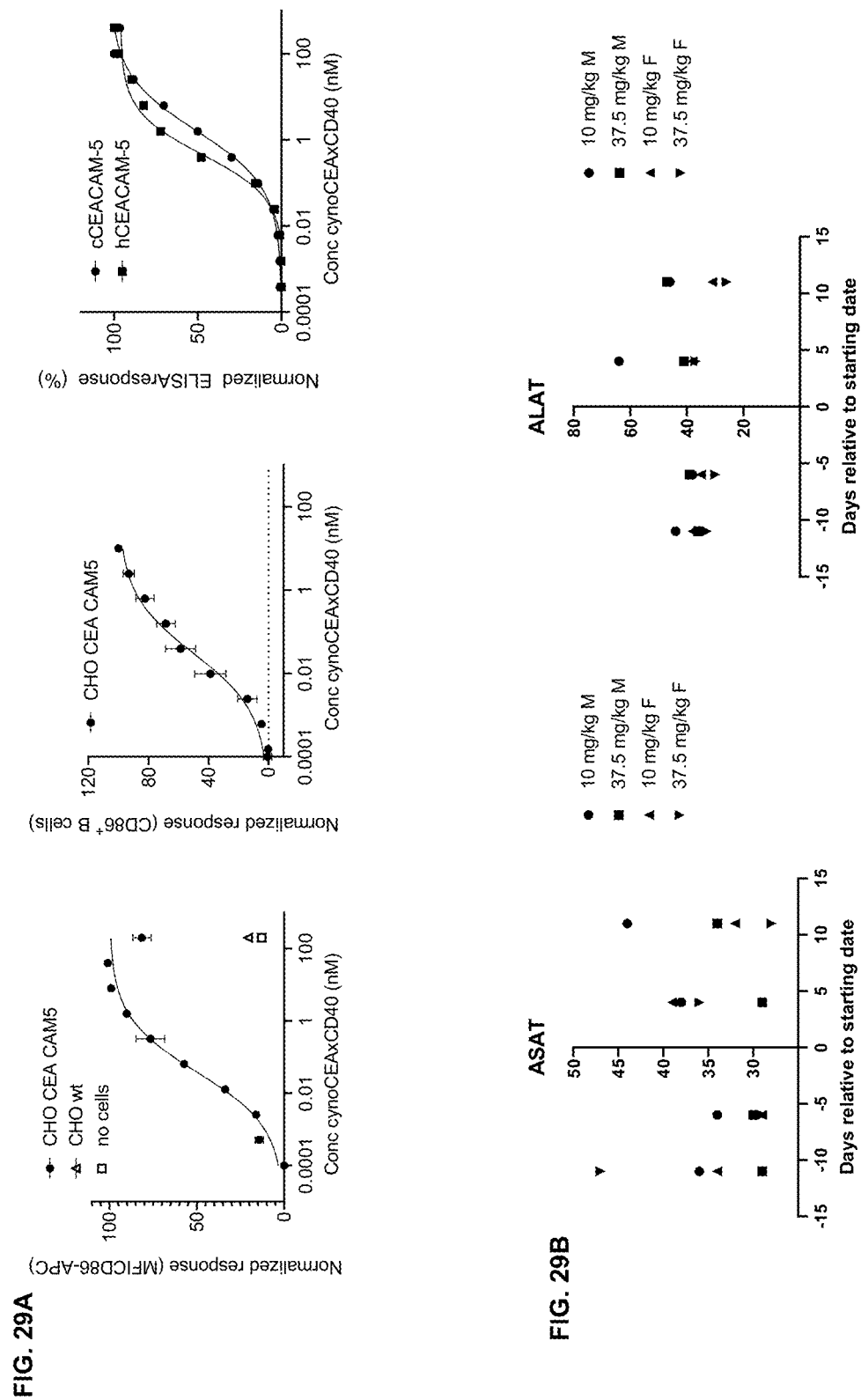

The cynoCEA×CD40 bispecific antibody (AC_05355) was administered once weekly via intravenous infusion for 2 weeks to cynomolgus monkeys at two different dose levels (10 mg/kg and 37.5 mg/kg). One female and one male were evaluated at each dose level.
Results
FIG. 29 shows that CEA×CD40 bsAbs in the RUBY™ format (AC_05355) induce upregulation of CD86 on cynomolgus and human B cells to a similar degree. The CEA-conditional activation of CD40 on cynomolgus B cells and human B cells is similar to what is observed with the human CEA×CD40 bsAb in RUBY™ (AC_05355) used for the in vitro assays. The cynoCEA×CD40 bsAb binds with similar affinity to human and cynomolgus monkey CEA (hCEA vs cCEA, right panel).
FIG. 29 also shows that in cynomolgus monkeys there were no findings associated with cyoCEA×CD40 bsAb (AC_05355) at the evaluated dose levels.

Example 21—Receptor Binding

Materials and Methods
Dual ELISA showing simultaneous binding of CD40× TAA RUBY™ bsAb to its respective antigen targets (CD40×CEA bsAb=ffAC_05337 and cynoCEA×CD40 bsAb=AC_05355). ELISA plates were coated with the target, bsAb was added followed by detection using biotinylated target.
Results
FIG. 30 shows that the bispecific antibodies were successfully generated in the RUBY™ format and the generated bsAbs displayed good binding to their respective antigen targets as illustrated by the ELISA binding evaluations.

Example 22: Anti-Tumor Effect of CD40-CEACAM5 Bispecific Antibody ffAC_05337

Figure 31:
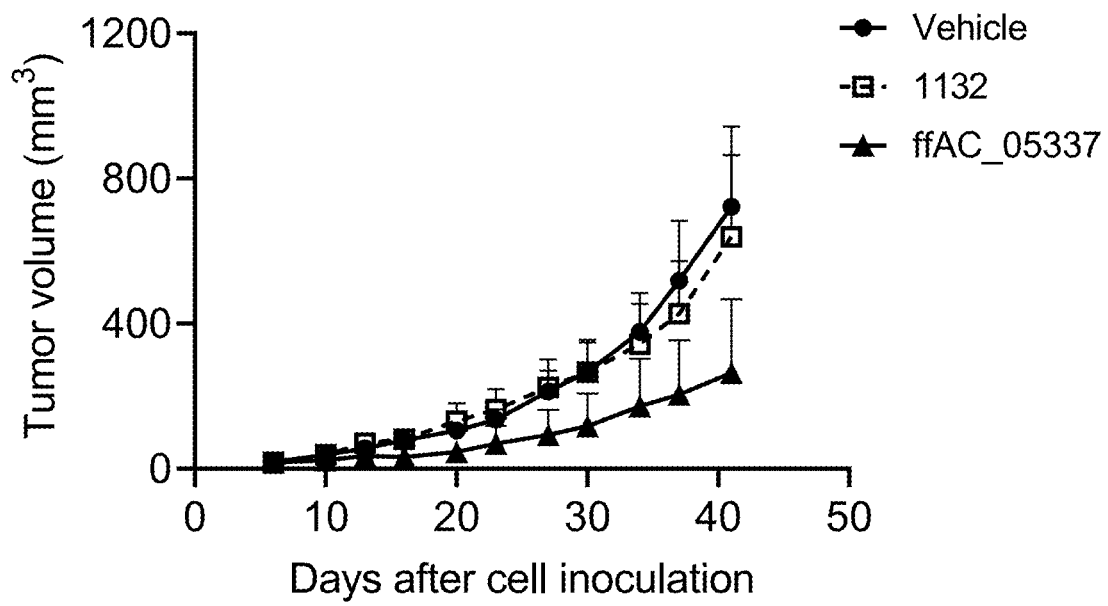
FIG. 31. MC38-CEACAM5 2 tumor growth and survival. hCD40tg mice inoculated with MC38-CEACAM5 2 tumors were dosed with the indicated treatments on days 7, 10, and 13 post-inoculation. Tumors were frequently measured, and the graphs shows the mean tumor volume (+SD) of each group until the first mouse in any of the treatment groups reached a tumor volume above the ethical limit, and the % surviving mice in each treatment group.
Figure 31:
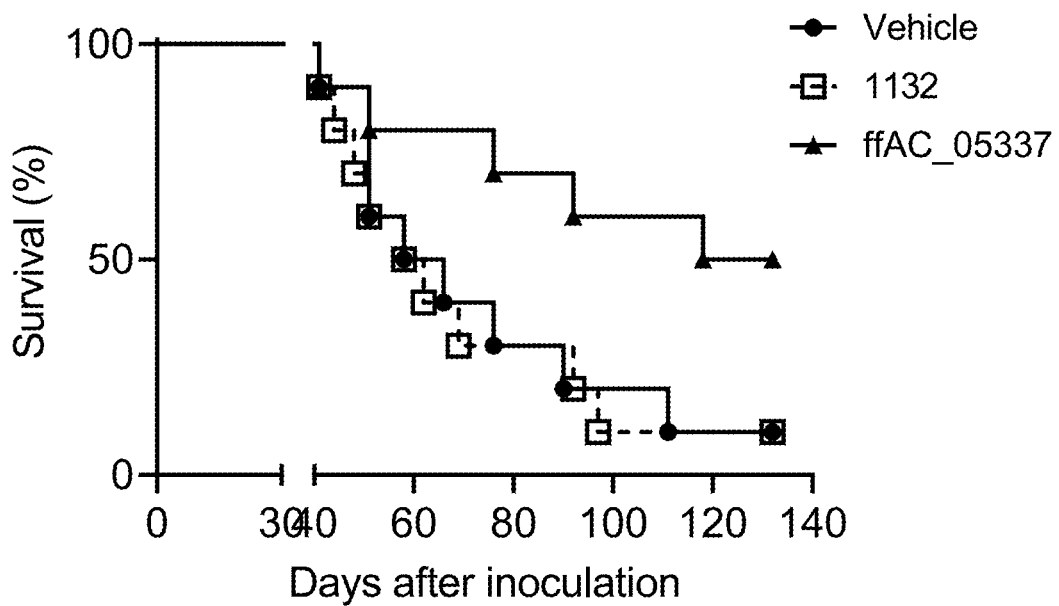

Background and Aim
ffAC_05337 is a CD40-CEA bispecific antibody in the RUBY™ format. The antibody has been LALA-mutated to silence Fcγ receptor binding.
The aim of this study was to evaluate the anti-tumor effect of ffAC_05337 and a CD40 mAb in human CD40 transgenic (hCD40tg) mice inoculated with a CEACAM5-transfected murine tumor cell line called MC38-CEACAM5 2.
Materials and Methods
Female hCD40tg mice of 9 weeks of age were inoculated with $1\times10^6$ MC38-CEACAM5 2 cells (obtained from Kerafast) s.c. in the right flank. On days 7, 10, and 13 after inoculation, the mice were administered i.p. with 100 µg of wildtype CD40 monospecific antibody, 1132, or 167 µg of the CD40-CEACAM5 bsAb ffAC_05337. A group of vehicle-treated mice was also included. The tumors were frequently measured with a caliper in width (w), length (l) and height (h) and the tumor volume was calculated using the formula: (w/2×l/2×h/2×π×(4/3)).
Results and Conclusions
The data demonstrated that treatment with the CD40-CEACAM5 bsAb ffAC_05337 but not the CD40 mAb 1132 reduced the MC38-CEACAM5 tumor volume compared to vehicle-treated mice (FIG. 31). Further, treatment with ffAC_05337 but not 1132 led to improved survival compared to vehicle-treated mice (FIG. 31).

Example 23—Functional Assays Using Cells Obtained from Primary Human Gastric Cancer Patients Dissociated primary cells from gastric cancer patients were purchased from Discovery Life Sciences (Huntsville, AL). Directly after thawing, DTCs were counted using NucleoCounter® NC-200™ (Chemometec, Denmark) and 20,000 viable cells were pipetted into each well. The cancer cells were used to assess functionality in the CD40 bioassay, or alternatively the ability of the primary cancer cells to activate the immune cells in the same tumor sample was analyzed. 200,000 viable cells were pipetted into a Nunc UpCell 96-well plate (Thermo Scientific, 174897). Next, CD40×CEA bsAb (ffAC_05337) or controls were added into the wells. The plate was incubated for 48 hours in a 37° C., 5% CO2 incubator. Next, the cells were harvested, and analyzed by flow cytometry.

TABLE 28

FACs panel for activation staining

| CD40 | APC | 555591 | BD Pharmingen |
| CD86 | PE | 555658 | BD Pharmingen |
| CD45 | V450 | 560367 | BD Horizon |
| CD14 | PerCP-Cy5.5 | 562692 | BD Pharmingen |
| CD83 | PE-Cy7 | 561132 | BD Pharmingen |
| CD3 | FITC | 555332 | BD Pharmingen |
| CD56 | FITC | 562794 | BD Pharmingen |

Results

Figure 32:
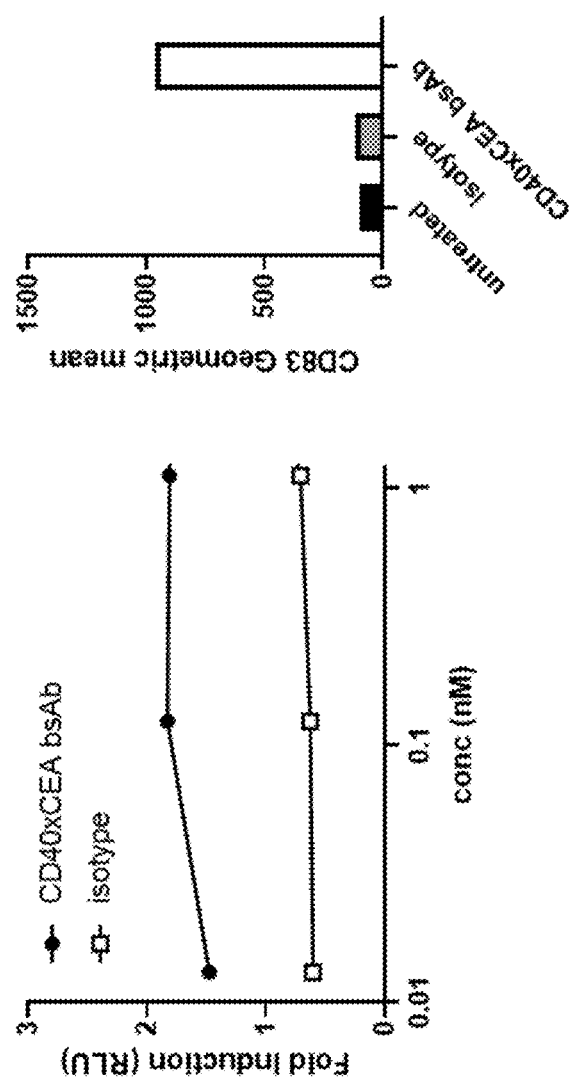
FIG. 32. Dissociated cells from human gastric cancer tumors were analyzed for: (left) their CEA-expression (gated on total viable cells), (middle) ability to provide cross-linking to CD40×CEA Neo-X-Prime bsAb (ffAC_05337) in a CD40 reporter assay, and (right, 1 nM CD40×CEA) CD83 upregulation following stimulation of the tumor infiltrating immune cells (gated on viable CD45+ CD3-CD56– cells) using CD40×CEA Neo-X-Prime bsAb or isotypexCD40 bsAb (data from 1 representative experiment out of four).
Figure 32:
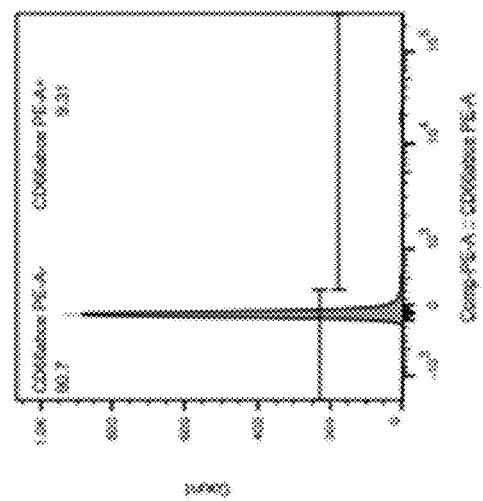
Figure 33A:
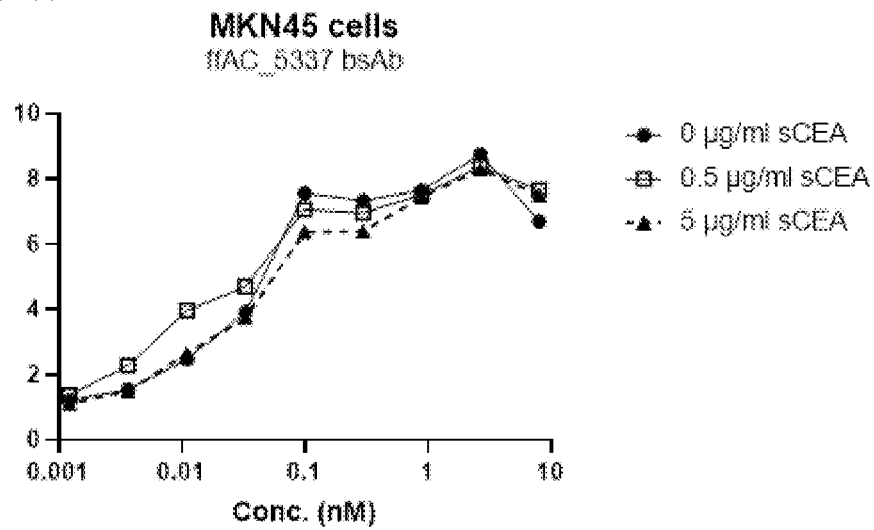
FIGS. 33A-33D. Effect of the bispecific antibody ffAC_0337 on CD40 reporter cells when co-cultured with tumor cells with different CEA receptor density in the presence and absence of soluble CEA. MKN45 CEA high expressing cells (FIG. 33A), LSW74T, CEA intermediate expressing cells (FIG. 33B), HT29 and LOVO, CEA low expressing cells (FIGS. 33C-33D). The response was calculated as fold induction to background.
Figure 33C:
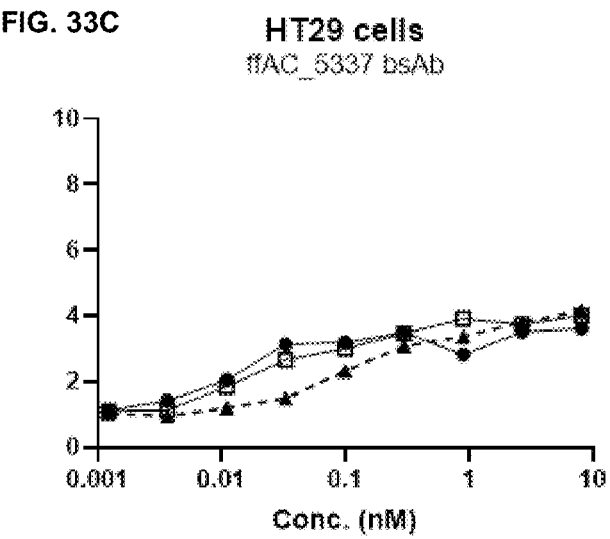
Figure 33B:
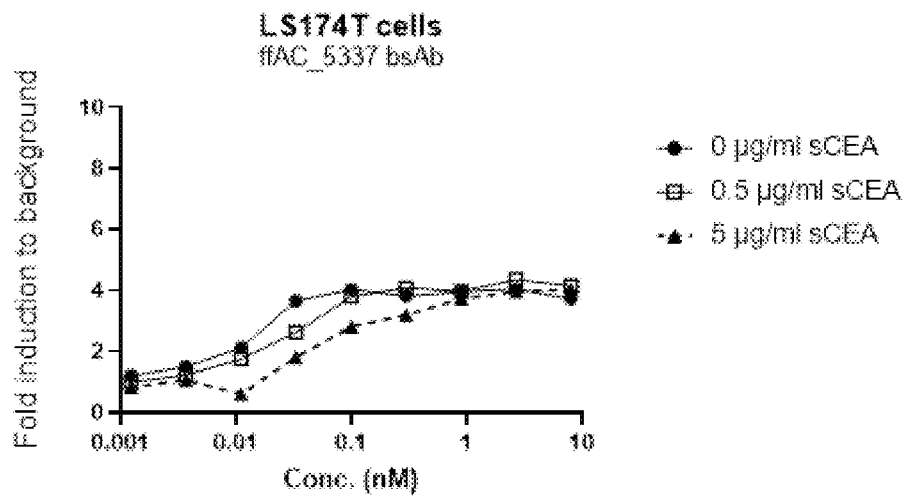
Figure 33D:
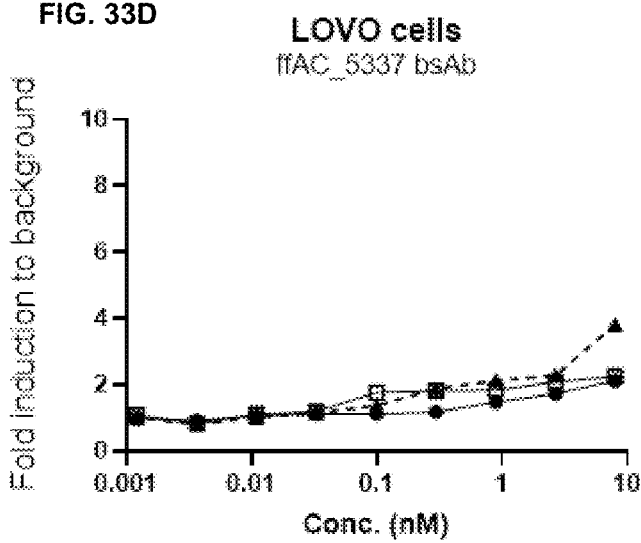

First, it was demonstrated that the CEA densities in patient derived tumors were sufficient to provide cross-linking and induce CD40 stimulation using a reporter cell assay. The results demonstrated that patient derived cancer cells can induce similar cross-linking and CD40 activation as the cell lines (FIG. 32). Secondly, when culturing dissociated cells from patient derived gastric tumors, it was demonstrated that a CD40×CEA bsAb (ffAC_05337) could activate tumor infiltrating immune cells (FIG. 32).

Example 24—Evaluation of the CD40 Agonistic Function in the Presence of Soluble CEA Using the CD40 Reporter Assay Aim and Background The aim of this study was to assess the CD40 agonistic function of the bispecific antibody ffAC_05337 using the CD40 reporter assay in the presence of CEA expressing cells and physiological relevant soluble CEA concentrations. CD40 crosslinking will be mediated by simultaneous binding of CD40, expressed on CD40 reporter cells, and CEA expressed on CHO cells or CEA expressing human tumor cells. In addition, since high levels of soluble CEA can be detected systemically in cancer patients, the agonistic function was assessed in the presence of physiological relevant concentrations of soluble CEA.

Materials and Methods

Agonistic function of the ffAC_05337 was evaluated using a CD40 reporter assay (Promega, CD40 Bioassay Kit CS JA2155). The assay was performed according to the manufacturer's protocol. In brief, CD40 reporter cells and titrating concentrations of ffAC_05337 were diluted in RPMI containing 10% FCS and added to the assay plates before the addition of CEA transfected CHO, CHO wt or CEA expressing human tumor cells. In addition, the assay was performed in the presence of 0.5, 1, 5, 25 or 50 ug/ml soluble CEA. The assay plates were incubated for 6 h at 37° C. until addition of Bio-Glo™ Luciferase Assay Detection solution and analyzed in the BMG ELISA plate reader.

Results and Conclusions

Figure 34:
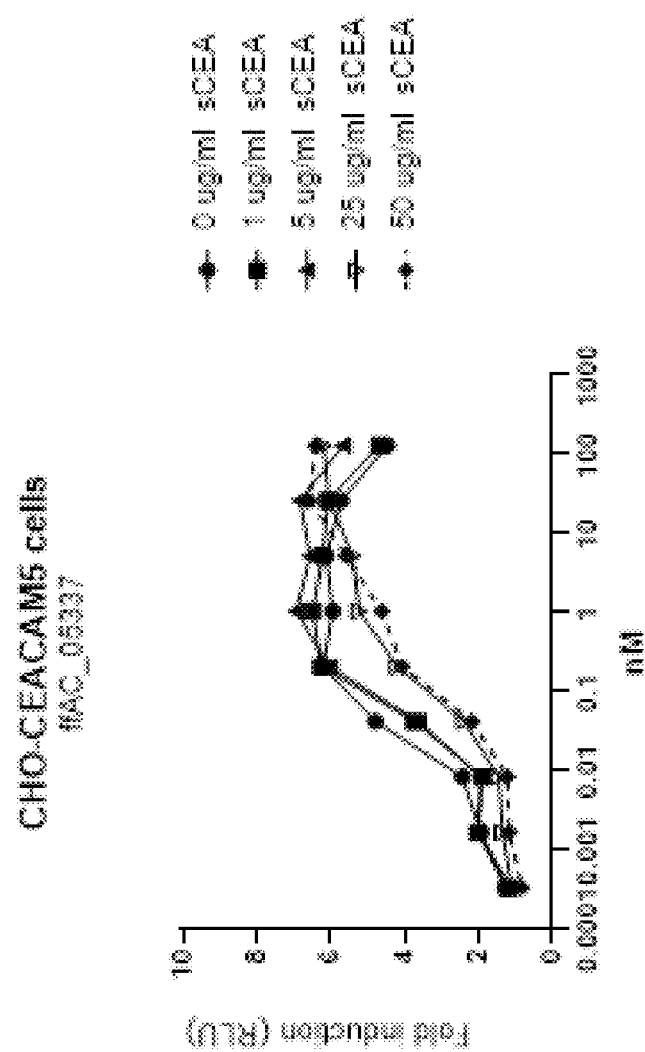
FIG. 34. Effect of the bispecific antibody ffAC_05337 on CD40 reporter cells co-cultured with CEA expressing CHO cells and titrated antibodies in the presence or absence of soluble CEA. The response was calculated as fold induction to background.

The results show that the bispecific antibody ffAC_05337 induce CD40 activation in the presence of CEA and the potency and efficacy is unaffected by the presence of soluble CEA in the cultures (FIGS. 33 and 34). A minor decrease in the efficacy of ffAC_05337 can be observed in the presence of 25 and 50 ug/ml soluble CEA (FIG. 34).

The invention includes, but is not limited to, the embodiments of the following numbered paragraphs:

1. A bispecific polypeptide comprising a first binding domain, designated B1, which is capable of binding specifically to CD40, and a second binding domain, designated B2, which is capable of specifically binding to carcinoembryonic antigen (CEA).

2. The bispecific polypeptide according to paragraph 1, wherein the first and/or second binding domains are/is selected from the group consisting of antibodies and antigen-binding fragments thereof, and CD40 ligands.

3. The bispecific polypeptide according to paragraph 2 wherein the antigen-binding fragment is selected from the group consisting of: Fv fragments (such as a single chain Fv fragment, or a disulphide-bonded Fv fragment), Fab-like fragments (such as a Fab fragment; a Fab' fragment or a F(ab)2 fragment) and domain antibodies.

4. The bispecific polypeptide according to any one of the preceding paragraphs wherein the polypeptide is a bispecific antibody.

5. The bispecific polypeptide according to any one of the preceding paragraphs wherein:
   (a) binding domain B1 and/or binding domain B2 is an intact IgG antibody;
   (b) binding domain B1 and/or binding domain B2 is an Fv fragment;
   (c) binding domain B1 and/or binding domain B2 is a Fab fragment; and/or
   (d) binding domain B1 and/or binding domain B2 is a single domain antibody.

6. The bispecific polypeptide according to paragraph 5, wherein the bispecific antibody comprises a human Fc region or a variant of a said region, where the region is an IgG1, IgG2, IgG3 or IgG4 region, preferably an IgG1 or IgG4 region.

7. The bispecific polypeptide according to paragraph 6, wherein the Fc exhibits no or very low affinity for FcγR.

8. The bispecific polypeptide according to paragraph 7, wherein the Fc region is a variant of a human IgG1 Fc region comprising a mutation at one or more of the following positions: L234, L235, P239, D265, N297 and/or P329.

9. The bispecific polypeptide according to paragraph 8, wherein alanine is present at the mutated position(s).

10. The bispecific polypeptide according to paragraph 9, wherein the Fc region is a variant of a human IgG1 Fc region comprising the double mutations L234A and L235A.

11. The bispecific polypeptide according to any one of paragraphs 4-10, wherein the bispecific antibody is selected from the groups consisting of:
   (a) bivalent bispecific antibodies, such as IgG-scFv bispecific antibodies (for example, wherein B1 is an intact IgG and B2 is an scFv attached to B1 at the N-terminus of a light chain and/or at the C-terminus of a light chain and/or at the N-terminus of a heavy chain and/or at the C-terminus of a heavy chain of the IgG, or vice versa);
   (b) monovalent bispecific antibodies, such as a Duo-Body® or a 'knob-in-hole' bispecific antibody (for example, an scFv-KIH, scFv-KIHr, a BiTE-KIH or a BiTE-KIHr);
   (c) scFv$_2$-Fc bispecific antibodies (for example, ADAP-TIR™ bispecific antibodies);
   (d) BiTE/scFv$_2$ bispecific antibodies;
   (e) DVD-Ig bispecific antibodies;

(f) DART-based bispecific antibodies (for example, DART$_2$-Fc or DART);

(g) DNL-Fab3 bispecific antibodies; and (h) scFv-HSA-scFv bispecific antibodies.

12. The bispecific polypeptide according to paragraph 11, wherein the bispecific antibody is an IgG-scFv bispecific antibody.

13. The bispecific polypeptide according to any one of the preceding paragraphs, wherein binding domain B1 and binding domain B2 are fused directly to each other.

14. The bispecific polypeptide according to any one of the preceding paragraphs, wherein binding domain B1 and binding domain B2 are joined via a polypeptide linker.

15. The bispecific polypeptide according to paragraph 14, wherein the linker is selected from the group consisting of the amino acid sequence SGGGGSGGGGS (SEQ ID NO: 337), SGGGGSGGGGSAP (SEQ ID NO: 338), NFSQP (SEQ ID NO: 339), KRTVA (SEQ ID NO: 340), GGGSGGGG (SEQ ID NO: 341), GGGGSGGGGS (SEQ ID NO: 342), GGGGSGGGGSGGGGS (SEQ ID NO: 343), GSTSGSGKPGSGEGSTKG (SEQ ID NO: 344), THTCPPCPEPKSSDK (SEQ ID NO: 345), GGGS (SEQ ID NO: 346), EAAKEAAKGGGGS (SEQ ID NO: 347), EAAKEAAK (SEQ ID NO: 348), or (SG)m, where m=1 to 7.

16. The bispecific polypeptide according to any one of the preceding paragraphs, wherein one of B1 or B2 is an immunoglobulin molecule, and one of B1 or B2 is a Fab fragment, wherein the Fab fragment is fused to the C-terminus of the heavy chain of the immunoglobulin via the light chain of the Fab fragment.

17. The bispecific polypeptide according to any one of the preceding paragraphs, wherein the bispecific polypeptide comprises one or more mutations to promote association of the heavy chain polypeptide of the immunoglobulin with the light chain polypeptide of the immunoglobulin and/or to promote association of the heavy chain polypeptide of the Fab with the light chain polypeptide of the Fab.

18. The bispecific polypeptide according to paragraph 17, wherein the one or more mutations prevent the formation of aggregates and a Fab by-product.

19. The bispecific polypeptide according to paragraph 17 or 18, wherein the mutations prevent formation of aggregates and Fab by-products by generating steric hindrance and/or incompatibility between charges.

20. The bispecific polypeptide according to any one of paragraphs 17-19, wherein the polypeptide comprises one or more mutation pairs each comprising two functionally compatible mutations.

21. The bispecific polypeptide according to any one of the preceding paragraphs, wherein the polypeptide can modulate the activity of and/or activate myeloid cells.

22. The bispecific polypeptide according to any one of the preceding paragraphs, wherein the polypeptide is incapable of inducing antibody-dependent cell cytotoxicity (ADCC), antibody-dependent cellular phagocytosis (ADCP) and/or complement-dependent cytotoxicity (CDC).

23. The bispecific polypeptide according to any one of the preceding paragraphs, wherein the polypeptide is capable of inducing tumour immunity.

24. The bispecific polypeptide according to any one of the preceding paragraphs, wherein the polypeptide is capable of inducing:

(a) tumour-specific immune activation; and/or (b) activation of dendritic cells; and/or (c) internalisation of associated tumour debris and/or extracellular vesicles containing CEA antigens as well as tumour neoantigens; and/or (d) cross-presentation of peptides derived from internalised tumour antigens on MHC; and/or (e) priming and activation of effector T cells; and/or (f) direct tumoricidal effects, selected from the list consisting of: apoptosis, necroptosis, antibody-dependent cellular cytotoxicity (ADCC) and complement-dependent cytotoxicity (CDC).

25. The bispecific polypeptide according to any one of the preceding paragraphs, wherein the bispecific polypeptide is capable of:

(a) activation of a B-cell, in the presence of a CEA; and/or (b) activation of dendritic cells in the presence of CEA; and/or (c) capable of increased dendritic cell cross-presentation of neoantigens; and/or (d) inducing proliferation of neoantigen specific T cells.

26. The bispecific polypeptide according to any one of the preceding paragraphs, wherein the bispecific polypeptide promotes uptake of tumor derived material, derived from tumor cells overexpressing CEA.

27. The bispecific polypeptide according to any one of the preceding paragraphs, wherein the B-cell activation is characterised by CD86 upregulation.

28. The bispecific polypeptide according to any one of the preceding paragraphs wherein binding domain B1 binds to human CD40 with a $K_D$ of less than $2\times10^{-7}$M or less than $1.5\times10^{-7}$M or less than $8.5\times10^{-8}$M or less than $8\times10^{-8}$M or less than $7.5\times10^{-8}$M or less than $7\times10^{-8}$M or less than $9\times10^{-8}$M or less than $9\times10^{-9}$M or less than $5\times10^{-10}$M or less than $3\times10^{-10}$M, preferably less than $8.5\times10^{-8}$M, more preferably less than $5\times10^{-10}$M or less than $3\times10^{-10}$M.

29. The bispecific polypeptide according to any one of the preceding paragraphs, wherein binding domain B1 comprises one or more heavy chain CDR sequences selected from those in Table C(1) and/or wherein binding domain B1 comprises one or more light chain CDR sequences selected from those in Table C(2).

30. The bispecific polypeptide according to any one of the preceding paragraphs, wherein binding domain B1 comprises one, two or three light chain CDR sequences from a particular row for an individual antibody reference in Table C(2), and/or one, two or three heavy chain CDR sequences from the corresponding row for the antibody with the same reference in Table C(1).

31. The bispecific polypeptide according to any one of the preceding paragraphs wherein binding domain B1 comprises all three heavy chain CDR sequences of a particular antibody reference as shown in Table C(1), and/or all three light chain CDR sequences of an antibody reference as shown in Table C(2), or wherein binding domain B1 comprises a heavy chain VH sequence and/or a light chain VL sequence as shown in Table A.

32. The bispecific polypeptide according to any one of the preceding paragraphs, wherein B1 comprises any one, two, three, four, five or all six features independently selected from the following:

(a) a heavy chain CDR1 sequence which consists of the sequence "G, F, T, F, S, S, Y, A";

(b) a heavy chain CDR2 sequence which is 8 amino acids in length and comprises the consensus sequence: "I, G/S, S/G, Y/S, G/S, G/S, G/Y/S, T";

(c) a heavy chain CDR3 sequence which is 9 to 12 amino acids in length and which comprises the consensus sequence of: "A, R, Y/R/G, Y/P/V/-, N/S/V, F/Y/W, G/H/S, -/S, -/V, M/F, D, Y"
(d) a light chain CDR1 sequence which consists of the sequence: "Q, S, I, S, S, Y";
(e) a light chain CDR2 sequence which consists of the sequence: "A, A, S";
(f) a light chain CDR3 sequence which is 9 amino acids in length and comprises the consensus sequence: "Q, Q, Y/S, G/Y, R/S/V, N/A/Y/T, P, P/F/Y, T".

33. A bispecific polypeptide according to any one of the preceding paragraphs wherein binding domain B1 comprises:
(a) the three CDRs of the heavy chain and/or the three CDRs of the light chain of antibody 1132/1133 (SEQ ID NOs: 73, 74 and 75; and/or 90 and 92, and AAS); or
(b) the three CDRs of the heavy chain and/or the three CDRs of the light chain of antibody 1107/1108 (SEQ ID NOs: 73, 78 and 80; and/or SEQ ID NOs: 90 and 95, and AAS); or
(c) the three CDRs of the heavy chain and/or the three CDRs of the light chain of antibody 1150/1151 (SEQ ID NOs: 73, 76 and 77; and/or SEQ ID NOs: 90 and 93, and AAS); or
(d) the three CDRs of the heavy chain and/or the three CDRs of the light chain of antibody 1140/1135 (SEQ ID NOs: 73, 78 and 79; and/or SEQ ID NOs: 90 and 94, and AAS); or
(e) the three CDRs of the heavy chain and/or the three CDRs of the light chain of antibody G12 or G12_mut or ffAC_05337 (SEQ ID NOs: 81, 82 and 83; and/or SEQ ID NOs: 96 and 98, and GNI); or
(f) the three CDRs of the heavy chain and/or the three CDRs of the light chain of antibody APX005 (SEQ ID NOs: 84, 85 and 86; and/or SEQ ID NOs: 99 and 101, and RAS); or
(g) the three CDRs of the heavy chain and/or the three CDRs of the light chain of antibody 21.4.1 (SEQ ID NOs: 87, 88 and 89; and/or SEQ ID NOs: 102 and 104, and TAS).

34. The bispecific polypeptide according to any one of the preceding paragraphs wherein binding domain B1 comprises:
(a) the heavy chain variable region and/or the light chain variable region of antibody 1132/1133 (SEQ ID NOs: 3 and 1); or
(b) the heavy chain variable region and/or the light chain variable region of antibody 1107/1108 (SEQ ID NOs: 15 and 13); or
(c) the heavy chain variable region and/or the light chain variable region of antibody 1150/1151 (SEQ ID NOs: 7 and 5); or
(d) the heavy chain variable region and/or the light chain variable region of antibody 1140/1135 (SEQ ID NOs: 11 and 9); or
(e) the heavy chain variable region and/or the light chain variable region of antibody G12 (SEQ ID NOs: 19 and 17); or
(f) the heavy chain variable region and/or the light chain variable region of antibody APX005 (SEQ ID NOs: 23 and 21); or
(g) the heavy chain variable region and/or the light chain variable region of antibody 21.4.1 (SEQ ID NOs: 27 and 25); or
(h) the heavy chain variable region and/or the light chain variable region of antibody G12_mut (SEQ ID NOs: 29 and 17); or
(i) the heavy chain variable region and/or the light chain variable region of antibody ffAC_05337 (SEQ ID NOs: 431 and 430).

35. The bispecific polypeptide according to any one of the preceding paragraphs wherein binding domain B1 comprises the light chain of antibody 1132/1133 (SEQ ID NO: 372 or 379) and/or the heavy chain of antibody 1132/1133 (SEQ ID NO: 371 or 378).

36. The bispecific polypeptide according to any one of the preceding paragraphs wherein binding domain B1 comprises the light chain of antibody G12 (SEQ ID NO: 381) and/or the heavy chain of antibody G12 (SEQ ID NO: 380) or the light chain of antibody G12_mut (SEQ ID NO: 383) and/or the heavy chain of antibody G12_mut (SEQ ID NO: 382).

37. The bispecific polypeptide according to any one of the preceding paragraphs wherein binding domain B1 comprises the light chain of antibody ffAC_05337 (SEQ ID NO: 430) and/or the heavy chain of antibody ffAC_05337 (SEQ ID NO: 431).

38. The bispecific polypeptide according to any one of the preceding paragraphs, wherein the CEA is a tumor-associated CEA.

39. The bispecific polypeptide according to any one of the preceding paragraphs, wherein the CEA is a carcinoembryonic antigen-related cell adhesion molecule (CEACAM).

40. The bispecific polypeptide according to paragraph 39, wherein the CEACAM is one or more selected from the listing consisting of: CEACAM1; CEACAM6; and CEACAM5.

41. The bispecific polypeptide according to paragraph 40, wherein the CEACAM is CEACAM5.

42. The bispecific polypeptide according to any one of the preceding paragraphs, wherein B2 which is capable of specifically binding to CEA on a target cell.

43. The bispecific polypeptide according to paragraph 42, wherein the target cell is a cancer cell and/or a tumour cell.

44. The bispecific polypeptide according to paragraph 43, wherein the CEA on the target cell is an intermediate level of CEA or a high level of CEA.

45. The bispecific polypeptide according to paragraph 44, wherein the intermediate level of CEA is characterised by the target cell expressing about 10,000 or more CEA receptors per target cell, preferably about 50,000 or more CEA receptors per target cell.

46. The bispecific polypeptide according to paragraph 44, wherein the high level of CEA is characterised by the target cell expressing about 200,000 of more CEA receptors per target cell, preferably about 300,000 of more CEA receptors per target cell.

47. The bispecific polypeptide according to any one of the preceding paragraphs wherein binding domain B2 binds to human CEA with a $K_D$ of less than $2 \times 10^{-6}$ M or less than $1.5 \times 10^{-8}$ M or less than $2.5 \times 10^{-9}$ M or less than $2 \times 10^{-9}$ M or less than $1.5 \times 10^{-12}$ M or less than $1 \times 10^{-12}$ M, preferably less than $1.5 \times 10^{-8}$ M or less than $2.5 \times 10^{-9}$ M or less than $1.5 \times 10^{-12}$ M.

48. The bispecific polypeptide according to any one of the preceding paragraphs wherein binding domain B2 binds preferentially to CEA on a cell over soluble CEA.

49. The bispecific polypeptide according to any one of the preceding paragraphs, wherein binding domain B2 comprises one or more heavy chain CDR sequences selected from those in Table D(1a) and/or Table D(1b) and/or wherein binding domain B2 comprises one or more light chain CDR sequences selected from those in Table D(2).

50. The bispecific polypeptide according to any one of the preceding paragraphs, wherein binding domain B2 comprises one, two or three light chain CDR sequences from a particular row for an individual antibody reference in Table D(2), and/or one, two or three heavy chain CDR sequences from the corresponding row for the antibody with the same reference in Table D(1a) and/or Table D(1b).

51. The bispecific polypeptide according to any one of the preceding paragraphs wherein binding domain B2 comprises all three heavy chain CDR sequences of a particular antibody reference as shown in Table D(1a) and/or Table D(1b), and/or all three light chain CDR sequences of an antibody reference as shown in Table D(2), or wherein binding domain B1 comprises a heavy chain VH sequence and/or a light chain VL sequence as shown in Table B.

52. The bispecific polypeptide according to any one of the preceding paragraphs, wherein B2 comprises any one, two, three, four, five or all six features independently selected from the following:
   (a) a heavy chain CDR1 sequence which consists of the sequence: "G, F, T, F, S, S, S, Y" or which comprises the consensus sequence of: "G, F, T, F, G/S, S, Y, Y/A";
   (b) a heavy chain CDR2 sequence which consists of the sequence: "I, G, S, G, S, Y, S, T" or which comprises the consensus sequence of: "I, S, G, Y/S, G, Y/G, S, T";
   (c) a heavy chain CDR3 sequence which comprises the consensus sequence of: "A, R, Y, P, S, V, P/L, F, P, Q, S, P/H/L, H/P/L, L/F/V/W, D, Y" or which comprises the consensus sequence of: "A, R, H/Y, G, Y, G/S/T, V/H, L/F, D, Y";
   (d) a light chain CDR1 sequence which consists of the sequence: "Q, S, I, S, S, Y" or which comprises the consensus sequence of: "Q, S, I, R/S, S, Y";
   (e) a light chain CDR2 sequence which consists of the sequence: "A, A, S";
   (f) a light chain CDR3 sequence which consists of the sequence: "Q, Q, A, G, N, P, H, T" or which comprises the consensus sequence of: "Q, Q, G/Y, T/P/A, W/-, Y/-, F/V, P, F/Y, T".

53. A bispecific polypeptide according to any one of the preceding paragraphs wherein binding domain B2 comprises:
   (a) the three CDRs of the heavy chain and/or the three CDRs of the light chain of antibody AC_05059 (SEQ ID NOs: 216, 217 and 218 or 280, 281 and 218 and/or SEQ ID NOs: 90 and 311, and AAS)
   (b) the three CDRs of the heavy chain and/or the three CDRs of the light chain of antibody AC_05060 (SEQ ID NOs: 219, 220 and 221 or 282, 283 and 221 and/or SEQ ID NOs: 312 and 313, and AAS)
   (c) the three CDRs of the heavy chain and/or the three CDRs of the light chain of antibody AC_05061 (SEQ ID NOs: 222, 223 and 224 or 284, 285 and 224 and/or SEQ ID NOs: 90 and 314, and AAS)
   (d) the three CDRs of the heavy chain and/or the three CDRs of the light chain of antibody AC_05062 (SEQ ID NOs: 222, 223 and 225 or 284, 285 and 225 and/or SEQ ID NOs: 315 and 94, and SAS)
   (e) the three CDRs of the heavy chain and/or the three CDRs of the light chain of antibody AC_05064 (SEQ ID NOs: 222, 223 and 226 or 284, 285 and 226 and/or SEQ ID NOs: 90 and 317, and AAS)
   (f) the three CDRs of the heavy chain and/or the three CDRs of the light chain of antibody AC_05079 (SEQ ID NOs: 216, 217 and 227 or 280, 281 and 227 and/or SEQ ID NOs: 90 and 311, and AAS)
   (g) the three CDRs of the heavy chain and/or the three CDRs of the light chain of antibody AC_05080 (SEQ ID NOs: 216, 217 and 228 or 280, 281 and 228 and/or SEQ ID NOs: 90 and 311, and AAS)
   (h) the three CDRs of the heavy chain and/or the three CDRs of the light chain of antibody AC_05081 (SEQ ID NOs: 216, 217 and 229 or 280, 281 and 229 and/or SEQ ID NOs: 90 and 311, and AAS)
   (i) the three CDRs of the heavy chain and/or the three CDRs of the light chain of antibody AC_05082 (SEQ ID NOs: 222, 223 and 230 or 284, 285 and 230 and/or SEQ ID NOs: 90 and 311, and AAS)
   (j) the three CDRs of the heavy chain and/or the three CDRs of the light chain of antibody AC_05083 (SEQ ID NOs: 222, 223 and 231 or 284, 285 and 231 and/or SEQ ID NOs: 318 and 319, and AAS)
   (k) the three CDRs of the heavy chain and/or the three CDRs of the light chain of antibody AC_05084 (SEQ ID NOs: 222, 223 and 232 or 284, 285 and 232 and/or SEQ ID NOs: 90 and 320, and AAS)
   (l) the three CDRs of the heavy chain and/or the three CDRs of the light chain of antibody AC_05085 (SEQ ID NOs: 219, 233 and 234 or 286, 287 and 234 and/or SEQ ID NOs: 90 and 311, and AAS)
   (m) the three CDRs of the heavy chain and/or the three CDRs of the light chain of antibody AC_05086 (SEQ ID NOs: 216, 217 and 235 or 280, 281 and 235 and/or SEQ ID NOs: 90 and 311, and AAS)
   (n) the three CDRs of the heavy chain and/or the three CDRs of the light chain of antibody AC_05087 (SEQ ID NOs: 216, 217 and 236 or 280, 281 and 236 and/or SEQ ID NOs: 90 and 311, and AAS)
   (o) the three CDRs of the heavy chain and/or the three CDRs of the light chain of antibody AC_05088 (SEQ ID NOs: 216, 217 and 237 or 280, 281 and 237 and/or SEQ ID NOs: 90 and 311, and AAS)
   (p) the three CDRs of the heavy chain and/or the three CDRs of the light chain of antibody AC_05089 (SEQ ID NOs: 216, 217 and 238 or 280, 281 and 238 and/or SEQ ID NOs: 90 and 311, and AAS)
   (q) the three CDRs of the heavy chain and/or the three CDRs of the light chain of antibody AC_05090 or ffAC_05337 (SEQ ID NOs: 216, 217 and 239 or 280, 281 and 239 and/or SEQ ID NOs: 90 and 311, and AAS)
   (r) the three CDRs of the heavy chain and/or the three CDRs of the light chain of antibody AC_05091 (SEQ ID NOs: 216, 217 and 240 or 280, 281 and 240 and/or SEQ ID NOs: 90 and 311, and AAS)
   (s) the three CDRs of the heavy chain and/or the three CDRs of the light chain of antibody AC_05092 (SEQ ID NOs: 216, 217 and 218 or 280, 281 and 218 and/or SEQ ID NOs: 321 and 311, and AAS)
   (t) the three CDRs of the heavy chain and/or the three CDRs of the light chain of antibody AC_05093 (SEQ ID NOs: 216, 217 and 241 or 280, 281 and 241 and/or SEQ ID NOs: 90 and 311, and AAS)
   (u) the three CDRs of the heavy chain and/or the three CDRs of the light chain of antibody AC_05094 (SEQ ID NOs: 216, 217 and 242 or 280, 281 and 242 and/or SEQ ID NOs: 90 and 311, and AAS)
   (v) the three CDRs of the heavy chain and/or the three CDRs of the light chain of antibody AC_05095 (SEQ ID NOs: 216, 217 and 243 or 280, 281 and 243 and/or SEQ ID NOs: 90 and 311, and AAS)
   (w) the three CDRs of the heavy chain and/or the three CDRs of the light chain of antibody AC_05096 (SEQ ID NOs: 216, 217 and 244 or 280, 281 and 244 and/or SEQ ID NOs: 90 and 311, and AAS)
(x) the three CDRs of the heavy chain and/or the three CDRs of the light chain of antibody AC_05097 (SEQ ID NOs: 217, 216 and 245 or 280, 281 and 245 and/or SEQ ID NOs: 90 and 311, and AAS)
(y) the three CDRs of the heavy chain and/or the three CDRs of the light chain of antibody AC_05098 (SEQ ID NOs: 219, 220 and 246 or 282, 283 and 246 and/or SEQ ID NOs: 312 and 313, and AAS)
(z) the three CDRs of the heavy chain and/or the three CDRs of the light chain of antibody AC_05099 (SEQ ID NOs: 222, 223 and 224 or 288, 285 and 224 and/or SEQ ID NOs: 90 and 311, and AAS)
(aa) the three CDRs of the heavy chain and/or the three CDRs of the light chain of antibody AC_05100 (SEQ ID NOs: 222, 223 and 247 or 288, 285 and 247 and/or SEQ ID NOs: 90 and 311, and AAS)
(ab) the three CDRs of the heavy chain and/or the three CDRs of the light chain of antibody Fab1 (SEQ ID NOs: 248, 249 and 250 or 289, 290 and 250 and/or SEQ ID NOs: 90 and 322, and AAS)
(ac) the three CDRs of the heavy chain and/or the three CDRs of the light chain of antibody Fab2 (SEQ ID NOs: 251, 252 and 253 or 291, 292 and 253 and/or SEQ ID NOs: 90 and 323, and AAS)
(ad) the three CDRs of the heavy chain and/or the three CDRs of the light chain of antibody Fab3 (SEQ ID NOs: 254, 255 and 256 or 293, 294 and 256 and/or SEQ ID NOs: 324 and 326, and GAS)
(ae) the three CDRs of the heavy chain and/or the three CDRs of the light chain of antibody Fab4 (SEQ ID NOs: 257, 258 and 259 or 295, 296 and 259 and/or SEQ ID NOs: 90 and 327, and AAS)
(af) the three CDRs of the heavy chain and/or the three CDRs of the light chain of antibody Fab5 (SEQ ID NOs: 260, 261 and 262 or 297, 298 and 262 and/or SEQ ID NOs: 324 and 328, and GAS)
(ag) the three CDRs of the heavy chain and/or the three CDRs of the light chain of antibody Fab6 (SEQ ID NOs: 263, 264 and 265 or 299, 300 and 265 and/or SEQ ID NOs: 324 and 329, and GAS)
(ah) the three CDRs of the heavy chain and/or the three CDRs of the light chain of antibody Fab7 (SEQ ID NOs: 266, 267 and 268 or 301, 302 and 268 and/or SEQ ID NOs: 90 and 330, and AAS)
(ai) the three CDRs of the heavy chain and/or the three CDRs of the light chain of antibody Fab8 (SEQ ID NOs: 269, 270 and 271 or 303, 304 and 271 and/or SEQ ID NOs: 90 and 331, and AAS)
(aj) the three CDRs of the heavy chain and/or the three CDRs of the light chain of antibody Fab9 (SEQ ID NOs: 272, 335 and 273 or 305, 306 and 273 and/or SEQ ID NOs: 90 and 332, and AAS)
(ak) the three CDRs of the heavy chain and/or the three CDRs of the light chain of antibody Fab10 (SEQ ID NOs: 274, 275 and 276 or 307, 308 and 276 and/or SEQ ID NOs: 90 and 333, and AAS) and/or
(al) the three CDRs of the heavy chain and/or the three CDRs of the light chain of antibody Fab11 (SEQ ID NOs: 277, 278 and 279 or 309, 310 and 279 and/or SEQ ID NOs: 324 and 334, and GAS).

54. The bispecific polypeptide according to any one of the preceding paragraphs wherein binding domain B2 comprises:

(a) the heavy chain variable region and/or the light chain variable region of antibody AC_05059 (SEQ ID NO: 33 and/or SEQ ID NO: 31)
(b) the heavy chain variable region and/or the light chain variable region of antibody AC_05060 (SEQ ID NO: 37 and/or SEQ ID NO: 35)
(c) the heavy chain variable region and/or the light chain variable region of antibody AC_05061 (SEQ ID NO: 41 and/or SEQ ID NO: 39)
(d) the heavy chain variable region and/or the light chain variable region of antibody AC_05062 (SEQ ID NO: 45 and/or SEQ ID NO: 43)
(e) the heavy chain variable region and/or the light chain variable region of antibody AC_05064 (SEQ ID NO: 49 and/or SEQ ID NO: 47)
(f) the heavy chain variable region and/or the light chain variable region of antibody AC_05079 (SEQ ID NO: 53 and/or SEQ ID NO: 51)
(g) the heavy chain variable region and/or the light chain variable region of antibody AC_05080 (SEQ ID NO: 57 and/or SEQ ID NO: 55)
(h) the heavy chain variable region and/or the light chain variable region of antibody AC_05081 (SEQ ID NO: 61 and/or SEQ ID NO: 59)
(i) the heavy chain variable region and/or the light chain variable region of antibody AC_05082 (SEQ ID NO: 65 and/or SEQ ID NO: 63)
(j) the heavy chain variable region and/or the light chain variable region of antibody AC_05083 (SEQ ID NO: 69 and/or SEQ ID NO: 67)
(k) the heavy chain variable region and/or the light chain variable region of antibody AC_05084 (SEQ ID NO: 106 and/or SEQ ID NO: 71)
(l) the heavy chain variable region and/or the light chain variable region of antibody AC_05085 (SEQ ID NO: 110 and/or SEQ ID NO: 108)
(m) the heavy chain variable region and/or the light chain variable region of antibody AC_05086 (SEQ ID NO: 114 and/or SEQ ID NO: 112)
(n) the heavy chain variable region and/or the light chain variable region of antibody AC_05087 (SEQ ID NO: 118 and/or SEQ ID NO: 116)
(o) the heavy chain variable region and/or the light chain variable region of antibody AC_05088 (SEQ ID NO: 122 and/or SEQ ID NO: 120)
(p) the heavy chain variable region and/or the light chain variable region of antibody AC_05089 (SEQ ID NO: 126 and/or SEQ ID NO: 124)
(q) the heavy chain variable region and/or the light chain variable region of antibody AC_05090 (SEQ ID NO: 130 and/or SEQ ID NO: 128)
(r) the heavy chain variable region and/or the light chain variable region of antibody AC_05091 (SEQ ID NO: 134 and/or SEQ ID NO: 132)
(s) the heavy chain variable region and/or the light chain variable region of antibody AC_05092 (SEQ ID NO: 138 and/or SEQ ID NO: 136)
(t) the heavy chain variable region and/or the light chain variable region of antibody AC_05093 (SEQ ID NO: 142 and/or SEQ ID NO: 140)
(u) the heavy chain variable region and/or the light chain variable region of antibody AC_05094 (SEQ ID NO: 146 and/or SEQ ID NO: 144)
(v) the heavy chain variable region and/or the light chain variable region of antibody AC_05095 (SEQ ID NO: 150 and/or SEQ ID NO: 148)

(w) the heavy chain variable region and/or the light chain variable region of antibody AC_05096 (SEQ ID NO: 154 and/or SEQ ID NO: 152)
(x) the heavy chain variable region and/or the light chain variable region of antibody AC_05097 (SEQ ID NO: 158 and/or SEQ ID NO: 156)
(y) the heavy chain variable region and/or the light chain variable region of antibody AC_05098 (SEQ ID NO: 162 and/or SEQ ID NO: 160)
(z) the heavy chain variable region and/or the light chain variable region of antibody AC_05099 (SEQ ID NO: 166 and/or SEQ ID NO: 164)
(aa) the heavy chain variable region and/or the light chain variable region of antibody AC_05100 (SEQ ID NO: 170 and/or SEQ ID NO: 168)
(ab) the heavy chain variable region and/or the light chain variable region of antibody Fab1 (SEQ ID NO: 174 and/or SEQ ID NO: 172)
(ac) the heavy chain variable region and/or the light chain variable region of antibody Fab2 (SEQ ID NO: 178 and/or SEQ ID NO: 176)
(ad) the heavy chain variable region and/or the light chain variable region of antibody Fab3 (SEQ ID NO: 182 and/or SEQ ID NO: 180)
(ae) the heavy chain variable region and/or the light chain variable region of antibody Fab4 (SEQ ID NO: 186 and/or SEQ ID NO: 184)
(af) the heavy chain variable region and/or the light chain variable region of antibody Fab5 (SEQ ID NO: 190 and/or SEQ ID NO: 188)
(ag) the heavy chain variable region and/or the light chain variable region of antibody Fab6 (SEQ ID NO: 194 and/or SEQ ID NO: 192)
(ah) the heavy chain variable region and/or the light chain variable region of antibody Fab7 (SEQ ID NO: 198 and/or SEQ ID NO: 196)
(ai) the heavy chain variable region and/or the light chain variable region of antibody Fab8 (SEQ ID NO: 202 and/or SEQ ID NO: 200)
(aj) the heavy chain variable region and/or the light chain variable region of antibody Fab9 (SEQ ID NO: 206 and/or SEQ ID NO: 204)
(ak) the heavy chain variable region and/or the light chain variable region of antibody Fab10 (SEQ ID NO: 210 and/or SEQ ID NO: 208)
(al) the heavy chain variable region and/or the light chain variable region of antibody Fab11 (SEQ ID NO: 214 and/or SEQ ID NO: 212)
(am) the heavy chain variable region and/or the light chain variable region of antibody mAb2 (SEQ ID NO: 387 and/or SEQ ID NO: 385) and/or
(an) the heavy chain variable region and/or the light chain variable region of antibody ffAC_05337 (SEQ ID NO: 433 and/or SEQ ID NO: 432).

55. The bispecific polypeptide according to any one of the preceding paragraphs wherein binding domain B2 comprises:
(a) the light chain and/or the heavy chain of antibody AC_05059 (SEQ ID NO: 388 and/or SEQ ID NO: 389)
(b) the light chain and/or the heavy chain of antibody AC_05060 (SEQ ID NO: 390 and/or SEQ ID NO: 391)
(c) the light chain and/or the heavy chain of antibody AC_05061 (SEQ ID NO: 392 and/or (SEQ ID NO: 393)
(d) the light chain and/or the heavy chain of antibody AC_05062 (SEQ ID NO: 394 and/or SEQ ID NO: 395)
(e) the light chain and/or the heavy chain of antibody AC_05064 (SEQ ID NO: 396 and/or SEQ ID NO: 397)
(f) the light chain and/or the heavy chain of antibody AC_05079 (SEQ ID NO: 398 and/or SEQ ID NO: 399)
(g) the light chain and/or the heavy chain of antibody AC_05081 (SEQ ID NO: 400 and/or SEQ ID NO: 401)
(h) the light chain and/or the heavy chain of antibody AC_05088 (SEQ ID NO: 402 and/or SEQ ID NO: 403)
(i) the light chain and/or the heavy chain of antibody AC_05089 (SEQ ID NO: 404 and/or SEQ ID NO: 405)
(j) the light chain and/or the heavy chain of antibody AC_05090 (SEQ ID NO: 406 and/or SEQ ID NO: 407)
(k) the light chain and/or the heavy chain of antibody AC_05091 (SEQ ID NO: 408 and/or SEQ ID NO: 409)
(l) the light chain and/or the heavy chain of antibody AC_05093 (SEQ ID NO: 410 and/or SEQ ID NO: 411)
(m) the light chain and/or the heavy chain of antibody AC_05094 (SEQ ID NO: 412 and/or SEQ ID NO: 413)
(n) the light chain and/or the heavy chain of antibody AC_05096 (SEQ ID NO: 414 and/or SEQ ID NO: 415)
(o) the light chain and/or the heavy chain of antibody AC_05097 (SEQ ID NO: 416 and/or SEQ ID NO: 417)
(p) the light chain and/or the heavy chain of antibody Fab1 (SEQ ID NO: 418 and/or SEQ ID NO: 419)
(q) the light chain and/or the heavy chain of antibody Fab3 (SEQ ID NO: 420 and/or
(SEQ ID NO: 421).

56. The bispecific polypeptide according to any one of the preceding paragraphs wherein the bispecific polypeptide:
comprises a Chain H1 comprising a sequence selected from the listing consisting of: SEQ ID NO: 359; SEQ ID NO: 362; SEQ ID NO: 365; and/or SEQ ID NO: 367; and/or
comprises a Chain L1 comprising a sequence selected from the listing consisting of: SEQ ID NO: 360; SEQ ID NO: 363; SEQ ID NO: 372; and/or SEQ ID NO: 368; and/or
comprises a Chain H2 comprising a sequence selected from the listing consisting of: SEQ ID NO: 361; SEQ ID NO: 364; SEQ ID NO: 366; and/or SEQ ID NO: 369.

57. A polypeptide comprising a binding domain, designated B2, as defined in any one of paragraphs 1 to 56, which is capable of specifically binding to CEA.

58. A bispecific polypeptide comprising a first binding domain, designated B3, which is capable of binding specifically to a target antigen that is not CD40, and a second binding domain, designated B2, as defined in any of paragraph 1 to 57, which is capable of specifically binding to CEA.

59. An isolated nucleic acid molecule encoding a bispecific polypeptide according to any one of paragraphs 1-56 or 58 or a polypeptide according to paragraph 57, or a component polypeptide chain thereof.

60. The nucleic acid molecule according to paragraph 59 wherein the molecule is a cDNA molecule.

61. The nucleic acid molecule according to paragraph 59 or 60 encoding an antibody heavy chain or variable region thereof.

62. The nucleic acid molecule according to any one of paragraphs 59 to 61 encoding an antibody light chain or variable region thereof.

63. The vector comprising a nucleic acid molecule according to any one of paragraphs 59 to 62.

64. The vector according to paragraph 63 wherein the vector is an expression vector.

65. A recombinant host cell comprising a nucleic acid molecule according to any one of paragraphs 59 to 62 or a vector according to paragraph 63 or 64.

66. The host cell according to paragraph 65 wherein the host cell is a bacterial cell.

67. The host cell according to paragraph 65 wherein the host cell is a mammalian cell.

68. The host cell according to paragraph 67 wherein the host cell is a human cell.

69. A method for producing bispecific polypeptide according to any one of paragraphs 1-56 or 58 or a polypeptide according to paragraph 57, the method comprising culturing a host cell as defined in any one of paragraphs 65 to 68 under conditions which permit expression of the bispecific polypeptide or component polypeptide chain thereof.

70. A pharmaceutical composition comprising an effective amount of bispecific polypeptide according to any one of paragraphs 1-56 or 58 or an effective amount of a polypeptide according to paragraph 59, and a pharmaceutically-acceptable diluent, carrier or excipient.

71. The pharmaceutical composition according to paragraph 70 adapted for parenteral delivery.

72. The pharmaceutical composition according to paragraph 70 adapted for intravenous delivery.

73. A bispecific polypeptide according to any one of paragraphs 1-56 or 58 or a polypeptide according to paragraph 57, for use in medicine.

74. A bispecific polypeptide according to any one of paragraphs 1-56 or 58 or a polypeptide according to paragraph 57, for use in treating cancer and/or a tumour and/or a non-cancer condition in a subject.

75. Use of a bispecific polypeptide according to any one of paragraphs 1-56 or 58 or a polypeptide according to paragraph 57, in the preparation of a medicament for treating a cancer and/or a tumour and/or a non-cancer condition in a subject.

76. The bispecific polypeptide or polypeptide for use according to paragraph 74 or the use according to paragraph 75, wherein the polypeptide is for use in combination with one or more additional therapeutic agents.

77. The bispecific polypeptide or polypeptide for use according to paragraph 76 or the use according to paragraph 76, wherein the one or more additional therapeutic agents is/are an immunotherapeutic agent that binds a target selected from the group consisting of PD-1/PD-L1, VGFR, EGFR, HER2, CTLA-4, CD137, OX40, GITR, LAG3, TIM3, CD27, VISTA and KIR.

78. The bispecific polypeptide or polypeptide for use according to any one of paragraphs 74, 76 or 77 or the use according to any one of paragraphs 75-77, for administration systemically.

79. A method for the treatment and/or diagnosis of a cancer and/or a tumour and/or a non-cancer condition in a subject, comprising the step of administering to the subject an effective amount of a bispecific polypeptide according to any one of paragraphs 1-56 or 58 or a polypeptide according to paragraph 57.

80. A method according to paragraph 79, wherein the method comprises administering the bispecific polypeptide systemically or the polypeptide systemically.

81. A method according to paragraph 79 or 80, further comprising administering to the subject one or more additional therapeutic agents.

82. A method according to paragraph 81, wherein the one or more additional therapeutic agents is/are an immunotherapeutic agent that binds a target selected from the group consisting of PD-1/PD-L1, VGFR, EGFR, HER2, CTLA-4, CD137, OX40, GITR, LAG3, TIM3, CD27 and KIR.

83. The bispecific polypeptide or polypeptide for use according to any one of paragraphs 74 or 76-78, the use according to any one of paragraphs 75-78, or the method according to any one of paragraphs 80-83, wherein the cancer and/or the tumour comprises target cells comprising expression of CEA.

84. The bispecific polypeptide or polypeptide for use according to paragraph 83, the use according to paragraph 83, or the method according to paragraph 83, wherein the expression of CEA is an intermediate level of CEA expression or a high level of CEA expression.

85. The bispecific polypeptide or polypeptide for use according to paragraph 84, the use according to paragraph 84, or the method according to paragraph 84, wherein the intermediate level of CEA expression is characterised by the target cell expressing about 10,000 or more CEA receptors per target cell, preferably about 50,000 or more CEA receptors per target cell.

86. The bispecific polypeptide or polypeptide for use according to paragraph 84, the use according to paragraph 84, or the method according to paragraph 84, wherein the high level of CEA expression is characterised by the target cell expressing about 200,000 of more CEA receptors per target cell, preferably about 300,000 of more CEA receptors per target cell.

87. The bispecific polypeptide or polypeptide for use according to any one of paragraphs 74 or 76-86, the use according to any one of paragraphs 75-86, or the method according to any one of paragraphs 79-86, wherein the cancer and/or the tumour is one or more cancer and/or tumour selected from the list consisting of: prostate cancer and/or a prostate tumour; breast cancer and/or a breast tumour; lung cancer and/or a lung tumour; colorectal cancer and/or a colorectal tumour; melanomas; bladder cancer and/or a bladder tumour; brain/CNS cancer and/or a brain/CNS tumour; cervical cancer and/or a cervical tumour; oesophageal cancer and/or a oesophageal tumour; gastric cancer and/or a gastric tumour; head/neck cancer and/or a head/neck tumour; kidney cancer and/or a kidney tumour; liver cancer and/or a liver tumour; carcinoma; leukaemia; lymphomas; ovarian cancer and/or an ovarian tumour; pancreatic cancer and/or a pancreatic tumour; tonsil cancer and/or a tonsil tumour; and sarcomas.

88. The bispecific polypeptide or polypeptide for use according to paragraph 87, the use according to paragraph 87, or the method according to paragraph 87, wherein the one or more cancer and/or tumour selected from the list consisting of: breast cancer and/or a breast tumour; lung cancer and/or a lung tumour; colorectal cancer and/or a colorectal tumour; gastric cancer and/or a gastric tumour; and/or pancreatic cancer and/or a pancreatic tumour.

89. The bispecific polypeptide or polypeptide for use according to any one of paragraphs 74 or 76-88, the use according to any one of paragraphs 75-88, or the method according to any one of paragraphs 79-88, wherein the tumour is a solid tumour.

90. The bispecific polypeptide or polypeptide for use according to any one of paragraphs 74 or 76-78, the use according to any one of paragraphs 75-78, or the method according to any one of paragraphs 79-82, wherein the one or more non-cancer condition is selected from the list consisting of: ulcerative colitis, pancreatitis; cirrhosis; COPD; Crohn's disease; and/or hypothyroidism.

91. The bispecific polypeptide or polypeptide for use according to any one of paragraphs 74 or 76-90, the use according to any one of paragraphs 75-90, or the method according to any one of paragraphs 79-90, wherein the subject is human.

92. A bispecific polypeptide substantially as described herein with reference to the description and figures.

93. A polypeptide substantially as described herein with reference to the description and figures.

94. A polynucleotide substantially as described herein with reference to the description and figures.

95. A pharmaceutical composition substantially as described herein with reference to the description and figures.

96. A bispecific polypeptide for use or a polypeptide for use, substantially as described herein with reference to the description and figures.

97. Use of a bispecific polypeptide substantially as described herein with reference to the description and figures.

98. A method of treatment substantially as described herein with reference to the description and figures.

The invention claimed is:

1. A method for the treatment of a cancer and/or a tumour in a subject, comprising the step of administering to the subject an effective amount of a bispecific antibody, wherein said bispecific antibody comprises a first binding domain, designated B1, which is capable of binding specifically to CD40, and a second binding domain, designated B2, which is capable of specifically binding to carcinoembryonic antigen (CEA), wherein binding domain B1 comprises the three CDRs of the heavy chain and the three CDRs of the light chain of antibody ffAC 05337 (SEQ ID NOs: 81, 82 and 83; and SEQ ID NO: 96, GNI, and SEQ ID NO: 98); and wherein binding domain B2 comprises the three CDRs of the heavy chain and the three CDRs of the light chain of antibody ffAC 05337 (SEQ ID NOs: 216, 217 and 239 and SEQ ID NO: 90, AAS, and SEQ ID NO: 311).

2. The method according to claim 1, wherein the bispecific antibody comprises a human Fc region or a variant of a human Fc region, where the region is an IgG1, IgG2, IgG3 or IgG4 region.

3. The method according to claim 1, wherein the bispecific antibody is capable of inducing:
(a) tumour-specific immune activation; and/or
(b) activation of dendritic cells; and/or
(c) internalisation of associated tumour debris and/or extracellular vesicles containing CEA antigens as well as tumour neoantigens; and/or
(d) cross-presentation of peptides derived from internalised tumour antigens on MHC; and/or
(e) priming and activation of effector T cells; and/or
(f) direct tumoricidal effects, selected from the list consisting of: apoptosis, necroptosis, antibody-dependent cellular cytotoxicity (ADCC) and complement-dependent cytotoxicity (CDC).

4. The method according to claim 1, wherein the CEA is a carcinoembryonic antigen-related cell adhesion molecule (CEACAM).

5. The method according to claim 1, wherein binding domain B1 comprises the heavy chain variable region and the light chain variable region of antibody ffAC_05337 (SEQ ID NO: 431 and 430) and wherein binding domain B2 comprises the heavy chain variable region and the light chain variable region of antibody ffAC_05337 (SEQ ID NO: 433 and 432).

6. The method according to claim 1, wherein the cancer and/or the tumour is one or more cancer and/or tumour selected from the list consisting of: prostate cancer; breast cancer; lung cancer; colorectal cancer; melanomas; bladder cancer; brain/CNS cancer; cervical cancer; oesophageal cancer; gastric cancer; head/neck cancer; kidney cancer; liver cancer; carcinoma; leukaemia; lymphomas; ovarian cancer; pancreatic cancer; tonsil cancer; and sarcomas.

7. The method according to claim 4, wherein the CEACAM is CEACAM5.

* * * * *